(12) United States Patent
Berdini et al.

(10) Patent No.: US 8,399,442 B2
(45) Date of Patent: *Mar. 19, 2013

(54) PHARMACEUTICAL COMPOUNDS

(75) Inventors: Valerio Berdini, Cambridge (GB); Jayne Elizabeth Curry, Cambridge (GB); Neil James Gallagher, Basel (CH); Adrian Liam Gill, Buxton (GB); John Francis Lyons, Cambridge (GB)

(73) Assignee: Astex Therapeutics Limited, Cambridge (GB)

( * ) Notice: Subject to any disclaimer, the term of this patent is extended or adjusted under 35 U.S.C. 154(b) by 869 days.

This patent is subject to a terminal disclaimer.

(21) Appl. No.: 12/159,054

(22) PCT Filed: Dec. 29, 2006

(86) PCT No.: PCT/GB2006/004954
§ 371 (c)(1),
(2), (4) Date: Dec. 19, 2008

(87) PCT Pub. No.: WO2007/077435
PCT Pub. Date: Jul. 12, 2007

(65) Prior Publication Data
US 2010/0004232 A1 Jan. 7, 2010

Related U.S. Application Data

(60) Provisional application No. 60/755,339, filed on Dec. 30, 2005, provisional application No. 60/806,218, filed on Jun. 29, 2006.

(30) Foreign Application Priority Data

Dec. 30, 2005 (GB) .................................. 0526607.7

(51) Int. Cl.
*A61K 31/33* (2006.01)
(52) U.S. Cl. ...................................................... 514/183
(58) Field of Classification Search .................... 514/183
See application file for complete search history.

(56) References Cited

U.S. PATENT DOCUMENTS

| 5,952,368 | A | 9/1999 | Kertesz et al. |
| 6,350,746 | B1 | 2/2002 | Buckman et al. |
| 6,358,978 | B1 | 3/2002 | Ritzeler et al. |
| 6,696,437 | B1 | 2/2004 | Lubisch et al. |
| 7,087,616 | B2 | 8/2006 | Fischer et al. |
| 7,977,477 | B2 | 7/2011 | Berdini et al. |
| 8,110,573 | B2 | 2/2012 | Berdini et al. |
| 2003/0207883 | A1 | 11/2003 | Renhowe et al. |
| 2004/0048868 | A1 | 3/2004 | Edwards et al. |
| 2004/0082798 | A1 | 4/2004 | Alonso-Alija et al. |
| 2004/0214814 | A1 | 10/2004 | Bebbington et al. |
| 2004/0242559 | A1 | 12/2004 | Ugolini et al. |
| 2005/0009894 | A1 | 1/2005 | Babin et al. |
| 2006/0293336 | A1 | 12/2006 | Sutton et al. |
| 2007/0021472 | A1 | 1/2007 | Zhu et al. |
| 2007/0105900 | A1 | 5/2007 | Berdini et al. |
| 2007/0135477 | A1 | 6/2007 | Berdini et al. |
| 2007/0208007 | A1 | 9/2007 | Saitou et al. |
| 2008/0132495 | A1 | 6/2008 | Berdini et al. |
| 2008/0312223 | A1 | 12/2008 | Berdini et al. |
| 2010/0055094 | A1 | 3/2010 | Curry et al. |
| 2011/0105501 | A1 | 5/2011 | Gallagher et al. |
| 2011/0159111 | A1 | 6/2011 | Curry et al. |
| 2011/0224203 | A1 | 9/2011 | Berdini et al. |
| 2012/0190673 | A1 | 7/2012 | Berdini et al. |

FOREIGN PATENT DOCUMENTS

| EP | 0169051 A2 | 1/1986 |
| EP | 0711768 A1 | 5/1996 |
| EP | 1264820 A1 | 12/2002 |
| EP | 1460067 A1 | 9/2004 |
| JP | 2007/045752 A | 2/2007 |
| WO | 94/14435 A1 | 7/1994 |
| WO | 94/29300 A1 | 12/1994 |

(Continued)

OTHER PUBLICATIONS

Kuehl et al 'Multiple Myeloma: Evolving Genetic Events and Host Interactions' Nature Reviews, vol. 2, p. 175-187, 2002.*

(Continued)

*Primary Examiner* — Brandon Fetterolf
*Assistant Examiner* — Christopher R Stone
(74) *Attorney, Agent, or Firm* — Heslin Rothenberg Farley & Mesiti P.C.

(57) ABSTRACT

A method for the treatment of: A. a disease state or condition mediated by a kinase which is BCR-abl, VEGFR, PDGFR, EGFR, FLT3, JAK, C-abl, PDK1, Chk, FGFR, Ret, Eph, or Src; or B. a cancer in which the cancer cells thereof contain a drug resistant kinase mutation which is: (a) a threonine gatekeeper mutation; or (b) a drug-resistant gatekeeper mutation; or (c) an imatinib resistant mutation; or (d) a nilotinib resistant mutation; or (e) a dasatinib resistant mutation; or (f) a T670l mutation in KIT; or (g) a T674l mutation in PDGFR; or (h) T790M mutation in EGFR; or (i) a T315l mutation in abl; or C. a cancer which expresses a mutated molecular target which is a mutated form of BCRabl, c-kit, PDGF, EGF receptor or ErbB2; which method comprises administering to a patient in need thereof a therapeutically effective amount of a compound of the formula (1 or 1'): or a salt, solvate, tautomer or N-oxide thereof.

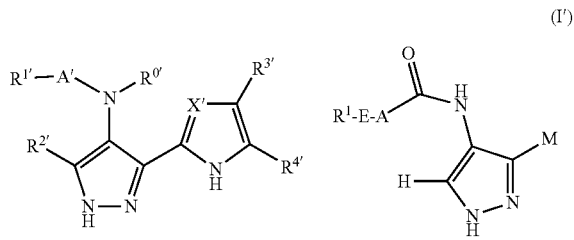

(1')

26 Claims, 8 Drawing Sheets

FOREIGN PATENT DOCUMENTS

| | | |
|---|---|---|
| WO | 96/00218 A1 | 1/1996 |
| WO | 97/12615 A1 | 4/1997 |
| WO | 97/36585 A1 | 10/1997 |
| WO | 99/46244 A1 | 9/1999 |
| WO | 99/50247 A1 | 10/1999 |
| WO | 99/61426 A1 | 12/1999 |
| WO | 00/39108 A1 | 7/2000 |
| WO | 00/43384 A1 | 7/2000 |
| WO | 00/59902 A2 | 10/2000 |
| WO | 00/64888 A1 | 11/2000 |
| WO | 01/02385 A1 | 1/2001 |
| WO | 01/19788 A2 | 3/2001 |
| WO | 01/19798 A2 | 3/2001 |
| WO | 01/57022 A2 | 8/2001 |
| WO | 01/64642 A2 | 9/2001 |
| WO | 01/64643 A2 | 9/2001 |
| WO | 01/79198 A1 | 10/2001 |
| WO | 02/00647 A1 | 1/2002 |
| WO | 02/00651 A2 | 1/2002 |
| WO | 02/00655 A1 | 1/2002 |
| WO | 02/059111 A2 | 8/2002 |
| WO | 02/072549 A1 | 9/2002 |
| WO | 02/096426 A1 | 12/2002 |
| WO | 03/002566 A1 | 1/2003 |
| WO | 03/004488 A1 | 1/2003 |
| WO | 03/006465 A1 | 1/2003 |
| WO | 03/035065 A1 | 5/2003 |
| WO | 03/044014 A1 | 5/2003 |
| WO | 03/053941 A2 | 7/2003 |
| WO | 03/066629 A2 | 8/2003 |
| WO | WO 03/082831 A1 * | 10/2003 |
| WO | 2004/041277 A1 | 5/2004 |
| WO | 2004/050636 A2 | 6/2004 |
| WO | 2004/052370 A2 | 6/2004 |
| WO | 2004/054515 A2 | 7/2004 |
| WO | 2004/056815 A1 | 7/2004 |
| WO | 2005/002552 A2 | 1/2005 |
| WO | 2005/002576 A2 | 1/2005 |
| WO | 2005/005414 A2 | 1/2005 |
| WO | 2005/028624 A2 | 3/2005 |
| WO | 2005/047266 A1 | 5/2005 |
| WO | 2006/070195 A1 | 7/2006 |
| WO | 2006/071940 A2 | 7/2006 |
| WO | 2006/092430 A1 | 9/2006 |
| WO | 2006/094209 A2 | 9/2006 |
| WO | 2006/094235 A1 | 9/2006 |
| WO | 2006/124780 A2 | 11/2006 |
| WO | 2007/019416 A1 | 2/2007 |
| WO | 2007/063031 A2 | 6/2007 |
| WO | 2008/001101 A2 | 1/2008 |
| WO | 2008/001115 A2 | 1/2008 |
| WO | 2008/003857 A1 | 1/2008 |

OTHER PUBLICATIONS

Vippagunta et al 'Crystalline Solids' Advanced Drug Delivery Reviews, vol. 48, p. 3-26, 2001.*
Souillac, Pierre, et al., Characterization of Delivery Systems, Differential Scanning Calorimetry, Encyclopedia of Controlled Drug Delivery, Wiley, 1999, pp. 212-227.
Vippagunta, Sudha R., et al., Crystalline solids, Advanced Drug Delivery Reviews, 2001, pp. 3-26.
Morissette, Sherry L., et al., High-throughput crystallization: polymorphs, salts, co-crystals and solvates of pharmaceutical solids, Advanced Drug Delivery Reviews, 2004, pp. 275-300.
Essassi et al.: Synthese et Hererocyclisation Des (Pyrazolyl-3-(5))-2 Benzimidazoles en Catalyse Par Transfert de Phase, *Bull. Soc. Chim. Belg.* vol. 96, pp. 63-67, 1987.
Blankley et al.: Antihypertensive Activity of 6-Arylpyrido[2,3-d] Pyrimidim-7-Amine Derivatives. 2. 7-Acyl Amide Analogues, *Journal of Medicinal Chemistry*, vol. 26, No. 3, Mar. 1, 1983, pp. 403-411.
Abd El-Wareth A O Sarhan et al.: Synthesis, Characterization and Reactions of 2-Deoxo-5-Deazaalloxazines, *Bioorganic & Medicinal Chemistry*, vol. 9, Jan. 1, 2001, pp. 2993-2998.
Mesguiche et al.: 4-Alkoxy-2,6-Diaminopyrimidine Derivatives: Inhibitors of Cyclin Dependent Kinases 1 and 2, *Bioorganic & Medicinal Chemistry Letters*, vol. 13, Jan. 1, 2003, pp. 217-222.
GB Search Report for GB 0315657.7 filed Jul. 3, 2003.
GB Search Report for GB 0324919.0 filed Oct. 24, 2003.
International Search Report for PCT/GB2004/002824 filed Jul. 5, 2004.
European Supplementary Search Report for EP Application No. 04 743 172.1, (2008).
GB search report for GB 0428552.4 filed Dec. 30, 2004.
GB search report for GB 0428554.0 filed Dec. 30, 2004.
International Search Report for PCT/GB2005/005097 filed Dec. 30, 2005.
GB search report for GB 0526607.7 filed Dec. 30, 2005.
International Search Report for PCT/GB2006/004954 filed Dec. 29, 2006.

* cited by examiner

PHARMACEUTICAL COMPOUNDS

CROSS REFERENCE TO RELATED APPLICATIONS

This application is a national phase filing under 35 U.S.C. §371 of PCT International Application PCT/GB2006/004954, filed Dec. 29, 2006 and published under PCT Article 21(2) in English as WO 2007/077435 on Jul. 12, 2007. PCT/GB2006/004954 claimed priority from United States Provisional Applications 60/755,339, filed Dec. 30, 2005, and 60/806,218, filed Jun. 29, 2006. PCT/GB2006/004954 also claimed priority from British application No. 0526607.7, filed Dec. 30, 2005. The entire contents of each of the prior applications are incorporated herein by reference.

This invention relates to new therapeutic uses of acylamino-pyrazolylbenzoimidazoles and ureido-pyrazolylbenzoimidazoles, and their analogues and in particular the compound 1-cyclopropyl-3-[3-(5-morpholin-4-ylmethyl-1H-benzoimidazol-2-yl)-1H-pyrazol-4-yl]-urea and its salts and crystalline forms.

BACKGROUND OF THE INVENTION

The compound 1-cyclopropyl-3-[3-(5-morpholin-4-ylmethyl-1H-benzoimidazol-2-yl)-1H-pyrazol-4-yl]-urea free base and various salts thereof are disclosed in our earlier International patent application filed 30 Dec. 2005 claiming priority from U.S. Ser. No. 60/640,475 and GB0428552.4 as being inhibitors of Cyclin Dependent Kinases (CDK kinases), Aurora kinases and Glycogen Synthase Kinase-3 (GSK3).

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

Cyclin Dependent Kinases

The process of eukaryotic cell division may be broadly divided into a series of sequential phases termed G1, S, G2 and M. Correct progression through the various phases of the cell cycle has been shown to be critically dependent upon the spatial and temporal regulation of a family of proteins known as cyclin dependent kinases (cdks) and a diverse set of their cognate protein partners termed cyclins. Cdks are cdc2 (also known as cdk1) homologous serine-threonine kinase proteins that are able to utilise ATP as a substrate in the phosphorylation of diverse polypeptides in a sequence dependent context. Cyclins are a family of proteins characterised by a homology region, containing approximately 100 amino acids, termed the "cyclin box" which is used in binding to, and defining selectivity for, specific cdk partner proteins.

Modulation of the expression levels, degradation rates, and activation levels of various cdks and cyclins throughout the cell cycle leads to the cyclical formation of a series of cdk/cyclin complexes, in which the cdks are enzymatically active. The formation of these complexes controls passage through discrete cell cycle checkpoints and thereby enables the process of cell division to continue. Failure to satisfy the prerequisite biochemical criteria at a given cell cycle checkpoint, i.e. failure to form a required cdk/cyclin complex, can lead to cell cycle arrest and/or cellular apoptosis. Aberrant cellular proliferation, as manifested in cancer, can often be attributed to loss of correct cell cycle control. Inhibition of cdk enzymatic activity therefore provides a means by which abnormally dividing cells can have their division arrested and/or be killed. The diversity of cdks, and cdk complexes, and their critical roles in mediating the cell cycle, provides a broad spectrum of potential therapeutic targets selected on the basis of a defined biochemical rationale.

Progression from the G1 phase to the S phase of the cell cycle is primarily regulated by cdk2, cdk3, cdk4 and cdk6 via association with members of the D and E type cyclins. The D-type cyclins appear instrumental in enabling passage beyond the G1 restriction point, where as the cdk2/cyclin E complex is key to the transition from the G1 to S phase. Subsequent progression through S phase and entry into G2 is thought to require the cdk2/cyclin A complex. Both mitosis, and the G2 to M phase transition which triggers it, are regulated by complexes of cdk1 and the A and B type cyclins.

During G1 phase Retinoblastoma protein (Rb), and related pocket proteins such as p130, are substrates for cdk(2, 4, & 6)/cyclin complexes. Progression through G1 is in part facilitated by hyperphosphorylation, and thus inactivation, of Rb and p130 by the cdk(4/6)/cyclin-D complexes. Hyperphosphorylation of Rb and p130 causes the release of transcription factors, such as E2F, and thus the expression of genes necessary for progression through G1 and for entry into S-phase, such as the gene for cyclin E. Expression of cyclin E facilitates formation of the cdk2/cyclin E complex which amplifies, or maintains, E2F levels via further phosphorylation of Rb. The cdk2/cyclin E complex also phosphorylates other proteins necessary for DNA replication, such as NPAT, which has been implicated in histone biosynthesis. G1 progression and the G1/S transition are also regulated via the mitogen stimulated Myc pathway, which feeds into the cdk2/cyclin E pathway. Cdk2 is also connected to the p53 mediated DNA damage response pathway via p53 regulation of p21 levels. p21 is a protein inhibitor of cdk2/cyclin E and is thus capable of blocking, or delaying, the G1/S transition. The cdk2/cyclin E complex may thus represent a point at which biochemical stimuli from the Rb, Myc and p53 pathways are to some degree integrated. Cdk2 and/or the cdk2/cyclin E complex therefore represent good targets for therapeutics designed at arresting, or recovering control of, the cell cycle in aberrantly dividing cells.

The exact role of cdk3 in the cell cycle is not clear. As yet no cognate cyclin partner has been identified, but a dominant negative form of cdk3 delayed cells in G1, thereby suggesting that cdk3 has a role in regulating the G1/S transition.

Although most cdks have been implicated in regulation of the cell cycle there is evidence that certain members of the cdk family are involved in other biochemical processes. This is exemplified by cdk5 which is necessary for correct neuronal development and which has also been implicated in the phosphorylation of several neuronal proteins such as Tau, NUDE-1, synapsin1, DARPP32 and the Muncl 8/Syntaxin1A complex. Neuronal cdk5 is conventionally activated by binding to the p35/p39 proteins. Cdk5 activity can, however, be deregulated by the binding of p25, a truncated version of p35. Conversion of p35 to p25, and subsequent deregulation of cdk5 activity, can be induced by ischemia, excitotoxicity, and β-amyloid peptide. Consequently p25 has been implicated in the pathogenesis of neurodegenerative diseases, such as Alzheimer's, and is therefore of interest as a target for therapeutics directed against these diseases.

Cdk7 is a nuclear protein that has cdc2 CAK activity and binds to cyclin H. Cdk7 has been identified as component of the TFIIH transcriptional complex which has RNA polymerase II C-terminal domain (CTD) activity. This has been associated with the regulation of HIV-1 transcription via a Tat-mediated biochemical pathway. Cdk8 binds cyclin C and has been implicated in the phosphorylation of the CTD of RNA polymerase II. Similarly the cdk9/cyclin-T1 complex (P-TEFb complex) has been implicated in elongation control of RNA polymerase II. PTEF-b is also required for activation of transcription of the HIV-1 genome by the viral transactivator Tat through its interaction with cyclin T1. Cdk7, cdk8, cdk9 and the P-TEFb complex are therefore potential targets for anti-viral therapeutics.

At a molecular level mediation of cdk/cyclin complex activity requires a series of stimulatory and inhibitory phosphorylation, or dephosphorylation, events. Cdk phosphorylation is performed by a group of cdk activating kinases (CAKs) and/or kinases such as weel, Myt1 and Mik1. Dephosphorylation is performed by phosphatases such as cdc25(a & c), pp 2a, or KAP.

Cdk/cyclin complex activity may be further regulated by two families of endogenous cellular proteinaceous inhibitors: the Kip/Cip family, or the INK family. The INK proteins specifically bind cdk4 and cdk6. p16$^{ink4}$ (also known as MTS1) is a potential tumour suppressor gene that is mutated, or deleted, in a large number of primary cancers. The Kip/Cip family contains proteins such as p21$^{Cip1, Waf1}$, p27$^{Kip1}$ and p57$^{kip2}$. As discussed previously p21 is induced by p53 and is able to inactivate the cdk2/cyclin(E/A) and cdk4/cyclin(D1/D2/D3) complexes. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of cdks, and their associated proteins, in co-ordinating and driving the cell cycle in proliferating cells have been outlined above. Some of the biochemical pathways in which cdks play a key role have also been described. The development of monotherapies for the treatment of proliferative disorders, such as cancers, using therapeutics targeted generically at cdks, or at specific cdks, is therefore potentially highly desirable. Cdk inhibitors could conceivably also be used to treat other conditions such as viral infections, autoimmune diseases and neuro-degenerative diseases, amongst others. Cdk targeted therapeutics may also provide clinical benefits in the treatment of the previously described diseases when used in combination therapy with either existing, or new, therapeutic agents. Cdk targeted anticancer therapies could potentially have advantages over many current antitumour agents as they would not directly interact with DNA and should therefore reduce the risk of secondary tumour development.

Diffuse Large B-Cell Lymphomas (DLBCL)

Cell cycle progression is regulated by the combined action of cyclins, cyclin-dependent kinases (CDKs), and CDK-inhibitors (CDKi), which are negative cell cycle regulators. p27KIP1 is a CDKi key in cell cycle regulation, whose degradation is required for G1/S transition. In spite of the absence of p27KIP1 expression in proliferating lymphocytes, some aggressive B-cell lymphomas have been reported to show an anomalous p27KIP1 staining. An abnormally high expression of p27KIP1 was found in lymphomas of this type. Analysis of the clinical relevance of these findings showed that a high level of p27KIP1 expression in this type of tumour is an adverse prognostic marker, in both univariate and multivariate analysis. These results show that there is abnormal p27KIP1 expression in Diffuse Large B-cell Lymphomas (DLBCL), with adverse clinical significance, suggesting that this anomalous p27KIP1 protein may be rendered non-functional through interaction with other cell cycle regulator proteins. (Br. J. Cancer. 1999 July; 80(9): 1427-34. p27KIP1 is abnormally expressed in Diffuse Large B-cell Lymphomas and is associated with an adverse clinical outcome. Saez A, Sanchez E, Sanchez-Beato M, Cruz M A, Chacon I, Munoz E, Camacho F I, Martinez-Montero J C, Mollejo M, Garcia J F, Piris M A. Department of Pathology, Virgen de la Salud Hospital, Toledo, Spain.)

Chronic Lymphocytic Leukemia

B-Cell chronic lymphocytic leukaemia (CLL) is the most common leukaemia in the Western hemisphere, with approximately 10,000 new cases diagnosed each year (Parker S L, Tong T, Bolden S, Wingo P A: Cancer statistics, 1997. Ca. Cancer. J. Clin. 47:5, (1997)). Relative to other forms of leukaemia, the overall prognosis of CLL is good, with even the most advanced stage patients having a median survival of 3 years.

The addition of fludarabine as initial therapy for symptomatic CLL patients has led to a higher rate of complete responses (27% v 3%) and duration of progression-free survival (33 v 17 months) as compared with previously used alkylator-based therapies. Although attaining a complete clinical response after therapy is the initial step toward improving survival in CLL, the majority of patients either do not attain complete remission or fail to respond to fludarabine. Furthermore, all patients with CLL treated with fludarabine eventually relapse, making its role as a single agent purely palliative (Rai K R, Peterson B, Elias L, Shepherd L, Hines J, Nelson D, Cheson B, Kolitz J, Schiffer C A: A randomized comparison of fludarabine and chlorambucil for patients with previously untreated chronic lymphocytic leukemia. A CALGB SWOG, CTG/NCI-C and ECOG Inter-Group Study. Blood 88:141a, 1996 (abstr 552, suppl 1). Therefore, identifying new agents with novel mechanisms of action that complement fludarabine's cytotoxicity and abrogate the resistance induced by intrinsic CLL drug-resistance factors will be necessary if further advances in the therapy of this disease are to be realized.

The most extensively studied, uniformly predictive factor for poor response to therapy and inferior survival in CLL patients is aberrant p53 function, as characterized by point mutations or chromosome 17p13 deletions. Indeed, virtually no responses to either alkylator or purine analog therapy have been documented in multiple single institution case series for those CLL patients with abnormal p53 function. Introduction of a therapeutic agent that has the ability to overcome the drug resistance associated with p53 mutation in CLL would potentially be a major advance for the treatment of the disease.

Flavopiridol and CYC 202, inhibitors of cyclin-dependent kinases induce in vitro apoptosis of malignant cells from B-cell chronic lymphocytic leukemia (B-CLL).

Flavopiridol exposure results in the stimulation of caspase 3 activity and in caspase-dependent cleavage of p27(kip1), a negative regulator of the cell cycle, which is overexpressed in B-CLL (Blood. 1998 Nov. 15; 92(10):3804-16 Flavopiridol induces apoptosis in chronic lymphocytic leukemia cells via activation of caspase-3 without evidence of bcl-2 modulation or dependence on functional p53. Byrd J C, Shinn C, Waselenko J K, Fuchs E J, Lehman T A, Nguyen P L, Flinn I W, Diehl L F, Sausville E, Grever M R).

Aurora Kinases

Relatively recently, a new family of serine/threonine kinases known as the Aurora kinases has been discovered that are involved in the G2 and M phases of the cell cycle, and which are important regulators of mitosis.

The precise role of Aurora kinases has yet to be elucidated but that they play a part in mitotic checkpoint control, chromosome dynamics and cytokinesis (Adams et al., *Trends Cell Biol.*, 11: 49-54 (2001). Aurora kinases are located at the centrosomes of interphase cells, at the poles of the bipolar spindle and in the mid-body of the mitotic apparatus.

Three members of the Aurora kinase family have been found in mammals so far (E. A. Nigg, *Nat. Rev. Mol. Cell. Biol.* 2: 21-32, (2001)). These are:
Aurora A (also referred to in the literature as Aurora 2);
Aurora B (also referred to in the literature as Aurora 1); and
Aurora C (also referred to in the literature as Aurora 3).

The Aurora kinases have highly homologous catalytic domains but differ considerably in their N-terminal portions (Katayama H, Brinkley W R, Sen S.; The Aurora kinases: role in cell transformation and tumorigenesis; Cancer Metastasis Rev. 2003 December; 22(4):451-64).

The substrates of the Aurora kinases A and B have been identified as including a kinesin-like motor protein, spindle apparatus proteins, histone H3 protein, kinetochore protein and the tumour suppressor protein p53.

Aurora A kinases are believed to be involved in spindle formation and become localised on the centrosome during the early G2 phase where they phosphorylate spindle-associated proteins (Prigent et al., *Cell*, 114: 531-535 (2003). Hirota et al, *Cell*, 114:585-598, (2003) found that cells depleted of Aurora A protein kinase were unable to enter mitosis. Furthermore, it has been found (Adams, 2001) that mutation or disruption of the Aurora A gene in various species leads to mitotic abnormalities, including centrosome separation and maturation defects, spindle aberrations and chromosome segregation defects.

The Aurora kinases are generally expressed at a low level in the majority of normal tissues, the exceptions being tissues with a high proportion of dividing cells such as the thymus and testis. However, elevated levels of Aurora kinases have been found in many human cancers (Giet et al., *J. Cell. Sci.* 112: 3591-361, (1999) and Katayama (2003). Furthermore, Aurora A kinase maps to the chromosome 20q13 region that has frequently been found to be amplified in many human cancers.

Thus, for example, significant Aurora A over-expression has been detected in human breast, ovarian and pancreatic cancers (see Zhou et al., *Nat. Genet.* 20: 189-193, (1998), Tanaka et al., *Cancer Res.*, 59: 2041-2044, (1999) and Han et al., *cancer Res.*, 62: 2890-2896, (2002).

Moreover, Isola, *American Journal of Pathology* 147,905-911 (1995) has reported that amplification of the Aurora A locus (20q13) correlates with poor prognosis for patients with node-negative breast cancer.

Amplification and/or over-expression of Aurora-A is observed in human bladder cancers and amplification of Aurora-A is associated with aneuploidy and aggressive clinical behaviour, see Sen et al, *J. Natl. Cancer Inst*, 94: 1320-1329 (2002).

Elevated expression of Aurora-A has been detected in over 50% of colorectal cancers, (see Bischoff et al., *EMBO J.*, 17: 3052-3065, (1998) and Takahashi et al., *Jpn. J. Cancer Res.*, 91: 1007-1014 (2000)) ovarian cancers (see Gritsko et al. *Clin. Cancer Res.*, 9: 1420-1426 (2003), and gastric tumours Sakakura et al., *British Journal of Cancer,* 84: 824-831 (2001).

Tanaka et al. *Cancer Research,* 59: 2041-2044 (1999) found evidence of over-expression of Aurora A in 94% of invasive duct adenocarcinomas of the breast.

High levels of Aurora A kinase have also been found in renal, cervical, neuroblastoma, melanoma, lymphoma, pancreatic and prostate tumour cell lines Bischoff et al. (1998), EMBO J., 17: 3052-3065 (1998); Kimura et al. J. Biol. Chem., 274: 7334-7340 (1999); Zhou et al., Nature Genetics, 20: 189-193 (1998); Li et al., Clin Cancer Res. 9 (3): 991-7 (2003)].

Aurora-B is highly expressed in multiple human tumour cell lines, including leukemic cells [Katayama et al., Gene 244: 1-7)]. Levels of this enzyme increase as a function of Duke's stage in primary colorectal cancers [Katayama et al., J. Natl Cancer Inst., 91: 1160-1162 (1999)].

High levels of Aurora-3 (Aurora-C) have been detected in several tumour cell lines, even though this kinase tends to be restricted to germ cells in normal tissues (see Kimura et al. *Journal of Biological Chemistry,* 274: 7334-7340 (1999)). Over-expression of Aurora-3 in approximately 50% of colorectal cancers has also been reported in the article by Takahashi et al., *Jpn J. Cancer Res.* 91: 1007-1014 (2001)].

Other reports of the role of Aurora kinases in proliferative disorders may be found in Bischoff et al., *Trends in Cell Biology* 9: 454-459 (1999); Giet et al. Journal of Cell Science, 112: 3591-3601 (1999) and Dutertre, et al. *Oncogene,* 21: 6175-6183 (2002).

Royce et al report that the expression of the Aurora 2 gene (known as STK15 or BTAK) has been noted in approximately one-fourth of primary breast tumours. (Royce M E, Xia W, Sahin A A, Katayama H, Johnston D A, Hortobagyi G, Sen S, Hung M C; STK15/Aurora-A expression in primary breast tumours is correlated with nuclear grade but not with prognosis; *Cancer.* 2004 Jan. 1; 100(1):12-9).

Endometrial carcinoma (EC) comprises at least two types of cancer: endometrioid carcinomas (EECs) are estrogen-related tumours, which are frequently euploid and have a good prognosis. Nonendometrioid carcinomas (NEECs; serous and clear cell forms) are not estrogen related, are frequently aneuploid, and are clinically aggressive. It has also been found that Aurora was amplified in 55.5% of NEECs but not in any EECs (P< or =0.001) (Noreno-Bueno G, Sanchez- Estevez C, Cassia R, Rodriguez-Perales S, Diaz-Uriarte R, Dominguez O, Hardisson D, Andujar M, Prat J, Matias-Guiu X, Cigudosa J C, Palacios *J. Cancer Res.* 2003 Sep. 15; 63(18):5697-702).

Reichardt et al (*Oncol Rep.* 2003 September-October; 10(5):1275-9) have reported that quantitative DNA analysis by PCR to search for Aurora amplification in gliomas revealed that five out of 16 tumours (31%) of different WHO grade (1× grade II, 1× grade III, 3× grade IV) showed DNA amplification of the Aurora 2 gene. It was hypothesized that amplification of the Aurora 2 gene may be a non-random genetic alteration in human gliomas playing a role in the genetic pathways of tumourigenesis.

Results by Hamada et al (*Br. J. Haematol.* 2003 May; 121(3):439-47) also suggest that Aurora 2 is an effective candidate to indicate not only disease activity but also tumourigenesis of non-Hodgkin's lymphoma. Retardation of tumour cell growth resulting from the restriction of this gene's functions could be a therapeutic approach for non-Hodgkin's lymphoma.

In a study by Gritsko et al (*Clin Cancer Res.* 2003 April; 9(4): 1420-6)), the kinase activity and protein levels of Aurora A were examined in 92 patients with primary ovarian tumours. In vitro kinase analyses revealed elevated Aurora A kinase activity in 44 cases (48%). Increased Aurora A protein levels were detected in 52 (57%) specimens. High protein levels of Aurora A correlated well with elevated kinase activity.

Results obtained by Li et al (*Clin. Cancer Res.* 2003 March; 9(3):991-7) showed that the Aurora A gene is overexpressed in pancreatic tumours and carcinoma cell lines and suggest that overexpression of Aurora A may play a role in pancreatic carcinogenesis.

Similarly, it has been shown that Aurora A gene amplification and associated increased expression of the mitotic kinase it encodes are associated with aneuploidy and aggressive clinical behaviour in human bladder cancer. (*J. Natl. Cancer Inst.* 2002 Sep. 4; 94(17):1320-9).

Investigation by several groups (Dutertre S, Prigent C., Aurora-A overexpression leads to override of the microtubule-kinetochore attachment checkpoint; *Mol. Interv.* 2003 May; 3(3):127-30 and Anand S, Penrhyn-Lowe S, Venkitaraman A R., Aurora-A amplification overrides the mitotic spindle assembly checkpoint, inducing resistance to Taxol, *Cancer Cell.* 2003 January; 3(1):51-62) suggests that overexpression of Aurora kinase activity is associated with resistance to some current cancer therapies. For example overexpression of Aurora A in mouse embryo fibroblasts can reduce the sensitivity of these cells to the cytotoxic effects of taxane derivatives. Therefore Aurora kinase inhibitors may find particular use in patients who have developed resistance to existing therapies.

On the basis of work carried out to date, it is apparent that inhibition of Aurora kinases, particularly Aurora kinase A and Aurora kinase B, will prove an effective means of arresting tumour development.

Harrington et al (*Nat. Med.* 2004 March; 10(3):262-7) have demonstrated that an inhibitor of the Aurora kinases suppresses tumour growth and induces tumour regression in vivo. In the study, the Aurora kinase inhibitor blocked cancer cell proliferation, and also triggered cell death in a range of cancer cell lines including leukaemic, colorectal and breast cell lines. In addition, it has shown potential for the treatment of leukemia by inducing apoptosis in leukemia cells. VX-680 potently killed treatment-refractory primary Acute Myelogenous Leukemia (AML) cells from patients (Andrews, *Oncogene*, 2005, 24, 5005-5015).

Recent reports indicate that Aurora kinases A and B are overexpressed in human leukaemia cells and that a small molecule Aurora kinase inhibitor is active against the growth of primary acute myeloid cells in vitro (Harrington et al, 2004). Moreover it has recently been reported that the product of the PML gene that is disrupted in acute promyelocytic leukaemia by a t(15:17) translocation (PML3), interacts with Aurora A and suppresses its kinase activity. Further evidence is emerging that PML is a tumour suppressor and that its disruption is not limited to leukaemias but may also be common in lymphomas and some solid tumors (Xu et al, *Molecular Cell* 17: 721-732, 2005).

Cancers which may be particularly amenable to Aurora inhibitors include breast, bladder, colorectal, pancreatic, ovarian, non-Hodgkin's lymphoma, gliomas and nonendometrioid endometrial carcinomas. Leukemias particularly amenable to Aurora inhibitors include Acute Myelogenous Leukemia (AML), chronic myelogenous leukaemia (CML), B-cell lymphoma (Mantle cell), and Acute Lymphoblastic Leukemia (ALL). Further leukemias include acute promyelocytic leukaemia.

Overexpression of Aurora kinase A has been identified as an independent predictor of poor prognosis in patients with medulloblastoma, a highly malignant primitive neuroectodermal tumor of the cerebellum (Neben et al., *Cancer Research*, 64: 3103-3111 (2004).

Glycogen Synthase Kinase

Glycogen Synthase Kinase-3 (GSK3) is a serine-threonine kinase that occurs as two ubiquitously expressed isoforms in humans (GSK3α & beta GSK3β). GSK3 has been implicated as having roles in embryonic development, protein synthesis, cell proliferation, cell differentiation, microtubule dynamics, cell motility and cellular apoptosis. As such GSK3 has been implicated in the progression of disease states such as diabetes, cancer, Alzheimer's disease, stroke, epilepsy, motor neuron disease and/or head trauma. Phylogenetically GSK3 is most closely related to the cyclin dependent kinases (CDKs).

The consensus peptide substrate sequence recognised by GSK3 is (Ser/Thr)-X-X-X-(pSer/pThr), where X is any amino acid (at positions (n+1), (n+2), (n+3)) and pSer and pThr are phospho-serine and phospho-threonine respectively (n+4). GSK3 phosphorylates the first serine, or threonine, at position (n). Phospho-serine, or phospho-threonine, at the (n+4) position appear necessary for priming GSK3 to give maximal substrate turnover. Phosphorylation of GSK3α at Ser21, or GSK3β at Ser9, leads to inhibition of GSK3. Mutagenesis and peptide competition studies have led to the model that the phosphorylated N-terminus of GSK3 is able to compete with phospho-peptide substrate (S/TXXXpS/pT) via an autoinhibitory mechanism. There are also data suggesting that GSK3β and GSKβ may be subtly regulated by phosphorylation of tyrosines 279 and 216 respectively. Mutation of these residues to a Phe caused a reduction in in vivo kinase activity. The X-ray crystallographic structure of GSK3β has helped to shed light on all aspects of GSK3 activation and regulation.

GSK3 forms part of the mammalian insulin response pathway and is able to phosphorylate, and thereby inactivate, glycogen synthase. Upregulation of glycogen synthase activity, and thereby glycogen synthesis, through inhibition of GSK3, has thus been considered a potential means of combating type II, or non-insulin-dependent diabetes mellitus (NIDDM): a condition in which body tissues become resistant to insulin stimulation. The cellular insulin response in liver, adipose, or muscle tissues, is triggered by insulin binding to an extracellular insulin receptor. This causes the phosphorylation, and subsequent recruitment to the plasma membrane, of the insulin receptor substrate (IRS) proteins. Further phosphorylation of the IRS proteins initiates recruitment of phosphoinositide-3 kinase (PI3K) to the plasma membrane where it is able to liberate the second messenger phosphatidylinosityl 3,4,5-trisphosphate (PIP3). This facilitates co-localisation of 3-phosphoinositide-dependent protein kinase 1 (PDK1) and protein kinase B (PKB or Akt) to the membrane, where PDK1 activates PKB. PKB is able to phosphorylate, and thereby inhibit, GSK3α and/or GSKβ through phosphorylation of Ser9, or ser21, respectively. The inhibition of GSK3 then triggers upregulation of glycogen synthase activity. Therapeutic agents able to inhibit GSK3 may thus be able to induce cellular responses akin to those seen on insulin stimulation. A further in vivo substrate of GSK3 is the eukaryotic protein synthesis initiation factor 2B (eIF2B). eIF2B is inactivated via phosphorylation and is thus able to suppress protein biosynthesis. Inhibition of GSK3, e.g. by inactivation of the "mammalian target of rapamycin" protein (mTOR), can thus upregulate protein biosynthesis. Finally there is some evidence for regulation of GSK3 activity via the mitogen activated protein kinase (MAPK) pathway through phosphorylation of GSK3 by kinases such as mitogen activated protein kinase activated protein kinase 1 (MAPKAP-K1 or RSK). These data suggest that GSK3 activity may be modulated by mitogenic, insulin and/or amino acid stimulii.

It has also been shown that GSK3β is a key component in the vertebrate Wnt signalling pathway. This biochemical pathway has been shown to be critical for normal embryonic development and regulates cell proliferation in normal tissues. GSK3 becomes inhibited in response to Wnt stimulii. This can lead to the de-phosphorylation of GSK3 substrates such as Axin, the adenomatous polyposis coli (APC) gene product and β-catenin. Aberrant regulation of the Wnt pathway has been associated with many cancers. Mutations in APC, and/or β-catenin, are common in colorectal cancer and other tumours. β-catenin has also been shown to be of importance in cell adhesion. Thus GSK3 may also modulate cellular adhesion processes to some degree. Apart from the biochemical pathways already described there are also data implicating GSK3 in the regulation of cell division via phosphorylation of cyclin-D1, in the phosphorylation of transcription factors such as c-Jun, CCAAT/enhancer binding protein α (C/EBPα), c-Myc and/or other substrates such as Nuclear Factor of Activated T-cells (NFATc), Heat Shock Factor-1 (HSF-1) and the c-AMP response element binding protein (CREB). GSK3 also appears to play a role, albeit tissue specific, in regulating cellular apoptosis. The role of GSK3 in modulating cellular apoptosis, via a pro-apoptotic mechanism, may be of particular relevance to medical conditions in which neuronal apoptosis can occur. Examples of these are head trauma, stroke, epilepsy, Alzheimer's and motor neuron diseases, progressive supranuclear palsy, corticobasal degeneration, and Pick's disease. In vitro it has been shown that GSK3 is able to hyper-phosphorylate the microtubule associated protein Tau. Hyperphosphorylation of Tau disrupts its normal binding to microtubules and may also lead to the formation of intra-cellular Tau filaments. It is believed that the progressive accumulation of these filaments leads to eventual neuronal dysfunction and degeneration. Inhibition of Tau phosphorylation, through inhibition of GSK3, may thus provide a means of limiting and/or preventing neurodegenerative effects.

C-Abl

A chromosomal translocation event which fuses a BCR encoded sequence to a truncated c-abl gene greatly increases c-abl's tyrosine kinase activity and is the transforming agent in 95% of all Chronic Myeloid Leukaemia (CML) patients. This translocation occurs between chromosomes 9 and 22 resulting in an altered chromosome 22, the Philadelphia (Ph+) chromosome, which can be distinguished by cytogenetic methods. The fusion of BCR and Abl gene sequences results in the oligomerization of the Bcr-Abl gene product, increased trans-autophosphorylation and activation. An auto-inhibitory domain of the c-abl protein is also deleted as a result of the gene fusion. The sub-cellular localization of c-abl is also affected as a result of the gene fusion. The oncogenic effects of Bcr-Abl are complicated, but are believed to involve induction of G1 to S phase transition through activation of Ras, Erk and Jun pathways. Bcr-Abl also affects cell survival through the PI3K/Akt pathway. The oncogenic effects of Bcr-Abl have been demonstrated in animal models which indicate that the Bcr-Abl protein is able to establish CML symptoms in mice.

CML is a fatal disease, which progresses through three stages: chronic phase, accelerated phase, and blast crisis. CML is characterized in early stages by the proliferation of terminally differentiated neutrophils. As the disease progresses an excessive number of myeloid or lymphoid progenitor cells are produced. This chronic phase of the disease may last for years before advancing to an acute blast stage, characterized by multiple additional genetic mutations. CML primarily affects adults who have a mean survival of 5 years after the disease is manifested. CML has been successfully treated in early phases by an ATP competitive inhibitor of c-abl, imatinib (Gleevec). A 95% remission rate was demonstrated for this drug in a phase I clinical trial. Durable responses to imatinib have been observed for CML patients in the chronic phase, however remissions in blast phase only last 2-6 months. Unfortunately the development of acquired resistance to imatinib in CML patients is estimated to be as high as 15%/year.

Kinase domain mutations in BCR-ABL represent the most common mechanism of acquired resistance to imatinib, occurring in 500-90% of cases. The most common cause of imatinib resistance is through the development of point mutations in the c-abl kinase domain, which directly or indirectly affect imatinib binding. More than 25 distinct Abl kinase domain mutations have been identified in imatinib treated CML patients and are associated with clinical resistance to imatinib (Hematology Shah 2005 (1): 183). These mutations have varying degrees of sensitivity to imatinib. Imatinib has been shown to bind to the ABL kinase domain in the inactive, or closed, conformation and to induce a variety of conformational changes to the protein upon binding. While some resistance-associated mutations occur at amino acid positions implicated in directly contacting imatinib, the majority are felt to prevent the kinase domain from adopting the specific conformation to which imatinib binds. Studies have shown that some mutations confer only a moderate degree of resistance, and as a result, dose escalation is predicted to recapture responses in some cases. Co-administration of second generation BCR-ABL inhibitors (e.g. BMS354825, AMN-107) have been shown to effectively inhibit many imatinib resistant c-abl mutants. However there are no drugs in the clinic which have been shown to be efficacious against the most imatinib resistant c-abl mutation, T315I.

The Philadelphia chromosome is also found in a form of acute lymphoblastic leukemia (ALL). It seems highly probable that this form of ALL is due to the same chromosomal and molecular mechanisms as CML.

FMS-Like Tyrosine-kinase 3 (FLT3)

FLT3 (short for fns-like tyrosine-kinase 3) is a class III receptor tyrosine kinase (RTK) structurally related to the receptors for platelet derived growth factor (PDGF), colony stimulating factor 1 (CSF1), and KIT ligand (KL). FLT3 contains an intracellular tyrosine kinase domain split in two by a specific hydrophilic insertion termed a kinase insert.

FLT3 and its specific ligand FLT3-ligand (FL) plays a role in regulation of haematopoietic progenitor cells and is expressed on haematopoietic cells including CD34-positive bone marrow cells, corresponding to multipotential, myeloid and B-lymphoid progenitor cells, and on monocytic cells.

Activating mutations of FLT3 are one of the most frequent mutations observed in acute myeloid leukaemia. The most frequent mutations are referred to as length mutations (LM) or internal tandem duplications (ITD) and consist of a duplicated sequence or insert belonging to exon 11 and sometimes involving intron 11 and exon 12.

Internal tandem duplications and/or insertions and, rarely, deletions in the FLT3-gene are implicated in 20-25% of all acute myeloid leukemias (AML) and 5-10% myelodysplastic syndromes (ADS) and some cases with acute lymphoblastic leukemia (ALL).

The mutation of the FLT3 protein causes constitutive activation of the tyrosine kinase activity due to disruption of a negative regulatory domain. This activation results in stimulation of several growth factor dependent pathways including the raf-MEK-ERK pathway and contributes to the growth and survival of the leukaemic cells. Thus inhibition of the kinase activity of FLT3 would be an effective treatment for diseases such as those described above which are dependent upon the FLT3 activity.

3-Phosphoinositide-Dependent protein Kinase-1 (PDK1)

The 3-phosphoinositide-dependent protein kinase-1 (PDK1) plays a key role in regulating the activity of a number of kinases belonging to the AGC subfamily of protein kinases (Alessi, D. et al., Biochem. Soc. Trans, 29, p1-14, 2001). These include protein kinase B (PKB/AKT), p70 ribosomal S6 kinase (S6K) (Avruch, J. et al., Prog. Mol. Subcell. Biol., 2001, p 115-154, 2001) and p90 ribosomal S6 kinase (Frodin, M. et al., EMBO J., 19, p2924-2934, 2000). Kinase activity of serum and glucocordicoid regulated kinase (SGK) can also be phosphorylated and activated by PDK-1. Other potential substrates include protein kinase C, cAMP-dependent protein kinase (PKA), PRK1 and Protein kinase G.

PDK1 mediated signalling is activated in response to insulin and growth factors and as a consequence of attachment of the cell to the extracellular matrix (integrin signalling). Once activated these enzymes mediate many diverse cellular events by phosphorylating key regulatory proteins that play important roles controlling processes such as cell survival, growth, proliferation and glucose regulation (Lawlor, M. A. et al., J. Cell Sci., 114, p2903-2910, 2001), (Lawlor, M. A. et al., EMBO J., 21, p3728-3738, 2002). PDK-1 inhibitors therefore may provide novel therapeutic treatment for diseases such as diabetes and cancer.

PDK1 is a 556 amino acid protein, with an N-terminal catalytic domain and a C-terminal pleckstrin homology (PH) domain, which activates its substrates by phosphorylating these kinases at their activation loop (Belham, C. et al., Curr. Biol., 9, pR93-96, 1999). Many human cancers including prostate and NSCL have elevated PDK1 signalling pathway function resulting from a number of distinct genetic events such as PTEN mutations or over-expression of certain key regulatory proteins [(Graff, J. R., Expert Opin. Ther. Targets, 6, p 103-13, 2002), (Brognard, J., et al., Cancer Res., 61 p 3986-97, 2001)]. Inhibition of PDK1 as a potential mechanism to treat cancer was demonstrated by transfection of a PTEN negative human cancer cell line (IJ87MG) with antisense oligonucleotides directed against PDK1. The resulting decrease in PDK1 protein levels led to a reduction in cellular proliferation and survival (Flynn, P., et al., Curr. Biol., 10, p 1439-42, 2000). Therefore inhibition of PDK-1 could offer an attractive target for cancer therapy.

PDK-1-mediated phosphorylation of PKB/AKT, which is largely present in an inactive form in unstimulated cells, converts the enzyme to a catalytically active form. This occurs through the phosphorylation of the activation loop domain of AKT at threonine-309 in AKT2 and theonine-308 in AKT1. Although AKT displays low, basal levels of activation in normal, unstimulated cells, AKT often becomes constitutively activated in tumor cells. This occurs through the up-regulation of a variety of different signalling molecules or the presence of oncogenenic mutations commonly found in cancer cells that can promote the activation of AKT, such as P1-3 kinase, growth factor receptors (e.g., EGFR family members), Ras, Src, and BCR-ABL activation. Loss of the tumor suppressor PTEN is another means of greatly increasing AKT activity in cancer cells (Besson, A. et al., Eur. J. Biochem. (1999), Vol. 263, No. 3, pp. 605-611). PTEN mutation or down regulation of PTEN protein is found in a large number of tumors and cancer cell lines. PTEN is a phosphatase that removes the D-3 phosphate from the products of P1-3 kinase such as phosphatidylinositol 3,4,5-trisphosphate and phosphatidylinositol-3,4-bisphosphate (Myers, M. P. et al., Proc. Natl. Acad. Sci. USA (1998), Vol. 95, No. 23, pp. 13513-13518; Stambolic, V. et al., Cell (1998), Vol. 95 p29-39). Loss of PTEN, therefore has the effect of increasing products of P1-3 kinase and promoting constitutive activation of AKT. Cancers with highly upregulated levels of AKT may be especially sensitive to the effects of PDK-1/AKT pathway inhibitors.

Therefore PDK1 is a critical mediator of the PI3K signalling pathway, which regulates a multitude of cellular function including growth, proliferation and survival. Consequently inhibition of this pathway could affect many defining requirements for cancer progression, as such it is anticipated that a PDK1 inhibitor will have an effect on the growth of a very wide range of human cancers.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels. (Folkman, EXS, 79, 1-81 (1997); Folkman, Nature Medicine, 1, 27-31 (1995); Folkman and Shing, J. Biol. Chem., 267, 10931 (1992)).

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, Ann. Rhum. Dis., 51, 919 (1992)). In diabetes (and in many different eye diseases), new vessels invade the macula or retina or other ocular structures, and may cause blindness (Brooks, et al., Cell, 79, 1157 (1994)). The process of atherosclerosis has been linked to angiogenesis (Kahlon, et al., Can. J. Cardiol., 8, 60 (1992)). Tumor growth and metastasis have been found to be angiogenesis-dependent (Folkman, Cancer Biol, 3, 65 (1992); Denekamp, Br. J. Rad., 66,181 (1993); Fidler and Ellis, Cell, 79,185 (1994)).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly, et al., *Cell*, 79, 315 (1994); Ingber, et al., *Nature*, 348, 555 (1990)), ocular diseases (Friedlander, et al., *Science*, 270, 1500 (1995)), arthritis (Peacock, et al., *J. Exp. Med.*, 175, 1135 (1992); Peacock et al., *Cell. Immun.*, 160, 178 (1995)) and hemangioma (Taraboletti, et al., *J. Natl. Cancer Inst.*, 87, 293 (1995)).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al., *The Oncologist*, 5(90001), 1-2 (2000)). VEGFR(s) are protein tyrosine kinases (PTKs). PTKs catalyze the phosphorylation of specific tyrosine residues in proteins involved in cell function thus regulating cell growth, survival and differentiation. (Wilks, A. F., *Progress in Growth Factor Research*, 2, 97-111 (1990); Courtneidge, S. A., *Dev. Supp*. 1, 57-64 (1993); Cooper, J. A., *Semin. Cell Biol.*, 5(6), 377-387 (1994); Paulson, R. F., *Semin. Immunol.*, 7(4), 267-277 (1995); Chan, A. C., *Curr. Opin.Immunol.*, 8(3), 394-401 (1996)).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T., et al., *J. Cell Biol.*, 129, 895-898 (1995)).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G., *The Oncologist*, 5(90001), 3-10 (2000)).

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

Janus Kinases (JAKs)

The Janus kinases (JAKs) consist of four known mammalian family members, JAK1, JAK2, JAK3 and TYK2 and are intra cellular tyrosine kinases. The JAK-STAT pathway is activated through specific membrane bound receptors. Upon cytokine and growth factor binding, JAKs are recruited to the intracellular domains of the receptors and phosphorylate cytoplasmic proteins including the Signal Transducers and Activators of Transcription (STATs). Specific cytokine receptors recruit and activate distinct pairs of JAK and STAT proteins. The STATs dimerize on phosphorylation and directly activate transcription after nuclear translocation.

JAK2 is the primary tyrosine kinase activated by erythropoietin (EPO) and is essential for definitive erythropoiesis (Parganas et al., Cell 1998; 93(3): 385-95).

Constitutive activation of the JAK-STAT pathway through mechanisms such as point mutations resulting in deregulation of JAK2 activity have been shown to result in ligand independent survival and hypersensitivity and have been observed in some leukaemic cell types (Levine et al., 2005; Jelinek., 2005; Staerk et al 2005).

An activating mutation in the tyrosine kinase JAK2 has been observed in polycythemia vera, essential thrombocythemia and myeloid metaplasia with myelofibrosis (Levine et al., Cancer Cell 2005; 7, 387-97). JAK2 mutation 1849G>T is rare in acute leukaemias but can be found in CMML, Philadelphia chromosome-negative CML, and megakaryocytic leukaemia (Jelinek, Blood 2005; 106: 3370-3). Chronic Myelomonocytic Leukemias (CMML) include two types: an adult type referred to as CMML and a form of childhood leukemia called Juvenile Myelomonocytic Leukemia (JMML) or Juvenile Chronic Myelogenous Leukemia (JCML). CMML leukemias have features that are characteristic of myelogenous leukemia. In the past, CMML was sometimes classified and referred to as a type of myelodysplastic syndrome (MDS). CMML is more rapidly progressive than "typical" chronic myelogenous leukemia and less rapidly progressive than a type of acute leukemia known as acute myelomonocytic leukemia. Juvenile myelomonocytic leukemia differs in several ways from the adult CMML.

A high proportion (>50%) of patients with myeloproliferative disorders (PD; (polycythemia vera, essential thrombocythemia, idiopathic myelofibrosis) carry a dominant gain-of-function V617F mutation in the JH2 kinase-like domain of JAK2. The majority of Polycythemia Vera (PV) patients harbor a unique somatic mutation (V617F) in the pseudokinase domain of JAK2, which leads to constitutive signaling (Staerk et al, J. Biol. Chem., 10.1074/jbc.C500358200). This mutation leads to deregulation of the kinase activity, and thus to constitutive tyrosine phosphorylation activity. The incidence of the V617F mutation in different studies ranges from 65-97% in polycythemia vera, from 41-57% in patients with essential thrombocythemia, and from 23-95% in patients with idiopathic myelofibrosis. In MPD the mutation is heterozygous in most patients and homozygous only in a minor subset. Mitotic recombination probably causes both 9p LOH and the transition from heterozygosity to homozygosity. The same mutation was also found in roughly 20% of Ph-negative atypical CML, in more than 10% of CMML, in about 15% of patients with megakaryocytic AML (AML M7), and ⅕ patients with juvenile myelomonocytic leukemia (JMML). The V617F mutation seems to occur exclusively in hematopietic malignancies of the myeloid lineage.

JAK2 has been described in a novel somatic point mutation (a G-C to T-A transversion, at nucleotide 1849 of exon 12, resulting in the substitution of valine to phenylalanine at codon 617; JAK2V617F) in classic, BCR/ABL-negative MPD including polycythemia vera (PV), essential thrombocythemia (ET), and myelofibrosis with myeloid metaplasia (MMM) (Blood, 15 Nov. 2005, Vol. 106, No. 10, pp. 3335-3336). Following the initial wave of studies that reported a relatively high incidence of JAK2V617F in PV (65%-97%), ET (23%-57%), and MMM (35%-57%), subsequent studies disclosed the occurrence of the same mutation in a spectrum of atypical MPDs as well as in myelodysplastic syndrome (MDS), albeit at a much lower mutational frequency (3%-33%). In one of these latter studies, JAK2V617F and other oncogenic kinase mutations including BCR/ABL and FIP1L1-PDGFRA were shown to be mutually exclusive events.

Checkpoint Kinase 1 (Chk 1) and Checkpoint Kinase 2 (Chk2)

Checkpoint kinase 1 (Chk 1) and Checkpoint kinase 2 (Chk2) are unrelated serine/threonine kinases involved in the DNA damage checkpoint at the G2M boundary (M. J. O'Connell et al, EMBO J., 1997, 16, 545-554). Chk1 is an essential DNA damage and replication checkpoint kinase. It is phosphorylated by ataxia-telangiectasia mutated and Rad3-related kinase (ATR) in response to formation of single-stranded DNA and other DNA lesions (and replication stress) which is induced during DNA damage processing. This phosphorylation correlates with its ability to arrest cells in G2 (Walworth and Bemards 1996). Chk1 phosphorylates Cdc25 phosphatase inhibiting the removal of two inactivating phosphates on cyclin dependent kinases (CDKs) (Zeng et al, Nature, 1998, 395, 507-510) leading to cell cycle arrest. DNA damaging agents available in the clinic, which cause p53-dependent cell cycle arrest and apoptosis, may have reduced efficacy against p53 mutant tumour cells. If Chk1 activity is also inhibited in p53-negative cancers, all ability to arrest and repair DNA in response to DNA damage is removed, resulting in mitotic catastrophe and enhancing the effect of the DNA damaging agents (Koniaras et al., Oncogene 2001; 20(51): 7453-63.).

Thus combining the inhibition of CHK1/2 with DNA targeting agents such as topoisomerase inhibitors, alkylating agents, antimetabolites, DNA binders cisplatin, cyclophosphamide, doxorubicin, irinotecan, fludarabine mitomycin C and radiotherapy, may be beneficial by overcoming some of the mechanisms used by cancer cell to evade current chemotherapy.

Chk2 similarly plays a critical role in the DNA damage checkpoint via double-strand breaks and ataxia-telangiectasia mutated kinase (ATM). Chk2 inhibition therefore could also protect normal sensitive tissues from some chemotherapeutic agents. Targeting Chk1 and Chk2 may significantly increase the therapeutic window of DNA damaging agents available in the clinic.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signaling molecules which act as autocrine as well as paracrine factors. Autocrine FGF signaling may be particularly important in the progression of steroid hormone-dependent cancers to a hormone independent state (Powers, et al., Endocr. Relat. Cancer, 7, 165-197 (2000)).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Ozawa, et al., Teratog. Carcinog. Mutagen., 21, 27-44 (2001)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors numbered 1 to 4 (FGFR1 to FGFR4). Upon ligand binding, the receptors dimerize and auto- or trans-phosphorylate specific cytoplasmic tyrosine residues to transmit an intracellular signal that ultimately regulates nuclear transcription factor effectors.

Disruption of the FGFR1 pathway should affect tumor cell proliferation since this kinase is activated in many tumor types in addition to proliferating endothelial cells. The overexpression and activation of FGFR1 in tumor-associated vasculature has suggested a role for these molecules in tumor angiogenesis.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signaling in intramembranous bone formation. For example, in Apert (AP) syndrome, characterized by premature cranial suture ossification, most cases are associated with point mutations engendering gain-of-function in fibroblast growth factor receptor 2 (Lemonnier, et al., J. Bone Miner. Res., 16, 832-845 (2001)).

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene (Meyers, et al., Am. J. Hum. Genet., 58, 491-498 (1996); Plomp, et al., Am. J. Med. Genet., 75, 245-251 (1998)), and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of fibroblast growth factor receptor 2 (Yu, et al., Proc. Natl. Acad. Sci. U.S.A., 97, 14536-14541 (2000)).

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas (Powers, C. J., et al., Endocr. Rel. Cancer, 7, 165 (2000), Qiu, W., et. al., World Journal Gastroenterol, 11(34) 2005). Accordingly, FGFR3 inhibitors would be useful in the treatment of multiple myeloma, bladder and cervical carcinomas.

As such, compounds which inhibit FGFR will be useful in providing a means of preventing the growth or inducing apoptosis of neoplasias and in tumours, particularly by inhibiting angiogenesis. Therefore, the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Over expression of FGFR4 has been linked to poor prognosis in both prostate and thyroid carcinomas (Ezzat, S., et al. The Journal of Clinical Investigation, 109, 1 (2002), Wang et al. Clinical Cancer Research, 10 (2004)). In addition a germline polymorphism (Gly388Arg) is associated with increased incidence of lung, breast, colon and prostate cancers (Wang et al. Clinical Cancer Research, 10 (2004)).

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. Clin Cancer Res. 2006 12(22): 6652-6662.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis (Inoue, et al., 1997 & 2002; Barrios, et al. 1997)). TGFβ1 and PDGF have been reported to be involved in the fibrogenic process (reviewed by Atamas & White, 2003) and further published work suggests the elevation of FGF's and consequent increase in fibroblast proliferation, may be in response to elevated TGFβ1 (Khalil, et al., 2005).

The potential therapeutic relevance of this pathway in fibrotic conditions is suggested by the reported clinical effect of Pirfenidone (Arata, et al., 2005) in idiopathic pulmonary fibrosis (IPF).

Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

RET

The Ret proto-oncogene encodes a receptor tyrosine kinase that is expressed during development in a variety of tissues, including the peripheral and central nervous systems and the kidney. The abnormalities present in ret null mice suggest that Ret is critical for the migration and innervation of enteric neurons to the hindgut, and for proliferation and branching of the ureteric bud epithelium during kidney development (Nature 367, 380-383, 1994).

Mutations in the RET receptor tyrosine kinase provides a classic example of phenotypic heterogeneity in a variety of diseases. Gain-of-function mutations of RET are associated with human cancer and in particular cause inherited and non-inherited thyroid cancer. Gene rearrangements juxtaposing the tyrosine kinase domain of RET to heterologous gene partners have been found in sporadic papillary carcinomas of the thyroid (PTC). These rearrangements generate chimeric RET/PTC oncogenes. In germline cancers, point mutations of RET are responsible for multiple endocrine neoplasia type 2 (MEN 2A and 2B) and familial medullary thyroid carcinoma (FMTC). Both MEN 2 mutations and PTC gene rearrangements potentiate the intrinsic tyrosine kinase activity of RET and, ultimately, activate targets downstream of RET.

Thus somatic gene rearrangements of RET have been found in papillary thyroid carcinoma (PTC) and germline point mutations in multiple endocrine neoplasia (MEN) types 2A and 2B and familial medullary thyroid carcinoma (FMTC). Conversely, loss-of-function mutations are responsible for the development of Hirschsprung's disease, a congenital malformation of the enteric nervous system. (Naoya Asai et al, Pathology International, Volume 56 Page 164, April 2006)

Eph

The largest subfamily of receptor tyrosine kinases (RTKs), the Eph family, and their ligands (ephrins), play important roles in physiologic and pathologic vascular processes. Both the Ephs (receptors) and ephrins (ligands) are divided into two groups, A and B subfamilies (Eph Nomenclature Committee, 1997). The binding of ephrin ligands to Eph receptors is dependent on cell-cell interactions. The interactions of ephrins and Ephs have recently been shown to function via bi-directional signalling. The ephrins binding to Eph receptors initiate phosphorylation at specific tyrosine residues in the cytoplasmic domain of the Eph receptors. In response to Eph receptor binding, the ephrin ligand also undergoes tyrosine phosphorylation, so-called 'reverse' signalling (Holland, S. J., et al., Nature, 383, 722-725 (1996); Bruckner et al, Science 275: 1640-1643 (1997)).

Eph RTKs and their ephrin ligands play important roles in embryonic vascular development. Disruption of specific Eph receptors and ligands (including ephrin-B2) leads to defective vessel remodelling, organisation, and sprouting resulting in embryonic death (Wang, H. U., et al., Cell, 93: 741-753

(1998); Adams, R. H., et al., Genes Dev, 13, 295-306 (1999); Gale and Yancopoulos, Genes Dev, 13, 1055-1066 (1999); Helbling, P. M., et al., Development, 127, 269-278 (2000)). Coordinated expression of the Eph/ephrin system determines the phenotype of embryonic vascular structures: ephrin-B2 is present on arterial endothelial cells (ECs), whereas EphB4 is present on venQus ECs (Gale and Yancopoulos, Genes Dev, 13, 1055-1066 (1999); Shin, D., et al., DevBiol, 230, 139-150 (2001)). Recently, specific Ephs and ephrins have been implicated in tumour growth and angiogenesis.

The Ephs and ephrins have been found to be overexpressed in many human tumours. In particular, the role of EphB2 has been identified in small cell lung carcinoma (Tang, X. X., et al., Clin Cancer Res, 5, 455-460 (1999)), human neuroblastomas (Tang, X. X., et al., Clin Cancer Res, 5, 1491-1496 (1999)) and colorectal cancers (Liu, W., et al., Brit. J. Canc., 90, 1620-1626 (2004)), and higher expression levels of Ephs and ephrins, including EphB2, have been found to correlate with more aggressive and metastatic tumours (Nakamoto, M. and Bergemann, A. D., Microsc. Res Tech, 59, 58-67 (2002)).

Consequently, inhibition of EphB2 will serve to disrupt angiogenesis, and in particular in certain tumours where overexpression occurs.

As discussed previously, there are also publications that teach that inhibitors of angiogenesis, working by diverse mechanisms, are beneficial in diseases such as cancer and metastasis (O'Reilly, et al., Cell, 79, 315 (1994); Ingber, et al., Nature, 348, 555 (1990)), ocular diseases (Friedlander, et al., Science, 270,1500 (1995)), arthritis (Peacock, et al., J. Exp. Med., 175, 1135 (1992); Peacock et al., Cell. Immun., 160, 178 (1995)) and hemangioma (Taraboletti, et al., J. Natl. Cancer Inst., 87, 293 (1995)).

SRC

The Src family kinases (SFK) comprises nine members of which three (Src, Fyn Yes) are ubiquitously expressed. Src itself is implicated in the pathogenesis of human malignancies. Activated mutants of c-Src can transform human cells in culture and Src protein expression and/or activity is increased in epithelial cancers. In colon cancer there is frequent elevation of Src activity compared to adjacent normal mucosa. Furthermore the Src activation is often elevated in metastases compared to the primary tumour implying a possible role for the protein in invasion and metastasis. Moreover Src expression is strongly correlated with disease progression. Similarly Src expression and activation are also elevated in breast, pancreatic, oesophageal, ovarian, lung, head and neck and gastric cancers compared to normal tissues.

EGFR and PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. One driver for growth is the epidermal growth factor (EGF), and the receptor for EGF (EGFR) has been implicated in the development and progression of a number of human solid tumours including those of the lung, breast, prostate, colon, ovary, head and neck. EGFR is a member of a family of four receptors, namely EGFR (HER1 or ErbB1), ErbB2 (HER2/neu), ErbB3 (HER3), and ErbB4 (HER4). These receptors are large proteins that reside in the cell membrane, each having a specific external ligand binding domain, a transmembrane domain and an internal domain which has tyrosine kinase enzyme activity. When EGF attaches to EGFR, it activates the tyrosine kinase, triggering reactions that cause the cells to grow and multiply. EGFR is found at abnormally high levels on the surface of many types of cancer cells, which may divide excessively in the presence of EGF. Inhibition of EGRF activity has therefore been a target for chemotherapeutic research in the treatment of cancer. Such inhibition can be effected by direct interference with the target EGRF on the cell surface, for example by the use of antibodies, or by inhibiting the subsequent tyrosine kinase activity.

Examples of agents which target EGRF tyrosine kinase activity include the tyrosine kinase inhibitors gefitinib and erlotinib. Gefitinib which has the chemical name 4-(3-chloro-4-fluoroanilino)-7-methoxy-6-(3-morpholinopropoxy) quinazoline, is used for the treatment of non-small-cell lung cancer, and is also under development for other solid tumours that over-express EGF receptors such as breast and colorectal cancer. Erlotinib, which has the chemical name N-(3-ethynylphenyl)-6,7-bis(2-methoxyethoxy)-4-quinazoline, has also been used for the treatment of non-small-cell lung cancer, and is being developed for the treatment of various other solid tumours such as pancreatic cancer.

Another growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment of chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. In addition, sorafenib (BAY 43-9006) which has the chemical name 4-(4-(3-(4-chloro-3(trifluoromethyl)phenyl)ureido)phenoxy)-N2-methylpyridine-2-carboxamide, targets both the Raf signalling pathway to inhibit cell proliferation and the VEGFR/PDGFR signalling cascades to inhibit tumour angiogenesis. Sorafenib is being investigated for the treatment of a number of cancers including liver and kidney cancer.

There are conditions which are dependent on activation of PDGFR such as hypereosinophilic syndrome. PDGFR activation is also associated with other malignancies, which include chronic myelomonocytic leukemia (CMML). In another disorder, dermatofibrosarcoma protuberans, an infiltrative skin tumor, a reciprocal translocation involving the gene encoding the PDGF-B ligand results in constitutive secretion of the chimeric ligand and receptor activation. Imatinib has which is a known inhibitor of PDGFR has activity against all three of these diseases.

WO 02/34721 from Du Pont discloses a class of indeno [1,2-c]pyrazol-4-ones as inhibitors of cyclin dependent kinases.

WO 01/81348 from Bristol Myers Squibb describes the use of 5-thio-, sulphinyl- and sulphonylpyrazolo[3,4-b]-pyridines as cyclin dependent kinase inhibitors.

WO 00/62778 also from Bristol Myers Squibb discloses a class of protein tyrosine kinase inhibitors.

WO 01/72745A1 from Cyclacel describes 2-substituted 4-heteroaryl-pyrimidines and their preparation, pharmaceutical compositions containing them and their use as inhibitors of cyclin-dependant kinases (cdks) and hence their use in the treatment of proliferative disorders such as cancer, leukaemia, psoriasis and the like.

WO 99/21845 from Agouron describes 4-aminothiazole derivatives for inhibiting cyclin-dependent kinases (cdks), such as CDK1, CDK2, CDK4, and CDK6. The invention is also directed to the therapeutic or prophylactic use of pharmaceutical compositions containing such compounds and to methods of treating malignancies and other disorders by administering effective amounts of such compounds.

WO 01/53274 from Agouron discloses as CDK kinase inhibitors a class of compounds which can comprise an amide-substituted benzene ring linked to an N-containing heterocyclic group.

WO 01/98290 (Pharmacia & Upjohn) discloses a class of 3-aminocarbonyl-2-carboxamido thiophene derivatives as protein kinase inhibitors. The compounds are stated to have multiple protein kinase activity.

WO 01/53268 and WO 01/02369 from Agouron disclose compounds that mediate or inhibit cell proliferation through the inhibition of protein kinases such as cyclin dependent kinase or tyrosine kinase. The Agouron compounds have an aryl or heteroaryl ring attached directly or though a CH=CH or CH=N group to the 3-position of an indazole ring.

WO 00/39108 and WO 02/00651 (both to Du Pont Pharmaceuticals) describe broad classes of heterocyclic compounds that are inhibitors of trypsin-like serine protease enzymes, especially factor Xa and thrombin. The compounds are stated to be useful as anticoagulants or for the prevention of thromboembolic disorders.

US 2002/0091116 (Zhu et al.), WO 01/1978 and WO 01/64642 each disclose diverse groups of heterocyclic compounds that have activity against Factor Xa.

WO 03/035065 (Aventis) discloses a broad class of benzimidazole derivatives as protein kinase inhibitors but does not disclose activity against CDK kinases or GSK kinases.

WO 97/36585 and U.S. Pat. No. 5,874,452 (both to Merck) disclose biheteroaryl compounds that are inhibitors of farnesyl transferase.

WO 03/066629 (Vertex) discloses benzimidazolylpyrazole amines as GSK-3 inhibitors.

WO 97/12615 (Warner Lambert) discloses benzimidazoles as 15-lipoxygenase inhibitors.

WO 2004/54515 (SmithKline Beecham Corporation) discloses a class of benzimidazoles as thrombopoietin mimetics.

WO 2004/41277 (Merck) discloses a class of amino-benzimidazoles as androgen receptor modulators.

WO 2005/028624 (Plexxikon) discloses molecular scaffolds for compounds having activity against protein kinases.

SUMMARY OF THE INVENTION

In a first aspect, the invention provides the use of a compound for the manufacture of a medicament for the prophylaxis or treatment of:
A. a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. csrc); or B. a cancer in which the cancer cells thereof contain a drug resistant kinase mutation which is:
   (a) a threonine gatekeeper mutation; or
   (b) a drug-resistant gatekeeper mutation; or
   (c) an imatinib resistant mutation; or
   (d) a nilotinib resistant mutation; or
   (e) a dasatinib resistant mutation; or
   (f) a T670I mutation in KIT; or
   (g) a T674I mutation in PDGFR; or
   (h) T790M mutation in EGFR; or
   (i) a T315I mutation in abl; or
C. a cancer which expresses a mutated molecular target which is a mutated form of BCRabl, c-kit, PDGF, EGF receptor or ErbB2; or
D. a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2;
wherein the compound is:
I. A Compound of the Formula (I):

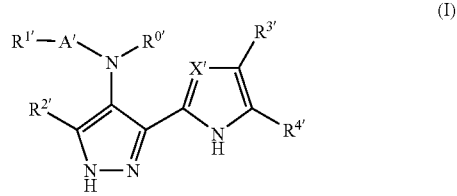

(I)

or a salt, solvate, tautomer or N-oxide thereof;
wherein
X' is $CR^{5'}$ or N;
A' is a bond or —$(CH_2)_m$—$(B')_n$—;
B' is C=O, $NR^g$(C=O) or O(C=O) wherein $R^g$ is hydrogen or $C_{1-4}$ hydrocarbyl optionally substituted by hydroxy or $C_{1-4}$ alkoxy;
m is 0, 1 or 2;
n is 0 or 1;
$R^{0'}$ is hydrogen or, together with $NR^g$ when present, forms a group —$(CH_2)_p$— wherein p is 2 to 4;
$R^{1'}$ is hydrogen, a carbocyclic or heterocyclic group having from 3 to 12 ring members, or an optionally substituted $C_{1-8}$ hydrocarbyl group;
$R^{2'}$ is hydrogen, halogen, methoxy, or a $C_{1-4}$ hydrocarbyl group optionally substituted by halogen, hydroxyl or methoxy;
$R^{3'}$ and $R^{4'}$ together with the carbon atoms to which they are attached form an optionally substituted fused carbocyclic or heterocyclic ring having from 5 to 7 ring members of which up to 3 can be heteroatoms selected from N, O and S; and
$R^{5'}$ is hydrogen, a group $R^{2'}$ or a group $R^{10'}$ wherein $R^{10'}$ is selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$;

and salts, N-oxides, tautomers and solvates thereof: or

II. A Compound of the Formula (I'):

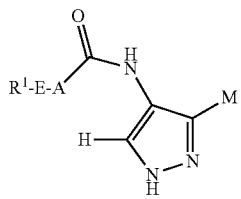

(I')

or a salt, solvate, tautomer or N-oxide thereof, wherein M is selected from a group D1 and a group D2:

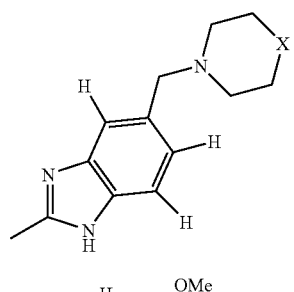

(D1)

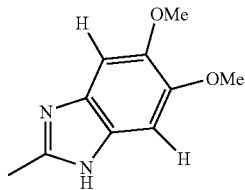

(D2)

and wherein:

(A) when M is a group D1:

X is selected from O, NH and $NCH_3$;

A is selected from a bond and a group $NR^2$ where $R^2$ is hydrogen or methyl;

E is selected from a bond, $CH_2$, CH(CN) and $C(CH_3)_2$;

$R^1$ is selected from:

(i) a cycloalkyl group of 3 to 5 ring members optionally substituted by hydroxy, fluorine, amino, methylamino, methyl or ethyl;

(ii) a saturated heterocyclic group of 4 to 6 ring members containing 1 or 2 heteroatom ring members selected from O, N, S and $SO_2$, the heterocyclic group being optionally substituted by $C_{1-4}$ alkyl, amino or hydroxy; but excluding unsubstituted 4-morpholinyl, unsubstituted tetrahydropyran-4-yl, unsubstituted 2-pyrrolidinyl, and unsubstituted and 1-substituted piperidine-4-yl;

(iii) a 2,5-substituted phenyl group of the formula:

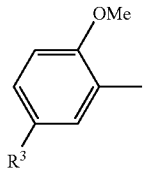

wherein (a) when X is NH or N—$CH_3$, $R^3$ is selected from chlorine and cyano; and (b) when X is O, $R^3$ is CN;

(iv) a group $CR^6R^7R^8$ wherein $R^6$ and $R^7$ are each selected from hydrogen and methyl, and $R^8$ is selected from hydrogen, methyl, $C_{1-4}$ alkylsulphonylmethyl, hydroxymethyl and cyano;

(v) a pyridazin-4-yl group optionally substituted by one or two substituents selected from methyl, ethyl, methoxy and ethoxy;

(vi) a substituted imidazothiazole group wherein the substituents are selected from methyl, ethyl, amino, fluorine, chlorine, amino and methylamino; and (vii) an optionally substituted 1,3-dihydro-isoindol-2-yl or optionally substituted 2,3-dihydro-indol-1-yl group wherein the optional substituents in each case are selected from halogen, cyano, amino, $C_{1-4}$ mono- and dialkylamino, $CONH_2$ or CONH—$C_{1-4}$ alkyl $C_{1-4}$ alkyl and $C_{1-4}$ alkoxy wherein the $C_{1-4}$ alkyl and $C_{1-4}$ alkoxy groups are optionally substituted by hydroxy, methoxy, or amino;

(viii) 3-pyridyl optionally substituted by one or two substituents selected from hydroxy, halogen, cyano, amino, $C_{1-4}$ mono- and dialkylamino, $CONH_2$ or CONH—$C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino, but excluding the compounds 2-oxo-1,2-dihydro-pyridine-3-carboxylic acid [3-(5-morpholin-4-ylmethyl-1H-benzoimidazol-2-yl)-1H-pyrazol-4-yl]-amide and 2,6-dimethoxy-N-[3-(5-morpholin-4-ylmethyl-1H-benzoimidazol-2-yl)-1H-pyrazol-4-yl]-nicotinamide;

(ix) thiomorpholine or an S-oxide or S,S-dioxide thereof optionally substituted by one or two substituents selected from halogen, cyano, amino, $C_{1-4}$ mono- and dialkylamino, $CONH_2$ or CONH—$C_{1-4}$ alkyl $C_{1-4}$ alkyl and $C_{1-4}$ alkoxy wherein the $C_{1-4}$ alkyl and $C_{1-4}$ alkoxy groups are optionally substituted by hydroxy, methoxy, or amino; and when E-A is $NR^2$, $R^1$ is additionally selected from:

(x) 2-fluorophenyl, 3-fluorophenyl, 4-fluorophenyl, 2,4-difluorophenyl, 3,4-difluorophenyl, 2,5-difluorophenyl, 3,5-difluorophenyl, 2,4,6-trifluorophenyl, 2-methoxyphenyl, 5-chloro-2-methoxyphenyl, cyclohexyl, unsubstituted 4-tetrahydropyranyl and tert-butyl;

(xi) a group $NR^{10}R^{11}$ where $R^{10}$ and $R^{11}$ are each $C_{1-4}$ alkyl or $R^{10}$ and $R^{11}$ are linked so that $NR^{10}R^{11}$ forms a saturated heterocyclic group of 4 to 6 ring members optionally containing a second heteroatom ring member selected from O, N, S and $SO_2$, the heterocyclic group being optionally substituted by $C_{1-4}$ alkyl, amino or hydroxy;

(xii) pyridone optionally substituted by one or two substituents selected from hydroxy, halogen, cyano, amino, $C_{1-4}$ mono- and dialkylamino, $CONH_2$, CONH—$C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino;

when E-A is C(CH$_3$)$_2$NR$^2$ or CH$_2$—NR$^2$, R$^1$ is additionally selected from:
(xiii) unsubstituted 2-furyl and 2,6-difluorophenyl; and
when E-A is C(CH$_3$)$_2$NR$^2$, R$^1$ is additionally selected from:
(xiv) unsubstituted phenyl; and
when E is CH$_2$, R$^1$ is additionally selected from:
(xv) unsubstituted tetrahydropyran-4-yl; and
(B) when M is a group D2:
A is selected from a bond and a group NR$^2$ where R$^2$ is hydrogen or methyl;
E is selected from a bond, CH$_2$, CH(CN) and C(CH$_3$)$_2$;
R$^1$ is selected from:
(xvi) a 2-substituted 3-furyl group of the formula:

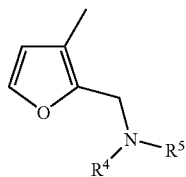

wherein R$^4$ and R$^5$ are the same or different and are selected from hydrogen and C$_{1-4}$ alkyl, or R$^4$ and R$^5$ are linked so that NR$^4$R$^5$ forms a 5- or 6-membered saturated heterocyclic group optionally containing a second heteroatom or group selected from O, NH, NMe, S or SO$_2$, the 5- or 6-membered saturated ring being optionally substituted by hydroxy, fluorine, amino, methylamino, methyl or ethyl;
(xvii) a 5-substituted 2-furyl group of the formula:

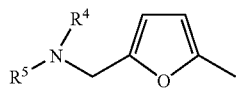

wherein R$^4$ and R$^5$ are the same or different and are selected from hydrogen and C$_{1-4}$ alkyl, or R$^4$ and R$^5$ are linked so that NR$^4$R$^5$ forms a 5- or 6-membered saturated heterocyclic group optionally containing a second heteroatom or group selected from O, NH, NMe, S or SO$_2$, the 5- or 6-membered saturated heterocyclic group being optionally substituted by hydroxy, fluorine, amino, methylamino, methyl or ethyl; with the proviso that the compound is not 5-piperidin-1-ylmethyl-furan-2-carboxylic acid [3-(5,6-dimethoxy-1H-benzoimidazol-2-yl)-1H-pyrazol-4-yl]-amide;
(xviii) a group of the formula:

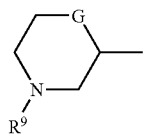

wherein R$^9$ is hydrogen, methyl, ethyl or isopropyl; G is CH, O, S, SO, SO$_2$ or NH and the group is optionally substituted by one, two or three substituents selected from C$_{1-4}$ hydrocarbyl, hydroxy, C$_{1-4}$ hydrocarbyloxy, fluorine, amino, mono- and di-C$_{1-4}$ alkylamino and wherein the C$_{1-4}$ hydrocarbyl and C$_{1-4}$ hydrocarbyloxy groups are each optionally substituted by hydroxy, fluorine, amino, mono- or di-C$_{1-4}$ alkylamino; and (xix) a 3,5-disubstituted phenyl group of the formula:

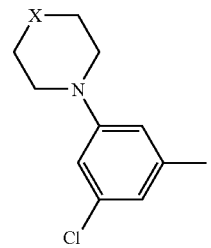

wherein X is selected from O, NH and NCH$_3$; and
(C) when M is a Group D1:
and X is O; A is a group NR$^2$ where R$^2$ is hydrogen; E is a bond; and R$^1$ is 2,6-difluorophenyl; then the compound of the formula (I) is an acid addition salt selected from salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, hydrochloric, isethionic, isobutyric, lactic (e.g. (+)-L-lactic and (±)-DL-lactic), lactobionic, laurylsulphonic, maleic, malic, (–)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

Compounds of the formula (I) correspond to the compounds of formula (I) disclosed in our earlier application PCT/GB2004/002824 (WO 2005/002552), the contents of which are incorporated herein by reference. The moieties X', A', B', R$^{0'}$, R$^{1'}$, R$^{2'}$, R$^{3'}$, R$^{4'}$ and R$^{5'}$ in formula (I') correspond to the moieties X, A, B, R$^0$, R$^1$, R$^2$, R$^3$, R$^4$ and R$^5$ in formula (I) of PCT/GB2004/002824.

Particular compounds of the formula (I) are the compounds of the sub-groups, embodiments and examples of formula (I) as defined in PCT/GB2004/002824 (WO 2005/002552).

Compounds of the formula (I') correspond to the compounds of formula (I') disclosed in our International patent application number PCT/GB2005/005097 (WO 2006/070195), the contents of which are incorporated herein by reference.

Particular compounds of the formula (I') are the compounds of the sub-groups, embodiments and examples of formula (I) as defined in PCT/GB2005/005097 (WO 2006/070195).

In further aspects, the invention provides:
The use of a compound of the formula (I), (I') or sub-groups, individual species, salts or crystalline forms thereof as defined herein for the manufacture of a medicament for the prophylaxis or treatment of a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc).

The use of a compound of the formula (I), (I') or sub-groups, individual species, salts or crystalline forms thereof as defined herein for the manufacture of a medicament for the prophylaxis or treatment of a disease state or condition mediated by a kinase which is BCR-abl, VEGFR, Flt3, JAK, C-abl, PDK1, Chk1, Chk2, FGFR (e.g. FGFR$^3$), Ret, Eph (e.g. EphB2 or EphB4), or cSrc.

The use of a compound of the formula (I), (I') or subgroups, individual species, salts or crystalline forms thereof as defined herein for the manufacture of a medicament for the treatment or prophylaxis of a disease state or condition which is a malignancy driven by BCR-abl.

The use of a compound of the formula (I), (I') or subgroups, individual species, salts or crystalline forms thereof as defined herein for the manufacture of a medicament for the treatment or prophylaxis of a disease state or condition which is a malignancy driven by BCR-abl and wherein the malignancy is selected from Philadelphia chromosome positive malignancies, for example Philadelphia chromosome-positive leukamias such as Philadelphia chromosome positive CML and Philadelphia chromosome positive ALL; and myeloproliferative syndrome.

The use of a compound of the formula (I), (I') or subgroups, individual species, salts or crystalline forms thereof as defined herein for the manufacture of a medicament for the treatment or prophylaxis of a disease state or condition mediated by VEGFR.

The use of a compound of the formula (I), (I') or subgroups, individual species, salts or crystalline forms thereof as defined herein for the manufacture of a medicament for the treatment or prophylaxis of a disease state or condition mediated by VEGFR; wherein the disease state or condition is an ocular disease or condition such as the disease and conditions selected from age-related macular degeneration (e.g. wet form of age-related macular degeneration); ischemic proliferative retinopathies (e.g. retinopathy of prematurity (ROP) and diabetic retinopathy); and hemangioma.

The use of a compound of the formula (I), (I') or subgroups, individual species, salts or crystalline forms thereof as defined herein for the manufacture of a medicament for the treatment or prophylaxis of a disease state or condition mediated by a kinase which is Flt3, JAK, C-abl, PDK1, Chk1 or Chk2.

The use of a compound of the formula (I), (I') or subgroups, individual species, salts or crystalline forms thereof as defined herein for the manufacture of a medicament for the treatment or prophylaxis of a disease state or condition mediated by a kinase which is Flt3, JAK, C-abl, PDK1, Chk1 or Chk2; and wherein the disease state or condition is any one or more diseases or conditions (in any combination) selected from polycythemia vera, essential thrombocythemia, idiopathic myelofibrosis, juvenile myelomonocytic leukemia (JMML), Chronic Myelomonocytic Leukemias (CMML), megakaryocytic leukaemia, megakaryocytic AML (AML M7), Philadelphia chromosome-negative CML and imatinib resistant CML.

The use of a compound of the formula (I), (I') or subgroups, individual species, salts or crystalline forms thereof as defined herein for the manufacture of a medicament for the treatment or prophylaxis of a disease state or condition mediated by a kinase which is Flt3, JAK, C-abl, PDK1, Chk1 or Chk2; wherein the disease state or condition is selected from myeloproliferative disorders (MPD) such as polycythemia vera, essential thrombocythemia and idiopathic myelofibrosis including myelofibrosis with myeloid metaplasia (MMM).

The use of a compound of the formula (I), (I') or subgroups, individual species, salts or crystalline forms thereof as defined herein for the manufacture of a medicament for the treatment or prophylaxis of a disease state or condition mediated by a kinase which is FGFR (e.g. FGFR$^3$), Ret, Eph (e.g. EphB2 or EphB4), or cSrc.

The use of a compound of the formula (I), (I') or subgroups, individual species, salts or crystalline forms thereof as defined herein for the manufacture of a medicament for the treatment or prophylaxis of a disease state or condition mediated by a kinase which is FGFR (e.g. FGFR$^3$), Ret, Eph (e.g. EphB2 or EphB4), or cSrc; and wherein the disease state or condition is (in any combination) selected from papillary thyroid carcinoma, multiple endocrine neoplasia (MEN) types 2A and 2B, familial medullary thyroid carcinoma (FMTC), Hirschsprung's disease, Apert (AP) syndrome, Crouzon syndrome, Jackson-Weiss syndrome, Beare-Stevenson cutis gyrata syndrome, Pfeiffer Syndrome (PS), multiple myelomas, head and neck cancers and epithelial cancers.

The use of a compound of the formula (I), (I') or subgroups, individual species, salts or crystalline forms thereof as defined herein for the manufacture of a medicament for the treatment or prophylaxis of a disease state or condition mediated by a kinase which is FGFR (e.g. FGFR3), Ret, Eph (e.g. EphB2 or EphB4), or cSrc; and wherein the disease state or condition is selected from abnormalities in human skeletal development such as Apert (AP) syndrome, Crouzon syndrome, Jackson-Weiss syndrome, Beare-Stevenson cutis gyrata syndrome and Pfeiffer Syndrome (PS).

The use of a compound of the formula (I), (I') or subgroups, individual species, salts or crystalline forms thereof as defined herein for the manufacture of a medicament for the treatment or prophylaxis of a disease state or condition mediated by a kinase which is FGFR (e.g. FGFR3), Ret, Eph (e.g. EphB2 or EphB4), or cSrc; and wherein the disease state or condition is selected from thyroid cancers such as papillary thyroid carcinoma, familial medullary thyroid carcinoma (FMTC), multiple endocrine neoplasia (MEN) types 2A and 2B.

The use of a compound of the formula (I), (I') or subgroups, individual species, salts or crystalline forms thereof as defined herein for the manufacture of a medicament for the treatment or prophylaxis of a cancer in which the cancer cells thereof contain a drug resistant kinase mutation which is:
(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T670I mutation in KIT; or
(g) a T674I mutation in PDGFR; or
(h) T790M mutation in EGFR; or
(i) a T315I mutation in abl The use of a compound of the formula (I), (I') or subgroups, individual species, salts or crystalline forms thereof as defined herein for the manufacture of a medicament for the treatment or prophylaxis of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T674I mutation in PDGFR; or
(f) T790M mutation in EGFR.

The use of a compound of the formula (I), (I') or subgroups, individual species, salts or crystalline forms thereof as defined herein for the manufacture of a medicament for the treatment or prophylaxis of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T674I mutation in PDGFR.

The use of a compound of the formula (I), (I') or subgroups, individual species, salts or crystalline forms thereof as defined herein for the manufacture of a medicament for the treatment or prophylaxis of a cancer in which the cancer cells thereof contain a drug resistant kinase mutation which is:
(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T670I mutation in KIT; or
(g) a T674I mutation in PDGFR; or
(h) T790M mutation in EGFR; or
(i) a T315I mutation in abl;
wherein the medicament is for the treatment or prophylaxis of any one of more (in any combination) of gastrointestinal stromal tumors (GISTs), chronic myelomonocytic leukaemia (CMML), the hypereosinophilic syndrome, and dermatofibrosarcoma protuberans.

The use of a compound of the formula (I), (I') or subgroups, individual species, salts or crystalline forms thereof as defined herein for the manufacture of a medicament for the treatment or prophylaxis of a cancer in which the cancer cells thereof contain a drug resistant kinase mutation which is:
(c) an imatinib resistant mutation; or
(d) a nilotinib resistant mutation; or
(e) a dasatinib resistant mutation; or
wherein the medicament is for the treatment or prophylaxis of nilotinib-, dasatinib- or imatinib-resistant CML.

The use of a compound of the formula (I), (I') or subgroups, individual species, salts or crystalline forms thereof as defined herein for the manufacture of a medicament for the treatment or prophylaxis of a cancer which expresses a mutated molecular target which is a mutated form of BCRabl, c-kit, PDGF, EGF receptor or ErbB2.

The use of a compound of the formula (I), (I') or subgroups, individual species, salts or crystalline forms thereof as defined herein for the manufacture of a medicament for the treatment or prophylaxis of a disease mediated by a kinase containing a mutation in a region of the protein that binds to or interacts with other cancer agents but does not bind to or interact with the compounds of formula (I) or (I'), for example a mutated kinase selected from c-abl, c-kit, PDGPR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2.

The use of a compound as defined in any one of claims 1 to 106 for the manufacture of a medicament for the prophylaxis or treatment of any one or more (in any combination) of diseases and conditions selected from ocular diseases or conditions (such as age-related macular degeneration [e.g. wet form of age-related macular degeneration]; ischemic proliferative retinopathies [e.g. retinopathy of prematurity (ROP) and diabetic retinopathy]; and hemangioma); myeloproliferative disorders (MPD) (such as polycythemia vera, essential thrombocythemia and idiopathic myelofibrosis including myelofibrosis with myeloid metaplasia (MMM)); juvenile myelomonocytic leukemia (JMML); Chronic Myelomonocytic Leukemias (CMML); megakaryocytic leukaemia (including megakaryocytic AML (AML M7)); Philadelphia chromosome-negative CML; imatinib resistant CML; nilotinib-resistant CML; dasatinib-resistant CML; gastrointestinal stromal tumours (GISTs); glioblastomas such as glioblastoma multiformi, chronic myelomonocytic leukemia (CMML); the hypereosinophilic syndrome; dermatofibrosarcoma protuberans; Philadelphia chromosome positive malignancies (for example Philadelphia chromosome-positive leukamias such as Philadelphia chromosome positive CML and Philadelphia chromosome positive ALL); myeloproliferative syndrome; multiple myelomas, epithelial cancers, head and neck cancers, abnormalities in human skeletal development (such as Apert (AP) syndrome, Crouzon syndrome, Jackson-Weiss syndrome, Beare-Stevenson cutis gyrata syndrome and Pfeiffer Syndrome (PS)), thyroid cancers (such as papillary thyroid carcinoma, familial medullary thyroid carcinoma (FMTC), multiple endocrine neoplasia (MEN) types 2A and 2B); and Hirschsprung's disease.

The use of a compound of the formula (I), (I') or subgroups, individual species, salts or crystalline forms thereof as defined herein for the manufacture of a medicament for the treatment or prophylaxis of any one or more (in any combination) of diseases and conditions selected from ocular diseases or conditions (such as age-related macular degeneration [e.g. wet form of age-related macular degeneration]; ischemic proliferative retinopathies [e.g. retinopathy of prematurity (ROP) and diabetic retinopathy]; and hemangioma); myeloproliferative disorders (MPD) (such as polycythemia vera, essential thrombocythemia and idiopathic myelofibrosis including myelofibrosis with myeloid metaplasia (MMM)); juvenile myelomonocytic leukemia (JMML); Chronic Myelomonocytic Leukemias (CMML); megakaryocytic leukaemia (including megakaryocytic AML (AML M7)); Philadelphia chromosome-negative CML; imatinib resistant CML; gastrointestinal stromal tumors (GISTs); glioblastomas such as glioblastoma multiformi, chronic myelomonocytic leukemia (CMML); the hypereosinophilic syndrome; dermatofibrosarcoma protuberans; Philadelphia chromosome positive malignancies (for example Philadelphia chromosome-positive leukamias such as Philadelphia chromosome positive CML and Philadelphia chromosome positive ALL); myeloproliferative syndrome; multiple myelomas, epithelial cancers, head and neck cancers, abnormalities in human skeletal development (such as Apert (AP) syndrome, Crouzon syndrome, Jackson-Weiss syndrome, Beare-Stevenson cutis gyrata syndrome and Pfeiffer Syndrome (PS)), thyroid cancers (such as papillary thyroid carcinoma, familial medullary thyroid carcinoma (FMTC), multiple endocrine neoplasia (MEN) types 2A and 2B); and Hirschsprung's disease.

The use of a compound of the formula (I), (I') or sub-groups, individual species, salts or crystalline forms thereof as defined herein for the manufacture of a medicament for the treatment or prophylaxis of any one or more ocular diseases or conditions such as the diseases and conditions (in any combination) selected from age-related macular degeneration (e.g. wet form of age-related macular degeneration); ischemic proliferative retinopathies (e.g. retinopathy of prematurity (ROP) and diabetic retinopathy); and hemangioma.

The use of a compound of the formula (I), (I') or sub-groups, individual species, salts or crystalline forms thereof as defined herein for the manufacture of a medicament for the treatment or prophylaxis of any one or more diseases or conditions (in any combination) selected from any one or more diseases or conditions (in any combination) selected from myeloproliferative disorders (MPD) such as polycythemia vera, essential thrombocythemia and idiopathic myelofibrosis including myelofibrosis with myeloid metaplasia (MMM); juvenile myelomonocytic leukemia (JMML); Chronic Myelomonocytic Leukemias (CMML); megakaryocytic leukaemia including megakaryocytic AML (AML M7); Philadelphia chromosome-negative CML; and imatinib resistant CML.

The use of a compound of the formula (I), (I') or sub-groups, individual species, salts or crystalline forms thereof as defined herein for the manufacture of a medicament for the treatment or prophylaxis of malignancies driven by BCR-abl, particularly Philadelphia chromosome positive malignancies, for example Philadelphia chromosome-positive leukemias such as Philadelphia chromosome positive CML and Philadelphia chromosome positive ALL.

The use of a compound of the formula (I), (I') or sub-groups, individual species, salts or crystalline forms thereof as defined herein for the manufacture of a medicament for the treatment or prophylaxis of myeloproliferative syndrome.

The use of a compound of the formula (I), (I') or sub-groups, individual species, salts or crystalline forms thereof as defined herein for the manufacture of a medicament for the treatment or prophylaxis of any one or more diseases or conditions (in any combination) selected from multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B and Hirschsprung's disease.

The use of a compound of the formula (I), (I') or sub-groups, individual species, salts or crystalline forms thereof as defined herein for the manufacture of a medicament for the treatment or prophylaxis of a disease state or condition selected from gastrointestinal stromal tumors (GISTs); glioblastomas such as glioblastoma multiformi, chronic myelomonocytic leukemia (CMML); the hypereosinophilic syndrome; dermatofibrosarcoma protuberans.

The use of a compound of the formula (I), (I') or sub-groups, individual species, salts or crystalline forms thereof as defined herein for the manufacture of a medicament for the treatment or prophylaxis of a disease state or condition selected from imatinib resistant CML; nilotinib-resistant CML; and dasatinib-resistant CML.

The use of a compound of the formula (I), (I') or sub-groups, individual species, salts or crystalline forms thereof as defined herein for the manufacture of a medicament for the treatment or prophylaxis of imatinib resistant CML.

The use of a compound of the formula (I), (I') or sub-groups, individual species, salts or crystalline forms thereof as defined herein for the manufacture of a medicament for the treatment or prophylaxis of myelofibrosis with myeloid metaplasia (MMM).

A method for the prophylaxis or treatment of:
A. a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc); or
B. a cancer in which the cancer cells thereof contain a drug resistant kinase mutation which is:
 (a) a threonine gatekeeper mutation; or
 (b) a drug-resistant gatekeeper mutation; or
 (c) an imatinib resistant mutation; or
 (d) a nilotinib resistant mutation; or
 (e) a dasatinib resistant mutation; or
 (f) a T6701 mutation in KIT; or
 (g) a T6741 mutation in PDGFR; or
 (h) T790M mutation in EGFR; or
 (i) a T315I mutation in abl; or
C. a cancer which expresses a mutated molecular target which is a mutated form of BCRabl, c-kit, PDGF, EGF receptor or ErbB2; or
D. a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2;

which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc); which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by a kinase which is BCR-abl, VEGFR, Flt3, JAK, C-abl, PDK1, Chk1, Chk2, FGFR (e.g. FGFR3), Ret, Eph (e.g. EphB2 or EphB4), or cSrc; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition which is a malignancy driven by BCR-abl; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition which is a malignancy driven by BCR-abl; and wherein the malignancy is selected from Philadelphia chromosome positive malignancies, for example Philadelphia chromosome-positive leukamias such as Philadelphia chromosome positive CML and Philadelphia chromosome positive ALL; and myeloproliferative syndrome; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by VEGFR; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by VEGFR; wherein the disease state or condition is an ocular disease or condition such as the disease and conditions selected from age-related macular degeneration (e.g. wet form of age-related macular degeneration); ischemic proliferative retinopathies (e.g. retinopathy of prematurity (ROP) and diabetic retinopathy); and hemangioma; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by a kinase which is Flt3, JAK, C-abl, PDK1, Chk1 or Chk2; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by a kinase which is Flt3, JAK, C-abl, PDK1, Chk1 or Chk2; and wherein the disease state or condition is any one or more diseases or conditions (in any combination) selected from polycythemia vera, essential thrombocythemia, idiopathic myelofibrosis, juvenile myelomonocytic leukemia (JMML), Chronic Myelomonocytic Leukemias (CMML), megakaryocytic leukaemia, megakaryocytic AML (AML M7), Philadelphia chromosome-negative CML and imatinib resistant CML; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by a kinase which is Flt3, JAK, C-abl, PDK1, Chk1 or Chk2; wherein the disease state or condition is selected from myeloproliferative disorders (MPD) such as polycythemia vera, essential thrombocythemia and idiopathic myelofibrosis including myelofibrosis with myeloid metaplasia (NMM); which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by a kinase which is FGFR (e.g. FGFR$^3$), Ret, Eph (e.g. EphB2 or EphB4), or cSrc; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by a kinase which is FGFR (e.g. FGFR$^3$), Ret, Eph (e.g. EphB2 or EphB4), or cSrc; and wherein the disease state or condition is (in any combination) selected from papillary thyroid carcinoma, multiple endocrine neoplasia (MEN) types 2A and 2B, familial medullary thyroid carcinoma (FMTC), Hirschsprung's disease, Apert (AP) syndrome, Crouzon syndrome, Jackson-Weiss syndrome, Beare-Stevenson cutis gyrata syndrome, Pfeiffer Syndrome (PS), multiple myelomas, head and neck cancers and epithelial cancers; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by a kinase which is FGFR (e.g. FGFR3), Ret, Eph (e.g. EphB2 or EphB4), or cSrc; and wherein the disease state or condition is selected from abnormalities in human skeletal development such as Apert (AP) syndrome, Crouzon syndrome, Jackson-Weiss syndrome, Beare-Stevenson cutis gyrata syndrome and Pfeiffer Syndrome (PS); which method comprises administering to a patient in need of such treatment an effective amount of a compound of the formula (I), (I') or sub-groups, individual species, salts or crystalline forms thereof as defined herein.

A method for the prophylaxis or treatment of a disease state or condition mediated by a kinase which is FGFR (e.g. FGFR$^3$), Ret, Eph (e.g. EphB2 or EphB4), or cSrc; and wherein the disease state or condition is selected from thyroid cancers such as papillary thyroid carcinoma, familial medullary thyroid carcinoma (FMTC), multiple endocrine neoplasia (MEN) types 2A and 2B; which method comprises administering to a patient in need of such treatment an effective amount of a compound of the formula (I), (I') or sub-groups, individual species, salts or crystalline forms thereof as defined herein.

A method for the prophylaxis or treatment of a cancer in which the cancer cells thereof contain a drug resistant kinase mutation which is:
(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T670I mutation in KIT; or
(g) a T6741 mutation in PDGFR; or
(h) T790M mutation in EGFR; or
(i) a T315I mutation in abl
which method comprises administering to a patient in need of such treatment an effective amount of a compound of the formula (I), (I') or sub-groups, individual species, salts or crystalline forms thereof as defined herein.

A method for the prophylaxis or treatment of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T674I mutation in PDGFR; or
(f) T790M mutation in EGFR;
which method comprises administering to a patient in need of such treatment an effective amount of a compound of the formula (I), (I') or sub-groups, individual species, salts or crystalline forms thereof as defined herein.

A method for the prophylaxis or treatment of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T674I mutation in PDGFR; or
which method comprises administering to a patient in need of such treatment an effective amount of a compound of the formula (I), (I') or sub-groups, individual species, salts or crystalline forms thereof as defined herein.

A method for the treatment or prophylaxis of a cancer in which the cancer cells thereof contain a drug resistant kinase mutation which is:
(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T670I mutation in KIT; or
(g) a T674I mutation in PDGFR; or
(h) T790M mutation in EGFR; or
(i) a T315I mutation in abl;
wherein the medicament is for the treatment or prophylaxis of any one of more (in any combination) of gastrointestinal stromal tumors (GISTs), chronic myelomonocytic leukaemia (CMML), the hypereosinophilic syndrome, and dermatofibrosarcoma protuberans; which method comprises administering to a patient in need of such treatment an effective amount of a compound of the formula (I), (I') or sub-groups, individual species, salts or crystalline forms thereof as defined herein.

A method for the treatment or prophylaxis of a cancer in which the cancer cells thereof contain a drug resistant kinase mutation which is:
(c) an imatinib resistant mutation; or
(d) a nilotinib resistant mutation; or
(e) a dasatinib resistant mutation; or
wherein the medicament is for the treatment or prophylaxis of nilotinib-, dasatinib- or imatinib-resistant CML; which method comprises administering to a patient in need of such treatment an effective amount of a compound of the formula (I), (I') or sub-groups, individual species, salts or crystalline forms thereof as defined herein.

A method for the prophylaxis or treatment of a cancer which expresses a mutated molecular target which is a mutated form of BCRabl, c-kit, PDGF, EGF receptor or ErbB2; which method comprises administering to a patient in need of such treatment an effective amount of a compound of the formula (I), (I') or sub-groups, individual species, salts or crystalline forms thereof as defined herein.

A method for the prophylaxis or treatment of a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2; which method comprises administering to a patient in need of such treatment an effective amount of a compound of the formula (I), (I') or sub-groups, individual species, salts or crystalline forms thereof as defined herein.

A method for the prophylaxis or treatment of any one or more (in any combination) of diseases and conditions selected from ocular diseases or conditions (such as age-related macular degeneration [e.g. wet form of age-related macular degeneration]; ischemic proliferative retinopathies [e.g. retinopathy of prematurity (ROP) and diabetic retinopathy]; and hemangioma); myeloproliferative disorders (MPD) (such as polycythemia vera, essential thrombocythemia and idiopathic myelofibrosis including myelofibrosis with myeloid metaplasia (MMM)); juvenile myelomonocytic leukemia (JMML); Chronic Myelomonocytic Leukemias (CMML); megakaryocytic leukaemia (including megakaryocytic AML (AML M7)); Philadelphia chromosome-negative CML; imatinib resistant CML; nilotinib-resistant CML; dasatinib-resistant CML; gastrointestinal stromal tumours (GISTs); glioblastomas such as glioblastoma multiformi, chronic myelomonocytic leukemia (CMML); the hypereosinophilic syndrome; dermatofibrosarcoma protuberans; Philadelphia chromosome positive malignancies (for example Philadelphia chromosome-positive leukamias such as Philadelphia chromosome positive CML and Philadelphia chromosome positive ALL); myeloproliferative syndrome; multiple myelomas, epithelial cancers, head and neck cancers, abnormalities in human skeletal development (such as Apert (AP) syndrome, Crouzon syndrome, Jackson-Weiss syndrome, Beare-Stevenson cutis gyrata syndrome and Pfeiffer Syndrome (PS)), thyroid cancers (such as papillary thyroid carcinoma, familial medullary thyroid carcinoma (FMTC), multiple endocrine neoplasia (MEN) types 2A and 2B); and Hirschsprung's disease; which method comprises administering to a patient in need of such treatment an effective amount of a compound of the formula (I), (I') or sub-groups, individual species, salts or crystalline forms thereof as defined herein.

A method for the prophylaxis or treatment of any one or more (in any combination) of diseases and conditions selected from ocular diseases or conditions (such as age-related macular degeneration [e.g. wet form of age-related macular degeneration]; ischemic proliferative retinopathies [e.g. retinopathy of prematurity (ROP) and diabetic retinopathy]; and hemangioma); myeloproliferative disorders (MPD) (such as polycythemia vera, essential thrombocythemia and idiopathic myelofibrosis including myelofibrosis with myeloid metaplasia (MMM)); juvenile myelomonocytic leukemia (JMML);

Chronic Myelomonocytic Leukemias (CMML); megakaryocytic leukaemia (including megakaryocytic AML (AML M7)); Philadelphia chromosome-negative CML; imatinib resistant CML; gastrointestinal stromal tumors (GISTs); glioblastomas such as glioblastoma multiformi, chronic myelomonocytic leukemia (CMML); the hypereosinophilic syndrome; dermatofibrosarcoma protuberans; Philadelphia chromosome positive malignancies (for example Philadelphia chromosome-positive leukamias such as Philadelphia chromosome positive CML and Philadelphia chromosome positive ALL); myeloproliferative syndrome; multiple myelomas, epithelial cancers, head and neck cancers, abnormalities in human skeletal development (such as Apert (AP) syndrome, Crouzon syndrome, Jackson-Weiss syndrome, Beare-Stevenson cutis gyrata syndrome and Pfeiffer Syndrome (PS)), thyroid cancers (such as papillary thyroid carcinoma, familial medullary thyroid carcinoma (FMTC), multiple endocrine neoplasia (MEN) types 2A and 2B); and Hirschsprung's disease; which method comprises administering to a patient in need of such treatment an effective amount of a compound of the formula (I), (I') or sub-groups, individual species, salts or crystalline forms thereof as defined herein.

A method for the prophylaxis or treatment of any one or more ocular diseases or conditions such as the diseases and conditions (in any combination) selected from age-related macular degeneration (e.g. wet form of age-related macular degeneration); ischemic proliferative retinopathies (e.g. retinopathy of prematurity (ROP) and diabetic retinopathy); and hemangioma; which method comprises administering to a patient in need of such treatment an effective amount of a compound of the formula (I), (I') or sub-groups, individual species, salts or crystalline forms thereof as defined herein.

A method for the prophylaxis or treatment of any one or more diseases or conditions (in any combination) selected from any one or more diseases or conditions (in any combination) selected from myeloproliferative disorders (MPD) such as polycythemia vera, essential thrombocythemia and idiopathic myelofibrosis including myelofibrosis with myeloid metaplasia (MMM); juvenile myelomonocytic leukemia (JMML); Chronic Myelomonocytic Leukemias (CMML); megakaryocytic leukaemia including megakaryocytic AML (AML M7); Philadelphia chromosome-negative CML; and imatinib resistant CML; which method comprises administering to a patient in need of such treatment an effective amount of a compound of the formula (I), (I') or sub-groups, individual species, salts or crystalline forms thereof as defined herein.

A method for the prophylaxis or treatment of Philadelphia chromosome positive malignancies, for example Philadelphia chromosome-positive leukamias such as Philadelphia chromosome positive CML and Philadelphia chromosome positive ALL; which method comprises administering to a patient in need of such treatment an effective amount of a compound of the formula (I), (I') or sub-groups, individual species, salts or crystalline forms thereof as defined herein.

A method for the prophylaxis or treatment of myeloproliferative syndrome; which method comprises administering to a patient in need of such treatment an effective amount of a compound of the formula (I), (I') or sub-groups, individual species, salts or crystalline forms thereof as defined herein.

A method for the prophylaxis or treatment of any one or more diseases or conditions (in any combination) selected from multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B and Hirschsprung's disease; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition selected from gastrointestinal stromal tumors (GISTs); glioblastomas such as glioblastoma multiformi, chronic myelomonocytic leukemia (CMML); the hypereosinophilic syndrome; dermatofibrosarcoma protuberans; which method comprises administering to a patient in need of such treatment an effective amount of a compound of the formula (I), (I') or sub-groups, individual species, salts or crystalline forms thereof as defined herein.

A method for the prophylaxis or treatment of a disease state or condition selected from imatinib resistant CML; nilotinib-resistant CML; and dasatinib-resistant CML; which method comprises administering to a patient in need of such treatment an effective amount of a compound of the formula (I), (I') or sub-groups, individual species, salts or crystalline forms thereof as defined herein.

A method for the prophylaxis or treatment of imatinib resistant CML; which method comprises administering to a patient in need of such treatment an effective amount of a compound of the formula (I), (I') or sub-groups, individual species, salts or crystalline forms thereof as defined herein.

A method for the prophylaxis or treatment of myelofibrosis with myeloid metaplasia (MMM); which method comprises administering to a patient in need of such treatment an effective amount of a compound of the formula (I), (I') or sub-groups, individual species, salts or crystalline forms thereof as defined herein.

A compound of the formula (I), (I') or sub-groups, individual species, salts or crystalline forms thereof as defined herein; for use in the prophylaxis or treatment of:
A. a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR$^3$), Ret, Eph (e.g. EpbB2 or EphB4), or Src (e.g. csrc); or
B. a cancer in which the cancer cells thereof contain a drug resistant kinase mutation which is:
 (a) a threonine gatekeeper mutation; or
 (b) a drug-resistant gatekeeper mutation; or
 (c) an imatinib resistant mutation; or
 (d) a nilotinib resistant mutation; or
 (e) a dasatinib resistant mutation; or
 (f) a T670I mutation in KIT; or
 (g) a T674I mutation in PDGFR; or
 (h) T790M mutation in EGFR; or
 (i) a T315I mutation in abl; or C. a cancer which expresses a mutated molecular target which is a mutated form of BCRabl, c-kit, PDGF, EGF receptor or ErbB2; or D. a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2.

A compound of the formula (I), (I') or sub-groups, individual species, salts or crystalline forms thereof as defined herein for use in the prophylaxis or treatment of a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Cbk2), FGFR (e.g. FGFR3), Ret, Eph (e.g. EphB2 or EphB4), or Src (e.g. cSrc).

A compound of the formula (I), (I') or sub-groups, individual species, salts or crystalline forms thereof as defined herein for use in the prophylaxis or treatment of a disease state or condition mediated by any a kinase which is BCR-abl, VEGFR, Flt3, JAK, C-abl, PDK1, Cbk1, Chk2, FGFR (e.g. FGFR3), Ret, Eph (e.g. EphB2 or EphB4), or cSrc.

A compound of the formula (I), (I') or sub-groups, individual species, salts or crystalline forms thereof as defined herein for use in the treatment or prophylaxis of a disease state or condition which is a malignancy driven by BCR-abl.

A compound of the formula (I), (I') or sub-groups, individual species, salts or crystalline forms thereof as defined herein for use in the treatment or prophylaxis of a disease state or condition which is a malignancy driven by BCR-abl and wherein the malignancy is selected from Philadelphia chromosome positive malignancies, for example Philadelphia chromosome-positive leukamias such as Philadelphia chromosome positive CML and Philadelphia chromosome positive ALL; and myeloproliferative syndrome.

A compound of the formula (I), (I') or sub-groups, individual species, salts or crystalline forms thereof as defined herein for use in the treatment or prophylaxis of a disease state or condition mediated by VEGFR.

A compound of the formula (I), (I') or sub-groups, individual species, salts or crystalline forms thereof as defined herein for use in the treatment or prophylaxis of a disease state or condition mediated by VEGFR; wherein the disease state or condition is an ocular disease or condition such as the disease and conditions selected from age-related macular degeneration (e.g. wet form of age-related macular degeneration); ischemic proliferative retinopathies (e.g. retinopathy of prematurity (ROP) and diabetic retinopathy); and hemangioma.

A compound of the formula (I), (I') or sub-groups, individual species, salts or crystalline forms thereof as defined herein for the manufacture of a medicament for the treatment or prophylaxis of a disease state or condition mediated by a kinase which is Flt3, JAK, C-abl, PDK1, Chk1 or Chk2.

A compound of the formula (I), (I') or sub-groups, individual species, salts or crystalline forms thereof as defined herein for use in the treatment or prophylaxis of a disease state or condition mediated by a kinase which is Flt3, JAK, C-abl, PDK1, Chk1 or Chk2; and wherein the disease state or condition is any one or more diseases or conditions (in any combination) selected from polycythemia vera, essential thrombocythemia, idiopathic myelofibrosis, juvenile myelomonocytic leukemia (JMML), Chronic Myelomonocytic Leukemias (CMML), megakaryocytic leukaemia, megakaryocytic AML (AML M7), Philadelphia chromosome-negative CML and imatinib resistant CML.

A compound of the formula (I), (I') or sub-groups, individual species, salts or crystalline forms thereof as defined herein for use in the treatment or prophylaxis of a disease state or condition mediated by a kinase which is Flt3, JAK, C-abl, PDK1, Cbk1 or Chk2; wherein the disease state or condition is selected from myeloproliferative disorders (MPD) such as polycythemia vera, essential thrombocythemia and idiopathic myelofibrosis including myelofibrosis with myeloid metaplasia (MMM).

A compound of the formula (I), (I') or sub-groups, individual species, salts or crystalline forms thereof as defined herein for use in the treatment or prophylaxis of a disease state or condition mediated by a kinase which is FGFR (e.g. FGFR$^3$), Ret, Eph (e.g. EphB2 or EphB4), or cSrc.

A compound of the formula (I), (I') or sub-groups, individual species, salts or crystalline forms thereof as defined herein for use in the treatment or prophylaxis of a disease state or condition mediated by a kinase which is FGFR (e.g. FGFR$^3$), Ret, Eph (e.g. EphB2 or EphB4), or cSrc; and wherein the disease state or condition is (in any combination) selected from papillary thyroid carcinoma, multiple endocrine neoplasia (MEN) types 2A and 2B, familial medullary thyroid carcinoma (FMTC), Hirschsprung's disease, Apert (AP) syndrome, Crouzon syndrome, Jackson-Weiss syndrome, Beare-Stevenson cutis gyrata syndrome, Pfeiffer Syndrome (PS), multiple myelomas, head and neck cancers and epithelial cancers.

A compound of the formula (I), (I') or sub-groups, individual species, salts or crystalline forms thereof as defined herein for use in the treatment or prophylaxis of a disease state or condition mediated by a kinase which is FGFR (e.g. FGFR$^3$), Ret, Eph (e.g. EphB2 or EphB4), or cSrc; and wherein the disease state or condition is selected from thyroid cancers such as papillary thyroid carcinoma, familial medullary thyroid carcinoma (FMTC), multiple endocrine neoplasia (MEN) types 2A and 2B.

A compound of the formula (I), (I') or sub-groups, individual species, salts or crystalline forms thereof as defined herein for use in the treatment or prophylaxis of a cancer in which the cancer cells thereof contain a drug resistant kinase mutation which is:

(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T670I mutation in KIT; or
(g) a T674I mutation in PDGFR; or
(h) T790M mutation in EGFR; or
(i) a T315I mutation in abl.

A compound of the formula (I), (I') or sub-groups, individual species, salts or crystalline forms thereof as defined herein for the manufacture of a medicament for the treatment or prophylaxis of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T674I mutation in PDGFR; or
(f) T790M mutation in EGFR.

A compound of the formula (I), (I') or sub-groups, individual species, salts or crystalline forms thereof as defined herein for use in the treatment or prophylaxis of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T674I mutation in PDGFR.

A compound of the formula (I), (I') or sub-groups, individual species, salts or crystalline forms thereof as defined herein for use in the treatment or prophylaxis of a cancer in which the cancer cells thereof contain a drug resistant kinase mutation which is:
(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T6701 mutation in KIT; or
(g) a T6741 mutation in PDGFR; or
(h) T790M mutation in EGFR; or
(i) a T315I mutation in abl;
wherein the cancer is any one of more (in any combination) of gastrointestinal stromal tumors (GISTs), chronic myelomonocytic leukaemia (CMML), the hypereosinophilic syndrome, and dermatofibrosarcoma protuberans.

A compound of the formula (I), (I') or sub-groups, individual species, salts or crystalline forms thereof as defined herein for use in the treatment or prophylaxis of a cancer in which the cancer cells thereof contain a drug resistant kinase mutation which is:
(c) an imatinib resistant mutation; or
(d) a nilotinib resistant mutation; or
(e) a dasatinib resistant mutation; or
and wherein the cancer is a nilotinib-, dasatinib- or imatinib-resistant CML.

A compound of the formula (I), (I') or sub-groups, individual species, salts or crystalline forms thereof as defined herein for use in the treatment or prophylaxis of a cancer which expresses a mutated molecular target which is a mutated form of BCRabl, c-kit, PDGF, EGF receptor or ErbB2.

A compound of the formula (I), (I') or sub-groups, individual species, salts or crystalline forms thereof as defined herein for use in the treatment or prophylaxis of a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EpbB5, EphB6, c-Src and kinases of the JAK family such as TYK2.

A compound as defined in any one of claims 1 to 106 for the manufacture of a medicament for the prophylaxis or treatment of any one or more (in any combination) of diseases and conditions selected from ocular diseases or conditions (such as age-related macular degeneration [e.g. wet form of age-related macular degeneration]; ischemic proliferative retinopathies [e.g. retinopathy of prematurity (ROP) and diabetic retinopathy]; and hemangioma); myeloproliferative disorders (MPD) (such as polycythemia vera, essential thrombocythemia and idiopathic myelofibrosis including myelofibrosis with myeloid metaplasia (MMM)); juvenile myelomonocytic leukemia (JMML); Chronic Myelomonocytic Leukemias (CMML); megakaryocytic leukaemia (including megakaryocytic AML (AML M7)); Philadelphia chromosome-negative CML; imatinib resistant CML; nilotinib-resistant CML; dasatinib-resistant CML; gastrointestinal stromal tumours (GISTs); glioblastomas such as glioblastoma multiformi, chronic myelomonocytic leukemia (CMML); the hypereosinophilic syndrome; dermatofibrosarcoma protuberans; Philadelphia chromosome positive malignancies (for example Philadelphia chromosome-positive leukamias such as Philadelphia chromosome positive CML and Philadelphia chromosome positive ALL); myeloproliferative syndrome; multiple myelomas, epithelial cancers, head and neck cancers, abnormalities in human skeletal development (such as Apert (AP) syndrome, Crouzon syndrome, Jackson-Weiss syndrome, Beare-Stevenson cutis gyrata syndrome and Pfeiffer Syndrome (PS)), thyroid cancers (such as papillary thyroid carcinoma, familial medullary thyroid carcinoma (FMTC), multiple endocrine neoplasia (MEN) types 2A and 2B); and Hirschsprung's disease.

A compound of the formula (I), (I') or sub-groups, individual species, salts or crystalline forms thereof as defined herein for use in the treatment or prophylaxis of any one or more (in any combination) of diseases and conditions selected from ocular diseases or conditions (such as age-related macular degeneration [e.g. wet form of age-related macular degeneration]; ischemic proliferative retinopathies [e.g. retinopathy of prematurity (ROP) and diabetic retinopathy]; and hemangioma); myeloproliferative disorders (MPD) (such as polycythemia vera, essential thrombocythemia and idiopathic myelofibrosis including myelofibrosis with myeloid metaplasia (MMM)); juvenile myelomonocytic leukemia (JMML); Chronic Myelomonocytic Leukemias (CMML); megakaryocytic leukaemia (including megakaryocytic AML (AML M7)); Philadelphia chromosome-negative CML; imatinib resistant CML; gastrointestinal stromal tumors (GISTs); glioblastomas such as glioblastoma multiformi, chronic myelomonocytic leukemia (CMML); the hypereosinophilic syndrome; dermatofibrosarcoma protuberans; Philadelphia chromosome positive malignancies (for example Philadelphia chromosome-positive leukamias such as Philadelphia chromosome positive CML and Philadelphia chromosome positive ALL); myeloproliferative syndrome; multiple myelomas, epithelial cancers, head and neck cancers, abnormalities in human skeletal development (such as Apert (AP) syndrome, Crouzon syndrome, Jackson-Weiss syndrome, Beare-Stevenson cutis gyrata syndrome and Pfeiffer Syndrome (PS)), thyroid cancers (such as papillary thyroid carcinoma, familial medullary thyroid carcinoma (FMTC), multiple endocrine neoplasia (MEN) types 2A and 2B); and Hirschsprung's disease.

A compound of the formula (I), (I') or sub-groups, individual species, salts or crystalline forms thereof as defined herein for use in the treatment or prophylaxis of any one or more ocular diseases or conditions such as the diseases and conditions (in any combination) selected from age-related macular degeneration (e.g. wet form of age-related macular degeneration); ischemic proliferative retinopathies (e.g. retinopathy of prematurity (ROP) and diabetic retinopathy); and hemangioma.

A compound of the formula (I), (I') or sub-groups, individual species, salts or crystalline forms thereof as defined herein for use in the treatment or prophylaxis of any one or more diseases or conditions (in any combination) selected from any one or more diseases or conditions (in any combination) selected from myeloproliferative disorders (MPD) such as polycythemia vera, essential thrombocythemia and idiopathic myelofibrosis including myelofibrosis with myeloid metaplasia (MMM); juvenile myelomonocytic leukemia (JMML); Chronic Myelomonocytic Leukemias (CMML); megakaryocytic leukaemia including megakaryocytic AML (AML M7); Philadelphia chromosome-negative CML; and imatinib resistant CML.

A compound of the formula (I), (I') or sub-groups, individual species, salts or crystalline forms thereof as defined herein for use in the treatment or prophylaxis of malignancies driven by BCR-abl, particularly Philadelphia chromosome positive malignancies, for example Philadelphia chromosome-positive leukamias such as Philadelphia chromosome positive CML and Philadelphia chromosome positive ALL.

A compound of the formula (I), (I') or sub-groups, individual species, salts or crystalline forms thereof as defined herein for use in the prophylaxis of myeloproliferative syndrome.

A compound of the formula (I), (I') or sub-groups, individual species, salts or crystalline forms thereof as defined herein for use in the treatment or prophylaxis of any one or more diseases or conditions (in any combination) selected from multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B and Hirschsprung's disease.

A compound of the formula (I), (I') or sub-groups, individual species, salts or crystalline forms thereof as defined herein for use in the treatment or prophylaxis of a disease state or condition selected from gastrointestinal stromal tumors (GISTs); glioblastomas such as glioblastoma multiformi, chronic myelomonocytic leukemia (CMML); the hypereosinophilic syndrome; dermatofibrosarcoma protuberans.

A compound of the formula (I), (I') or sub-groups, individual species, salts or crystalline forms thereof as defined herein for use in the treatment or prophylaxis of a disease state or condition selected from imatinib resistant CML; nilotinib-resistant CML; and dasatinib-resistant CML.

A compound of the formula (I), (I') or sub-groups, individual species, salts or crystalline forms thereof as defined herein for use in the treatment or prophylaxis of imatinib resistant CML.

A compound of the formula (I), (I') or sub-groups, individual species, salts or crystalline forms thereof as defined herein for use in the treatment or prophylaxis of myelofibrosis with myeloid metaplasia (MMM).

A method for the diagnosis and treatment of a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR$^3$), Ret, Eph (e.g. EphB2 or EphB4), or Src (e.g. cSrc); which method comprises (i) screening a patient to determine whether a disease or condition from which the patient is or may be suffering is one which would be susceptible to treatment with a compound having activity against the Inase; and (ii) where it is indicated that the disease or condition from which the patient is thus susceptible, thereafter administering to the patient a compound compound of the formula (I), (I') or sub-groups, individual species, salts or crystalline forms thereof as defined herein.

The use of a compound of the formula (I), (I') or sub-groups, individual species, salts or crystalline forms thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR$^3$), Ret, Eph (e.g. EphB2 or EphB4), or Src (e.g. cSrc).

A compound of the formula (I), (I') or sub-groups, individual species, salts or crystalline forms thereof as defined herein for use in the treatment or prophylaxis of a disease state or condition in a patient who has been screened and has been determined as suffering from, or being at risk of suffering from, a disease or condition which would be susceptible to treatment with a compound having activity against a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR$^3$), Ret, Eph (e.g. EphB2 or EphB4), or Src (e.g. cSrc).

A method for the diagnosis and treatment of a cancer in which the cancer cells thereof contain a drug resistant kinase mutation which is:
(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T670I mutation in KIT; or
(g) a T674I mutation in PDGFR; or
(h) T790M mutation in EGFR; or
(i) a T315I mutation in abl;
which method comprises (i) screening a patient to determine whether a cancer from which the patient is or may be suffering is one in which the cancer cells thereof contain the drug resistant kinase mutation; and (ii) where it is indicated that the cancer cells do contain the drug resistant mutation, thereafter administering to the patient a compound of the formula (I), (I') or sub-groups, individual species, salts or crystalline forms thereof as defined herein.

The use of a compound of the formula (I), (I') or sub-groups, individual species, salts or crystalline forms thereof as defined herein for the manufacture of a medicament for the treatment or prophylaxis of a cancer in a patient who has been screened and has been determined as suffering from, or being at risk of suffering from, a cancer in which the cancer cells thereof contain a drug resistant kinase mutation which is:
(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T670I mutation in KIT; or
(g) a T674I mutation in PDGFR; or
(h) T790M mutation in EGFR; or
(i) a T315I mutation in abl.

A compound of the formula (I), (I') or sub-groups, individual species, salts or crystalline forms thereof as defined herein for use in the treatment or prophylaxis of a cancer in a patient who has been screened and has been determined as suffering from or being at risk of suffering from, a cancer in which the cancer cells thereof contain a drug resistant kinase mutation which is:
(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T670I mutation in KIT; or
(g) a T674I mutation in PDGFR; or
(h) T790M mutation in EGFR; or
(i) a T315I mutation in abl.

A method for the diagnosis and treatment of a cancer which expresses a mutated molecular target which is a mutated form of BCRabl, c-kit, PDGF, EGF receptor or ErbB2; which method comprises (i) screening a patient to determine whether a cancer from which the patient is or may be suffering is one which expresses the said mutated molecular target; and (ii) where it is indicated that the cancer cells do express the said mutated molecular target, thereafter administering to the patient a compound of the formula (I), (I') or sub-groups, individual species, salts or crystalline forms thereof as defined herein.

The use of a compound of the formula (I), (I') or sub-groups, individual species, salts or crystalline forms thereof as defined herein for the manufacture of a medicament for the treatment or prophylaxis of a cancer in a patient who has been screened and has been determined as suffering from, or being at risk of suffering from a cancer which expresses a mutated molecular target which is a mutated form of BCRabl, c-kit, PDGF, EGF receptor or ErbB2.

A compound of the formula (I), (I') or sub-groups, individual species, salts or crystalline forms thereof as defined herein for use in the treatment or prophylaxis of a cancer in a patient who has been screened and has been determined as suffering from, or being at risk of suffering from a cancer which expresses a mutated molecular target which is a mutated form of BCRabl, c-kit, PDGF, EGF receptor or ErbB2.

A method of modulating a cellular process (for example cell division) by modulating (e.g. inhibiting) the activity of a kinase selected from BCR-abl, VEGFR, PDGFR, EGFR, Flt3, JAK (e.g. JAK2 or JAK3), C-abl, PDK1, Chk (e.g. Chk1 or Chk2), FGFR (e.g. $FGFR^3$), Ret, Eph (e.g. EphB2 or EphB4), and Src (e.g. cSrc) using a compound of the formula (I), (I') or sub-groups, individual species, salts or crystalline forms thereof as defined herein.

A compound of the formula (I), (I') or sub-groups, individual species, salts or crystalline forms thereof as defined herein for use as a modulator (e.g. inhibitor) of a kinase selected from BCR-abl, VEGFR, PDGFR, EGFR, Flt3, JAK (e.g. JAK2 or JAK3), C-abl, PDK1, Chk (e.g. Chk1 or Chk2), FGFR (e.g. $FGFR^3$), Ret, Eph (e.g. EphB2 or EphB4), and Src (e.g. cSrc).

The use of a compound of the formula (I), (I') or sub-groups, individual species, salts or crystalline forms thereof as defined herein for the manufacture of a medicament for modulating (e.g. inhibiting) the activity of a kinase selected from BCR-abl, VEGFR, PDGFR, EGFR, Flt3, JAK (e.g. JAK2 or JAK3), C-abl, PDK1, Chk (e.g. Chk1 or Chk2), FGFR (e.g. $FGFR^3$), Ret, Eph (e.g. EphB2 or EphB4), and Src (e.g. cSrc).

A method for the diagnosis and treatment of a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2; which method comprises (i) screening a patient to determine whether a disease or condition from which the patient is or may be suffering is one which mediated by a kinase containing a mutation in a region of the protein that binds to or interacts with other cancer agents but does not bind to or interact with the compounds of formula (I) or (I'); where it is indicated that the disease or condition is as defined herein, thereafter administering to the patient a compound of the formula (I), (I') or sub-groups, individual species, salts or crystalline forms thereof as defined herein.

The use of a compound of the formula (I), (I') or sub-groups, individual species, salts or crystalline forms thereof as defined herein for the manufacture of a medicament for the treatment or prophylaxis of a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2.

A compound of the formula (I), (I') or sub-groups, individual species, salts or crystalline forms thereof as defined herein for use in the treatment or prophylaxis of a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EpbB1, EphB2, EphB3, EphB5, EphB6, c-Src and kinases of the JAK family such as TYK2.

A compound of the formula (I), (I') or sub-groups, individual species, salts or crystalline forms thereof as defined herein for use in the treatment or prophylaxis of nilotinib-, dasatinib- or imatinib-resistant CML.

The use of a compound of the formula (I), (I') or sub-groups, individual species, salts or crystalline forms thereof as defined herein for the manufacture of a medicament for the treatment or prophylaxis of nilotinib-, dasatinib- or imatinib-resistant CML.

A method for the prophylaxis or treatment of nilotinib-, dasatinib- or imatinib-resistant CML; which method comprises administering to a patient in need of such treatment an effective amount of a compound of the formula (I), (I') or sub-groups, individual species, salts or crystalline forms thereof as defined herein.

The use of 1-cyclopropyl-3-[3-(5-morpholin-4-ylmethyl-1H-benzoimidazol-2-yl)-1H-pyrazol-4-yl]-urea or a salt or crystalline form thereof as defined herein for the manufacture of a medicament for the prophylaxis or treatment of a disease state or condition as defined herein.

A method for the prophylaxis of a disease state or condition as defined herein, which method comprises administering to a patient in need thereof, an effective amount of 1-cyclopropyl-3-[3-(5-morpholin-4-ylmethyl-1H-benzoimidazol-2-yl)-1H-pyrazol-4-yl]-urea or a salt or crystalline form thereof as defined herein.

1-Cyclopropyl-3-[3-(5-morpholin-4-ylmethyl-1H-benzoimidazol-2-yl)-1H-pyrazol-4-yl]-urea or a salt or crystalline form thereof as defined herein for use in the prophylaxis or treatment of a disease state or condition as defined herein.

The use of a compound of the formula (I), (I') or sub-groups, individual species, salts or crystalline forms thereof as defined herein for the manufacture of a medicament for alleviating or reducing the incidence of a disease state or condition as defined herein.

A method for alleviating or reducing the incidence of a disease state or condition as defined herein, which method comprises administering to a patient (e.g. a patient in need thereof) a compound (e.g. in a therapeutically effective amount) of the formula (I), (I') or sub-groups, individual species, salts or crystalline forms thereof as defined herein.

A compound of the formula (I), (I') or sub-groups, individual species, salts or crystalline forms thereof as defined herein for use in alleviating or reducing the incidence of a disease state or condition as defined herein.

In addition, the invention also provides the use of the compounds of Formula (I) or (I') in the treatment of the ocular diseases such as age-related macular degeneration in particular wet form of age-related macular degeneration and hemangioma, and Philadelphia chromosome positive ALL.

Also provided are methods of treatment of polycythemia vera; essential thrombocythemia; idiopathic myelofibrosis; juvenile myelomonocytic leukemia (JMML); Chronic Myelomonocytic Leukemias (CMML); megakaryocytic leukaemia including megakaryocytic AML (AML M7); Philadelphia chromosome-negative CML, imatinib resistant CML, gastrointestinal stromal tumors (GISTs), the hypereosinophilic syndrome or dermatofibrosarcoma protuberans by administering to a patient in need of such treatment a compound of the formula (I) as defined herein and in PCT/GB2004/002824 (WO 2005/002552) or a compound of the formula (I').

Also provided are methods of treatment of ocular diseases such as age-related macular degeneration in particular wet form of age-related macular degeneration and hemangioma, and Philadelphia chromosome positive ALL, by administering to a patient in need of such treatment a compound of the formula (I) as defined herein and in PCT/GB2004/002824 (WO 2005/002552) or a compound of the formula (I').

The invention provides the use of a compound of formula (I) or (I') for the manufacture of a medicament for the treatment of ocular diseases such as age-related macular degeneration in particular wet form of age-related macular degeneration, Ischemic proliferative retinopathies such as retinopathy of prematurity (ROP) and diabetic retinopathy and hemangioma.

Also provided are methods of treatment of ocular diseases such as age-related macular degeneration in particular wet form of age-related macular degeneration, Ischemic proliferative retinopathies such as retinopathy of prematurity (ROP) and diabetic retinopathy and hemangioma by administering to a patient in need of such treatment a compound of the formula (I) as defined herein and in PCT/GB2004/002824 (WO 2005/002552) or a compound of the formula (I').

The invention provides the use of a compound of formula (I) or (I') for the manufacture of a medicament for the treatment of Philadelphia chromosome positive ALL.

Also provided are methods of treatment of Philadelphia chromosome positive ALL by administering to a patient in need of such treatment a compound of the formula (I) as defined herein and in PCT/GB2004/002824 (WO 2005/002552) or a compound of the formula (I').

In further aspects, the invention provides:

A compound of the formula (I) or (I') and any sub-groups and examples thereof as defined herein for use in the treatment of multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B and Hirschsprung's disease.

The use of a compound of the formula (I') or (I") and any sub-groups and examples thereof as defined herein for the manufacture of a medicament for the treatment of multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B or Hirschsprung's disease.

A method for the treatment of multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B or Hirschsprung's disease, which method comprises administering to a patient in need thereof a compound of the formula (I) or (I') and any sub-groups and examples thereof as defined herein.

General Preferences and Definitions

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

References to compounds of the invention include compounds of Formula (I) and/or Formula (I') or Formula (I$^0$) and/or salts (e.g. lactate or citrate salts) thereof.

References to the prophylaxis or treatment of a disease state or condition such as cancer include within their scope alleviating or reducing the incidence of cancer.

Compounds of the Formula (I)

The following general preferences and definitions shall apply to each of the moieties $R^1$ to $R^{10}$, and their various sub-groups, sub-definitions, examples and embodiments of formula (I) unless the context indicates otherwise. In this specification, a superscript letter following the number of an R group indicates that the R group is a sub-group of the R group designated solely by the number. Thus, for example $R^{1a}$, $R^{1b}$ and $R^{1c}$ are all sub groups of $R^1$, and, analogously, $R^{9a}$ and $R^{9b}$ are subgroups of $R^9$. Thus, unless indicated otherwise, the general preferences, definitions and examples set out for, e.g. $R^1$ apply also to its sub-groups $R^{1a}$, $R^{1b}R^{1c}$ etcetera, and similarly with the other R groups.

Any references to formula (I) herein shall also be taken to refer to formulae (II) to (VIII) and any other sub-group of compounds within formula (I) unless the context requires otherwise.

The term upregulation of Aurora kinase as used herein is defined as including elevated expression or over-expression of Aurora kinase, including gene amplification (i.e. multiple gene copies) and increased expression by a transcriptional effect, and hyperactivity and activation of Aurora kinase, including activation by mutations.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups $R^{10}$ as defined herein.

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cyclohexenyl, cycloheptenyl and cyclooctenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about four heteroatoms typically selected from nitrogen, sulphur and oxygen. Typically the heteroaryl ring will contain up to 4 heteroatoms, more typically up to 3 heteroatoms, usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a a 5- or 6-membered ring containing 1, 2 or 3 ring heteroatoms;
e) a pyrazole ring fused to a a 5- or 6-membered ring containing 1 or 2 ring heteroatoms;
f) an imidazole ring fused to a 5- or 6-membered ring containing 1 or 2 ring heteroatoms;
g) an oxazole ring fused to a 5- or 6-membered ring containing 1 or 2 ring heteroatoms;
h) an isoxazole ring fused to a 5- or 6-membered ring containing 1 or 2 ring heteroatoms;
i) a thiazole ring fused to a 5- or 6-membered ring containing 1 or 2 ring heteroatoms;
j) an isothiazole ring fused to a 5- or 6-membered ring containing 1 or 2 ring heteroatoms;
k) a thiophene ring fused to a 5- or 6-membered ring containing 1, 2 or 3 ring heteroatoms;
l) a furan ring fused to a 5- or 6-membered ring containing 1, 2 or 3 ring heteroatoms;
m) an oxazole ring fused to a 5- or 6-membered ring containing 1 or 2 ring heteroatoms;
n) an isoxazole ring fused to a 5- or 6-membered ring containing 1 or 2 ring heteroatoms;
o) a cyclohexyl ring fused to a 5- or 6-membered ring containing 1, 2 or 3 ring heteroatoms; and
p) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to Imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclic groups include saturated groups such as piperidine, pyrrolidine, azetidine, morpholine, piperazine and N-alkyl piperazines.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NRC$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; or two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S;

$R^c$ is selected from hydrogen and $C_{1-4}$ hydrocarbyl; and $X^1$ is O, S or $NR^c$ and $X^2$ is =O, =S or =$NR^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{11}$ may be selected such that they contain no more than 20 non-hydrogen atoms, for example, no more than 15 non-hydrogen atoms, e.g. no more than 12, or 11, or 10, or 9, or 8, or 7, or 6, or 5 non-hydrogen atoms.

Where the carbocyclic and heterocyclic groups have a pair of substituents on adjacent ring atoms, the two substituents may be linked so as to form a cyclic group. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group. Examples of such linked substituent groups include:

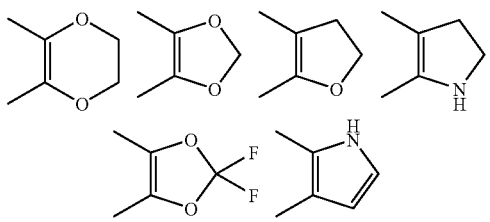

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone, except where otherwise stated. In certain cases, as defined herein, one or more of the carbon atoms making up the carbon backbone may be replaced by a specified atom or group of atoms. Examples of hydrocarbyl groups include alkyl, cycloalkyl, cycloalkenyl, carbocyclic aryl, alkenyl, alk-ynyl, cycloalkylalkyl, cycloalkenylalkyl, and carbocyclic aralkyl, aralkenyl and aralkynyl groups. Such groups can be unsubstituted or, where stated, substituted by one or more substituents as defined herein. The examples and preferences expressed below apply to each of the hydrocarbyl substituent groups or hydrocarbyl-containing substituent groups referred to in the various definitions of substituents for compounds of the formula (I) unless the context indicates otherwise.

Preferred non-aromatic hydrocarbyl groups are saturated groups such as alkyl and cycloalkyl groups.

Generally by way of example, the hydrocarbyl groups can have up to eight carbon atoms, unless the context requires otherwise. Within the sub-set of hydrocarbyl groups having 1 to 8 carbon atoms, particular examples are $C_{1-6}$ hydrocarbyl groups, such as $C_{1-4}$ hydrocarbyl groups (e.g. $C_{1-3}$ hydrocarbyl groups or $C_{1-2}$ hydrocarbyl groups), specific examples being any individual value or combination of values selected from $C_1$, $C_2$, $C_3$, $C_4$, $C_5$, $C_6$, $C_7$ and $C_8$ hydrocarbyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-6}$ cycloalkyl groups.

Examples of alkenyl groups include, but are not limited to, ethenyl(vinyl), 1-propenyl, 2-propenyl(allyl), isopropenyl, butenyl, buta-1,4-dienyl, pentenyl, and hexenyl. Within the sub-set of alkenyl groups the alkenyl group will have 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

Examples of alkynyl groups include, but are not limited to, ethynyl and 2-propynyl(propargyl) groups. Within the sub-set of alkynyl groups having 2 to 8 carbon atoms, particular examples are $C_{2-6}$ alkynyl groups, such as $C_{2-4}$ allynyl groups.

Examples of carbocyclic aryl groups include substituted and unsubstituted phenyl groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members, more usually 3, 4, 5 or 6 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$), and ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members.

The definition "$R^a$-$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, $OC(NR^c)$, $SC(NR^c)$, $NR^cC(NR^c)$, C(O)O, C(O)S, $C(O)NR^c$, C(S)O, C(S)S, $C(S)NR^c$, $C(NR^c)O$, $C(NR^c)S$, $C(NR^c)NR^c$, OC(O)O, SC(O)O, $NR^cC(O)O$, OC(S)O, SC(S)O, $NR^cC(S)O$, $OC(NR^c)O$, $SC(NR^c)O$, $NR^cC(NR^c)O$, OC(O)S, SC(O)S, $NR^cC(O)S$, OC(S)S, SC(S)S, $NR^cC(S)S$, $OC(NR^c)S$, $SC(NR^c)S$, $NR^cC(NR^c)S$, $OC(O)NR^c$, $SC(O)NR^c$, $NR^cC(O)NR^c$, $OC(S)NR^c$, $SC(S)NR^c$, $NR^cC(S)NR^c$, $OC(NR^c)NR^c$, $SC(NR^c)NR^c$, $NR^cC(NR^c)NR^c$, S, SO, $SO_2$, $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-8}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofliran and the alkoxy group is a $C_{1-4}$ alkoxy group, more typically a $C_{1-3}$ alkoxy group such as methoxy, ethoxy or n-propoxy.

Alkoxy groups substituted by a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-8}$ hydrocarbyl group, examples of hydrocarbyl groups $R^a$-$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl and trifluoromethyl), or hydroxy (e.g. hydroxymethyl and hydroxyethyl), $C_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $SO_2NR^c$ include aminosulphonyl, $C_{1-4}$ alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$-$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Particular and Preferred Compounds of the Formula (I)

In formula (I), X can be $CR^5$ or N. In one particular embodiment, X is N. In another particular embodiment, X is CH. Preferably X is N.

$R^0$ can be hydrogen or, together with the group $R^g$ when present, can form a bridging group —$(CH_2)_p$— wherein p is 2 to 4, more usually 2-3, e.g. 2. Preferably $R^1$ is hydrogen.

When $R^0$ and the group $R^g$ form a bridging group —$(CH_2)_p$—, the entity —$(CH_2)_m$—$(B)_n$—$NR^0$— can be represented thus:

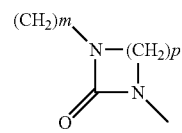

When A is a bond or a group —$(CH_2)_m$—$(B)_n$— wherein n is 0, X can be N or $CR^5$ wherein $R^5$ is hydrogen or a group $R^{10}$. More preferably, X is N.

When A is a bond or a group —(CH$_2$)$_m$—(B)$_n$— wherein n is 1, it is preferred that X is N or CR$^5$ wherein R$^5$ is hydrogen or a group R$^2$. More preferably, X is N.

Where R$^5$ is other than hydrogen, more particularly when n is 1, it is preferably a small substituent containing no more than 14 atoms, for example a C$_{1-4}$ alkyl or C$_{3-6}$ cycloalkyl group such as methyl, ethyl, propyl and butyl, or cyclopropyl and cyclobutyl.

A is a bond or —(CH$_2$)$_m$—(B)$_n$— wherein B is C=O, NR$^g$(C=O) or O(C=O), m is 0, 1 or 2; and n is 0 or 1. In one preferred group of compounds of the invention, m is 0 or 1, n is 1 and B is C=O or NR$^g$(C=O), preferably C=O. More preferably, m is 0, n is 1 and B is C=O. It is presently preferred that when B is NR$^g$(C=O), R$^g$ is hydrogen.

It will be appreciated that the moiety R$^1$-A-NH linked to the 4-position of the pyrazole ring can take the form of an amine R$^1$—(CH$_2$)$_m$—NH, an amide R$^1$—(CH$_2$)$_m$—C(=O)NH, a urea R$^1$; —(CH$_2$)$_m$—NHC(=O)NH or a carbamate R$^1$—(CH$_2$)$_m$—OC(=O)NH wherein in each case m is 0, 1 or 2, preferably 0 or 1 and most preferably 0.

R$^1$ is hydrogen, a carbocyclic or heterocyclic group having from 3 to 12 ring members, or an optionally substituted C$_{1-8}$ hydrocarbyl group as hereinbefore defined. Examples of carbocyclic and heterocyclic, and optionally substituted hydrocarbyl groups are as set out above.

For example, R$^1$ can be a monocyclic or bicyclic group having from 3 to 10 ring members.

Where R$^1$ is a monocyclic group, typically it has 3 to 7 ring members, more usually 3 to 6 ring members, for example, 3, 4, 5 or 6.

When the monocyclic group R$^1$ is an aryl group, it will have 6 ring members and will be an unsubstituted or substituted phenyl ring.

When the monocyclic group R$^1$ is a non-aromatic carbocyclic group, it can have from 3 to 7 ring members, more usually 3 to 6 ring members, for example, 3, or 4, or 5 or 6 ring members. The non-aromatic carbocyclic group may be saturated or partially unsaturated but preferably it is saturated, i.e. R$^1$ is a cycloalkyl group.

When the monocyclic group R$^1$ is a heteroaryl group, it will have 5 or 6 ring members. Examples of heteroaryl groups having 5 and 6 ring members are set out above, and particular examples are described below.

In one sub-group of compounds, the heteroaryl group has 5 ring members.

In another sub-group of compounds, the heteroaryl group has 6 ring members.

The monocyclic heteroaryl groups R$^1$ typically have up to 4 ring heteroatoms selected from N, O and S, and more typically up to 3 ring heteroatoms, for example 1, or 2, or 3 ring heteroatoms.

When R$^1$ is a non-aromatic monocyclic heterocyclic group, it may be any one of the groups listed hereinabove or hereinafter. Such groups typically have from 4 to 7 ring members and more preferably 5 or 6 ring members. The non-aromatic monocyclic heterocyclic groups typically contain up to 3 ring heteroatoms, more usually 1 or 2 ring heteroatoms, selected from N, S and O. The heterocyclic group may be saturated or partially unsaturated, but preferably it is saturated. Particular examples of non-aromatic monocyclic heterocyclic groups are the particular and preferred examples defined in the "General Preferences and Definitions" section above, and as set out in the tables and examples below.

Where R$^1$ is a bicyclic group, typically it has 8 to 10 ring members, for example 8, or 9, or 10 ring members. The bicyclic group can be an aryl or heteroaryl group and examples of such groups include groups comprising a 5-membered ring fused to another 5-membered ring; a 5-membered ring fused to a 6-membered ring; and a 6-membered ring fused to another 6-membered ring. Examples of groups in each of these categories are set out above in the "General Preferences and Definitions" section.

A bicyclic aryl or heteroaryl group can comprise two aromatic or unsaturated rings, or one aromatic and one non-aromatic (e.g. partially saturated) ring.

Bicyclic heteroaryl groups typically contain up to 4 heteroatom ring members selected from N, S and O. Thus, for example, they may contain 1, or 2, or 3, or 4 heteroatom ring members.

In the monocyclic and bicyclic heterocyclic groups R$^1$, examples of combinations of heteroatom ring members include N; NN; NNN; NNNN; NO; NNO; NS, NNS, O, S, OO and Ss.

Particular examples of R$^1$ include optionally substituted or unsubstituted heteroaryl groups selected from pyrazolo[1,5-a]pyridinyl (e.g. pyrazolo[1,5-a]pyridin-3-yl), furanyl (e.g. 2-furanyl and 3-furanyl), indolyl (e.g. 3-indolyl, 4-indolyl and 7-indolyl), oxazolyl, thiazolyl (e.g. thiazol-2-yl and thiazol-5-yl), isoxazolyl (e.g. isoxazol-3-yl and isoxazol-4-yl), pyrrolyl (e.g. 3-pyrrolyl), pyridyl (e.g. 2-pyridyl), quinolinyl (e.g. quinolin-8-yl), 2,3-dihydro-benzo[1,4]dioxine (e.g. 2,3-dihydro-benzo[1,4]dioxin-5-yl), benzo[1,3]dioxole (e.g. benzo[1,3]dioxol-4-yl), 2,3-dihydrobenzofuranyl (e.g. 2,3-dihydrobenzofuran-7-yl), imidazolyl and thiophenyl (e.g. 3-thiophenyl).

Other examples of R$^1$ include substituted or unsubstituted heteroaryl groups selected from pyrazolo[1,5-a]pyrimidine, isobenzofuran, [1,2,4]triazolo[1,5-a]pyrimidine, tetrazolyl, tetrahydroisoquinolinyl (e.g. 1,2,3,4-tetrahydroisoquinolin-7-yl), pyrimidinyl, pyrazolyl, triazolyl, 4,5,6,7-tetrahydrobenzo[d]isoxazole, phthalazine, 2H-phthalazin-1-one, benzoxazole, cinnoline, quinoxaline, naphthalene, benzo[c]isoxazole, imidazo[2,1-b]thiazole, pyridone, tetrahydroquinolinyl (e.g. 1,2,3,4-tetrahydroquinolin-6-yl), and 4,5,6,7-tetrahydro-benzofuran groups.

Preferred R$^1$ heteroaryl groups include pyrazolo[1,5-a]pyridinyl, furanyl, 2,3-dihydrobenzofuranyl, thiophenyl, indolyl, thiazolyl, isoxazolyl and 2,3-dihydro-benzo[1,4]dioxine groups.

Preferred aryl groups R$^1$ are optionally substituted phenyl groups.

Examples of non-aromatic groups R$^1$ include monocyclic cycloalkyl and azacycloalkyl groups such as cyclohexyl, cyclopentyl and piperidinyl, particularly cyclohexyl and 4-piperidinyl groups. Other examples of non-aromatic groups R$^1$ include monocyclic oxacycloalkyl groups such as tetrahydropyranyl and aza-oxa cycloalkyl groups such as morpholino (e.g. 2-morpholino and 4-morpholino).

Preferred substituted and unsubstituted C$_{1-8}$ hydrocarbyl groups include trifluoromethyl and tertiary butyl groups.

One sub-set of preferred R$^1$ groups includes phenyl, pyrazolo[1,5-a]pyridinyl and 2,3-dihydro-benzo[1,4]dioxine groups.

Another sub-set of preferred R$^1$ groups includes unsubstituted and substituted phenyl, pyrazolo[1,5-a]pyridinyl, 2,3-dihydro-benzo[1,4]dioxine, indol-4-yl, 2,3-dihydrobenzofuranyl, tert-butyl, furanyl, pyrazolo[1,5-a]pyridin-3-yl, pyrazolo[1,5-a]pyrimidin-3-yl, oxazolyl, isoxazolyl, benzoxazol-2-yl, 2H-tetrazol-5-yl, pyrazin-2-yl, pyrazolyl, benzyl, α,α-dimethylbenzyl, α-aminobenzyl, α-methylaminobenzyl, 4,5,6,7-tetrahydro-benzo[d]isoxazol-3-yl, 2H-phthalazin-1-one-4-yl, benzoxazol-7-yl, quinazolinyl, 2-naphthyl, cyclopropyl, benzo[c]isoxazol-3-yl, 4-piperidinyl, 5-thiazolyl, 2-pyridyl, 3-pyridyl, 3-pyrrolyl, isoxazolyl, imidazo[2,1-b]thiazolyl, 4-pyrimidinyl, cyclohexyl, tetrahydropyran-4-yl, tetrahydroquinolinyl, 4,5,6,7-tetrahydro-benzofuranyl and morpholinyl groups.

The group $R^1$ can be an unsubstituted or substituted carbocyclic or heterocyclic group in which one or more substituents can be selected from the group $R^{10}$ as hereinbefore defined. In one embodiment, the substituents on $R^1$ may be selected from the group $R^{10a}$ consisting of halogen, hydroxy, trifluoromethyl, cyano, nitro, carboxy, heterocyclic groups having 5 or 6 ring members and up to 2 heteroatoms selected from O, N and S, a group $R^a$-$R^b$ wherein $R^a$ is a bond, O, CO, $X^3C(X^4)$, $C(X^4)X^3$, $X^3C(X^4)X^3$, S, SO, or $SO_2$, and $R^b$ is selected from hydrogen, heterocyclic groups having 5 or 6 ring members and up to 2 heteroatoms selected from O, N and S, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having 5 or 6 ring members and up to 2 heteroatoms selected from O, N and S; wherein one or more carbon atoms of the $C_{1-8}$ hydrocarbyl group may optionally be replaced by O, S, SO, $SO_2$, $X^3C(X^4)$, $C(X^4)X^3$ or $X^3C(X^4)X^3$; $X^3$ is O or S; and $X^4$ is $=$O or $=$S.

In a further embodiment, the substituents on $R^1$ may be selected from the group $R^{10b}$ consisting of halogen, hydroxy, trifluoromethyl, cyano, nitro, carboxy, a group $R^a$-$R^b$ wherein $R^a$ is a bond, O, CO, $X^3C(X^4)$, $C(X^4)X^3$, $X^3C(X^4)X^3$, S, SO, or $SO_2$, and $R^b$ is selected from hydrogen and a $C_{1-8}$ hydrocarbyl group optionally substituted by one or more substituents selected from hydroxy, oxo, halogen, cyano, nitro, carboxy; wherein one or more carbon atoms of the $C_{1-8}$ hydrocarbyl group may optionally be replaced by O, S, SO, $SO_2$, $X^3C(X^4)$, $C(X^4)X^3$ or $X^3C(X^4)X^3$; $X^3$ is O or S; and $X^4$ is $=$O or $=$S.

In another embodiment, the substituents on $R^1$ may be selected from halogen, hydroxy, trifluoromethyl, a group $R^a$-$R^b$ wherein $R^1$ is a bond or O, and $R^b$ is selected from hydrogen and a $C_{1-4}$ hydrocarbyl group optionally substituted by one or more substituents selected from hydroxyl and halogen.

One sub-set of substituents that may be present on a group $R^1$ (e.g. an aryl or heteroaryl group $R^1$) includes fluorine, chlorine, methoxy, methyl, oxazolyl, morpholino, trifluoromethyl, bromomethyl, chloroethyl, pyrrolidino, pyrrolidinylethoxy, pyrrolidinylmethyl, difluoromethoxy and morpholinomethyl.

Another sub-set of substituents that may be present on a group $R^1$ includes fluorine, chlorine, methoxy, ethoxy, methyl, ethyl, isopropyl, tert-butyl, amino, oxazolyl, morpholino, trifluoromethyl, bromomethyl, chloroethyl, pyrrolidino, pyrrolidinylethoxy, pyrrolidinylmethyl, difluoromethoxy, trifluoromethoxy, morpholino, N-methylpiperazino, piperazine, piperidino, pyrrolidino, and morpholinomethyl.

The moiety $R^1$ may be substituted by more than one substituent. Thus, for example, there may be 1 or 2 or 3 or 4 substituents, more typically 1, 2 or 3 substituents. In one embodiment, where $R^1$ is a six membered ring (e.g. a carbocyclic ring such as a phenyl ring), there may be a single substituent which may be located at any one of the 2-, 3- and 4-positions on the ring. In another embodiment, there may be two or three substituents and these may be located at the 2-, 3-, 4- or 6-positions around the ring. By way of example, a phenyl group $R^1$ may be 2,6-disubstituted, 2,3-disubstituted, 2,4-disubstituted 2,5-disubstituted, 2,3,6-trisubstituted or 2,4,6-trisubstituted.

In one embodiment, a phenyl group $R^1$ may be disubstituted at positions 2- and 6- with substituents selected from fluorine, chlorine and $R^a$-$R^b$, where $R^a$ is O and $R^b$ is $C_{1-4}$ alkyl, with fluorine being a particular substituent.

In one subgroup of compounds, the group $R^1$ is a five membered heteroaryl group containing 1 or 2 ring heteroatoms selected from O, N and S. Particular heteroaryl groups include furan, thiophene, pyrrole, oxazole, isoxazole and thiazole groups. The heteroaryl groups may be unsubstituted or substituted by one or more substituent groups as hereinbefore defined.

One preferred group of five membered heteroaryl groups consists of optionally substituted isoxazole and thiazole groups.

In another sub-group of compounds, $R^1$ is a pyrazolopyridine group, for example, a pyrazolo[1,5-a]pyridine group, such as a 3-pyrazolo[1,5-a]pyridinyl group.

Particular examples of groups $R^1$ include the groups A1 to A183 (e.g. A1 to A60) set out in Table 1 on pages 37 to 46 in PCT/GB2004/002824 (WO 2005/002552).

One preferred sub-set of compounds of the invention is the sub-set wherein $R^1$ is a group selected from A1 to A34.

Another preferred sub-set of compounds of the invention is the sub-set wherein $R^1$ is a group selected from A1 to A24, A26 to A34, A38 to A46, A48 to A57, A59 to A64, A66 to A114, A116 to A165, A167 to A168 and A170 to A183.

One particularly preferred sub-set of groups $R^1$ includes 2,6-difluorophenyl, 2-chloro-6-fluorophenyl, 2-fluoro-6-methoxyphenyl, 2,6-dichlorophenyl, 2,4,6-trifluorophenyl, 2-chloro-6-methyl, 2,3-dihydro-benzo[1,4]dioxin-5-yl and pyrazolo[1,5-a]pyridin-3-yl. Compounds containing groups $R^1$ selected from this sub-set have particularly good cdk inhibitory activity.

Another particularly preferred sub-set of groups $R^1$ includes 2,6-difluorophenyl, 2-methoxyphenyl, 2,6-difluoro-4-methoxyphenyl, 2-fluoro-6-methoxyphenyl, 2-fluoro-5-methoxyphenyl, 2,6-dimethoxyphenyl, 2,4-dimethoxyphenyl, 2-chloro-6-fluorophenyl, 2,6-dichlorophenyl, 2,4,6-trifluorophenyl, 2-chloro-6-methyl, 2,3-dihydro-benzo[1,4]dioxin-5-yl and pyrazolo[1,5-a]pyridin-3-yl.

In the context of the inhibition of cdk kinases, one currently most preferred group $R^1$ is 2,6-difluorophenyl.

$R^2$ is hydrogen, halogen, methoxy, or a $C_{1-4}$ hydrocarbyl group optionally substituted by halogen, hydroxyl or methoxy. Preferably $R^2$ is hydrogen, chlorine or methyl, and most preferably $R^2$ is hydrogen.

In the compounds of the formula (I), $R^3$ and $R^4$, together with the carbon atoms to which they are attached, form a fused heterocyclic or carbocyclic group having from 5 to 7 ring members, of which up to 3 can be heteroatoms selected from N, O and S. The fused carbocyclic or heterocyclic ring can be optionally substituted by 0 to 4 groups $R^{10}$ as defined herein. The fused heterocyclic or carbocyclic group can be aromatic or non-aromatic but preferably is aromatic.

In one preferred group of compounds, $R^3$ and $R^4$ together with the carbon atoms to which they are attached form a fused carbocyclic group having from 5 to 7 ring members.

Fused five and six membered carbocyclic or heterocyclic groups are particularly preferred. Examples of fused heterocyclic rings include five and six membered rings such as thiazolo, isothiazolo, oxazolo, isoxazolo, pyrrolo, pyrido, thieno, furano, pyrimido, pyrazolo, pyrazino, tetrahydroazepinone and imidazolo fused rings. It is preferred that the fused heterocyclic group is selected from six membered ring groups, one particularly preferred group being the pyrido group.

Examples of fused carbocyclic rings include five and six membered rings such as benzo, dihydro or tetrahydro-benzo and cyclopenta-fused rings. Six membered rings are preferred. One particularly preferred group is the benzo group.

Particular examples of ring systems formed by the five membered ring and $R^3$ and $R^4$ are ring systems (i) to (iv) set out below. Ring system (i) is generally preferred.

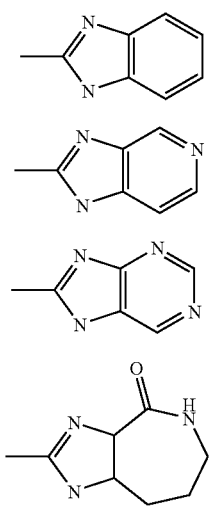

The fused carbocyclic or heterocyclic group can be optionally substituted by one or more groups $R^{10}$ as hereinbefore defined.

In one embodiment, the substituents on the fused carbocyclic or heterocyclic group may be selected from halogen, hydroxy, trifluoromethyl, cyano, nitro, carboxy, amino, monocyclic carbocyclic and heterocyclic groups having from 3 to 7 (typically 5 or 6) ring members, a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, a carbocyclic or heterocyclic group with 3-7 ring members and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, a carbocyclic or heterocyclic group with 3-7 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; and $R^c$, $X^1$ and $X^2$ are as hereinbefore defined, or two adjacent groups $R^{10}$ together with the carbon atoms or heteroatoms to which they are attached may form a 5-membered heteroaryl ring or a 5- or 6-membered non-aromatic heterocyclic ring, wherein the said heteroaryl and heterocyclic groups contain up to 3 heteroatom ring members selected from N, O and S.

Preferred $R^{10}$ groups on the fused carbocyclic or heterocyclic group formed by $R^3$ and $R^4$ include halogen (e.g. fluorine and chlorine), a group $R^a$-$R^b$ wherein $R^a$ is a bond, O, CO, $C(X^2)X^1$, and $R^b$ is selected from hydrogen, heterocyclic groups having 3-7 ring members (preferably 5 or 6 ring mbers) and a $C_{1-4}$ hydrocarbyl group (e.g. a saturated hydrocarbyl group such as an alkyl or cycloalkyl group) optionally substituted by one or more substituents selected from hydroxy, carboxy, amino, mono- or di-$C_{1-4}$ hydrocarbylamino, and heterocyclic groups with 3-7 ring members (e.g. 5 or 6 ring members). Particular compounds of the formula (I) are those defined in, for example, the compounds of formulae (II) to (IXa) and any sub-groups thereof in PCT/GB2004/002824 (WO 2005/002552), the compounds listed in PCT/GB2004/002824 (WO 2005/002552) and the compounds exemplified in the Examples section of PCT/GB2004/002824 (WO 2005/002552).

A preferred compound of the formula (I) is 1-(2,6-difluorophenyl)-N-[3-(5-morpholin-4-ylmethyl-1H-benzimidazol-2-yl)-1H-pyrazol-4-yl]-urea and its salts, N-oxides, tautomers and solvates, and in particular its salts.

Particular compounds of the formula (I) include Examples 3-305 of WO 2005/002252 as laid out below.

In many of the compounds shown below that contain an NH moiety (e.g. amide and urea NH groups, benzoniidazole NH groups and pyrazole NH groups), the hydrogen atom is not explicitly shown. However, in such cases, it is to be understood that the hydrogen atom is present. For example, in many of the compounds, a hydrogen atom is not explicitly shown at the 1-position of the pyrazole ring—i.e. the pyrazole ring appears thus:

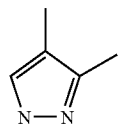

In such cases, it is to be understood that a hydrogen atom is present at the 1-position, i.e. the above structure is equivalent to:

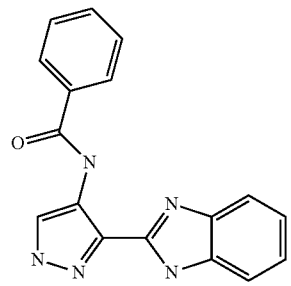

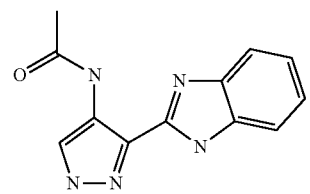

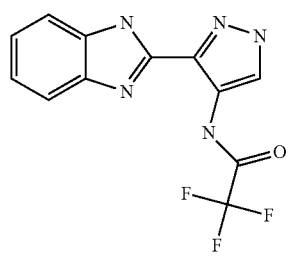

63
-continued
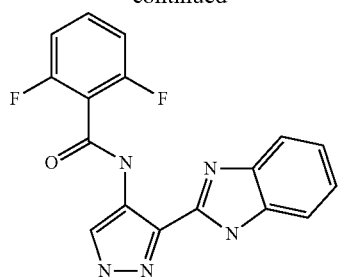
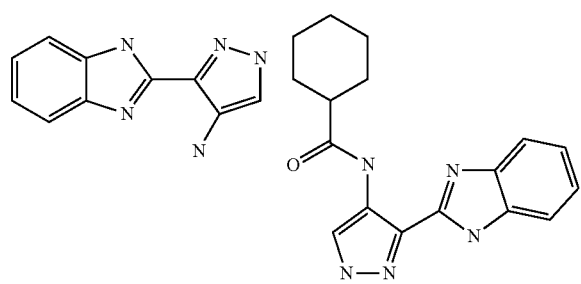
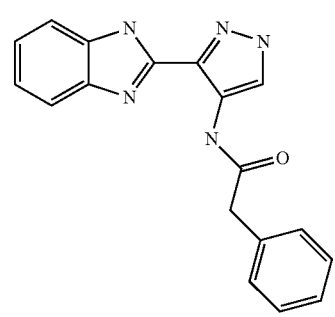
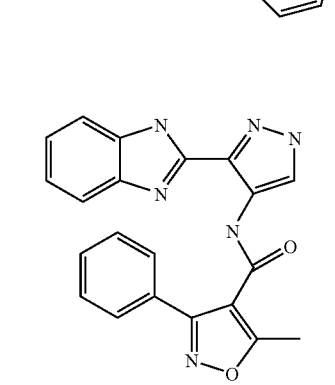

64
-continued
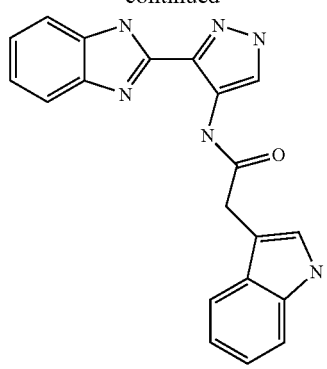
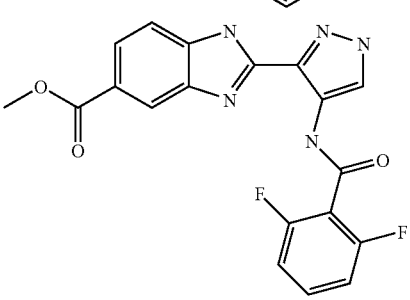
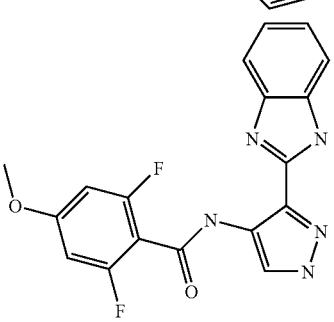
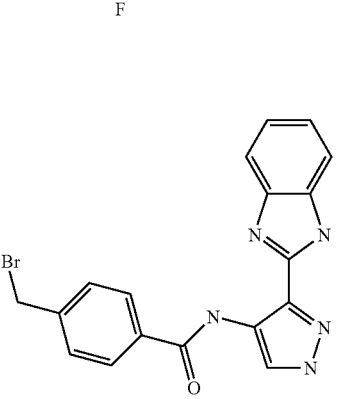
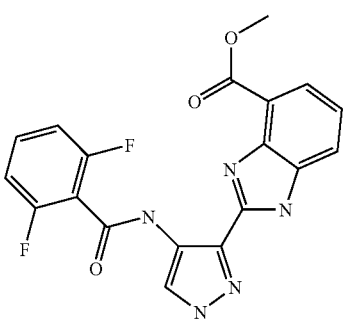

65
-continued
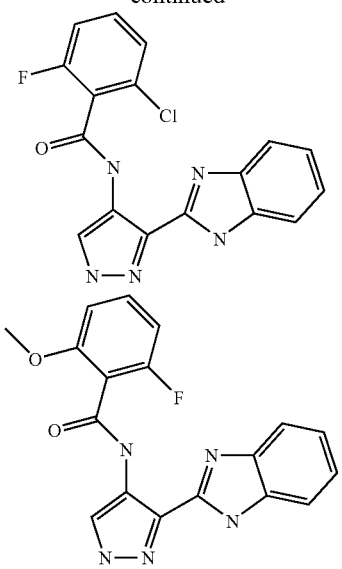
66
-continued
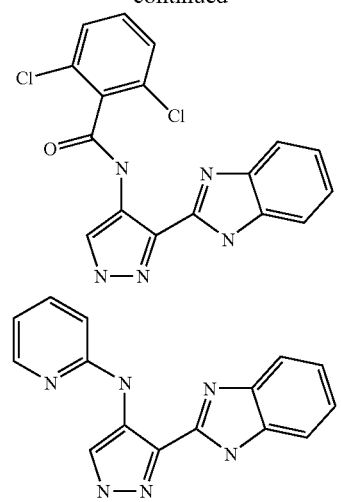
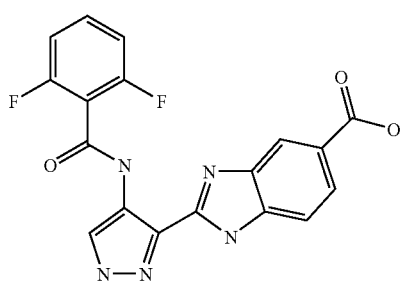
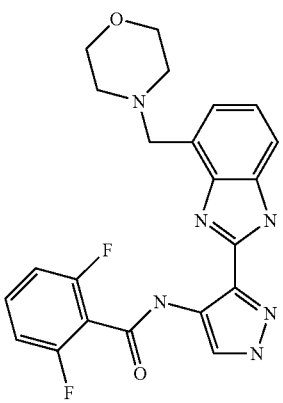
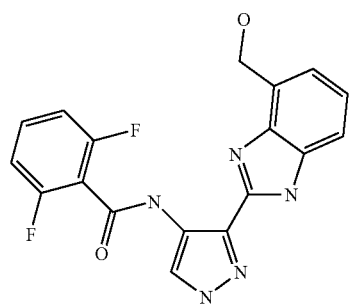
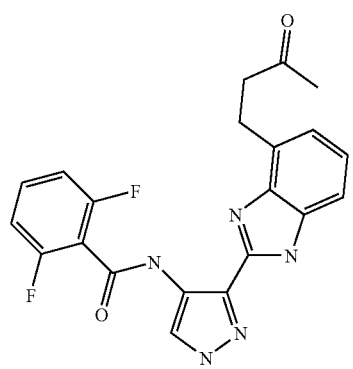

67
-continued
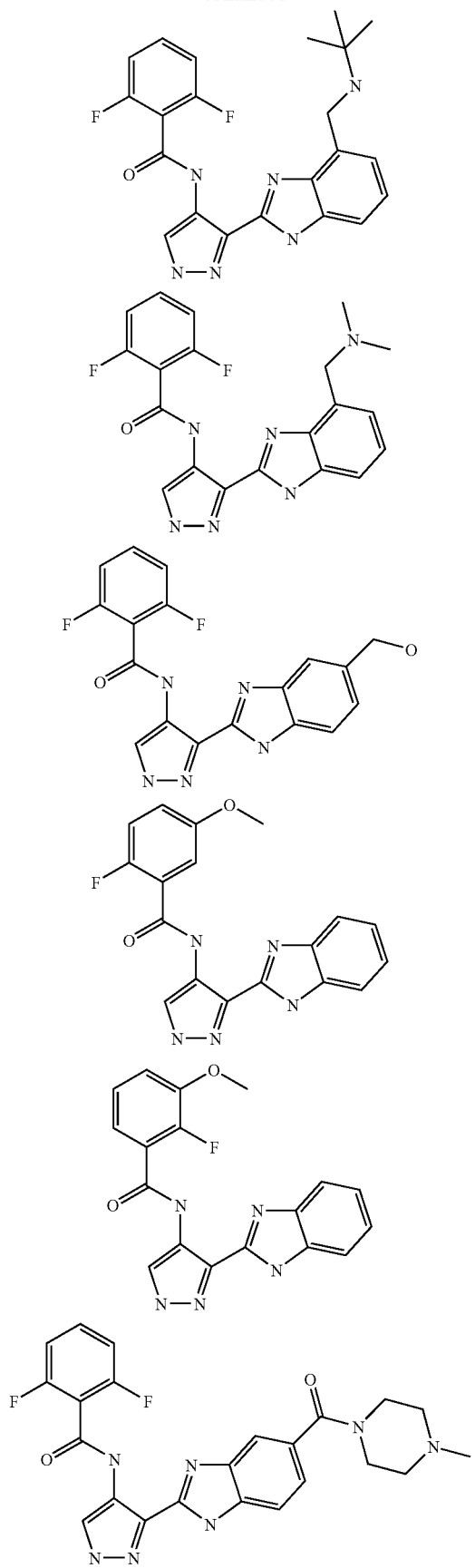
68
-continued
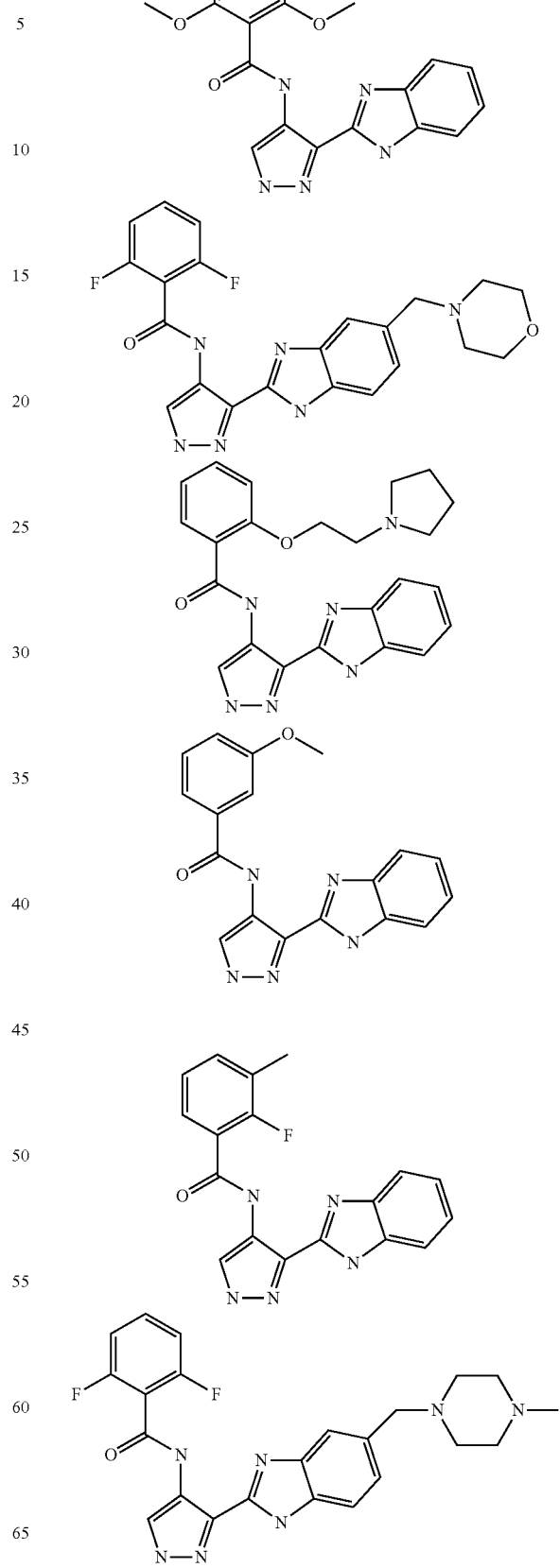

69
-continued
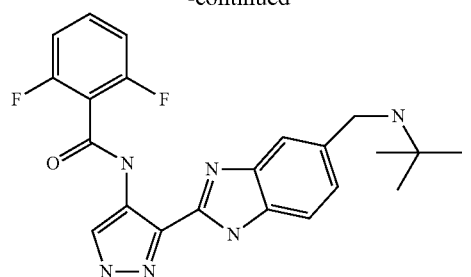
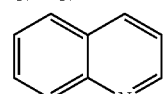
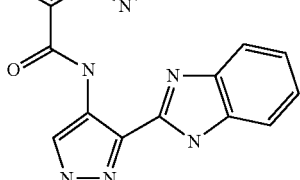
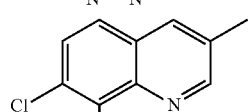
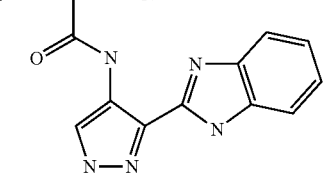
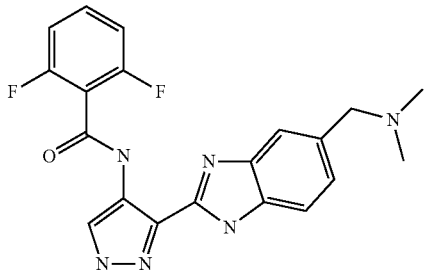
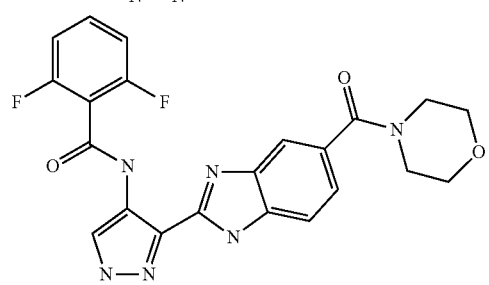
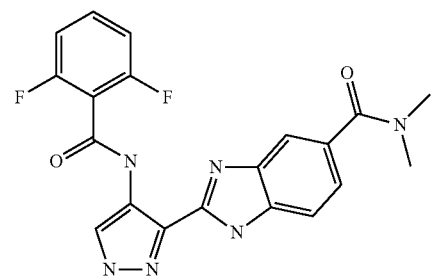
70
-continued
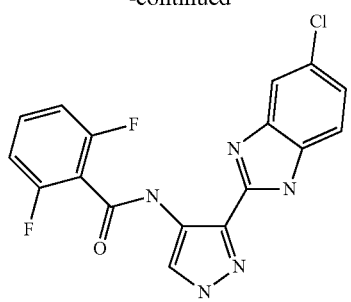
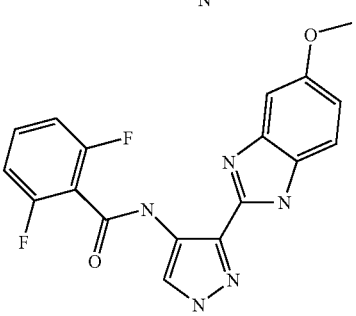
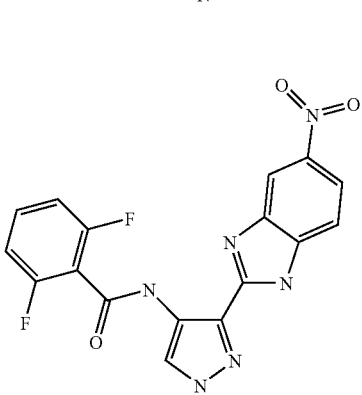
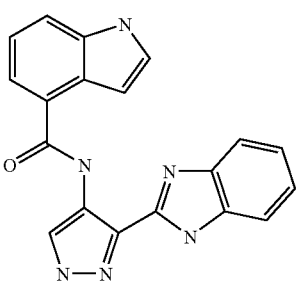
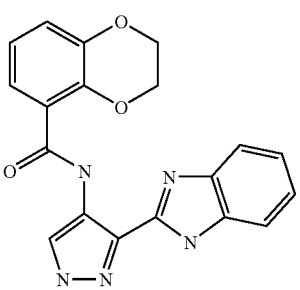

71
-continued
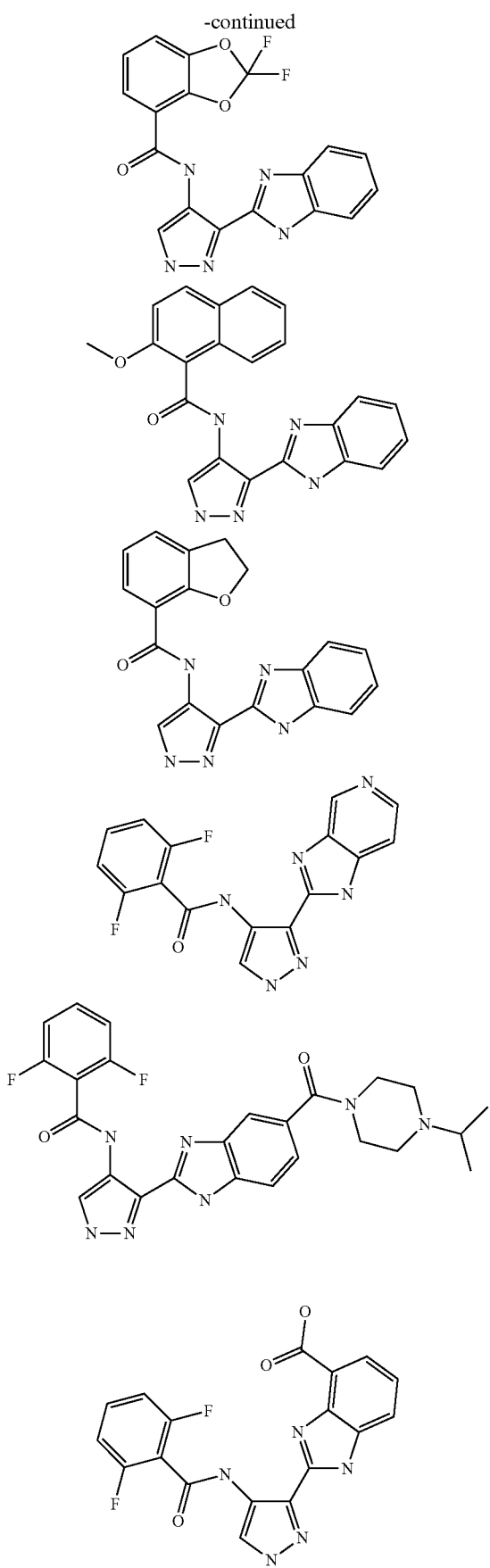
72
-continued
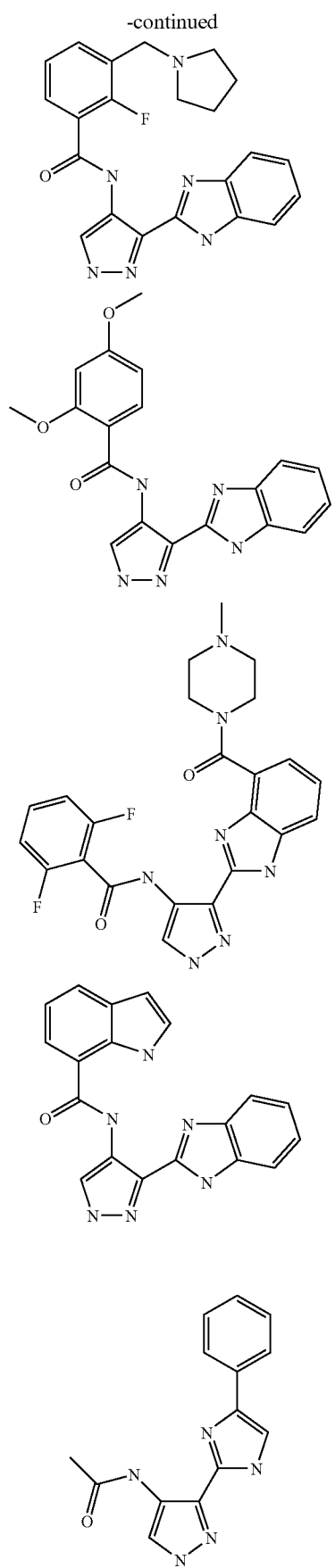

73
-continued
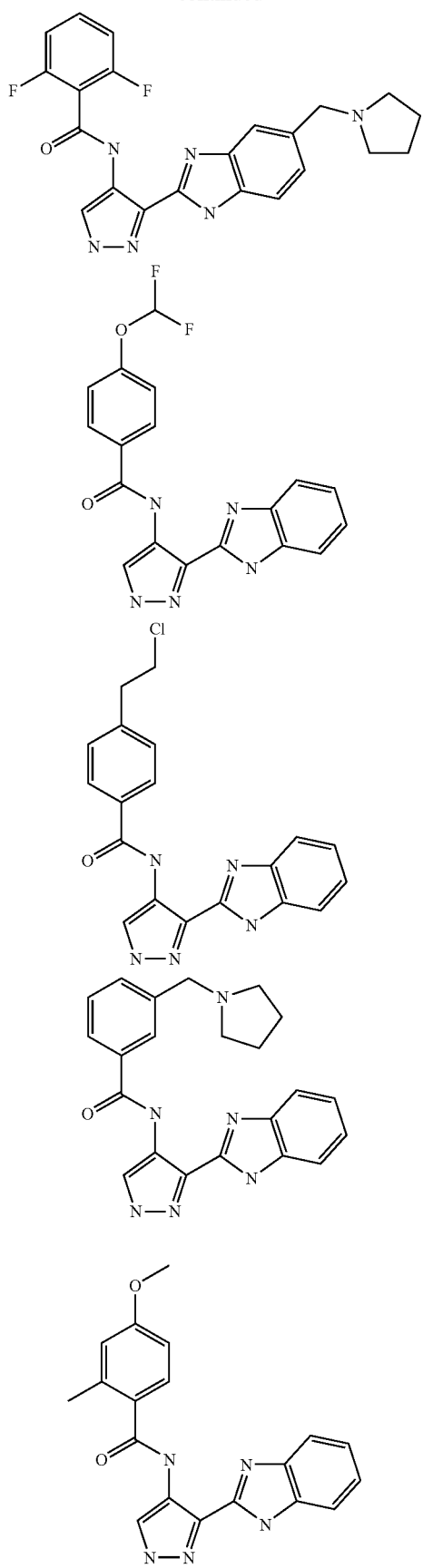
74
-continued
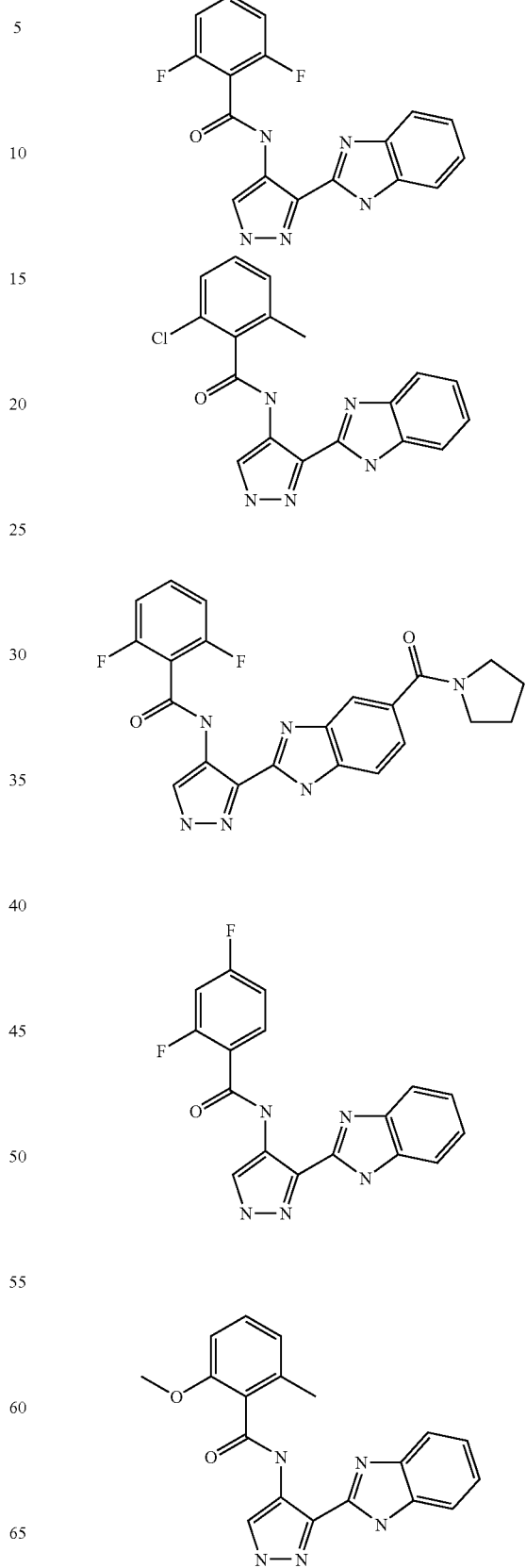

75
-continued
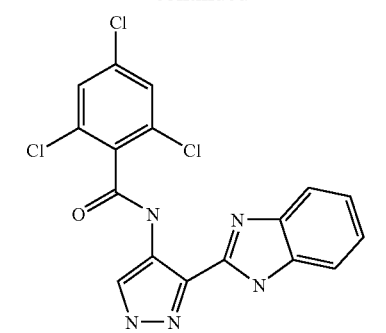
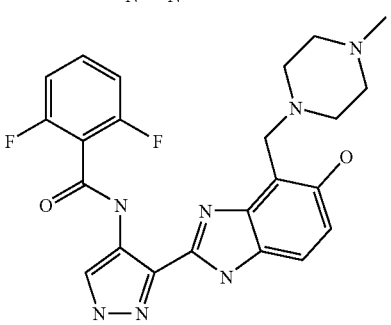
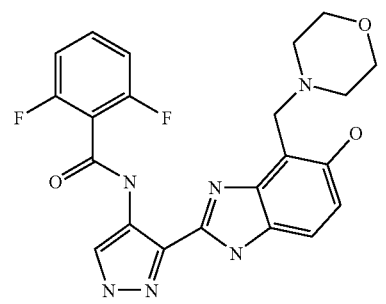
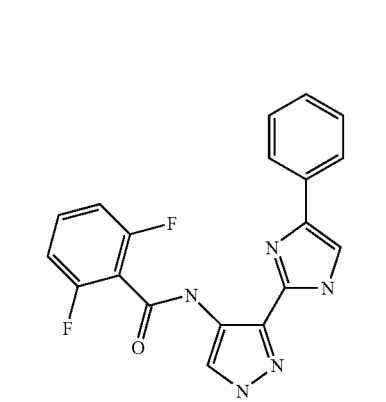
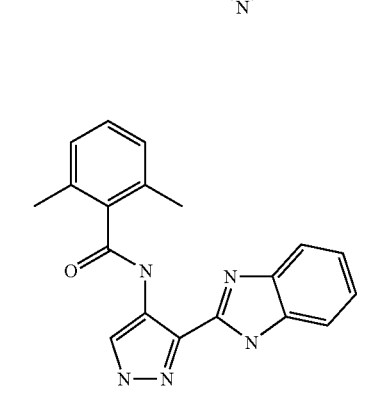
76
-continued
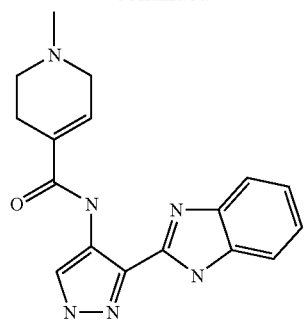
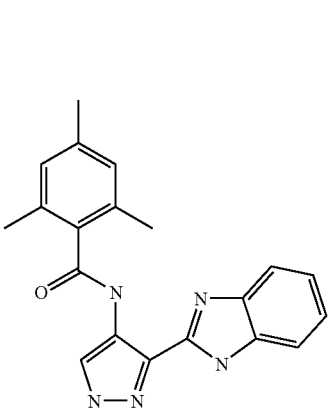
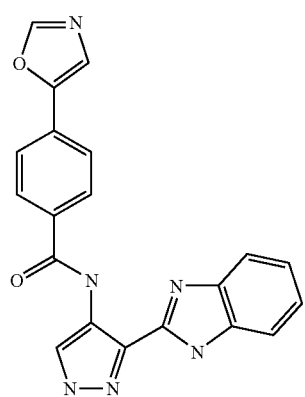
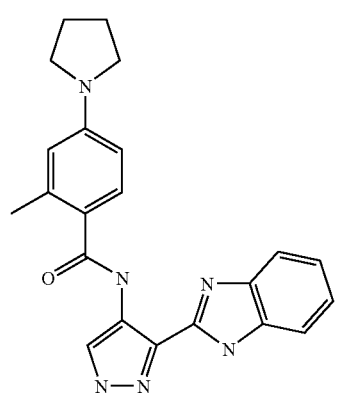

-continued
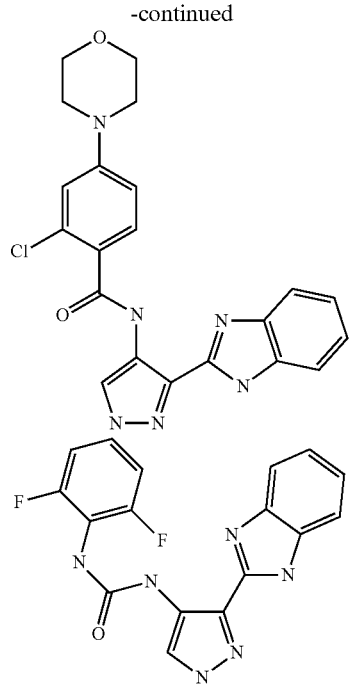
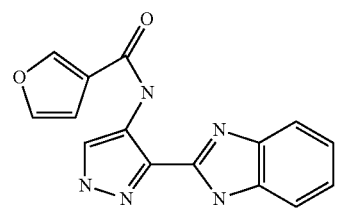
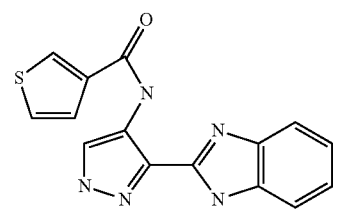
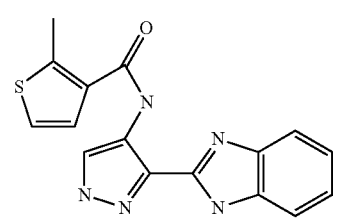
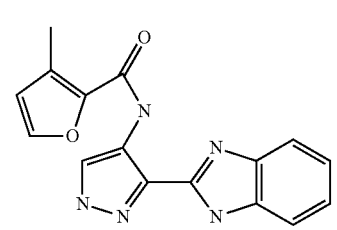
-continued
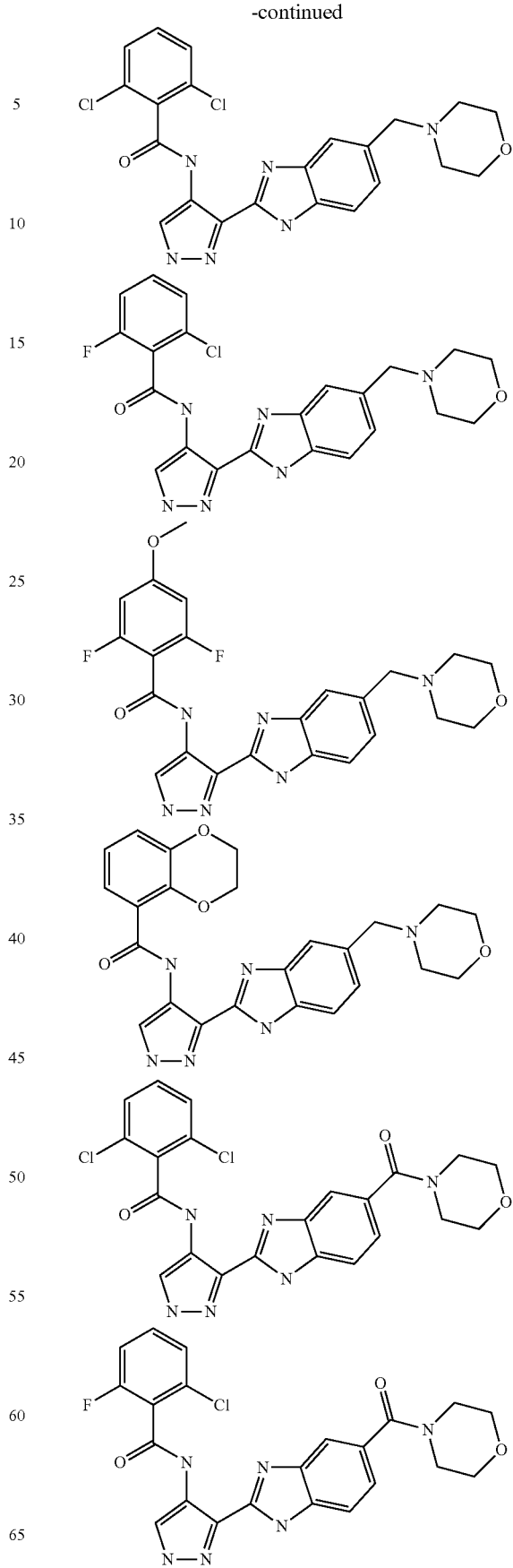

-continued
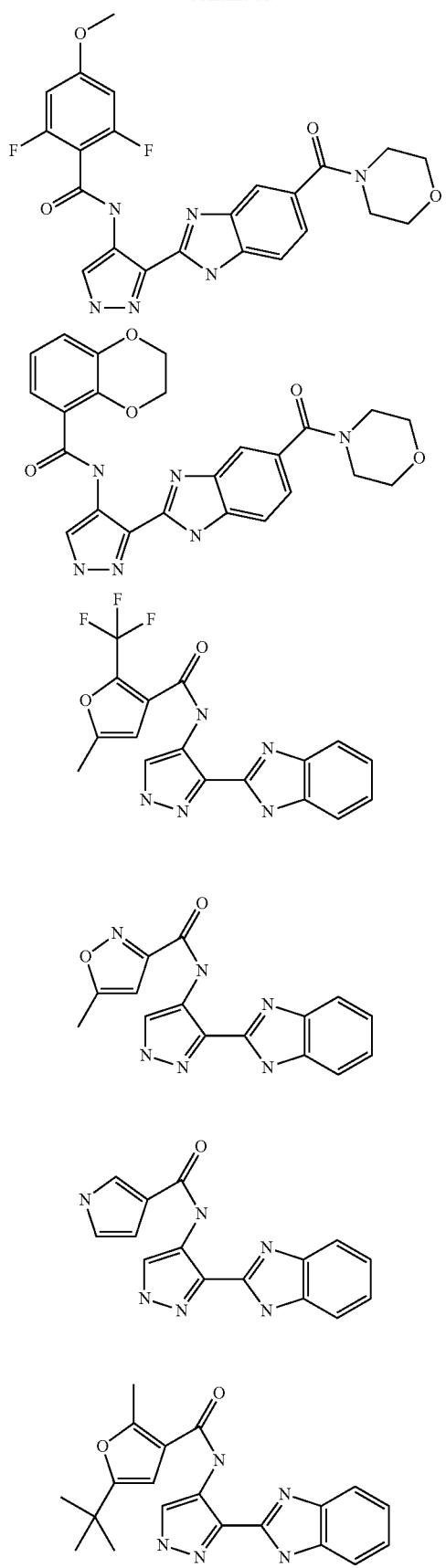
-continued
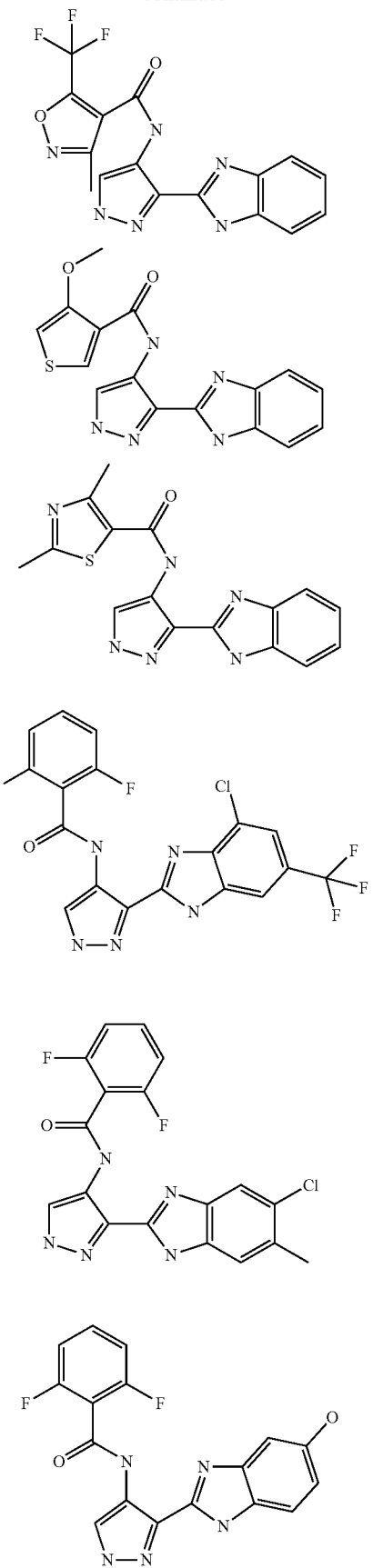

81
-continued
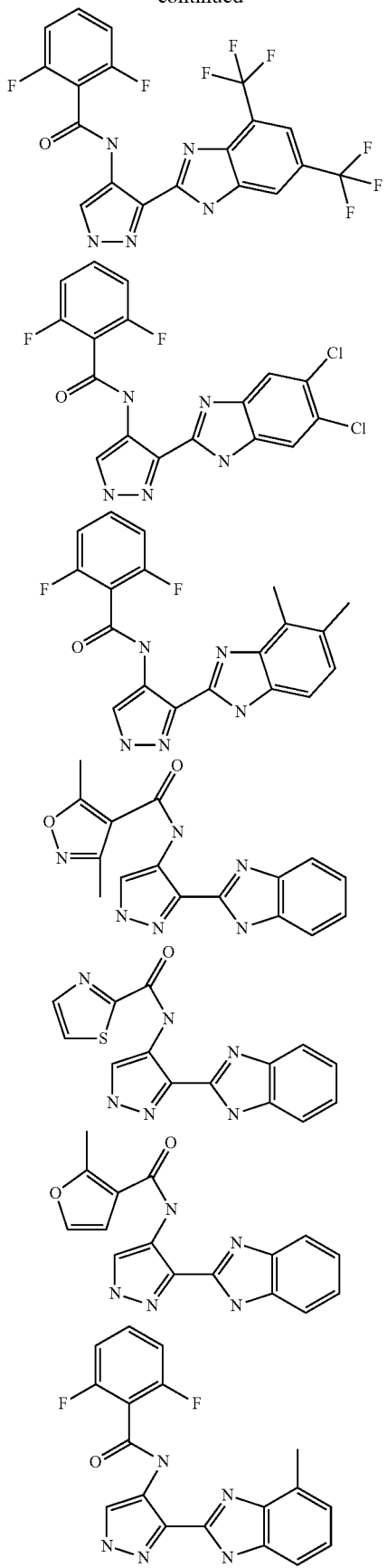
82
-continued
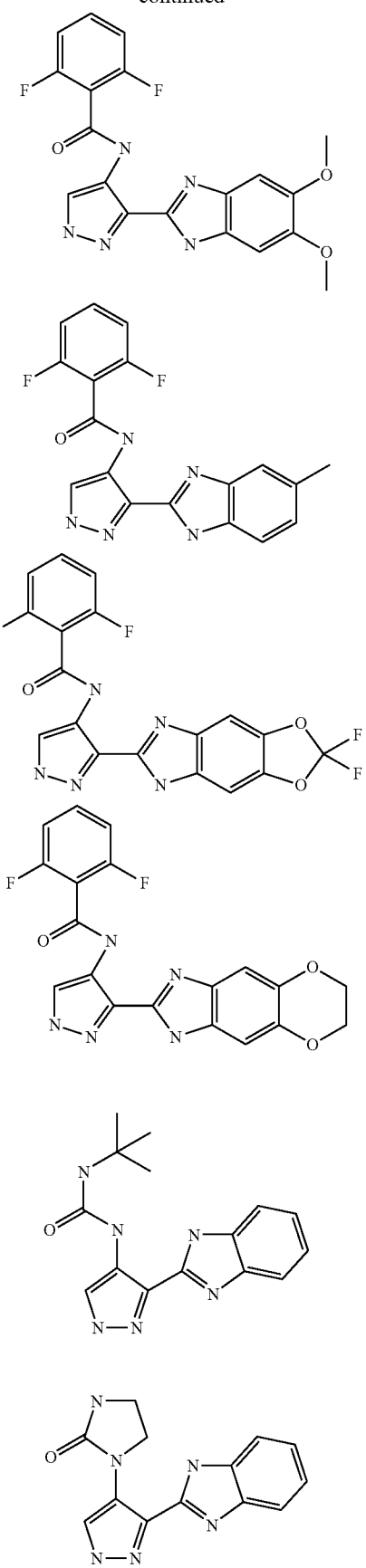

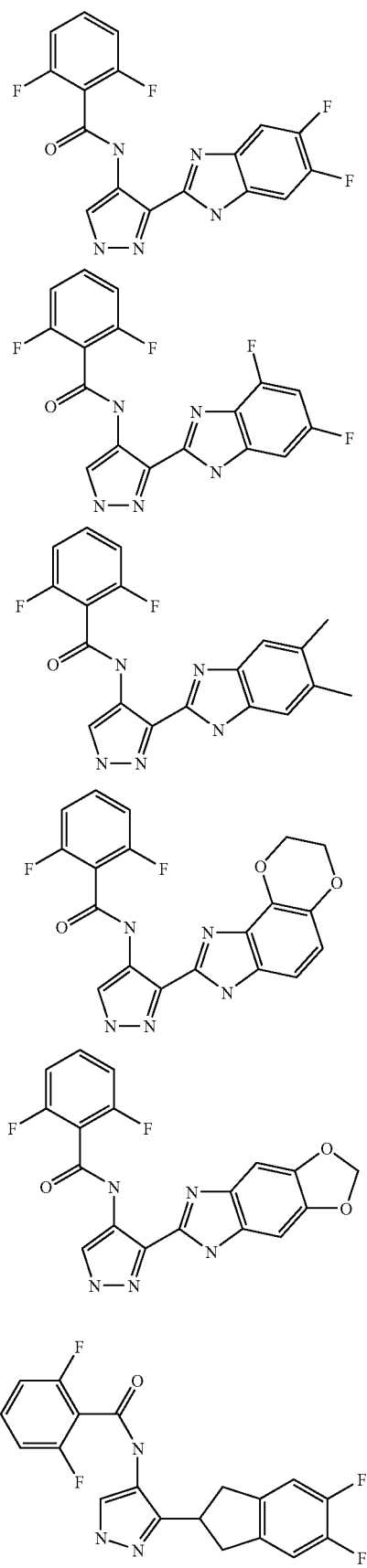
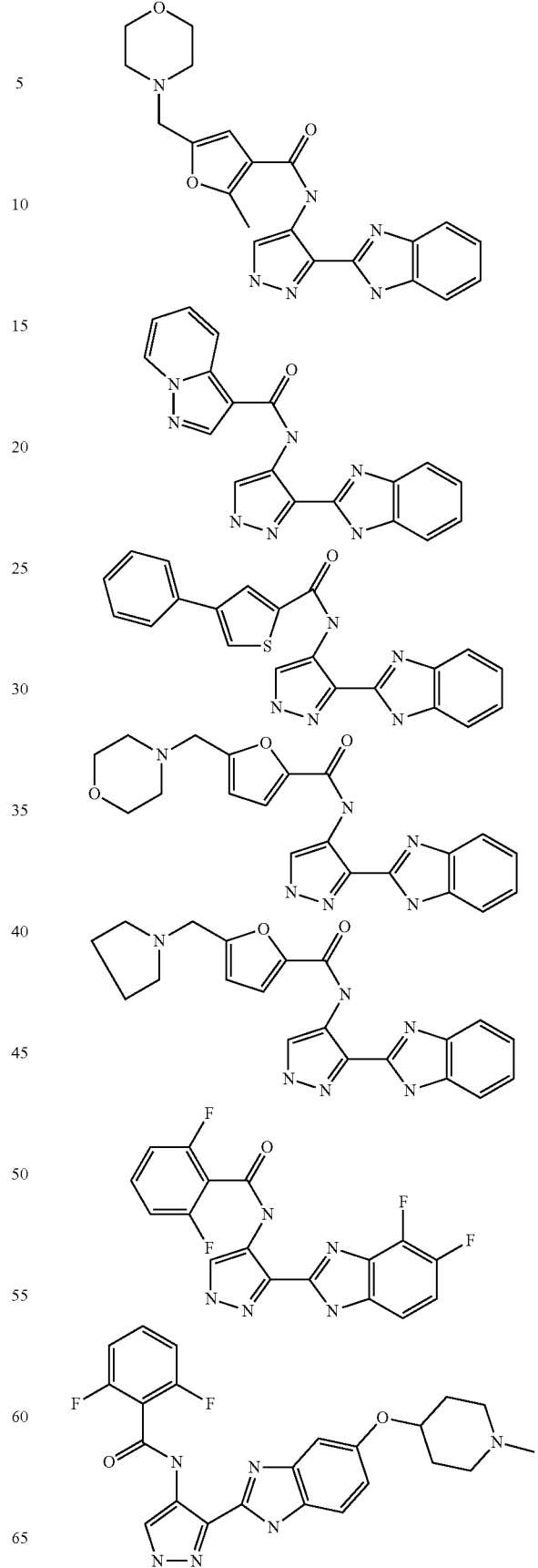

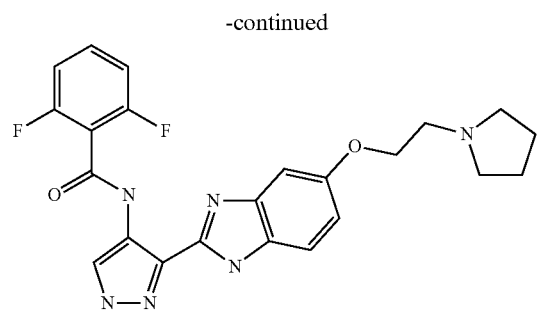
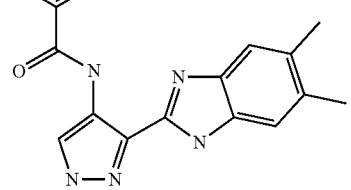
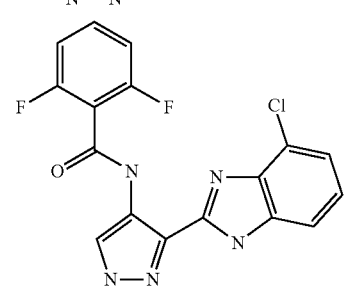
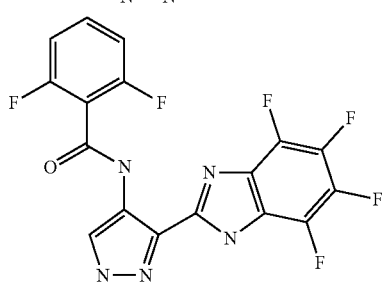
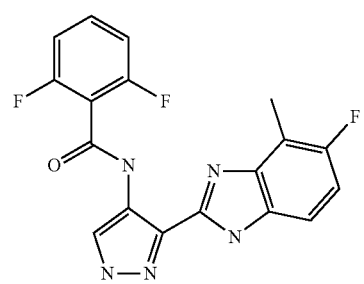
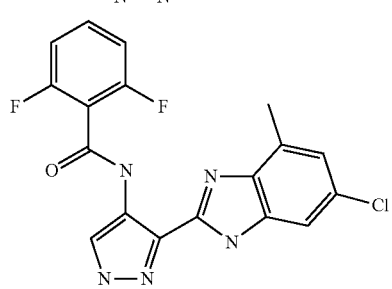
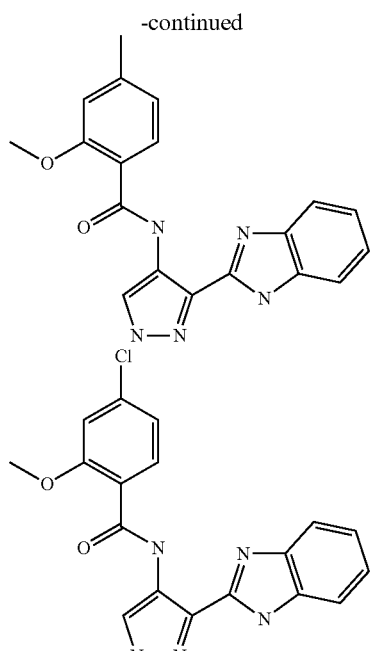
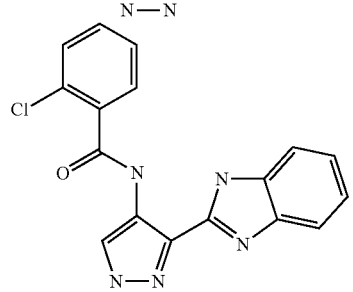
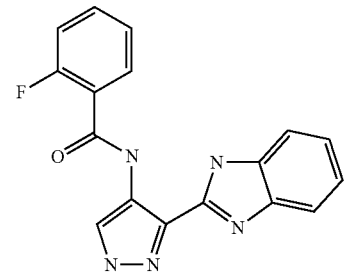
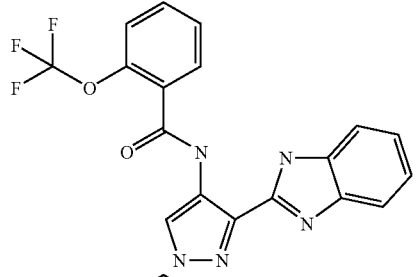
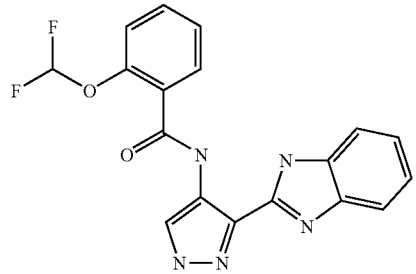

87
-continued
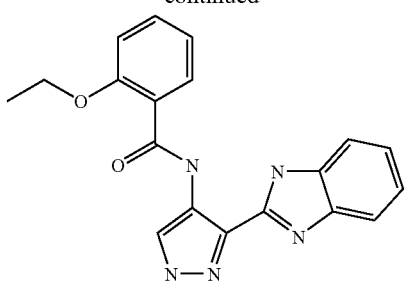
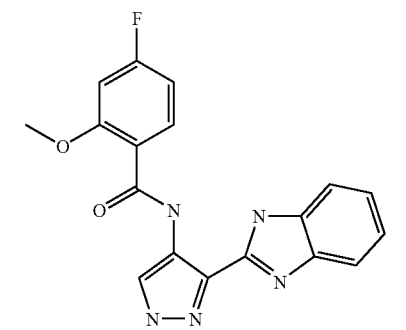
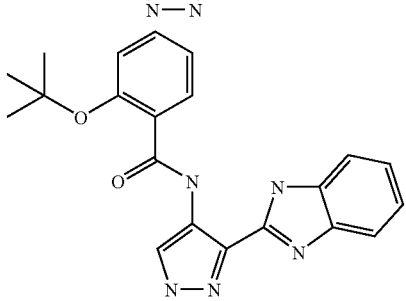
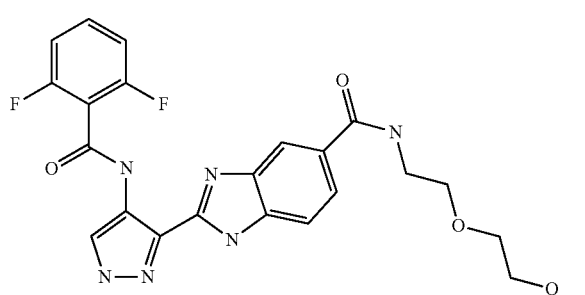
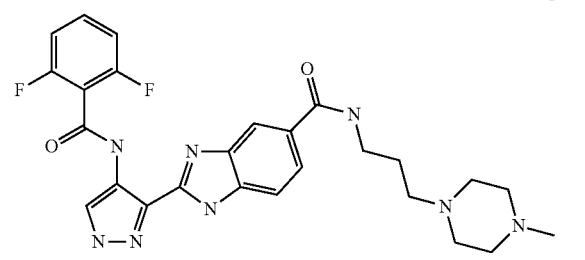
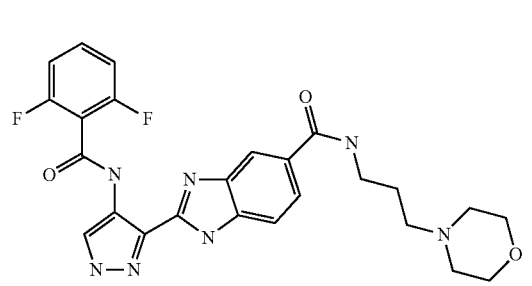
88
-continued
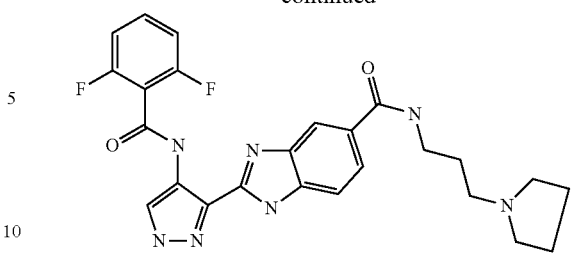
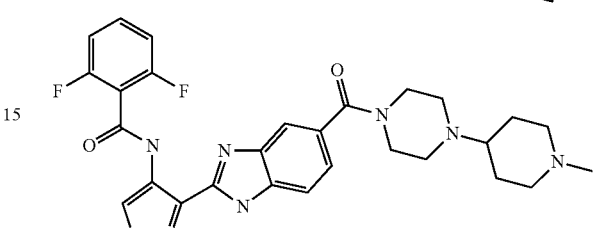
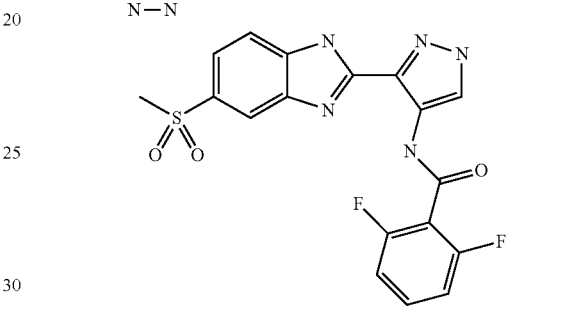
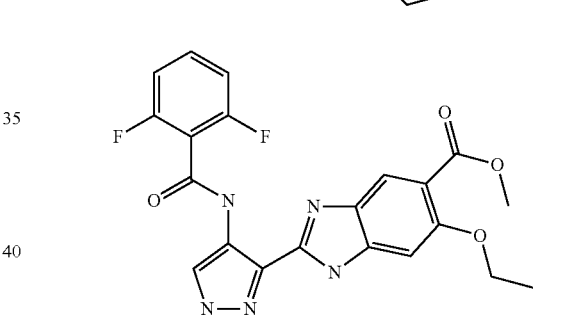
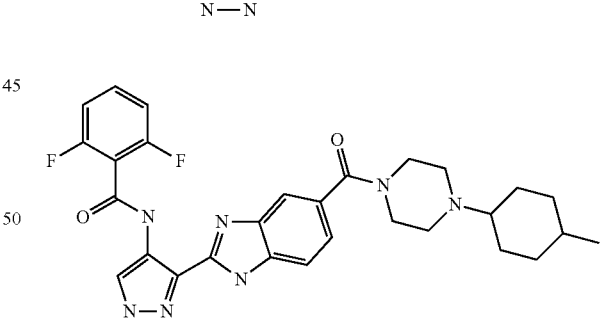
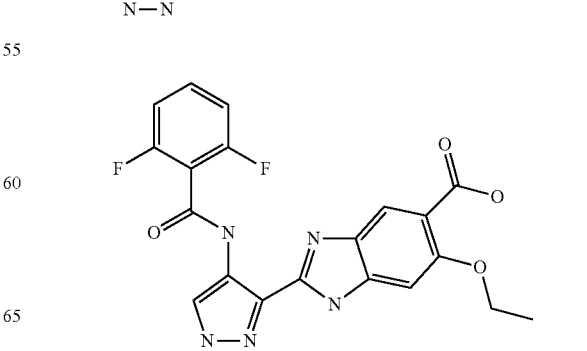

89
-continued
90
-continued
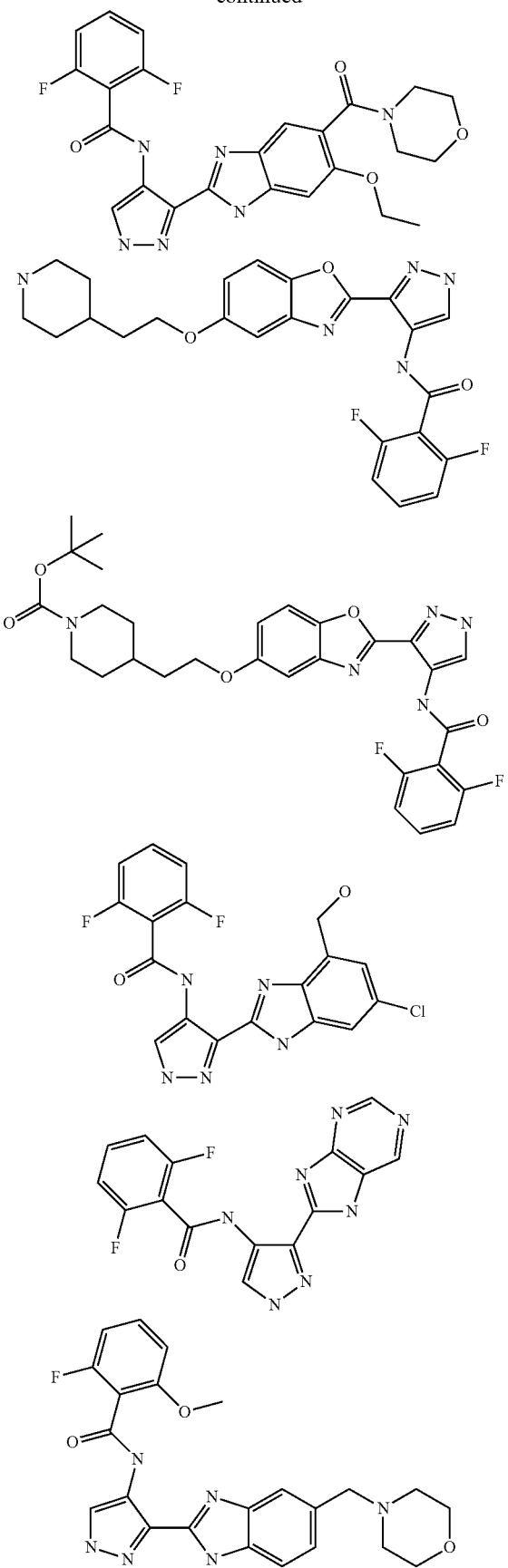
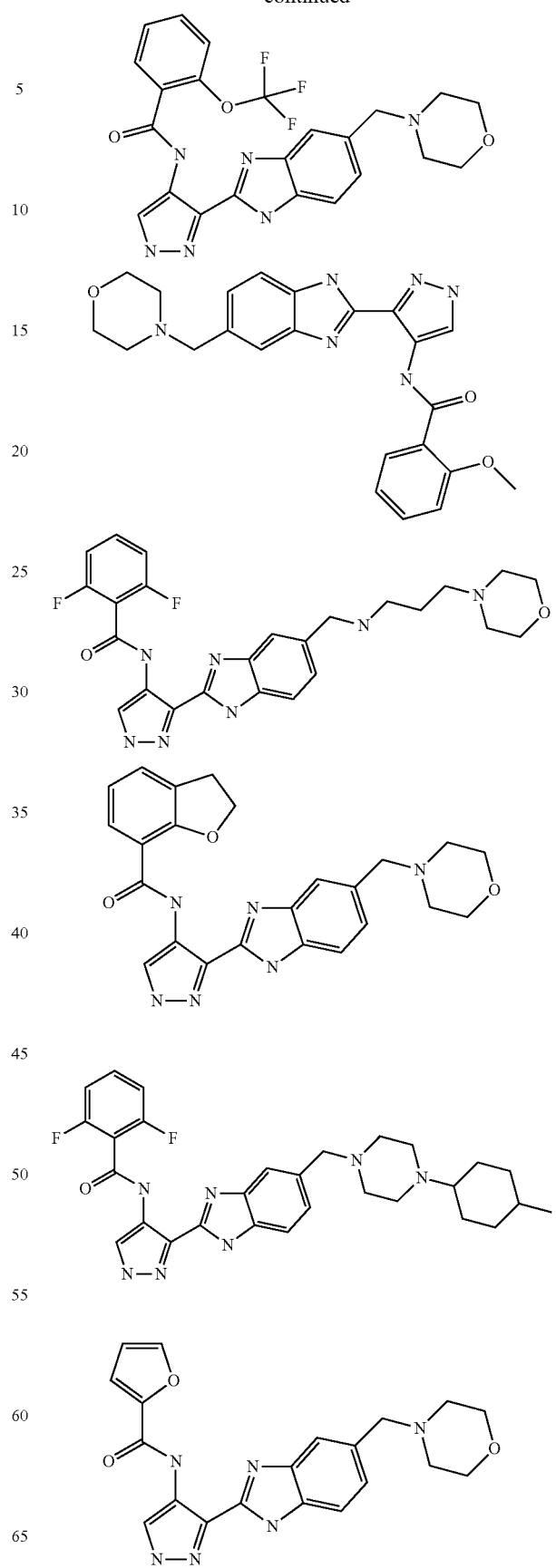

91
-continued
92
-continued
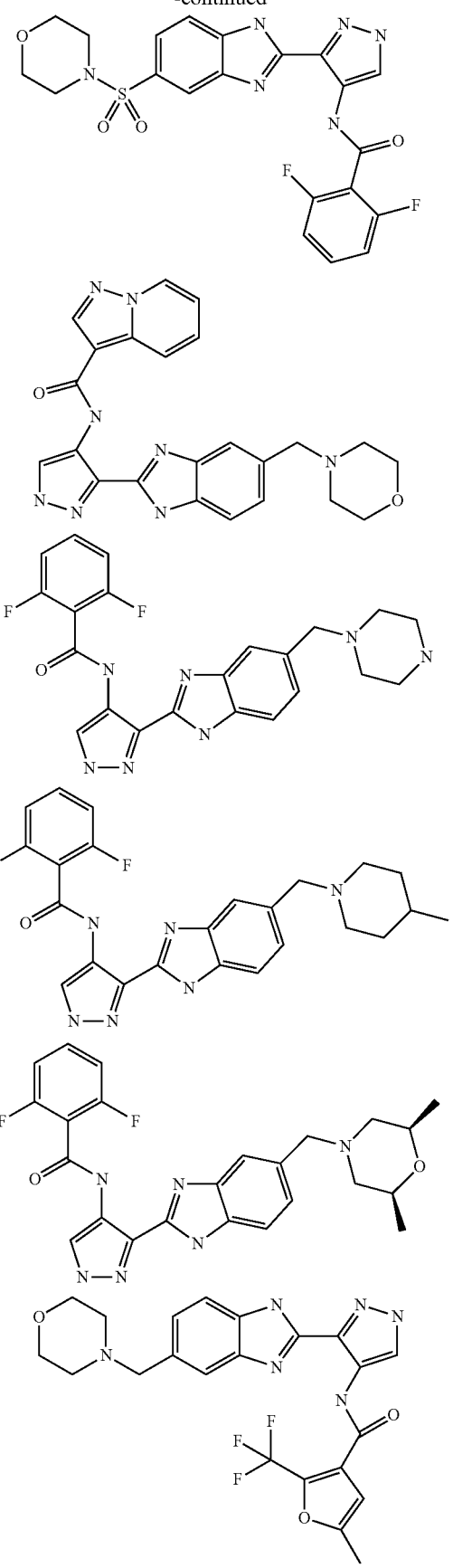
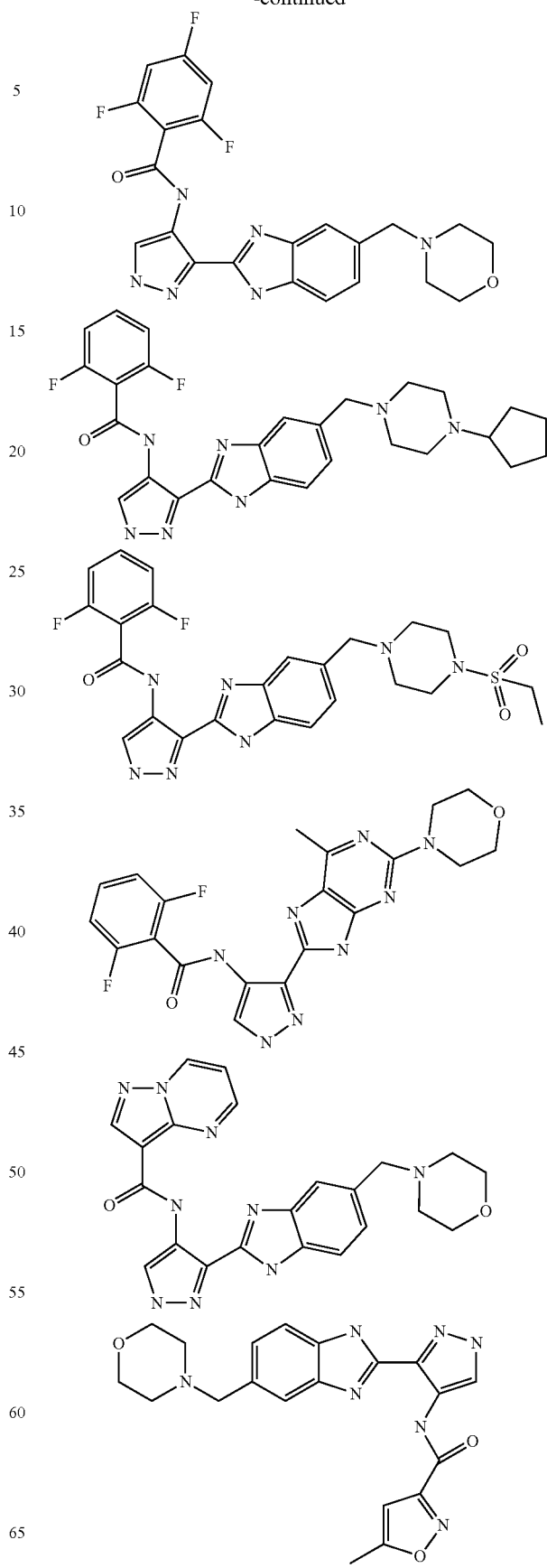

93
-continued
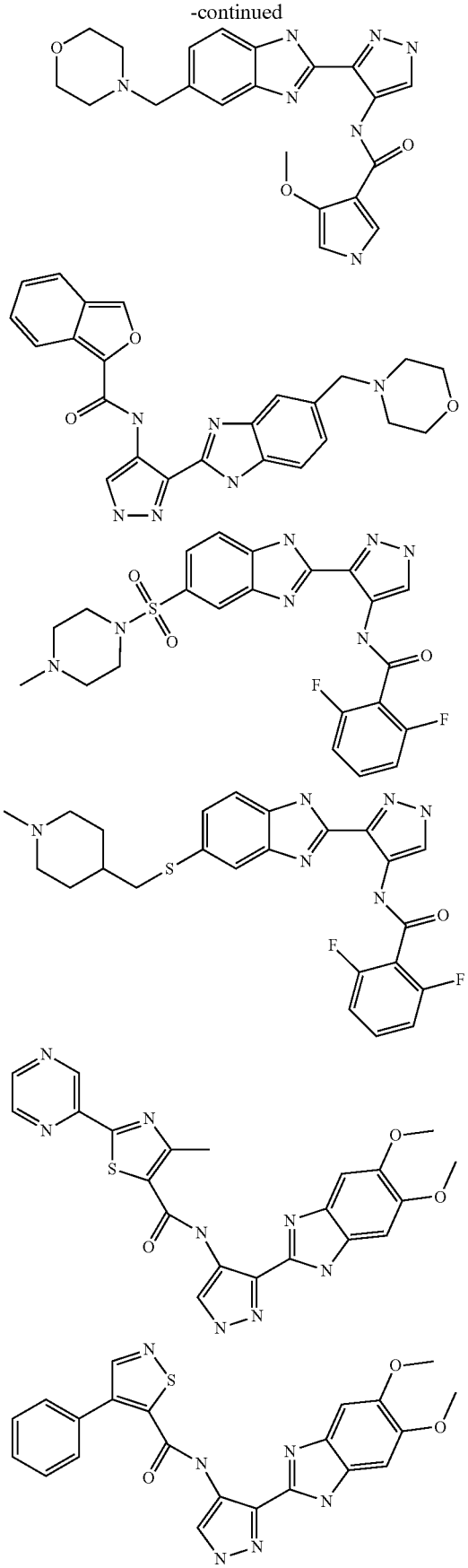
94
-continued
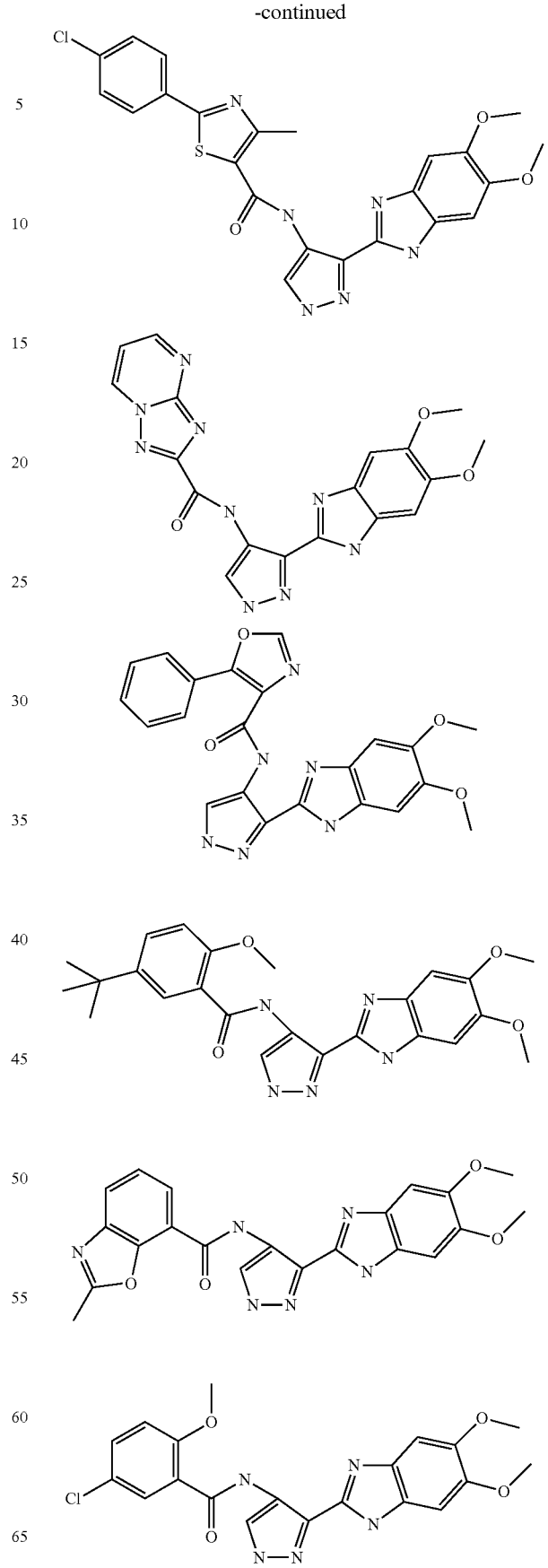

95
-continued
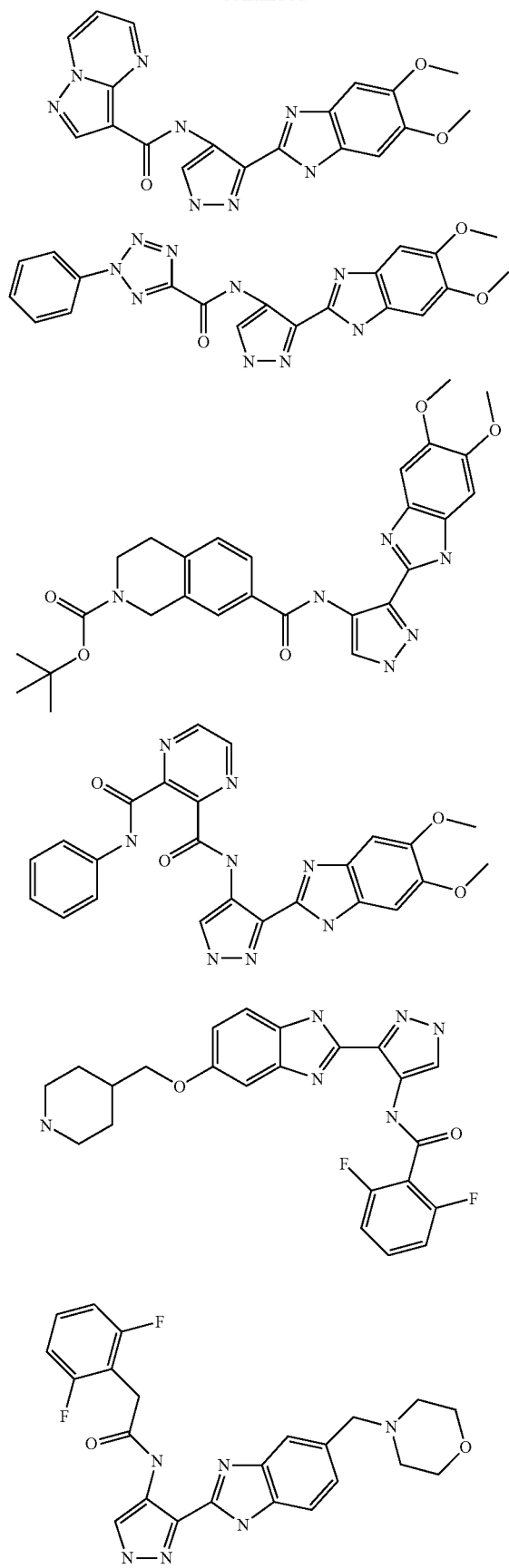
96
-continued
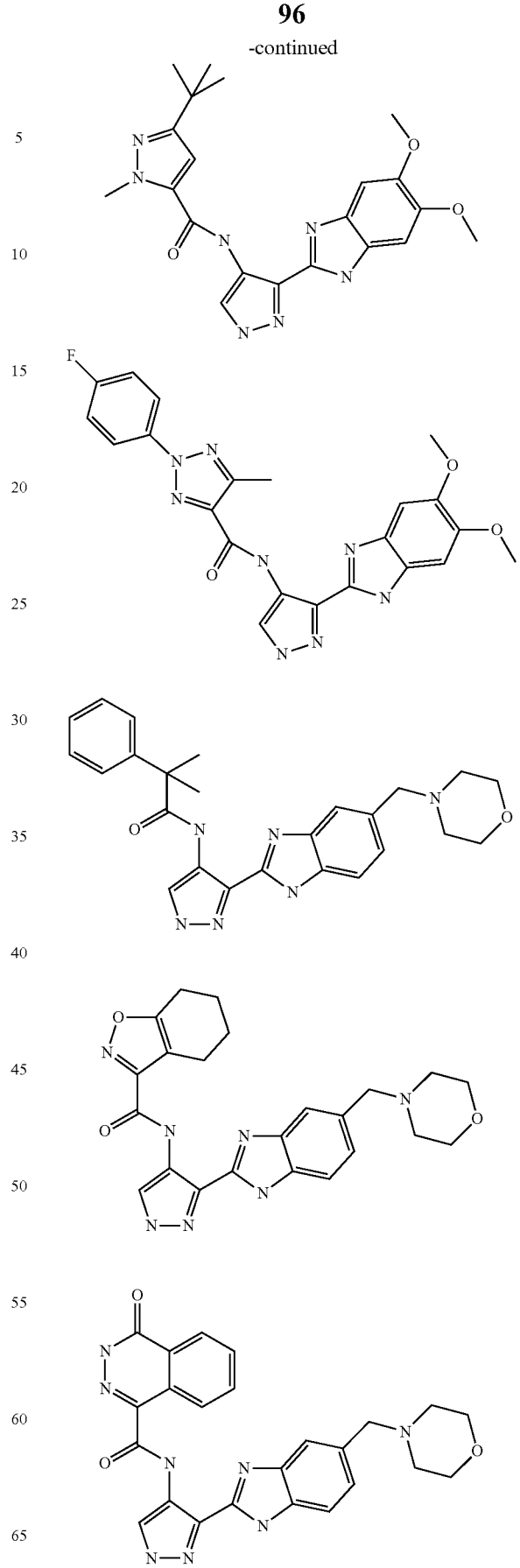

97
-continued
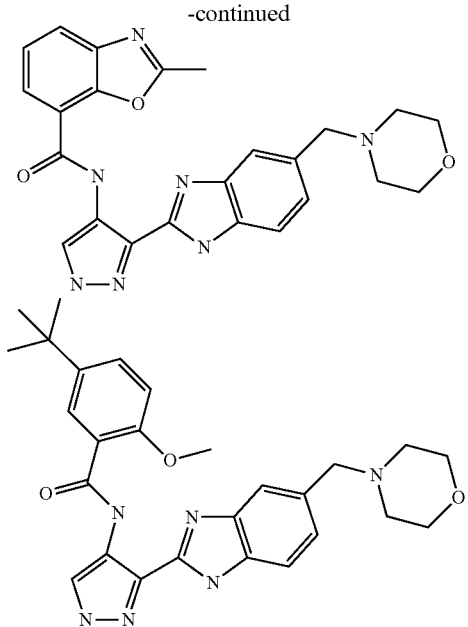
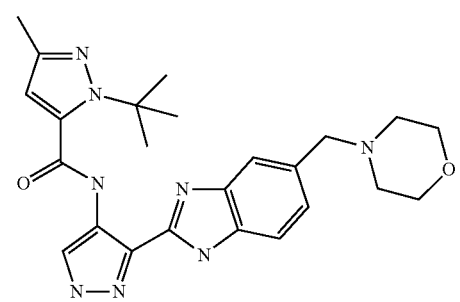
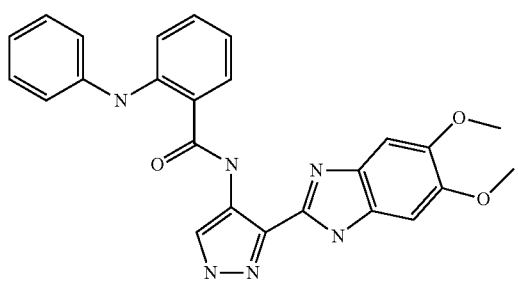
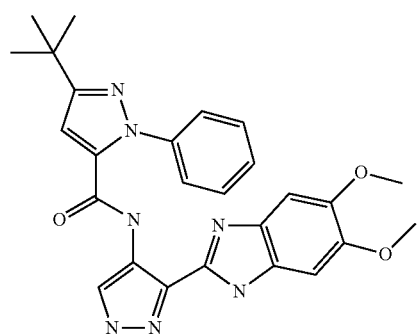
98
-continued
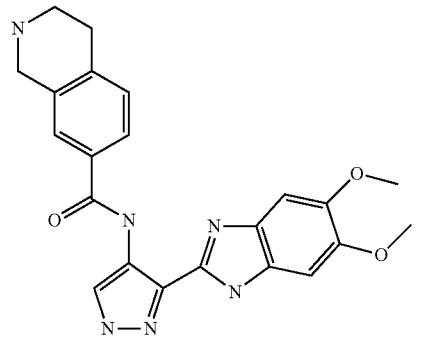
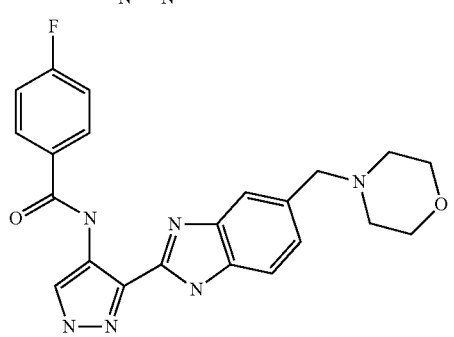
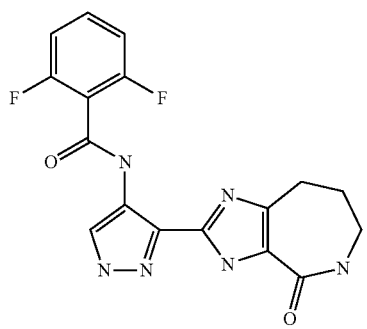
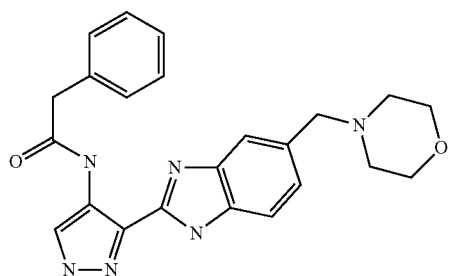
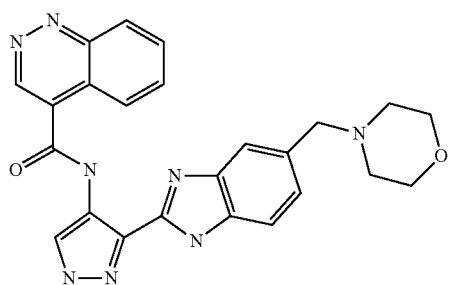

99
-continued
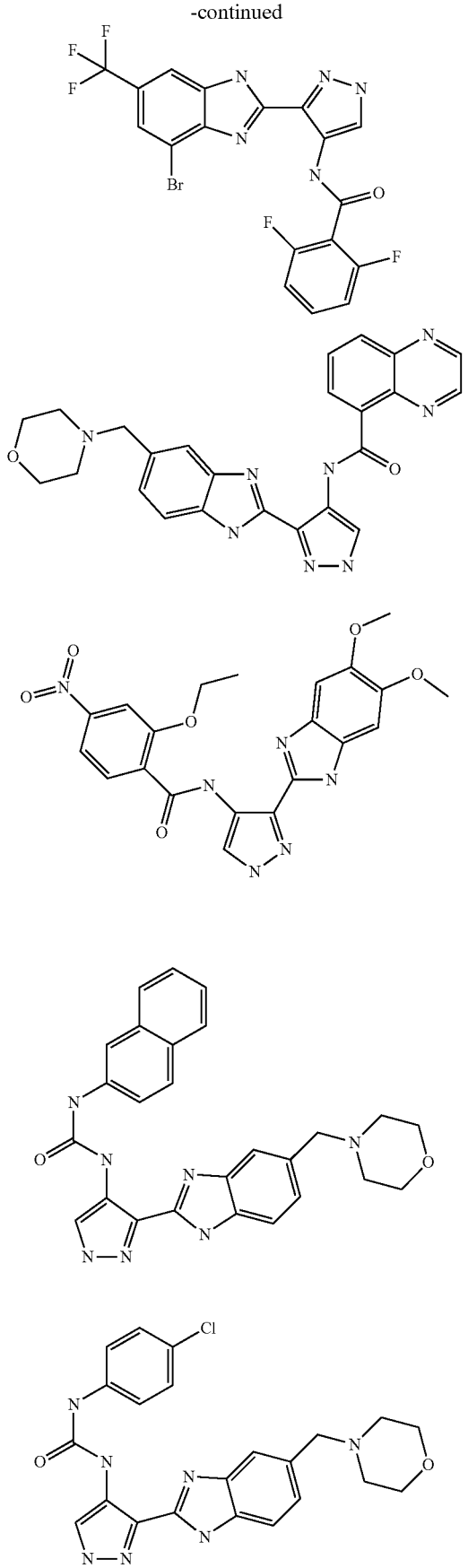
100
-continued
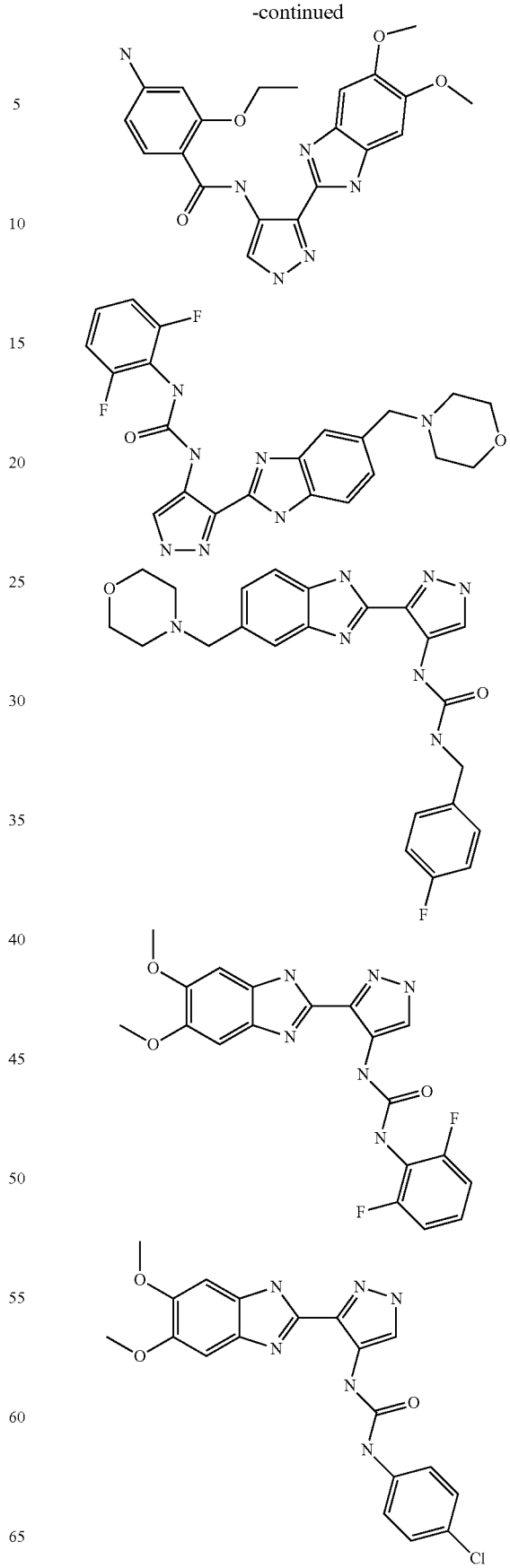

101
-continued
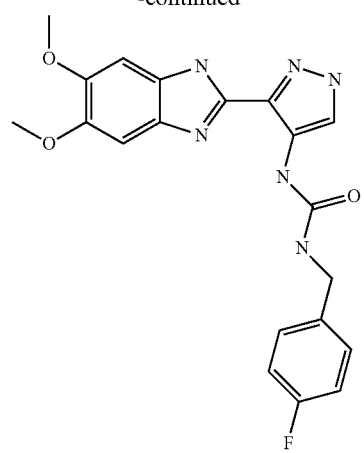
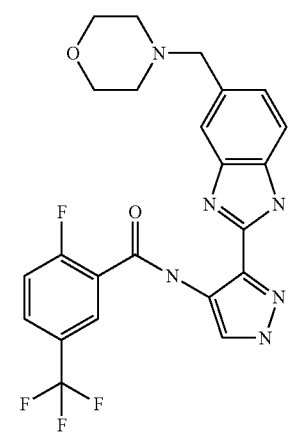
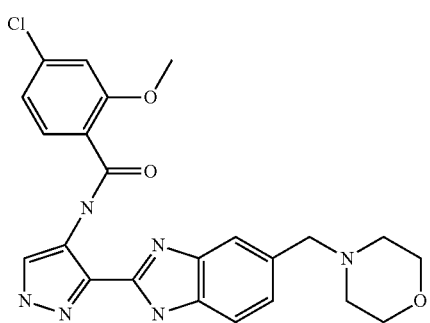
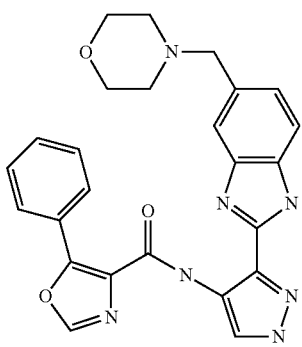
102
-continued
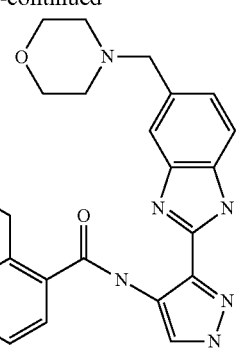
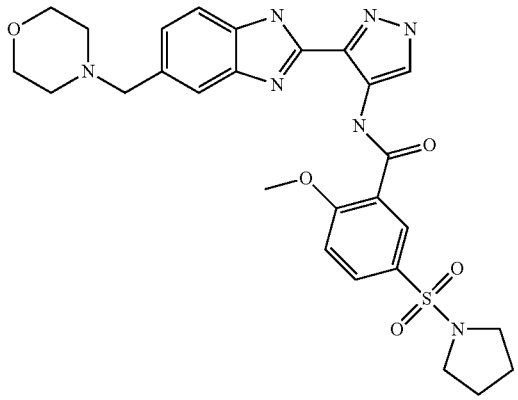
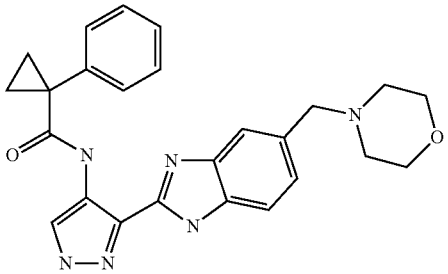
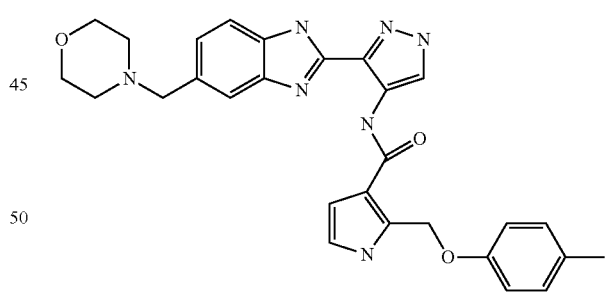
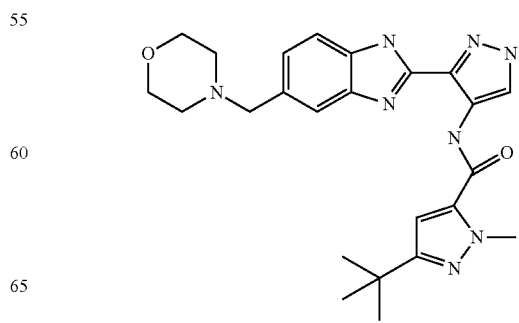

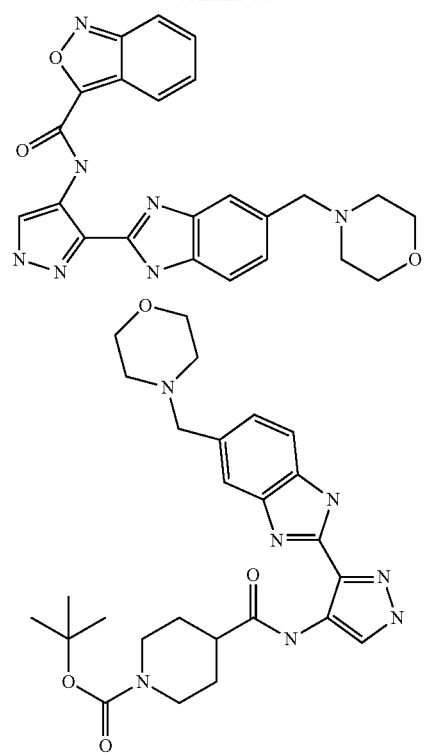
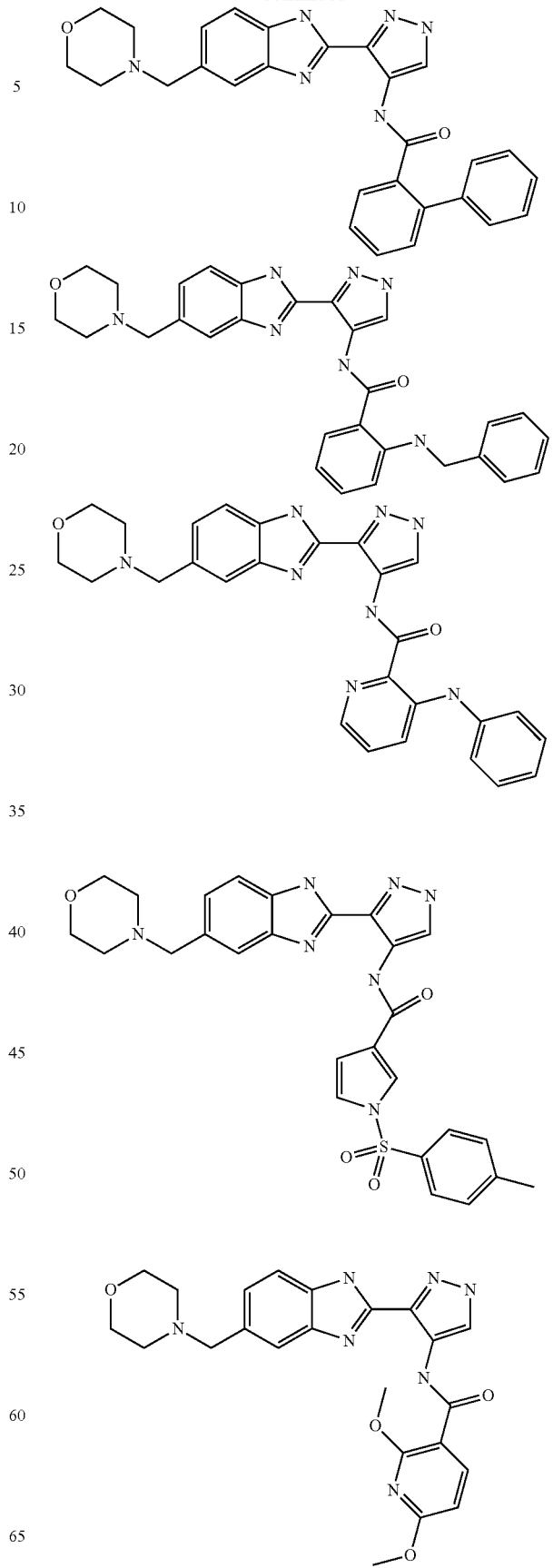

105
-continued
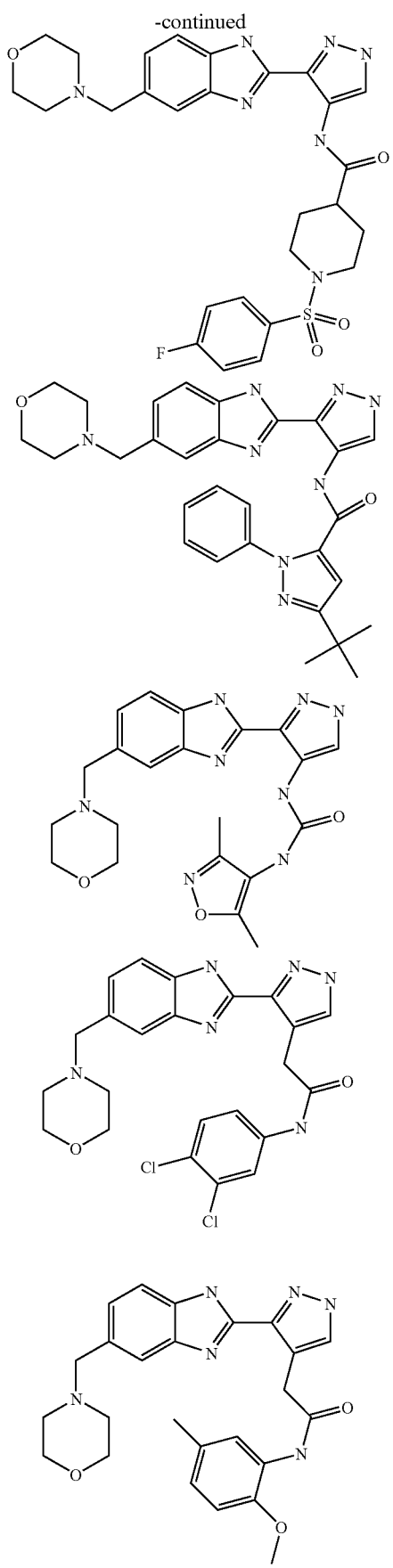
106
-continued
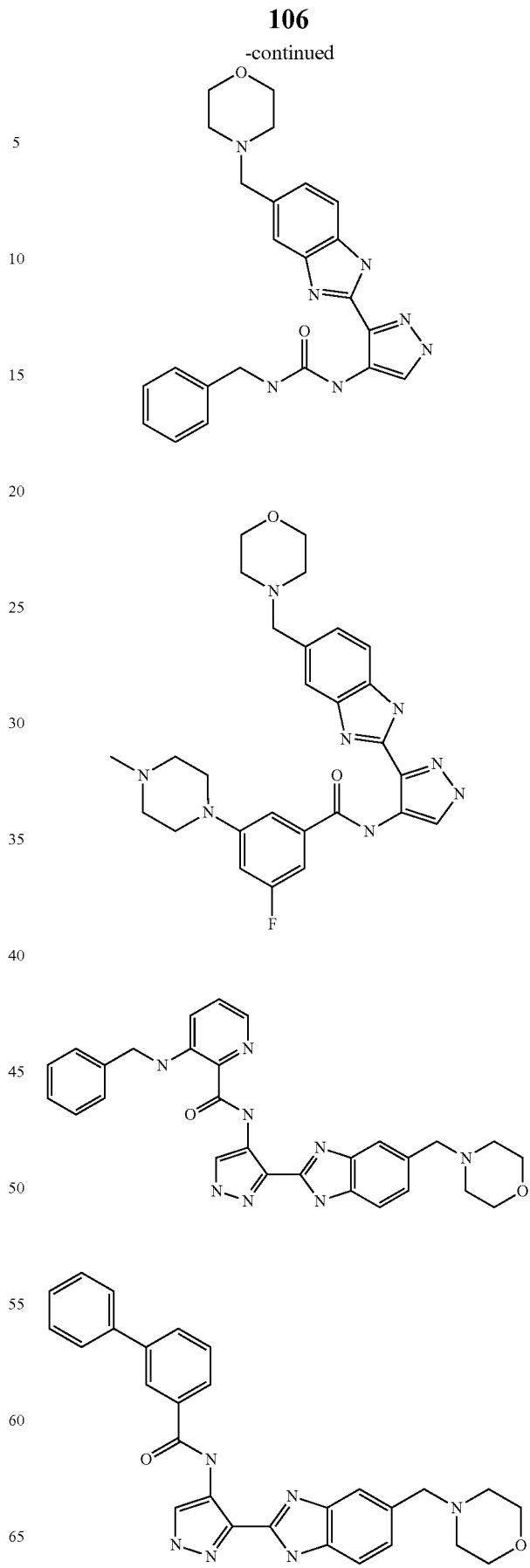

107
-continued
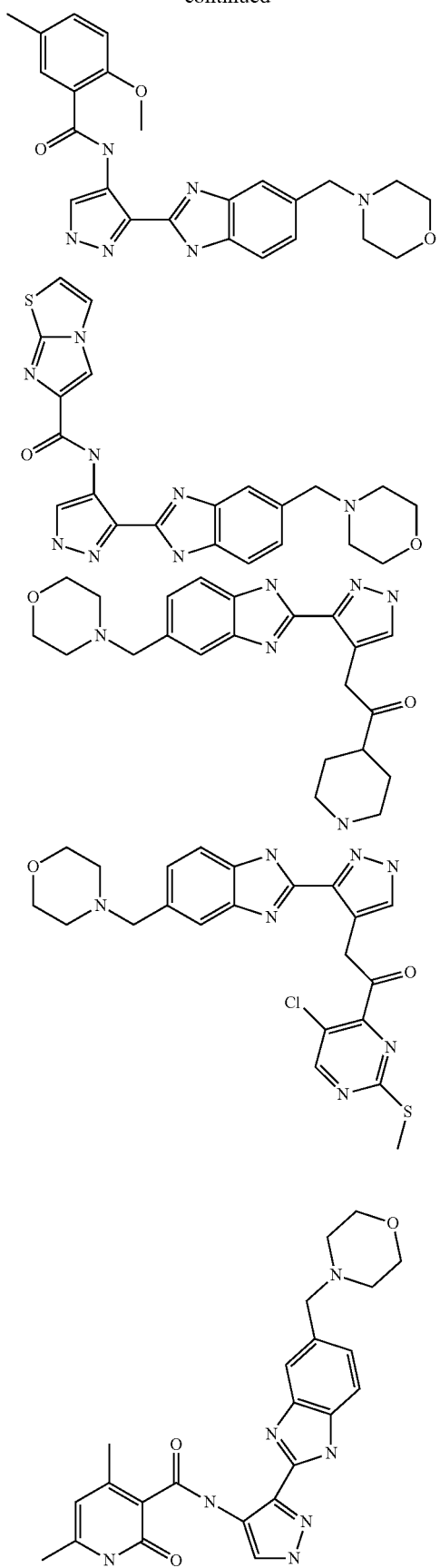
108
-continued
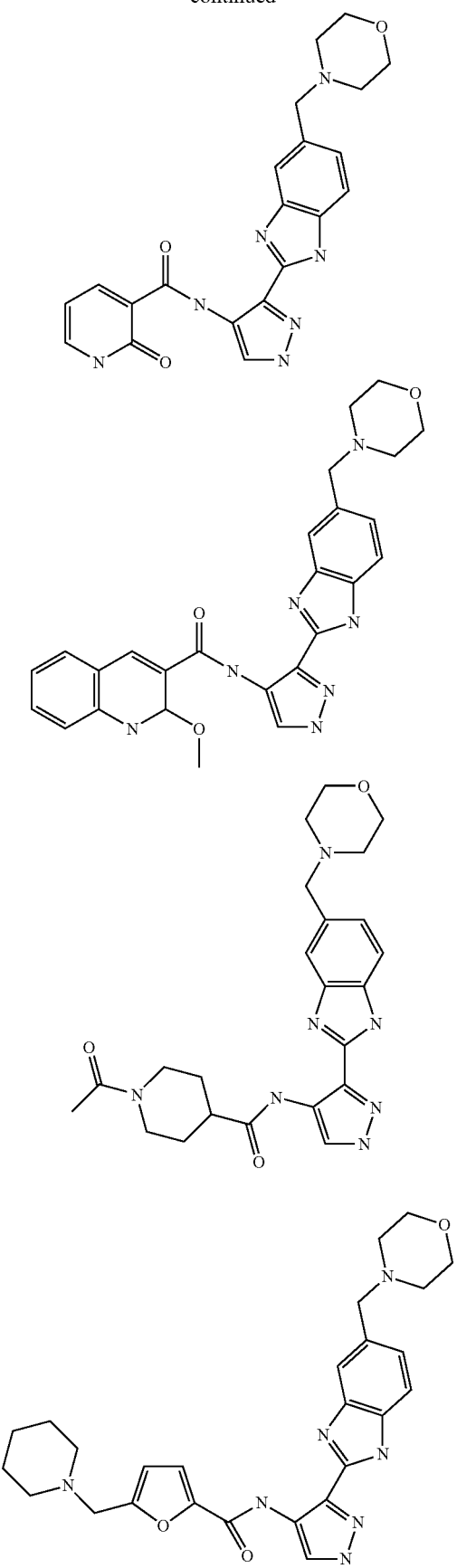

109
-continued
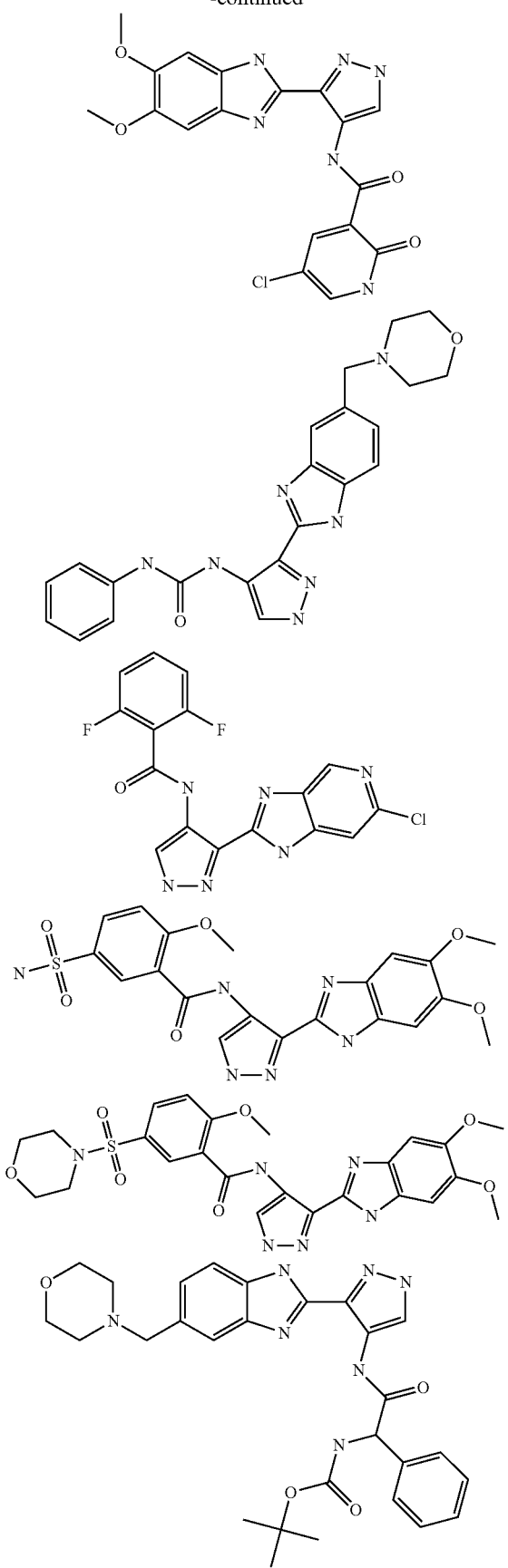
110
-continued
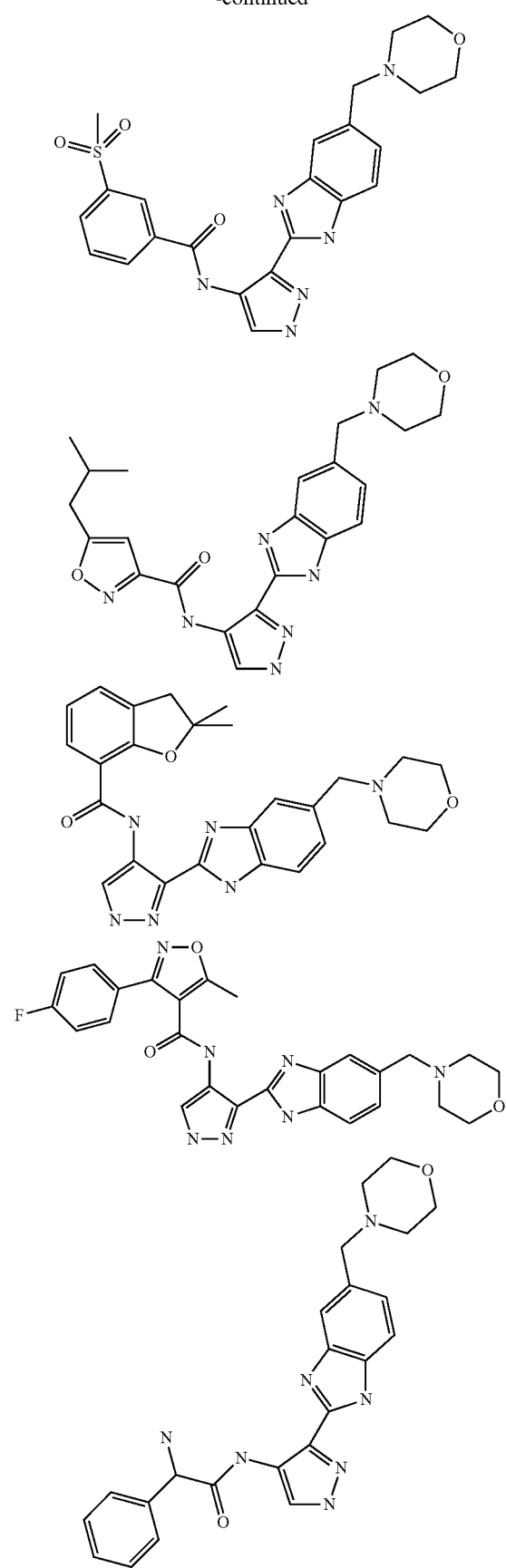

111
-continued
112
-continued
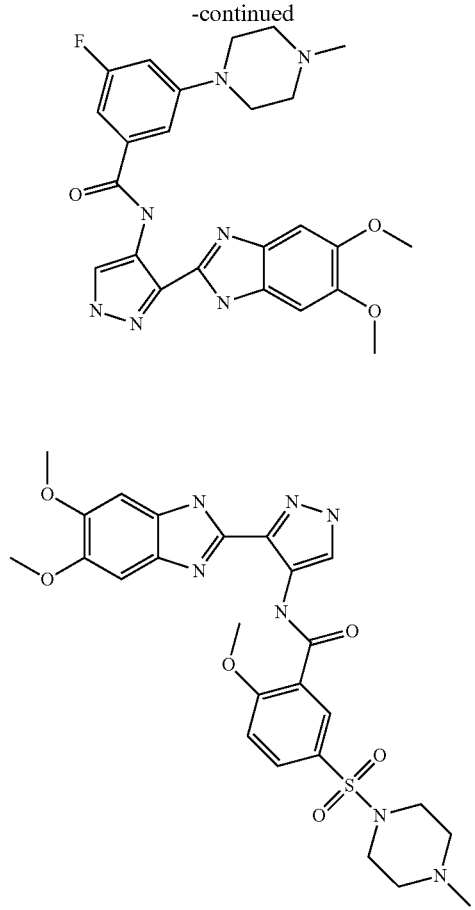
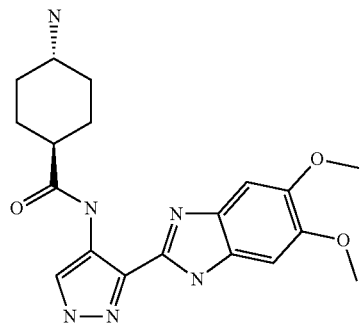
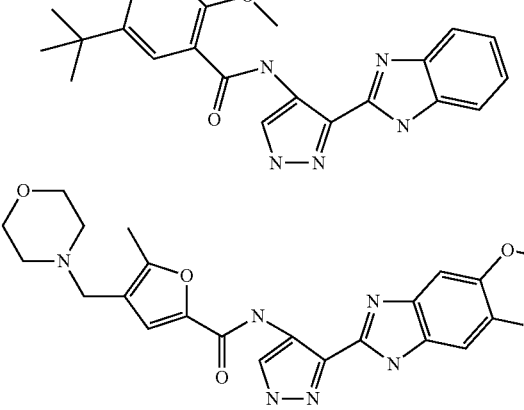
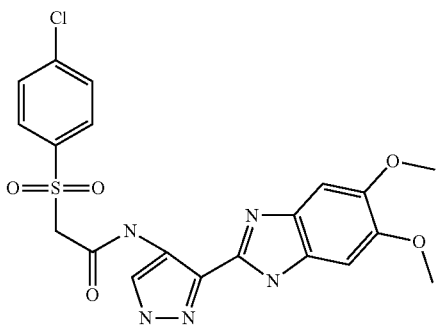
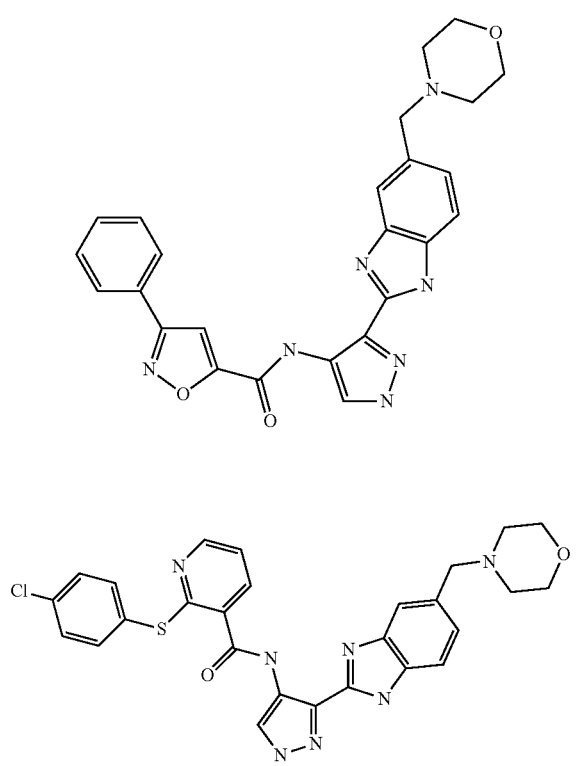
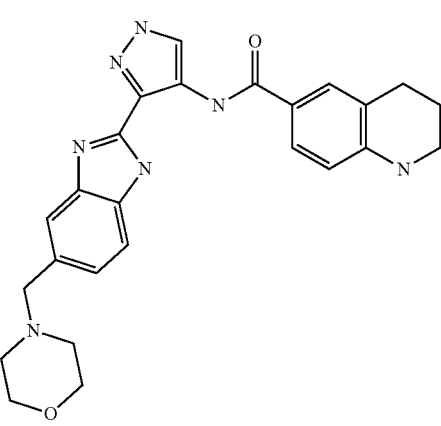

113
-continued
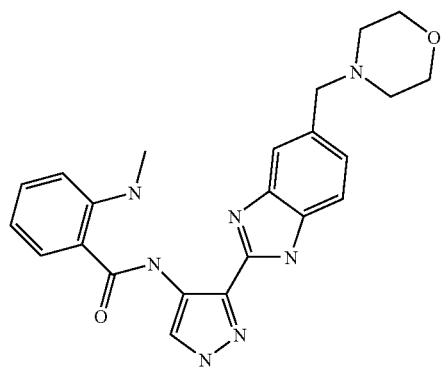
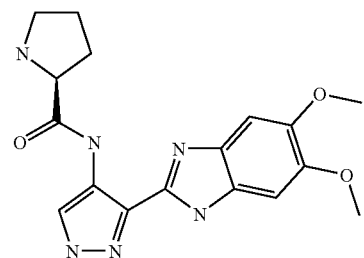
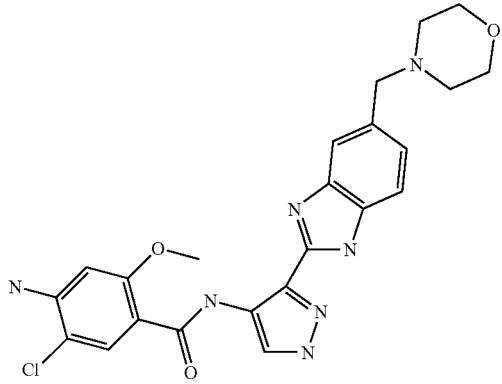
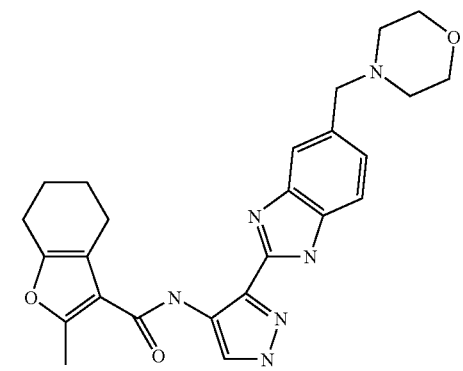
114
-continued
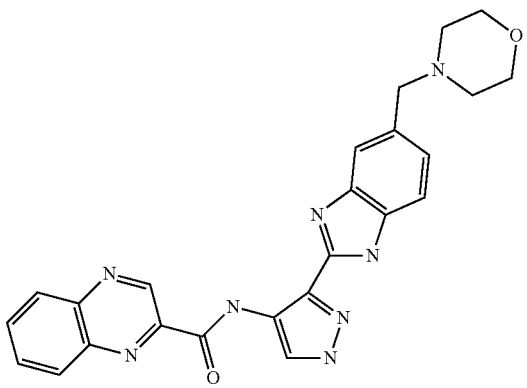
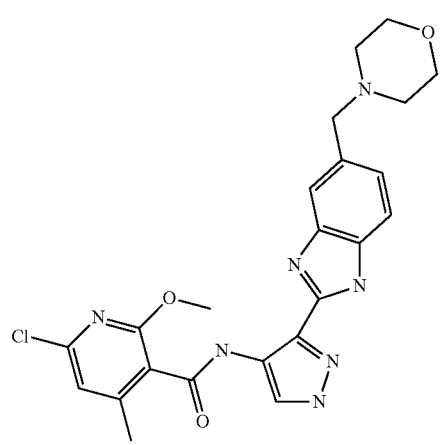
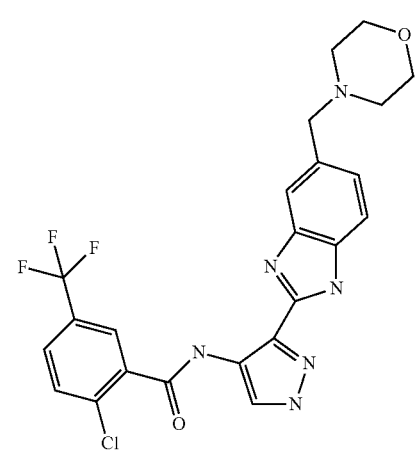
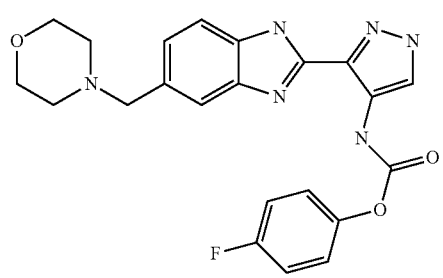

115
-continued
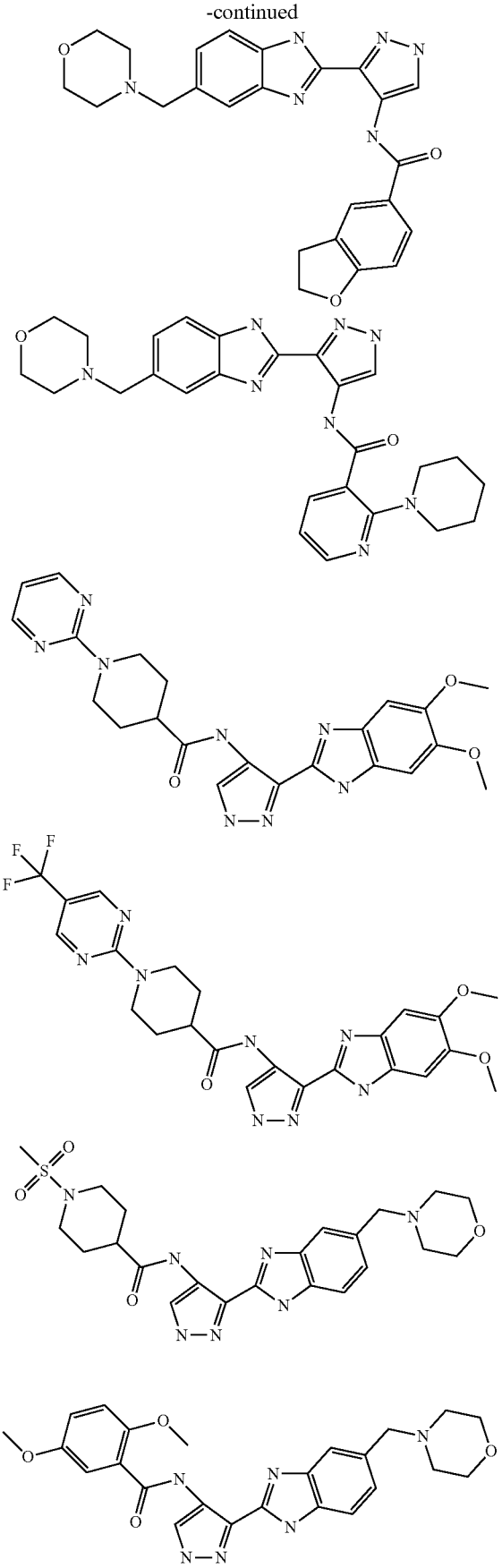
116
-continued
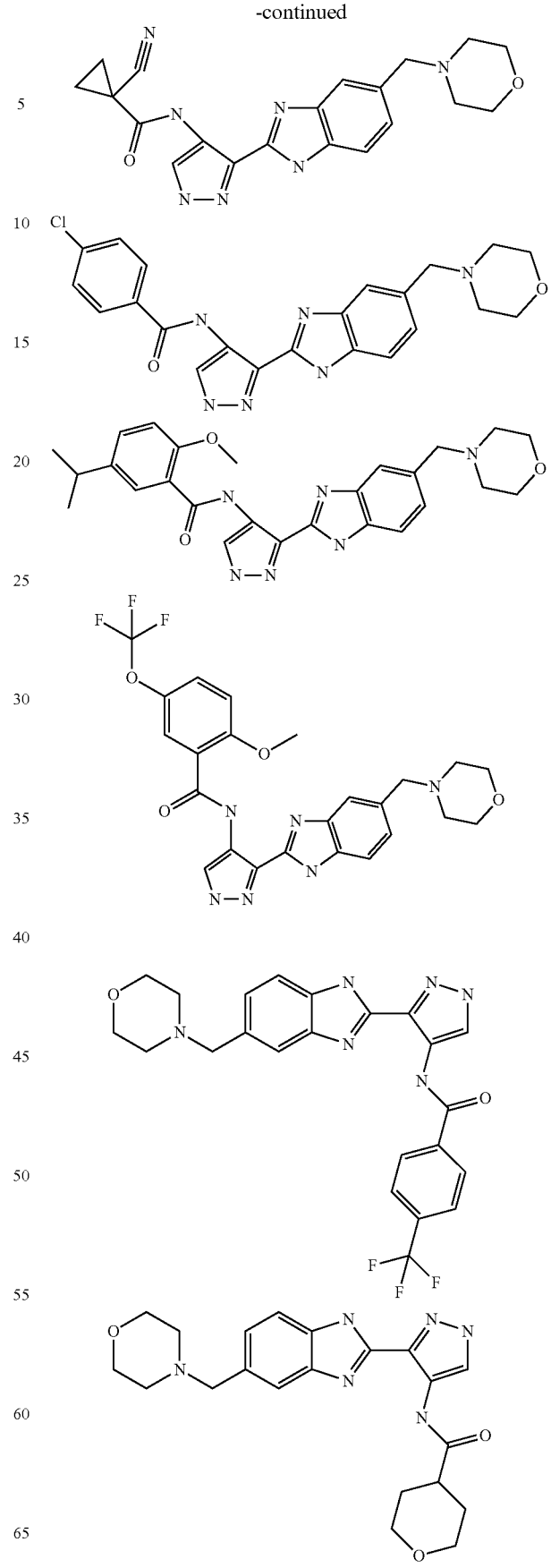

| 117 -continued | 118 -continued |
|---|---|
| 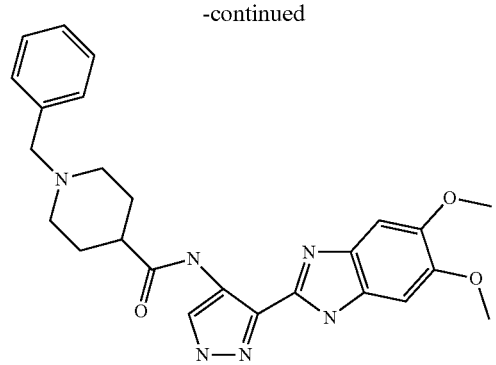 | 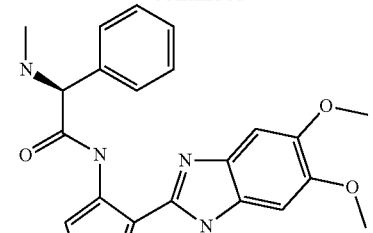 |
| 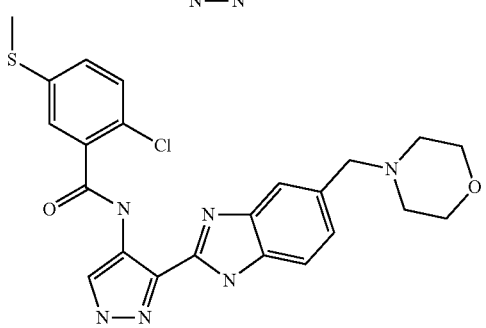 | 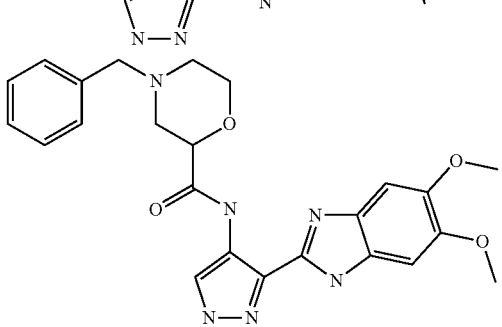 |
| 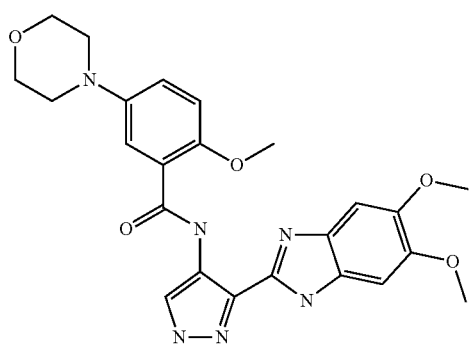 | 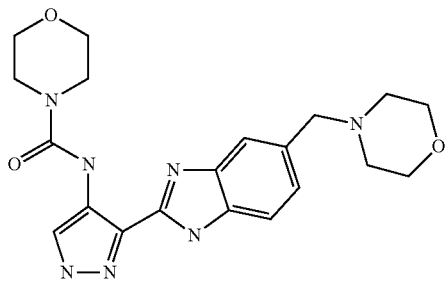 |
| 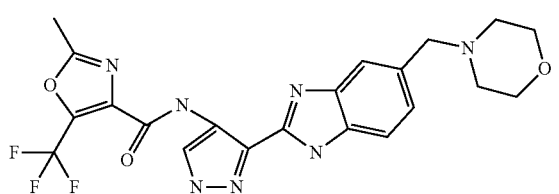 | 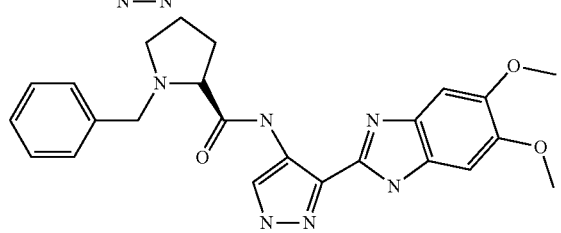 |
| 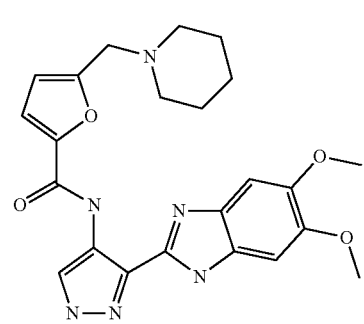 | 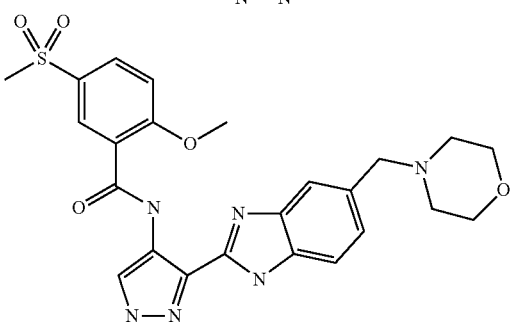 |
| | 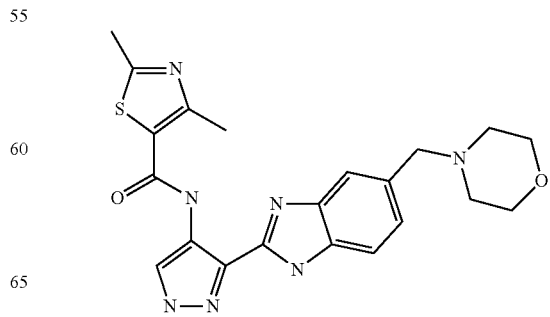 |

119
-continued
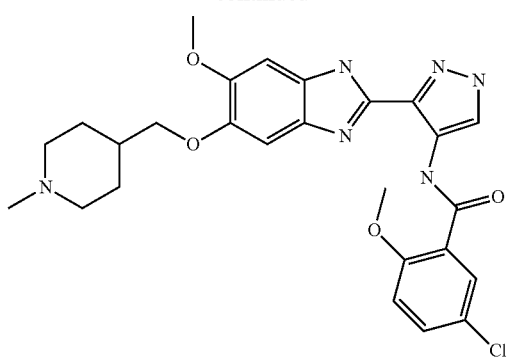 [SMILES: COc1cc2[nH]c(-c3n[nH]cc3NC(=O)c3cc(Cl)ccc3OC)nc2cc1OCC1CCN(C)CC1]
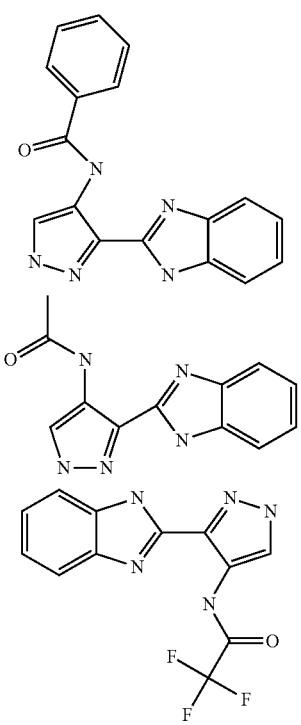
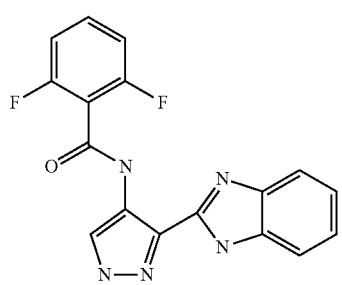
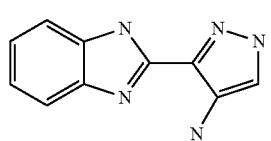
120
-continued
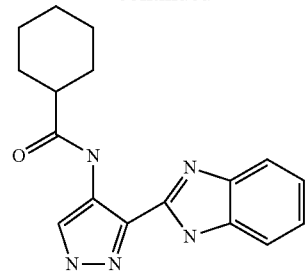
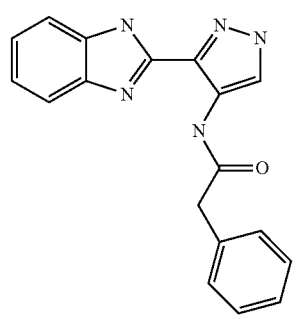
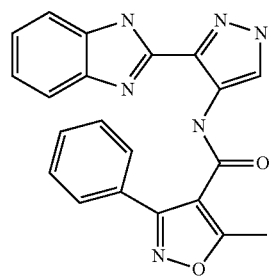
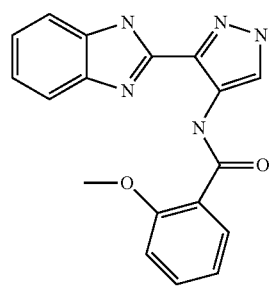
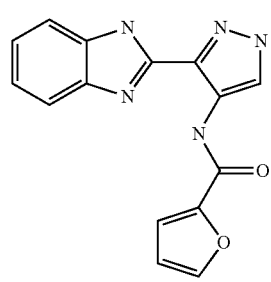

121
-continued
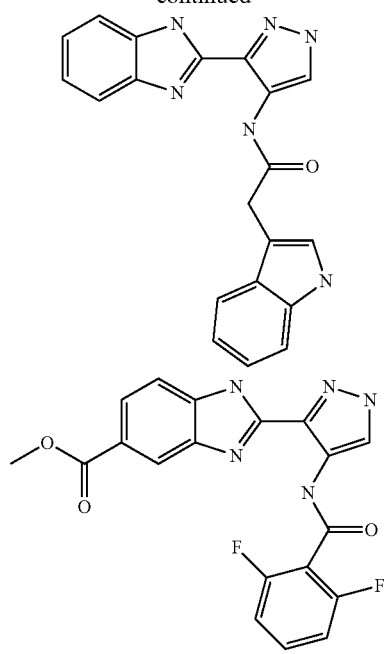
122
-continued
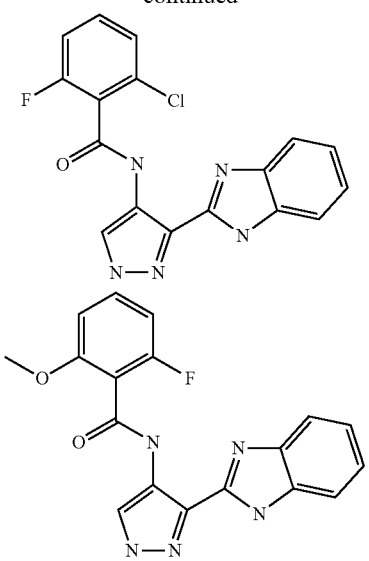
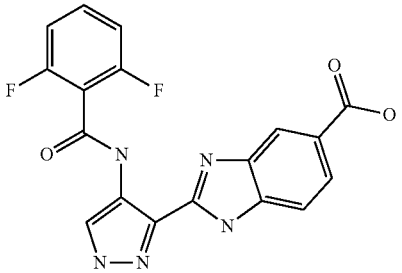
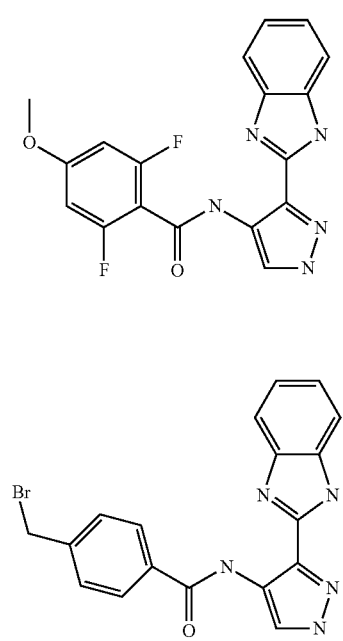
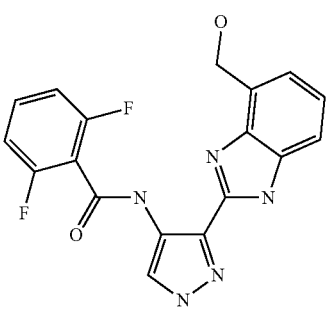
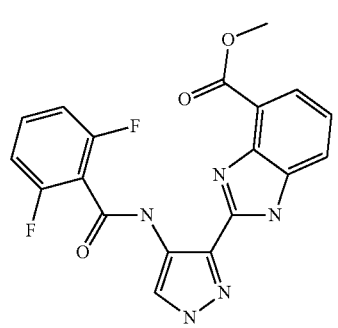
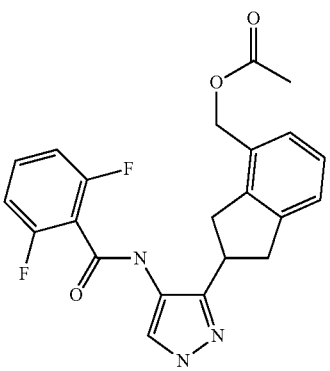

123
-continued
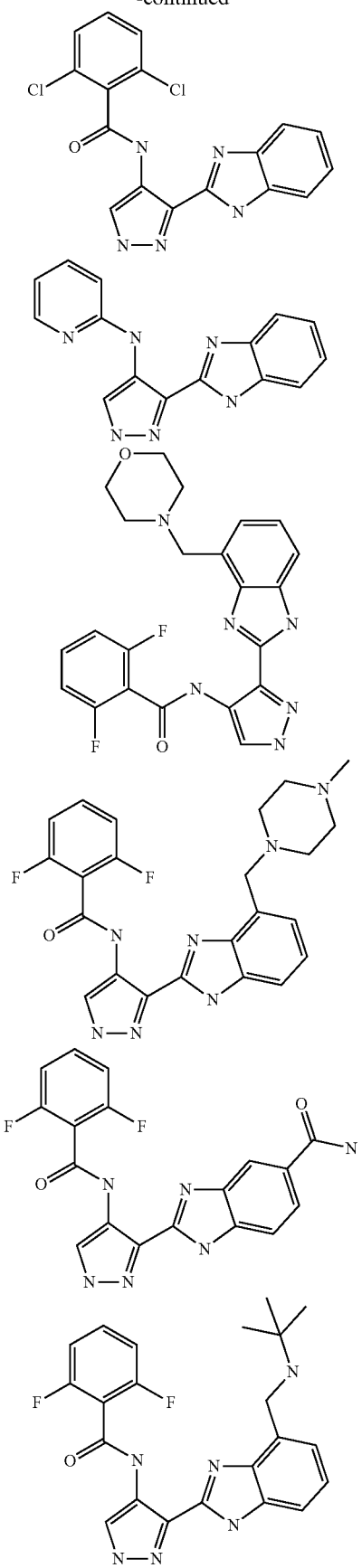
124
-continued
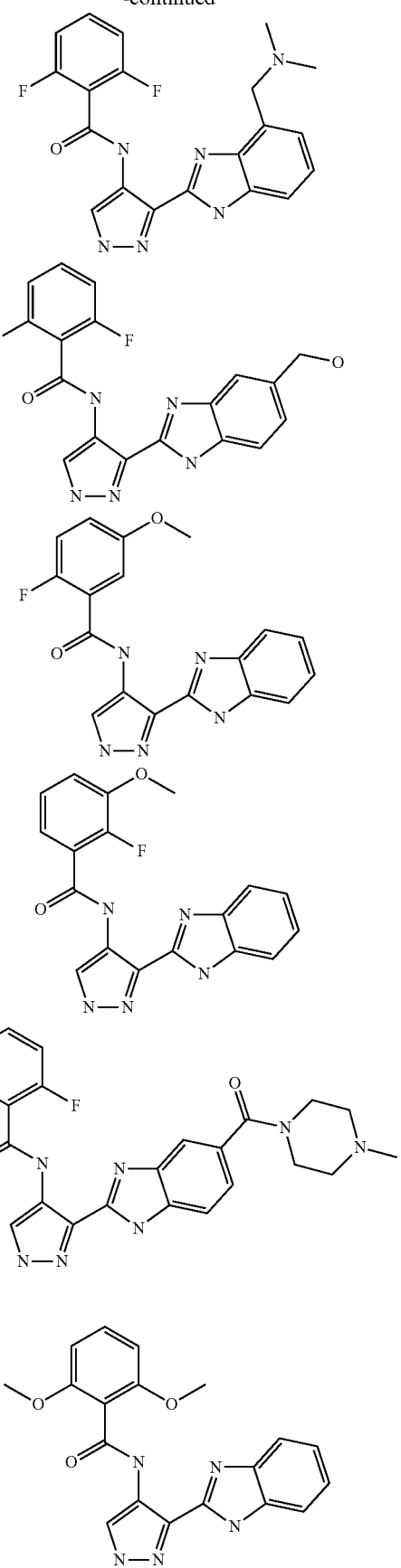

125
-continued
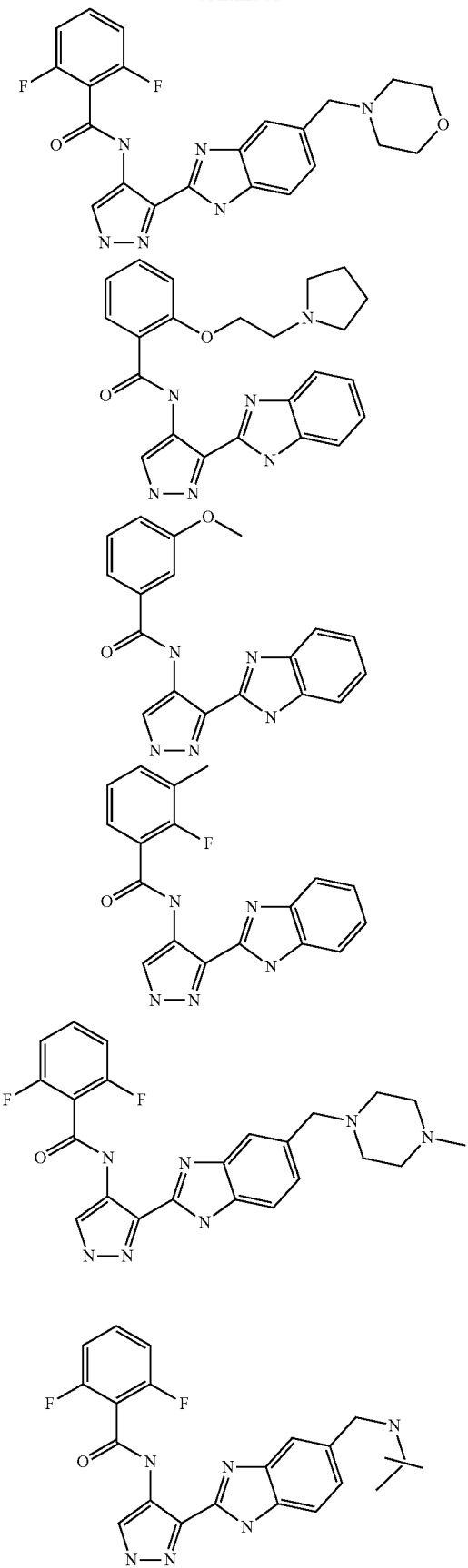
126
-continued
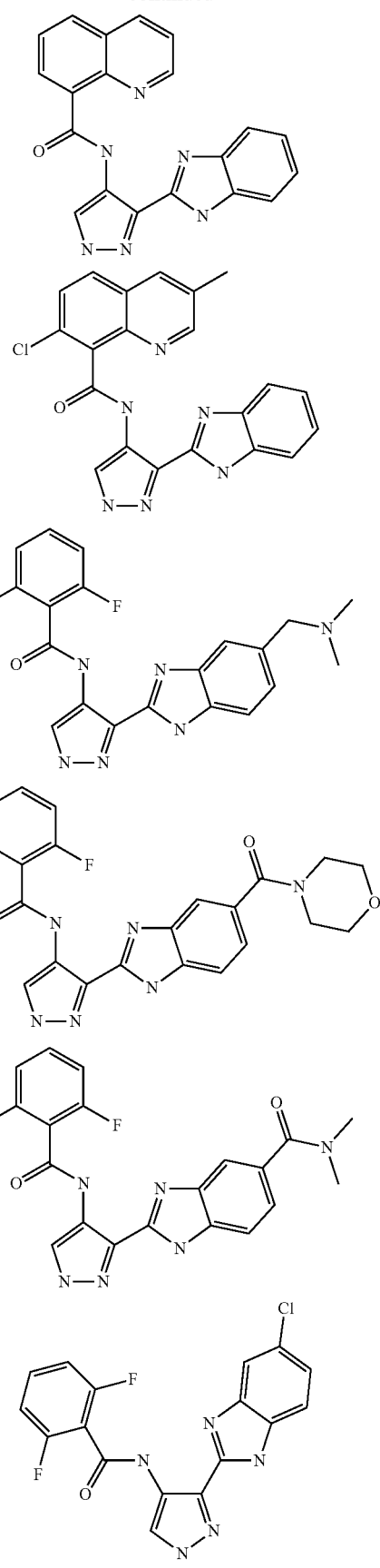

127
-continued
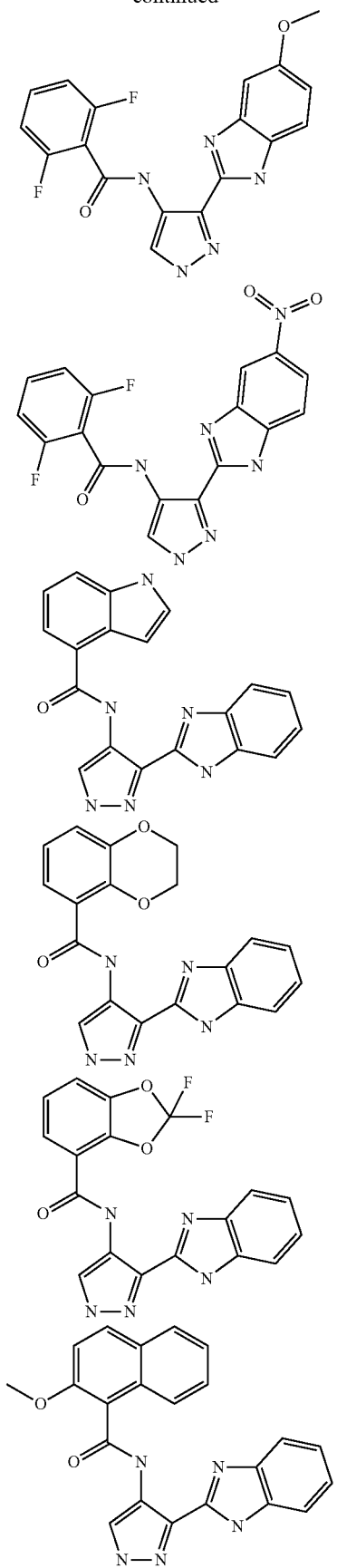
128
-continued
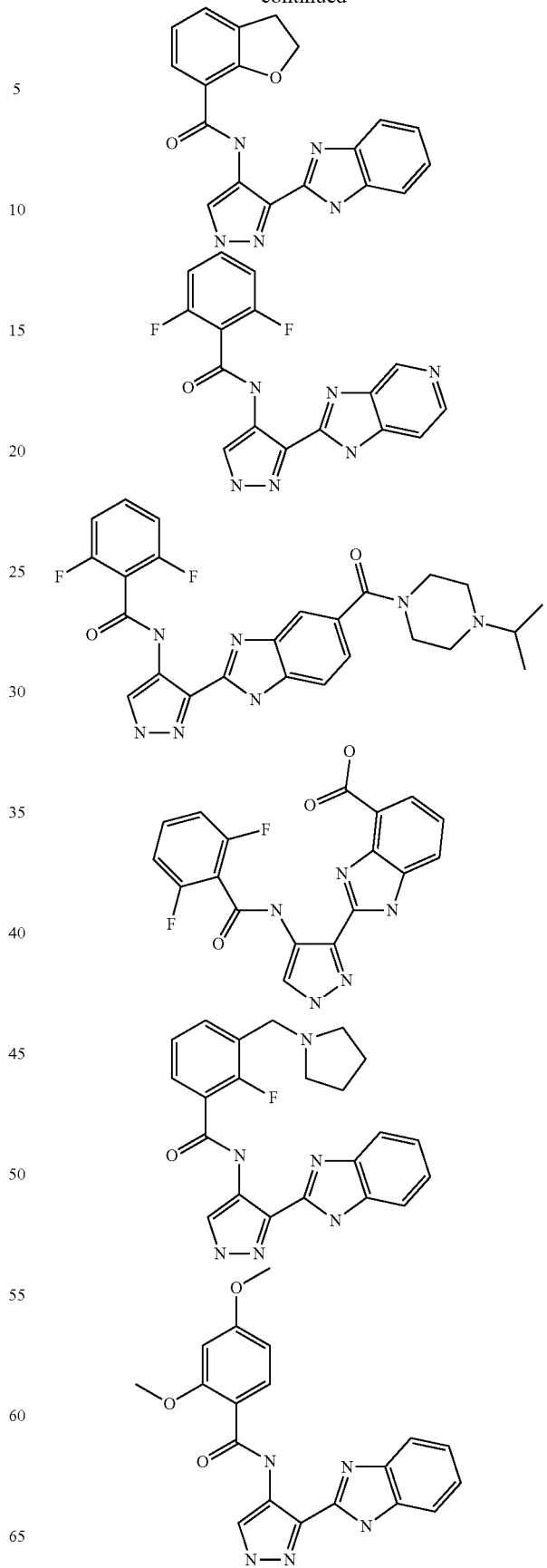

129
-continued
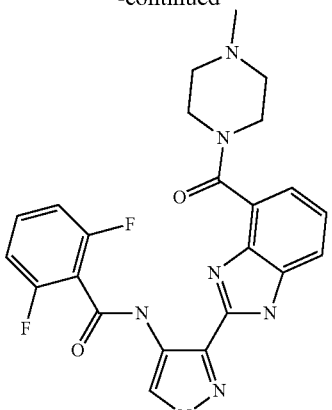
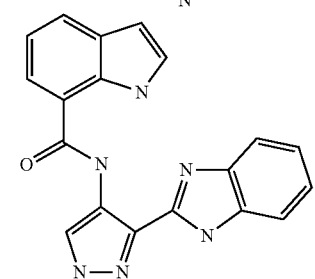
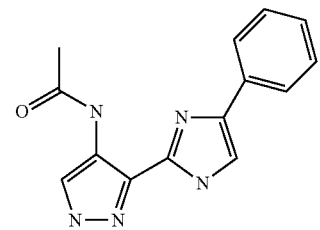
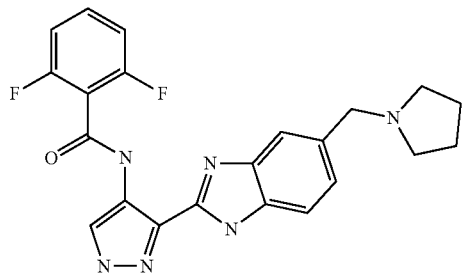
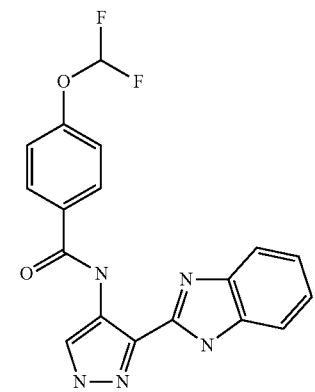
130
-continued
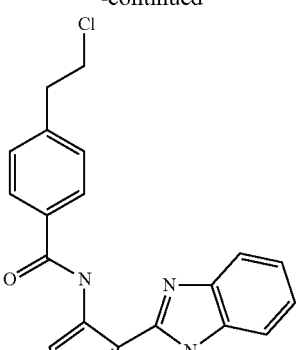
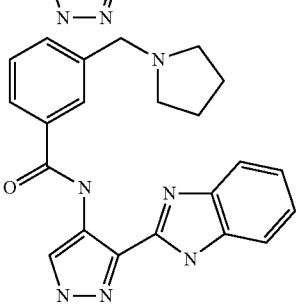
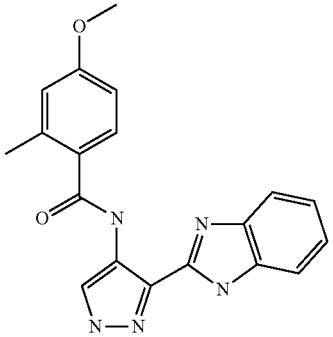
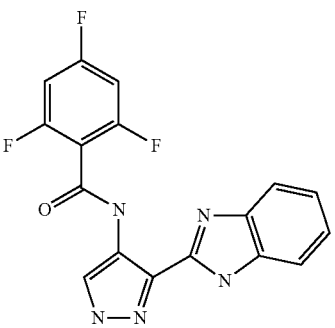
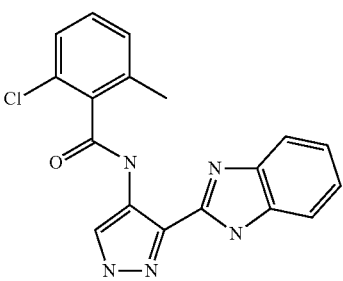

131
-continued
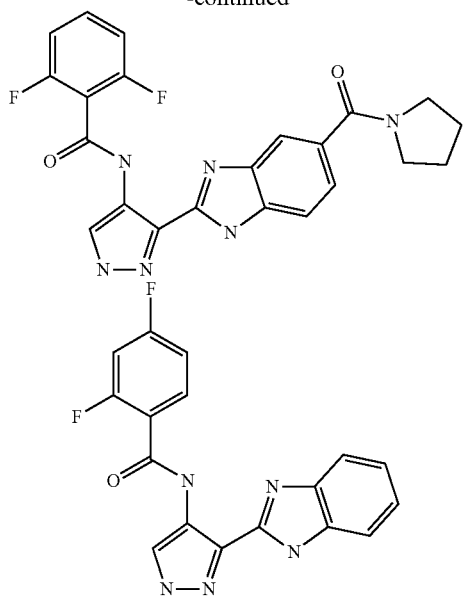
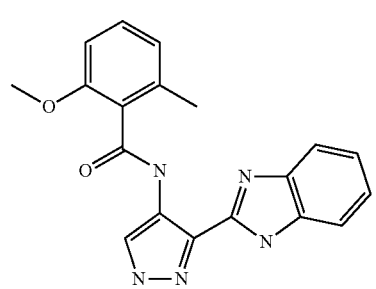
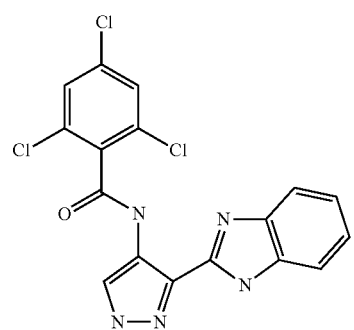
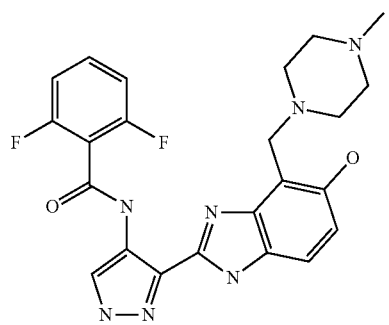
132
-continued
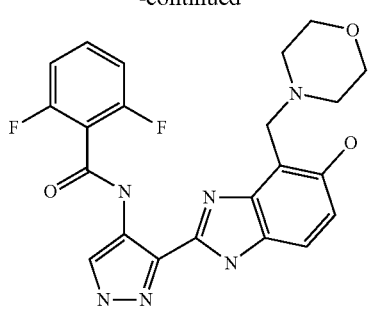
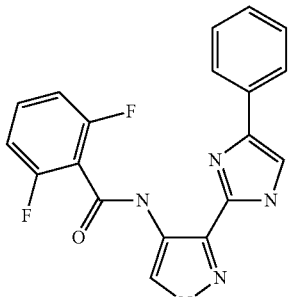
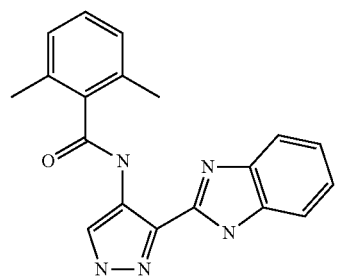
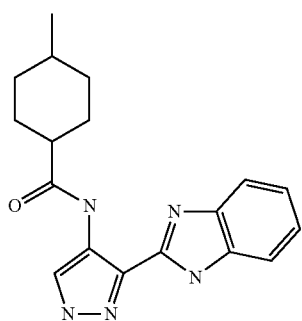
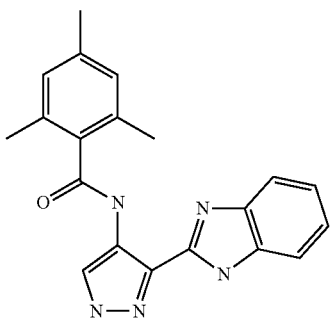

133
-continued
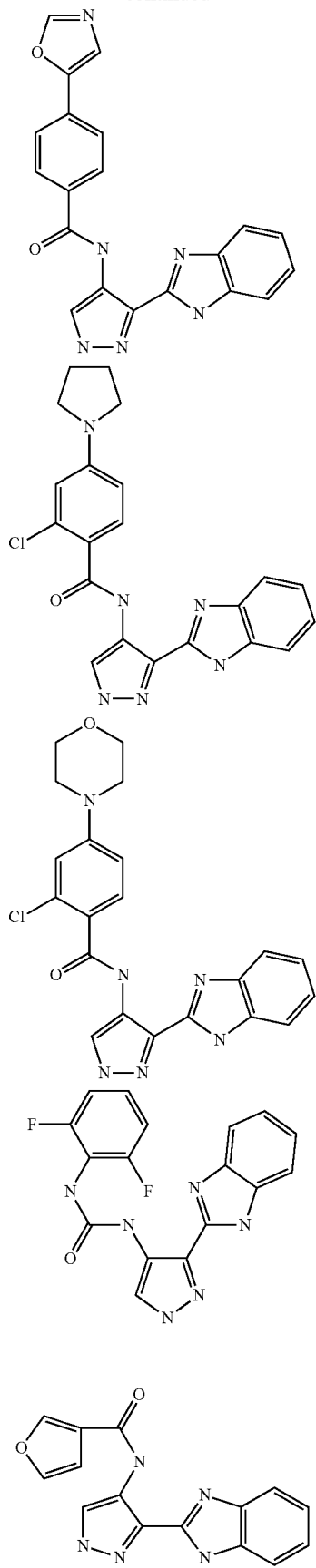
134
-continued
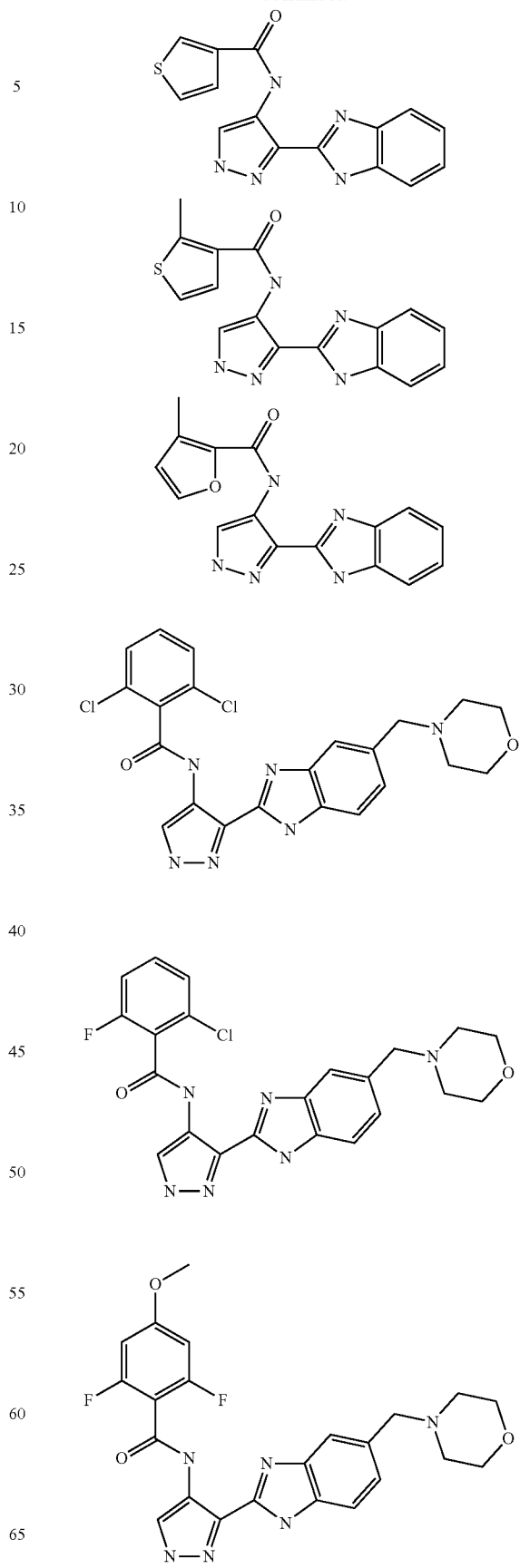

135
-continued
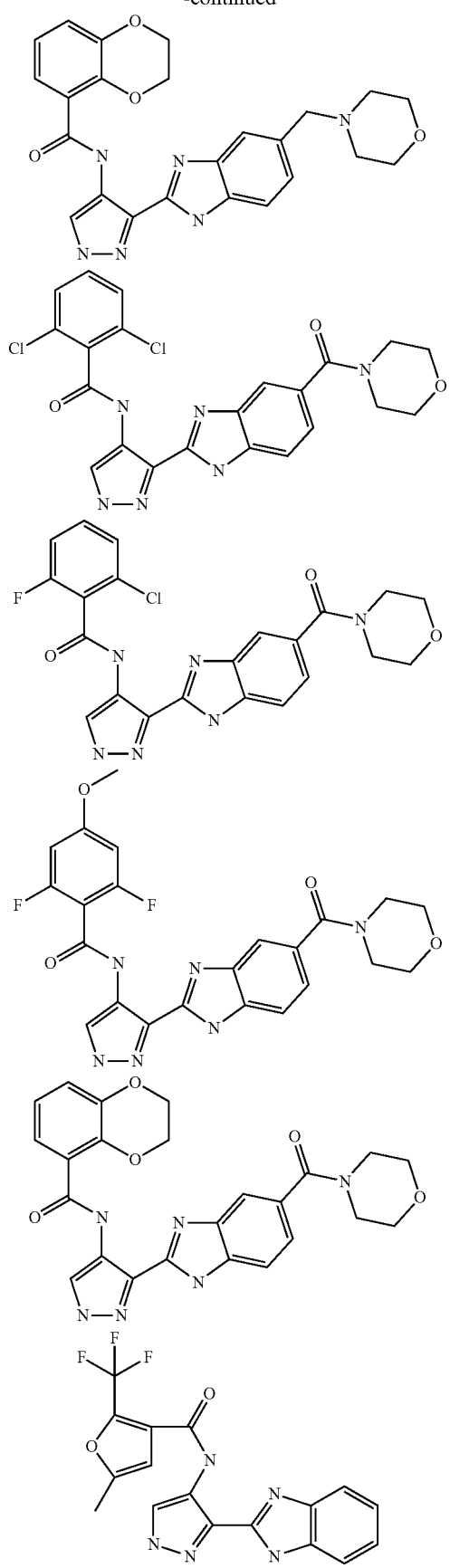
136
-continued
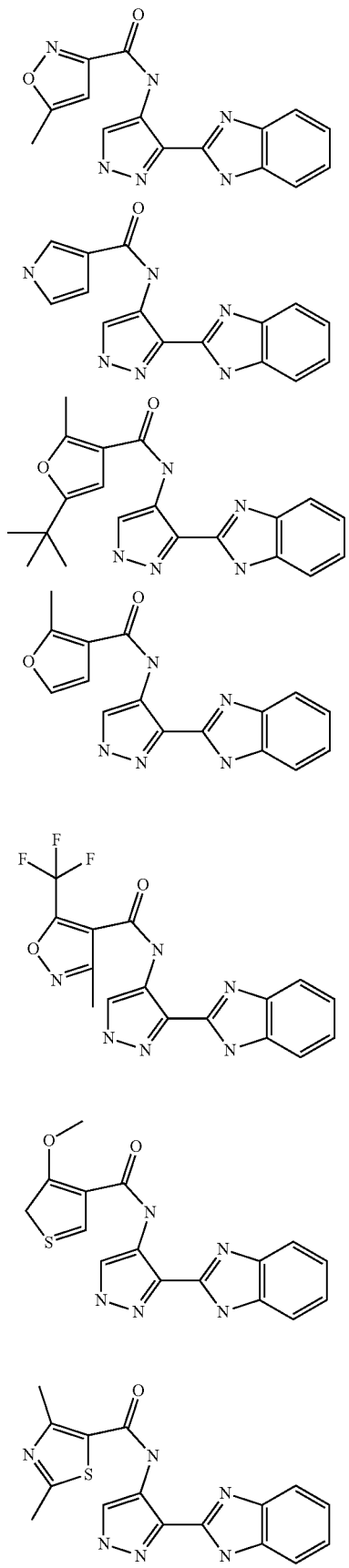

137
-continued
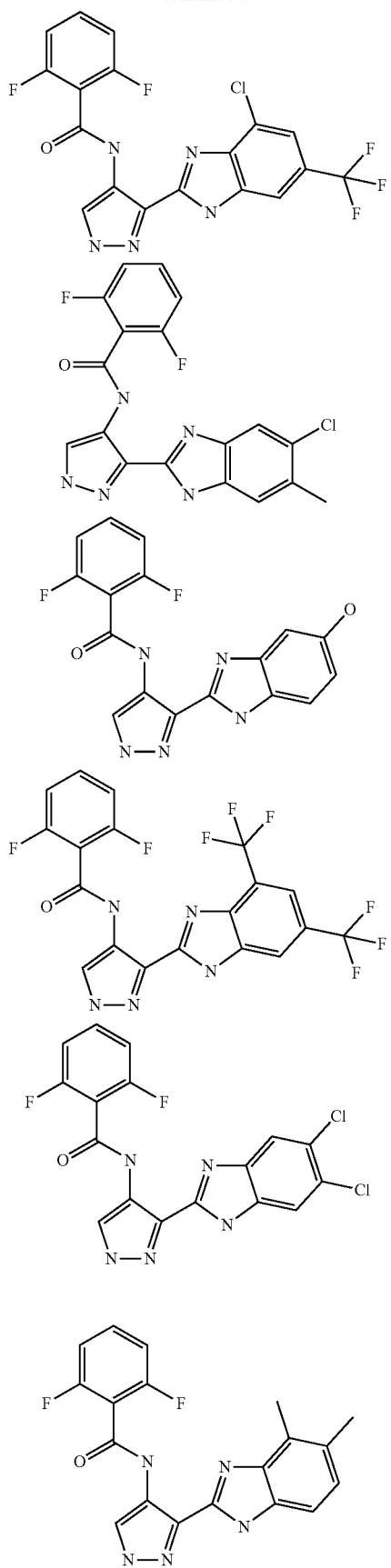
138
-continued
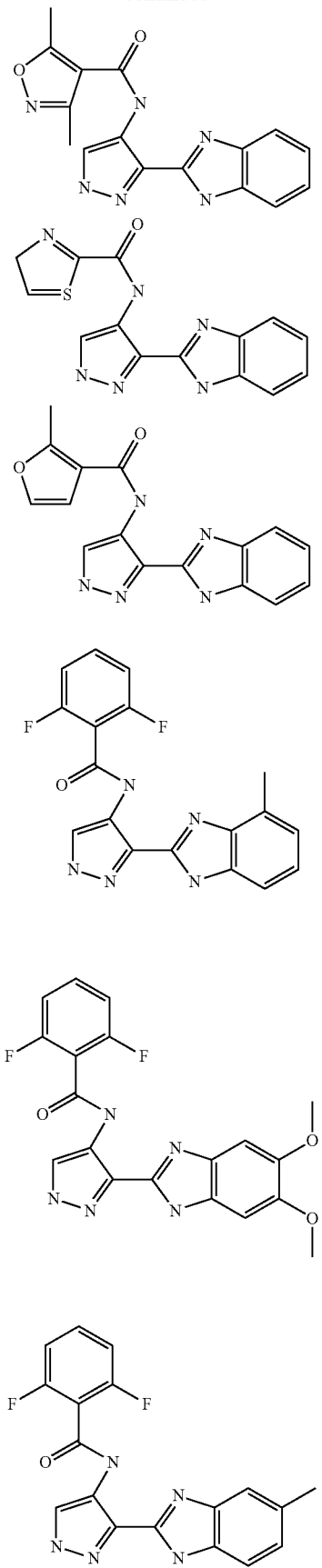

-continued
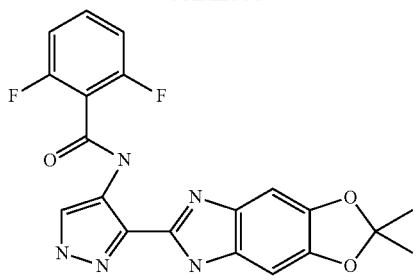
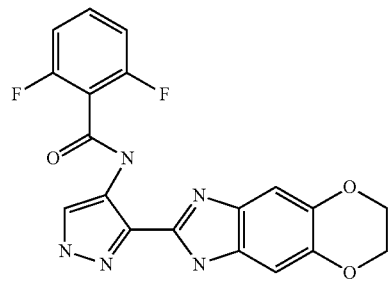
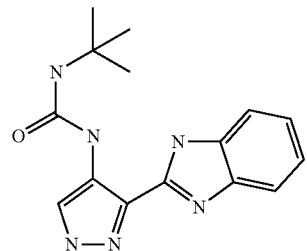
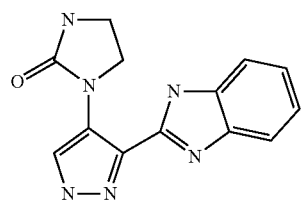
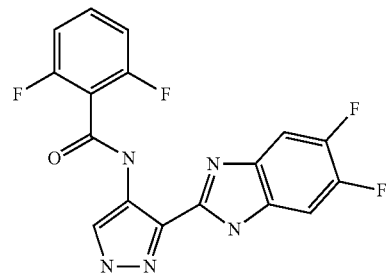
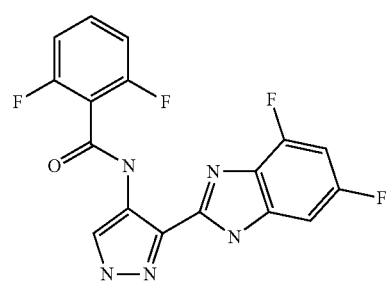
-continued
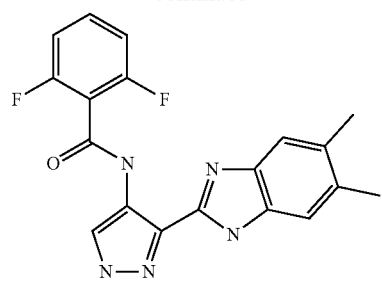
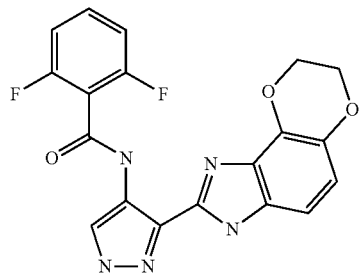
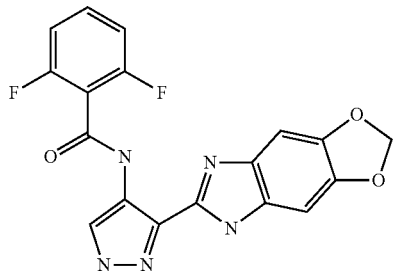
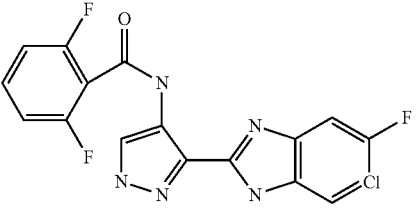
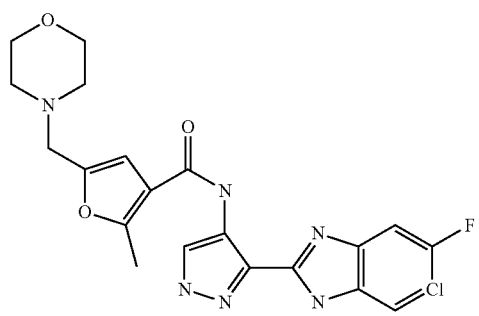
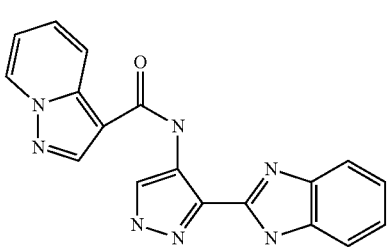

141
-continued
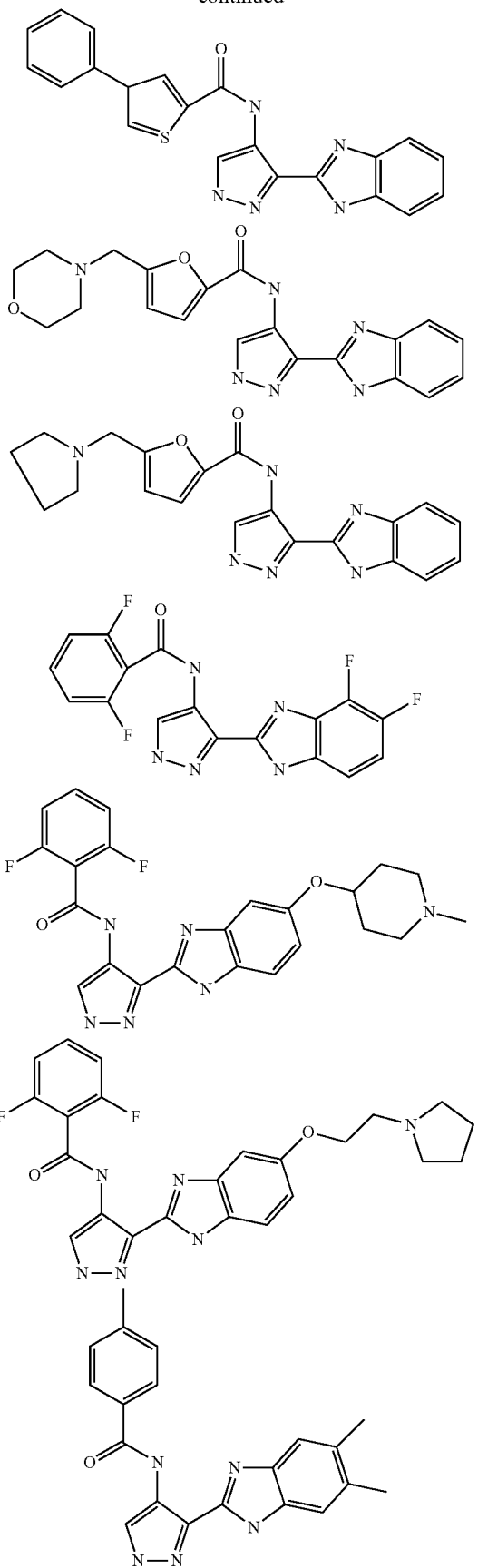
142
-continued
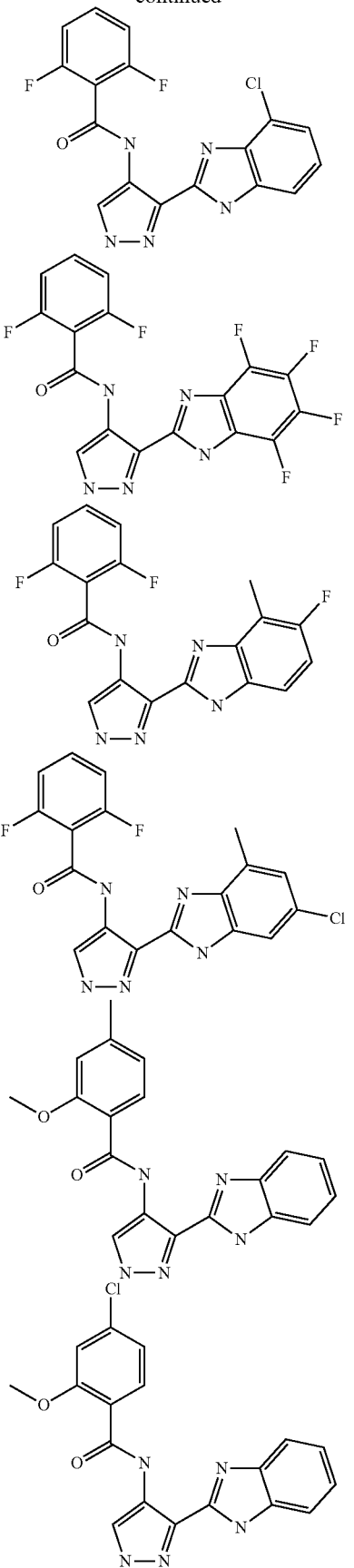

143
-continued
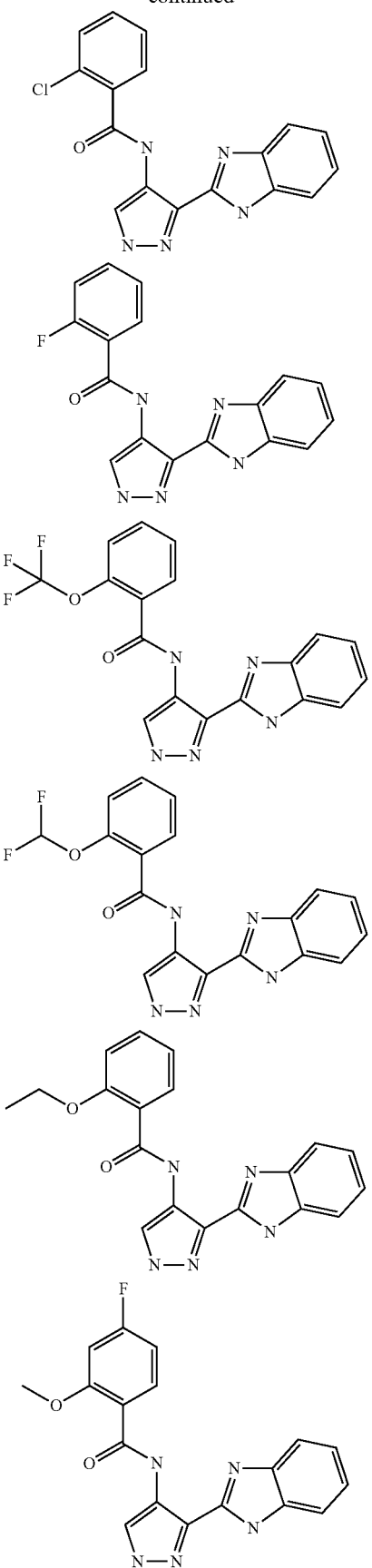
144
-continued
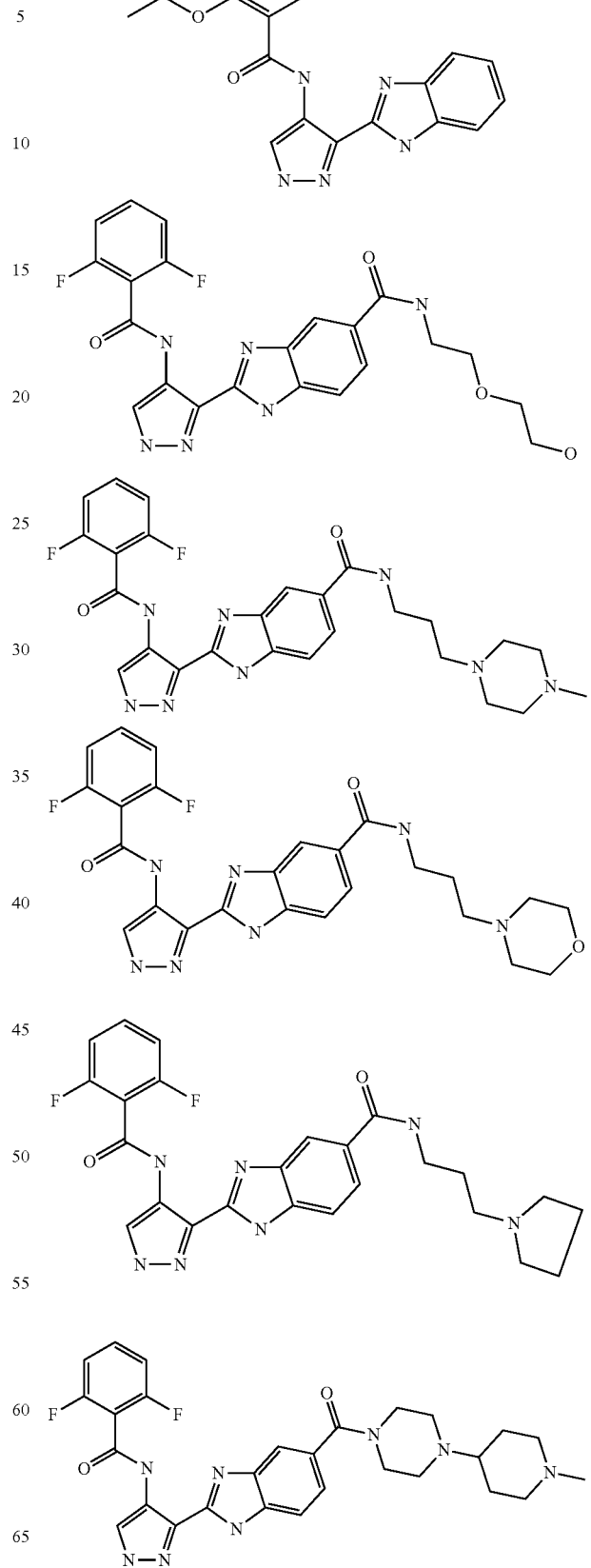

145
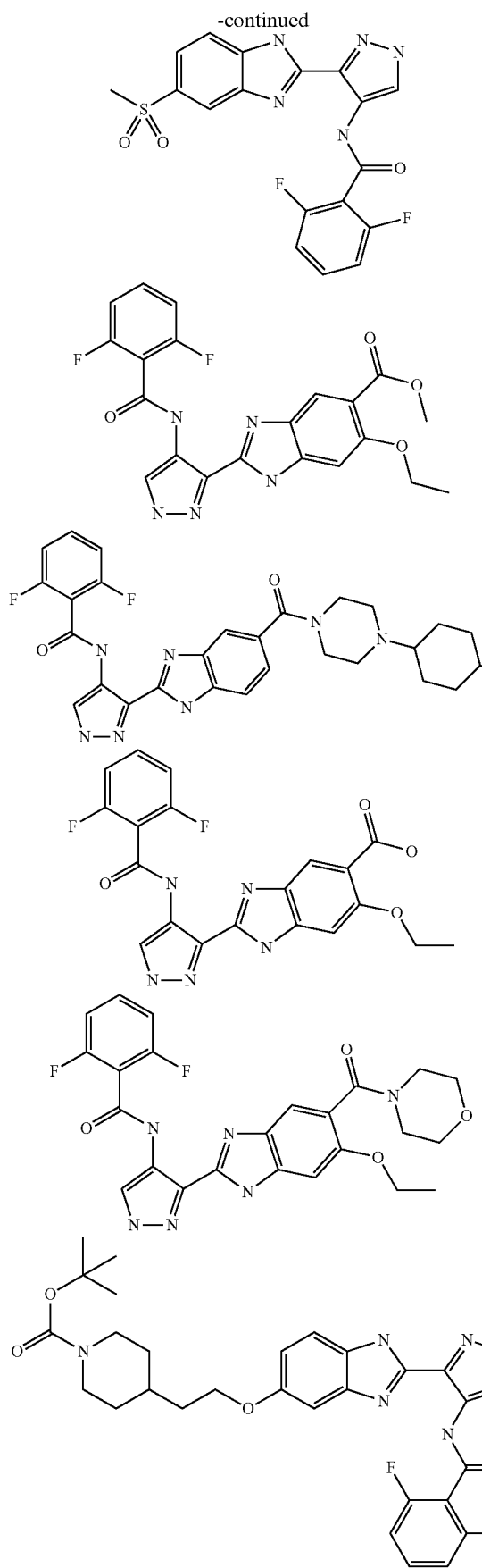
146
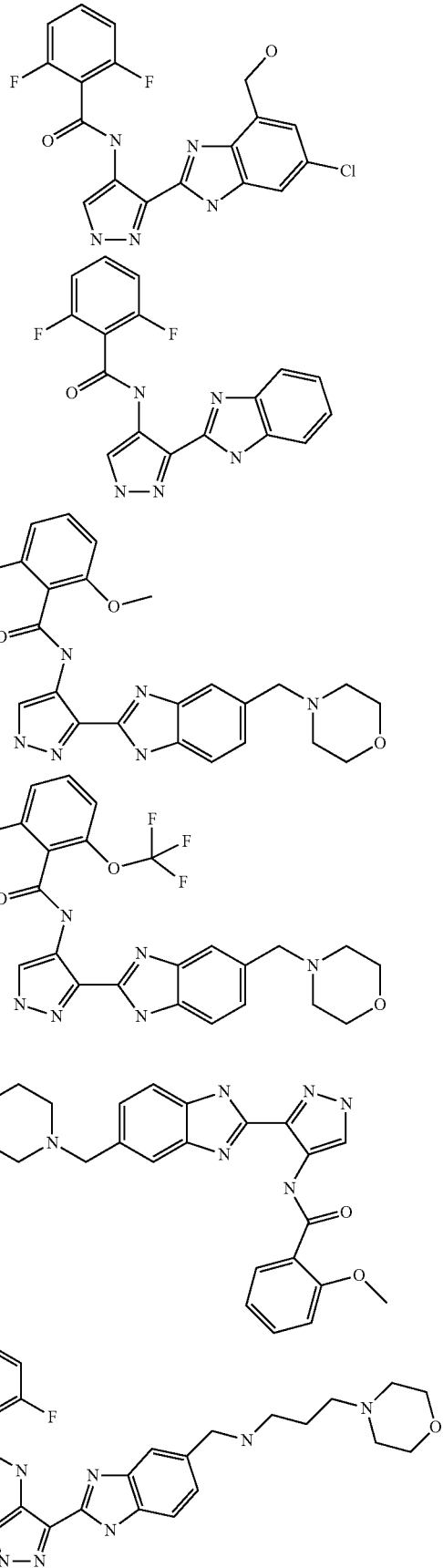

147
-continued
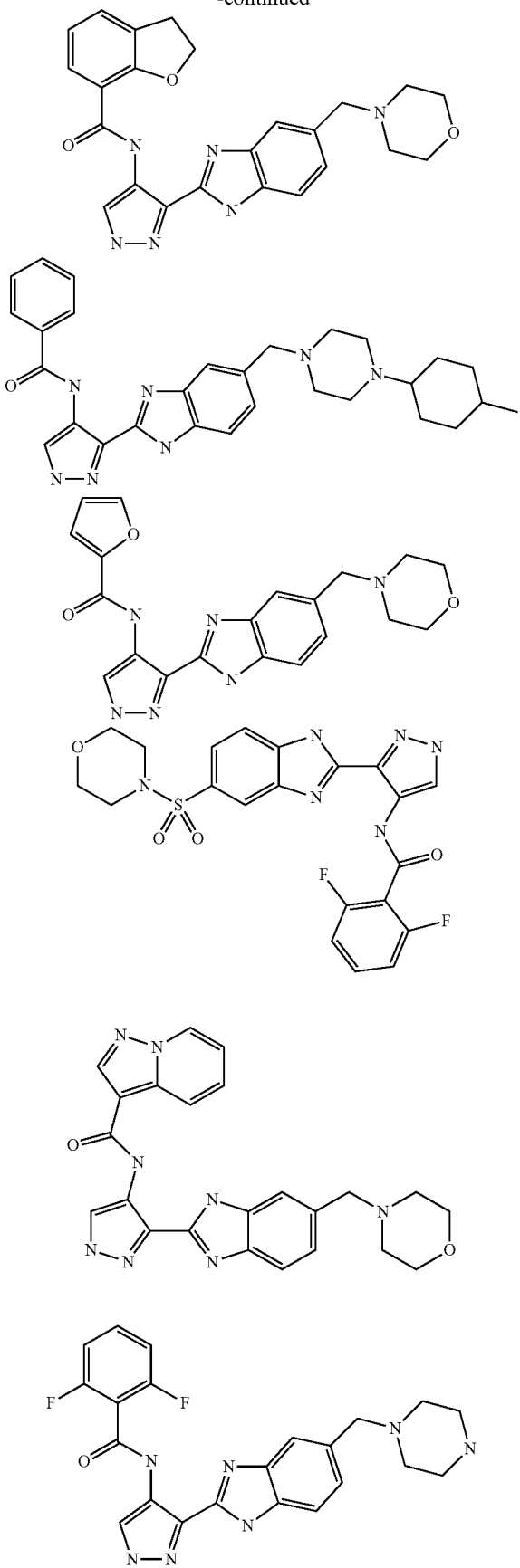
148
-continued
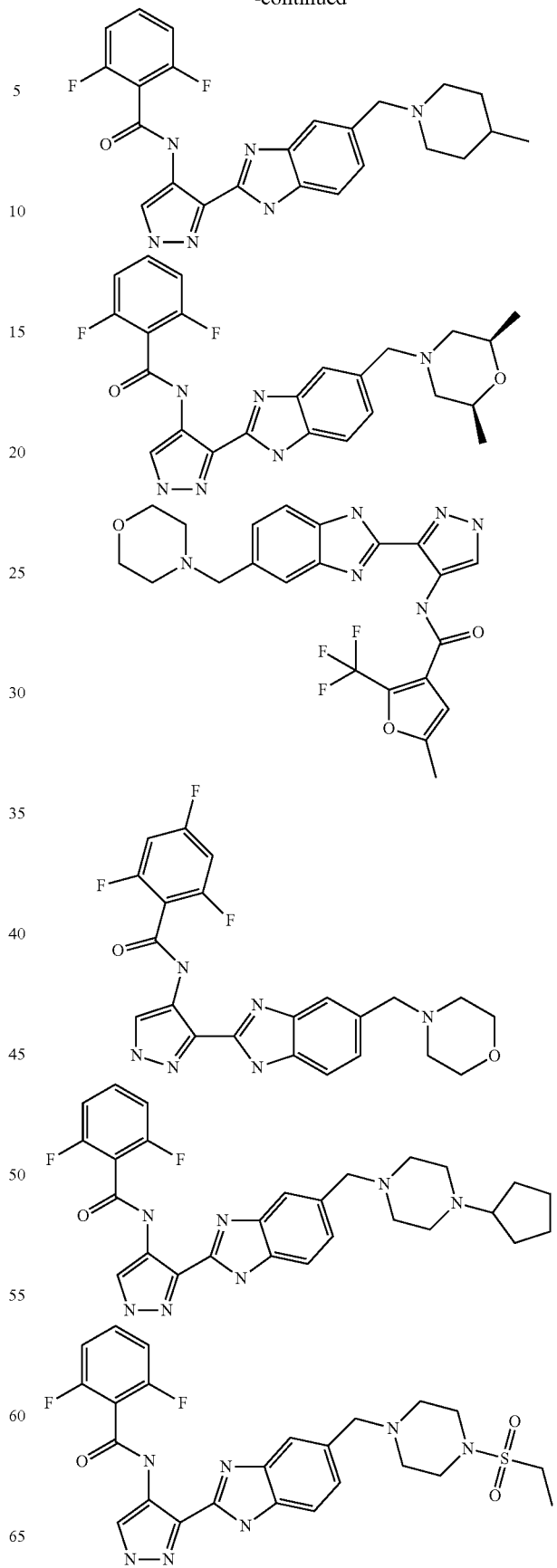

149
-continued
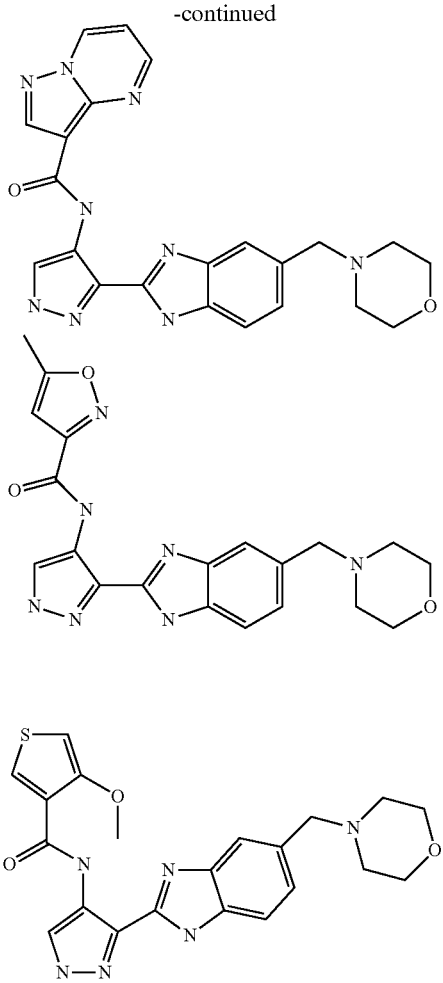
150
-continued
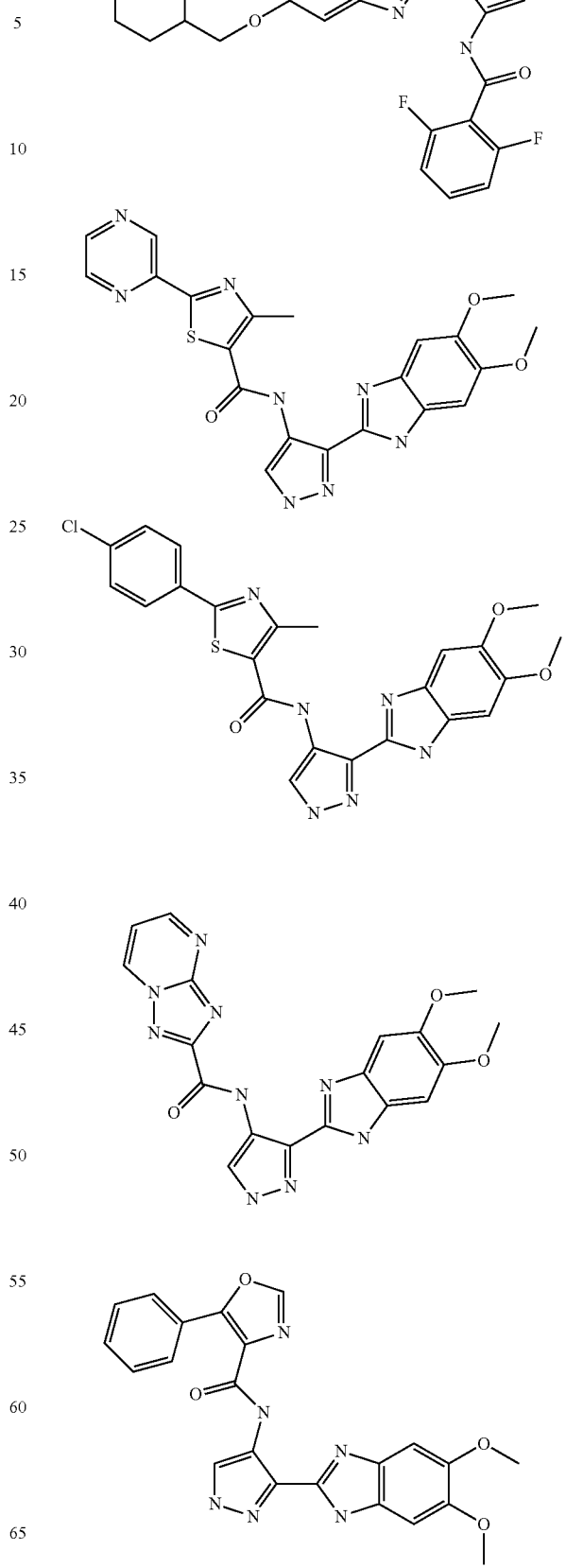

151
-continued
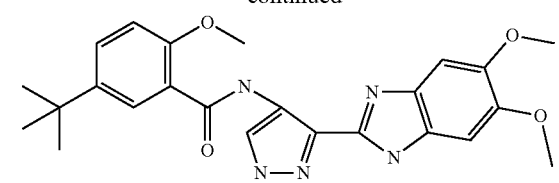
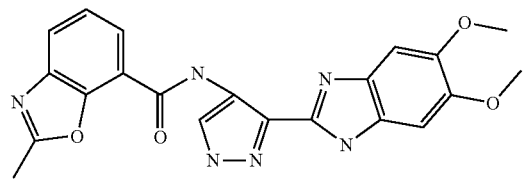
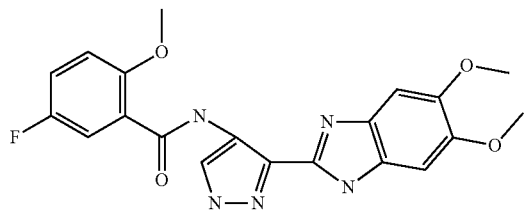
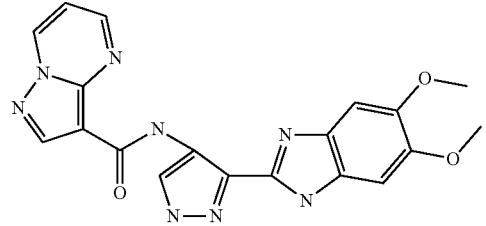
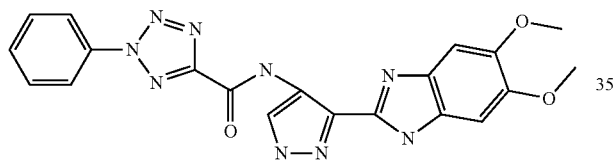
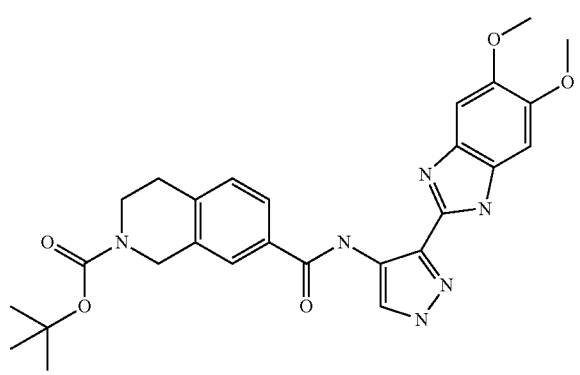
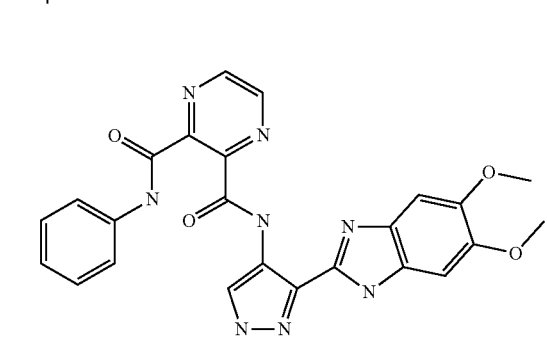
152
-continued
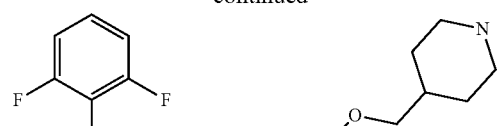
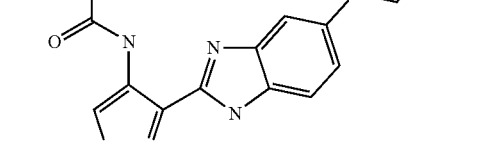
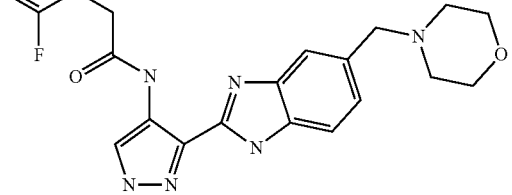
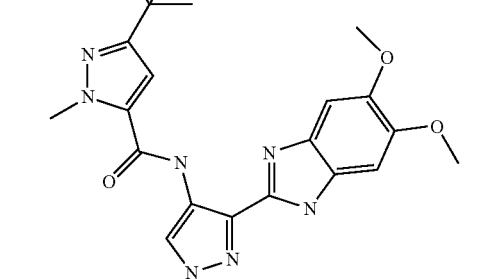
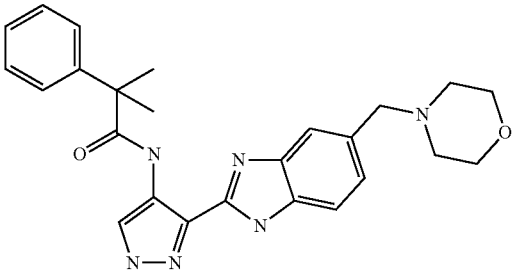

153
-continued
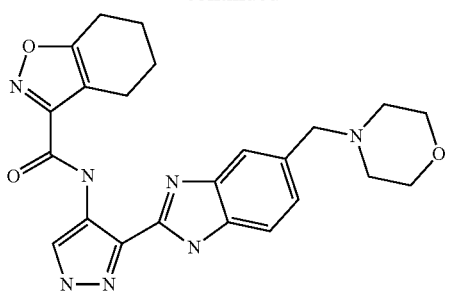
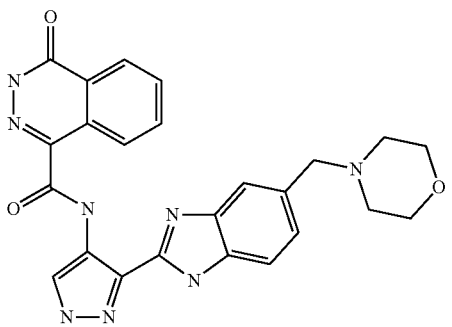
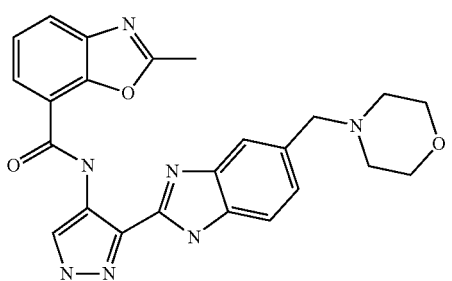
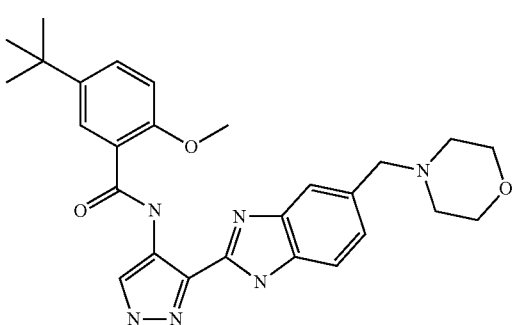
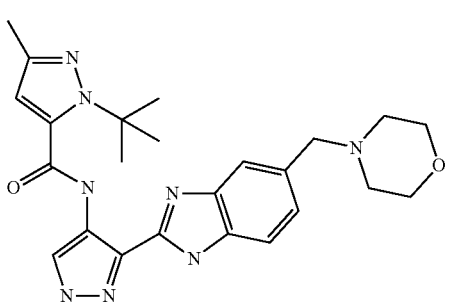
154
-continued
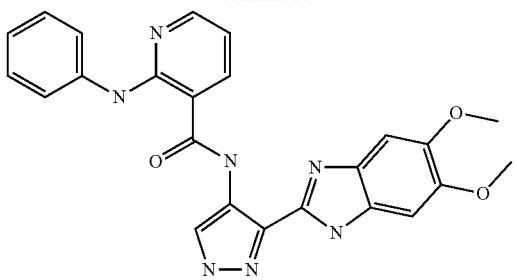
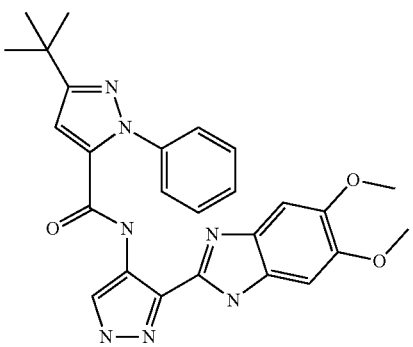
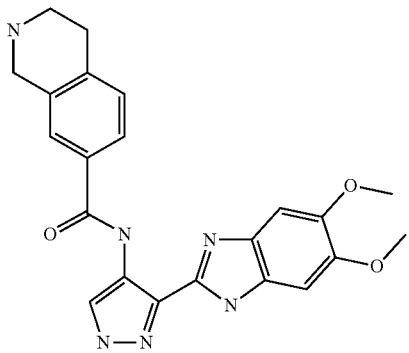
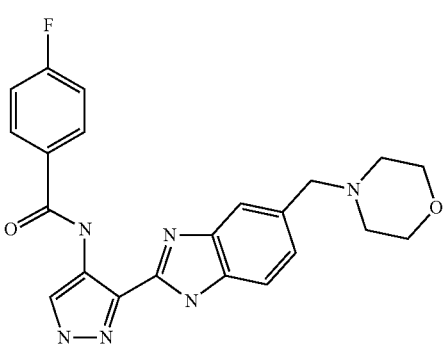
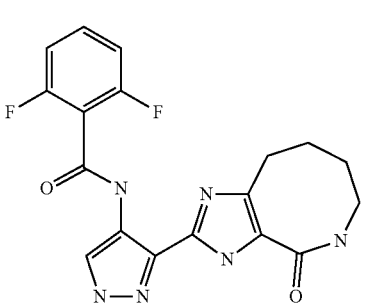

155
-continued
156
-continued
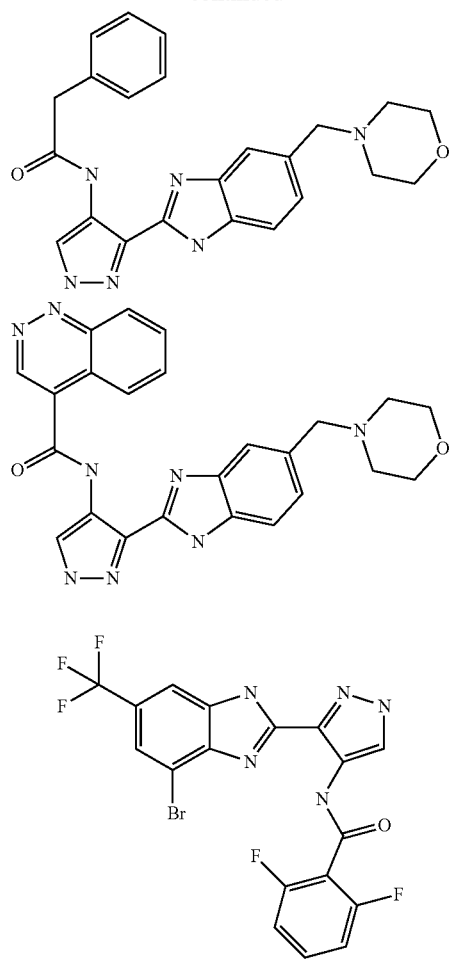
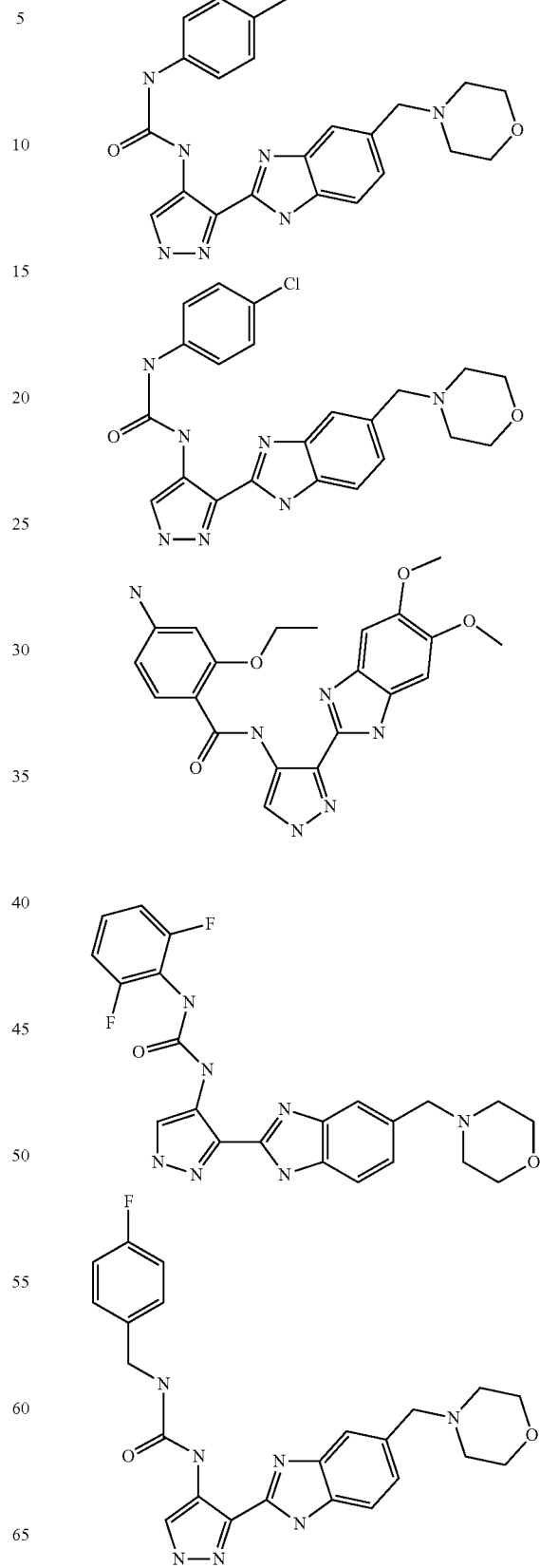

157
-continued
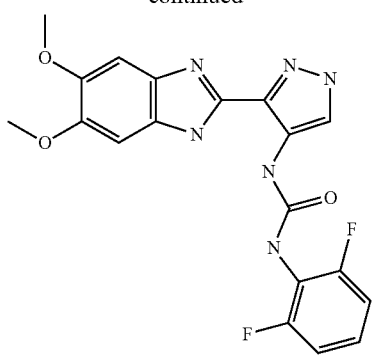
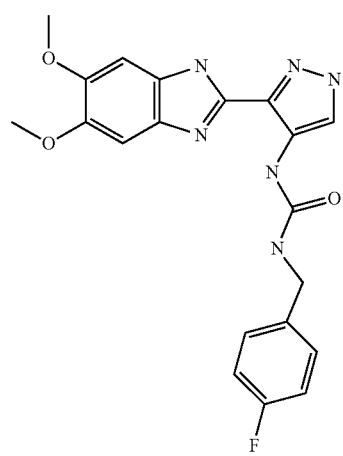
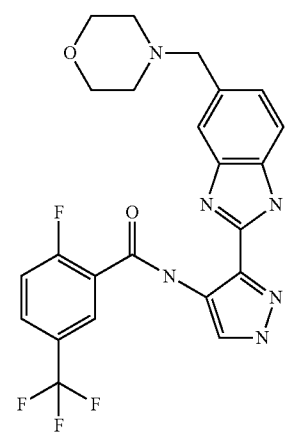
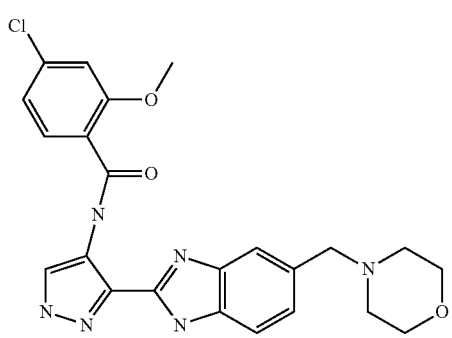
158
-continued
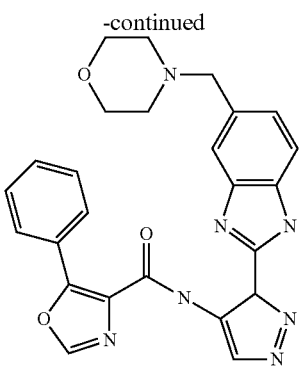
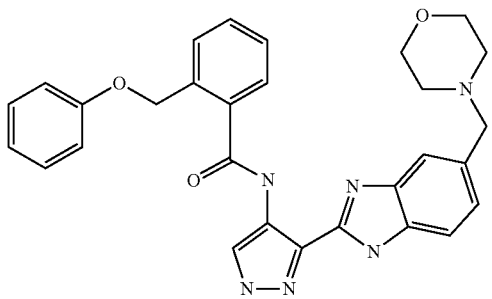
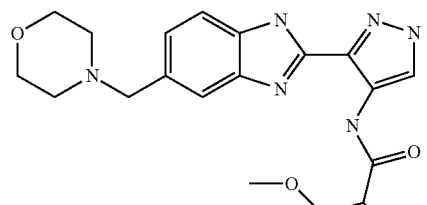
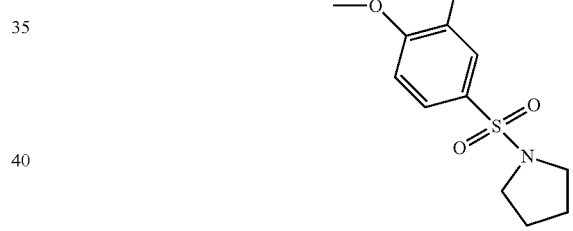
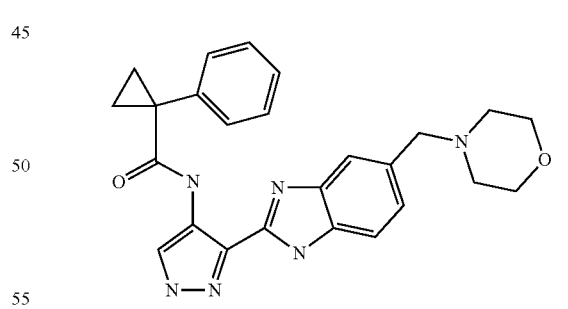

159
-continued
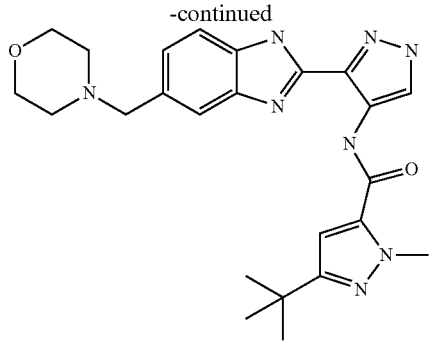
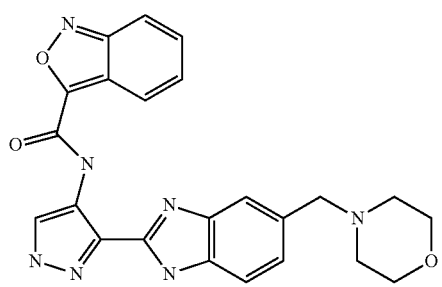
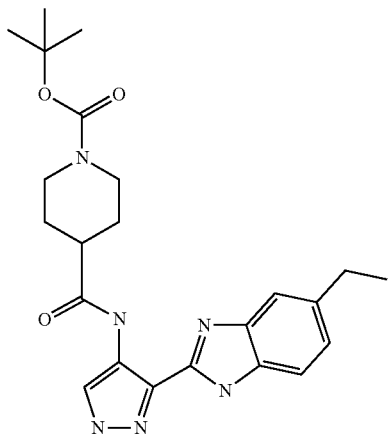
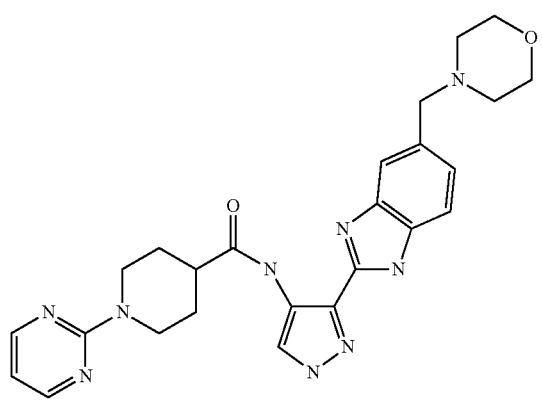
160
-continued
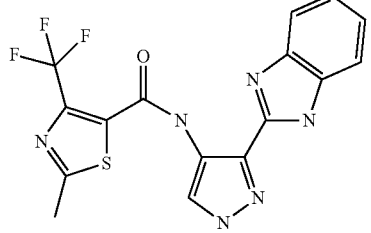
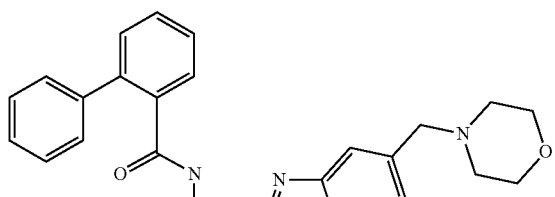
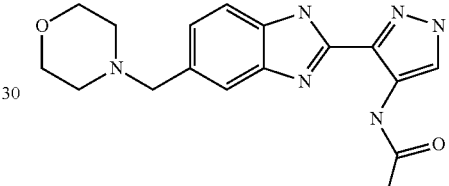
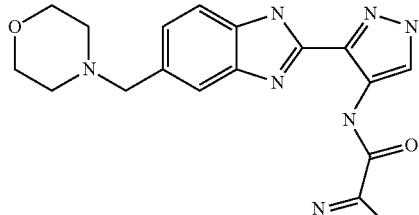
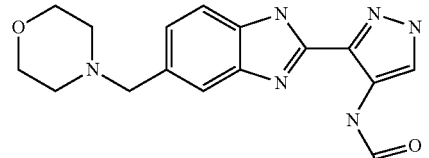

161
-continued
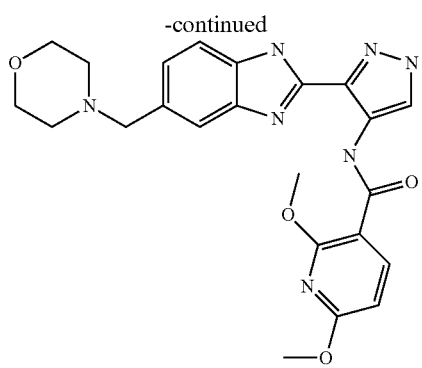
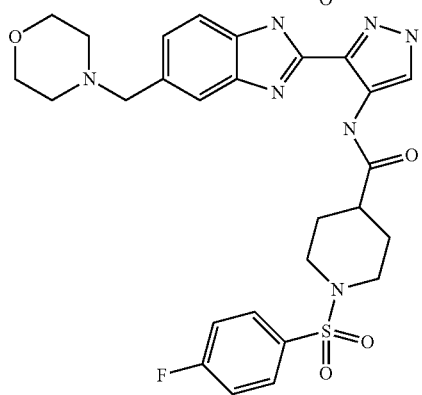
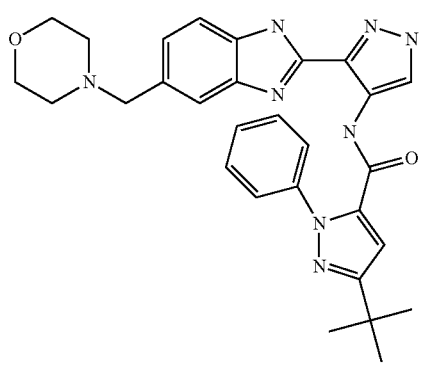
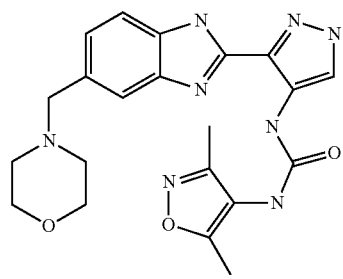
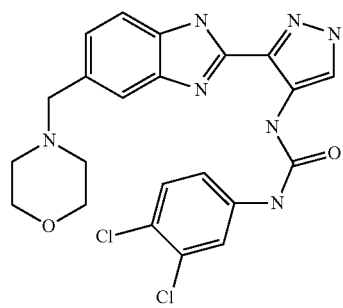
162
-continued
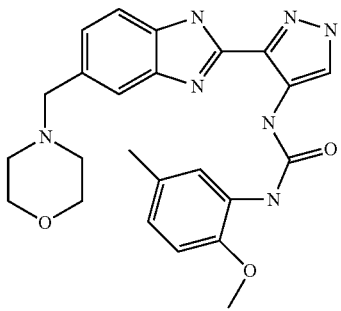
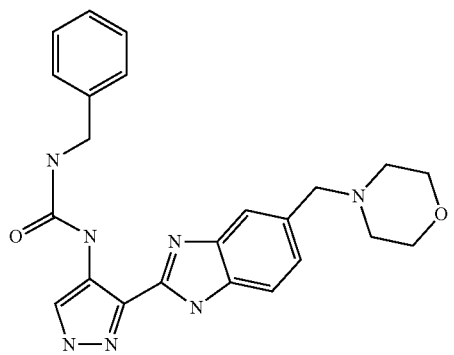
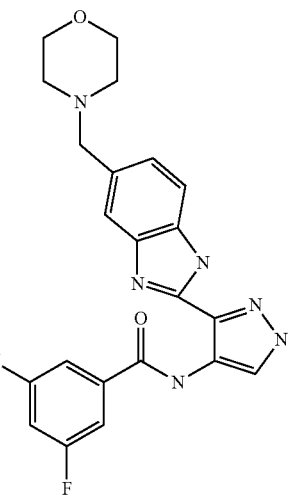
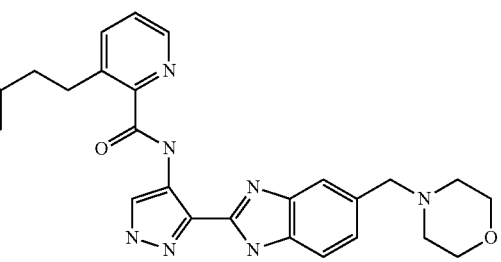

163
-continued
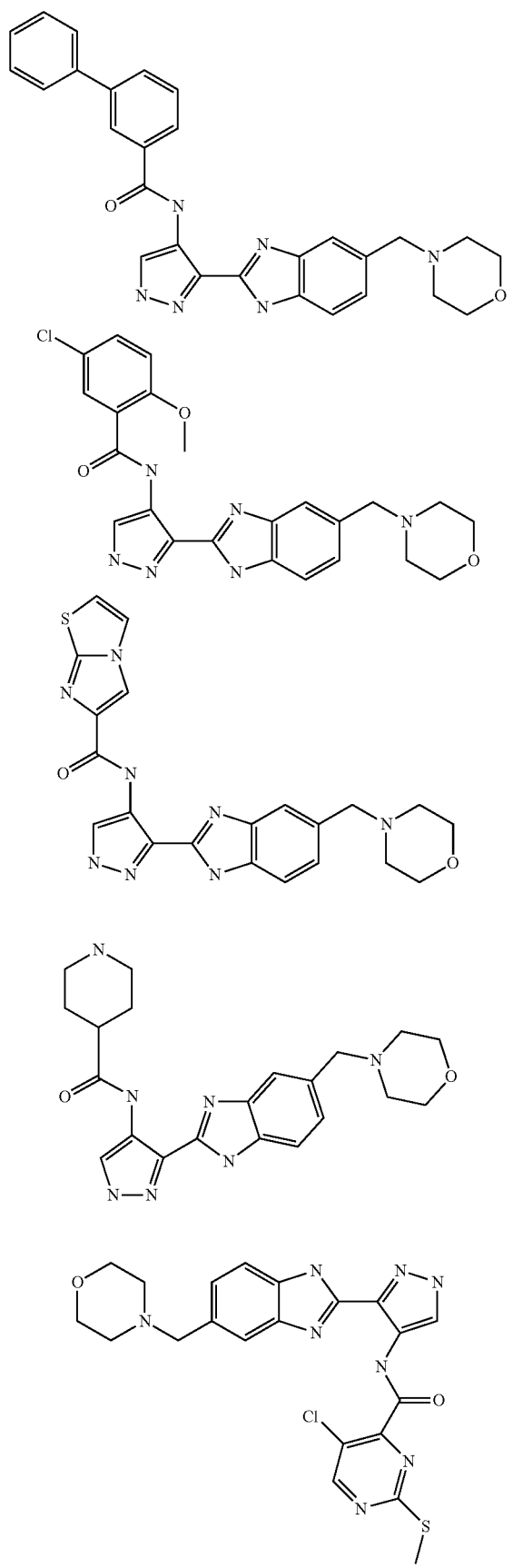
164
-continued
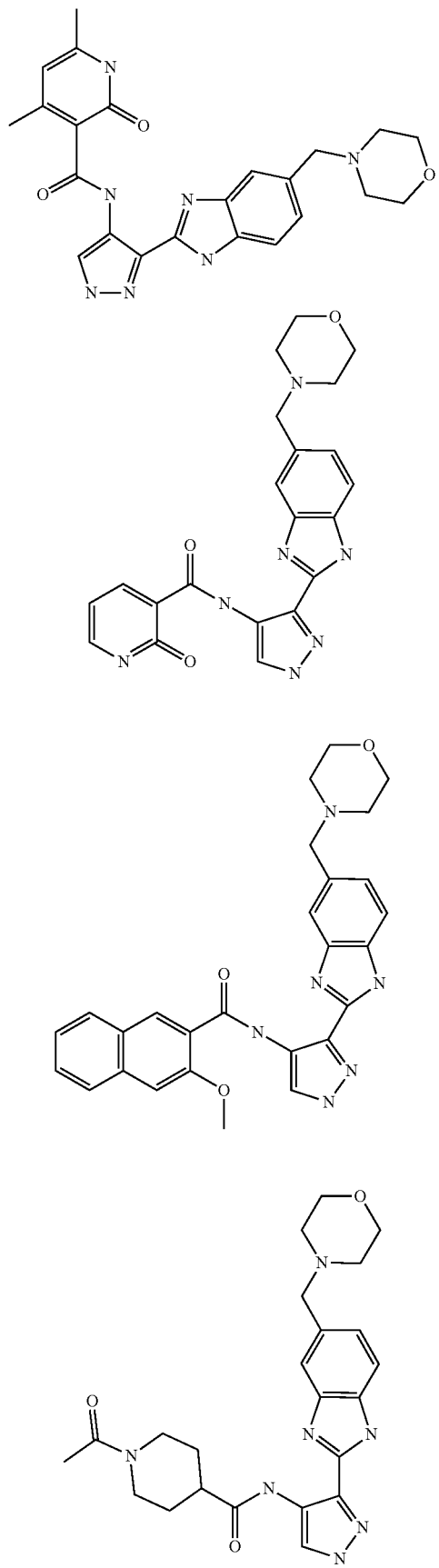

165
-continued
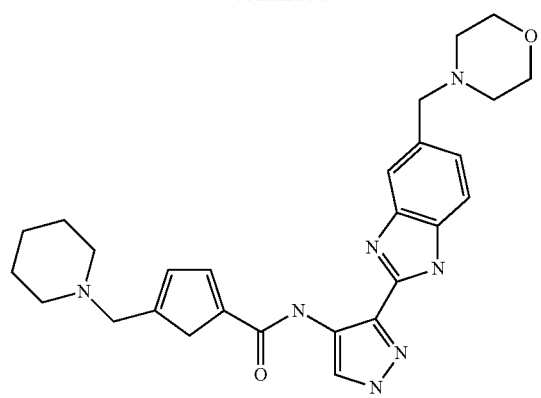
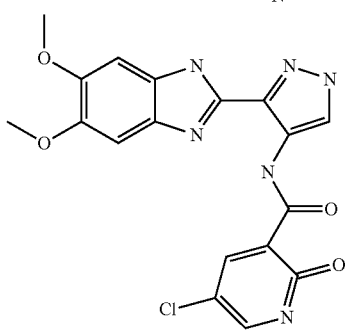
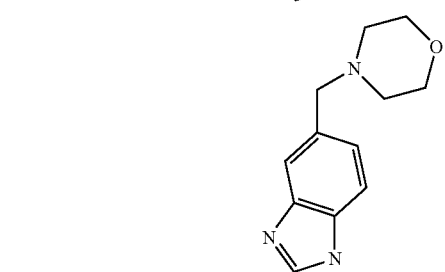
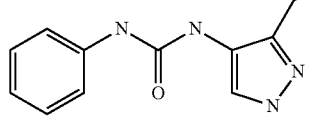
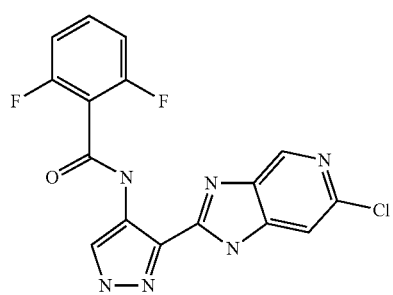
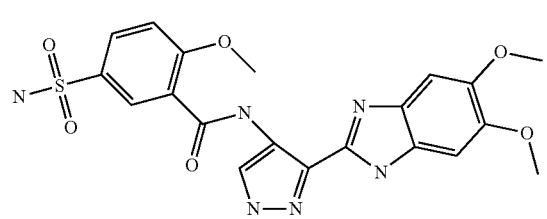
166
-continued
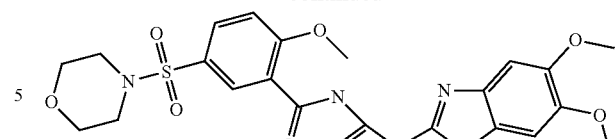
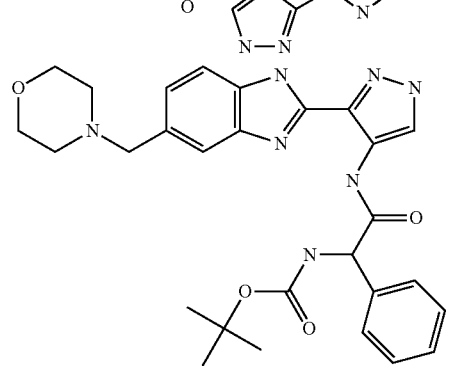
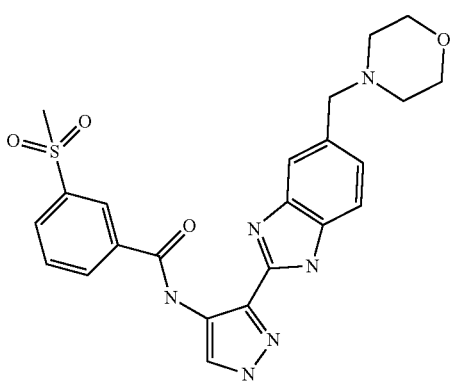
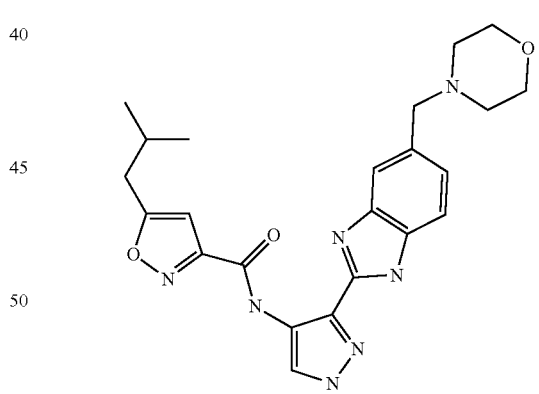
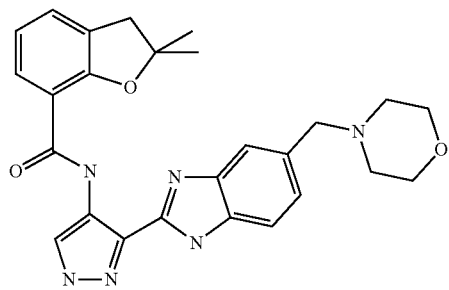

167
-continued
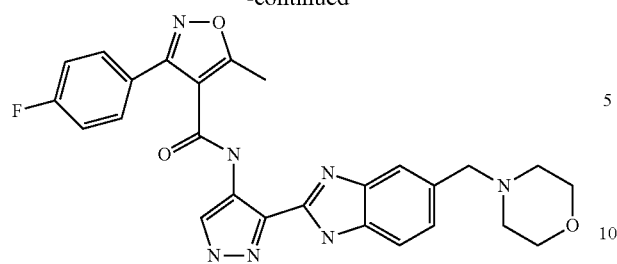
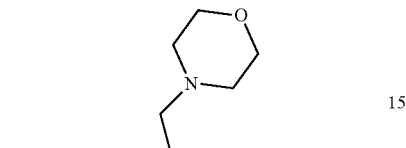
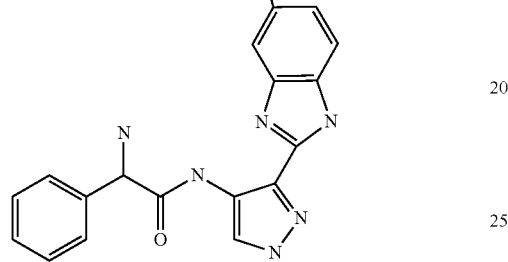
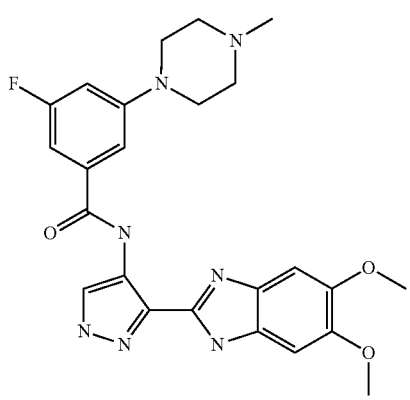
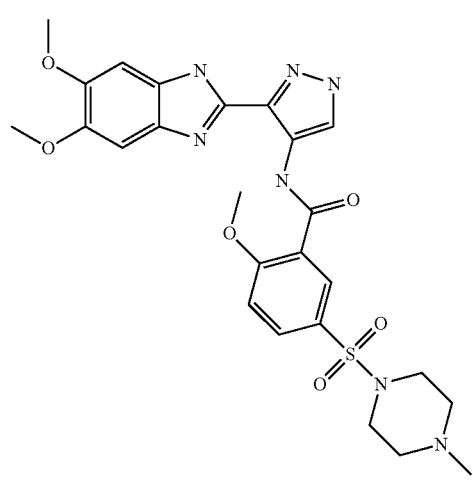
168
-continued
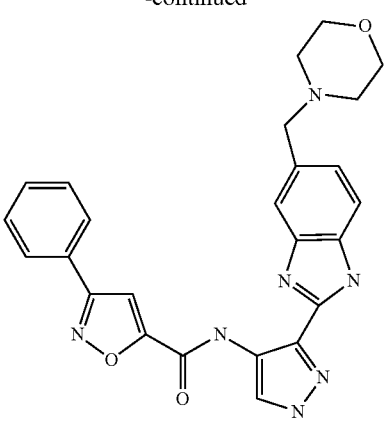
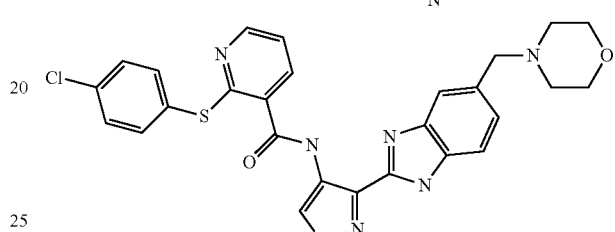
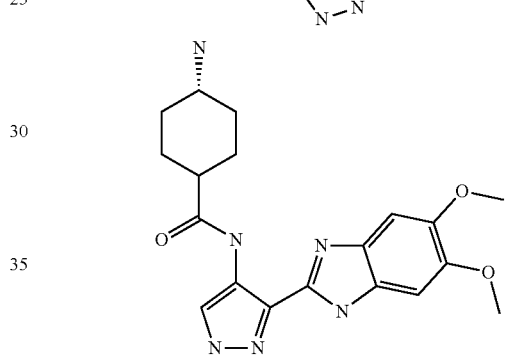
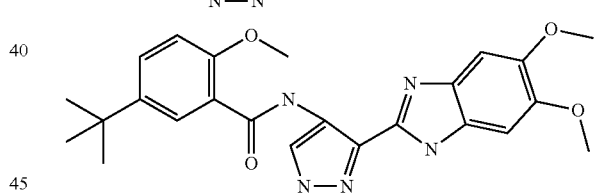
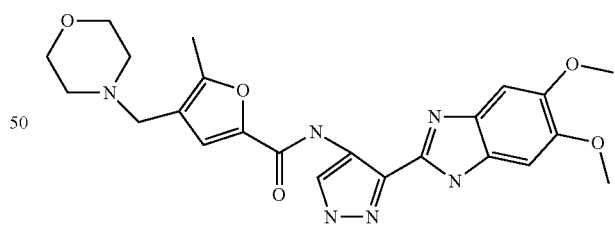
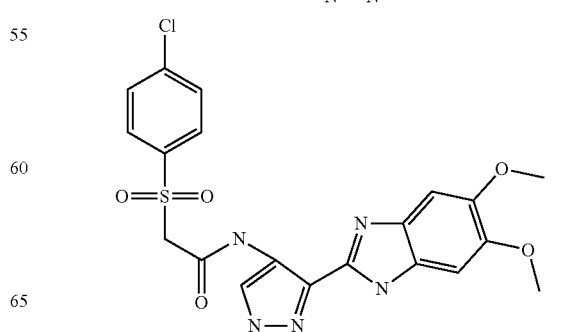

169
-continued
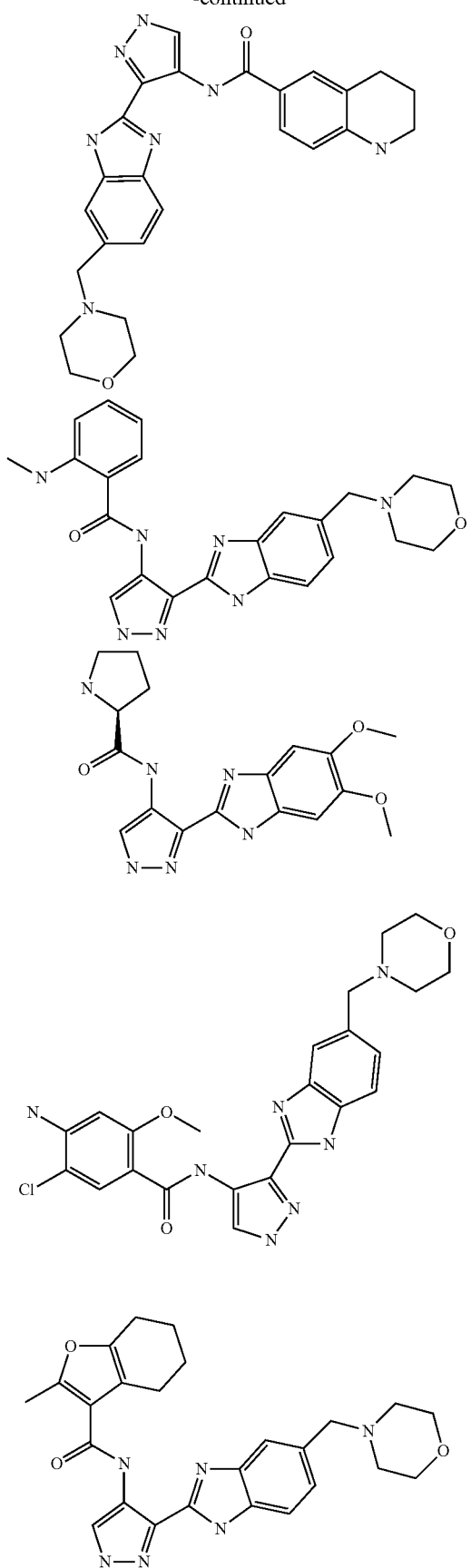
170
-continued
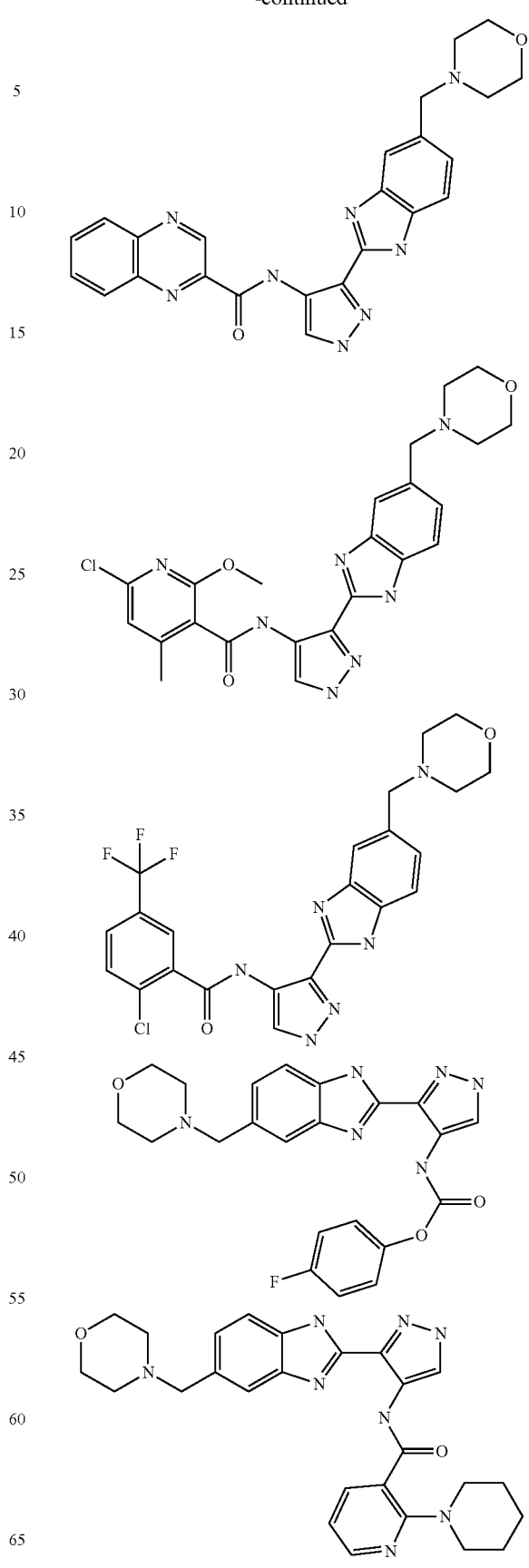

171
-continued
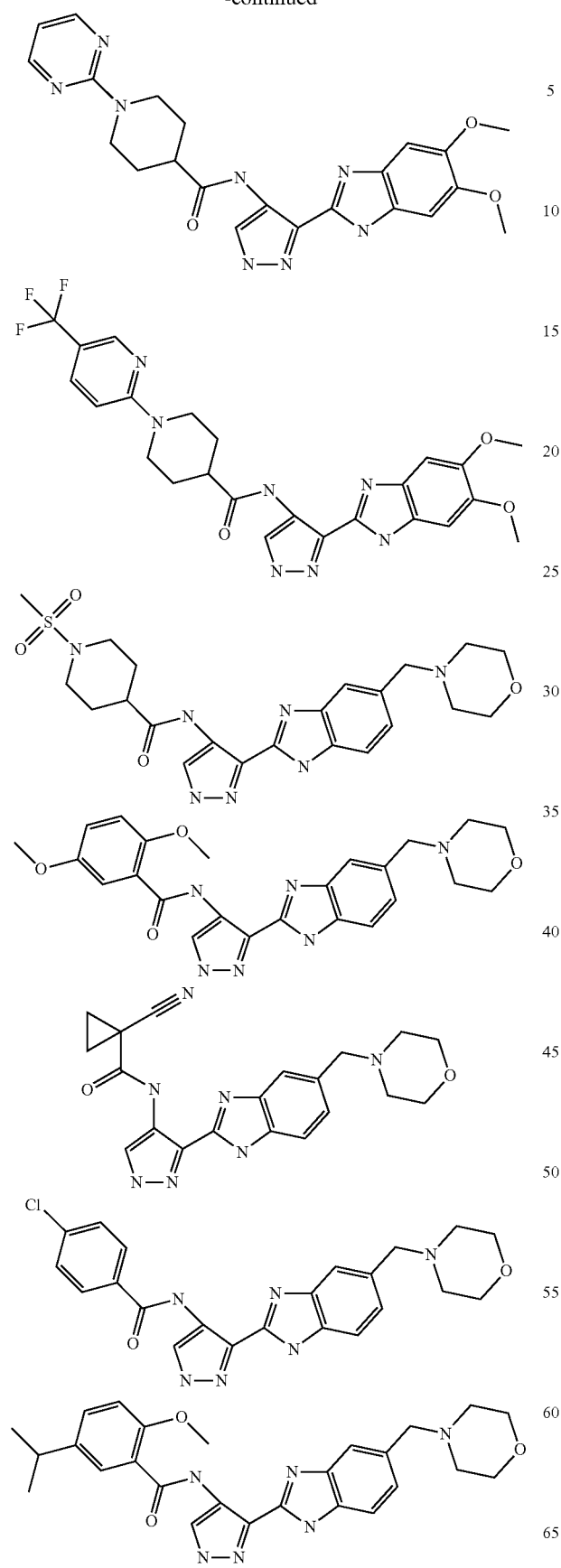
172
-continued
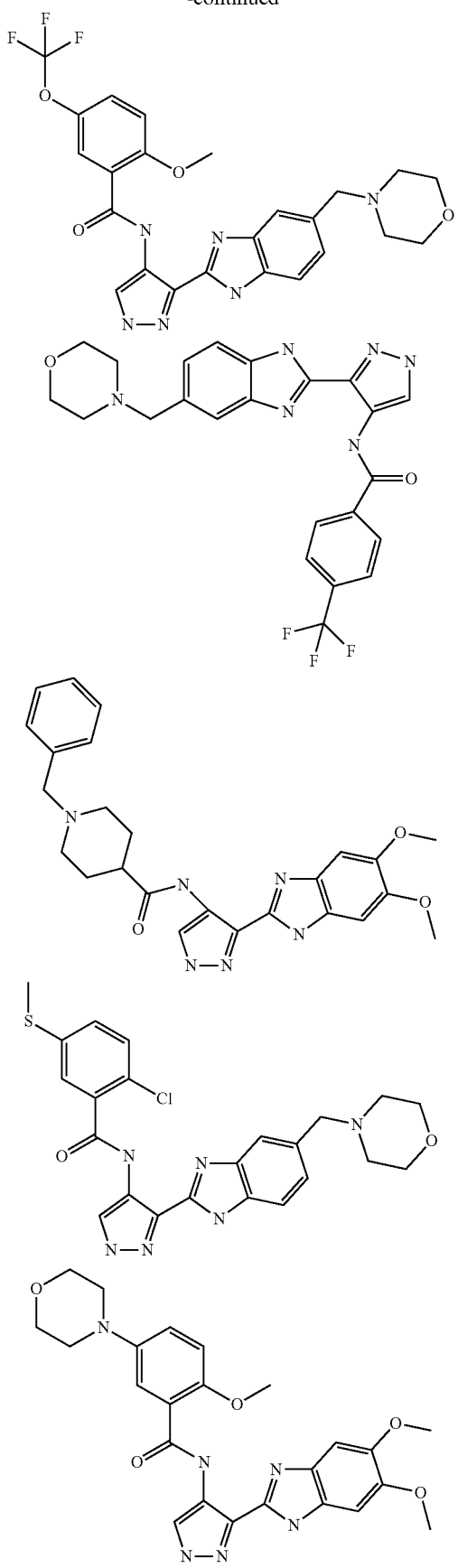

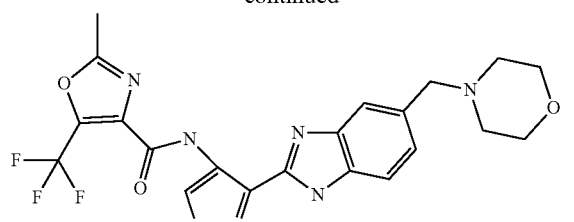
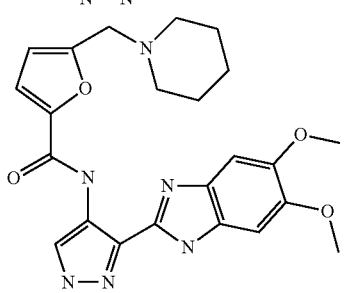
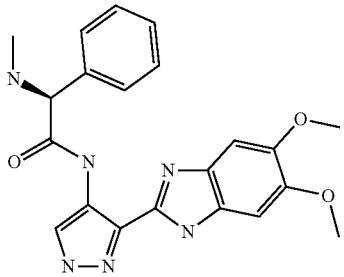
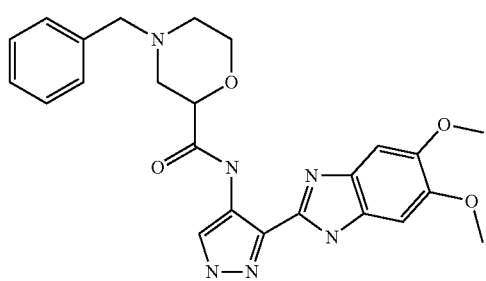
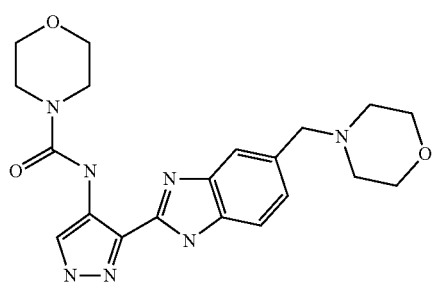
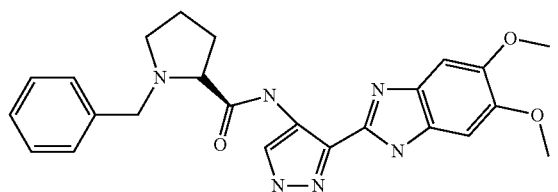
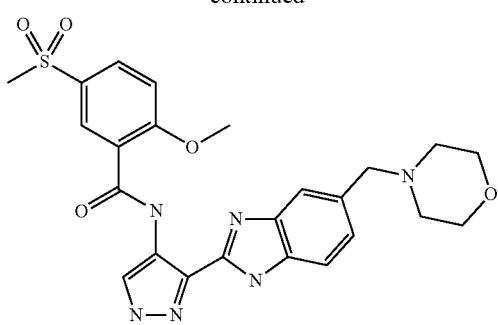
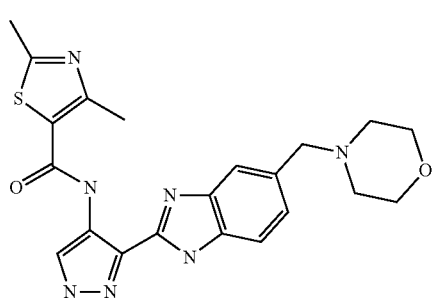
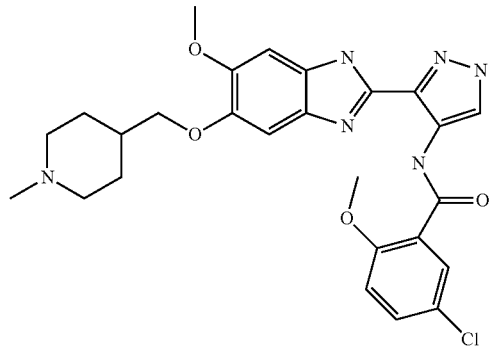
These compounds can be prepared as described in WO 2005/002552 at pages 109-257.
Particular compounds of the formula (I) for use in the present invention are the compounds of formula (II) from WO 2005/002552:
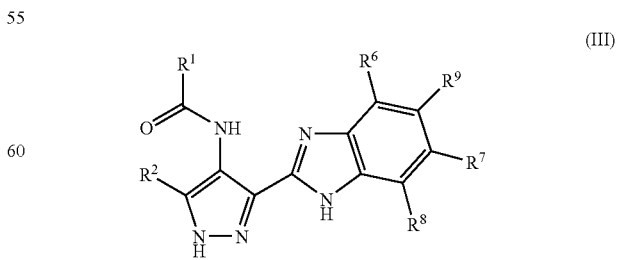
(III)
wherein $R^1$, $R^2$ and $R^6$ to $R^9$ are as defined herein.

A further group of compounds for use in the invention can be represented by the formula (Va) of WO2005/002552:

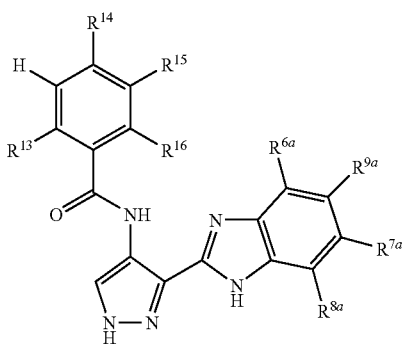

(Va)

wherein $R^{6a}$ to $R^{9a}$, $R^{13}$, $R^{14}$ and $R^{16}$, and subgroups thereof, are defined in WO2005/002552.

Another group of compounds for use in the invention are the compounds of formula (VII) and (VIIa) of WO2005/002552:

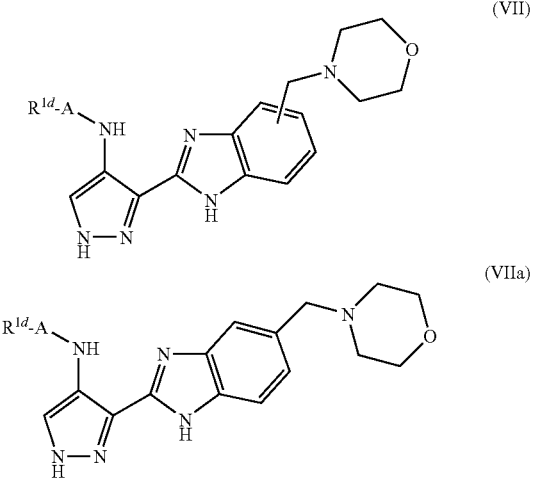

(VII)

(VIIa)

wherein $R^{1d}$ is a group $R^1$, $R^{1a}$, $R^{1b}$ or $R^{1c}$ as defined therein.
Formula (I')
General Preferences and Definitions for Compounds of the Formula (I')

The following general preferences and definitions shall apply to each of the moieties D1, D2, A, E, X, $X^a$ and $R^1$ to $R^9$ in formula (I') and their various sub-groups, sub-definitions, examples and embodiments unless the context indicates otherwise.

Any references to formula (I') herein shall also be taken to refer to formulae (II') to (VIII') and any other sub-group of compounds within formula (I') unless the context requires otherwise.

The term upregulation of Aurora kinase as used herein is defined as including elevated expression or over-expression of Aurora kinase, including gene amplification (i.e. multiple gene copies) and increased expression by a transcriptional effect, and hyperactivity and activation of Aurora kinase, including activation by mutations.

The term "saturated" as used herein refers to rings where there are no multiple bonds between ring atoms.

The term "hydrocarbyl" as used herein, whether on its own or as part of a composite term such as "hydrocarbyloxy" is a generic term encompassing aliphatic and alicyclic groups having an all-carbon backbone. Examples of hydrocarbyl groups include alkyl, cycloalkyl, cycloalkenyl, alkenyl, alkynyl, cycloalkylalkyl, cycloalkenylalkyl. Particular hydrocarbyl groups are saturated groups such as alkyl and cycloalkyl groups.

Examples of hydrocarbyloxy groups include alkoxy, cycloalkoxy, cycloalkenoxy, alkenyloxy, alkynyloxy, cycloalkylalkyloxy, cycloalkenylalkyoxy. Particular hydrocarbyloxy groups are saturated groups such as alkoxy.

The prefix "$C_{1-n}$" (where n is an integer) as used herein refers to the number of carbon atoms in a given group. Thus, a $C_{1-4}$ hydrocarbyl group contains from 1 to 4 carbon atoms, whilst a $C_{1-3}$ hydrocarbyloxy group contains from 1 to 3 carbon atoms, and so on.

Examples of $C_{1-4}$ hydrocarbyl groups include $C_{1-3}$ hydrocarbyl groups or $C_{1-2}$ hydrocarbyl groups, specific examples being any individual value or combination of values selected from $C_1$, $C_2$, $C_3$ and $C_4$ hydrocarbyl groups.

The term "alkyl" covers both straight chain and branched chain alkyl groups. Examples of alkyl groups are methyl, ethyl, propyl, isopropyl, n-butyl, isobutyl, and tert-butyl.

Examples of cycloalkyl groups are those derived from cyclopropane, cyclobutane and cyclopentane.

Examples of alkenyl groups are ethenyl(vinyl), 1-propenyl, 2-propenyl(allyl), isopropenyl, butenyl and buta-1,4-dienyl.

Examples of cycloalkenyl groups are cyclopropenyl and cyclobutenyl.

Examples of alkynyl groups are ethynyl and 2-propynyl (propargyl) groups.

Examples of cycloalkylalkyl and cycloalkenylalkyl include cyclopropylmethyl.

Examples of alkoxy groups are methoxy, ethoxy, n-propyloxy, i-propyloxy, n-butoxy, isobutoxy and tert-butoxy.

When an alkyl group forms part of a mono-alkylamino or dialkylamino group, the alkyl group may be any of the examples of alkyl groups set out above. Particular alkylamino and dialkylamino groups are methylamino, dimethylamino, ethylamino, diethylamino, n-propylamino, isopropylamino, butylamino, isobutylamino and i-butylamino. Particular alkyl- and dialkylamino groups are methylamino and dimethylamino.

The term "saturated heterocyclic group" as used herein refers to a heterocyclic group containing no multiple bonds between adjacent ring members. The saturated heterocyclic groups may contain 1 or 2 heteroatom ring members selected from O, S and N.

Depending on the context, the heterocylic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

The saturated heterocyclic groups are typically monocyclic and usually contain 4, 5 or 6 ring members unless otherwise stated.

A particular example of saturated heterocyclic groups containing 4 ring members is the azetidine group.

Examples of saturated heterocyclic groups containing 5 ring members include pyrrolidine (e.g. 1-pyrrolidinyl, 2-pyrrolidinyl and 3-pyrrolidinyl), pyrrolidone, tetrahydrofuran, and tetrahydrothiophene.

Examples of saturated heterocyclic groups containing 6 ring members include morpholine, thiomorpholine, thiomorpholine S-oxide, thiomorpholine S,S-dioxide, piperidine (e.g. 1-piperidinyl, 2-piperidinyl, 3-piperidinyl and 4-piperidinyl), piperidone, dioxane, tetrahydropyran (e.g. 4-tetrahydropyranyl), piperazone, piperazine, and N-alkyl piperazines such as N-methyl piperazine.

Specific Embodiments of and Preferences for D1, D2, A, E, $R^1$ to $R^9$ and X in Sub-groups (A) and (B) of Formula (I')

In one general embodiment, M is a group D1.

In another general embodiment, M is a group D2.

X is selected from O, NH and NCH$_3$. In one particular embodiment X is O.

A is selected from a bond and a group $NR^2$ where $R^2$ is hydrogen or methyl.

In one embodiment, A is a bond.

In another embodiment, A is a group $NR^2$ where $R^2$ is hydrogen or methyl.

E is selected from a bond, $CH_2$, $CH(CN)$ and $C(CH_3)_2$.

In one sub-group of compounds E is a bond.

In another sub-group of compounds E is $CH_2$.

In a further sub-group of compounds E is $CH(CN)$.

In another sub-group of compounds E is $C(CH_3)_2$.

When M is a group D1, $R^1$ can be selected from groups (i), (ii), (iii), (iv), (v), (vi), (vii), (viii), (ix), (x), (xi), (xii), (xiii), (xiv) and (xv).

Each individual group in the list of groups (i) to (xv) represents a separate embodiment of the invention.

In embodiment (i) $R^1$ is a cycloalkyl group of 3 to 5 ring members optionally substituted by hydroxy, fluorine, amino, methylamino, methyl or ethyl.

Particular cycloalkyl groups are optionally substituted cyclopropyl and cyclobutyl groups, more typically optionally substituted cyclopropyl groups. In a preferred embodiment, $R^1$ is an unsubstituted cyclopropyl group.

In embodiment (ii), $R^1$ is a saturated heterocyclic group of 4 to 6 ring members containing 1 or 2 heteroatom ring members selected from O, N, S and SO$_2$, the heterocyclic group being optionally substituted by $C_{1-4}$ alkyl, amino or hydroxy; but excluding unsubstituted 4-morpholinyl, unsubstituted tetrahydropyran-4-yl, unsubstituted 2-pyrrolidinyl, and unsubstituted and 1-substituted piperidine-4-yl.

Examples of saturated heterocyclic groups are as set out in the General Preferences and Definitions section above.

Particular examples of saturated heterocyclic groups include:

five membered rings containing a single heteroatom ring member selected from O, N and S (other than unsubstituted 2-pyrrolidinyl);

six membered rings containing two heteroatom ring members selected from O, N and S (other than unsubstituted 4-morpholinyl).

The saturated heterocyclic groups may be substituted or unsubstituted. In one embodiment, they are unsubstituted. In another embodiment, they are substituted by one or two $C_{1-4}$ alkyl groups, for example one or two methyl groups.

One particular saturated heterocyclic group is an optionally substituted tetrahydrofuran group (e.g. tetrahydrofuran-2-yl and tetrahydrofuran-3-yl), more preferably an unsubstituted tetrahydrofuran group.

In embodiment (iii) $R^1$ is a 2,5-substituted phenyl group of the formula:

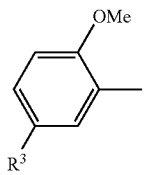

wherein (a) when X is NH or N—CH$_3$, $R^3$ is selected from chlorine and cyano; and (b) when X is O, $R^3$ is CN.

In one sub-group of compounds within embodiment (iii), X is N—CH$_3$ and $R^3$ is selected from chlorine and cyano.

In another sub-group of compounds within embodiment (iii), X is O and $R^3$ is CN.

In embodiment (iv) $R^1$ is a group $CR^6R^7R^8$ wherein $R^6$ and $R^7$ are each selected from hydrogen and methyl, and $R^8$ is selected from hydrogen, methyl, $C_{1-4}$ alkylsulphonylmethyl, hydroxymethyl and cyano.

Within embodiment (iv), particular examples of $R^1$ are methyl, cyanomethyl, HOCH$_2$C(CH$_3$)$_2$— and 2-methylsulphonylethyl.

Within embodiment (iv), further particular examples of $R^1$ are methyl and isopropyl.

In embodiment (v) $R^1$ is a pyridazin-4-yl group optionally substituted by one or two substituents selected from methyl, ethyl, methoxy and ethoxy. The pyridazinyl group may be a pyridazin-3-yl or pyridazin-4-yl group but typically is a pyridazin-4-yl. Particular substituents are methoxy groups and, for example, the pyridazinyl group may bear two methoxy substituents.

In embodiment (vi) $R^1$ is a substituted imidazothiazole group wherein the substituents are selected from methyl, ethyl, amino, fluorine, chlorine, amino and methylamino. A particular substituent is methyl.

In embodiment (vii) $R^1$ is an optionally substituted 1,3-dihydro-isoindol-2-yl or optionally substituted 2,3-dihydro-indol-1-yl group wherein the optional substituents in each case are selected from halogen, cyano, amino, $C_{1-4}$ mono- and dialkylamino, CONH$_2$ or CONH—$C_{1-4}$ alkyl $C_{1-4}$ alkyl and $C_{1-4}$ alkoxy wherein the $C_{1-4}$ alkyl and $C_{1-4}$ alkoxy groups are optionally substituted by hydroxy, methoxy, or amino.

Particular substituents are selected from methyl, ethyl, fluorine, chlorine (preferably only on the aryl ring of the dihydroindole or dihydroisoindole), CONH$_2$, amino, methylamino, dimethylamino and methoxy.

In one sub-group of compounds in embodiment (vii), the dihydroisoindole or dihydroindole are each unsubstituted.

In embodiment (viii) $R^1$ is 3-pyridyl optionally substituted by one or two substituents selected from hydroxy, halogen, cyano, amino, $C_{1-4}$ mono- and dialkylamino, CONH$_2$ or CONH—$C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino; but excluding the compounds 2-oxo-1,2-dihydro-pyridine-3-carboxylic acid [3-(5-morpholin-4-ylmethyl-1H-benzoimidazol-2-yl)-1H-pyrazol-4-yl]-amide and 2,6-dimethoxy-N-[3-(5-morpholin-4-ylmethyl-1H-benzoimidazol-2-yl)-1H-pyrazol-4-yl]-nicotinamide.

In one embodiment $R^1$ is 3-pyridyl optionally substituted by one or two substituents selected from hydroxy, halogen, cyano, amino, $C_{1-4}$ mono- and dialkylamino, CONH$_2$ or CONH—$C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino but where R$^1$ is 3-pyridyl, X is O, A is a bond and E is a bond the pyridyl has one or two substituents selected from halogen, cyano, amino, C$_{1-4}$ mono- and dialkylamino, CONH$_2$ or CONH—C$_{1-4}$ alkyl, C$_{1-4}$ alkyl and C$_{2-4}$ alkoxy wherein the C$_{1-4}$ alkyl and C$_{1-4}$ alkoxy groups are optionally substituted by hydroxy, methoxy, or amino.

Particular substituents are selected from methyl, ethyl, fluorine, chlorine, CONH$_2$, amino, methylamino, dimethylamino and methoxy. Further particular substituents are selected from methyl, ethyl, fluorine, chlorine, CONH$_2$, amino, methylamino, and dimethylamino.

In one sub-group of compounds, the 3-pyridyl group is unsubstituted.

In embodiment (ix) R$^1$ is thiomorpholine or an S-oxide or S,S-dioxide thereof optionally substituted by one or two substituents selected from halogen, cyano, amino, C$_{1-4}$ mono- and dialkylamino, CONH$_2$ or CONH—C$_{1-4}$ alkyl C$_{1-4}$ alkyl and C$_{1-4}$ alkoxy wherein the C$_{1-4}$ alkyl and C$_{1-4}$ alkoxy groups are optionally substituted by hydroxy, methoxy, or amino.

In one sub-group of compounds, the thiomorpholine or S-oxide or S,S-dioxide thereof is unsubstituted.

In embodiment (x), E-A is NR$^2$ and R$^1$ is selected from: 2-fluorophenyl, 3-fluorophenyl, 4-fluorophenyl, 2,4-difluorophenyl, 3,4-difluorophenyl, 2,5-difluorophenyl, 3,5-difluorophenyl, 2,4,6-trifluorophenyl, 2-methoxyphenyl, 5-chloro-2-methoxyphenyl, cyclohexyl, unsubstituted 4-tetrahydropyranyl and tert-butyl.

In embodiment (xi) E-A is NR$^2$ and R$^1$ is a group NR$^{10}$R$^{11}$ where R$^{10}$ and R$^{11}$ are each C$_{1-4}$ alkyl or R$^{10}$ and R$^{11}$ are linked so that NR$^{10}$R$^{11}$ forms a saturated heterocyclic group of 4 to 6 ring members optionally containing a second heteroatom ring member selected from O, N, S and SO$_2$, the heterocyclic group being optionally substituted by C$_{1-4}$ alkyl, amino or hydroxy.

Within this embodiment, one sub-group of compounds is the group of compounds wherein R$^{10}$ and R$^{11}$ are each C$_{1-4}$ alkyl, particularly methyl.

Another sub-group of compounds is the group of compounds wherein R$^{10}$ and R$^{11}$ are linked so that NR$^{10}$R$^{11}$ forms a saturated heterocyclic group of 4 to 6 ring members optionally containing a second heteroatom ring member selected from O, N, S and SO$_2$, the heterocyclic group being optionally substituted by C$_{1-4}$ alkyl, amino or hydroxy. The saturated heterocyclic group can be any of the nitrogen containing saturated heterocyclic groups listed above in the General Preferences and Definitions section but particular saturated heterocyclic groups include pyrrolidinyl, morpholinyl, piperazinyl and N—C$_{1-4}$ alkyl-piperazinyl groups. Such groups are typically unsubstituted or substituted by one or two methyl groups and, in one particular embodiment, are unsubstituted.

In embodiment (xii), E-A is NR$^2$ and R$^1$ is a pyridone group optionally substituted by one or two substituents selected from hydroxy, halogen, cyano, amino, C$_{1-4}$ mono- and dialkylamino, CONH$_2$, CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino.

The pyridone group may be N-substituted, for example with an alkyl group such as methyl, and may otherwise be unsubstituted.

In embodiment (xiii), E-A is C(CH$_3$)$_2$NR$^2$ or CH$_2$—NR$^2$ and R$^1$ is selected from unsubstituted 2-furyl and 2,6-difluorophenyl.

In embodiment (xiv), E-A is C(CH$_3$)$_2$NR$^2$ and R$^1$ is unsubstituted phenyl.

In embodiment (xv), E is CH$_2$ and R$^1$ is unsubstituted tetrahydropyran-4-yl.

When M is a group D2, R$^1$ can be selected from groups (xvi), (xvii), (xviii) and (xix).

Each individual group in the list of groups (xvi) to (xix) represents a separate embodiment of the invention.

In embodiment (xvi) R$^1$ is a 2-substituted 3-furyl group of the formula:

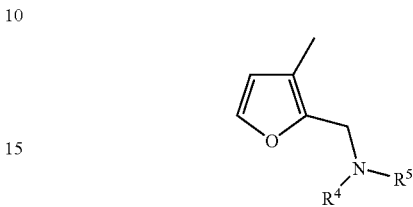

wherein R$^4$ and R$^5$ are the same or different and are selected from hydrogen and C$_{1-4}$ alkyl, or R$^4$ and R$^5$ are linked so that NR$^4$R$^5$ forms a 5- or 6-membered saturated heterocyclic group optionally containing a second heteroatom or group selected from O, NH, NMe, S or SO$_2$, the 5- or 6-membered saturated ring being optionally substituted by hydroxy, fluorine, amino, methylamino, methyl or ethyl.

In one embodiment R$^1$ is a 2-substituted 3-furyl group of the formula:

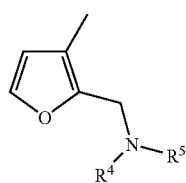

wherein R$^4$ and R$^5$ are the same or different and are selected from hydrogen and C$_{1-4}$ alkyl, or R$^4$ and R$^5$ are linked so that NR$^4$R$^5$ forms a 5- or 6-membered saturated heterocyclic group optionally containing a second heteroatom or group selected from O, NH, NMe, S or SO$_2$, the 5- or 6-membered saturated ring being optionally substituted by hydroxy, fluorine, amino, methylamino, methyl or ethyl but where A is bond and E is a bond, R$^4$ and R$^5$ are not linked so that NR$^4$R$^5$ forms a unsubstituted piperidine Particular saturated heterocyclic groups are as set out above in the General Preferences and Definitions section but particular saturated heterocyclic groups include pyrrolidinyl, morpholinyl, piperazinyl and N—C$_{1-4}$ alkyl-piperazinyl groups. Such groups are typically unsubstituted or substituted by one or two methyl groups and, in one particular embodiment, are unsubstituted.

Particular examples of compounds wherein R$^4$ and R$^5$ are selected from hydrogen and C$_{1-4}$ alkyl are methylamino and dimethylamino groups, more typically a dimethylamino group.

In embodiment (xvii), R$^1$ is a 5-substituted 2-furyl group of the formula:

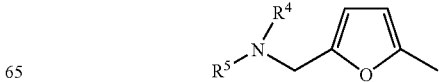

wherein $R^4$ and $R^5$ are the same or different and are selected from hydrogen and $C_{1-4}$ alkyl, or $R^4$ and $R^5$ are linked so that $NR^4R^5$ forms a 5- or 6-membered saturated heterocyclic group optionally containing a second heteroatom or group selected from O, NH, NMe, S or $SO_2$, the 5- or 6-membered saturated heterocyclic group being optionally substituted by hydroxy, fluorine, amino, methylamino, methyl or ethyl; with the proviso that the compound is not 5-piperidin-1-ylmethyl-furan-2-carboxylic acid [3-(5,6-dimethoxy-1H-benzoimidazol-2-yl)-1H-pyrazol-4-yl]-amide.

Particular saturated heterocyclic groups are as set out above in the General Preferences and Definitions section but particular saturated heterocyclic groups include pyrrolidinyl, morpholinyl, piperazinyl and N—$C_{1-4}$ alkyl-piperazinyl groups. Such groups are typically unsubstituted or substituted by one or two methyl groups and, in one particular embodiment, are unsubstituted.

In embodiment (xviii), $R^1$ is a group of the formula:

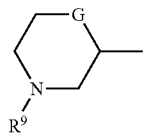

wherein $R^9$ is hydrogen, methyl, ethyl or isopropyl; G is CH, O, S, SO, $SO_2$ or NH and the group is optionally substituted by one, two or three substituents selected from $C_{1-4}$ hydrocarbyl, hydroxy, $C_{1-4}$ hydrocarbyloxy, fluorine, amino, mono- and di-$C_{1-4}$ alkylamino and wherein the $C_{1-4}$ hydrocarbyl and $C_{1-4}$ hydrocarbyloxy groups are each optionally substituted by hydroxy, fluorine, amino, mono- or di-$C_{1-4}$ alkylamino.

In one sub-group of compounds within embodiment (xix), G is selected from O and CH.

In embodiment (xviii), the group $R^1$ is typically unsubstituted or substituted by one or two methyl groups, and more typically is unsubstituted.

In embodiment (xix) $R^1$ is a 3,5-disubstituted phenyl group of the formula:

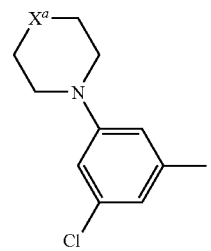

wherein $X^a$ is as X is selected from O, NH and $NCH_3$.
Preferably Xa is N—$CH_3$.

Particular examples of the moiety $R^1$-A- are shown in Table X, the asterisk indicating the point of attachment to the carbonyl group C=O in the group $R^1$-E-A-C(=O)—NH—.

TABLE X

Examples of the Moiety $R^1$-E-A-

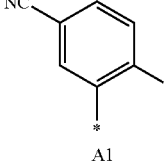 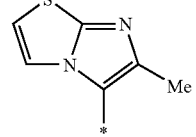  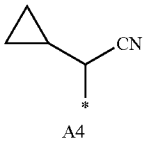 [SMILES: *C(C#N)C1CC1]
A1 — A2 — A3 — A4

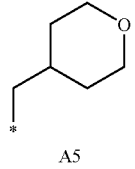 [SMILES: *CC1CCOCC1] 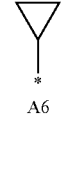 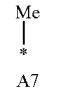 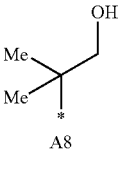
A5 — A6 — A7 — A8

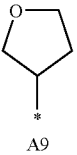  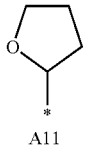 
A9 — A10 — A11 — A12

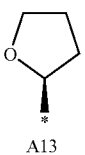 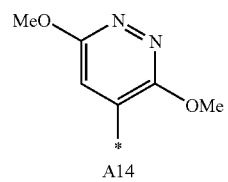 [SMILES: *c1cc(OC)nnc1OC] 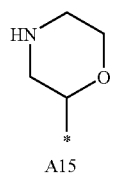 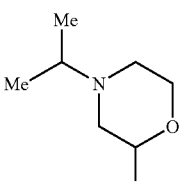
A13 — A14 — A15 — A16

TABLE X-continued
Examples of the Moiety R¹-E-A-
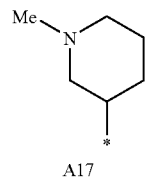
A17
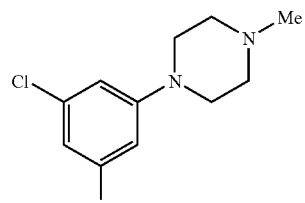
A18
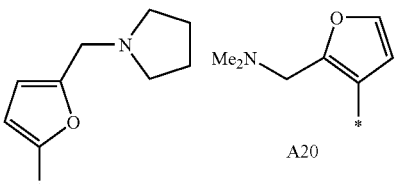
A19  A20
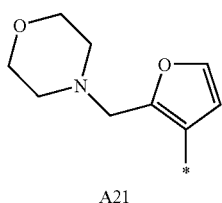 [SMILES: *c1ccoc1CN1CCOCC1]
A21
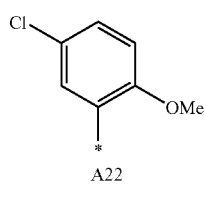 [SMILES: *c1cc(Cl)ccc1OC]
A22
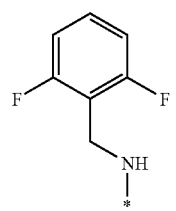
A23
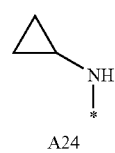
A24
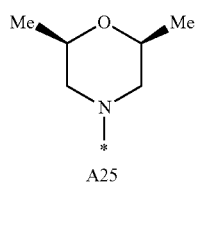
A25
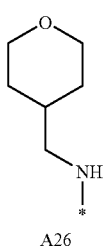 [SMILES: *NCC1CCOCC1]
A26
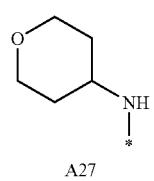 [SMILES: *NC1CCOCC1]
A27
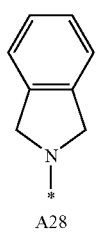
A28
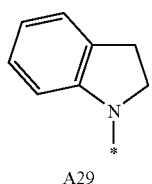 [SMILES: *N1CCc2ccccc21]
A29
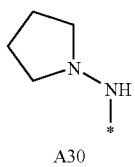
A30
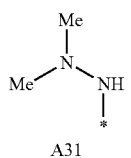
A31
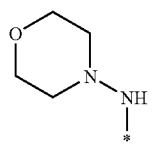
A32
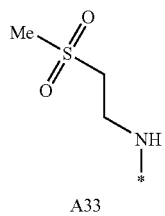
A33
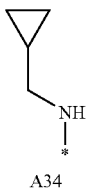 [SMILES: *NCC1CC1]
A34
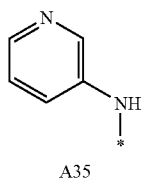 [SMILES: *Nc1cccnc1]
A35
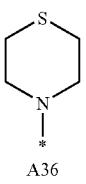 [SMILES: *N1CCSCC1]
A36
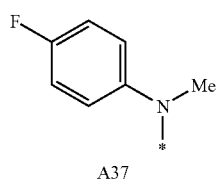 [SMILES: *N(C)c1ccc(F)cc1]
A37
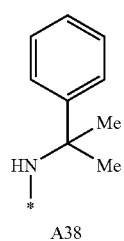
A38
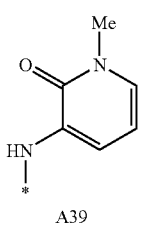
A39
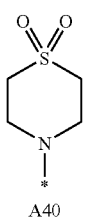 [SMILES: *N1CCS(=O)(=O)CC1]
A40

TABLE X-continued
Examples of the Moiety R¹-E-A-
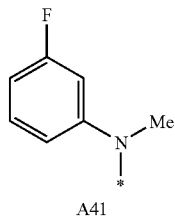 [SMILES: *N(C)c1cccc(F)c1]
A41
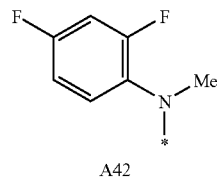 [SMILES: *N(C)c1ccc(F)cc1F]
A42
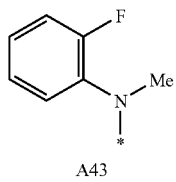 [SMILES: *N(C)c1ccccc1F]
A43
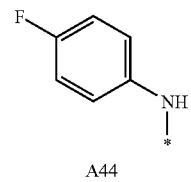 [SMILES: *Nc1ccc(F)cc1]
A44
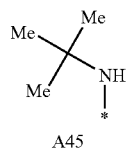
A45
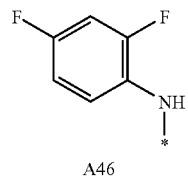
A46
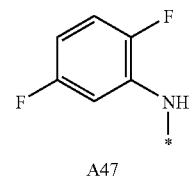
A47
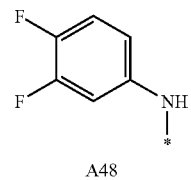
A48
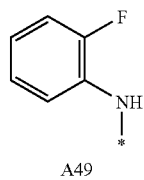 [SMILES: *Nc1ccccc1F]
A49
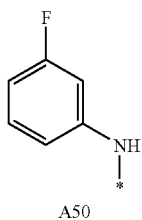 [SMILES: *Nc1cccc(F)c1]
A50
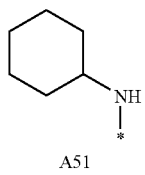 [SMILES: *NC1CCCCC1]
A51
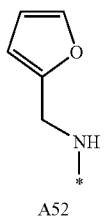
A52
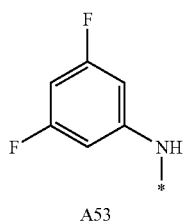
A53
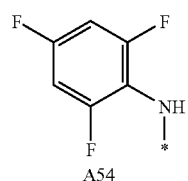 [SMILES: *Nc1c(F)cc(F)cc1F]
A54
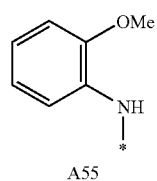 [SMILES: *Nc1ccccc1OC]
A55
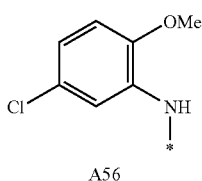 [SMILES: *Nc1cc(Cl)ccc1OC]
A56
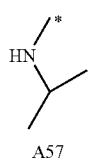
A57
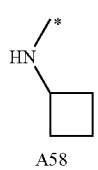
A58
A59

In Table X, preferred groups R¹-E-A- include A1, A4, A10, A11, A13, A20, A22, A23, A24, A29, A30, A31, A32, A38, A42, A43, A44, A46, A47, A49, A54 and A56.

In another embodiment the group R¹-E-A is A57, A58 or A59.

A preferred sub-set of groups R¹-E-A- includes A1, A4, A20, A24, A30, A44, A46 and A54. Within this sub-set, one particular group R¹-A- is the group A24.

One sub-group of compounds for the new therapeutic uses of the invention is represented by the formula (II'):

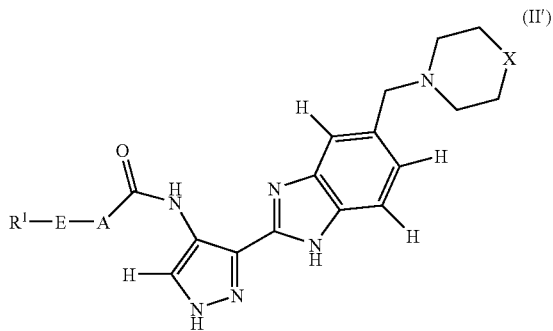

wherein R¹, E, A and X are as defined herein.

Within formula (II'), one subset of compounds is the subset wherein X is O.

One sub-group of compounds of the formula (II') can be represented by the formula (III'):

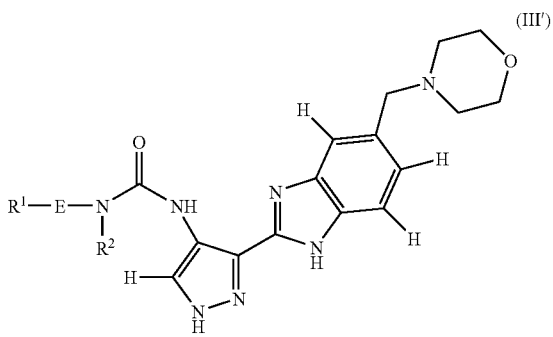

Within formula (III), one sub-set of compounds is the sub-set wherein E is a bond.

Another sub-set of compounds within formula (III') is the sub-set wherein E is $CH_2$ or $C(CH_3)_2$.

In one particularly preferred embodiment within formula (III'), E is a bond, R² is H and R¹ is a cycloalkyl group (i) as defined herein. In one embodiment the cycloalkyl group can be cyclopropyl or cyclobutyl. More preferably R¹ is a cyclopropyl group.

For the avoidance of doubt, it is to be understood that each general and specific preference, embodiment and example of the groups R¹ may be combined with each general and specific preference, embodiment and example of the groups R² and/or R³ and/or R⁴ and/or R⁵ and/or R⁶ and/or R⁷ and/or R⁸ and/or R⁹ and/or R¹⁰ and/or R¹¹ and/or D1 and/or D2 and/or A and/or E and/or X and/or $X^a$ and any sub-groups thereof as defined herein and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Compounds of Sub-Group (C) of Formula (I')

In one sub-group of compounds of the formula (I) for the new therapeutic uses of the invention (i.e. sub-group (C) of formula (I)), M is a group D1; X is O; A is a group NR² where R² is hydrogen; E is a bond; R¹ is 2,6-difluorophenyl; and the compound is an acid addition salt formed from a selected group of acids.

Accordingly, in one embodiment, the invention provides for the new therapeutic uses of the invention an acid addition salt of 1-(2,6-difluorophenyl)-N-[3-(5-morpholin-4-ylmethyl-1H-benzimidazol-2-yl)-1H-pyrazol-4-yl]-urea which is a salt formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, hydrochloric, isethionic, isobutyric, lactic (e.g. (+)-L-lactic and (±)-DL-lactic), lactobionic, laurylsulphonic, maleic, malic, (−)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

In one embodiment, the acid addition salt is formed from an acid selected from the group consisting of adipic, alginic, ascorbic (e.g. L-ascorbic), aspartic (e.g. L-aspartic), benzoic, camphoric (e.g. (+) camphoric), capric, caprylic, carbonic, cyclamic, dodecanoate, dodecylsulphuric, ethane-1,2-disulphonic, galactaric, gentisic, glucoheptonic, D-gluconic, glutamic (e.g. L-glutamic), α-oxoglutaric, glycolic, hippuric, isobutyric, laurylsulphonic, mucic, naphthalene-1,5-disulphonic, nicotinic, oleic, orotic, oxalic, palmitic, pamoic, sebacic, stearic, tartaric (e.g. (+)-L-tartaric), thiocyanic and xinafoic acids.

In another embodiment, the acid addition salt is formed from an acid selected from the group consisting of acetic, adipic, ascorbic, aspartic, citric, DL-lactic, fumaric, gluconic, glucuronic, hippuric, hydrochloric, glutamic, DL-malic, p-toluenesulphonic, methanesulphonic (mesylate), ethanesulphonic (esylate), sebacic, stearic, succinic and tartaric acids.

In a further embodiment, the acid addition salt is formed from an acid selected from the group consisting of adipic, ascorbic, aspartic, gluconic, hippuric, glutamic, sebacic, stearic and tartaric acids.

In another particular embodiment, the compound is an acid addition salt formed with hydrochloric acid.

Preferred salts for the new therapeutic uses of the invention are salts having a solubility in a given liquid carrier (e.g. water) of greater than 25 mg/ml of the liquid carrier (e.g. water), more typically greater than 50 mg/ml and preferably greater than 100 mg/ml. Such salts are particularly advantageous for administration in a liquid form, for example by injection or infusion.

Salts of the invention that have a solubility of greater than 25 mg/ml include the D-glucuronate, mesylate, esylate and DL-lactate salts, the latter three of which have solubilities in excess of 100 mg/ml.

Accordingly, in one particular embodiment, there is provided for the new therapeutic uses of the invention a mesylate salt of 1-(2,6-difluorophenyl)-N-[3-(5-morpholin-4-ylmethyl-1H-benzimidazol-2-yl)-1H-pyrazol-4-yl]-urea.

In another particular embodiment, there is provided for the new therapeutic uses of the invention an esylate (ethanesulphonate) salt of 1-(2,6-difluorophenyl)-N-[3-(5-morpholin-4-ylmethyl-1H-benzimidazol-2-yl)-1H-pyrazol-4-yl]-urea.

In a further particular embodiment, there is provided for the new therapeutic uses of the invention a DL lactate salt of 1-(2,6-difluorophenyl)-N-[3-(5-morpholin-4-ylmethyl-1H-benzimidazol-2-yl)-1H-pyrazol-4-yl]-urea. In one embodiment, the lactate salt is the L-lactate.

The free base or parent compound from which the compounds (i.e. acid addition salts) of sub-group (C) of Formula (I) of the invention are derived has the formula (IA):

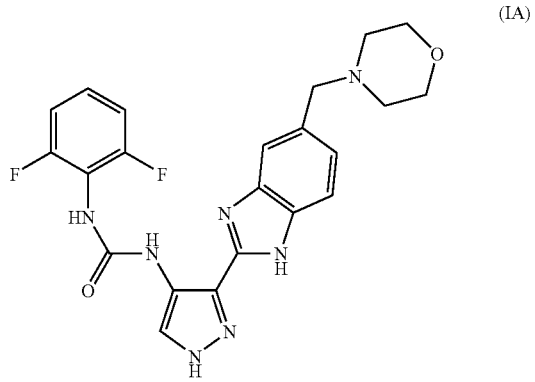 [SMILES: O=C(Nc1c[nH]nc1-c1nc2cc(CN3CCOCC3)ccc2[nH]1)Nc1c(F)cccc1F]

Particular compounds of the invention are as illustrated in the examples below.

One preferred compound for the new therapeutic uses of the invention is 1-cyclopropyl-3-[3-(5-morpholin-4-ylmethyl-1H-benzoimidazol-2-yl)-1H-pyrazol-4-yl]-urea and salts (e.g. the lactate or citrate salts or mixtures thereof), solvates and tautomers thereof.

In one embodiment, the salt of 1-cyclopropyl-3-[3-(5-morpholin-4-ylmethyl-1H-benzoimidazol-2-yl)-1H-pyrazol-4-yl]-urea may be the acetate, mesylate, ethanesulphonate, DL-lactate, adipate, D-glucuronate, D-gluconate or hydrochloride salt.

Other Aspects of the Invention

In other aspects of the invention, there are provided:

A compound of the formula (I) or (II') and sub-groups, embodiments and examples thereof as defined herein and as defined in PCT/GB2004/002824 (WO 2005/002552), and wherein $R^1$, $R^2$, $R^3$, $R^4$, A and X are as defined in PCT/GB2004/002824 (WO 2005/002552), and salts thereof (for example the acetate, mesylate, ethanesulphonate, DL-lactate, adipate, D-glucuronate, D-gluconate or hydrochloride salt) for use in the treatment of polycythemia vera, essential thrombocythemia, or idiopathic myelofibrosis.

A compound of the formula (I) or (I') and sub-groups, embodiments and examples thereof as defined herein and as defined in PCT/GB2004/002824 (WO 2005/002552), and wherein $R^1$, $R^2$, $R^3$, $R^4$, A and X are as defined in PCT/GB2004/002824 (WO 2005/002552), and salts thereof (for example the acetate, mesylate, ethanesulphonate, DL-lactate, adipate, D-glucuronate, D-gluconate or hydrochloride salt) for use in the treatment of juvenile myelomonocytic leukemia (JMML) or Chronic Myelomonocytic Leukemias (CMML).

A compound of the formula (I) or (I') and sub-groups, embodiments and examples thereof as defined herein or as defined in PCT/GB2004/002824 (WO 2005/002552), and wherein $R^1$, $R^2$, $R^3$, $R^4$, A and X are as defined in PCT/GB2004/002824 (WO 2005/002552), and salts thereof (for example the acetate, mesylate, ethanesulphonate, DL-lactate, adipate, D-glucuronate, D-gluconate or hydrochloride salt) for use in the treatment of megakaryocytic leukaemia including megakaryocytic AML (AML M7) or Philadelphia chromosome-negative or imatinib resistant CML.

A compound of the formula (I) or (I') and sub-groups, embodiments and examples thereof as defined herein and as defined in PCT/GB2004/002824 (WO 2005/002552), PCT/GB2004/002824 (WO 2005/002552), and wherein $R^1$, $R^2$, $R^3$, $R^4$, A and X are as defined in PCT/GB2004/002824 (WO 2005/002552), and salts thereof (for example the acetate, mesylate, ethanesulphonate, DL-lactate, adipate, D-glucuronate, D-gluconate or hydrochloride salt) for use in the treatment of gastrointestinal stromal tumors (GISTs), the hypereosinophilic syndrome or dermatofibrosarcoma protuberans The Compound of Formula (I⁰) and Salts and Crystalline Forms Thereof A particularly preferred compound falling within the scope of both formulae (I) and (I') above is the compound 1-cyclopropyl-3-[3-(5-morpholin-4-ylmethyl-1H-benzoimidazol-2-yl)-1H-pyrazol-4-yl]-urea and its salts, tautomers and crystalline forms.

The invention provides inter alia the lactate and citrate salts of the compound 1-cyclopropyl-3-[3-(5-morpholin-4-ylmethyl-1H-benzoimidazol-2-yl)-1H-pyrazol-4-yl]-urea and crystalline forms thereof for the new uses defined herein.

The invention also provides for use according to the invention the products of novel processes for preparing the compound, the lactate salts and crystalline forms thereof, as well as novel chemical intermediates for use in the processes.

The invention further provides therapeutic uses of the compound and its salts, as well as novel therapeutic uses of analogues of 1-cyclopropyl-3-[3-(5-morpholin-4-ylmethyl-1H-benzoimidazol-2-yl)-1H-pyrazol-4-yl]-urea.

More particularly, the invention provides for the novel uses described herein, a salt of 1-cyclopropyl-3-[3-(5-morpholin-4-ylmethyl-1H-benzoimidazol-2-yl)-1H-pyrazol-4-yl]-urea selected from the lactate, citrate and mixtures thereof.

The free base of 1-cyclopropyl-3-[3-(5-morpholin-4-ylmethyl-1H-benzoimidazol-2-yl)-1H-pyrazol-4-yl]-urea from which the salts are derived has the formula (I⁰):

(I⁰):

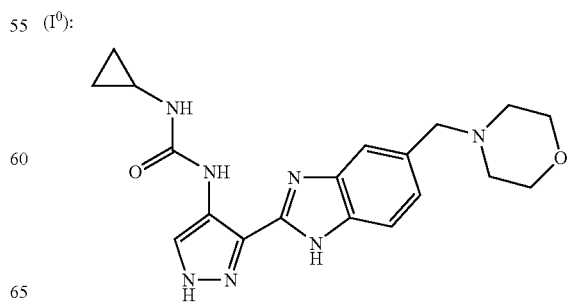

The compound of the formula (I⁰) may be referred to in this application by its chemical name, 1-cyclopropyl-3-[3-(5-morpholin-4-ylmethyl-1H-benzoimidazol-2-yl)-1H-pyrazol-4-yl]-urea, or, for convenience, as "the compound (I⁰)", "the compound of formula (I⁰)". Each of these synonyms refers to the compound shown in formula (I⁰) above and having the chemical name 1-cyclopropyl-3-[3-(5-morpholin-4-ylmethyl-1H-benzoimidazol-2-yl)-1H-pyrazol-4-yl]-urea.

References to the compound 1-cyclopropyl-3-[3-(5-morpholin-4-ylmethyl-1H-benzoimidazol-2-yl)-1H-pyrazol-4-yl]-urea free base and its lactate or citrate salts or mixtures thereof include within their scope all solvates, tautomers and isotopes thereof and, where the context admits, N-oxides, other ionic forms and prodrugs. Therefore reference to the alternative tautomer of formula (I), 1-cyclopropyl-3-[3-(6-morpholin-4-ylmethyl-1H-benzoimidazol-2-yl)-1H-pyrazol-4-yl]-urea is to be understood to refer to compound (I).

Lactate and Citrate Salts, Mixtures and Crystals of the compound of formula (I⁰)

For convenience the salts formed from L-lactic acid, and citric acid may be referred to herein as the L-lactate salts and citrate salts respectively.

In one particular embodiment the salt is the L-lactate or D-lactate, preferably L-lactate.

In another embodiment, the salt is a salt formed with citric acid.

More particularly the salts are a mixture of the L-lactate salts and citrate salts.

In the solid state, the lactate (particularly the L-lactate) or citrate salts of the invention can be crystalline or amorphous or a mixture thereof.

In one embodiment, the lactate (particularly the L-lactate) or citrate salts are amorphous.

In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

In another embodiment, the lactate (particularly the L-lactate) or citrate salts are substantially crystalline i.e. they may be from 50% to 100% crystalline, and more particularly they may be at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

In a further embodiment, the lactate or citrate salts are selected from the group consisting of lactate (particularly the L-lactate) or citrate salts that are from 50% to 100% crystalline, for example at least 50% crystalline, at least 60% crystalline, at least 70% crystalline, at least 80% crystalline, at least 90% crystalline, at least 95% crystalline, at least 98% crystalline, at least 99% crystalline, at least 99.5% crystalline, and at least 99.9% crystalline, for example 100% crystalline.

More preferably the lactate (particularly the L-lactate) or citrate salts may be those (or may be selected from the group consisting of those) that are 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

One example of a substantially crystalline salt is a crystalline salt formed with L-lactic acid.

Another example of a substantially crystalline salt is a crystalline salt formed with citric acid.

The salts of the invention, in the solid state, can be solvated (e.g. hydrated) or non-solvated (e.g. anhydrous).

In one embodiment, the salts are non-solvated (e.g. anhydrous).

A further example of a non-solvated salt is the crystalline salt formed with lactic acid (particularly L-lactic acid) as defined herein.

In one embodiment the crystalline form of the salt of Formula (I) is selected from L-lactate salt and citrate salt, in particular the L-lactate salt.

The term "anhydrous" as used herein does not exclude the possibility of the presence of some water on or in the salt (e.g. a crystal of the salt). For example, there may be some water present on the surface of the salt (e.g. salt crystal), or minor amounts within the body of the salt (e.g. crystal). Typically, an anhydrous form contains fewer than 0.4 molecules of water per molecule of compound, and more preferably contains fewer than 0.1 molecules of water per molecule of compound, for example 0 molecules of water.

In another embodiment, the lactate particularly the L-lactate) or citrate salts are solvated. Where the salts are hydrated, they can contain, for example, up to three molecules of water of crystallisation, more usually up to two molecules of water, e.g. one molecule of water or two molecules of water. Non-stoichiometric hydrates may also be formed in which the number of molecules of water present is less than one or is otherwise a non-integer. For example, where there is less than one molecule of water present, there may be for example 0.4, or 0.5, or 0.6, or 0.7, or 0.8, or 0.9 molecules of water present per molecule of compound.

Other solvates include alcoholates such as ethanolates and isopropanolates.

In one embodiment, the lactic acid salt (particularly the L-lactate) is solvated for example with water and/or ethanol.

The lactate (particularly the L-lactate) or citrate salts of the present invention can be synthesized from the parent compound 1-cyclopropyl-3-[3-(5-morpholin-4-ylmethyl-1H-benzoimidazol-2-yl)-1H-pyrazol-4-yl]-urea by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002.

Generally, such salts can be prepared by reacting the parent compound 1-cyclopropyl-3-[3-(5-morpholin-4-ylmethyl-1H-benzoimidazol-2-yl)-1H-pyrazol-4-yl]-urea with the appropriate acid in water or in an organic solvent, or in a mixture of the two; generally, non-aqueous media such as ether, ethyl acetate, ethanol, isopropanol, or acetonitrile are used.

In another aspect, the invention provides a method of preparing a lactate (particularly the L-lactate) or citrate salt of 1-cyclopropyl-3-[3-(5-morpholin-4-ylmethyl-1H-benzoimidazol-2-yl)-1H-pyrazol-4-yl]-urea, which method comprises forming a solution of 1-cyclopropyl-3-[3-(5-morpholin-4-ylmethyl-1H-benzoimidazol-2-yl)-1H-pyrazol-4-yl]-urea free base in a solvent (typically an organic solvent) or mixture of solvents, and treating the solution with an acid to form a precipitate of the salt.

The acid may be added as a solution in a solvent which is miscible with the solvent in which the free base is dissolved. The solvent in which the free base is initially dissolved may be one in which the salt thereof is insoluble. Alternatively, the solvent in which the free base is initially dissolved may be one in which the salt is at least partially soluble, a different solvent in which the salt is less soluble subsequently being added such that the salt precipitates out of solution.

In an alternative method of forming a salt, 1-cyclopropyl-3-[3-(5-morpholin-4-ylmethyl-1H-benzoimidazol-2-yl)-1H-pyrazol-4-yl]-urea is dissolved in a solvent comprising a volatile acid and optionally a co-solvent, thereby to form a solution of the salt with the volatile acid, and the resulting solution is then concentrated or evaporated to isolate the salt.

In another aspect, the invention provides a method of forming a lactate (particularly the L-lactate) or citrate salt of 1-cyclopropyl-3-[3-(5-morpholin-4-ylmethyl-1H-benzoimidazol-2-yl)-1H-pyrazol-4-yl]-urea as defined herein, which method comprises treating a compound of the formula (I):

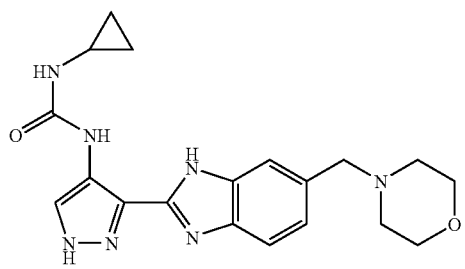

(I)

with an organic or inorganic acid as defined herein in an organic solvent, and optionally isolating the salt thus formed.

The lactate particularly the L-lactate) or citrate salt is typically precipitated from the organic solvent as it is formed and hence can be isolated by separation of the solid from the solution, e.g. by filtration.

One salt form of the invention can be converted to the free base and optionally to another salt form by methods well known to the skilled person. For example, the free base can be formed by passing the salt solution through a column containing an amine stationary phase (e.g. a Strata-NH$_2$ column). Alternatively, a solution of the salt in water can be treated with sodium bicarbonate to decompose the salt and precipitate out the free base. The free base may then be combined with another acid by one of the methods described above or elsewhere herein.

The lactate (particularly the L-lactate) or citrate salts have a number of advantages over the corresponding free base. For example, the salts will enjoy one or more of the following advantages over the free base in that they:
 will be more soluble in particular they will have improved solubility in aqueous solution and hence will be better for i.v. administration (e.g. by infusion)
 will allow control of solution pH and therefore better for i.v. administration;
 will have better stability for example thermal stabililty (e.g. improved shelf life);
 will have advantages for production;
 will have better physicochemical properties;
 may have improved anti-cancer activity; and
 may have an improved therapeutic index.

The crystalline lactate salt (particularly the L-lactate) of the invention is particularly advantageous as it is:
 non-hygroscopic
 anhydrous and does not form hydrates
 single polymorphic form
 crystalline
 stable to storage
 has sharp melting point and no form changes in DSC experiment.
 has good solubility in water, and gives better solubility in buffer systems.

The term 'stable' or 'stability' as used herein includes chemical stability and solid state (physical) stability. The term 'chemical stability' means that the compound can be stored in an isolated form, or in the form of a formulation in which it is provided in admixture with for example, pharmaceutically acceptable carriers, diluents or adjuvants as described herein, under normal storage conditions, with little or no chemical degradation or decomposition. 'Solid-state stability' means the compound can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g. hydration, dehydration, solvatisation, desolvatisation, crystallisation, recrystallisation or solid-state phase transition).

Preferred salts for use in the preparation of liquid (e.g. aqueous) pharmaceutical compositions are the salts of the invention (i.e. the lactate or citrate or mixtures thereof as defined herein) having a solubility in a given liquid carrier (e.g. water or buffered systems) of greater than 1 mg/ml, typically greater than 5 mg/ml of the liquid carrier (e.g. water), more typically greater than 15 mg/ml, more typically greater than 20 mg/ml and preferably greater than 25 mg/ml.

In another aspect, there is provided, for the novel uses as defined herein, a pharmaceutical composition comprising an aqueous solution containing the lactate salt (particularly the L-lactate) or citrate salt or mixtures thereof of 1-cyclopropyl-3-[3-(5-morpholin-4-ylmethyl-1H-benzoimidazol-2-yl)-1H-pyrazol-4-yl]-urea (such as) in a concentration of greater than 1 mg/ml, typically greater than 5 mg/ml of the liquid carrier (e.g. water or buffered systems), more typically greater than 15 mg/ml, more typically greater than 20 mg/ml and preferably greater than 25 mg/ml.

In a preferred embodiment, the pharmaceutical composition comprises an aqueous solution containing the L-lactate salt of 1-cyclopropyl-3-[3-(5-morpholin-4-ylmethyl-1H-benzoimidazol-2-yl)-1H-pyrazol-4-yl]-urea in a concentration of greater than 1 mg/ml, typically greater than 5 mg/ml of the liquid carrier (e.g. water), more typically greater than 15 mg/ml, typically, greater than 20 mg/ml and preferably greater than 25 mg/ml.

In another aspect, the invention provides, for the novel uses as defined herein, an aqueous solution of the lactate salt (particularly the L-lactate) or citrate salt or mixtures thereof of 1-cyclopropyl-3-[3-(5-morpholin-4-ylmethyl-1H-benzoimidazol-2-yl)-1H-pyrazol-4-yl]-urea, wherein the aqueous solution has a pH of 2 to 6, for example 2 to 5, and more particularly 4 to 6 such as 4 to 5.

In the aqueous solutions defined above, the salt may be any of the salts described herein but, in one preferred embodiment is the L-lactate salt. In one preferred embodiment, the salt is a mixture of L-lactate and citrate salts.

The invention also provides, for the novel uses as defined herein, an aqueous solution of 1-cyclopropyl-3-[3-(5-morpholin-4-ylmethyl-1H-benzoimidazol-2-yl)-1H-pyrazol-4-yl]-urea in protonated form together with one or more counter ions and optionally one or more further counter ions. In one embodiment one of the counter ions is selected from lactate and citrate. In another embodiment one of the counter ions is from the formulation buffer as described herein such as citrate. In a further embodiment there may be one or more further counter ions such as a chloride ion (e.g. from saline).

The invention therefore provides, for the novel uses as defined herein, an aqueous solution of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate, and optionally one or more further counter ions such as a chloride ion.

In the situation where there is more than one counter ions the aqueous solution of 1-cyclopropyl-3-[3-(5-morpholin-4-ylmethyl-1H-benzoimidazol-2-yl)-1H-pyrazoyl-4-yl]-urea in protonated form will potentially contain a mixture of counter ions for example a mixture of L-lactate and citrate counter ions and optionally one or more further counter ions such as a chloride ion.

The invention therefore provides, for the novel uses as defined herein, an aqueous solution of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate and optionally one or more further counter ions such as a chloride ion, and a mixture thereof.

The invention also provides, for the novel uses as defined herein, an aqueous solution of 1-cyclopropyl-3-[3-(5-morpholin-4-ylmethyl-1H-benzoimidazol-2-yl)-1H-pyrazoyl-4-yl]-urea in protonated form together with one or more counter ions and optionally one or more IV excipients for dilution to achieve isotonic formulation. In one embodiment one of the counter ions is selected from L-lactate and citrate. In another embodiment one of the counter ions is from the formulation buffer as described herein such as citrate. In a further embodiment there may be one or more IV excipients as detailed in the United States Pharmacopeia and the National Formulary such as a hexose sugar e.g. dextrose (D-glucose). The invention therefore provides an aqueous solution of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate, and optionally one or more IV excipients such as dextrose. In the situation where there is more than one counter ions the aqueous solution of 1-cyclopropyl-3-[3-(5-morpholin-4-ylmethyl-1H-benzoimidazol-2-yl)-1H-pyrazol-4-yl]-urea in protonated form will potentially contain a mixture of counter ions for example a mixture of lactate and citrate counter ions and optionally one or more further IV excipients such as a dextrose. The invention therefore provides an aqueous solution of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate and optionally one or more further IV excipients such as a dextrose, and a mixture thereof.

The aqueous solutions can be formed inter alia by dissolving a lactate salt in a solution of citrate ions (e.g. a citrate buffer) or by dissolving a citrate salt in a solution of lactate ions. The lactate and citrate ions may be present in the solution in a lactate:citrate ratio of from 10:1 or less, for example 10:1 to 1:10, more preferably less then 8:1, or less than 7:1, or less than 6:1, or less than 5:1 or less than 4:1 or less than 3:1 or less than 2:1 or less than 1:1, more particularly from 1:1 to 1:10. In one embodiment, the lactate and citrate ions are present in the solution in a lactate:citrate ratio of from 1:1 to 1:10, for example 1:1 to 1:8, or 1:1 to 1:7 or 1:1 to 1:6 or 1:1 to 1:5, e.g. approximately 1:4.4.

The aqueous solutions of the salts may be buffered or unbuffered but in one embodiment are buffered.

In another aspect, there is provided, for the novel uses of the invention as defined herein, a pharmaceutical composition comprising a lyophilised formulation containing the lactate salt or citrate salt or mixtures thereof of 1-cyclopropyl-3-[3-(5-morpholin-4-ylmethyl-1H-benzoimidazol-2-yl)-1H-pyrazol-4-yl]-urea, wherein the formulation has a pH of 2 to 6, for example 2 to 5, and more particularly 4 to 6 such as 4 to 5.

In one preferred embodiment the lyophilised formulation defined above, the salt is the L-lactate.

The invention also provides, for the novel uses of the invention as defined herein, a lyophilised formulation of 1-cyclopropyl-3-[3-(5-morpholin-4-ylmethyl-1H-benzoimidazol-2-yl)-1H-pyrazol-4-yl]-urea in protonated form together with one or more counter ions. In one embodiment one of the counter ions is L-lactate. In another embodiment one of the counter ions is from the formulation buffer as described herein such as citrate.

The invention therefore provides, for the novel uses of the invention as defined herein, a lyophilised formulation of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate. In the situation where there is more than one counter ions the aqueous solution of 1-cyclopropyl-3-[3-(5-morpholin-4-ylmethyl-1H-benzoimidazol-2-yl)-1H-pyrazol-4-yl]-urea in protonated form will potentially contain a mixture of counter ions for example a mixture of L-lactate and citrate counter ions.

The invention therefore provides, for the novel uses of the invention as defined herein, a lyophilised formulation of 1-cyclopropyl-3-[3-(5-morpholin-4-ylmethyl-1H-benzoimidazol-2-yl)-1H-pyrazol-4-yl]-urea in protonated form together with one or more counter ions selected from lactate, citrate and a mixture thereof.

In one preferred embodiment the lyophilised formulation defined above, the salt is a L-lactate and the buffer salt is citrate.

In one embodiment, the lactate and citrate ions are present in the lyophilised formulation in a lactate:citrate ratio of from 10:1 or less, for example 10:1 to 1:10, more preferably less then 8:1, or less than 7:1, or less than 6:1, or less than 5:1 or less than 4:1 or less than 3:1 or less than 2:1 or less than 1:1, more particularly from 1:1 to 1:10, for example 1:1 to 1:8, or 1:1 to 1:7 or 1:1 to 1:6 or 1:1 to 1:5, e.g. approximately 1:4.4.

The lyophilised formulation of the salts may be buffered or unbuffered but in one embodiment are buffered.

In the context of the salt formed with lactic acid, a preferred buffer is a buffer formed from citric acid and corrected with NaOH or HCl to the correct pH, for example at a solution pH of approximately 4.5. At this pH and in the citrate buffer, the free base has a solubility of about 80 mg/ml respectively.

The lyophilised formulation is then reconstituted into a sterile aqueous solution containing an IV excipient such as saline or dextrose, preferably dextrose.

The salts of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms therefore also form part of the invention.

The compound 1-cyclopropyl-3-[3-(5-morpholin-4-ylmethyl-1H-benzoimidazol-2-yl)-1H-pyrazol-4-yl]-urea may also form N-oxides. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compound 1-cyclopropyl-3-[3-(5-morpholin-4-ylmethyl-1H-benzoimidazol-2-yl)-1H-pyrazol-4-yl]-urea, from which the lactate or citrate salts of the invention are derived, may exist in a number of different tautomeric forms and references in this application to the compound include all such forms.

More particularly, in the lactate or citrate salts of 1-cyclopropyl-3-[3-(5-morpholin-4-ylmethyl-1H-benzoimidazol-2-yl)-1H-pyrazol-4-yl]-urea of the invention, the benzoimidazole group may take either of the following two tautomeric forms A and B. For simplicity, the general formula (I) illustrates forms A but the formula is to be taken as embracing all four tautomeric forms.

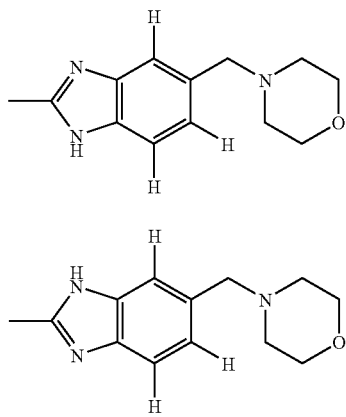

Moreover, in the context of the lactate or citrate salts of 1-cyclopropyl-3-[3-(6-morpholin-4-ylmethyl-1H-benzoimidazol-2-yl)-1H-pyrazol-4-yl]-urea, references to the alternative tautomer, are clearly references to the lactate or citrate salts of the same compound as 1-cyclopropyl-3-[3-(5-morpholin-4-ylmethyl-1H-benzoimidazol-2-yl)-1H-pyrazol-4-yl]-urea.

The pyrazole ring may also exhibit tautomerism and can exist in the two tautomeric forms C and D below.

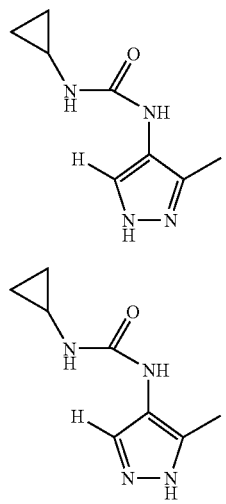

In addition cis and trans conformations of the urea are possible.

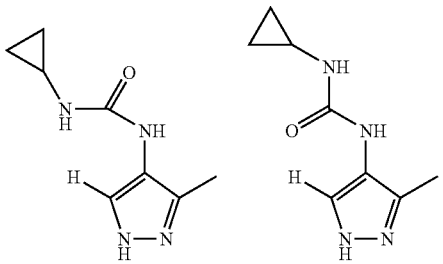

References to the lactate or citrate salts (e.g. the L-lactate salt) of 1-cyclopropyl-3-[3-(5-morpholin-4-ylmethyl-1H-benzoimidazol-2-yl)-1H-pyrazol-4-yl]-urea and the salts of the invention also include variants with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Also encompassed by references to 1-cyclopropyl-3-[3-(5-morpholin-4-ylmethyl-1H-benzoimidazol-2-yl)-1H-pyrazol-4-yl]-urea and the salts of the invention are any polymorphic forms, solvates (e.g. hydrates), complexes (e.g. inclusion complexes or clathrates with compounds such as cyclodextrins, or complexes with metals) thereof.

Crystal Structures of 1-Cyclopropyl-3-[3-(5-morpholin-4-ylmethyl-1H-benzoimidazol-2-yl)-1H-pyrazol-4-yl]-urea As described above, the lactate or citrate salts of 1-cyclopropyl-3-[3-(5-morpholin-4-ylmethyl-1H-benzoimidazol-2-yl)-1H-pyrazol-4-yl]-urea can be amorphous or substantially crystalline. In one particular embodiment, the lactate or citrate salts are substantially crystalline, the term "substantially crystalline" having the meaning defined above. In particular the lactate salt of 1-cyclopropyl-3-[3-(5-morpholin-4-ylmethyl-1H-benzoimidazol-2-yl)-1H-pyrazol-4-yl]-urea is substantially crystalline.

The crystals described herein and the crystal structures and their employment for the novel uses of the invention as defined herein form further aspects of the invention.

Where the lactate salt (particularly the L-lactate) of 1-cyclopropyl-3-[3-(5-morpholin-4-ylmethyl-1H-benzoimidazol-2-yl)-1H-pyrazol-4-yl]-urea is substantially crystalline, one single crystalline form may predominate, although other crystalline forms may be present in minor and preferably negligible amounts.

The crystalline forms of 1-cyclopropyl-3-[3-(5-morpholin-4-ylmethyl-1H-benzoimidazol-2-yl)-1H-pyrazol-4-yl]-urea contain less than or equal to about 5% by weight other crystalline forms of 1-cyclopropyl-3-[3-(5-morpholin-4-ylmethyl-1H-benzoimidazol-2-yl)-1H-pyrazol-4-yl]-urea, in particular containing less than or equal to about 1% by weight of other crystalline forms.

In a preferred embodiment, the invention provides a substantially crystalline salt (e.g. a lactate salt (particularly the L-lactate) as defined herein) of 1-cyclopropyl-3-[3-(5-morpholin-4-ylmethyl-1H-benzoimidazol-2-yl)-1H-pyrazol-4-yl]-urea containing a single crystalline form of the salt and no more than 5% by weight of any other crystalline forms of the salt.

Preferably, the single crystalline form is accompanied by less than 4%, or less than 3%, or less than 2% of other crystalline forms, and in particular contains less than or equal to about 1% by weight of other crystalline forms. More preferably, the single crystalline form is accompanied by less than 0.9%, or less than 0.8%, or less than 0.7%, or less than 0.6%, or less than 0.5%, or less than 0.4%, or less than 0.3%, or less than 0.2%, or less than 0.1%, or less than 0.05%, or less than 0.01%, by weight of other crystalline forms, for example 0% by weight of other crystalline forms.

The crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD.

Determination of the crystal structure of a compound can be performed by X-ray crystallography which can be carried out according to the conventional methods such as those described herein and in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal.

The crystal structure of the lactate salt and the dihydrate free base of 1-cyclopropyl-3-[3-(5-morpholin-4-ylmethyl-1H-benzoimidazol-2-yl)-1H-pyrazol-4-yl]-urea has been determined by X-ray crystallography—see Examples 5 and 7 below.

Tables 1 and 3 give coordinate data for crystals of 1-cyclopropyl-3-[3-(5-morpholin-4-ylmethyl-1H-benzoimidazol-2-yl)-1H-pyrazol-4-yl]-urea in Crystallographic Information File (CIF) Format (see Hall, Allen and Brown, *Acta Cryst.* (1991). A47, 655-685; http://www.iucr.ac.uk/iucr-top/cif/home.html). Alternative file formats such as a PDB file format (e.g. format consistent with that of the EBI Macromolecular Structure Database (Hinxton, UK)) may be used or preferred by others of skill in the art. However it will be apparent that the use of a different file format to present or manipulate the coordinates of the Tables is within the scope of the present invention. The numbers in brackets in the Tables represents the deviation (s.u., standard uncertainty). The crystal structure of the lactate salt is illustrated in FIGS. 4 and 5.

In one embodiment the invention provides, for the novel uses of the invention as defined herein, a lactate salt (particularly the L-lactate) of 1-cyclopropyl-3-[3-(5-morpholin-4-yl-methyl-1H-benzoimidazol-2-yl)-1H-pyrazol-4-yl]-urea which is crystalline and has a crystal structure as defined by the coordinates in Table 3 herein.

In another embodiment the invention provides, for the novel uses of the invention as defined herein, a lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and has a crystal structure as set out in FIGS. 4 and 5.

In another embodiment the invention provides, for the novel uses of the invention as defined herein, a lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and has a crystal structure that belongs belong to an orthorhombic space group $P2_12_12_1$ (# 19) and has crystal lattice parameters at 97 (2) K a=9.94 (10), b=15.03 (10), c=16.18 (10) Å, $\alpha=\beta=\gamma=90°$.

In another embodiment the invention provides, for the novel uses of the invention as defined herein, a lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and has crystal lattice parameters at room temperature a=10.08 (10), b=15.22 (10), c=16.22 (10) Å, $\alpha=\beta=\gamma=90°$.

Accordingly, in another embodiment, the invention provides, for the novel uses of the invention as defined herein, a lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and:
 (a) has a crystal structure as set out in FIGS. 4 and 5; and/or
 (b) has a crystal structure as defined by the coordinates in Table 3 herein; and/or
 (c) has crystal lattice parameters at 97 (2) K a=9.94 (10), b=15.03 (10), c=16.18 (10) Å, $\alpha=\beta=\gamma=90°$; and/or
 (d) has crystal lattice parameters at room temperature a=10.08 (10), b=15.22 (10), c=16.22 (10) Å, $\alpha=\beta=\gamma=90°$; and/or
 (e) has a crystal structure that belongs belong to an orthorhombic space group $P2_12_12_1$ (#19).

The substantially crystalline salts preferably are substantially free of residual organic solvent used, e.g. to recrystallise or otherwise purify the salt, or other solvent such as water.

In one embodiment the crystals of the lactate salt (particularly the L-lactate) of the compounds of Formula (I) and (I'), in particular lactate salt of 1-cyclopropyl-3-[3-(5-morpholin-4-ylmethyl-1H-benzoimidazol-2-yl)-1H-pyrazol-4-yl]-urea are crystals which contain less than 10% by weight of residual solvent (e.g. water or an organic solvent), for example less than 5% residual solvent.

In one embodiment, the crystalline salts (e.g. the lactate salts-particularly the L-lactate) are anhydrous, the term "anhydrous" having the meaning defined above.

In another embodiment the crystalline lactate salt of 1-cyclopropyl-3-[3-(5-morpholin-4-ylmethyl-1H-benzoimidazol-2-yl)-1H-pyrazol-4-yl]-urea contains residual organic solvent e.g. ethanol in the range of about 0 to 5% by weight for example about 2% ethanol.

Alternatively, the crystalline structure of a compound can be analysed by the solid state technique of X-ray Powder Diffraction (XRPD). XRPD can be carried out according to the conventional methods such as those described herein (see Examples 6 and 8) and in Introduction to X-ray Powder Diffraction, Ron Jenkins and Robert L. Snyder (John Wiley & Sons, New York, 1996). The presence of defined peaks (as opposed to random background noise) in an XRPD diffractogram indicates that the compound has a degree of crystallinity.

A compound's X-ray powder pattern is characterised by the diffraction angle (2θ) and/or interplanar spacing (d) parameters of an X-ray diffraction spectrum or pattern. These are related by Bragg's equation, nλ=2d Sin θ, (where n=1; %=wavelength of the radiation or cathode used; d=interplanar spacing; and θ=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually mean ones which coincide in the range of 2θ±0.2°. The peaks mean main peaks and include peaks not larger than medium at diffraction angles other than those stated above.

Both the lactate salt and free base forms of 1-cyclopropyl-3-[3-(5-morpholin-4-ylmethyl-1H-benzoimidazol-2-yl)-1H-pyrazol-4-yl]-urea have been characterised by XRPD. In each case, the powder X-ray diffraction patterns are expressed in terms of the diffraction angle (2θ), inter planar spacing (d) and/or relative intensities. Tables 2, 3 and 4 show the interplanar spacing (d) values of the X-ray diffraction spectrum that correspond to the diffraction angle values of the free base, lactate salt and dihydrate free base forms of 1-cyclopropyl-3-[3-(5-morpholin-4-ylmethyl-1H-benzoimidazol-2-yl)-1H-pyrazol-4-yl]-urea.

Therefore 1-cyclopropyl-3-[3-(5-morpholin-4-ylmethyl-1H-benzoimidazol-2-yl)-1H-pyrazol-4-yl]-urea has X-ray powder diffraction patterns essentially as shown in FIG. 3, 6, 7 or 8 and/or Tables 2, 4 or 5.

The invention therefore provides, for the novel uses of the invention as defined herein, crystals of salts (e.g. lactate—particularly the L-lactate) of 1-cyclopropyl-3-[3-(5-morpholin-4-ylmethyl-1H-benzoimidazol-2-yl)-1H-pyrazol-4-yl]-urea having an X-ray powder diffraction patterns which are substantially as in FIG. 3, 6, 7 or 8. Preferably the compound of the present invention is a compound which exhibits peaks at the same diffraction angles as those of the X-ray powder diffraction pattern shown in FIG. 3, 6, 7 or 8 and/or Table 2 and/or Table 4 and/or Table 5 and optionally has same the relative intensity.

The invention further provides, for the novel uses of the invention as defined herein, a crystal of 1-cyclopropyl-3-[3-(5-morpholin-4-ylmethyl-1H-benzoimidazol-2-yl)-1H-pyrazol-4-yl]-urea lactic acid salt (particularly the L-lactate) which has an X-ray powder diffraction pattern essentially as shown in FIG. 6. Accordingly, in another embodiment, the invention provides, for the novel uses of the invention as defined herein, a substantially crystalline lactate salt (particularly the L-lactate) of 1-cyclopropyl-3-[3-(5-morpholin-4-ylmethyl-1H-benzoimidazol-2-yl)-1H-pyrazol-4-yl]-urea which exhibits peaks at the same diffraction angles as those of the X-ray powder diffraction pattern shown in FIG. 6. Preferably the peaks have the same relative intensity as the peaks in FIG. 6. Therefore the invention provides, for the novel uses of the invention as defined herein, a substantially crystalline lactic acid salt (particularly the L-lactate) of 1-cyclopropyl-3-[3-(5-morpholin-4-ylmethyl-1H-benzoimidazol-2-yl)-1H-pyrazol-4-yl]-urea having an X-ray powder diffraction pattern substantially as shown in FIG. 6.

The X-ray powder diffraction pattern of the lactate salt may be characterised by the presence of peaks at the diffraction angles (2θ) and interplanar spacings (d), and preferably the intensities shown in Table 4.

Therefore the invention provides, for the novel uses of the invention as defined herein, a crystal of cyclopropyl-3-[3-(6-morpholin-4-ylmethyl-1H-benzoimidazol-2-yl)-1H-pyrazol-4-yl]-urea lactate (particularly the L-lactate), which shows an X-ray powder diffraction pattern having characteristic peaks at a diffraction angle (2θ±1.0 degree such as ±0.2 degree, in particular ±0.1 degree) of Table 4.

The invention also provides, for the novel uses of the invention as defined herein, crystals of cyclopropyl-3-[3-(6-morpholin-4-ylmethyl-1H-benzoimidazol-2-yl)-1H-pyrazol-4-yl]-urea lactate salt (particularly the L-lactate) having an X-ray powder diffraction pattern showing major peaks of diffraction angles 2θ of 17.50, 18.30, 19.30, 19.60, and 21.85±1.0 degree such as ±0.2 degree, in particular ±0.1 degree.

Therefore in one embodiment the invention provides, for the novel uses of the invention as defined herein, a crystalline form of cyclopropyl-3-[3-(6-morpholin-4-ylmethyl-1H-benzoimidazol-2-yl)-1H-pyrazol-4-yl]-urea lactate salt (particularly the L-lactate) characterized by peaks in the X-ray diffraction pattern at 12.40, 15.20, 15.60, 17.50, 18.30, 18.50, 19.30, 19.60, 21.85, and 27.30±1.0 degrees two-theta.

The crystal of cyclopropyl-3-[3-(6-morpholin-4-ylmethyl-1H-benzoimidazol-2-yl)-1H-pyrazol-4-yl]-urea lactate salt (particularly the L-lactate) is also characterised in that the characterisitic X-ray powder diffraction pattern is represented by the spacings between lattice planes, d (Å) of Table 4.

In a further embodiment the invention provides, for the novel uses of the invention as defined herein, a crystal of cyclopropyl-3-[3-(6-morpholin-4-ylmethyl-1H-benzoimidazol-2-yl)-1H-pyrazol-4-yl]-urea lactate salt (particularly the L-lactate), which possess an X-ray powder diffraction pattern whose characteristic peaks appear as the lattice spacing (d) of the powder X-ray diffraction at 5.06, 4.85, 4.60, 4.53, and 4.07, more particularly lattice spacing (d) of the powder X-ray diffraction at 7.13, 5.83, 5.68, 5.06, 4.85, 4.79, 4.60, 4.53, 4.07, and 3.26 angstrom.

Therefore, in another embodiment, the invention provides, for the novel uses of the invention as defined herein, a substantially crystalline L-lactate salt (particularly the L-lactate) of 1-cyclopropyl-3-[3-(5-morpholin-4-ylmethyl-1H-benzoimdazol-2-yl)-1H-pyrazol-4-yl]-urea having an X-ray powder diffraction pattern characterised by the presence of major peaks at the diffraction angles (2θ) of 17.50, 18.30, 19.30, 19.60, and 21.85 degrees, more particularly 12.40, 15.20, 15.60, 17.50, 18.30, 18.50, 19.30, 19.60, 21.85, and 27.30 degrees, and interplanar spacings (d) of 5.06, 4.85, 4.60, 4.53, and 4.07, more particularly 7.13, 5.83, 5.68, 5.06, 4.85, 4.79, 4.60, 4.53, 4.07, and 3.26 angstrom.

In a further embodiment, the invention provides, for the novel uses of the invention as defined herein, a substantially crystalline L-lactate salt of 1-cyclopropyl-3-[3-(5-morpholin-4-ylmethyl-1H-benzoimidazol-2-yl)-1H-pyrazol-4-yl]-urea having an X-ray powder diffraction pattern characterised by the presence of peaks at the diffraction angles (2θ) and interplanar spacings (d), and preferably the intensities shown in Table 4.

The crystalline salts of the invention can also be characterised by differential scanning calorimetry (DSC).

The lactate salt has been analysed by DSC and exhibits onset at 190° C. and a peak at 194-197° C.

Accordingly, in another aspect, the invention provides, for the novel uses of the invention as defined herein, a lactate salt (particularly the L-lactate) of which is anhydrous and exhibits onset at 190° C. and/or an endothermic peak at 194-197° C. when subjected to DSC.

The term "onset" as used herein in connection with DSC refers to the start of an endothermic peak in the DSC scan, where the peak is the point of maximum heat output.

Therefore a further aspect of the invention concerns the novel uses of the lactate salt (particularly the L-lactate) of 1-cyclopropyl-3-[3-(5-morpholin-4-ylmethyl-1H-benzoimidazol-2-yl)-1H-pyrazol-4-yl]-urea which exhibits peaks at the same diffraction angles as those of the X-ray powder diffraction pattern shown in FIG. 6, 7 or 8 and further exhibits onset at 190° C. and/or an endothermic peak accompanying decomposition in the vicinity of peak at 194-197° C. according to thermal analysis (DSC).

The behaviour of the salts of the invention in conditions of high humidity can be analysed by standard gravimetric vapour sorption (GVS) methods, for example as described in Example 4.

The lactate salt can exist in a stable anhydrous crystalline form in conditions of high relative humidity does not undergo changes in crystal structure under such conditions.

The salts of the invention can be further characterised by infra-red spectroscopy, e.g. FTIR.

The infra-red spectrum of the lactate salt (KBr disc method) contains characteristic peaks at 3229, 2972 and 1660 $cm^{-1}$.

Accordingly, in a further embodiment, the invention provides, for the novel uses of the invention as defined herein, a (preferably substantially crystalline) lactic acid salt (particularly the L-lactate) of 1-cyclopropyl-3-[3-(5-morpholin-4-ylmethyl-1H-benzoimidazol-2-yl)-1H-pyrazol-4-yl]-urea that exhibits an infra-red spectrum, when analysed using the KBr disc method, that contains characteristic peaks at 3229, 2972 and 1660 $cm^{-1}$.

As will be evident from the foregoing paragraphs, the lactate salt particularly the L-lactate) of the invention can be characterised by a number of different physicochemical parameters. Accordingly, in a preferred embodiment, the invention provides a L-lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and is characterised by any one or more (in any combination) or all of the following parameters, namely that the salt:

(a) has a crystal structure as set out in FIGS. 4 and 5; and/or
(b) has a crystal structure as defined by the coordinates in Table 3 herein; and/or
(c) has crystal lattice parameters at 97 (2) K a=9.94 (10), b=15.03 (10), c=16.18 (10) Å, $\alpha=\beta=\gamma=90°$; and/or
(d) has crystal lattice parameters at room temperature a=10.08 (10), b=15.22 (10), c=16.22 (10) Å, $\alpha=\beta=\gamma=90°$; and/or
(e) has a crystal structure that belongs belong to an orthorhombic space group $P2_12_12_1$ (# 19); and/or
(f) has an X-ray powder diffraction pattern characterised by the presence of major peaks at the diffraction angles (2θ) of 17.50, 18.30, 19.30, 19.60, and 21.85 degrees, more particularly 12.40, 15.20, 15.60, 17.50, 18.30, 18.50, 19.30, 19.60, 21.85, and 27.30 degrees, and/or interplanar spacings (d) of 5.06, 4.85, 4.60, 4.53, and 4.07, more particularly 7.13, 5.83, 5.68, 5.06, 4.85, 4.79, 4.60, 4.53, 4.07, and 3.26 angstrom; and/or
(g) exhibits peaks at the same diffraction angles as those of the X-ray powder diffraction pattern shown in FIG. 6 or Table 4 and optionally wherein the peaks have the same relative intensity as the peaks in FIG. 6; or Table 4 and/or
(h) has an X-ray powder diffraction pattern substantially as shown in FIG. 6; and/or
(i) is anhydrous and exhibits onset at 190° C. and/or an endothermic peak at 194-197° C. when subjected to DSC; and/or
(j) exhibits an infra-red spectrum, when analysed using the KBr disc method, that contains characteristic peaks at 3229, 2972 and 1660 $cm^{-1}$.

Crystal Structures of 1-Cyclopropyl-3-[3-(5-morpholin-4-ylmethyl-1H-benzoimidazol-2-yl)-1H-pyrazol-4-yl]-urea free base The free base of 1-cyclopropyl-3-[3-(5-morpholin-4-ylmethyl-1H-benzoimidazol-2-yl)-1H-pyrazol-4-yl]-urea can also be amorphous or substantially crystalline. In one particular embodiment, the free base is substantially crystalline, the term "substantially crystalline" having the meaning defined above. In one embodiment, the free base of 1-cyclopropyl-3-[3-(5-morpholin-4-ylmethyl-1H-benzoimidazol-2-yl)-1H-pyrazol-4-yl]-urea exists in a dihydrate crystalline form.

The novel uses of crystals described herein and the crystal structures form further aspects of the invention.

The crystal structure of the free base dihydrate of 1-cyclopropyl-3-[3-(5-morpholin-4-ylmethyl-1H-benzoimidazol-2-yl)-1H-pyrazol-4-yl]-urea has been determined by X-ray crystallography.

In one embodiment, the invention provides, for the novel uses of the invention as defined herein, the dihydrate free base of 1-cyclopropyl-3-[3-(5-morpholin-4-ylmethyl-1H-benzoimidazol-2-yl)-1H-pyrazol-4-yl]-urea which is crystalline and (i) has a crystal structure as defined by the coordinates in Table 2 herein; and/or (ii) wherein the crystals belong to a monoclinic space group $P2_1/n$ (# 14) with crystal lattice parameters a=7.66 (10), b=15.18 (10), c=17.71 (10) Å, $\beta=98.53 (2)°$, $\alpha=\gamma=90°$.

The free base forms of 1-cyclopropyl-3-[3-(5-morpholin-4-ylmethyl-1H-benzoimidazol-2-yl)-1H-pyrazol-4-yl]-urea have been characterised by XRPD. Therefore free base forms of 1-cyclopropyl-3-[3-(5-morpholin-4-ylmethyl-1H-benzoimidazol-2-yl)-1H-pyrazol-4-yl]-urea have X-ray powder diffraction patterns essentially as shown in FIG. 3, 6, 7 or 8 and/or Tables 3, 5 or 6 in Examples 70 and 72.

Accordingly, in one embodiment, the invention provides, for the novel uses of the invention as defined herein, crystals of 1-cyclopropyl-3-[3-(5-morpholin-4-ylmethyl-1H-benzoimidazol-2-yl)-1H-pyrazol-4-yl]-urea free base exhibiting X-ray powder diffraction patterns containing peaks at the same diffraction angles as those of the X-ray powder diffraction pattern shown in FIG. 3, 6, 7 or 8 and/or Table 3 and/or Table 5 and/or Table 6 and wherein the peaks optionally have the same relative intensity.

The invention also provides, for the novel uses of the invention as defined herein, a crystal of 1-cyclopropyl-3-[3-(5-morpholin-4-ylmethyl-1H-benzoimidazol-2-yl)-1H-pyrazol-4-yl]-urea free base, which shows an X-ray powder diffraction pattern having characteristic peaks at a diffraction angle (2θ±1.0 degree such as ±0.2 degree, in particular ±0.1 degree) of Table 2.

In a further embodiment the invention, for the novel uses of the invention as defined herein, provides a crystal of 1-cyclopropyl-3-[3-(5-morpholin-4-ylmethyl-1H-benzoimidazol-2-yl)-1H-pyrazol-4-yl]-urea free base, which possess an X-ray powder diffraction pattern whose characteristic peaks appear as the lattice spacing (d) of Table 2.

The free base of 1-cyclopropyl-3-[3-(5-morpholin-4-ylmethyl-1H-benzoimidazol-2-yl)-1H-pyrazol-4-yl]-urea exhibits peaks at the same diffraction angles as those of the X-ray powder diffraction pattern shown in FIG. 3 and/or Table 2 and further exhibits an exothermic peak accompanying decomposition in the vicinity of 193° C. according to thermal analysis (DSC).

Biological Activity

The lactate or citrate salts of compound of the formulae (I°) are inhibitors of aurora kinase. For example they inhibit Aurora A and/or Aurora B.

The lactate or citrate salts of compound of the invention also have activity against cyclin dependent kinases. For example, they have activity against CDK2, CDK4, CDK5, CDK6 and CDK 9 kinases, and in particular CDK2.

The lactate or citrate salts of the compound of the invention also have activity against glycogen synthase kinase-3 (GSK-3).

As a consequence of their activity in modulating or inhibiting CDK and Aurora kinases and glycogen synthase kinase, they will be useful in providing a means of arresting, or recovering control of, the cell cycle in abnormally dividing cells. It is therefore anticipated that, in addition to the novel uses defined herein, the compound will prove useful in treating or preventing proliferative disorders such as cancers. The compound of the invention will be useful in treating conditions such as viral infections, type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions where the lactate or citrate salts of the compound of the invention will be useful consists of viral infections, autoimmune diseases and neurodegenerative diseases.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. RB−ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma. In addition hematopoietic tumours of lymphoid lineage can include small cell lymphocytic lymphoma.

The cancers may be cancers which are sensitive to inhibition of any one or more cyclin dependent kinases.

Whether or not a particular cancer is one which is sensitive to inhibition by a cyclin dependent kinase or an aurora kinase may be determined by means of a cell growth assay as set out in the examples below or by a method as set out in the section headed "Methods of Diagnosis".

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

It has also been discovered that some cyclin-dependent kinase inhibitors can be used in combination with other anticancer agents. For example, the cyclin-dependent kinase inhibitor flavopiridol has been used with other anticancer agents in combination therapy.

Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes breast cancer, ovarian cancer, colon cancer, prostate cancer, oesophageal cancer, squamous cancer and non-small cell lung carcinomas.

As the lactate or citrate salts of the compound have activity against Aurora kinase, particular examples of cancers where the Aurora kinase inhibiting compounds of the invention will be useful include:

human breast cancers (e.g. primary breast tumours, node-negative breast cancer, invasive duct adenocarcinomas of the breast, non-endometrioid breast cancers);
ovarian cancers (e.g. primary ovarian tumours);
pancreatic cancers;
human bladder cancers;
colorectal cancers (e.g. primary colorectal cancers);
gastric tumours;
renal cancers;
cervical cancers:
neuroblastomas;
melanomas;
lymphomas;
prostate cancers;
leukemia;
non-endometrioid endometrial carcinomas;
gliomas; and
non-Hodgkin's lymphoma.

Cancers which may be particularly amenable to Aurora inhibitors include breast, bladder, colorectal, pancreatic, ovarian, non-Hodgkin's lymphoma, gliomas and nonendometrioid endometrial carcinomas.

A particular sub-set of cancers which may be particularly amenable to Aurora inhibitors consist of breast, ovarian, colon, liver, gastric and prostate cancers.

Another subset of cancers that Aurora inhibitors may be particularly amenable to treat are hematological cancers, in particular leukemia. Therefore, in a further embodiment the lactate or citrate salts of compound of formula (I) are used to treat hematological cancers, in particular leukemia. Particular leukemias are selected from Acute Myelogenous Leukemia (AML), chronic myelogenous leukaemia (CML), B-cell lymphoma (Mantle cell), and Acute Lymphoblastic Leukemia (ALL—also known as acute lymphocytic leukemia). In one embodiment the leukemias are selected from relapsed or refractory acute myelogenous leukemia, myelodysplastic syndrome, acute lymphocytic leukemia and chronic myelogenous leukemia. Further leukemias include acute promyelocytic leukaemia.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma).

One particular cancer is chronic lymphocytic leukaemia.

Another particular cancer is mantle cell lymphoma.

Another particular cancer is diffuse large B cell lymphoma.

The compounds of the invention having aurora kinase inhibitory activity will be particularly useful in the treatment or prevention of cancers of a type associated with or characterised by the presence of elevated levels of aurora kinases, for example the cancers referred to in this context in the introductory section of this application. Such cancers include medulloblastoma.

The lactate (particularly the L-lactate) or citrate salts of the compound of the formula (I) are inhibitors of VEGFR activity. In addition they are inhibitors of EpH and FGFR activity. As such, they will be useful in providing a means of preventing the growth or inducing apoptosis of neoplasias, particularly by inhibiting angiogenesis. It is therefore anticipated that the compound will prove useful in treating or preventing proliferative disorders such as cancers. In particular tumours with activating mutants of VEGFR or upregulation of VEGFR and patients with elevated levels of serum lactate dehydrogenase may be particularly sensitive to the inhibitors. Patients with activating mutants of any of the isoforms of the specific VEGFR as discussed herein may also find treatment with VEGFR inhibitors particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 may be particularly sensitive to the compounds of the invention and thus patients as discussed herein with such particular tumours may also find treatment with the compounds of the invention particularly beneficial. It may be preferred that the treatment is related to or directed at a mutated form of receptor tyrosine kinases, such as discussed above.

The lactate or citrate salts of the compound of the invention having Flt3, JAK, C-abl, PDK1, Chk1, and Chk2 inhibitory activity, will be particularly useful in the treatment or prevention of the following diseases and leukemias:
polycythemia vera;
essential thrombocythemia;
idiopathic myelofibrosis;
juvenile myelomonocytic leukemia (JMML);
Chronic Myelomonocytic Leukemias (CMML);
megakaryocytic AML (AML M7);
megakaryocytic leukaemia;
Philadelphia chromosome-negative CML;
Chronic Myeloid Leukaemia (CML);
imatinib resistant CML;
acute myeloid leukemias (AML);
myelodysplastic syndromes (MDS); and
acute lymphoblastic leukemia (ALL).

Therefore, in a further embodiment the lactate or citrate salts of compound of formula (I) are used to treat polycythemia vera; essential thrombocythemia; idiopathic myelofibrosis; juvenile myelomonocytic leukemia (JMML); Chronic Myelomonocytic Leukemias (CMML); megakaryocytic AML (AML M7); megakaryocytic leukaemia; Philadelphia chromosome-negative CML; or imatinib resistant CML.

In a further embodiment the lactate or citrate salts of compound of formula (I) are used to treat myeloproliferative disorders (MPD) such as polycythemia vera, essential thrombocythemia and idiopathic myelofibrosis including myelofibrosis with myeloid metaplasia (MMM).

In addition the compounds of the invention could be used in the treatment of diseases where malignancies are driven by BCR-abl in particular Philadelphia chromosome positive. In a further embodiment the lactate or citrate salts of compound of formula (I) are used to treat myeloproliferative syndrome, Philadelphia chromosome-positive leukamias such as Philadelphia chromosome positive CML and Philadelphia chromosome positive ALL. In particular the lactate or citrate salts of compound of formula (I) are used to treat Philadelphia chromosome positive ALL.

The lactate or citrate salts of the compound of the invention having VEGFR inhibitory activity, will be particularly useful in the treatment or prevention of ocular diseases such as age-related macular degeneration (AMD) in particular wet form of age-related macular degeneration, ischemic proliferative retinopathies such as retinopathy of prematurity (ROP) and diabetic retinopathy and hemangioma. Therefore, in a further embodiment the lactate or citrate salts of compound of formula (I) are used to treat ocular diseases such as age-related macular degeneration in particular wet form of age-related macular degeneration, Ischemic proliferative retinopathies such as retinopathy of prematurity (ROP) and diabetic retinopathy and hemangioma. It may be preferred that the treatment is related to or directed at a mutated form of a kinase, such as discussed herein. Diagnosis of tumours with such mutations could be performed using techniques known to a person skilled in the art and as described herein such as RTPCR and FISH.

The activity of the lactate or citrate salts of compound of the invention as inhibitors of cyclin dependent kinases, Aurora kinases, glycogen synthase kinase-3, VEGFR, Flt3, JAK, C-abl, PDK1, Chk1, and Chk2 can be measured using the assays set forth in the examples below and the level of activity exhibited by a given compound can be defined in terms of the $IC_{50}$ value.

The lactate or citrate salts of the compound of the invention having FGFR such as FGFR3, Ret, Eph such as EphB2 or EpbB4, or cSrc inhibitory activity, will be particularly useful in the treatment or prevention of the following diseases:
papillary thyroid carcinoma
multiple endocrine neoplasia (MEN) types 2A and 2B
familial medullary thyroid carcinoma (FMTC)
Hirschsprung's disease
Apert (AP) syndrome
Crouzon syndrome
Jackson-Weiss syndrome
Beare-Stevenson cutis gyrata syndrome
Pfeiffer Syndrome (PS)
multiple myelomas
head and neck cancers
epithelial cancers Therefore, in a further embodiment the lactate or citrate salts of compound of formula (I) are used to treat multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B and Hirschsprung's disease.

As the compounds have activity against FGFR particular cancers include multiple myeloma, bladder, hepatocellular, oral squamous cell carcinoma, cervical, prostate and thyroid carcinomas, lung, breast, and colon cancers. The compounds of the invention having FGFR such as FGFR1 inhibitory activity, will be particularly useful in the treatment or prevention of breast cancer in particular Classic Lobular Carcinomas (CLC). The compounds of the invention having FGFR such as FGFR2 or FGFR3 inhibitory activity will be particularly useful in the treatment or prevention of the skeletal diseases.

Furthermore, the compounds of the invention having FGFR such as FGFR1, FGFR2 or FGFR3 inhibitory activity, will be particularly useful in the treatment or prevention in pathologies in which progressive fibrosis is a symptom. Fibrotic conditions in which the compounds of the inventions may be useful in the treatment of in include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

Since compounds of the invention inhibit PDGFR they may also be useful in the treatment of a number of tumour and leukemia types including glioblastomas such as glioblastoma multiforme, prostate carcinomas, gastrointestinal stromal tumours, liver cancer, kidney cancer, chronic myeloid leukemia, chronic myelomonocytic leukemia (CMML) as well as hypereosinophilic syndrome, a rare proliferative hematological disorder and dermatofibrosarcoma protuberans, an infiltrative skin tumour.

The activity of the lactate or citrate salts of compound of the invention as inhibitors of FGFR such as FGFR3, Ret, Eph such as EphB2 or EphB4, or cSrc can be measured using the assays set forth in the examples below and the level of activity exhibited by a given compound can be defined in terms of the $IC_{50}$ value.

In further aspects, the invention provides:

A method for the prophylaxis or treatment of a disease state or condition mediated by VEGFR, Flt3, JAK, C-abl, PDK1, Chk1, or Chk2 which method comprises administering to a subject in need thereof a therapeutically effective amount of a lactate (particularly the L-lactate) or citrate salt of a compound of the formula ($I^0$).

A lactate (particularly the L-lactate) or citrate salt of a compound of the formula ($I^0$) for use in the prophylaxis or treatment of a disease state or condition mediated by VEGFR, Flt3, JAK, C-abl, PDK1, Chk1, or Chk2.

The use of a lactate (particularly the L-lactate) or citrate salt of a compound of the formula ($I^0$) for the manufacture of a medicament for the prophylaxis or treatment of a disease state or condition mediated by VEGFR, Flt3, JAK, C-abl, PDK1, Chk1, or Chk2.

A method for the prophylaxis or treatment of a disease state or condition mediated by FGFR such as FGFR3, Ret, Eph such as EphB2 or EphB4, or cSrc which method comprises administering to a subject in need thereof a therapeutically effective amount of a lactate (particularly the L-lactate) or citrate salt of a compound of the formula ($I^0$).

A lactate (particularly the L-lactate) or citrate salt of a compound of the formula ($I^0$) for use in the prophylaxis or treatment of a disease state or condition mediated by FGFR such as $FGFR^3$, Ret, Eph such as EphB2 or EphB4, or cSrc.

The use of a lactate (particularly the L-lactate) or citrate salt of a compound of the formula ($I^0$) for the manufacture of a medicament for the prophylaxis or treatment of a disease state or condition mediated by FGFR such as FGFR3, Ret, Eph such as EphB2 or EphB4, or cSrc.

Mutated Kinases

Drug resistant kinase mutations that arise in patient populations treated with kinase inhibitors can occur, in part, in the regions of the protein that bind to or interact with the particular inhibitor used in therapy. Such mutations reduce the capacity of the inhibitor to bind to and inhibit the kinase in question. This can occur at any of the amino acid residues which interact with the inhibitor or are important for supporting the binding of said inhibitor to the target. Another inhibitor that binds to a target kinase without requiring the interaction with the mutated amino acid residue will likely be unaffected by the mutation and will remain an effective inhibitor of the enzyme (Carter et al, PNAS, 2005, 102, 31, 11011-110116).

One common site at which drug resistant mutations occur is the so-called gate keeper residue. This particular residue forms a key site of interaction for several kinase inhibitors and their respective targets. For example, imatinib (Gleevec) binds in part to threonine 315 the gate keeper residue in the abl kinase domain. T315I mutations are one of the major forms of drug resistance arising in imatinib treated CML patients and may also be seen in patients with acute lymphoblastic leukemia. Thus an inhibitor of BCR-abl which does not require an interaction with the T315 for effective target inhibition will still be an effective inhibitor of the T315I imatinib resistant mutation.

Imatinib inhibits the tyrosine kinase activity of the receptors c-kit and PDGF-R in addition to blocking abl activity. Thus the drug has found utility in gastrointestinal tumours and hypereosinophilic syndrome, conditions which are dependent on activation of c-kit and PDGFR respectively. PDGF-R activation is associated with other malignancies, which respond to imatinib under different molecular circumstances. These include chronic myelomonocytic leukemia (CMML). In another disorder, dermatofibrosarcoma protuberans, an infiltrative skin tumor, a reciprocal translocation involving the gene encoding the PDGF-B ligand results in constitutive secretion of the chimeric ligand and receptor activation. Gleevec has activity against all three of these diseases.

In addition to the T315I resistant disease observed in CML, resistance due to similar gate-keeper mutations has been observed in both c-kit and PDGFr in imatinib-treated patients. Thus the T670I mutation in KIT and the T674I mutation in PDGFR are homologous to the T315I mutation in BCR-abl, and all three mutations confer resistance to clinical-stage ATP-competitive kinase inhibitors including BMS-354825 (dasatanib) and AMN-107 (nilotinib). The clinical importance of this mutation may grow considerably, as to date it appears to represent the primary mechanism of resistance to src/Abl inhibitors in patients. There are currently no effective kinase-targeted treatments for patients with threonine gate-keeper mutations.

Further, the T790M mutation in EGFR is homologous to the T315I mutation in BCR-abl, and this mutation may also confer resistance to clinical-stage ATP-competitive kinase inhibitors. Other clinical-stage ATP-competitive kinase inhibitors therefore include the EGRF inhibitors Iressa (gefitinib), and Tarceva (erlotinib), and SU-11248 (Sunitinib maleate, Sutent), a PDGFr and c-Kit inhibitor and other PDGFR inhibitors such as sorafenib.

Aurora kinase does not contain a threonine in the gate keeper region of the kinase active site. Thus many Aurora kinase inhibitors, including those of the current invention do not depend on this interaction to support the inhibition of the kinase activity. Accordingly, Aurora kinase inhibitors with a cross reactivity against abl, kit PDGFR or other kinases will be inhibitory to the drug resistant gate-keeper mutations, in particular threonine gate-keeper mutations, as well as the wild type variants and to be effective in resistant disease arising because of mutations in the gate-keeper region.

The compounds of the invention would therefore find particular application in relation to cancers which express a mutated molecular target such as BCRabl, c-kit, PDGF, EGF receptor, ErbB2. Diagnosis of tumours with such mutations could be performed using techniques known to a person skilled in the art and as described herein such as RTPCR and FISH.

Thus, since Aurora kinase does not represent a kinase harbouring a gatekeeper threonine, Aurora inhibitors may also be useful in the treatment of indications that are resistant to existing therapies by virtue of a mutation at that region of the protein. Such indications include gastrointestinal stromal tumors (GISTs), chronic myelomonocytic leukemia (CMML), the hypereosinophilic syndrome, a rare proliferative hematological disorder and dermatofibrosarcoma protuberans, an infiltrative skin tumour.

One aspect of the present invention is the use of a compound of formula (I), or formula (I') or formula ($I^0$) or sub-groups or examples thereof, for the inhibition of a kinase containing a mutation in a region of the protein that binds to or interacts with other cancer agents but does not bind to or interact with the compounds of formula (I).

A further aspect of the present invention is the method of treating a disease mediated by a kinase containing a mutation in a region of the protein that binds to or interacts with other cancer agents but does not bind to or interact with the compounds of formula (I), or formula (I') or formula ($I^0$) or sub-groups or examples thereof, with a compound of formula (I), or formula (I') or formula ($I^0$) or sub-groups or examples thereof.

Particular kinases for inhibition include c-abl, c-kit, PDGFR including PDGFR-beta and PDGFR-alpha, and ErbB family members such as EGFR (ErbB1), BER2 (ErbB2), ErbB3, and ErbB4, in particular c-abl, c-kit, and PDGFR.

Further kinases include those mentioned herein such as members of the Ephrin receptor family including EphA1, EphA2, EphA3, EphA4, EphA5, EphA8, EphA10, EphB1, EpbB2, EphB3, EphB5, EphB6, c-Src and kinases of the JAK family such as TYK2.

Other cancer agents include ATP-competitive kinase inhibitors such as Gleevec, BMS-354825, AMN-107, SU-11248 (Sunitinib maleate, Sutent), sorafenib (BAY 43-9006), Iressa (gefitinib), Tarceva (erlotinib), in particular Gleevec, BMS-354825 (dasatinib), and AMN-107 (nilotinib). Further kinase inhibitors are discussed in Davies et al, Biochem. J. 2000, 351, 95-105 and McInnes C., Fischer P. M. Curr. Pharm. Des. 2005 11:14 (1845-1863).

Particular regions to bind to or interact with other cancer agents include the kinase active site, the ATP binding site, and the gate keeper region in particular threonine gate keeper residue including T315 in abl, T670 in KIT, T674 in PDGFR, and T790 in EGFR. Particular regions of the kinase active site including the ATP binding pocket are discussed in Vulpetti A., Bosotti R. Farmaco 2004 59:10 (759-765), Knight et al, Chemistry & Biology, 12, 621-637 and Cherry M., Williams D. H. Curr. Med. Chem. 2004 11:6 (663-673).

A further aspect of the invention relates to the use of a compound of formula I for the inhibition of c-abl, c-kit, and PDGFR containing a mutation in the threonine gate keeper residue (i.e. T315 in abl, T670 in KIT, T674 in PDGFR).

Thus in a further embodiment of the invention the lactate or citrate salts of compound of formula (I), or formula ($I^0$) or formula ($I^0$) or sub-groups or examples thereof, are used to treat the gastrointestinal stromal tumors (GISTs), glioblastomas such as glioblastoma multiformi, the hypereosinophilic syndrome or dermatofibrosarcoma protuberans.

It follows from the foregoing paragraphs that, in further aspects, the invention provides:

A compound of the formula (I) as defined herein (e.g. in the form of a lactate or citrate salt thereof) for use in the treatment of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T674I mutation in PDGFR.

A compound of the formula (I) as defined herein (e.g. in the form of a lactate or citrate salt thereof) for use in the treatment of a cancer which expresses a mutated molecular target which is a mutated form of BCRabl, c-kit, PDGF, EGF receptor or ErbB2.

A compound of the formula (I) as defined herein (e.g. in the form of a lactate or citrate salt thereof) for use in the treatment of gastrointestinal stromal tumours (GISTs), chronic myelomonocytic leukemia (CMML), the hypereosinophilic syndrome and dermatofibrosarcoma protuberans.

A compound of the formula (I) as defined herein (e.g. in the form of a lactate or citrate salt thereof) for use in the treatment of a disease mediated by a kinase containing a mutation in a region of the protein that binds to or interacts with other cancer agents but does not bind to or interact with the compounds of formula (I), with a compound of formula (I), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, in particular c-abl, c-kit, PDGFR, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2.

The use of a compound of the formula (I) as defined herein (e.g. in the form of a lactate or citrate salt thereof) for the manufacture of a medicament for the treatment of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T6741 mutation in PDGFR.

The use of a compound of the formula (I) as defined herein (e.g. in the form of a lactate or citrate salt thereof) for the manufacture of a medicament for the treatment of a cancer which expresses a mutated molecular target which is a mutated form of BCRabl, c-kit, PDGF, EGF receptor or ErbB2.

The use of a compound of the formula (I) as defined herein (e.g. in the form of a lactate or citrate salt thereof) for the manufacture of a medicament for the treatment of gastrointestinal stromal tumours (GISTs), chronic myelomonocytic leukemia (CMML), the hypereosinophilic syndrome and dermatofibrosarcoma protuberans.

The use of a compound of the formula (I) as defined herein (e.g. in the form of a lactate or citrate salt thereof) for the manufacture of a medicament for the treatment of a disease mediated by a kinase containing a mutation in a region of the protein that binds to or interacts with other cancer agents but does not bind to or interact with the compounds of formula (I), with a compound of formula (I), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, in particular c-abl, c-kit, PDGFR, members of the Ephrin receptor family including EphA1, EphA2, EphA3, EphA4, EphA5, EphA8, EphA10, EphB1, EphB2, EphB3, EphB5, EpbB6, c-Src and kinases of the JAK family such as TYK2.

A method of treating a patient suffering from a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T6701 mutation in KIT; or
(e) a T6741 mutation in PDGFR;
which method comprises administering to the patient a compound of the formula (I) as defined herein (e.g. in the form of a lactate or citrate salt thereof).

A method for the treatment of a cancer which expresses a mutated molecular target which is a mutated form of BCRabl, c-kit, PDGF, EGF receptor or ErbB2, which method comprises administering to a patient in need thereof a compound of the formula (I) as defined herein (e.g. in the form of a lactate or citrate salt thereof).

A method for the treatment of gastrointestinal stromal tumours (GISTs), chronic myelomonocytic leukemia (CMML), the hypereosinophilic syndrome and dermatofibrosarcoma protuberans, comprises administering to a patient in need thereof a compound of the formula (I) as defined herein (e.g. in the form of a lactate or citrate salt thereof).

A method for the treatment of a disease mediated by a kinase containing a mutation in a region of the protein that binds to or interacts with other cancer agents but does not bind to or interact with the compounds of formula (I), with a compound of formula (I), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, in particular c-abl, c-kit, PDGFR, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2, which method comprises administering to a patient in need thereof a compound of the formula (I) as defined herein (e.g. in the form of a lactate or citrate salt thereof).

In a further aspect, the invention provides 1-cyclopropyl-3-[3-(5-morpholin-4-ylmethyl-1H-benzoimidazol-2-yl)-1H-pyrazol-4-yl]-urea or a salt (e.g. the L-lactate, citrate, acetate, mesylate, ethanesulphonate, DL-lactate, adipate, D-glucuronate, D-gluconate or hydrochloride salt), solvate, tautomer or N-oxide thereof for use in the treatment of juvenile myelomonocytic leukemia (JMML) or Chronic Myelomonocytic Leukemias (CMML).

The invention further provides 1-cyclopropyl-3-[3-(5-morpholin-4-ylmethyl-1H-benzoimidazol-2-yl)-1H-pyrazol-4-yl]-urea or a salt (e.g. the L-lactate, citrate, acetate, mesylate, ethanesulphonate, DL-lactate, adipate, D-glucuronate, D-gluconate or hydrochloride salt), solvate, tautomer or N-oxide thereof for use in the treatment of polycythemia vera, essential thrombocythemia, or idiopathic myelofibrosis.

The invention further provides 1-cyclopropyl-3-[3-(5-morpholin-4-ylmethyl-1H-benzoimidazol-2-yl)-1H-pyrazol-4-yl]-urea or a salt (e.g. the L-lactate, citrate, acetate, mesylate, ethanesulphonate, DL-lactate, adipate, D-glucuronate, D-gluconate or hydrochloride salt), solvate, tautomer or N-oxide thereof for use in the treatment of megakaryocytic leukaemia including megakaryocytic AML (AML M7) or Philadelphia chromosome-negative or imatinib resistant CML.

In the treatment of polycythemia vera; essential thrombocythemia; idiopathic myelofibrosis; juvenile myelomonocytic leukemia (JMML); Chronic Myelomonocytic Leukemias (CMML); megakaryocytic leukaemia including megakaryocytic AML (AML M7); Philadelphia chromosome-negative CML or imatinib resistant CML, the free base of 1-cyclopropyl-3-[3-(5-morpholin-4-ylmethyl-1H-benzoimidazol-2-yl)-1H-pyrazol-4-yl]-urea may be employed or, more preferably, a salt may be used. The salt may be the acetate, mesylate, ethanesulphonate, DL-lactate, adipate, D-glucuronate, D-gluconate or hydrochloride disclosed in our earlier applications U.S. Ser. No. 60/640,475 and GB 0428552.4, or it may be one of the salts disclosed herein, for example the L-lactate or citrate salts.

Also provided are methods of treatment of polycythemia vera; essential thrombocythemia; idiopathic myelofibrosis; juvenile myelomonocytic leukemia (JMML); Chronic Myelomonocytic Leukemias (CMML); megakaryocytic leukaemia including megakaryocytic AML (AML M7); Philadelphia chromosome-negative CML or imatinib resistant CML by administering to a patient in need of such treatment 1-cyclopropyl-3-[3-(5-morpholin-4-ylmethyl-1H-benzoimidazol-2-yl)-1H-pyrazol-4-yl]-urea or a salt thereof.

The invention also provides the compounds of the invention for use in the treatment of nilotinib resistant CML or dasatinib resistant CML.

Advantages of 1-cyclopropyl-3-[3-(5-morpholin-4-ylmethyl-1H-benzoimidazol-2-yl)-1H-pyrazol-4-yl]-urea (The Compound of formula (I°)

The compound of the formula (I°) has a number of advantages over prior art compounds. For example, the compound of formula (I°) is both more potent and more selective in its activities against different kinases including kinases implicated in cancer development and maintenance such as Jak 2, T315I abl and VEGFR kinases (see Table A), and demonstrate enhanced selectivity for and potency against Aurora A and B kinases in particular. Many of the other kinases targeted by the compound lie in oncogenic signalling pathways and have the potential to contribute in a positive way to the anti-tumour action of the compound (PDK1, Flt3, VEGFR2). In addition the potency against JAK2 and the c-abl T315I mutant could be of potential interest in leukemias and myeloproliferative diseases, including Gleevec resistant CML and polycythemia vera.

TABLE A

Inhibition of kinases in vitro

| Protein Kinase* | $IC_{50}$ (nM) |
|---|---|
| Aurora-A | 52% at 3 nM |
| Aurora-B | 58% at 3 nM |
| PDK1 | <10 |
| c-abl T315I mutant | <10 |
| JAK2 | <15 |
| Jak3$^c$ | <100 |
| Chk1 | <30 |
| c-abl | 57% at 30 nM |
| Chk2 | 41% at 30 nM |
| VEGFR2 (KDR) | <100 |
| Flt3 | <1000 |

In addition further kinases targeted by the compound could be of interest in particular in preventing or inhibiting angiogenesis and treating thyroid cancers (Table B).

TABLE B

Inhibition of further kinases in vitro

| Protein Kinase | $IC_{50}$ (nM) |
|---|---|
| FGFR3 | <30 |
| cSrc | <100 |
| EphB2 | <100 |
| EphB4 | <100 |
| Ret | <100 |
| PDGFRb | 400 nM |
| EGFR | 380 nM |

The compound of formula (I°) is also advantageous over prior art compounds in that it has different susceptibilities to P450 enzymes (Table C).

TABLE C

Inhibition of expressed cytochrome P450 isoforms in vitro.

| P450 isoform | IC50 (µM) |
|---|---|
| CYP1A2 | >10 |
| CYP2D6 | >10 |
| CYP3A4 | >10 |
| CYP2C9 | >10 |
| CYP2C19 | >10 |

In addition, compounds of the invention are also advantageous over prior art compounds in that they exhibit improvements with regard to drug metabolism and pharmacokinetic properties. In particular the compounds of the invention have reduced plasma protein binding. The binding of the compound of Examples 24, 62, 63 and 64 to plasma proteins was comparably moderate across all species tested, ranging from 61% in rat to 82% in mouse plasma. This could confer the advantage of having more free drug available in the systemic circulation to reach the appropriate site of action to exert its therapeutic effect. Increased free fraction to exert pharmacological action in tumours potentially leads to improved efficacy which thereby allows reduced dosages to be administered.

The compound of formula (I°) also demonstrates improved cell activity in proliferation and clonogenic assays (for example in the assay described in Examples 16 and 17), thereby indicating improved anti-cancer activity against a wide range of solid tumour and leukemic cell lines (Table D).

TABLE D

Inhibitory effect on tumour cell colony formation

| Origin | Origin | IC50 (nM) | p53 Status* |
|---|---|---|---|
| Colon | HCT 116 | 13 | + |
|  | HCT 116 N7 | 14 | − |
|  | HT-29 | 11 | − |
|  | SW620 | 14 | − |
| Ovarian | A2780 | 7.7 | + |
| Lung | A549 | 12 | + |
| Breast | MCF7 | 20 | + |
| Pancreatic | MIA-Pa—Ca-2 | 7.8 | − |

*+ indicates expression of wild type p53; − indicates no expression of p53 or that p53 is non-functional.

The compound of formula (I°) has a reduced toxicity and therefore a greater therapeutic window. In vitro studies with primary human mammary epithelial cells have demonstrated that following treatment of normal cells, cf. tumor cells, fewer become multinucleated or die after treatment, but instead undergo reversible G2/M arrest before re-entering the cell cycle once treatment is stopped. Data indicates that compound-treatment has different effects on tumor cells compared with normal cells. In checkpoint compromised tumor cells compound treatment leads to multinucleation, due to disruption of mitosis, inhibition of cytokinesis and bypass of the spindle checkpoint through Aurora kinase inhibition. It is this multinucleation that appears to lead to cell death. In contrast, in normal checkpoint competent cells treated with compound, fewer cells become multinucleated or die after 24 h compound treatment, instead the greater proportion undergo reversible G2/M arrest and then re-enter the cell cycle once the compound is removed. These differences in effects could reflect the fact that normal cells have checkpoints in place to halt the cell cycle if accurate chromosomal segregation does not take place, such as the post-mitotic p53-dependent checkpoint. In tumor cells these checkpoints are absent allowing mitosis to proceed and multinucleation to occur.

Furthermore, salt forms of the compound of formula (I°) demonstrate improved solubility in aqueous solution and better physicochemical properties, e.g. a lower logD.

Methods for the Preparation of Compounds of the Formula (I')

Compounds of the formula (I") can be prepared in accordance with synthetic methods well known to the skilled person.

For example, compounds of the formula (I") wherein A is a bond (i.e. where A and the carbonyl group form an amide bond), can be prepared by the reaction of a compound of the formula (X):

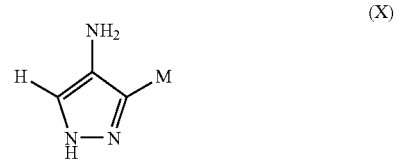

with a carboxylic acid R¹-E-CO₂H or a reactive derivative thereof under standard amide forming conditions.

The coupling reaction between the carboxylic acid and the amine (X) can be carried out in the presence of a reagent of the type commonly used in the formation of peptide linkages. Examples of such reagents include 1,3-dicyclohexylcarbodiimide (DCC) (Sheehan et al, *J. Amer. Chem. Soc.* 1955, 77, 1067), 1-ethyl-3-(3'-dimethylaminopropyl)-carbodiimide (EDC) (Sheehan et al, *J. Org. Chem.,* 1961, 26, 2525), uronium-based coupling agents such as O-(7-azabenzotriazol-1-yl)-N,N,N',N'-tetramethyluronium hexafluorophosphate (HATU) (L. A. Carpino, *J. Amer. Chem. Soc.,* 1993, 115, 4397) and phosphonium-based coupling agents such as 1-benzo-triazolyloxytris(pyrrolidino)phosphonium hexafluorophosphate (PyBOP) (Castro et al, *Tetrahedron Letters,* 1990, 31, 205). Carbodiimide-based coupling agents are advantageously used in combination with 1-hydroxyazabenzotriazole (HOAt) or 1-hydroxybenzotriazole (HOBt) (Konig et al, *Chem. Ber.,* 103, 708, 2024-2034). Preferred coupling reagents include EDC and DCC in combination with HOAt or HOBt.

The coupling reaction is typically carried out in a non-aqueous, non-protic solvent such as acetonitrile, dioxane, dimethylsulphoxide, dichloromethane, dimethylformamide or N-methylpyrrolidone, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine.

Amines of the formula (X) can be prepared by reduction of the corresponding nitro-compound of the formula (XI) under standard conditions. The reduction may be effected, for example by catalytic hydrogenation in the presence of a catalyst such as palladium on carbon in a polar solvent such as ethanol or dimethylformamide at room temperature.

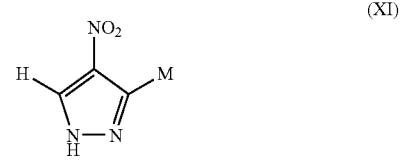

(XI)

The nitro-compounds of the formula (XI) can be prepared by reaction of the nitro-pyrazole carboxylic acid of the formula (XII):

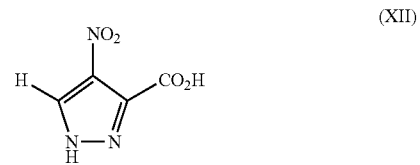 [SMILES: O=C(O)c1n[nH]cc1[N+](=O)[O-]]

(XII)

with either 4-morpholin-4-ylmethyl-benzene-1,2-diamine (to form compounds where M is D1) or 4,5-dimethoxy-benzene-1,2-diamine (to form compounds wherein M is D2).

The reaction between the diamine and the carboxylic acid (XII) can be carried out in the presence of a reagent such as DCC or EDC in the presence of HOBt as described above, under amide coupling conditions as described previously, to give an intermediate ortho-aminophenylamide (not shown) which is then cyclised to form the benzimidazole ring. The final cyclisation step is typically carried out by heating under reflux in the presence of acetic acid.

An illustrative reaction scheme, showing the preparation of compounds of the formula (X) where M is a group D1 is set out in Scheme 1.

Scheme 1

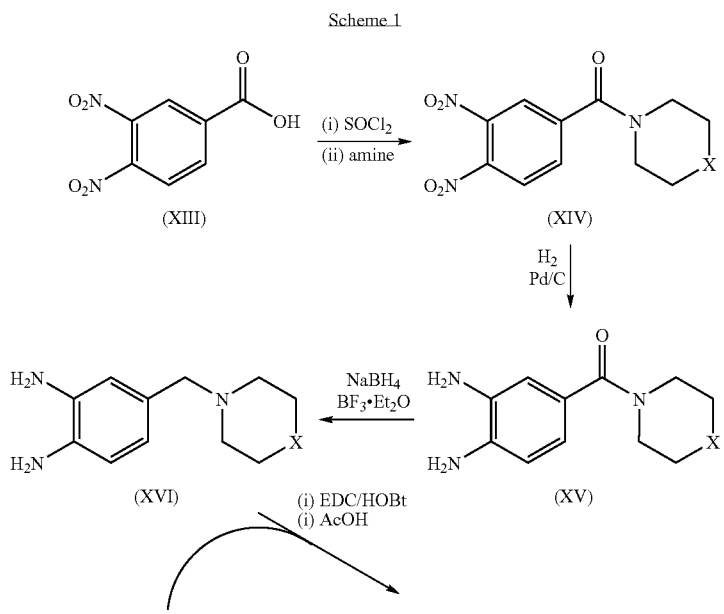

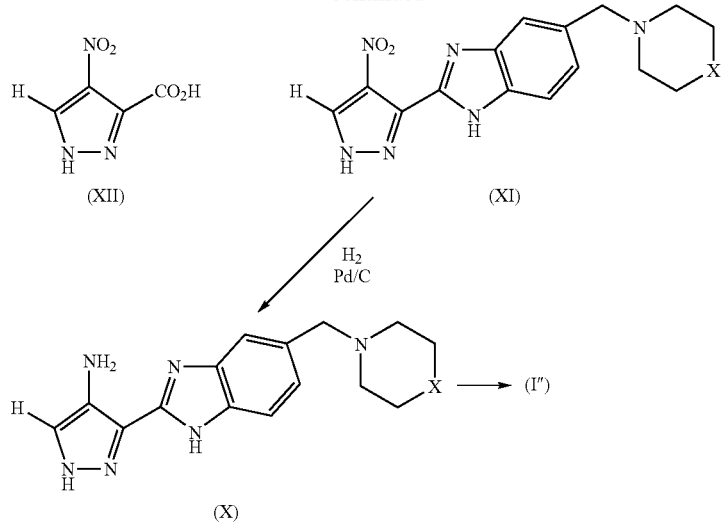

Typical conditions for each step in Scheme 1 may be found in the Examples section below.

Compounds wherein M is a group D2 can be made in an analogous manner but using 4,5-dimethoxy-benzene-1,2-diamine instead of the diamine (XVI) in Scheme 1.

In an alternative synthesis of compounds of the formula (I') wherein A is a bond, the diamines 4-morpholin-4-ylmethyl-benzene-1,2-diamine and 4,5-dimethoxy-benzene-1,2-diamine can also be reacted with carboxylic acids of the formula (XVII) where A is a bond to give compounds of the formula (I').

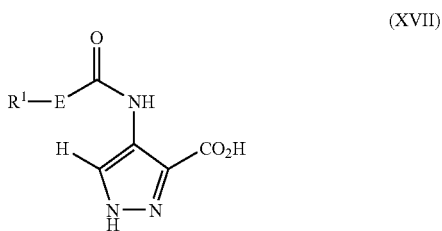

The reaction of the diamine with the carboxylic acid (XVII) can be carried out under conditions analogous to those described above for preparing the nitro-compounds (XI). Carboxylic acids of the formula (XVI) can be prepared by the sequence of reactions shown in Scheme 2.

As shown in Scheme 2, a substituted or unsubstituted 4-nitro-3-pyrazole carboxylic acid (XVIII) can be esterified by reaction with thionyl chloride to give the acid chloride intermediate followed by reaction with ethanol to form the ethyl ester (XIX). Alternatively, the esterification can be carried out by reacting the alcohol and carboxylic acid in the presence of an acidic catalyst, one example of which is thionyl chloride. The reaction is typically carried out at room temperature using the esterifying alcohol (e.g. ethanol) as the solvent. The nitro group can then be reduced using palladium on carbon according to standard methods to give the amine (XX). The amine (XX) is coupled with an appropriate carboxylic acid $R^1$-E-$CO_2$H under amide forming conditions the same as or analogous to those described above to give the amide (XXI). The ester group of the amide (XXI) can then be hydrolysed using an alkali metal hydroxide such as sodium hydroxide in a polar water miscible solvent such as methanol, typically at room temperature.

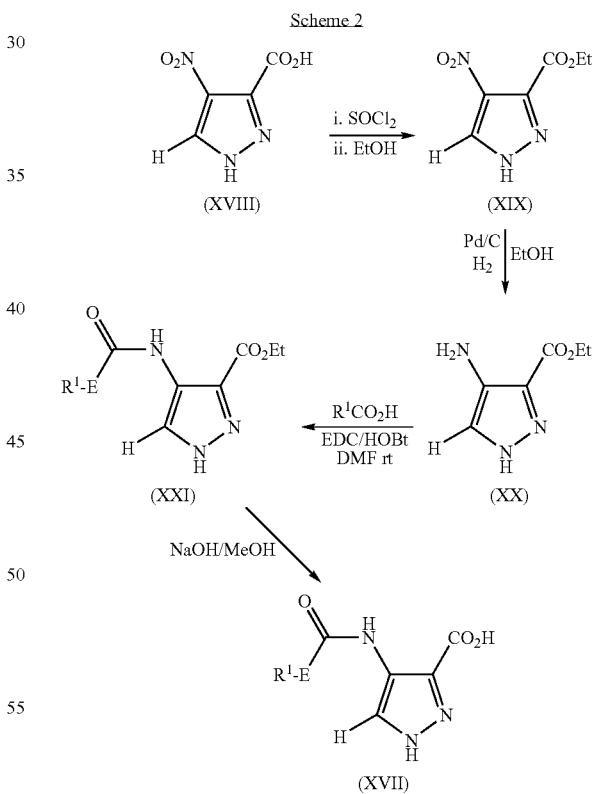

Compounds of the formula (I') in which A is $NR^2$ can be prepared using standard methods for the synthesis of ureas. For example, such compounds can be prepared by reacting an aminopyrazole compound of the formula (X) with a suitably substituted isocyanate of the formula $R^1$-E-N=C=O in a polar solvent such as DMF. The reaction is conveniently carried out at room temperature.

Alternatively, ureas of the formula (I') can be prepared by reacting an amine of the formula (X) with an amine of the formula R¹-E-NH₂ in the presence of carbonyl diimidazole (CDI). The reaction is typically carried out in a polar solvent such as THF with heating (for example using a microwave heater) to a temperature of up to about 150° C.

Instead of using CDI, the coupling of the two amines to form the urea can be effected using triphosgene (bis(trichloromethyl)carbonate) in the presence of a non-interfering base such as triethylamine in a solvent such as dichloromethane at room temperature or below.

As a further alternative to CDI, phosgene may be used instead of triphosgene.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999). A hydroxy group may be protected, for example, as an ether (—OR) or an ester (—OC(=O)R), for example, as: a t-butyl ether; a benzyl, benzhydryl(diphenylmethyl), or trityl (triphenylmethyl) ether; a trimethylsilyl or t-butyldimethylsilyl ether; or an acetyl ester (—OC(=O)CH₃, —OAc). An aldehyde or ketone group may be protected, for example, as an acetal (R—CH(OR)₂) or ketal (R₂C(OR)₂), respectively, in which the carbonyl group (>C=O) is converted to a diether (>C(OR)₂), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH₃); a benzyloxy amide (—NHCO—OCH₂C₆H₅, —NH-Cbz); as a t-butoxy amide (—NHCO—OC(CH₃)₃, —NH-Boc); a 2-biphenyl-2-propoxy amide (—NHCO—OC(CH₃)₂C₆H₄C₆H₅, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl(tosyl) and methanesulphonyl(mesyl) groups and benzyl groups such as a para-methoxybenzyl (PMB) group. A carboxylic acid group may be protected as an ester for example, as: an C₁₋₇ alkyl ester (e.g., a methyl ester; a t-butyl ester); a C₁₋₇ haloalkyl ester (e.g., a C₁₋₇ trihaloalkyl ester); a triC₁₋₇ alkylsilyl-C₁₋₇alkyl ester; or a C₅₋₂₀ aryl-C₁₋₇ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH₂NHC(=O)CH₃).

The acid addition salts constituting sub-group (C) of formula (I') can be formed during the synthesis of the parent compound 1-(2,6-difluorophenyl)-N-[3-(5-morpholin-4-ylmethyl-1H-benzimidazol-2-yl)-1H-pyrazol-4-yl]-urea, or by conversion of the free base of the parent compound to a desired salt, or by conversion of one salt of the parent compound to another desired salt of the parent compound. The parent compound 1-(2,6-difluorophenyl)-N-[3-(5-morpholin-4-ylmethyl-1H-benzimidazol-2-yl)-1H-pyrazol-4-yl]-urea (the compound of formula (IA)) can be prepared by the method illustrated in Scheme 3 below.

As shown in Scheme 3, the 3,4-dinitrocarboxylic acid (XIII, a commercially available compound, is converted to the morpholide (XXI). Formation of the amide can be accomplished by converting the acid (XIII) to an active derivative such as an acid chloride using standard methods. For example, the acid chloride can be formed by heating with excess thionyl chloride at the reflux temperature of the thionyl chloride and then removing excess thionyl chloride by azeotrope with toluene.

The morpholide (XXI) can be reduced to the dinitrobenzyl morpholine (XXIII) by treatment with a suitable reducing agent such as sodium borohydride in combination with boron trifluoride. The reduction reaction is typically carried out in an anhydrous solvent such as tetrahydrofuran at a reduced temperature, for example a temperature of 0-5° C. The dinitrobenzylmorpholine (XXIII) can then be reduced to the diaminobenzylmorpholine (XXIV) under standard conditions, for example by catalytic hydrogenation in the presence of a catalyst such as palladium on carbon in a polar solvent such as ethanol at room temperature.

The diaminobenzyl morpholine (XXIV) is then reacted with the commercially available 4-nitropyrazole-3-carboxylic acid to form the nitropyrazolyl-benzimidazole (XXV). The formation of the nitropyrazolyl-benzimidazole (XXV) may be achieved by first forming an amide bond between the carboxylic acid and the diaminobenzyl compound (XXIV) using a peptide coupling reagent such as O-(benzotriazol-1-yl)-N,N,N',N'-tetramethyluronium tetrafluoroborate (TBTU) capable of promoting amide bond formation with an aromatic amine group. The intermediate amide (not shown) is then cyclised to the nitro-pyrazolyl-benzimidazole (XXV) by heating in excess glacial acetic acid, for example at a temperature of approximately 65° C.

The nitropyrazolyl-benzimidazole (XXV) can be reduced to the corresponding amine (XXVI) under standard conditions. The reduction may be effected, for example by catalytic hydrogenation in the presence of a catalyst such as palladium on carbon in a polar solvent such as ethanol or dimethylformamide at room temperature. The amine (XXVI) can in turn be converted to the urea (IA) using standard methods for the synthesis of ureas, for example by reacting the amine (XXVI) with 2,6-difluorophenyl-isocyanate in a polar solvent such as THF at room temperature or below, for example at a temperature of 0-5° C.

The free base form of the urea (IA) can be used to prepare the acid addition salts of the invention.

Scheme 3

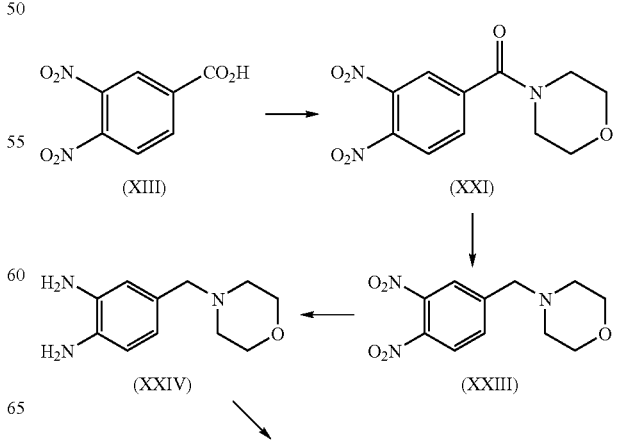

-continued

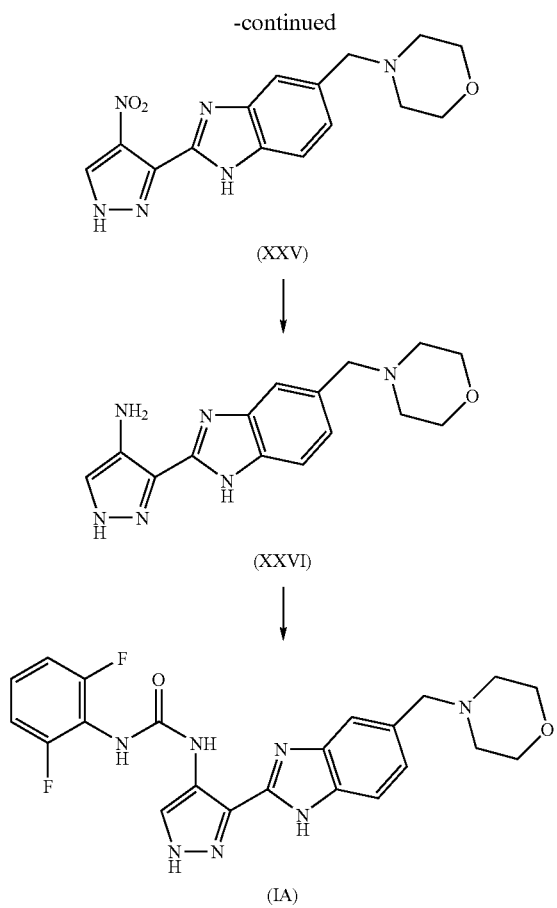

The salts of the present invention can be prepared from the free base by conventional methods such as the methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. For example, the salts can be prepared by reacting the free base with the appropriate acid in water or in an organic solvent, or in a mixture of the two; generally, nonaqueous media such as ether, ethyl acetate, methanol, ethanol, isopropanol, or acetonitrile are used.

In another aspect, the invention provides, for the novel uses of the invention as defined herein, an acid addition salt of 1-(2,6-difluorophenyl)-N-[3-(5-morpholin-4-ylmethyl-1H-benzimidazol-2-yl)-1H-pyrazol-4-yl]-urea prepared by a method which comprises forming a solution of 1-(2,6-difluorophenyl)-N-[3-(5-morpholin-4-ylmethyl-1H-benzimidazol-2-yl)-1H-pyrazol-4-yl]-urea free base in a solvent (typically an organic solvent) or mixture of solvents, and treating the solution with an acid to form a precipitate of the acid addition salt.

The acid is typically added as a solution in a solvent which is miscible with the solvent in which the free base is dissolved.

The solvent in which the free base is initially dissolved may be one in which the acid addition salt thereof is insoluble. Alternatively, the solvent in which the free base is initially dissolved may be one in which the acid addition salt is at least partially soluble, a different solvent in which the acid addition salt is less soluble subsequently being added such that the salt precipitates out of solution.

For example, in one method of preparing the salts of the invention, the free base is dissolved in a first solvent (which can be ethyl acetate or a mixture of ethyl acetate and an alcohol such as methanol) and a solution (e.g. a concentrated or saturated solution) of an acid such as hydrochloric acid in a second solvent (which can be an ether such as diethyl ether or dioxin) is then added such that a precipitate of the acid addition salt is formed, and the precipitate is then collected, for example by filtration.

Processes for Preparing 1-Cyclopropyl-3-[3-(5-morpholin-4-ylmethyl-1H-benzoimidazol-2-yl)-1H-pyrazol-4-yl]-urea In the examples of our earlier application WO 2005/002552 and in Schemes 1 and 3 above, it is disclosed that a [3-(5-morpholin-4-ylmethyl-1H-benzimidazol-2-yl)-1H-pyrazol-4-yl]-amide can be prepared by a sequence of steps including:
(i) reacting 4-morpholin-4-ylmethyl-benzene-1,2-diamine with 4-nitro-1H-pyrazole-3-carboxylic acid in the presence of 1-ethyl-3-(3'-dimethylaminopropyl)-carbodiimide (EDC) and 1-hydroxybenzotriazole (HOBt) in N,N-dimethyl formamide (DMF) to give 5-morpholin-4-ylmethyl-2-(4-nitro-1H-pyrazol-3-yl) 1H-benzimidazole; and
(ii) reducing the nitro group by treatment with palladium on carbon under a hydrogen atmosphere;
or
(i) reacting the 4-amino-1H-pyrazole-3-carboxylic ester with the appropriate carboxylic acid in the presence of 1-ethyl-3-(3'-dimethylaminopropyl)-carbodiimide (EDC) and 1-hydroxybenzotriazole (HOBt) in N,N-dimethyl formamide (DMF) or with the appropriate acid chloride in the presence of triethylamine to form the 4-amide-1H-pyrazole carboxylic acid; and
(ii) reacting 4-morpholin-4-ylmethyl-benzene-1,2-diamine with the appropriate 4-amide-1H-pyrazole carboxylic acid in the presence of 1-ethyl-3-(3'-dimethylaminopropyl)-carbodiimide (EDC) and 1-hydroxybenzotriazole (HOBt) in dimethyl formamide (DMF) to give the [3-(5-morpholin-4-ylmethyl-1H-benzimidazol-2-yl)-1H-pyrazol-4-yl]-amide.

It has now been found that instead of reacting the nitro-pyrazole compound with the diamine and then reducing the nitro group to the amine, or reacting the amide-pyrazole with the diamine, the amino-pyrazole may be reacted with the diamine provided that the amino group of the aminopyrazole is appropriately protected. The product of the reaction can then be cyclised to form the benzimidazole. In addition, it has been found that removal of the amine protecting group and cyclisation to the benzimidazole can be performed in one step.

Accordingly, a process for preparing a compound of the formula XXVII) or (XXVIII) or a salt thereof:

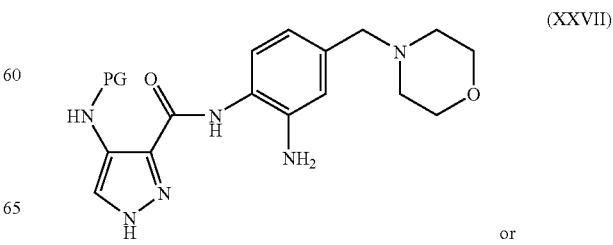

or

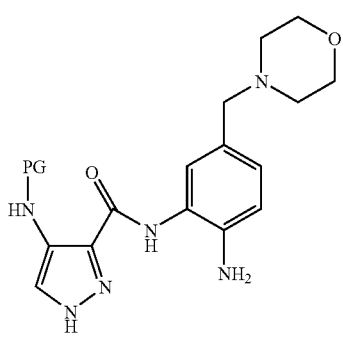

(XXVIII)

comprises:
(i) the reaction of a compound of the formula (XXIX):

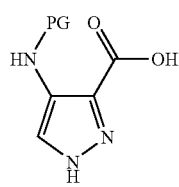

(XXIX)

where PG is an amine-protecting group:
(ii) with a compound of the formula (XXXI):

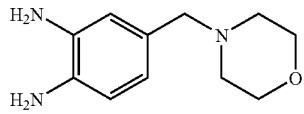

(XXXI)

in an organic solvent in the presence of a coupling agent such as EDC and HOBt:

Formula (XXVII) is a regioisomer of (XXVII).

The amine-protecting group PG can be any protecting group known for use in protecting amine groups under the conditions used in the above process, see for example Green et al. referred to above. Thus, for example, the nitrogen may be protected as an amide (NCO—R) or a urethane (NCO—OR), for example, as: a methyl amide (NCO—CH$_3$); a benzyloxy amide (NCO—OCH$_2$C$_6$H$_5$, —NH-Cbz); as a tert-butoxy amide (—NCO—OC(CH$_3$)$_3$, N-Boc); a 2-biphenyl-2-propoxy amide (NCO—OC(CH$_3$)$_2$C$_6$H$_4$C$_6$H$_5$, N-Bpoc), as a 9-fluorenylmethoxy amide (N-Fmoc), as a 6-nitroveratryloxy amide (N-Nvoc), as a 2-trimethylsilylethyloxy amide (N-Teoc), as a 2,2,2-trichloroethyloxy amide (N-Troc), as an allyloxy amide (N-Alloc), or as a 2-(phenylsulphonyl)ethyloxy amide (—N-Psec). Other protecting groups for amines include benzyl groups such as apara-methoxybenzyl (PMB) group. Preferred amine protecting groups are a urethane (NCO—OR), for example, a benzyloxy amide (NCO—OCH$_2$C$_6$H$_5$, —NH-Cbz), or a tert-butoxy amide (—NCO—OC(CH$_3$)$_3$, N-Boc); or an allyloxy amide (N-Alloc). In one embodiment, the protecting group PG is a protecting group APG, which is an amine protecting group that may be removed under acidic conditions. Such groups include the urethanes. A particularly preferred urethane protecting group is tert-butyloxycarbonyl which may be removed under acidic conditions.

In one embodiment, the protecting group PG is then removed from the compound of formula (XXVII) or (XXVIII) and replaced with a protecting group, APG, to form a compound of formula (XXVIIa) or (XXVIIa).

One particularly preferred compound of formula (XXIX) is the compound of the formula (XXXII) below:

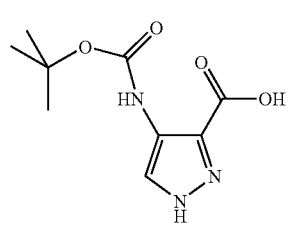

(XXXII)

The invention further provides a chemical intermediate per se of the formula (XXXII).

The invention also provides chemical intermediates per se of formula (XXVII) or (XXVIII), for example novel chemical intermediates of formula (XXVIIa) or (XXVIIIa) below. Therefore the invention provides 4-amino-1H-pyrazole-3-carboxylic acid (2-amino-4-morpholin-4-ylmethyl-phenyl)-amide or 4-amino-1H-pyrazole-3-carboxylic acid (2-amino-5-morpholin-4-ylmethyl-phenyl)-amide and protected forms thereof as a novel chemical intermediates. One particular preferred novel chemical intermediate of formula ((XXVII) is [3-(2-amino-4-morpholin-4-ylmethyl-phenylcarbamoyl)-1H-pyrazol-4-yl]-carbamic acid tert-butyl ester. One particularly preferred novel chemical intermediate of Formula (XXVIII) is [3-(2-amino-5-morpholin-4-ylmethylphenylcarbamoyl)-1H-pyrazol-4-yl]-carbamic acid tert-butyl ester.

When the protecting group PG is a tert-butyloxycarbonyl group, the overall yield from the process is in excess of 85%. Furthermore, the process is advantageous in that it makes use of relatively simple and inexpensive reagents and solvents and is also advantageous with respect to the ease of purification of the products.

In another aspect, the invention provides, for the novel uses of the invention as defined herein, 3-(5-morpholin-4-ylmethyl-1H-benzoimidazol-2-yl)-1H-pyrazol-4-ylamine or a salt thereof prepared by a process which comprises:

(i) treating a compound of the formula (XXVIIa) or (XXVIIa):

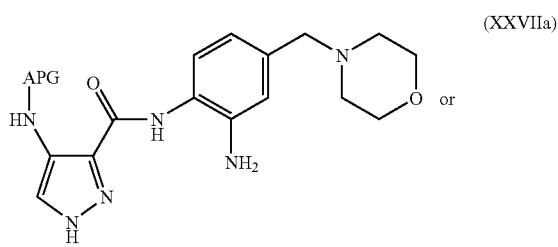

(XXVIIa)

or

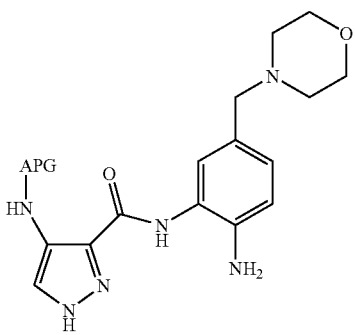

(XXVIIIa)

with an acid in a solvent, optionally with heating; and
(ii) neutralizing the reaction.

The amine-protecting group APG can be any protecting group known for use in protecting amine groups as defined above in relation to the compounds of the formulae (XXVII) or (XXVIII), and which is removable under the conditions used in the above process.

In step (i), the reaction with acid may be carried out with heating, for example to a temperature in the range 80 to 100° C. The solvent in which step (i) is carried out is an alcohol solvent, and it may be, for example, ethanol.

In step (i), the protecting group is preferably one such as the Boc group that can be removed by treatment with acid, the acid being selected so as be appropriate for protonation of the intermediate to activate the carbonyl group for the cyclisation reaction. Suitable acids include strong acids such as sulphuric acid, methanesulphonic acid or hydrochloric acid, and one particular acid is hydrochloric acid.

Following completion of the reaction in step (i), as judged for example by the disappearance of starting material (XIIIa), the reaction can be neutralized.

In step (ii), a non-interfering base is used. The term "non-interfering base" in the present context means a base such as sodium carbonate which will not react with compound produced. Step (ii) is typically carried out at room temperature.

In step (ii), the reaction is neutralized for example until the reaction is saturated with neutralizing agent and at pH 8.5.

Following step (ii), the compound can be reacted with carbonylating reagent such as 1,1'-carbonyldiimidazole (CDI) or a phosgene equivalent and then treated with cyclopropylamine. Phosgene equivalents include triphosgene or phosgene. A preferred carbonylating reagent is 1,1'-carbonyldiimidazole (CDI).

Alternatively, the urea can be prepared by reacting the aminopyrazole, 3-(5-morpholin-4-ylmethyl-1H-benzoimidazol-2-yl)-1H-pyrazol-4-ylamine, with phenyl chloroformate in the presence of a base such as pyridine in solvent e.g. THF to give the cyclic urea and then treating with cyclopropylamine, or by reacting the aminopyrazole with cyclopropylisocyanate which can be made from the Curtius rearrangement of cyclopropanecarboxylic acid azide (as described in U.S. Pat. No. 4,313,755 and U.S. Pat. No. 4,299,778).

Thus, in a further aspect, there is provided, for the novel uses of the invention as defined herein, 1-cyclopropyl-3-[3-(5-morpholin-4-ylmethyl-1H-benzoimidazol-2-yl)-1H-pyrazol-4-yl]-urea or a salt thereof prepared by a process which comprises:
(i) treating a compound of the formula ((XXVIIa) with an acid in a solvent, optionally with heating;
(ii) neutralizing the reaction;
(iii) reacting the product of step (ii) with carbonylating reagent;
(iv) reacting the product of step (iii) with cyclopropylamine.

Step (iii) is typically carried out under reflux, for example to a temperature of up to about 100° C., more typically up to 70-75° C. In step (iii), the reaction may be carried out in a polar aprotic solvent such as tetrahydrofuran. A carbonylating reagent can be a compound such as 1,1'-carbonyldiimidazole (CDI) or a phosgene equivalent such as triphosgene or phosgene. A preferred carbonylating reagent is 1,1'-carbonyldiimidazole (CDI).

Step (iv) is typically carried out with heating, for example to a temperature of up to about 100° C.

Following step (iv), the product may subjected to salt conversion or recrystallisation (e.g. using 2-propanol or ethanol as the solvent) to increase the purity and to give a crystalline form.

Step (iii) above gives rise to an intermediate compound of the formula (XXXIII) and/or its regioisomer (XXXIIIa):

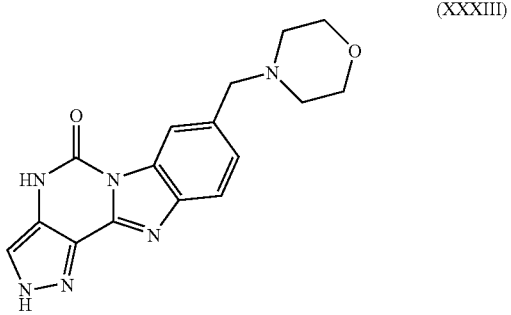

(XXXIII)

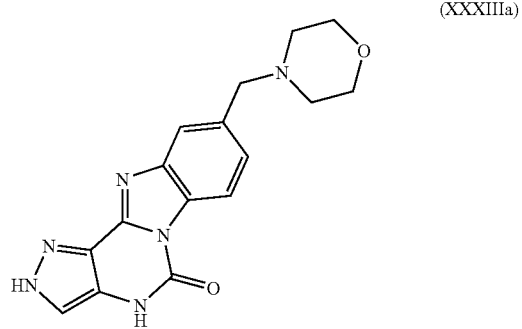

(XXXIIIa)

The intermediates of formulae (XXXIII) and (XXXIIIa), which can be isolated if required, are then reacted with cyclopropylamine to give a compound of the formula (XXX).

Accordingly, a process for the preparation of a compound of the formula (XXX) as defined herein comprises reacting a compound of the formula (XXXIII) or (XXXIIIa) with cyclopropylamine, and thereafter optionally forming an acid addition salt of the compound of the formula (XXX). The reaction is typically carried out in a polar aprotic solvent such as N-methylpyrrolidone, preferably at an elevated temperature such as a temperature in excess of 80° C., more typically in excess of 90° C., for example 95° C. to 105° C.

The foregoing process may also be used to prepare other compounds of the formula (I) and sub-groups thereof as defined herein where the moiety A in formula (I) is a group NH.

Accordingly, a process for preparing a compound of the formula (I) as defined herein, wherein the moiety A in formula (I) is a group NH, comprises the reaction of (i) a compound of the formula (XXXIII) and/or its regioisomer (XXXIIIa), or (ii) a compound of the formula (XXXIV) and/or its regioisomer (XXXIVa):

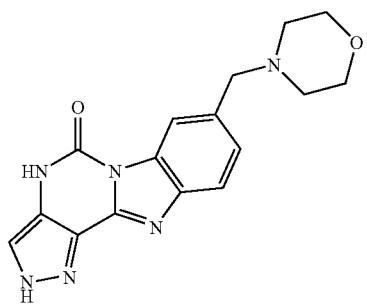
(XXXIII)

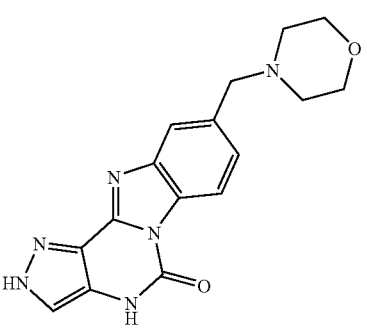
(XXXIIIa)

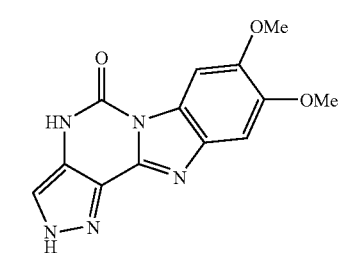
(XXXIV)

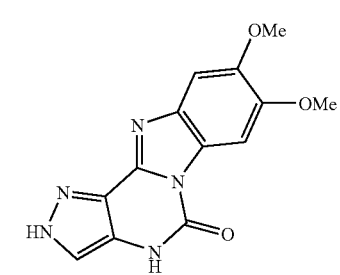
(XXXIVa)

with a compound of the formula $R^1$-E-$NH_2$, preferably in a polar aprotic solvent such as N-methylpyrrolidone, preferably at an elevated temperature such as a temperature in excess of 80° C., more typically in excess of 90° C., for example 95° C. to 105° C., and thereafter optionally forming an acid addition salt of the compound of formula (I).

The invention further provides chemical intermediates of the formulae (XXXIII), (XXXIIIa), (XXXIV) and (XXXIVa).

In further embodiments, the compound of formula ((XXVIIa) in the process for preparing 3-(5-morpholin-4-ylmethyl-1H-benzoimidazol-2-yl)-1H-pyrazol-4-ylamine or a salt thereof or process for preparing 1-cyclopropyl-3-[3-(5-morpholin-4-ylmethyl-1H-benzoimidazol-2-yl)-1H-pyrazol-4-yl]-urea or a salt thereof above, can be prepared by a process which comprises:

(i) reaction of a compound of the formula (XXIX), where PG is an amine-protecting group which is removable with acid, APG;

(ii) with a compound of the formula (XXXI) in an organic solvent in the presence of a coupling agent such as EDC and HOBt.

Optionally the processes described herein have the further step of recrystallising the salt to give a crystalline form, e.g. a crystalline form as defined herein.

Methods of Purification

The compound may be isolated and purified by a number of methods well known to those skilled in the art and examples of such methods include chromatographic techniques such as column chromatography (e.g. flash chromatography) and HPLC. Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

One such system for purifying compounds via preparative LC-MS is described in the experimental section below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Recrystallisation

Methods of recrystallisation of the lactate or citrate salt of 1-cyclopropyl-3-[3-(5-morpholin-4-ylmethyl-1H-benzoimidazol-2-yl)-1H-pyrazol-4-yl]-urea can be carried out by methods well known to the skilled person—see for example (P. Heinrich Stahl (Editor), Camille G. Wermuth (Editor), ISBN: 3-90639-026-8, Handbook of Pharmaceutical Salts: *Properties, Selection, and Use*, Chapter 8, Publisher Wiley-VCH). Products obtained from an organic reaction are seldom pure when isolated directly from the reaction mixture. If the compound (or a salt thereof) is solid, it may be purified and/or crystallized by recrystallization from a suitable solvent. A good recrystallization solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallizing solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for crystallization include crystallization from a vapour, which includes an evaporation step for example in a sealed tube or an air stream, and crystallization from melt (Crystallization Technology Handbook 2nd Edition, edited by A. Mersmann, 2001).

In particular the compound of formula ($I^0$) may subjected to recrystallisation (e.g. using 2-propanol or ethanol as the solvent) to increase the purity and to give a crystalline form.

Generally, the crystals obtained are analysed by an X-ray diffraction method such as X-ray powder diffraction (XRPD) or X-ray crystal diffraction.

Therefore, in a further embodiment the lactate salt of the compound prepared herein is optionally recrystallised to give a crystalline form, e.g. a crystalline form as defined herein.

Pharmaceutical Formulations

While it is possible for a compound (e.g. a compound of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt) to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF).

Thus, the present invention further provides, for the novel uses of the invention as defined herein, pharmaceutical compositions, as defined above, and pharmaceutical compositions made by a method comprising admixing a compound of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides, for the novel uses of the invention as defined herein, the lactate or citrate salt or mixtures thereof of 1-cyclopropyl-3-[3-(5-morpholin-4-ylmethyl-1H-benzoimidazol-2-yl)-1H-pyrazol-4-yl]-urea as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Examples of these are described in R. G. Strickly, Solubilizing Excipients in oral and injectable formulations, Pharmaceutical Research, Vol 21(2) 2004, p 201-230. In addition, they may contain co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

A drug molecule that is ionizable can be solubilized to the desired concentration by pH adjustment if the drug's pKa is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at 5-20 mg/ml, an isotonicifier, a pH 5-8 buffer, and optionally cholesterol.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of the formula (I) or 1-cyclopropyl-3-[3-(5-morpholin-4-ylmethyl-1H-benzoimidazol-2-yl)-1H-pyrazol-4-yl]-urea or all salts thereof such as the lactate or citrate salt thereof as defined herein. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediamietetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; poly-alcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

Pharmaceutical compositions of the present invention for parenteral injection can also comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If a compound not stable in aqueous media or has low solubility in aqueous media it can be formulated as a concentrate in organic solvents. The concentrate can then be diluted to a lower concentration in an aqueous system, and can be sufficiently stable for the short period of time during dosing. Therefore in another aspect, there is provided a pharmaceutical composition comprising a non aqueous solution composed entirely of one or more organic solvents, which can be dosed as is or more commonly diluted with a suitable IV excipient (saline, dextrose; buffered or not buffered) before administration (Solubilizing excipients in oral and injectable formulations, Pharmaceutical Research, 21(2), 2004, p201-

230). Examples of solvents and surfactants are propylene glycol, PEG300, PEG400, ethanol, dimethylacetamide (DMA), N-methyl-2-pyrrolidone (NMP, Pharmasolve), Glycerin, Cremophor EL, Cremophor RH 60 and polysorbate. Particular non aqueous solutions are composed of 70-80% propylene glycol, and 20-30% ethanol. One particular non aqueous solution is composed of 70% propylene glycol, and 30% ethanol. Another is 80% propylene glycol and 20% ethanol. Normally these solvents are used in combination and usually diluted at least 2-fold before IV bolus or IV infusion. The typical amounts for bolus IV formulations are ~50% for Glycerin, propylene glycol, PEG300, PEG400, and ~20% for ethanol. The typical amounts for IV infusion formulations are ~15% for Glycerin, 3% for DMA, and ~10% for propylene glycol, PEG300, PEG400 and ethanol.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing a compound of the formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The a compound of the formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt will generally be presented in unit dosage form and, as such, will typically contain sufficient compound to provide a desired level of biological activity. For example, a formulation intended for oral administration may contain from 0.1 milligrams to 2 grams of active ingredient, or 1 nanogram to 2 milligrams of active ingredient. Within this range, particular sub-ranges of compound are 0.1 milligrams to 2 grams of active ingredient (more usually from 10 milligrams to 1 gram, for example, 50 milligrams to 500 milligrams or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

A compound of the formula (I) or (I') or 1-cyclopropyl-3-[3-(5-morpholin-4-ylmethyl-1H-benzoimidazol-2-yl)-1H-pyrazol-4-yl]-urea or a salt thereof such as the lactate or citrate salt as defined herein will be useful in the prophylaxis or treatment of a range of disease states or conditions as defined herein, for example diseases or conditions mediated by disordered JAK signalling, abl kinase and Aurora kinases.

The compounds of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt are generally administered to a subject in need of such administration, for example a human or animal patient, preferably a human.

The compounds of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt may be administered over a prolonged term to maintain beneficial therapeutic effects or may be administered for a short period only. Alternatively they may be administered in a pulsatile or continuous manner.

A typical daily dose of the compound can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, such as 1 micrograms to 10 milligrams) per kilogram of bodyweight although higher or lower doses may be administered where required. The compound can be administered on a daily basis or on a repeat basis every 2, or 3, or 4, or 5, or 6, or 7, or 10 or 14, or 21, or 28 days for example. Ultimately, however, the quantity of compound administered and the type of composition used will be commensurate with the nature of the disease or physiological condition being treated and will be at the discretion of the physician.

An example of a daily dose of the compound comprises administering a compound of the formula (I) as defined herein, for example the lactate salt of compound I at a starting dosage of 1 mg/m$^2$/day-100 mg/m$^2$/day, in particular 1 mg/m$^2$/day-10 mg/m$^2$/day more particularly 3-6 mg/m$^2$/day (equivalent to 2.5-5 mg free base/m$^2$/day) or at an efficacious dose of the lactate salt of compound I of 2.5 mg/m$^2$/day-1.5 g/m$^2$/day, in particular 25 mg/m$^2$/day-600 mg/m$^2$/day, more particularly 200-500 mg/m$^2$/day such as 250 mg/m$^2$/day or 45-200 mg/m$^2$/day such as 45-150 mg/m$^2$/day or 56-185 mg/m$^2$/day (equivalent to 45-150 mg free base/m$^2$/day) although higher or lower doses may be administered where required. Ultimately, the quantity of compound administered and the type of composition used will be commensurate with the nature of the disease or physiological condition being treated and will be at the discretion of the physician.

In one particular dosing schedule, a patient will be given a continuous IV infusion of the compound or a salt thereof, for example the compound of formula (I), for periods of 2 hour to 120 hour, for example 2 to 96 hour in particular for 24 to 72 hour and the treatment repeated at a desired interval such as every one to three weeks.

More particularly, a patient may be given a continuous IV infusion of the compound or a salt thereof for periods of 24 hour daily for 5 days and the treatment repeated every week, or for periods of 24 hour and the treatment repeated every week, or for periods of 48 hour and the treatment repeated every two weeks or for periods of 72 hour and the treatment repeated every three weeks.

In another particular dosing schedule, a patient is given an infusion of the compound as an IV bolus over 2 hour once a day for a week every 1, 2, or 3 weeks or over 2 hour once every 1, 2, or 3 weeks.

Higher doses such as 1.5 g/m$^2$/day could be administered using a dosing regimen with frequent off-treatment periods such as 24 to 48 hour continuous IV fusion every one to two weeks. Lower dosages such could be administered using a dosing regimens with more sustained dosing (but still cyclical on/off) such as 48 to 72 hour continuous IV fusion every two to three weeks.

In particular, compounds of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt in particular the lactate salt could be administered to a patient at 250 mg/m$^2$/day for 72 hours by continuous IV infusion every 3 weeks.

In another embodiment, compounds of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt in particular the lactate salt could be administered to a patient over a five day treatment cycle.

Ultimately, however, the quantity of compound administered, the dosing regimen chosen and the type of composition used will be commensurate with the nature of the disease or physiological condition being treated and will be at the discretion of the physician.

The compounds of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt as defined herein can be administered as the sole therapeutic agent or they can be administered in combination therapy with one of more other compounds for treatment of a particular disease state, for example a neoplastic disease such as a cancer as hereinbefore defined. Examples of other therapeutic agents or therapies that may be administered or used together (whether concurrently or at different time intervals)

with the compounds of the invention include but are not limited to topoisomerase inhibitors, alkylating agents, antimetabolites, DNA binders, microtubule inhibitors (tubulin targeting agents), particular examples being cisplatin, cyclophosphamide, doxorubicin, irinotecan, fludarabine, 5FU, taxanes, mitomycin C and radiotherapy. In one embodiment the compounds of the formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt may be combined with a DNA targeting agents such as topoisomerase inhibitors, alkylating agents, antimetabolites, DNA binders particularly cisplatin, cyclophosphamide, doxorubicin, irinotecan, fludarabine mitomycin C and radiotherapy.

Other examples of therapeutic agents that may be administered together (whether concurrently or at different time intervals) with the compounds of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt as defined herein include monoclonal antibodies and signal transduction inhibitors.

For the case of CDK or Aurora inhibitors combined with other therapies, the two or more treatments may be given in individually varying dose schedules and via different routes. Thus, for example, the salt forms of compound I (e.g. the lactate or citrate salts and mixtures thereof) may be administered as solutions by the parenteral route whilst another therapeutic agent may be administered orally.

Where the compound of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt is administered in combination therapy with one, two, three, four or more other therapeutic agents (preferably one or two, more preferably one), the compounds can be administered simultaneously (either in the same or different pharmaceutical formulation) or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) or (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of the compounds of formula (I) and (I'), and in particular 1-cyclopropyl-3-[3-(5-morpholin-4-ylmethyl-1H-benzoimidazol-2-yl)-1H-pyrazol-4-yl]-urea and its salts and crystalline forms thereof such as the lactate or citrate salt, a patient may be screened to determine whether a disease or condition from which the patient is or may be suffering is:

A. a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR$^3$), Ret, Eph (e.g. EphB2 or EphB4), or Src (e.g. csrc); or B. a cancer in which the cancer cells thereof contain a drug resistant kinase mutation which is:
   (a) a threonine gatekeeper mutation; or
   (b) a drug-resistant gatekeeper mutation; or
   (c) an imatinib resistant mutation; or
   (d) a nilotinib resistant mutation; or
   (e) a dasatinib resistant mutation; or
   (f) a T670I mutation in KIT; or
   (g) a T674I mutation in PDGFR; or
   (h) T790M mutation in EGFR; or
     (i) a T315I mutation in abl; or C. a cancer which expresses a mutated molecular target which is a mutated form of BCRabl, c-kit, PDGF, EGF receptor or ErbB2; or D. a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2;

and is a disease state or condition which would be susceptible to treatment with a compound of the formula (I) or (I').

In a particular embodiment, prior to administration of a compound of the formula (I) or (I'), a patient may be screened to determine whether a disease or condition from which the patient is or may be suffering is one which would be susceptible to treatment with a compound having activity against BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases.

A biological sample taken from a patient may be analysed to determine whether a condition or disease, such as cancer, that the patient is or may be suffering from is one which is characterised by a genetic abnormality (e.g. contains a mutated form of a kinase as described above) or abnormal protein expression which leads to over-activation of a kinase or to sensitisation of a pathway to normal kinase activity. Alternatively or in addition, a biological sample taken from a patient may be analysed to determine whether a condition or disease, such as cancer, that the patient is or may be suffering from is one which is characterised by upregulation of a particular kinase and thus may be particularly sensitive to an inhibitor of that kinase. The term up-regulation includes elevated expression or over-expression, including gene amplification (i.e. multiple gene copies) and increased expression by a transcriptional effect, and hyperactivity and activation, including activation by mutations.

In the case of the kinases BCR-abl, VEGFR, PDGFR, EGFR, Flt3, JAK (e.g. JAK2 or JAK3), C-abl, PDK1, Chk (e.g. Chk1 or Cbk2), FGFR (e.g. FGFR3), Ret, Eph (e.g.

EphB2 or EphB4), or Src (e.g. cSrc) or a mutated form thereof as defined herein, a biological sample taken from a patient may be analysed to determine whether a condition or disease, such as cancer, that the patient is or may be suffering from is one which is characterised by a genetic abnormality or abnormal protein expression which leads to up-regulation of the levels or activity of the kinase or to sensitisation of a pathway to normal kinase activity, or to upregulation of the kinase signalling pathways such as kinase ligand levels or kinase ligand activity or to upregulation of a biochemical pathway downstream of kinase activation.

Examples of such abnormalities that result in activation or sensitisation of the kinase signal include loss of, or inhibition of apoptotic pathways, up-regulation of the receptors or ligands, or presence of mutant variants of the receptors or ligands e.g. PTK variants.

Tumours with mutants of FGFR1, FGFR2 or FGFR3 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions (Lemonnier, et al., J. Bone Miner. Res., 16, 832-845 (2001)). In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas (Powers, C. J., et al., Endocr. Rel. Cancer, 7, 165 (2000)). A particular mutation T6741 of the PDGF receptor has been identified in imatinib-treated patients.

In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. Clin Cancer Res. 2006 12(22): 6652-6662.

Alternatively, a biological sample taken from a patient may be analysed for loss of a negative regulator or suppressor of a particular kinase (e.g. BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases). In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

Thus, the patient may be subjected to a diagnostic test to detect a marker characteristic of over-expression, up-regulation or activation of a kinase. The term diagnosis includes screening. By marker we include genetic markers including, for example, the measurement of DNA composition to identify mutations of a particular kinase. The term marker also includes markers which are characteristic of up regulation of the activity of a kinase, including enzyme activity, enzyme levels, enzyme state (e.g. phosphorylated or not) and mRNA levels of the aforementioned proteins. The term up-regulation includes elevated expression or over-expression, including gene amplification (i.e. multiple gene copies) and increased expression by a transcriptional effect, and hyperactivity and activation, including activation by mutations.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

More specifically, the patient may be subjected to a diagnostic test to detect a marker characteristic of up-regulation of BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases. The term diagnosis includes screening. By marker we include genetic markers including, for example, the measurement of DNA composition to identify mutations of the kinases. The term marker also includes markers which are characteristic of up regulation of the kinases including enzyme activity, enzyme levels, enzyme state (e.g. phosphorylated or not) and mRNA levels of the aforementioned proteins.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in a kinase such as BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases may mean that the patient would be particularly suitable for treatment with an inhibitor of the kinase in question. Tumours may preferentially be screened for presence of a kinase variant prior to treatment. The screening process will typically involve direct sequencing, oligonucleotide microarray analysis, or a mutant specific antibody or by using the RT-PCR and FISH techniques described above.

In addition, mutant forms of, for example a kinase such as BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases, can be identified by direct sequencing of, for example, tumour biopsies using PCR and methods to sequence PCR products directly as hereinbefore described. The skilled person will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of cyclin E, or loss of p21 or p27, or detection of CDC4 variants, Aurora up-regulation and mutants of Aurora could be applicable in the present case.

Therefore, all of these techniques could also be used to identify tumours particularly suitable for treatment with the compounds of the invention.

In one embodiment of the invention, prior to administration of a compound of the formula (I), formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt, a patient may be screened to determine whether a disease or condition from which the patient is or may be suffering is one which would be susceptible to treatment with a compound having activity against Flt3, JAK, C-abl, PDK1, Chk1, and Chk2. These techniques may also be used for screening for diseases or conditions caused by the up-regulation or mutants of Flt3, JAK, C-abl, PDK1, Chk1, and Chk2 kinases.

In another embodiment of the invention, prior to administration of a compound of the formula (I), formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt, a patient may be screened to determine whether a disease or condition from which the patient is or may be suffering is one which would be susceptible to treatment with a compound having activity against FGFR, ret, Eph, cSRC, VEGFR, PDGFR kinases. These techniques may also be used for screening for diseases or conditions caused by the up-regulation or mutants of GFR, ret, Eph, cSRC, VEGFR, PDGFR kinases.

These techniques may also be used for screening for diseases or conditions caused by the up-regulation or mutants of VEGFR kinases, include, but are not limited to, standard methods such as reverse-transcriptase polymerase chain reaction (RT-PCR) or in-situ hybridisation.

Abnormal levels of proteins such as VEGFR can be measured using standard enzyme assays, for example, those assays described herein. Activation or overexpression could also be detected in a tissue sample, for example a tumour tissue, by measuring the tyrosine kinase activity with an assay such as that available from Chemicon International. The tyrosine kinase of interest would be immunoprecipitated from the sample lysate and its activity measured.

Alternative methods for the measurement of the over expression or activation of VEGFR including the isoforms thereof, include the measurement of microvessel density. This can for example be measured using methods described by Orre and Rogers (Int J Cancer 1999 84(2) 101-8). Assay methods also include the use of markers, for example, in the case of VEGFR these include CD31, CD34 and CD105 (Mineo et al. J Clin Pathol. 2004 57(6) 591-7).

Activating mutations of FLT3 are frequently observed in acute myeloid leukaemia, myelodysplastic syndromes (MDS) and some cases with acute lymphoblastic leukemia (ALL). Cancer patients with activating mutants of FLT3 can be screened for presence of the length mutations or internal tandem duplication mutations as an indication of those most sensitive to inhibitors of FLT3.

Activating mutations in the tyrosine kinase JAK2 has been observed in polycythemia vera, essential thrombocythemia and myeloid metaplasia with myelofibrosis. The methods descrined herein could be used to identify patients harbouring these mutations.

Patients with tumours harbouring cells expressing the resistance mutants of BCR-abl e.g. T315I can be identified using the methods described herein.

Therefore, in addition, the methods described herein could be used to diagnose mutations of JAK2 e.g. V617F, activating mutations of FLT3, mutants of C-Abl e.g. T315I.

In a further embodiment the compounds of the invention could be used to treat patients and/or tumours and/or leukemias which are Philadelphia chromosome positive (Ph+). This is a translocation which occurs between chromosomes 9 and 22 resulting in an altered chromosome 22. The translocation, often referred to as the BCR-abl translocation, can be distinguished by cytogenetic methods such as those known to the skilled person including those described herein, in particular FISH, and used to identify patients suitable for treatment with the compounds of the invention.

As the compounds of the invention are inhibitors of aurora kinase which is directly related to mitotic checkpoint defects, the compounds of the invention may be particularly suitable for treating patients suffering from a leukaemia exhibiting polyploidy as a manifestation of loss of chromosomal integrity, mitotic spindle defects or disease progression.

Genetic instability is a common feature in many leukemias resulting in aneuploidy. Centrosome aberrations have recently been described in several different hematological malignancies including acute myeloid leukemias, myelodysplastic syndromes, Hodgkin's as well as non-Hodgkin's lymphomas, chronic lymphocytic leukemias and multiple myelomas. Analagous to many solid tumors a correlation between centrosome abnormalities on the one hand and karyotype aberrations as well as clinical aggressiveness on the other hand seems to exist in myeloid malignancies, chronic lymphocytic leukemias and at least some types of non-Hodgkin's lymphomas.

Complex chromosomal aberrations are present in up to 30% of patients with primary myelodysplastic syndrome (MDS) or acute myeloid leukemia (AML) and are associated with a poor prognosis. Specific alterations in complex karyotypes are difficult to define by conventional cytogenetics alone. A more comprehensive view of the recurrent aberrations can be obtained when spectral karyotyping (SKY) and fluorescence in situ hybridization (FISH) with selected probes on bone marrow samples are used (Cancer Genet. Cytogenet., 2006, 165(1), 51-63, Trost D et al). A detailed analysis of specific breakpoints and deletions can reveal recurrent involvement of specific chromosomal bands harboring known tumor suppressor genes or oncogenes. Analysis of a large number of MDS and AML cases in a similar detailed manner with SKY and FISH will reveal whether new subgroups can be identified according to their genetic alterations. Correlation with clinical parameters may reveal the prognostic significance of these genetic subgroups. In MDS for example, the International Prognostic Scoring System combines blast percentage, karyotype, and number of cytopenias to generate a scoring system that reliably estimates survival and risk of transformation to acute myeloid leukemia for patients with MDS. This universally accepted scoring system is often combined with FAB or World Health Organization morphologic criteria to provide a more complete clinical picture and the most accurate prognostic assessment possible (Semin Oncol. 2005 August; 32(4 Suppl 5):S3-10, Bennett).

Genetic instability is a common feature of acute myeloid leukemia (AML) (Blood, 2003, 101(1), 289-91, Neben et al) and centrosome aberrations have been described as a possible cause of aneuploidy in many human tumors. To investigate whether centrosome aberrations correlate with cytogenetic findings in AML, a set of AML samples were examined using a centrosome-specific antibody to pericentrin. The AML samples analyzed displayed numerical and structural centrosome aberrations as compared with peripheral blood mononuclear cells. In comparison to AML samples with normal chromosome count, the extent of numerical and structural centrosome aberrations was higher in samples with numerical chromosome changes. When the frequency of centrosome aberrations was analyzed within cytogenetically defined risk groups, a correlation was found between the extent of centrosome abnormalities in all 3 risk groups. These results indicate that centrosome defects may contribute to the acquisition of chromosome aberrations and thereby to the prognosis in AML.

Thus a number of techniques known to the skilled person could be used to determine whether a tumour or leukaemia was associated with chromosomal aberrations.

Therefore an aspect of the invention is a method of detecting whether a patient is suffering from a disease, in particular cancer, exhibiting chromosomal aberrations and treating them with a compound of the invention.

The invention further provides a method of diagnosing whether a patient as suffering from a leukaemia exhibiting a chromosomal aberration and then administering a compound of the invention.

A further aspect of the invention is a method for the prophylaxis or treatment of (or alleviating or reducing the incidence of) cancer in a patient suffering from or suspected of suffering from cancer; which method comprises (i) subjecting a patient to a diagnostic test to determine whether the patient possesses chromosomal aberrations; and (ii) where the patient does possess the said chromosomal aberrations, thereafter administering to the patient a compound of the formula (I) as defined herein having aurora kinase inhibiting activity.

In another embodiment, prior to administration of the lactate or citrate salt of 1-cyclopropyl-3-[3-(5-morpholin-4-yl-methyl-1H-benzoimidazol-2-yl)-1H-pyrazol-4-yl]-urea, a patient may be screened to determine whether a disease or condition from which the patient is or may be suffering is one which would be susceptible to treatment with a compound having activity against Aurora and/or cyclin dependent kinases.

For example, a biological sample taken from a patient may be analysed to determine whether a condition or disease, such as cancer, that the patient is or may be suffering from is one which is characterised by a genetic abnormality or abnormal protein expression which leads to over-activation of CDKs or to sensitisation of a pathway to normal CDK activity. Examples of such abnormalities that result in activation or sensitisation of the CDK2 signal include up-regulation of cyclin E, (Harwell R M, Mull B B, Porter D C, Keyomarsi K.; J Biol. Chem. 2004 Mar. 26; 279(13):12695-705) or loss of p21 or p27, or presence of CDC4 variants (Rajagopalan H, Jallepalli P V, Rago C, Velculescu V E, Kinzler K W, Vogelstein B, Lengauer C.; Nature. 2004 Mar. 4; 428(6978):77-81). Tumours with mutants of CDC4 or up-regulation, in particular over-expression, of cyclin E or loss of p21 or p27 may be particularly sensitive to CDK inhibitors. Alternatively or in addition, a biological sample taken from a patient may be analysed to determine whether a condition or disease, such as cancer, that the patient is or may be suffering from is one which is characterised by upregulation of Aurora kinase and thus may be particularly sensitive to Aurora inhibitors. The term up-regulation includes elevated expression or over-expression, including gene amplification (i.e. multiple gene copies) and increased expression by a transcriptional effect, and hyperactivity and activation, including activation by mutations.

Thus, the patient may be subjected to a diagnostic test to detect a marker characteristic of over-expression, up-regulation or activation of Aurora kinase or the patient may be subjected to a diagnostic test to detect a marker characteristic of up-regulation of cyclin E, or loss of p21 or p27, or presence of CDC4 variants. The term diagnosis includes screening. By marker we include genetic markers including, for example, the measurement of DNA composition to identify mutations of Aurora or CDC4. The term marker also includes markers which are characteristic of up regulation of Aurora or cyclin E, including enzyme activity, enzyme levels, enzyme state (e.g. phosphorylated or not) and mRNA levels of the aforementioned proteins. Tumours with upregulation of cyclin E, or loss of p21 or p27 may be particularly sensitive to CDK inhibitors. Tumours may preferentially be screened for upregulation of cyclin E, or loss of p21 or p27 prior to treatment. Thus, the patient may be subjected to a diagnostic test to detect a marker characteristic of up-regulation of cyclin E, or loss of p21 or p27.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

It has been found, see Ewart-Toland et al., (Nat. Genet. 2003 August; 34(4):403-12), that individuals forming part of the sub-population possessing the Ile31 variant of the STK gene (the gene for Aurora kinase A) may have an increased susceptibility to certain forms of cancer. Therefore, such individuals suffering from cancer will benefit from the administration of compounds having Aurora kinase inhibiting activity. A patient suffering from, or suspected of suffering from, a cancer may therefore be screened to determine whether he or she forms part of the Ile31 variant sub-population. In addition, it has been found, Rajagopalan et al (Nature. 2004 Mar. 4; 428(6978):77-81), that there were mutations present in CDC4 (also known as Fbw7 or Archipelago) in human colorectal cancers and endometrial cancers (Spruck et al, Cancer Res. 2002 Aug. 15; 62(16):4535-9). Identification of individual carrying a mutation in CDC4 may mean that the patient would be particularly suitable for treatment with a CDK inhibitor. Tumours may preferentially be screened for presence of a CDC4 variant prior to treatment. The screening process will typically involve direct sequencing, oligonucleotide microarray analysis, or a mutant specific antibody.

Tumours with activating mutants of Aurora or up-regulation of Aurora including any of the isoforms thereof, may be particularly sensitive to Aurora inhibitors. Tumours may preferentially be screened for up-regulation of Aurora or for Aurora possessing the Ile31 variant prior to treatment (Ewart-Toland et al., Nat. Genet. 2003 August; 34(4):403-12). Ewart-Toland et al identified a common genetic variant in STK15 (resulting in the amino acid substitution F31I) that is preferentially amplified and associated with the degree of aneuploidy in human colon tumors. These results are consistent with an important role for the Ile31 variant of STK15 in human cancer susceptibility. In particular, this polymorphism in Aurora A has been suggested to be a genetic modifier for developing breast carcinoma (Sun et al, Carcinogenesis, 2004, 25(11), 2225-2230).

The aurora A gene maps to the chromosome 20q13 region that is frequently amplified in many cancers e.g. breast, bladder, colon, ovarian, pancreatic. Patients with a tumour that has this gene amplification might be particularly sensitive to treatments targeting aurora kinase inhibition Methods of identification and analysis of mutations and up-regulation of protein e.g. Aurora isoforms and chromosome 20q13 amplification are known to a person skilled in the art. Screening methods could include, but are not limited to, standard methods such as reverse-transcriptase polymerase chain reaction (RT-PCR) or in-situ hybridisation.

Tumours with mutants of CDC4 or up-regulation, in particular over-expression, of cyclin E or loss of p21 or p27 may be particularly sensitive to CDK inhibitors. Tumours may preferentially be screened for up-regulation, in particular over-expression, of cyclin E (Harwell R M, Mull B B, Porter D C, Keyomarsi K.; J Biol. Chem. 2004 Mar. 26; 279(13): 12695-705) or loss of p21 or p27 or for CDC4 variants prior to treatment (Rajagopalan H, Jallepalli P V, Rago C, Velculescu V E, Kinzler K W, Vogelstein B, Lengauer C.; Nature. 2004 Mar. 4; 428(6978):77-81).

Patients with mantle cell lymphoma (MCL) could be selected for treatment with a compound of the invention using diagnostic tests outlined herein. MCL is a distinct clinicopathologic entity of non-Hodgkin's lymphoma, characterized by proliferation of small to medium-sized lymphocytes with co-expression of CD5 and CD20, an aggressive and incurable clinical course, and frequent t(11;14)(q13;q32) translocation. Over-expression of cyclin D1 mRNA, found in mantle cell lymphoma (MCL), is a critical diagnostic marker. Yatabe et al (Blood. 2000 Apr. 1; 95(7):2253-61) proposed that cyclin D1-positivity should be included as one of the standard criteria for MCL, and that innovative therapies for this incurable disease should be explored on the basis of the new criteria. Jones et al (J Mol. Diagn. 2004 May; 6(2):84-9) developed a real-time, quantitative, reverse transcription PCR assay for cyclin D1 (CCND1) expression to aid in the diagnosis of mantle cell lymphoma (MCL). Howe et al (Clin Chem. 2004 January; 50(1):80-7) used real-time quantitative RT-PCR to evaluate cyclin D1 mRNA expression and found that quantitative RT-PCR for cyclin D1 mRNA normalized to CD19 mRNA can be used in the diagnosis of MCL in blood, marrow, and tissue. Alternatively, patients with breast cancer could be selected for treatment with a CDK inhibitor using diagnostic tests outline above. Tumour cells commonly overexpress cyclin E and it has been shown that cyclin E is overexpressed in breast cancer (Harwell et al, Cancer Res, 2000, 60, 481-489). Therefore breast cancer may in particular be treated with a CDK inhibitor as provided herein.

EXAMPLES

Figure 1:
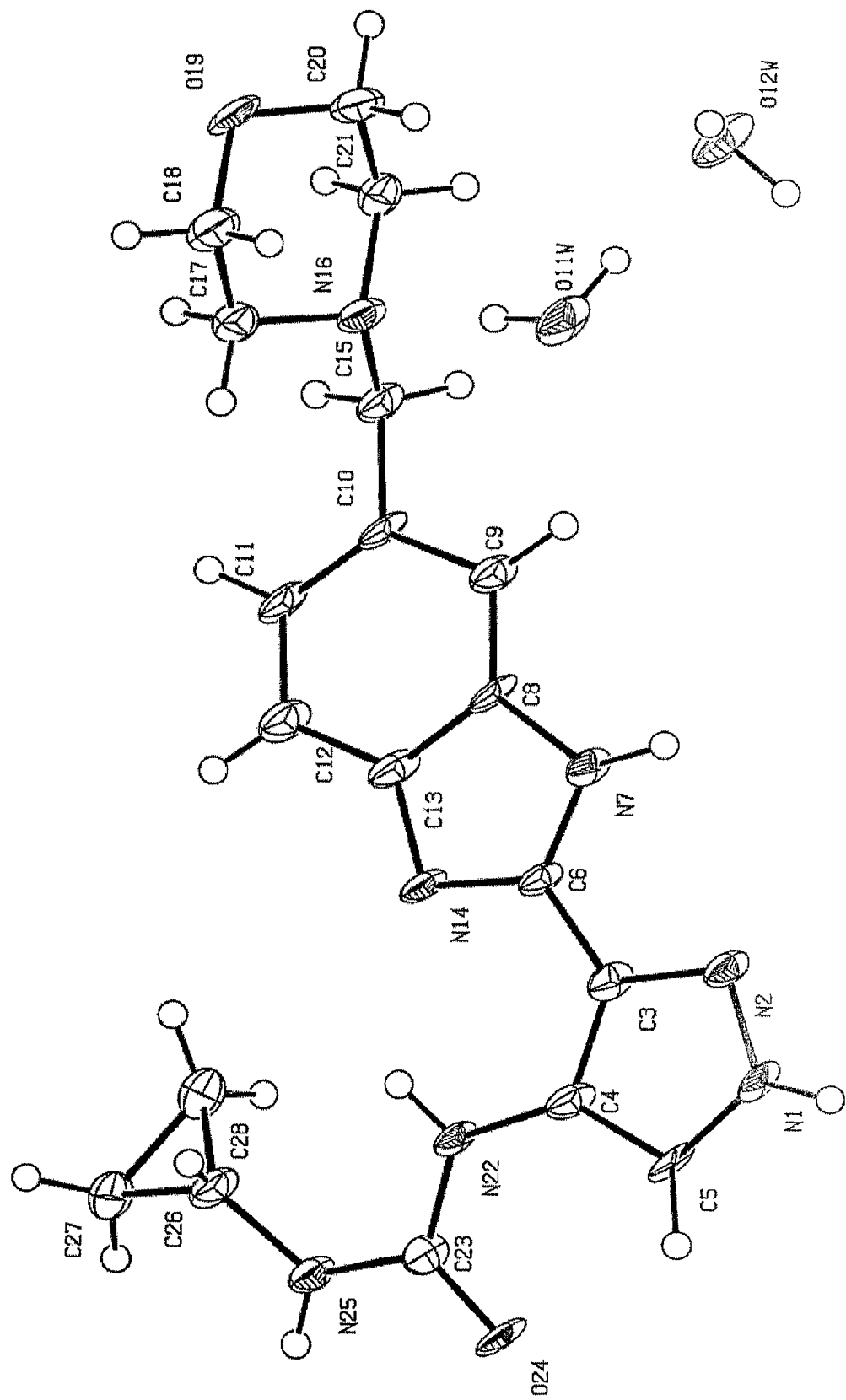
FIG. 1 is a thermal ellipsoid plot of the free base dihydrate of 1-cyclopropyl-3-[3-(5-morpholin-4-ylmethyl-1H-benzoimidazol-2-yl)-1H-pyrazol-4-yl]-urea as described in Example 69 below.

The invention will now be illustrated, but not limited, by reference to the specific embodiments described in the following examples.

In the examples, the following abbreviations are used.
AcOH acetic acid
BOC tert-butyloxycarbonyl
CDI 1,1-carbonyldiimidazole
DMAW90 Solvent mixture: DCM: MeOH, AcOH, $H_2O$ (90: 18:3:2)
DMAW120 Solvent mixture: DCM: MeOH, AcOH, $H_2O$ (120:18:3:2)
DMAW240 Solvent mixture: DCM: MeOH, AcOH, $H_2O$ (240:20:3:2)
DCM dichloromethane
DMF dimethylformamide
DMSO dimethyl sulphoxide
EDC 1-ethyl-3-(3'-dimethylaminopropyl)-carbodiimide
$Et_3N$ triethylamine
EtOAc ethyl acetate
$Et_2O$ diethyl ether HOAt 1-hydroxyazabenzotriazole
HOBt 1-hydroxybenzotriazole
MeCN acetonitrile
MeOH methanol
$SiO_2$ silica
TBTU N,N,N',N'-tetramethyl-O-(benzotriazol-1-yl)uronium tetrafluoroborate
THF tetrahydrofuran Analytical LC-MS System and Method Description In the examples, the compounds prepared were characterised by liquid chromatography and mass spectroscopy using the systems and operating conditions set out below. Where atoms with different isotopes are present, and a single mass quoted, the mass quoted for the compound is the monoisotopic mass (i.e. $^{35}Cl$; $^{79}Br$ etc.). Several systems were used, as described below, and these were equipped with, and were set up to run under, closely similar operating conditions. The operating conditions used are also described below.
Waters Platform LC-MS System:
HPLC System: Waters 2795
Mass Spec Detector: Micromass Platform LC
PDA Detector: Waters 2996 PDA
Analytical Acidic Conditions:
Eluent A: $H_2O$ (0.1% Formic Acid)
Eluent B: $CH_3CN$ (0.1% Formic Acid)
Gradient: 5-95% eluent B over 3.5 minutes
Flow: 0.8 ml/min
Column: Phenomenex Synergi 4µ MAX-RP 80A, 2.0×50 mm
Analytical Basic Conditions:
Eluent A: $H_2O$ (10 mM $NH_4HCO_3$ buffer adjusted to pH=9.2 with $NH_4OH$)
Eluent B: $CH_3CN$
Gradient: 05-95% eluent B over 3.5 minutes
Flow: 0.8 ml/min
Column: Phenomenex Luna C18(2) 5 µm 2.0×50 mm
Analytical Polar Conditions:
Eluent A: $H_2O$ (0.1% Formic Acid)
Eluent B: $CH_3CN$ (0.1% Formic Acid)
Gradient: 00-50% eluent B over 3 minutes
Flow: 0.8 ml/min
Column: Phenomenex Synergi 4µ MAX-RP 80A, 2.0×50 mm
Analytical Lipophilic Conditions:
Eluent A: $H_2O$ (0.1% Formic Acid)
Eluent B: $CH_3CN$ (0.1% Formic Acid)
Gradient: 55-95% eluent B over 3.5 minutes
Flow: 0.8 ml/min
Column: Phenomenex Synergi 4µ MAX-RP 80A, 2.0×50 mm
Analytical Long Acidic Conditions:
Eluent A: $H_2O$ (0.1% Formic Acid)
Eluent B: $CH_3CN$ (0.1% Formic Acid)
Gradient: 05-95% eluent B over 15 minutes
Flow: 0.4 ml/min
Column: Phenomenex Synergi 4µ MAX-RP 80A, 2.0×150 mm
Analytical Long Basic Conditions:
Eluent A: $H_2O$ (10 mM $NH_4HCO_3$ buffer adjusted to pH=9.2 with $NH_4OH$)
Eluent B: $CH_3CN$
Gradient: 05-95% eluent B over 15 minutes
Flow: 0.8 ml/min
Column: Phenomenex Luna C18(2) 5 µm 2.0×50 mm
Platform MS Conditions:
Capillary voltage: 3.6 kV (3.40 kV on ES negative)
Cone voltage: 25 V
Source Temperature: 120° C.
ScanRange: 100-800 amu
Ionisation Mode: Electro-Spray Positive or ElectroSpray Negative or ElectroSpray Positive & Negative
Waters Fractionlynx LC-MS System:
HPLC System: 2767 autosampler-2525 binary gradient pump
Mass Spec Detector: Waters ZQ
PDA Detector: Waters 2996 PDA
Analytical Acidic Conditions:
Eluent A: $H_2O$ (0.1% Formic Acid)
Eluent B: $CH_3CN$ (0.1% Formic Acid)
Gradient: 5-95% eluent B over 4 minutes
Flow: 2.0 ml/min
Column: Phenomenex Synergi 4µ MAX-RP 80A, 4.6×50 mm
Analytical Polar Conditions:
Eluent A: $H_2O$ (0.1% Formic Acid)
Eluent B: $CH_3CN$ (0.1% Formic Acid)
Gradient: 00-50% eluent B over 4 minutes
Flow: 2.0 ml/min
Column: Phenomenex Synergi 4µ MAX-RP 80A, 4.6×50 mm
Analytical Lipophilic Conditions:
Eluent A: $H_2O$ (0.1% Formic Acid)
Eluent B: $CH_3CN$ (0.1% Formic Acid)
Gradient: 55-95% eluent B over 4 minutes
Flow: 2.0 ml/min
Column: Phenomenex Synergi 4µ MAX-RP 80A, 4.6×50 mm
Fractionlynx MS conditions:
Capillary voltage: 3.5 kV (3.2 kV on ES negative)
Cone voltage: 25 V (30 V on ES negative)
Source Temperature: 120° C.
Scan Range: 100-800 amu
Ionisation Mode: ElectroSpray Positive or ElectroSpray Negative or ElectroSpray Positive & Negative Mass Directed Purification LC-MS System Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

One such system for purifying compounds via preparative LC-MS is described below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Preparative LC-MS Systems:
Waters Fractionlynx System:
Hardware:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
Software:
Masslynx 4.0
Waters MS Running Conditions:
Capillary voltage: 3.5 kV (3.2 kV on ES Negative)
Cone voltage: 25 V
Source Temperature: 120° C.
Multiplier: 500 V
Scan Range: 125-800 amu
Ionisation Mode: ElectroSpray Positive or ElectroSpray Negative
Agilent 1100 LC-MS Preparative System:
Hardware:
Autosampler: 1100 series "prepALS"
Pump: 1100 series "PrepPump" for preparative flow gradient and 1100 series "QuatPump" for pumping modifier in prep flow
UV detector: 1100 series "MWD" Multi Wavelength Detector
MS detector: 1100 series "LC-MSD VL"
Fraction Collector: 2×"Prep-FC"
Make Up pump: "Waters RMA"
Agilent Active Splitter
Software:
Chemstation: Chem32
Agilent MS Running Conditions:
Capillary voltage: 4000 V (3500 V on ES Negative)
Fragmentor/Gain: 150/1
Drying gas flow: 13.0 L/min
Gas Temperature: 350° C.
Nebuliser Pressure: 50 psig
Scan Range: 125-800 amu
Ionisation Mode: ElectroSpray Positive or ElectroSpray Negative
Chromatographic Conditions:
Columns:
1. Low pH chromatography:
Phenomenex Synergy MAX-RP, 10µ, 100×21.2 mm
(alternatively used Thermo Hypersil-Keystone HyPurity Aquastar, 5µ, 100×21.2 mm for more polar compounds)
2. High pH Chromatography:
Phenomenex Luna C18 (2), 10µ, 100×21.2 mm
(alternatively used Phenomenex Gemini, 5µ, 100×21.2 mm)
Eluents:
1. Low pH Chromatography:
Solvent A: $H_2O$+0.1% Formic Acid, pH~1.5
Solvent B: $CH_3CN$+0.1% Formic Acid
2. High pH Chromatography:
Solvent A: $H_2O$+10 mM $NH_4HCO_3$+$NH_4OH$, pH=9.2
Solvent B: $CH_3CN$
3. Make Up Solvent:
MeOH+0.2% Formic Acid (for both chromatography type)

Methods:
According to the analytical trace the most appropriate preparative chromatography type was chosen. A typical routine was to run an analytical LC-MS using the type of chromatography (low or high pH) most suited for compound structure. Once the analytical trace showed good chromatography a suitable preparative method of the same type was chosen. Typical running condition for both low and high pH chromatography methods were:

Flow rate: 24 ml/min

Gradient: Generally all gradients had an initial 0.4 min step with 95% A+5% B. Then according to analytical trace a 3.6 min gradient was chosen in order to achieve good separation (e.g. from 5% to 50% B for early retaining compounds; from 35% to 80% B for middle retaining compounds and so on)

Wash: 1.2 minute wash step was performed at the end of the gradient

Re-equilibration: 2.1 minutes re-equilibration step was ran to prepare the system for the next run Make Up flow rate: 1 ml/min Solvent:
All compounds were usually dissolved in 100% MeOH or 100% DMSO From the information provided someone skilled in the art could purify the compounds described herein by preparative LC-MS.

The starting materials for each of the Examples are commercially available unless otherwise specified.

Example 1

Synthesis of 5-cyano-2-methoxy-N-[3-(5-morpholin-4-ylmethyl-1H-benzoimidazol-2-yl)-1H-pyrazol-4-yl]-benzamide 1A. Synthesis of (3,4-Dinitro-phenyl)-morpholin-4-yl-methanone

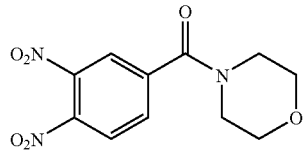 [SMILES: O=C(c1ccc([N+](=O)[O-])c([N+](=O)[O-])c1)N1CCOCC1]

A mixture of 3,4-dinitrobenzoic acid (10.0 g) and thionyl chloride (30 ml) was heated at reflux for 2 hours, cooled to ambient temperature and excess thionyl chloride removed through azeotrope with toluene. The residue was taken up in THF (100 ml) and morpholine (4.1 ml) and $Et_3N$ (7.2 ml) added concurrently to the mixture at 0° C. The mixture was stirred for 3 hours, water (100 ml) added and then extracted with EtOAc. The organic portion was washed with brine, dried ($MgSO_4$) and reduced in vacuo. Recrystallisation of the residue from MeOH gave (3,4-dinitro-phenyl)-morpholin-4-yl-methanone (8.23 g) as a yellow solid. ($^1$H NMR (300 MHz, DMSO-$d_6$) δ 8.3 (d, 1H), 8.3 (s, 1H), 8.0 (d, 1H), 3.7-3.5 (m, 8H)).

1B. Synthesis of (3,4-Diamino-phenyl-morpholin-4-yl-methanone

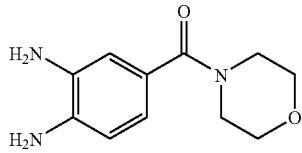

A mixture of (3,4-dinitro-phenyl)-morpholin-4-yl-methanone (1.0 g) and 10% Pd/C (150 mg) in MeOH (30 ml) was shaken under a hydrogen atmosphere at ambient temperature for 10 hours, then filtered through a plug of Celite and reduced in vacuo to give (3,4-diamino-phenyl)-morpholin-4-yl-methanone (900 mg). ($^1$H NMR (300 MHz, DMSO-$d_6$) δ 6.6 (s, 1H), 6.5 (s, 2H), 4.8 (s, 1.5H), 4.6 (s, 1.5H), 4.1 (s, 1H), 3.6 (m, 4H), 3.4 (m, 4H)).

1C. Synthesis of 4-Morpholin-4-ylmeth 1-benzene-1,2-diamine

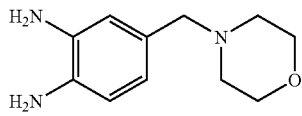

To a mixture of (3,4-dinitro-phenyl)-morpholin-4-yl-methanone (2.84 g) in dry THF (50 ml) was added NaBH$_4$ (954 mg) followed drop-wise by BF$_3$.Et$_2$O (3.2 ml). The mixture was stirred at ambient temperature for 3 hours and then quenched though addition of MeOH. The mixture was reduced in vacuo, partitioned between EtOAc and water and the organic portion washed with brine, dried (MgSO$_4$) and reduced in vacuo. The residue was purified via flash column chromatography eluting with EtOAc to give 4-(3,4-dinitro-benzyl)-morpholine (1.08 g).

A mixture of 4-(3,4-dinitro-benzyl)-morpholine (550 mg) and 10% Pd/C (75 mg) in MeOH (10 ml) was shaken under a hydrogen atmosphere at ambient temperature for 4 hours, then filtered through a plug of Celite and reduced in vacuo to give 4-morpholin-4-ylmethyl-benzene-1,2-diamine (483 mg) as the major component of a mixture.

1D. Synthesis of 5-morpholin-4-ylmethyl-2-(4-nitro-1H-pyrazol-3-yl)1H-benzimidazole

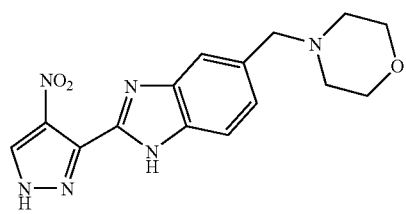 [SMILES: O=[N+]([O-])c1c[nH]nc1-c1nc2cc(CN3CCOCC3)ccc2[nH]1]

A mixture of 4-morpholin-4-ylmethyl-benzene-1,2-diamine (2.30 g, 11.1 mmol), 4-nitro-1H-pyrazole-3-carboxylic acid (1.57 g, 10.0 mmol), EDC (2.13 g, 11.1 mmol) and HOBt (1.50 g, 11.1 mmol) in dry DMF (25 ml) was stirred at ambient temperature for 24 hours. The mixture was reduced in vacuo and the crude residue dissolved in AcOH (40 ml) and heated at reflux for 3 h. The solvent was removed in vacuo and the residue was purified by flash column chromatography eluting with 0-20% MeOH in EtOAc to give 5-morpholin-4-ylmethyl-2-(4-nitro-1H-pyrazol-3-yl) IH-benzimidazole as a yellow solid. (1.0 g, 61%). (LC/MS: R$_t$ 1.83, [M+H]+329).

1E. Synthesis of 3-(5-morpholin-4-ylmethyl-1H-benzimidazol-2-yl)-1H-pyrazol-4-ylamine

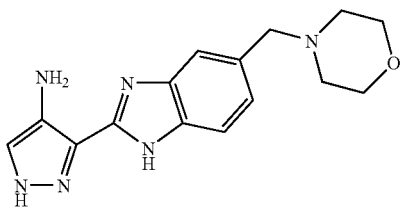 [SMILES: Nc1c[nH]nc1-c1nc2cc(CN3CCOCC3)ccc2[nH]1]

Palladium on carbon (10%, 0.08 g) was added to solution of 5-morpholin-4-ylmethyl-2-4-nitro-1H-pyrazol-3-yl) 1H-benzimidazole (0.82 g, 2.5 mmol) in DMF (30 ml) under an atmosphere of nitrogen. The mixture was shaken under a hydrogen atmosphere for 4 hours then filtered through Celite, washing with MeOH. The filtrate was concentrated in vacuo to give 3-(5-morpholin-4-ylmethyl-1H-benzimidazol-2-yl)-1H-pyrazol-4-ylamine as a brown solid (530 mg, 71%). (LC/MS: R$_t$ 1.94, [M+H]+299).

1F. Synthesis of 5-cyano-2-methoxy-benzoic acid

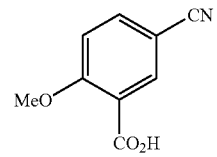 [SMILES: COc1ccc(C#N)cc1C(=O)O]

To a mixture of methyl-2-hydroxy-5-cyano-benzoate (2.g, 5.6 mmol), K$_2$CO$_3$ (4.68 g, 16.8 mmol) in acetone (50 ml) was added methyl iodide (0.7 ml, 5.6 mmol). The reaction was then heated at 65° C. overnight resulting in formation of a solid which was filtered off whilst hot and washed with acetone to give 5-cyano-2-methoxy-benzoic acid methyl ester (0.45 g). The crude product was dissolved in THF (5 ml) and then treated with LiOH (0.108 g 0.26 mmol) in water (5 ml) and stirred at room temperature overnight. The reaction was acidified with 2M HCl and extracted EtOAc (×2). The organic portion dried (MgSO$_4$) and reduced in vacuo to give 5-cyano-2-methoxy-benzoic acid (0.277 g). (LC/MS Acidic: R$_t$ 2.92, [M+H]$^+$ 178).

1G Synthesis of 5 cyano-2-methoxy-N-[3-(5-morpholin-4-ylmethyl-1H-benzoimidazol-2-yl)-1H-pyrazol-4-yl]-benzamide (Acid chloride method)

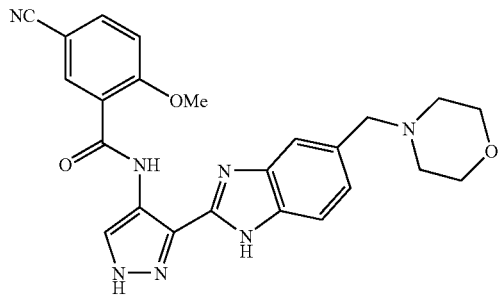

5-Cyano-2-methoxy-benzoic acid (Example 1F) (40 mg, 0.22 mmol) was dissolved in DCM (5 ml) and oxalyl chloride (34.4 mg, 0.264 mmol) was then added drop wise followed by DMF (1 drop). The reaction mixture was stirred at ambient temperature for 1 hour, reduced in vacuo, then re-evaporated using toluene (×2). A mixture of 3-(5-morpholin-4-ylmethyl-1H-benzimidazol-2-yl)-1H-pyrazol-4-ylamine (100 mg, 0.33 mmol), 5-cyano-2-methoxy-benzoyl chloride and diisopropylethylamine (1.83 µl, 0.9 mmol) in THF (5 ml) was stirred at 0° C. and then allowed to warm to room temperature over 2 hours. The reaction mixture was then concentrated in vacuo. The residue was purified by flash column chromatography SiO$_2$, 5-7% MeOH-DCM] to give 5-cyano-2-methoxy-N-[3-(5-morpholin-4-ylmethyl-1H-benzimidazol-2-yl)-1H-pyrazol-4-yl]-benzamide (12 mg). (LC/MS Acidic: R$_t$ 2.02 min [M−H]+458).

Example 2

Synthesis of 6-methyl-imadazol[2.1-b]thiazole-5-carboxylic acid [3-(5-morpholin-4-ylmethyl-1H-benzoimidazol-2-yl)-1H-pyrazol-4-yl]-amide

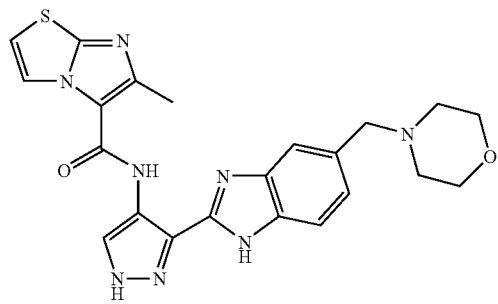 [SMILES: Cc1nc2sccn2c1C(=O)Nc1c[nH]nc1-c1nc2cc(CN3CCOCC3)ccc2[nH]1]

A mixture of 6-methyl-imidazo[2.1-b]thiazole-5-carboxylic acid (Bionet) (61 mg, 0.33 mmol), 3-(5-morpholin-4-ylmethyl-1H-benzimidazol-2-yl)-1H-pyrazol-4-ylamine (100 mg, 0.33 mmol), EDC (77 mg 0.39 mmol) and HOAt (54 mg, 0.39 mmol) was stirred in DMF (3 ml) at 80° C. for 1 h then at ambient temperature for 20 h. The mixture was reduced in vacuo and the residue was partitioned between EtOAc and saturated NaHCO. The organic portion was washed with brine, dried (MgSO$_4$) and reduced in vacuo. The residue was purified by preparative LC/MS to give 6-methyl-imidazo[2.1-b]thiazole-5-carboxylic acid [3-(5-morpholin-4-ylmethyl-1H-benzoimidazol-2-yl)-1H-pyrazol-4-yl]-amide (29 mg). (LC/MS Basic: R$_t$ 2.56 [M+H]+ 463).

Example 3

Synthesis of 2-cyano-N-[3-(5-morpholin-4-ylmethyl-1H-benzoimidaxol-2-yl)-1H-pyrazol-4-yl]-acetamide

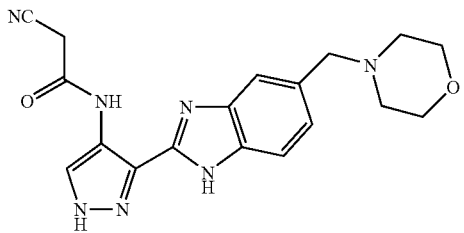

A mixture of cyano-acetic acid (23 mg, 0.28 mmol), 3-(5-morpholin-4-ylmethyl-1H-benzimidazol-2-yl)-1H-pyrazol-4-ylamine (70%, 100 mg, 0.23 mmol), TBTU (89 mg, 0.28 mmol) and DMF (2 ml) was stirred at 25° C. overnight. The mixture was then evaporated in vacuo. Flash chromatography, eluting with DCM-6% MeOH/DCM afforded 2-cyano-N-[3-(5-morpholin-4-ylmethyl-1H-benzoimidazol-2-yl)-1H-pyrazol-4-yl]-acetamide as a yellow solid (65 mg, 77%). (LC/MS (acidic method/final compound): R$_t$ 4.61, [M+H]+ 366).

Example 4

2-Cyano-2-cyclopropyl-N-[3-(5-morpholin-4-ylmethl-1H-benzoimidazol-2-yl)-1H-pyrazol-4-yl]-acetamide

4A. Synthesis of Cyano-Cyclopropyl-Acetic Acid

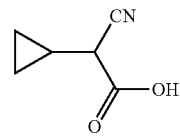

IN NaOH (3.26 ml, 3.26 mmol) was added to a solution of cyano-cyclopropyl-acetic acid ethyl ester (0.5 g, 3.26 mmol) in THF (15 ml). After 4 hours stirring at 25° C., the reaction mixture was evaporated in vacuo, re-dissolved in water (20 ml) and neutralized by the addition of 1N HCl solution (3.26 ml). This mixture was then extracted with EtOAc (3×20 ml) and the combined, dried (Na$_2$SO$_4$) organics evaporated in vacuo to give impure cyano-cyclopropyl-acetic acid as a clear oil. This material was used without any further purification in the preparation of Example 4B.

4B. 2-Cyano-2-cyclopropyl-N-[3-(5-morpholin-4-ylmethyl-1H-benzoimidazol-2-yl)-1H-pyrazol-4-yl]-acetamide

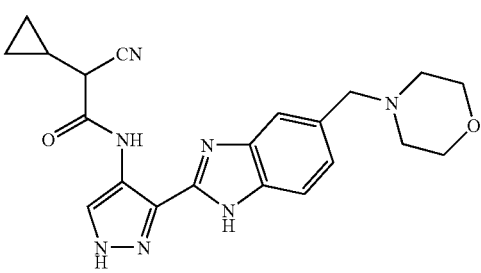 [SMILES: N#CC(C(=O)Nc1c[nH]nc1-c1nc2cc(CN3CCOCC3)ccc2[nH]1)C1CC1]

The product of Example 4A was reacted with 3-(5-morpholin-4-ylmethyl-1H-benzimidazol-2-yl)-1H-pyrazol-4-ylamine according to the method described in Example 3, except that the crude product was partitioned between DCM and saturated aqueous $NaHCO_3$ and was then purified by trituration with $Et_2O$. LC/MS (acidic method) $R_t$ 1.79 $[M+H]^+$ 406.

Examples 5-14

By following the methods of Examples 1, 2 and 3, modified where indicated in the Table below, the compounds of Examples 5 to 14 were prepared.

| Example | Structure | General Method of Preparation | Differences to General Method | LC/MS |
|---|---|---|---|---|
| 5 | 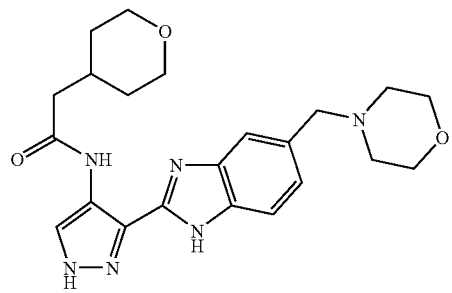 [SMILES: O=C(CC1CCOCC1)Nc1c[nH]nc1-c1nc2cc(CN3CCOCC3)ccc2[nH]1] | Ex. 1G | | $[M + H]^+$ 425 $R_t$ 1.77 Acidic |
| 6 | 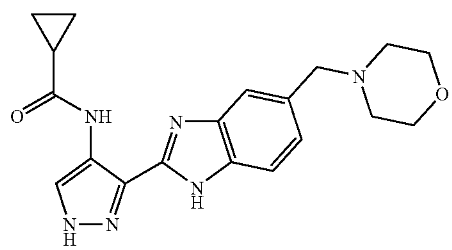 [SMILES: O=C(Nc1c[nH]nc1-c1nc2cc(CN3CCOCC3)ccc2[nH]1)C1CC1] | Ex. 1G | Purified by preparative LC/MS | $[M + H]^+$ 365 $R_t$ 2.45 Basic |
| 7 | 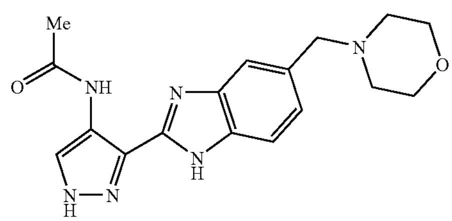 [SMILES: CC(=O)Nc1c[nH]nc1-c1nc2cc(CN3CCOCC3)ccc2[nH]1] | Ex 1G | Purified by preparative LC/MS | $[M + H]^+$ 339 $R_t$ 2.21 Basic |
| 8 | 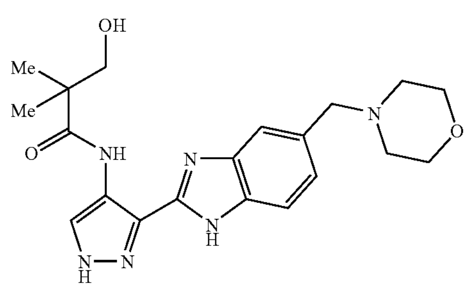 [SMILES: CC(C)(CO)C(=O)Nc1c[nH]nc1-c1nc2cc(CN3CCOCC3)ccc2[nH]1] | Ex. 2 | Purified by preparative LC/MS | $[M + H]^+$ 399 $R_t$ 1.74 Acidic |
| 9 | 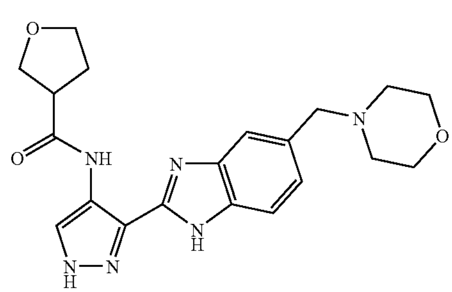 [SMILES: O=C(Nc1c[nH]nc1-c1nc2cc(CN3CCOCC3)ccc2[nH]1)C1CCOC1] | Ex. 2 | Purified by preparative LC/MS | $[M + H]^+$ 397 $R_t$ 1.64 Acidic |

| Example | Structure | General Method of Preparation | Differences to General Method | LC/MS |
|---|---|---|---|---|
| 10 | 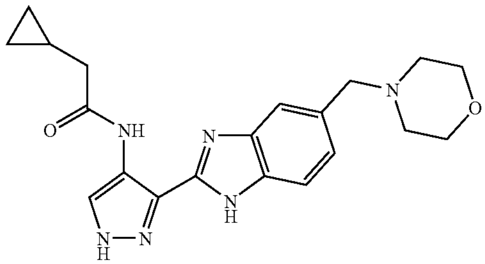 [SMILES: O=C(CC1CC1)Nc1c[nH]nc1-c1nc2cc(CN3CCOCC3)ccc2[nH]1] | Ex. 3 | Purified by column chromatography [SiO₂ eluting with DMAW 240-120] | [M + H]⁺ 381 R_t 1.85 Acidic |
| 11 | 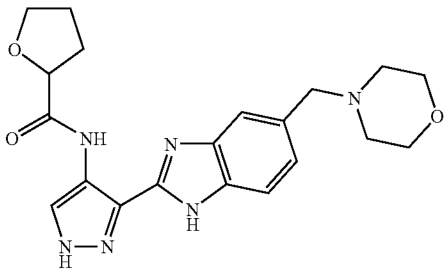 | Ex. 3 | Purified by column chromatography [SiO₂ eluting with DMAW 240-120] | [M + H]⁺ 397 R_t 1.76 Acidic |
| 12 | 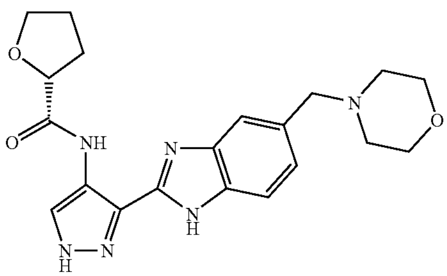 | Ex. 3 | Purified by column chromatography [SiO₂ eluting with DMAW 240-120] | [M + H]⁺ 397 R_t 1.76 Acidic |
| 13 | 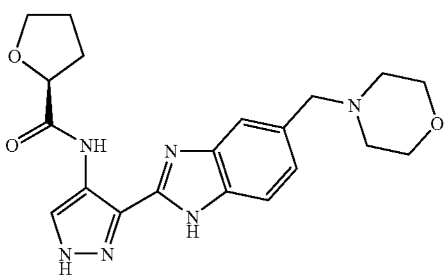 [SMILES: O=C(Nc1c[nH]nc1-c1nc2cc(CN3CCOCC3)ccc2[nH]1)[C@@H]1CCCO1] | Ex. 3 | Purified by column chromatography [SiO₂ eluting with DMAW 240-120] | [M + H]⁺ 397.24 R_t 1.79 Acidic |
| 14 | 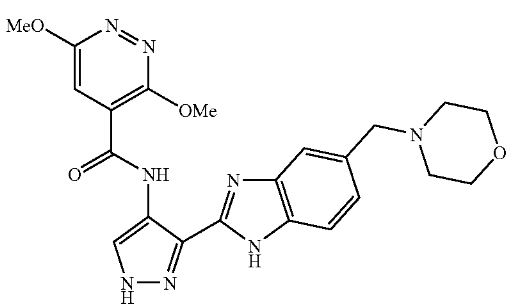 [SMILES: COc1cc(C(=O)Nc2c[nH]nc2-c2nc3cc(CN4CCOCC4)ccc3[nH]2)c(OC)nn1] | Ex. 3 | Purified by column chromatography [SiO₂ eluting with DMAW 240-120] | [M + H]⁺ 465.3 R_t 1.99 Acidic |

Example 15

Synthesis of N-[3-(5,6-dimethoxy-1H-benzimidazol-2-yl)-1H-pyrazol-4-yl]-rac-2-morpholine carboxamide-trifluoroacetate salt

15A. Synthesis of 5,6-dimethoxy-2-(4-nitro-1H-pyrazol-3-yl-1H-benzimidazole

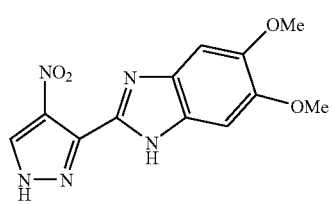

To a solution of EDC (4.81 g 25 mmol), HOBt (3.40 g, 25 mmol) and triethylamine (4.67 g, 46 mmol) in DMF (100 ml) was added 4-nitro-1H-pyrazole-3-carboxylic acid (3.63 g, 23.09 mmol) and 4,5-dimethoxy-benzene-1,2-diamine dihydrochloride (5.06 g, 20.99 mmol) and the mixture was stirred at room temperature overnight. The solvent was removed in vacuo and the resulting solid partitioned between EtOAc (50 ml) and saturated aqueous NaHCO$_3$ (50 ml). A precipitate was formed and removed by filtration. The filtrate was washed with water followed by diethyl ether and then azeotroped with MeOH and toluene to yield 4-nitro-1H-pyrazole-3-carboxylic acid (2-amino-4,5-dimethoxy-phenyl)-amide (2.35 g, 36%). 4-Nitro-1H-pyrazole-3-carboxylic acid (2-amino-4,5-dimethoxy-phenyl)-amide (2.35 g, 7.65 mmol) was dissolved in acetic acid (150 ml) and refluxed at 140° C. for 5 hours. The solution was left to cool and the solvent removed in vacuo. The resulting solid was partitioned between EtOAc (25 ml) and brine (25 ml). The organic layer was separated, dried (MgSO$_4$), filtered and the solvent removed in vacuo to yield 5,6-dimethoxy-2-(4-nitro-1H-pyrazol-3-yl)-1H-benzimidazol (2.08 g, 94%).

15B. Synthesis of 3-(5,6-dimethoxy-1H-benzimidazol-2-yl)-1H-pyrazol-4-ylamine

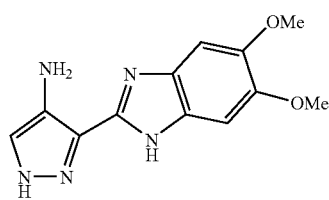 [SMILES: COc1cc2nc(-c3n[nH]cc3[N+](=O)[O-])[nH]c2cc1OC]

A mixture of 5,6-dimethoxy-2-(4-nitro-1H-pyrazol-3-yl)-1H-benzimidazole (2.08 g, 7.2 mmol) and 10% palladium on carbon (200 mg) in ethanol (150 ml) and DMF (50 ml) was hydrogenated at room temperature and pressure overnight. The reaction mixture was filtered through Celite and the solvent removed in vacuo. The resulting solid was azeotroped with methanol and toluene and the solvent removed in vacuo. The crude material was purified by flash chromatography, eluting with DCM: MeOH: acetic acid:water (120:18:3:2) [DMAW120] followed by DCM: MeOH: acetic acid:water (90:18:3:2) (DMAW90). Product fractions were combined and the solvent removed in vacuo to yield 3-(5,6-dimethoxy-1H-benzimidazol-2-yl)-1H-pyrazol-4-ylamine (~1 g, 53%).

15C. Synthesis of N-[3-(5,6-dimethoxy-1H-benzimidazol-2-yl)-1H-pyrazol-4-yl]-rac-4-BOC-2-morpholine carboxamide

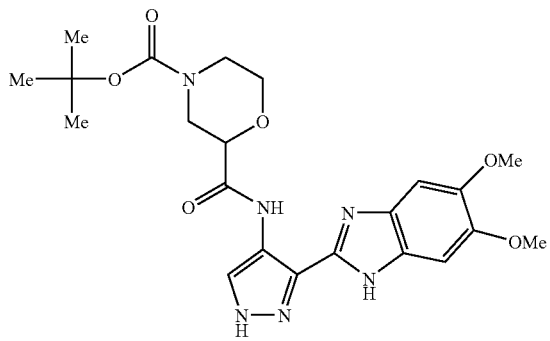 [SMILES: COc1cc2nc(-c3n[nH]cc3NC(=O)C3CN(C(=O)OC(C)(C)C)CCO3)[nH]c2cc1OC]

To a solution of EDC (125 mg, 0.54 mmol) and HOAt (74 mg, 0.54 mmol) in DMF (2 ml) was added 3-(5,6-dimethoxy-1H-benzimidazol-2-yl)-1H-pyrazol-4-ylamine (117 mg, 0.45 mmol) (Example 15B) and (rac)-BOC-2-carboxymorpholine (125 mg, 0.54 mmol) and the mixture stirred at room temperature overnight. The mixture was then partitioned between EtOAc and water. The organic layer was then washed successively with saturated aqueous sodium bicarbonate, brine and then dried (MgSO$_4$). The solution was evaporated to dryness in vacuo and the residue purified by flash column chromatography [SiO$_2$, gradient elution: EtOAc-hexanes (1:1)-EtOAc-MeOH (80:20)] to give N-[3-(5,6-dimethoxy-1H-benzimidazol-2-yl) 1H-pyrazol-4-yl]-rac-4-BOC-2-morpholine carboxamide (65 mg) as a colourless solid. (LC/MS (acidic method): R$_t$ 2.65 min, [M+H]$^+$ 473).

15D. Synthesis of N-[3-(5,6-dimethoxy-1H-benzimadazol-2-yl)-1H-pyrazol-4-yl]-rac-2-morpholine carboxamide-trifluoroacetate salt

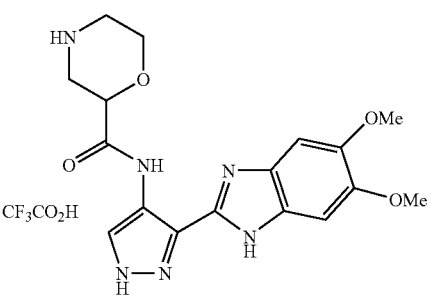 [SMILES: "CF3CO2H" ; COc1cc2nc(-c3n[nH]cc3NC(=O)C3CNCCO3)[nH]c2cc1OC]

N-[3-(5,6-dimethoxy-1H-benzimidazol-2-yl)-1H-pyrazol-4-yl]-rac-4-BOC-2-morpholine carboxamide (65 mg, 0.14 mmol) and anisole (60 μl, 0.56 mmol) were dissolved in a mixture of trifluoroacetic acid and dichloromethane (1:1;2 ml). After 3 hours at room temperature, the mixture was evaporated to dryness to give N-[3-(5,6-dimethoxy-1H-benzimidazol-2-yl)-1H-pyrazol-4-yl]-rac-2-morpholine carboxamide-trifluoroacetic acid salt (73 mg) as a colourless solid (LC/MS (acidic method): R$_t$ 1.42 min, [M−H$^+$]$^-$ 371.

Example 16

Synthesis of N-[3-(5,6-dimethoxy-1H-benzimidazol-2-yl)-1H-pyrazol-4-yl]-rac-4 isopropyl-2-morpholine Carboxamide

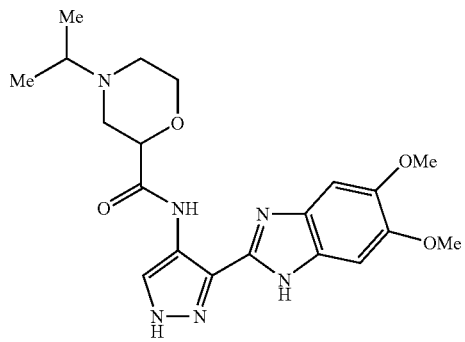 [SMILES: COc1cc2nc(-c3n[nH]cc3NC(=O)C3CN(C(C)C)CCO3)[nH]c2cc1OC]

To N-[3-(5,6-dimethoxy-1H-benzimidazol-2-yl)-1H-pyrazol-4-yl]-rac-2-morpholine carboxamide-trifluoroacetic acid salt (Example 15D) (34 mg, 0.07 mmol) and $K_2CO_3$ (20 mg, 0.14 mmol), in MeCN (1 ml) was added 2-iodopropane (17 µl, 0.15 mmol). The mixture was stirred at 80° C. for approximately 48 hours after which the mixture was concentrated and the residue purified by flash chromatography [$SiO_2$ gradient elution: DCM:MeOH (98:2) to DCM: MeOH: conc. aq. NH3 (90:10:1) to give N-[3-(5,6 dimethoxy-1H-benximidazol-2-yl)-1H-pyrazol-4-yl]-rac-4-isopropyl-2-morpholine carboxamide (12 mg) as a colourless gum (LC/MS (basic method): $R_t$ 2.52 min [M+H]$^+$ 415).

Example 17

Synthesis of N-[3-(5,6-dimethoxy-H-benzimidazol-2-yl)-1H-pyrazol-4-yl]-rac-1-methyl-piperidine 3-carboxamide

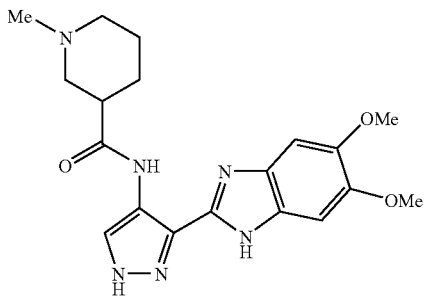 [SMILES: COc1cc2nc(-c3n[nH]cc3NC(=O)C3CCCN(C)C3)[nH]c2cc1OC]

To a solution of 3-(5,6-dimethoxy-1H-benzimidazol-2-yl)-1H-pyrazol-4-ylamine (65 mg, 0.25 mmol) (Example 15B) (rac)-1-methyl-piperidine-3-carboxylic acid-hydrocholoride salt (50 mg, 0.27 mmol) and disopropylethylamine (50 µl, 0.27 mmol) in DMF (1 ml) was added TBTU (97 mg, 0.30 mmol). The mixture was stirred at room temperature for approximately 16 hours after which 1N aqueous NaOH (1 ml) was added and the mixture stirred for a further 1 hours. The mixture was then evaporated to dryness in vacuo and the residue purified by flash column chromatography ($SiO_2$, eluting with a gradient of DCM:MeOH (98:2) to DCM: MeOH; conc. Aq. $NH_3$ (70:30:3) to give N-[3-(5,6-dimethoxy-1H-benzimidazol-2-yl)-1H-pyrazol-4-yl]-rac-1-methyl-piperidine 3-carboxamide (20 mg) as a colourless gum (LC/MS (basic method): $R_t$ 2.35 min, (M+H)+ 385).

Example 18

Synthesis of 3-chloro-N-(5,6-dimethoxy-1H-benzoimidazol-2-yl)-1H-pyrazol-4-yl-5-(4-methyl-piperazin-1-yl)-benzamide

18A. Synthesis of 3-Chloro-5-(4-methyl-piperazin-1-yl)-benzonitrile

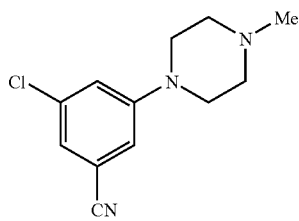 [SMILES: CN1CCN(c2cc(Cl)cc(C#N)c2)CC1]

5-Fluoro-3-chloro-benzonitrile (1 g, 6.4 mmol) was dissolved in DMSO (20 ml) followed by addition of $K_2CO_3$ (1.3 g, 9.6 mmol) and 1-methyl piperazine (1.4 ml, 12.8 mmol). The reaction mixture was heated at 80° C. for 20 hours. Diethyl ether was added to the crude material (10 ml) then acidified with 1N HCl. A precipitate was filtered off from the crude reaction mixture to give 3-chloro-5-(4-methyl-piperazin-1-yl)-benzonitrile (1.4 g, 93% yield) as a white solid (LC/MS: $R_t$ 1.83 [M+H]$^+$ 236, acidic method).

18B. Synthesis of 3-Chloro-5-(4-methyl-piperazin-1-yl)-benzoic acid

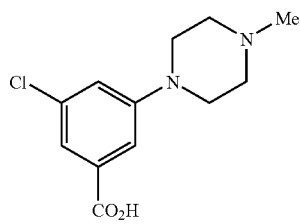 [SMILES: CN1CCN(c2cc(Cl)cc(C(=O)O)c2)CC1]

To 3-chloro-5-(4-methyl-piperazin-1-yl)-benzonitrile (1.4 g, 5.9 mmol) dissolved in ethanol (10 ml) was added 2M NaOH (20 ml) and reaction mixture was heated at reflux for 20 hours. The mixture was reduced in vacuo and the crude product was acidified in 1N HCl to pH 6 and partitioned between EtOAc and $H_2O$. The organic layer was evaporated to dryness in vacuo to give 0.7 g of the title compound as a white solid (LC/MS: $R_t$ 1.67, [M+H]$^+$ 256, acidic method).

18C. Synthesis of [3-chloro-N-[3-(5,6-dimethoxy-1H-Benzoimidaxol-2-yl)-1H-pyrazol-4-yl]-5-(4-methyl-piperazin-1-yl)-benzamide

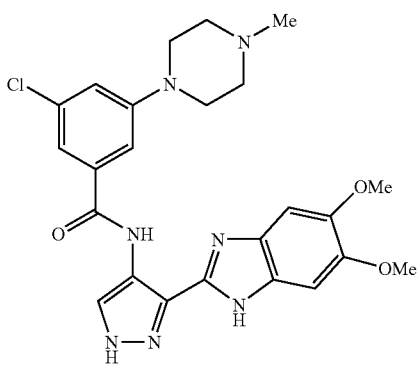 [SMILES: COc1cc2nc(-c3n[nH]cc3NC(=O)c3cc(Cl)cc(N4CCN(C)CC4)c3)[nH]c2cc1OC]

The compound was prepared in a manner analogous to Example 15C but using 3-chloro-5-(4-methyl-piperazin-1-yl)-benzoic acid (200 mg, 0.78 mmol) as a reagent in 15C in place of (rac)-BOC-2-carboxymorpholine. The crude product was purified by flash column chromatography [SiO₂ eluting with DMAW240-90 to give 92 mg (25% yield) of the title compound as a light brown solid (LC/MS: R$_t$ 2.07 [M+H]$^+$ 496).

Examples 19-21

By following the procedures set out in Example 15, modified where indicated, the compounds of Examples 19 to 21 were prepared.

| Example | Structure | General Method of Preparation | Differences to General Method | LC/MS |
|---|---|---|---|---|
| 19 | 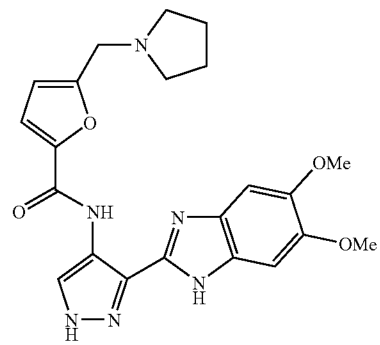 [SMILES: COc1cc2nc(-c3n[nH]cc3NC(=O)c3ccc(CN4CCCC4)o3)[nH]c2cc1OC] | Ex. 15C | Using 5-pyrrolidin-1-ylmethyl furan-2-carboxylic acid | [M + H]$^+$ 437 R$_t$ 2.62 Basic |
| 20 | 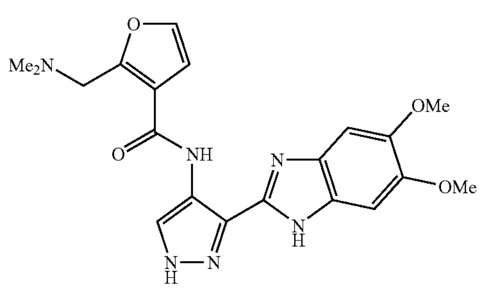 [SMILES: COc1cc2nc(-c3n[nH]cc3NC(=O)c3ccoc3CN(C)C)[nH]c2cc1OC] | Ex. 15C | Using 2-dimethylaminomethyl-furan-3-carboxylic acid Purified by preparative LC/MS | [M + H]$^+$ 411 R$_t$ 1.6 Acidic |
| 21 | 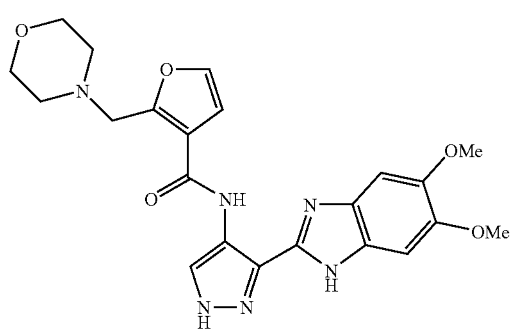 [SMILES: COc1cc2nc(-c3n[nH]cc3NC(=O)c3ccoc3CN3CCOCC3)[nH]c2cc1OC] | Ex 15C | No aqueous work up-purified by column chromatography [SiO₂ eluting with DMAW 240] Further purified by preparative LC/MS | [M + H]$^+$ 453.17 R$_t$ 1.75 Acidic |

Example 22

Synthesis of 5-chloro-2-methoxy-N-{3-[5-(4-methyl-piperazin-1-ylmethyl)-1H-benzoimidazol-2-yl]-1H-pyrazol-4-yl}-benzamide

22A. Synthesis of (3,4-dinitrophenyl)-(4-methylpiperazin-1-yl)-methanone

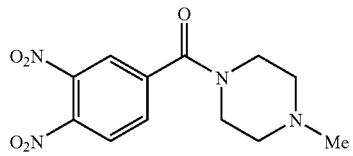 [SMILES: CN1CCN(C(=O)c2ccc([N+](=O)[O-])c([N+](=O)[O-])c2)CC1]

3,4-Dinitrobenzoic acid (50 g, 0.24 mol) was heated at reflux in $SOCl_2$ (160 ml) for 6 hours. The mixture was then evaporated to dryness in vacuo. The product was dissolved in THF and cooled to 5° C. To this solution, N-methylpiperazine (26.2 ml, 0.24 mol) and $Et_3N$ (42 ml) were added dropwise as a solution in THF (50 ml). After stirring overnight at room temperature, the solution was poured into water (1.5 L) and stirred at approximately 5° C. for 0.5 hours. The solid precipitate which formed was collected and dried to give (3,4-dinitrophenyl)-(4-methylpiperazin-1-yl)-methanone (40 g) as a yellow solid.

22B. Synthesis of 1-(3,4 diaminobenzyl)-4-methylpiperazine

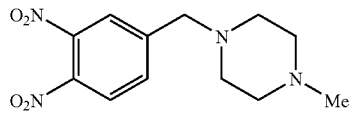 [SMILES: CN1CCN(Cc2ccc([N+](=O)[O-])c([N+](=O)[O-])c2)CC1]

To a cooled solution (5° C.) of (3,4-dinitrophenyl)-(4-methylpiperazin-1-yl)-methanone 12.2 g, 0.041 mol) in THF, was added powdered $NaBH_4$, followed by the dropwise addition of $BF_3.OEt_2$, while keeping the temperature below 5° C. The mixture was allowed to come to room temperature over 2 hours and then stirred for a further 2 hours at room temperature. MeOH was then added cautiously to the mixture (causing effervescence), the stirring was continued for 10 minutes and then the mixture concentrated. The residue was partitioned between EtOAc and saturated aqueous $NaHCO_3$. The organic layer was washed with water, brine and then dried ($MgSO_4$). The solution was evaporated in vacuo and the residue purified by flash chromatography on $SiO_2$ eluting with gradient DCM:MeOH (98:2) to DCM: MeOH: concentrated aqueous $NH_3$ (90:10:1) to give an orange crystalline solid (3.7 g). Recrystallisation from MeOH gave 1-(3,4-dinitrobenzyl)-4-methypiperazine (1 g) as an orange crystalline solid.

22C. Synthesis of 1-(3,4-diaminobenzyl)-4-methylpiperazine

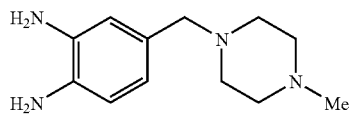

1-(3,4-dinitrobenzyl)-4-methylpiperazine (1 g) was dissolved in DMF:MeOH (1:1, 20 mil) and agitated with 10% Pd/C (50 mg) under an atmosphere of $H_2$ for 6 hours. The mixture was then filtered and evaporated to give a dark solid which was used immediately without any further purification.

22D. Synthesis of 5-chloro-2-methoxy-N-{3-[5-4-methyl-piperazin-1-ylmethyl)-1H-benzoimidazol-2-yl]-1H-pyrazol-4-yl}-benzamide

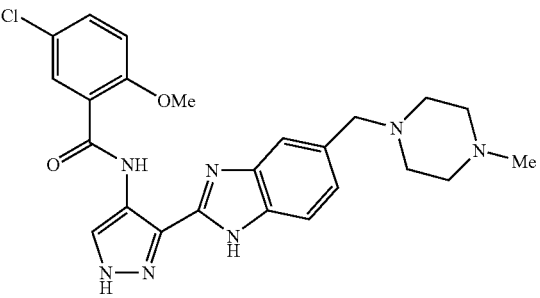 [SMILES: COc1ccc(Cl)cc1C(=O)Nc1c[nH]nc1-c1nc2cc(CN3CCN(C)CC3)ccc2[nH]1]

4-(5-chloro-2-methoxy-benzoylamino)-1H-pyrazole-3-carboxylic (1.17 g), the crude diamine, 1-(3,4-diaminobenzyl)-4-methylpiperazine (0.87 g), and TBTU (1.52 g) were dissolved in DMF (15 ml) and stirred for approximately 16 hours. The mixture was then evaporated to dryness to give a dark solid. The dark solid (100 mg) was dissolved in AcOH (4 ml) the mixture heated at 80° C. for 3 hours. The reaction mixture was evaporated in vacuo and the residue purified by flash chromatography ($SiO_2$, eluting with DMAW 120) to give 5-chloro-2-methoxy-N-{3-[5-(4-methyl-piperazin-1-ylmethyl)-1H-benzoimidazol-2-yl]-1H-pyrazol-4-yl}-benzamide as the di-acetic acid salt (35 mg). (LC/MS (acidic method/final compound): $R_t$ 6.63 [M+H]$^+$ 480).

Example 23

Synthesis of 1-(2,6-Difluoro-benzyl-3-[3-(5-morpholin-4-ylmethyl-1H-benzoimidazol-2-yl)-1H-pyrazol-4-yl]-urea

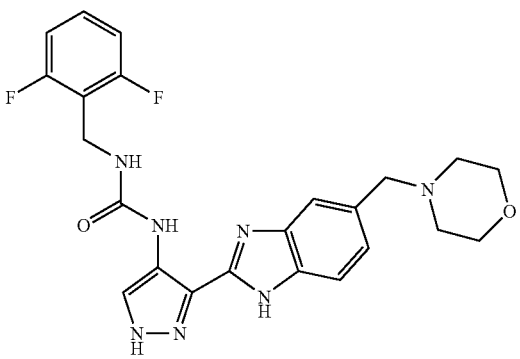 [SMILES: O=C(NCc1c(F)cccc1F)Nc1c[nH]nc1-c1nc2cc(CN3CCOCC3)ccc2[nH]1]

A mixture of 3-(5-morpholin-4-ylmethyl-1H-benzimidazol-2-yl)-1H-pyrazol-4-ylamine (Example 1E.), (100 mg, 0.33 mmol), and CDI (217 mg, 1.34 mmol) in THF (2 ml) was subjected to microwave irradiation (150° C., 150 W) for 15 minutes. 2,6-Difluoro-benzylamine (384 mg, 2.68 mmol) was then added and the reaction mixture irradiated again under identical conditions for a further 15 minutes. After cooling, the heterogeneous mixture was filtered, the filtrate was concentrated and the residue purified by column chromatography (SiO$_2$ eluting with gradient –DCM: MeOH: AcOH: H$_2$O (240:20:3:2) (DMAW240 to (120:18:3:2) (DMAW120) to give 1-(2,6-difluoro-benzyl)-[3(5-morpholin-4-ylmethyl-1H-benzimidazol-2-yl)-1H-pyrazol-4-yl]-urea (30 mg 19%). (LC/MS Acidic: R$_t$ 1.84 [M+H]$^+$ 468).

Examples 24-34

By following the general method set out in Example 23, but modified where indicated in the Table below, the compounds of Examples 24 to 34 were prepared.

| Example | Structure | Differences to General Method | LC/MS |
|---|---|---|---|
| 24 | 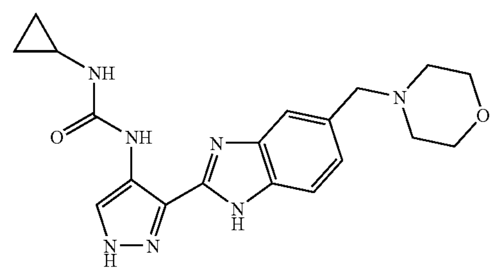 [SMILES: O=C(Nc1c[nH]nc1-c1nc2cc(CN3CCOCC3)ccc2[nH]1)NC1CC1] | Cyclopropylamine used as the amine | [M + H]$^+$ 382.24 R$_t$ 1.59 Acidic |
| 25 | 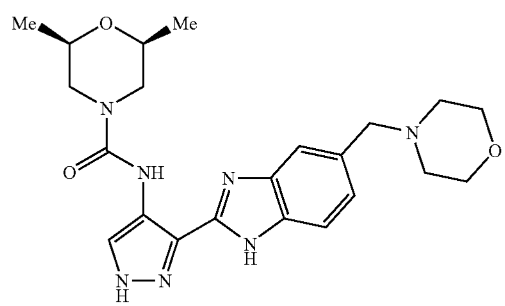 [SMILES: C[C@@H]1CN(C(=O)Nc2c[nH]nc2-c2nc3cc(CN4CCOCC4)ccc3[nH]2)C[C@H](C)O1] | | [M + H]$^+$ 440.31 R$_t$ 1.84 Acidic |
| 26 | 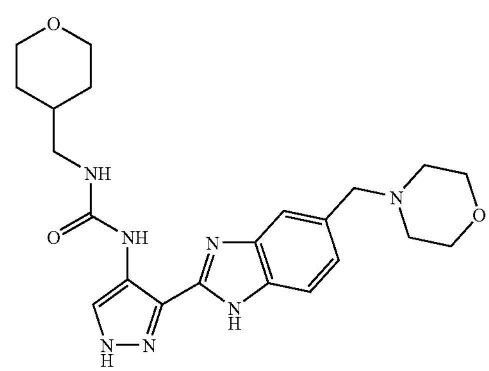 [SMILES: O=C(NCC1CCOCC1)Nc1c[nH]nc1-c1nc2cc(CN3CCOCC3)ccc2[nH]1] | Purified by preparative LC/MS | [M + H]$^+$ 440.34 R$_t$ 2.20 Polar |
| 27 | 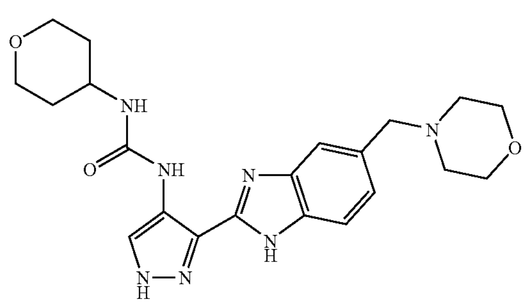 [SMILES: O=C(Nc1c[nH]nc1-c1nc2cc(CN3CCOCC3)ccc2[nH]1)NC1CCOCC1] | Purified by preparative LC/MS | [M + H]$^+$ 426.27 R$_t$ 1.57 Acidic |

-continued

| Example | Structure | Differences to General Method | LC/MS |
|---|---|---|---|
| 28 | 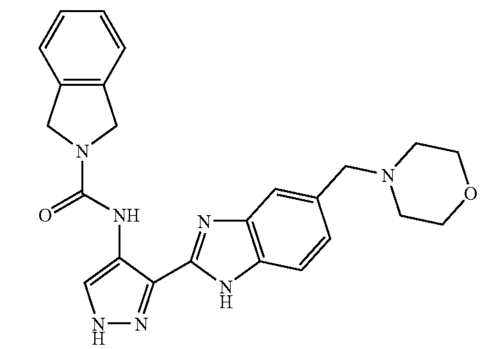 [SMILES: O=C(Nc1c[nH]nc1-c1nc2cc(CN3CCOCC3)ccc2[nH]1)N1Cc2ccccc2C1] | Crude product partitioned between EtOAc and sat. NaHCO$_3$. Purified by flash column chromatography on silica eluting with 100% EtOAc to 10% MeOH | [M + H]$^+$ 444 R$_t$ 6.67 Acidic |
| 29 | 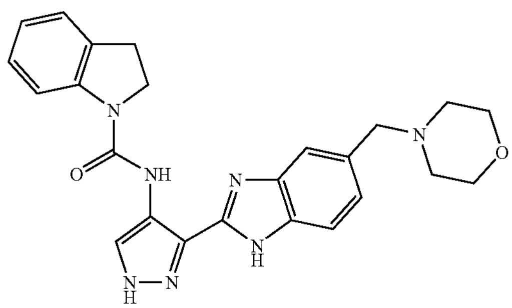 [SMILES: O=C(Nc1c[nH]nc1-c1nc2cc(CN3CCOCC3)ccc2[nH]1)N1CCc2ccccc21] | Crude product partitioned between EtOAc and sat. NaHCO$_3$. Purified by flash column chromatography on silica eluting with 100% EtOAc to 10% MeOH | [M + H]$^+$ 444 R$_t$ 6.98 Acidic |
| 30 | 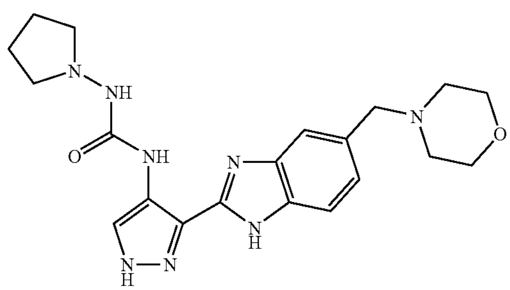 [SMILES: O=C(Nc1c[nH]nc1-c1nc2cc(CN3CCOCC3)ccc2[nH]1)NN1CCCC1] | 2.68 mmol DIPEA added. Work up-mixture stirred with 2M NaOH and extracted with DCM. Purified by flash column chromatography 2-5% MeOH-DCM, then LC/MS | [M + H]$^+$ 411 R$_t$ 2.45 Basic |
| 31 | 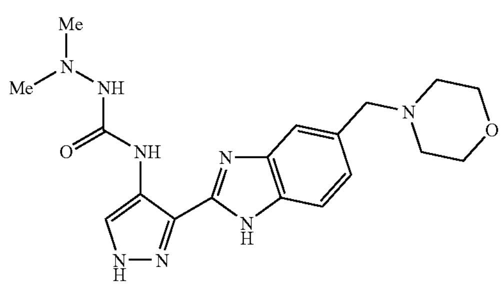 [SMILES: CN(C)NC(=O)Nc1c[nH]nc1-c1nc2cc(CN3CCOCC3)ccc2[nH]1] | 2.68 mmol DIPEA added Purified by preparative LC/MS | [M + H]$^+$ 385 R$_t$ 1.60 Acidic |
| 32 | 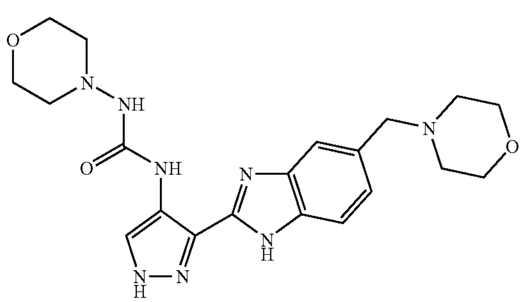 [SMILES: O=C(Nc1c[nH]nc1-c1nc2cc(CN3CCOCC3)ccc2[nH]1)NN1CCOCC1] | 2.68 mmol DIPEA added Purified by preparative LC/MS | [M + H]$^+$ 427 R$_t$ 1.69 Acidic |

| Example | Structure | Differences to General Method | LC/MS |
|---|---|---|---|
| 33 | 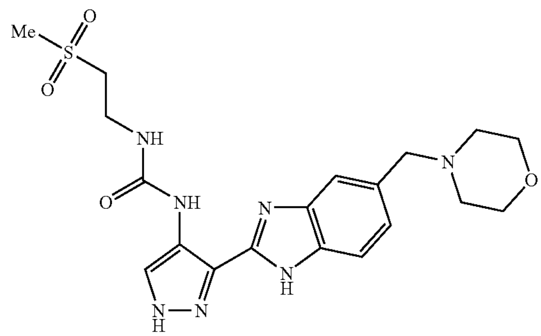 [SMILES: CS(=O)(=O)CCNC(=O)Nc1c[nH]nc1-c1nc2cc(CN3CCOCC3)ccc2[nH]1] | 2.68 mmol DIPEA added. Work up by partitioning between EtOAc and sat. NaHCO₃. Purified by column chromatography on silica (DMAW240-120) then preparative LC/MS | [M + H]⁺ 448 R_t 2.07 Basic |
| 34 | 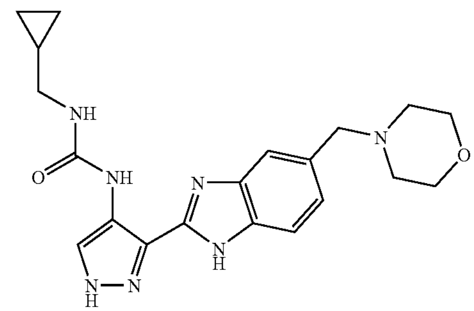 [SMILES: O=C(NCC1CC1)Nc1c[nH]nc1-c1nc2cc(CN3CCOCC3)ccc2[nH]1] | 2.68 mmol DIPEA added. Work up by partitioning between EtOAc and sat. NaHCO₃. Purified by preparative LC/MS | [M + H]⁺ 396 R_t 1.74 Basic |

Example 35

Synthesis of 1-[3-(5 morpholin-4-ylmethyl-1H-benzoimidazol-2-yl-1H-pyrazol-4-yl]-3-pyridin-3-yl-urea

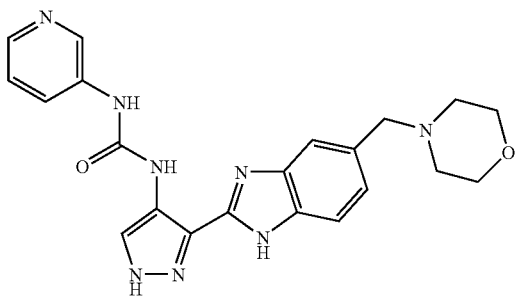 [SMILES: O=C(Nc1cccnc1)Nc1c[nH]nc1-c1nc2cc(CN3CCOCC3)ccc2[nH]1]

A mixture of 3-aminopyridine (31.5 mg, 0.33 mmol), Et₃N (0.195 ml, 1.32 mmol) in DCM (3 ml) was cooled to 0° C. and then treated with triphosgene (85 mg, 0.28 mmol). The reaction was stirred at ambient temperature for 1 hour, then 3-(5-morpholin-4-ylmethyl-1H-benzimidazol-2-yl)-1H-pyrazol-4-ylamine (100 mg, 0.33 mmol) was added and stirred at ambient temperature until the reaction was complete. The mixture was treated with 2M NaOH in MeOH for 30 minutes and then reduced in vacuo. The residue was purified by flash column chromatography [SiO₂, 2-20% MeOH/DCM] and then trituration with DCM followed by diethyl-ether to give 1-[3-(5-morpholin-4-ylmethyl-1H-benzoimadazol-2-yl)-1H-pyrazol-4-yl]-3-pyridin-3-yl-urea (20 mg). (LC/MS Basic: R_t 2.29, [M+H]⁺ 419).

Example 36

Synthesis of thiomorpholine-4-carboxylic acid [3-(5-morpholin-4-methyl-1H-benzoimidazol-2-yl)-1H-pyrazol-4-yl]-amide

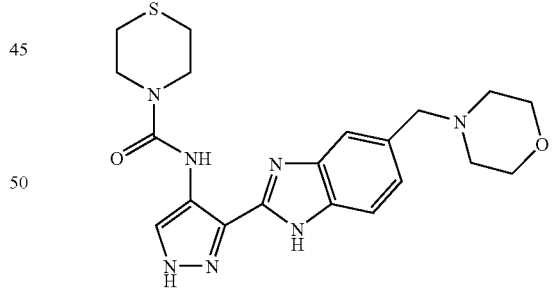

Phosgene (20% in toluene) (0.3 ml) was added at 0° C. to a solution of 3-(5-morpholin-4-ylmethyl-1H-benzimidazol-2-yl)-1H-pyrazol-4-ylamine (100 mg, 0.33 mmol) in a mixture of toluene/DCM (1:1). The reaction was stirred at ambient temperature for 1 hour then the excess phosgene was blown off by a stream of nitrogen. Thiomorpholine (35 mg, 0.33 mmol) was added and the reaction was stirred at ambient temperature for 1 hour then at 60° C. for 1 hour. The mixture was then concentrated in vacuo and the residue purified by preparative LC/MS to give thiomorpholine-4-carboxylic acid [3-(5-morpholin-4-ylmethyl-1H-benzoimidazol-2-yl)-1H-pyrazol-4-yl]-amide (LC/MS Polar: R_t 2.58, [M+H]+ 428).

Example 37

Synthesis of 1-(4-fluorophenyl)-1-methyl-3-[3-(5-morpholin-4-ylmethyl-1H-benzimadazol-2-yl)-1H-pyrazol-4-yl]-urea

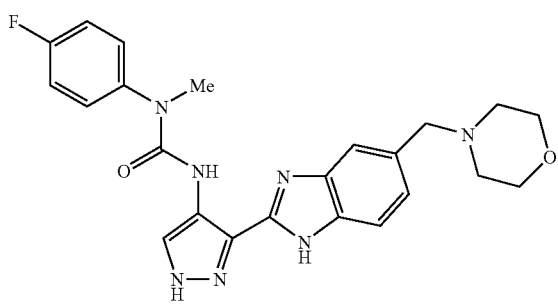 [SMILES: CN(C(=O)Nc1c[nH]nc1-c1nc2cc(CN3CCOCC3)ccc2[nH]1)c1ccc(F)cc1]

The procedure used to prepare the title compound was analogous to that described for Example 35 but using 4-fluoro-N-methylaniline instead of 3-aminopyridine, and conducting the reaction at 50° C. for 2 hours. The crude product was isolated as a precipitate from the cooled reaction mixture and was then purified by flash column chromatography [SiO$_2$ eluting with DCM:MeOH:AcOH:water (240:20:3:2)]. The resulting product was triturated with diethyl ether to give 1-(4-fluorophenyl)-1-methyl-3-[3-(5-morpholin-4-ylmethyl-1H-benzimidazol-2-yl)-1H-pyrazol-4-yl]-urea (3 mg) as a colourless solid. (LC/MS Acidic: R$_t$ 2.12, [M+H]$^+$ 450).

Examples 38-43

By following the methods described in Examples 35 and 37, modified where indicated in the Table below, the compounds of Examples 38 to 43 were prepared.

| Example | Structure | General Method of Preparation | Differences to General Method | LC/MS |
|---|---|---|---|---|
| 38 | 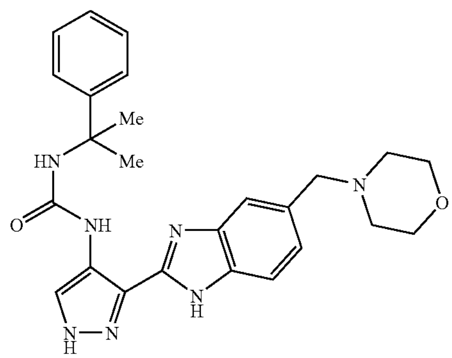 [SMILES: CC(C)(NC(=O)Nc1c[nH]nc1-c1nc2cc(CN3CCOCC3)ccc2[nH]1)c1ccccc1] | Ex. 35 | Work up by partitioning between EtOAc and sat. NaHCO$_3$. Purified by preparative LC/MS | [M + H]$^+$ 460 R$_t$ 2.03 Acidic |
| 39 | 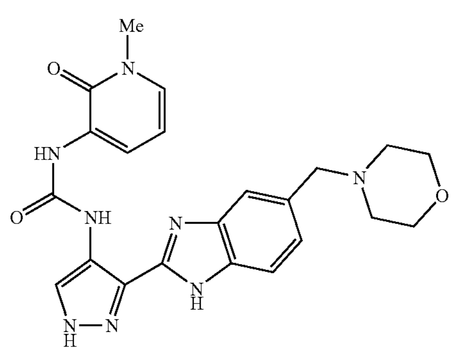 [SMILES: Cn1cccc(NC(=O)Nc2c[nH]nc2-c2nc3cc(CN4CCOCC4)ccc3[nH]2)c1=O] | Ex. 35 | Work up by partitioning between EtOAc and sat. NaHCO$_3$. Purified by preparative LC/MS | [M + H]$^+$ 449 R$_t$ 2.32 Polar |

-continued

| Example | Structure | General Method of Preparation | Differences to General Method | LC/MS |
|---|---|---|---|---|
| 40 | 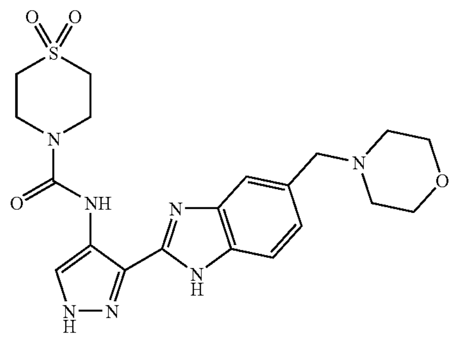 [SMILES: O=C(Nc1c[nH]nc1-c1nc2cc(CN3CCOCC3)ccc2[nH]1)N1CCS(=O)(=O)CC1] | Ex. 35 | Reaction heated to 60° C. Work up by partitioning EtOAc and sat. NaHCO$_3$. Purified by preparative LC/MS | [M + H]$^+$ 460 R$_t$ 2.22 Basic |
| 41 | 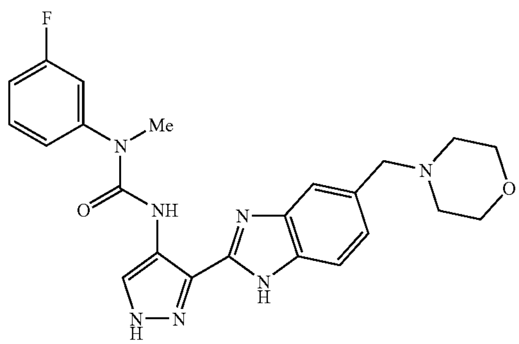 [SMILES: CN(C(=O)Nc1c[nH]nc1-c1nc2cc(CN3CCOCC3)ccc2[nH]1)c1cccc(F)c1] | Ex. 37 | | [M + H]$^+$ 450.24 R$_t$ 2.09 Acidic |
| 42 | 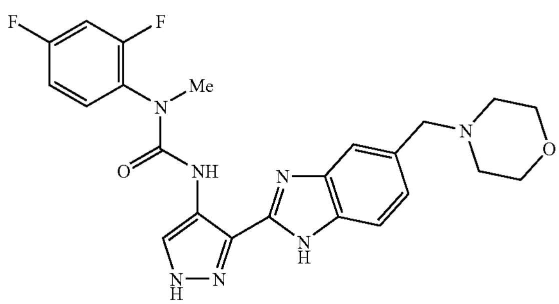 [SMILES: CN(C(=O)Nc1c[nH]nc1-c1nc2cc(CN3CCOCC3)ccc2[nH]1)c1ccc(F)cc1F] | Ex. 37 | | [M + H]$^+$ 468.38 R$_t$ 1.99 Acidic |
| 43 | 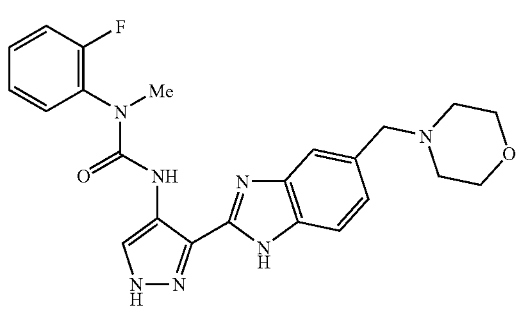 [SMILES: CN(C(=O)Nc1c[nH]nc1-c1nc2cc(CN3CCOCC3)ccc2[nH]1)c1ccccc1F] | Ex. 37 | Crude product isolated from the filtrate rather than the precipitate. Further purified by preparative LC/MS | [M + H]$^+$ 450.41 R$_t$ 2.68 Basic |

Example 44

Synthesis of 1-(4-fluorophenyl)-N-[3-(5-morpholin-4-ylmethyl-1H-benzimidazol-2-yl)-1H-pyrazol-4-yl]-urea

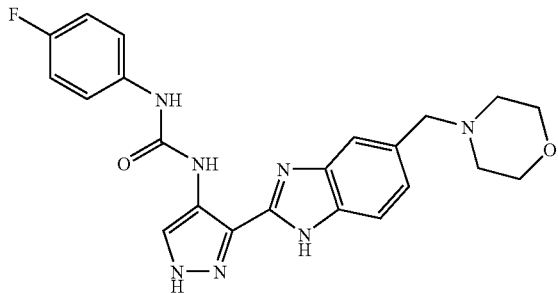 [SMILES: O=C(Nc1ccc(F)cc1)Nc1c[nH]nc1-c1nc2cc(CN3CCOCC3)ccc2[nH]1]

To 3-(5-morpholin-4-ylmethyl-1H-benzimidazol-2-yl)-1H-pyrazol-ylamine (Example 1E) (100 mg, 0.33 mmol), in THF (2 ml), was added 4-fluorophenyl isocyanate and the mixture was stirred for about 16 hours at room temperature. Resin-supported tris-amine (800 mg, 4 mmol/g) was added and the mixture agitated for a further 4 hours. The resin was removed by filtration, the filtrate was treated with 1N KOH (2 ml, MeOH:THF; 1:3) and the solution stirred for approximately 16 hours. The mixture was then partitioned between EtOAc and $H_2O$. The aqueous layer was further extracted with EtOAc and then the combined organic fractions washed with brine, dried ($MgSO_4$) and evaporated to dryness. The crude solid was dissolved in DCM and triturated with hexanes to give a solid which was collected by filtration. The solid was purified by flash column chromatography [$SiO_2$, EtOAc-MeOH (90:10)] to give 1-(4-fluorophenyl)-N-[3-(5-morpholin-4-ylmethyl-1H-benzimidazol-2-yl)-1H-pyrazol-4-yl]-urea (30 mg, 20%) as a yellow solid (LC/MS (acidic method): $R_t$ 2.01 min, $[M-H^+]^-$ 434).

Examples 45-56

By following the method described in Example 44, but modifying the conditions where indicated in the Table below, the compounds of Examples 45 to 56 were prepared.

| Example | Structure | Differences to General Method | LC/MS |
|---|---|---|---|
| 45 | 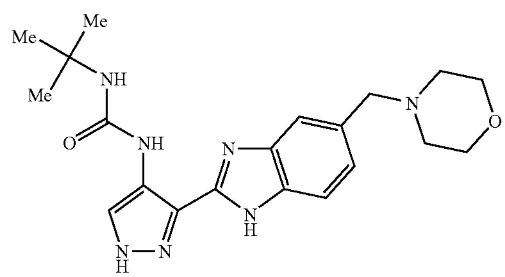 [SMILES: CC(C)(C)NC(=O)Nc1c[nH]nc1-c1nc2cc(CN3CCOCC3)ccc2[nH]1] | Reaction required heating (80°, 4 h) No chromatography required | $[M + H]^+$ 398 $R_t$ 1.79 Acidic |
| 46 | 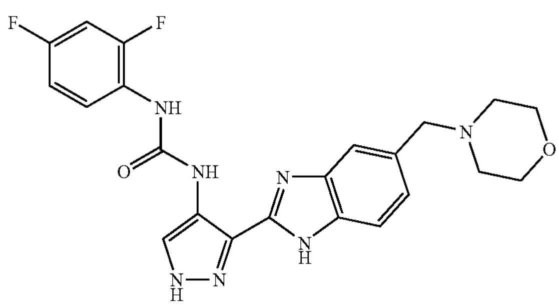 [SMILES: O=C(Nc1ccc(F)cc1F)Nc1c[nH]nc1-c1nc2cc(CN3CCOCC3)ccc2[nH]1] | | $[M + H]^+$ 454 $R_t$ 1.95 Acidic |
| 47 | 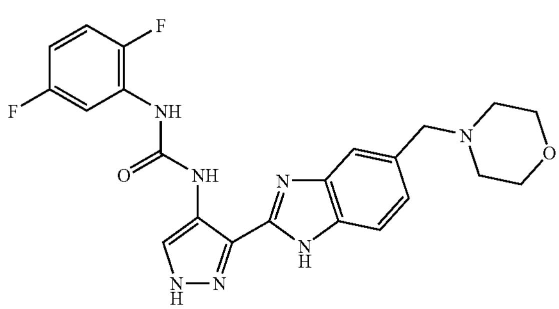 [SMILES: O=C(Nc1cc(F)ccc1F)Nc1c[nH]nc1-c1nc2cc(CN3CCOCC3)ccc2[nH]1] | | |

| Example | Structure | Differences to General Method | LC/MS |
|---|---|---|---|
| 48 | 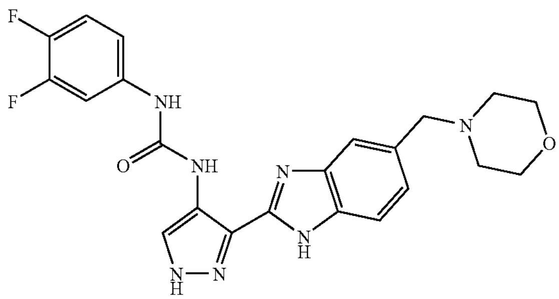 [SMILES: O=C(Nc1ccc(F)c(F)c1)Nc1c[nH]nc1-c1nc2cc(CN3CCOCC3)ccc2[nH]1] | Following chromatography on silica, impurity removed by precipitation from MeOH solution. | [M + H]+ 452 R_t 2.09 Acidic |
| 49 | 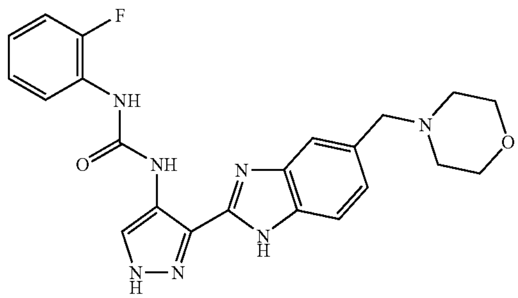 [SMILES: O=C(Nc1ccccc1F)Nc1c[nH]nc1-c1nc2cc(CN3CCOCC3)ccc2[nH]1] | Purified by preparative LC/MS | [M + H]+ 436 R_t 2.68 Basic |
| 50 | 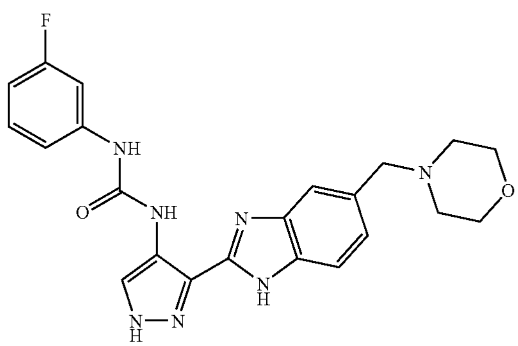 [SMILES: O=C(Nc1cccc(F)c1)Nc1c[nH]nc1-c1nc2cc(CN3CCOCC3)ccc2[nH]1] | Purified by preparative LC/MS | [M + H]+ 436 R_t 2.77 Basic |
| 51 | 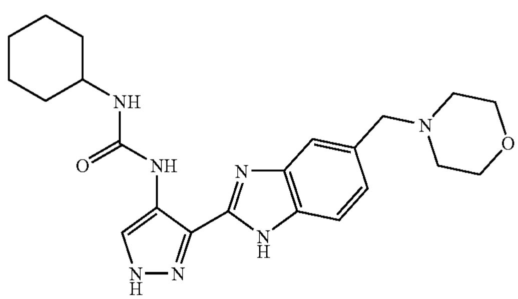 [SMILES: O=C(Nc1c[nH]nc1-c1nc2cc(CN3CCOCC3)ccc2[nH]1)NC1CCCCC1] | | [M + H]+ 422 R_t 1.89 Acidic |
| 52 | 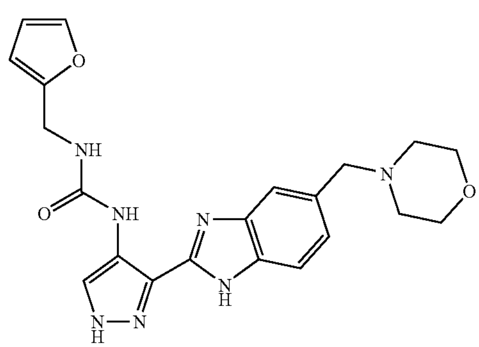 [SMILES: O=C(NCc1ccco1)Nc1c[nH]nc1-c1nc2cc(CN3CCOCC3)ccc2[nH]1] | | [M + H]+ 422 R_t 1.65 Acidic |

| Example | Structure | Differences to General Method | LC/MS |
|---|---|---|---|
| 53 | 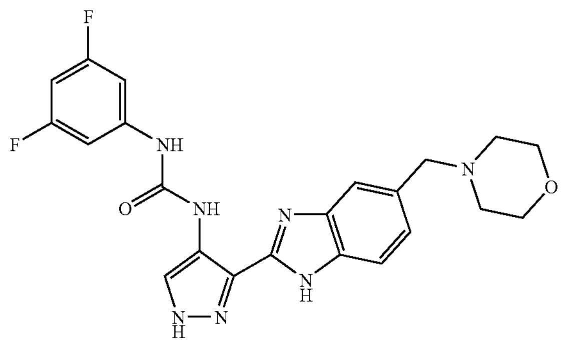 [SMILES: O=C(Nc1cc(F)cc(F)c1)Nc1c[nH]nc1-c1nc2cc(CN3CCOCC3)ccc2[nH]1] | Following chromatography on silica, impurity removed by precipitation from MeOH solution. | $[M+H]^+$ 452 $R_t$ 2.21 Acidic |
| 54 | 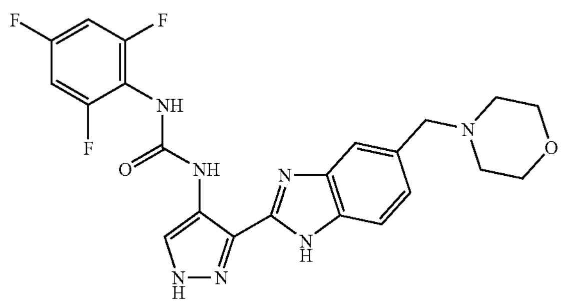 [SMILES: O=C(Nc1c[nH]nc1-c1nc2cc(CN3CCOCC3)ccc2[nH]1)Nc1c(F)cc(F)cc1F] | No tris-amine required. Purified by preparative LC/MS | $[M+H]^+$ 472 $R_t$ 1.89 Acidic |
| 55 | 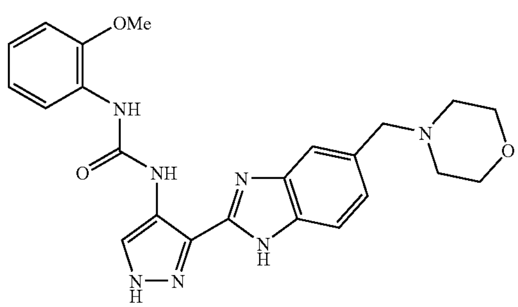 [SMILES: COc1ccccc1NC(=O)Nc1c[nH]nc1-c1nc2cc(CN3CCOCC3)ccc2[nH]1] | Reaction run for 1.5 hours 0° C. Mixture concentrated and purified directly by preparative LC/MS. | $[M+H]^+$ 448 $R_t$ 6.28 Acidic |
| 56 | 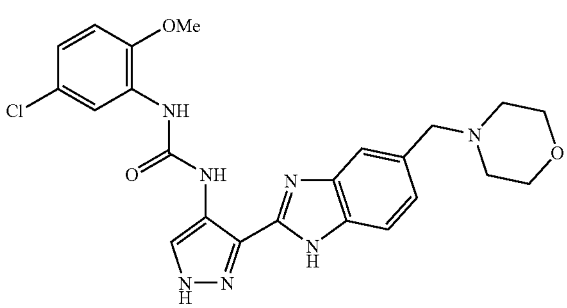 [SMILES: COc1ccc(Cl)cc1NC(=O)Nc1c[nH]nc1-c1nc2cc(CN3CCOCC3)ccc2[nH]1] | Reaction run for 1.5 hours at 0° C. Mixture concentrated and purified directly by preparative LC/MS. | $[M+H]^+$ 482 $R_t$ 7.28 Acidic |

Examples 57-59

By following the general method set out in Example 23, but modified where indicated in the Table below, the compounds of Examples 57 to 59 were prepared.

| Example | Structure | Procedure from Example | Differences to General Method | LC/MS |
|---------|-----------|------------------------|-------------------------------|-------|
| 57 | 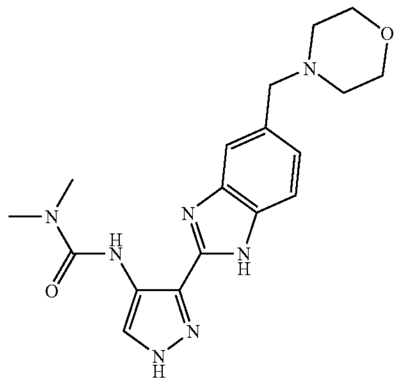 [SMILES: CN(C)C(=O)Nc1c[nH]nc1-c1nc2cc(CN3CCOCC3)ccc2[nH]1] | Example 23 using dimethylamine | | $[M - H^+]^-$ 368<br>$R_t$ 2.39<br>(Basic method) |
| 58 | 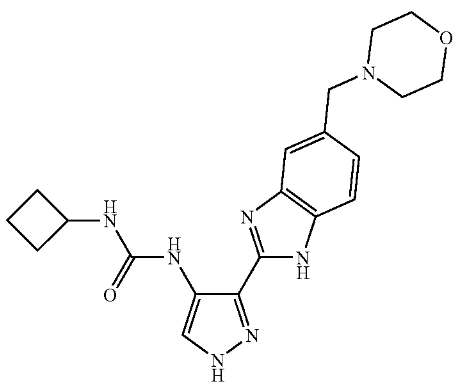 [SMILES: O=C(Nc1c[nH]nc1-c1nc2cc(CN3CCOCC3)ccc2[nH]1)NC1CCC1] | Example 23 using cyclobutylamine | | $[M + H^+]^+$ 396<br>$R_t$ 2.48<br>(Basic method) |
| 59 | 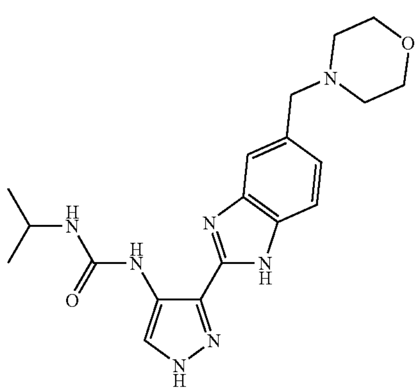 [SMILES: CC(C)NC(=O)Nc1c[nH]nc1-c1nc2cc(CN3CCOCC3)ccc2[nH]1] | Example 23 using isopropylamine | | $[M + H^+]^+$ 384<br>$R_t$ 2.40<br>(Basic method) |

Example 60

Synthesis of 1-(2,6-difluorophenyl)-N-[3-(5-morpholin-4-yl ethyl-1H-benzimidazol-2-yl)-1H-pyrazol-4-yl]-urea-hydrochloride salt

60A. Synthesis of (3,4-Dinitro-phenyl)-morpholin-4-yl-methanone

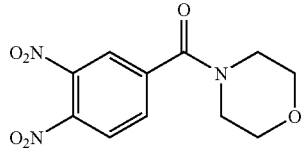 [SMILES: O=C(c1ccc([N+](=O)[O-])c([N+](=O)[O-])c1)N1CCOCC1]

A mixture of 3,4-dinitrobenzoic acid (1 mol. eq.) and thionyl chloride (9.2 mol. eq.) was heated at reflux for 6 hours, cooled to ambient temperature and excess thionyl chloride removed through azeotrope with toluene. The residue was taken up in THF (8 vol.) and then morpholine (1.0 mol. eq.) and Et$_3$N (1.1 mol. eq.) were added concurrently to the mixture at 0-5° C. The mixture was stirred for 1 hour at ambient temperature before being poured into water (25 vol.). The mixture was cooled to 3-7° C. and allowed to stand for 0.5 hours during which time the product appeared as a precipitate. The precipitate was collected by filtration, washed with water and dried to give 3,4-dinitro-phenyl)-morpholin-4-yl-methanone (75%) as a yellow solid. ($^1$H NMR (300 MHz, DMSO-d$_6$) δ 8.3 (d, 1H), 8.3 (s, 1M), 8.0 (d, 1H), 3.7-3.5 (m, 8H).

60B. Synthesis of 4-(3,4-Dinitro-benzyl)-morpholine

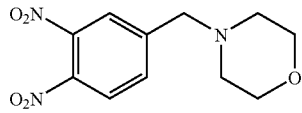 [SMILES: O=[N+]([O-])c1ccc(CN2CCOCC2)cc1[N+](=O)[O-]]

To a mixture of (3,4-dinitro-phenyl)-morpholin-4-yl-methanone (1 mol. eq.) in dry tetrahydrofuran (THF) (25 vol.), at 0-5° C., was added NaBH$_4$ (2 mol. eq.) followed drop-wise by BF$_3$.Et$_2$O (1.01 mol. eq.) so as to maintain the temperature at 0-5° C. The mixture was then stirred at ambient temperature for 3 hours and then quenched through addition of methanol. The mixture was then reduced in vacuo, partitioned between ethyl acetate and saturated aqueous NaHCO$_3$. The mixture was stirred rapidly for 30 minutes before separating the layers. The organic layer was washed successively with water and brine before being reduced in vacuo. The product was crystallised from methanol to give 4-(3,4-dinitro-benzyl)-morpholine (85%). (LC/MS (basic method): R$_t$ 2.80, [M+H]$^+$ 268).

60C. Synthesis of 4-Morpholin-4-ylmethyl-benzene-1,2-diamine

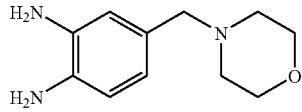

A mixture of 4-(3,4-dinitro-benzyl)-morpholine (1 mol. eq.) and 5% Pd/C (0.05 wt. eq.) in IMS (33 vol.) was stirred at 0-5° C. while the vessel was charged with hydrogen. The mixture was carefully warmed to 15-20° C. with stirring until the reaction was complete (<24 hours). The mixture was filtered and the filtrate evaporated to dryness to give 4-morpholin-4-ylmethyl-benzene-1,2-diamine (90%). The material was used immediately in the next step. (LC/MS (basic method): R$_t$ 1.64, [M–N(CH$_2$CH$_2$)$_2$O$^-$]$^+$ 121).

60D. Synthesis of 5-Morpholin-4-ylmethyl-2-(4-nitro-1H-pyrazol-3-yl)1H-benzimidazole

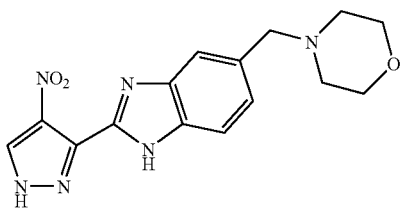 [SMILES: Nc1c[nH]nc1-c1nc2cc(CN3CCOCC3)ccc2[nH]1]

4-Morpholin-4-ylmethyl-benzene-1,2-diamine (1 mol. eq.) and 4-nitro-1H-pyrazole-3-carboxylic acid (1 mol. eq.) were dissolved in dimethylformamide (DMF) (10 vol.). 0-(Benzotriazol-1-yl)-N,N,N',N'-tetramethyluronium tetrafluoroborate (TBTU) (1.2 mol. eq.) was added and the mixture was stirred at ambient temperature for 24 hours. The mixture was concentrated in vacuo until no further solvent was seen to distil. The residue was then dissolved in glacial acetic acid (10 vol.) and heated at 65° C. for 12 hours. The mixture was concentrated in vacuo and then dissolved in water (6 vol.) at 75° C. The black solution was cooled to 0-5° C. over 2 hours during which time a solid was formed. The solid was removed by filtration and the aqueous filtrate was diluted with ethyl acetate (4 vol.) and tetrahydrofuran (2 vol.). Solid NaHCO$_3$ was added slowly to the stirred mixture until no further effervescence was observed and a pH of 6.8 was reached. The mixture was then stirred until a precipitation was observed. After standing the mixture at 0-5° C. for 2 hours, the solid was collected by filtration and washed with water (2 vol.) and ethyl acetate (2 vol.) and dried to give 5-morpholin-4-ylmethyl-2-(4-nitro-1H-pyrazol-3-yl)1H-benzimidazole as a brown solid (40%). (LC/MS (basic method): R$_t$ 1.93, [M–H$^+$]$^-$ 327).

60E. Synthesis of 3-(5-morpholin-4-ylmethyl-1H-benzimidazol-2-yl)-1H-pyrazol-ylamine

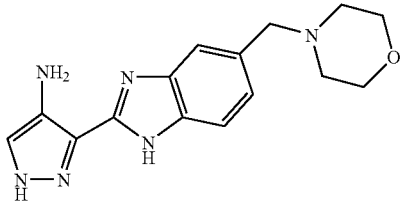

To 5-morpholin-4-ylmethyl-2-(4-nitro-1H-pyrazol-3-yl)1H-benzimidazole (1 mol. eq.) in DMF (36 vol.) under an atmosphere of nitrogen, was added 5% Pd/C (0.1 wt. eq.). The reaction vessel was charged with hydrogen and stirred at ambient temperature for 24 hours. The mixture was then filtered through celite, washing with methanol. The filtrate was concentrated in vacuo to give 3-(5-morpholin-4-ylmethyl-1H-benzimidazol-2-yl)-1H-pyrazol-4-ylamine as a brown solid (90%). (LC/MS (basic method): $R_t$ 1.94, $[M-H^+]^-$ 297. The product was used without any further purification.

60F. Synthesis of 1-(2,6-difluorophenyl)-N-[3-(5-morpholin-4-ylmethyl-1H-benzimidazol-yl)-1H-pyrazol-4-yl]-urea-hydrochloride salt

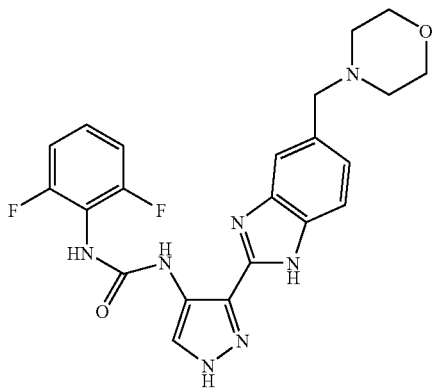 [SMILES: O=C(Nc1c[nH]nc1-c1nc2cc(CN3CCOCC3)ccc2[nH]1)Nc1c(F)cccc1F]

To a mixture of 3-(5-morpholin-4-ylmethyl-1H-benzimidazol-2-yl)-1H-pyrazol-4-ylamine (1 mol. eq.) in THF (10 vol.) was added 2,6-difluorophenyl isocyanate (1.3 mol. eq.) while stirring at 0-5° C. The mixture was then stirred for 16 hours at ambient temperature after which time the mixture was treated with 1M aq. KOH (4 vol.). After stirring for a further 2 hours the mixture was then concentrated in vacuo and partitioned between ethyl acetate and saturated aqueous $NaHCO_3$. The organic layer was washed with saturated brine, dried ($MgSO_4$), evaporated to dryness and then the residue purified by flash column chromatography [$SiO_2$, eluting with a gradient $CH_2Cl_2$-MeOH (98:2)-(90:10)] to give 1-(2,6-difluorophenyl)-N-[3-(5-morpholin-4-ylmethyl-1H-benzimidazol-2-yl)-1H-pyrazol-4-yl]-urea.

60G. Recrystallisation and characterization of the Free Base

Following chromatography on silica as described in Example 60E, the product was dissolved in a minimum amount of hot ethyl acetate, filtered and allowed to cool. The free base was thus obtained as a fine crystalline solid.

The compound 1-(2,6-difluorophenyl)-N-[3-(5-morpholin-4-ylmethyl-1H-benzimidazol-2-yl)-1H-pyrazol-4-yl]-urea has the following physicochemical parameters.

pKa values—3.42, 6.92 & 10.97 logP—3.24

$logP_{ion}$—0.36 logD (pH=6) 2.27

(pH=6.5) 2.68

(pH=7.4) 3.11

60H. Formation of Hydrochloride Salt

The product was dissolved in ethyl acetate and treated with excess saturated HCl in diethyl ether. The resulting precipitate was collected by filtration, washed with diethyl ether and dried to give 1-(2,6-difluorophenyl)-N-[3-(5-morpholin-4-ylmethyl-1H-benzimidazol-2-yl)-1H-pyrazol-4-yl]-urea—hydrochloride salt (59%) as a colourless solid. (LC/MS (acidic method): $R_t$ 1.80, $[M+H]^+$ 454).

By replacing the hydrogen chloride with other acids (e.g. DL lactic acid, ethane sulphonic acid and methane sulphonic acid) and changing the make up of the solvents as required, other salts of 1-(2,6-difluorophenyl)-N-[3-(5-morpholin-4-ylmethyl-1H-benzimidazol-2-yl)-1H-pyrazol-4-yl]-urea may be prepared.

60J. Comparison of the Solubilities of the Free Base and Hydrochloride salt

The solubilities of the free base and hydrochloride salt were measured and compared. The solubility of the free base at pH 7.4 (buffered aqueous solution) was found to be <0.001 mg/ml whereas the solubility of the hydrochloride salt at pH 7.1 (in buffered aqueous solution) was found to be 0.093 mg/ml. Thus, the hydrochloride salt has significant advantages in terms of solubility with respect to the free base.

Example 61

Determination of the Solubilities of Acid Addition Salts of 1-(2,6-difluorophenyl)-N-[3-(5-morpholin-4-ylmethyl-1H-benzimidazol-2-yl)-1H-pyrazol-4-yl]-urea The free base form of 1-(2,6-difluorophenyl)-N-[3-(5-morpholin-4-ylmethyl-1H-benzimidazol-2-yl)-1H-pyrazol-4-yl]-urea was combined with various acids by the procedure set out below in order to assess the solubilities of the resulting acid addition salts.

Procedure

Into an 8 ml vial was added the free base (59 mg, 0.13 mmol) and water (0.59 ml). To the vial was added the appropriate acid (1 eq., 0.13 mmol) and the vial was shaken at ambient temperature for 16 hours. After this time the vials were visually inspected. If a homogenous solution was observed, then the experiment was terminated, and it was concluded that the salt thus formed has a solubility greater than 100 mg/ml.

If solid remained, then a further 0.59 ml of water was added and the vial was shaken for 4 hours. If a homogenous solution was formed by this stage, it was concluded that the salt has a solubility of greater than 50 mg/ml.

If solid remained at this juncture, then a further 1.18 ml of water was added and the vial was shaken at ambient temperature. If this resulted in a homogenous solution, then it was concluded that the solubility is greater than 25 mg/ml. If solid still remained, it was concluded that the solubility of the salt is less than 25 mg/ml.

The free base was regenerated by passing the salt solution through a Strata-$NH_2$ column.

The results of the experiments are set out in the Table below.

| Solubilities of salts of 1-(2,6-difluorophenyl)-N-[3-(5-morpholin-4-ylmethyl-1H-benzimidazol-2-yl)-1H-pyrazol-4-yl]-urea | | | |
|---|---|---|---|
| >100 mg/ml | >50 mg/ml | >25 mg/ml | <25 mg/ml |
| Mesylate | | D-Glucuronate | Acetate |
| Ethanesulphonate | | | Adipate |
| DL-Lactate | | | L-(+)-Aspartate |
| | | | D-Gluconate |
| | | | L-Glutamate |
| | | | Hydrochloride |
| | | | Tosylate |
| | | | Free base |

On the basis of the results shown in the Table, it may be concluded that the mesylate, ethanesulphonate and DL-Lactate salts should prove to be particularly useful for preparing aqueous liquid compositions, for example for parenteral administration.

Example 62

Free Base and Salts of 1-Cyclopropyl-3-[3-(5-morpholin-4-ylmeth-1H-benzoimidazol-2-yl)-1H-pyrazol-4-yl]-urea The compound of Example 24, 1-cyclopropyl-3-[3-(5-morpholin-4-ylmethyl-1H-benzoimidazol-2-yl)-1H-pyrazol-4-yl]-urea, can be isolated in free base or acid addition salt form by the methods set out below or methods analogous thereto.

Free Base

Following chromatography on silica (see Example 24), the product of Example 24 was dissolved in a minimum volume of hot MeOH, filtered and allowed to cool. After ~16 h, the product was collected as a colourless crystalline solid.

Hydrochloride Salt (Generic Procedure)

Following chromatography on silica, the product (2.05 g) was dissolved in MeOH:EtOAc (1:10; 100 ml) and treated with 4N HCl in dioxane (1.1 mol. eq.). The resulting precipitate was collected by filtration and dried to give 1-cyclopropyl-3-[3-(5-morpholin-4-ylmethyl-1H-benzoimidazol-2-yl)-1H-pyrazol-4-yl]-urea hydrochloride (1.5 g). The product was dissolved in a minimum volume of MeOH and then triturated with $Et_2O$, until a cloudiness persisted for several seconds. After cooling overnight, the product was collected as a colourless crystalline solid.

Mesylate Salt

The product was collected as a colourless crystalline solid using the generic procedure described above but using methanesulphonic acid instead of hydrochloric acid.

Other Salts

It is anticipated other salts of interest could be prepared using the generic procedure described above.

Example 63

Determination of the Solubilities of the Free Base and Salts of 1-Cyclopropyl-3-[3-(5-morpholin-4-ylmethyl-1H-benzoimidazol-2-yl)-1H-pyrazol-4-yl]-urea The compound of Example 24, 1-cyclopropyl-3-[3-(5-morpholin-4-ylmethyl-1H-benzoimidazol-2-yl)-1H-pyrazol-4-yl]-urea was combined with various acids by the procedure set out below in order to assess the solubilities of the resulting acid addition salts.

Procedure

Into an 8 ml vial was added the free base (50 mg, 0.131 mmol) of the compound of Example 24 and water (0.5 ml). To the vial was added the appropriate acid (1 eq., 0.131 mmol) and the vial was shaken at ambient temperature for 14-16 hours. After this time the vials were visually inspected. If a homogeneous solution was observed, then the experiment was terminated, and it was concluded that the salt thus formed has a solubility greater than 100 mg/ml.

If solid remained, then a further 0.5 ml of water was added and the vial was shaken for 6 hours. If a homogenous solution was formed by this stage, it was concluded that the salt has a solubility of greater than 50 mg/ml.

If solid remained at this juncture, then a further 1 ml of water was added and the vial was shaken at ambient temperature. If this resulted in a homogenous solution, then it was concluded that the solubility is greater than 25 mg/ml. If solid still remained, it was concluded that the solubility of the salt is less than 25 mg/ml.

The free base was regenerated by passing the salt solution through a Strata-$NH_2$ column.

The results of the experiments are set out in the Table below.

| Solubilities of salts of 1-cyclopropyl-3-[3-(5-morpholin-4-ylmethyl-1H-benzoimidazol-2-yl)-1H-pyrazol-4-yl]-urea | | | |
|---|---|---|---|
| >100 mg/ml | >50 mg/ml | >25 mg/ml | <25 mg/ml |
| Acetate | | Tosylate | L-(+)-Aspartate |
| Mesylate | | | L-Glutamate |
| Ethanesulphonate | | | Free base |
| DL-Lactate | | | |
| Adipate | | | |
| D-Glucuronate | | | |
| D-Gluconate | | | |
| Hydrochloride | | | |

On the basis of the results shown in the Table, it may be concluded that the acetate, mesylate, ethanesulphonate, DL-lactate, adipate, D-glucuronate, D-gluconate and hydrochloride salts should prove to be particularly useful for preparing aqueous liquid compositions, for example for parenteral administration.

From data gathered to date, it is apparent that the compounds of the invention, and in particular the free base and salts of 1-cyclopropyl-3-[3-(5-morpholin-4-ylmethyl-1H-benzoimidazol-2-yl)-1H-pyrazol-4-yl]-urea (in particular the L-lactate), will have a number of advantages over prior art compounds. In particular, such advantages include one or more of the following:

Improved solubility in aqueous solution;
Better physicochemical properties in particular lower logD;
Differences in susceptibility to P450 enzymes;
Improvement in drug metabolism and pharmacokinetic properties;
Improved stability, e.g. improved shelf life and/or improved thermal stability;
Reduced dosage requirements;
Improved potency versus therapeutic targets and in particular Aurora A and B;
Improved cell activity in proliferation and clonogenic assays;

Improved anti-cancer activity; and
Improved therapeutic index.

In particular the L-lactic acid salt form of the compound had good stability at elevated temperatures, adequate aqueous solubility in acidic buffer systems and it was non-hygroscopic with no apparent polymorph or hydrate formation.

Example 64

Preparation of 1-Cyclopropyl-3-[3-(5-Morpholin-4-ylmethyl-1H-Benzoimidazol-2-yl)-1H-Pyrazol-4-yl]-Urea Lactate Salt To a solution of 1-cyclopropyl-3-[3-(5-morpholin-4-ylmethyl-1H-benzoimidazol-2-yl)-1H-pyrazol-4-yl]-urea (0.7 g, 1.83 mmol) in EtOAc-MeOH was added L-lactic acid (166 mg, 1.85 mmol). The mixture was stirred at ambient temperature then reduced in vacuo. This solid was purified by recrystallisation from boiling EtOH (20 mL) to give after drying 1-cyclopropyl-3-[3-(5-morpholin-4-ylmethyl-1H-benzoimidazol-2-yl)-1H-pyrazol-4-yl]-urea, L-lactate salt (0.48 g).

Example 65

Synthesis of the L-Lactate Salt of 1-cyclopropyl-3-[3-(5-morpholin-4-ylmethyl-1H-benzoimidazol-2-yl)-1H-pyrazol-4-yl]-urea The L-lactate salt of 1-cyclopropyl-3-[3-(5-morpholin-4-ylmethyl-1H-benzoimidazol-2-yl)-1H-pyrazol-4-yl]-urea may be prepared by the synthetic route shown in the Scheme below.

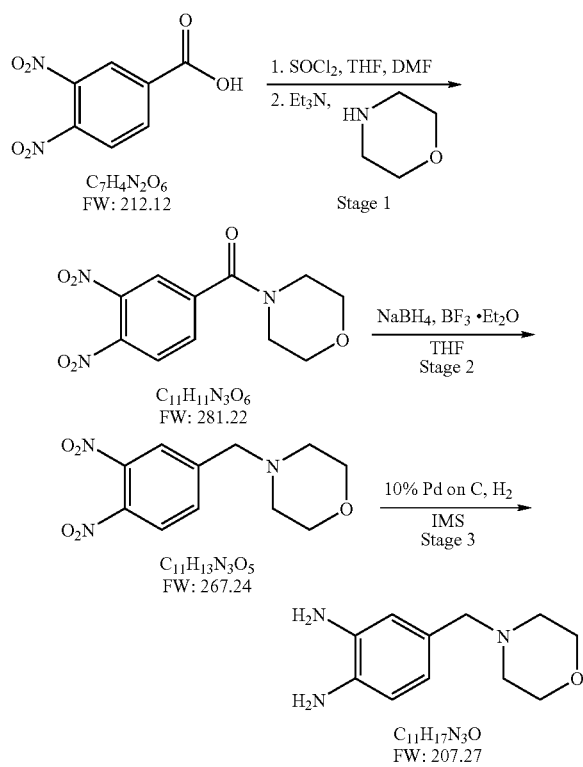

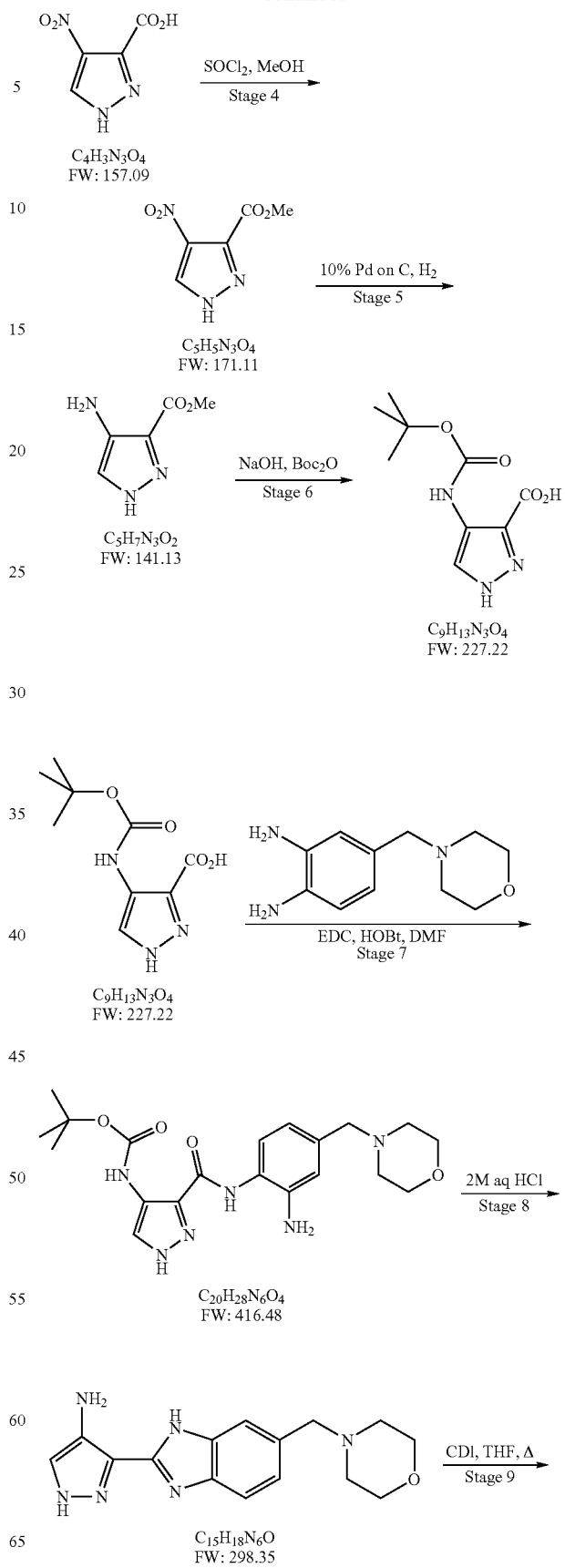

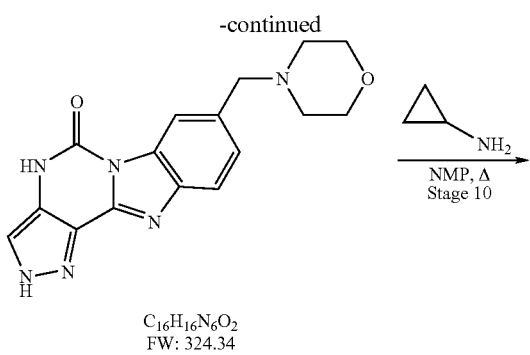

C₁₆H₁₆N₆O₂
FW: 324.34

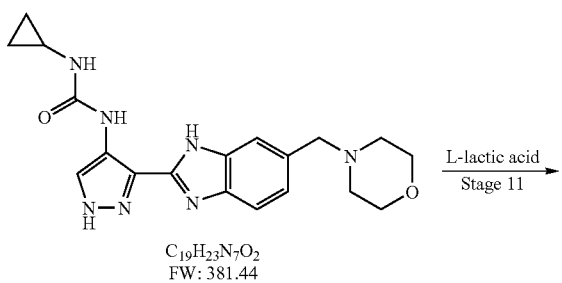

C₁₉H₂₃N₇O₂
FW: 381.44

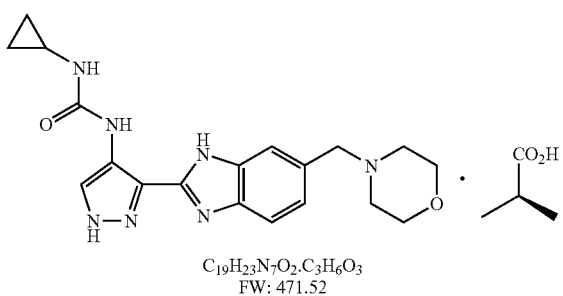

C₁₉H₂₃N₇O₂·C₃H₆O₃
FW: 471.52

Stage 1: Synthesis of
(3,4-dinitro-phenyl)-morpholin-4-yl-methanone

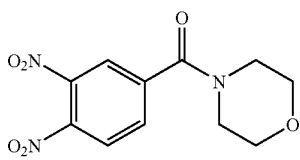

A solution of 3,4-dinitrobenzoic acid (10 g, 47 mmol, 1 eq.) and DMF (0.1 mL) in THF (100 mL) was treated with thionyl chloride (4.5 mL, 62 mmol, 1.3 eq.) then heated to reflux for 2.5 h. The mixture was cooled in ice then triethylamine (10 mL, 71 mmol, 1.1 eq.) was added over 20 min, keeping internal temperature <5° C. Morpholine (6.2 mL, 71 mmol, 1.5 eq) was added to the resulting thick yellow suspension over 15 min, keeping internal temperature <10° C. The ice-bath was removed and the mixture allowed to warm to r.t. After 15 min, a further portion of morpholine (1 mL, 11 mmol, 0.24 eq.) was added and the mixture stirred overnight. The mixture was diluted with water (250 mL) and cooled in ice. A beige solid was filtered off under suction, washed with a further portion of cold water (25 mL) and dried in vacuo to afford the title compound (12.7 g, 96%).

Stage 2: Synthesis of
4-(3,4-dinitro-benzyl)-morpholine

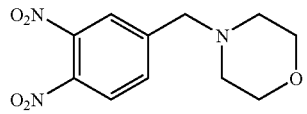 [SMILES: O=[N+]([O-])c1ccc(CN2CCOCC2)cc1[N+](=O)[O-]]

Sodium borohydride (3.36 g, 89 mmol, 2.1 eq.) was ground, placed in a nitrogen-flushed flask and suspended in THF (120 mL). After cooling to ~0° C., boron trifluoride etherate (11.3 mL, 89 mmol, 2.1 eq.) was added via syringe. This reaction is mildly exothermic and some hydrogen evolution was noted. 4-(3,4-Dinitrobenzoyl)morpholine (11.91 g, 42 mmol, 1.0 eq.) was added as a solid in one portion, the vessel being rinsed with an additional portion of THF (20 mL). The ice-bath was removed and the suspension stirred at r.t. for 3 h before cooling again in ice. Methanol (100 mL) was added cautiously (hydrogen evolution) then the mixture was brought to reflux for 1 h. The mixture was concentrated in vacuo then the residue was partitioned between ethyl acetate (100 mL) and 1:1 saturated sodium bicarbonate solution/water (100 mL). The organic phase was separated, washed with water (50 mL) then brine (100 mL) and dried (MgSO₄). The initial bicarbonate wash was extracted a second time with ethyl acetate (50 mL), this extract then being washed with the same aqueous washes used for the first extract before drying (MgSO₄), combination and concentration to afford 10.97 g of crude material. Recrystallisation from methanol (45 mL, 10 mL wash) gave the title compound (9.34 g, 83%).

Stage 3: Synthesis of
4-morpholin-4-ylmethyl-benzene-1,2-diamine

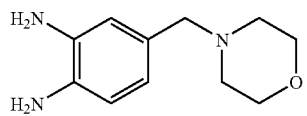

4-(3,4-Dinitrobenzyl)morpholine (21 g, 101 mmol) was suspended in ethanol (0.9 L) and the vessel purged with nitrogen. 10% Palladium on charcoal (1.05 g) was suspended in ethanol (25 mL) and added to the substrate. The mixture was cooled in ice then the atmosphere exchanged for hydrogen. The mixture was allowed to warm to 15-20° C. and hydrogenation continued at ambient pressure for 2 days. The vessel was purged with nitrogen then the mixture was filtered through Celite, rinsing with ethanol (0.3 L) in portions. Concentration afforded the title compound (15.8 g, 97%).

Stage 4: Synthesis of
4-nitro-1H-pyrazole-3-carboxylic acid methyl ester

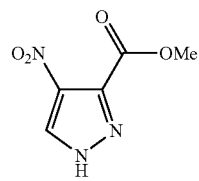 [SMILES: COC(=O)c1n[nH]cc1[N+](=O)[O-]]

A 20 L reaction vessel equipped with a digital thermometer and stirrer was charged with 4-nitro-1H-pyrazole-3-carboxylic acid (1.117 Kg, 7.1 μmol, 1 wt) and methanol (8.950 L, 8 vol). The reaction mixture was stirred under nitrogen, cooled to 0 to 5° C., thionyl chloride (0.581 L, 8.0 mol, 0.52 vol) added over 180 minutes and the resultant mixture allowed to warm to and stir at 18 to 22° C. overnight after which time $^1$H NMR analysis (d$_6$-DMSO) indicated reaction completion. The reaction mixture was concentrated under reduced pressure at 40 to 45° C., the residue treated with toluene and re-concentrated (3×2.250 L, 3×2 vol) under reduced pressure at 40 to 45° C. to give 4-nitro-1H-pyrazole-3-carboxylic acid methyl ester as an off-white solid (1.210 Kg, 99.5% th).

Stage 5: Synthesis of 4-amino-1H-pyrazole-3-carboxylic acid methyl ester

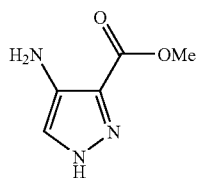

A 20 L reaction vessel equipped with a digital thermometer and stirrer was charged with palladium on carbon (10% wet paste, 0.170 Kg, 0.14 wt) under nitrogen. In a separate vessel, a slurry of 4-nitro-1H-pyrazole-3-carboxylic acid methyl ester (1.210 Kg, 7.07 mol, 1 wt) in ethanol (12.10 L, 10 vol) was warmed to 30 to 35° C. to effect dissolution and the solution added to the catalyst under nitrogen. Following a nitrogen-hydrogen purge sequence an atmosphere of hydrogen was introduced and the reaction mixture maintained at 28 to 30° C. until reaction completion (5 to 10 hours) was noted by $^1$H NMR analysis (d$_6$-DMSO). Following a purge cycle, the reaction mixture under nitrogen was filtered and the liquors concentrated under reduced pressure to give 4-amino-1H-pyrazole-3-carboxylic acid methyl ester (0.987 Kg, 98.9% th).

Stage 6: Synthesis of 4-tert-butoxycarbonylamino-1H-pyrazole-3-carboxylic acid

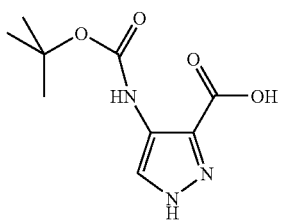 [SMILES: CC(C)(C)OC(=O)Nc1c[nH]nc1C(=O)O]

To a mixture of 4-amino-1H-pyrazole-3-carboxylic acid methyl ester (50.0 g, 355 mmol) in dioxane (500 mL) was added 2M aqueous NaOH solution (213 mL, 426 mmol), the mixture heated to 50° C. and stirred for 5 h. To this mixture was then added (BOC)$_2$O (81.4 g, 373 mmol), using a dioxane rinse (100 mL) and the mixture heated at 50° C. for a further 5 h, then stirred at ambient for 14 h. The dioxane was removed in vacuo and water (1 L) added. The mixture was taken to pH 2 using conc. aqueous HCl solution and the solid formed collected by filtration and dried on the filter. The solid was dried further through azeotrope with toluene (x3) and in the vacuum oven to give 4-tert-butoxycarbonylamino-1H-pyrazole-3-carboxylic acid (70.0 g, 87%) as a violet solid.

Stage 7: Synthesis of [3-(2-amino-4-morpholin-4-ylmethyl-phenylcarbamoyl)-1H-pyrazol-4-yl]-carbamic acid tert-butyl ester

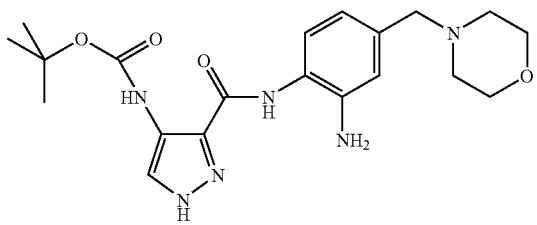 [SMILES: CC(C)(C)OC(=O)Nc1c[nH]nc1C(=O)Nc1ccc(CN2CCOCC2)cc1N]

A mixture of 4-tert-butoxycarbonylamino-1H-pyrazole-3-carboxylic acid (10.0 g, 44.1 mmol), 4-morpholin-4-ylmethyl-benzene-1,2-diamine (10.0 g, 48.5 mmol), EDC (10.14 g, 52.9 mmol) and HOBt (7.15 g, 52.9 mmol) in DMF (150 mL) was stirred at ambient temperature for 20 h and then the majority of the solvent removed in vacuo. The residue was partitioned between EtOAc (150 mL) and saturated aqueous NaHCO$_3$ (150 mL), the layers separated and the organic portion washed with brine, dried over MgSO$_4$ and reduced in vacuo to give [3-(2-amino-4-morpholin-4-ylmethyl-phenylcarbamoyl)-1H-pyrazol-4-yl]-carbamic acid tert-butyl ester (17.6 g, 96%) as a brown solid. LC/MS analysis indicates product contains 15% of the di-amide. This shows at approx. 5% level in $^1$H NMR. Di-amide is cleaved in subsequent step.

Stage 8: Synthesis of 3-(5-morpholin-4-ylmethyl-1H-benzoimidazol-2-yl)-1H-pyrazol-4-ylamine

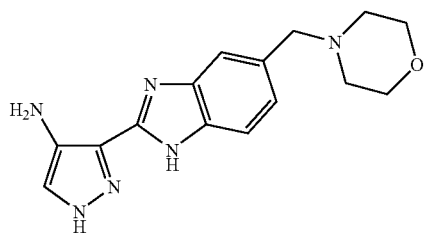 [SMILES: Nc1c[nH]nc1-c1nc2cc(CN3CCOCC3)ccc2[nH]1]

A mixture of [3-(2-amino-4-morpholin-4-ylmethyl-phenylcarbamoyl)-1H-pyrazol-4-yl]-carbamic acid tert-butyl ester (12.0 g, 28.8 mmol) and 2M aqueous HCl solution (50 μL) was heated at 85° C. for 14 h, then allowed to cool to ambient temperature. Solid Na$_2$CO$_3$ was carefully added until mixture was pH~8.5 and solution was saturated. A dark coloured gummy liquid was formed. The mixture was allowed to settle and the solvent decanted. To the remaining residue was added EtOH (60 mL), the mixture heated at reflux for 1 h and then hot filtered, washing with EtOH (2×20 mL), to remove inorganic residues. The filtrate was reduced in vacuo to give a glassy solid which was then stirred in Et$_2$O (60 mL) for 1 h and the resultant purple coloured powder collected by filtration and dried in vacuo to give 3-(5-morpholin-4-ylmethyl-1H-benzoimidazol-2-yl)-1H-pyrazol-4-ylamine (6.8 g, 80%, ~90% purity).

Stage 9: Synthesis of 7-morpholin-4-ylmethyl-2,4-dihydro-1,2,4,5a,10-pentaaza-cyclopenta[a]fluoren-5-one

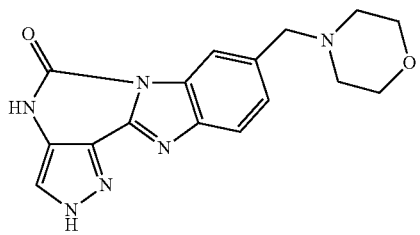 [SMILES: O=c1[nH]c2c[nH]nc2c2nc3ccc(CN4CCOCC4)cc3n12]

To a mixture of 3-(5-morpholin-4-ylmethyl-1H-benzoimidazol-2-yl)-1H-pyrazol-4-ylamine (3.2 g, 10.7 mmol) in anhydrous THF (50 mL) stirring at ambient temperature was added 1,1'-carbonyldiimidazole (1.78 g, 11 mmol). The mixture was heated at reflux for 14 h and then cooled to ambient. The solid formed was collected by filtration, washed with THF (20 mL) and dried in vacuo to give 7-morpholin-4-ylmethyl-2,4-dihydro-1,2,4,5a,10-pentaaza-cyclopenta[a]fluoren-5-one (2.34 g, 67%) as a pink solid.

Stage 10: Synthesis of 1-cyclopropyl-3-[3-(5-morpholin-4-ylmethyl-1H-benzoimidazol-2-yl)-1H-pyrazol-4-yl]-urea

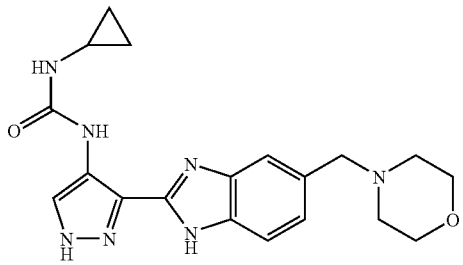 [SMILES: O=C(Nc1c[nH]nc1-c1nc2cc(CN3CCOCC3)ccc2[nH]1)NC1CC1]

To a mixture of 7-morpholin-4-ylmethyl-2,4-dihydro-1,2,4,5a,10-pentaaza-cyclopenta[a]-fluoren-5-one (10.7 g, 32.9 mmol) in NMP (65 mL) was added cyclopropylamine (6.9 mL, 99 mmol). The mixture was heated at 100° C. for 5 h. LC/MS analysis indicated ~75% conversion to product, therefore a further portion of cyclopropylamine (2.3 mL, 33 mmol) was added, the mixture heated at 100° C. for 4 h and then cooled to ambient. The mixture was diluted with water (100 mL) and extracted with EtOAc (100 mL). The organic portion was washed with sat. aq. NH$_4$Cl (2×50 mL) and brine (50 mL) and then the aqueous portions re-extracted with EtOAc (3×100 mL). The combined organic portions were dried over MgSO$_4$ and reduced in vacuo to give 1-cyclopropyl-3-[3-(5-morpholin-4-ylmethyl-1H-benzoimidazol-2-yl)-1H-pyrazol-4-yl]-urea as an orange glassy solid (9.10 g).

Stage 11: Synthesis of 1-cyclopropyl-3-[3-(5-morpholin-4-ylmethyl-1H-benzoimidazol-2-yl)-1H-pyrazol-4-yl]-urea L-lactate salt

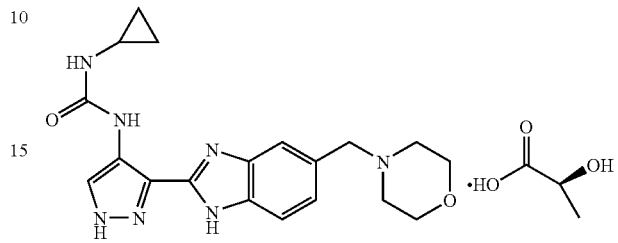

To a solution of 1-cyclopropyl-3-[3-(5-morpholin-4-ylmethyl-1H-benzoimidazol-2-yl)-1H-pyrazol-4-yl]-urea (9.10 g, 24 nmol) in EtOAc-iPrOH (1:1, 90 mL) was added L-lactic acid (2.25 g, 25 nmol). The mixture was stirred at ambient temperature for 24 h then reduced in vacuo. The residue was given consecutive slurries using toluene (100 mL) and Et$_2$O (100 mL) and the resultant solid collected and dried (8.04 g).

This solid was purified by recrystallisation from boiling iPrOH (200 mL) to give after drying 1-cyclopropyl-3-[3-(5-morpholin-4-ylmethyl-1H-benzoimidazol-2-yl)-1H-pyrazol-4-yl]-urea, L-lactate salt (5.7 g) as a beige solid.

Example 66A

Stage 1: Preparation of (3,4-dinitrophenyl)-morpholin-4-yl-methanone

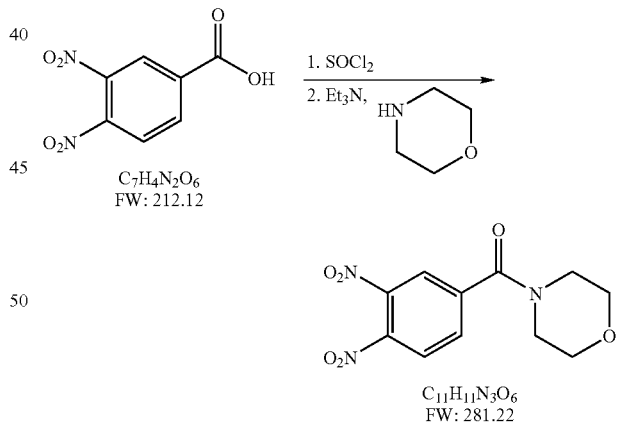

3,4-Dinitrobenzoic acid (1.000 Kg, 4.71 mol, 1.0 wt), tetrahydrofuran (10.00 L, 10.0 vol), and dimethyl for amide (0.010 L, 0.01 vol) were charged to a flask under nitrogen. Thionyl chloride (0.450 L, 6.16 mol, 0.45 vol) was added at 20 to 30° C. and the reaction mixture was heated to 65 to 70° C. Reaction completion was determined by $^1$H NMR analysis (d$_6$-DMSO), typically in 3 hours. The reaction mixture was cooled to 0 to 5° C. and triethylamine (1.25 L, 8.97 mol, 1.25 vol) was added at 0 to 10° C. Morpholine (0.62 L, 7.07 mol, 0.62 vol) was charged to the reaction mixture at 0 to 10° C. and the slurry was stirred for 30 minutes at 0 to 110° C.

Reaction completion was determined by $^1$H NMR analysis (d$_6$-DMSO). The reaction mixture was warmed to 15 to 20° C. and water (4.00 L, 4.0 vol) was added. This mixture was then charged to a 40 L flange flask containing water (21.00 L, 21.0 vol) at 15 to 25° C. to precipitate the product. The flask contents were cooled to and aged at 0 to 5° C. for 1 hour and the solids were collected by filtration. The filter-cake was washed with water (4×5.00 L, 4×5.0 vol) and the pH of the final wash was found to be pH 7. The wet filter-cake was analysed by $^1$H NMR for the presence of triethylamine hydrochloride. The filter-cake was dried at 40 to 45° C. under vacuum until the water content by KF<0.2% w/w, to yield (3,4-dinitrophenyl)-morpholin-4-yl-methanone (1.286 Kg, 97.0%, KF 0.069% w/w) as a yellow solid.

Stage 2: Preparation of 4-(3,4-dinitro-benzyl)-morpholine

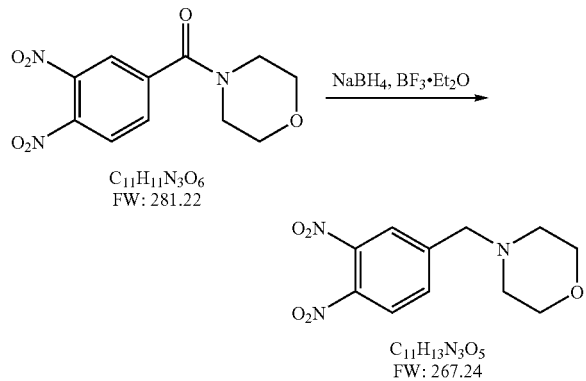

(3,4-Dinitrophenyl)-morpholin-4-yl-methanone (0.750 Kg, 2.67 mol, 1.0 wt) and tetrahydrofuran (7.50 L, 10.0 vol) were charged to a flask under nitrogen and cooled to 0 to 5° C. Borontrifluoride etherate (0.713 L, 5.63 mol, 0.95 vol) was added at 0 to 5° C. and the suspension was stirred at this temperature for 15 to 30 minutes. Sodium borohydride (0.212 Kg, 5.60 mol, 0.282 wt) was added in 6 equal portions over 90 to 120 minutes. (A delayed exotherm was noted 10 to 15 minutes after addition of the first portion. Once this had started and the reaction mixture had been re-cooled, further portions were added at 10 to 15 minute intervals, allowing the reaction to cool between additions). The reaction mixture was stirred at 0 to 5° C. for 30 minutes. Reaction completion was determined by $^1$H NMR analysis (d$_6$-DMSO). Methanol (6.30 L, 8.4 vol) was added dropwise at 0 to 10° C. to quench the reaction mixture (rapid gas evolution, some foaming). The quenched reaction mixture was stirred at 0 to 10° C. for 25 to 35 minutes then warmed to and stirred at 20 to 30° C. (exotherm, gas/ether evolution on dissolution of solid) until gas evolution had slowed. The mixture was heated to and stirred at 65 to 70° C. for 1 hour. The mixture was cooled to 30 to 40° C. and concentrated under vacuum at 40 to 45° C. to give crude 4-(3,4-dinitro-benzyl)-morpholine (0.702 Kg, 98.4%) as a yellow/orange solid.

4-(3,4-Dinitro-benzyl)-morpholine (2.815 kg, 10.53 mol, 1.0 wt) and methanol (12.00 L, 4.3 vol) were charged to a flask under nitrogen and heated to 65 to 70° C. The temperature was maintained until complete dissolution. The mixture was then cooled to and aged at 0 to 5° C. for 1 hour. The solids were isolated by filtration. The filter-cake was washed with methanol (2×1.50 L, 2×0.5 vol) and dried under vacuum at 35 to 45° C. to give 4-(3,4-dinitro-benzyl)-morpholine (2.353 Kg, 83.5% based on input Stage 2, 82.5% overall yield based on total input Stage 1 material,) as a yellow solid.

Stage 3: Preparation of 4-morpholin-4-yl-methyl-benzene-1,2-diamine

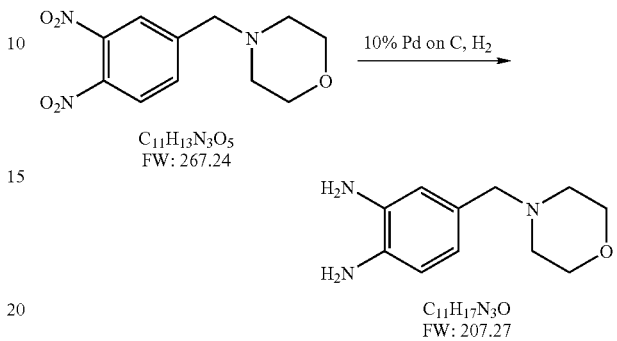

4-(3,4-Dinitro-benzyl)-morpholine (0.800 Kg, 2.99 mol, 1.0 wt), and ethanol (11.20 L, 14.0 vol) were charged to a suitable flask and stirred at 15 to 25° C. and a vacuum/nitrogen purge cycle was performed three times. 10% Palladium on carbon (10% Pd/C, 50% wet paste, 0.040 Kg, 0.05 wt wet weight) was slurried in ethanol (0.80 L, 1.0 vol) and added to the reaction. The mixture was cooled to 10 to 20° C. and a vacuum/nitrogen purge cycle was performed three times. A vacuum/hydrogen purge cycle was performed three times and the reaction was stirred under a hydrogen atmosphere at 10 to 20° C. Reaction completion was determined by $^1$H NMR analysis (d$_6$-DMSO), typically 14 to 20 hours. A vacuum/nitrogen purge cycle was performed three times and the reaction mixture was filtered through glass microfibre paper under nitrogen. The filter-cake was washed with ethanol (3×0.80 L, 3×1.0 vol) and the combined filtrate and washes were concentrated to dryness under vacuum at 35 to 45° C. to give 4-morpholin-4-yl-methyl-benzene-1,2-diamine (0.611 Kg 98.6%) as a brown solid.

Stage 4: Preparation of 4-nitro-1H-pyrazole-3-carboxylic acid methyl ester

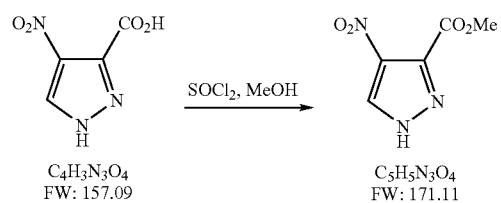 [SMILES: O=C(O)c1n[nH]cc1[N+](=O)[O-] ; COC(=O)c1n[nH]cc1[N+](=O)[O-]]

4-Nitro-1H-pyrazole-3-carboxylic acid (1.00 kg, 6.37 mol, 1.0 wt) and methanol (8.00 L, 8.0 vol) were charged to a flange flask equipped with a mechanical stirrer, condenser and thermometer. The suspension was cooled to 0 to 5° C. under nitrogen and thionyl chloride (0.52 L, 7.12 mol, 0.52 vol) was added at this temperature. The mixture was warmed to 15 to 25° C. over 16 to 24 hours. Reaction completion was determined by $^1$H NMR analysis (d$_6$-DMSO). The mixture was concentrated under vacuum at 35 to 45° C. Toluene (2.00 L, 2.0 vol) was charged to the residue and removed under vacuum at 35 to 45° C. The azeotrope was repeated twice using toluene (2.00 L, 2.0 vol) to give 4-nitro-1H-pyrazole-3-carboxylic acid methyl ester (1.071 Kg, 98.3%) as an off white solid.

Stage 5: Preparation of 4-amino-1H-pyrazole-3-carboxylic acid methyl ester

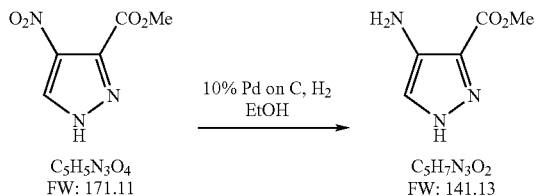 [SMILES: COC(=O)c1n[nH]cc1[N+](=O)[O-] ; COC(=O)c1n[nH]cc1N]

A suspension of 4-nitro-1H-pyrazole-3-carboxylic acid methyl ester (1.084 Kg, 6.33 mol, 1.0 wt) and ethanol (10.84 L, 10.0 vol) was heated to and maintained at 30 to 35° C. until complete dissolution occurred. 10% Palladium on carbon (10% Pd/C wet paste, 0.152 Kg, 0.14 wt) was charged to a separate flask under nitrogen and a vacuum/nitrogen purge cycle was performed three times. The solution of 4-nitro-1H-pyrazole-3-carboxylic acid methyl ester in ethanol was charged to the catalyst and a vacuum/nitrogen purge cycle was performed three times. A vacuum/hydrogen purge cycle was performed three times and the reaction was placed under an atmosphere of hydrogen. The reaction mixture was stirred at 28 to 30° C. until deemed complete by $^1$H NMR analysis ($d_6$-DMSO). The mixture was filtered under nitrogen and concentrated under vacuum at 35 to 45° C. to give 4-amino-1H-pyrazole-3-carboxylic acid methyl ester (0.883 Kg, 98.9%) as a purple solid.

Stage 6: Preparation of 4-tert-butoxycarbonylamino-1H-pyrazole-3-carboxylic acid

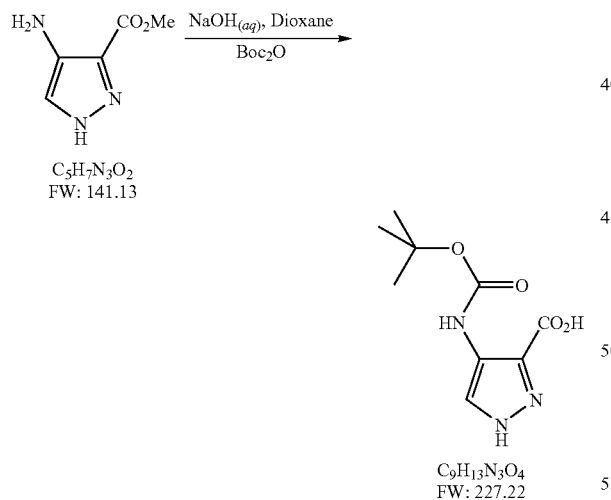

4-Amino-1H-pyrazole-3-carboxylic acid methyl ester (1.024 Kg, 7.16 mol, 1.0 wt) and dioxane (10.24 L, 10.0 vol) were charged to a flange flask equipped with a mechanical stirrer, condenser and thermometer. 2M aq. Sodium hydroxide solution (4.36 L, 8.72 mol, 4.26 vol) was charged at 15 to 25° C. and the mixture was heated to 45 to 55° C. The temperature was maintained at 45 to 55° C. until reaction completion, as determined by $^1$H NMR analysis ($d_6$-DMSO). Di-tert-butyl dicarbonate (Boc anhydride, 1.667 Kg, 7.64 mol, 1.628 wt) was added at 45 to 55° C. and the mixture was stirred for 55 to 65 minutes. $^1$H NMR IPC analysis ($d_6$-DMSO) indicated the presence of 9% unreacted intermediate. Additional di-tert-butyl dicarbonate (Boc anhydride, 0.141 Kg, 0.64 mol, 0.14 wt) was added at 55° C. and the mixture was stirred for 55 to 65 minutes. Reaction completion was determined by $^1$H NMR analysis ($d_6$-DMSO). The dioxane was removed under vacuum at 35 to 45° C. and water (17.60 L, 20.0 vol) was added to the residue. The pH was adjusted to pH 2 with 2M aq. hydrochloric acid (4.30 L, 4.20 vol) and the mixture was filtered. The filter-cake was slurried with water (10.00 L, 9.7 vol) for 20 to 30 minutes and the mixture was filtered. The filter-cake was washed with heptanes (4.10 L, 4.0 vol) and pulled dry on the pad for 16 to 20 hours. The solid was azeodried with toluene (5×4.00 L, 5×4.6 vol) then dried under vacuum at 35 to 45° C. to give 4-tert-butoxycarbonylamino-1H-pyrazole-3-carboxylic acid (1.389 Kg, 85.4%) as a purple solid.

Stage 7: Preparation of [3-(2-amino-4-morpholin-4-ylmethyl-phenylcarbamoyl)-1H-pyrazol-4-yl]-carbamic acid tert-butyl ester

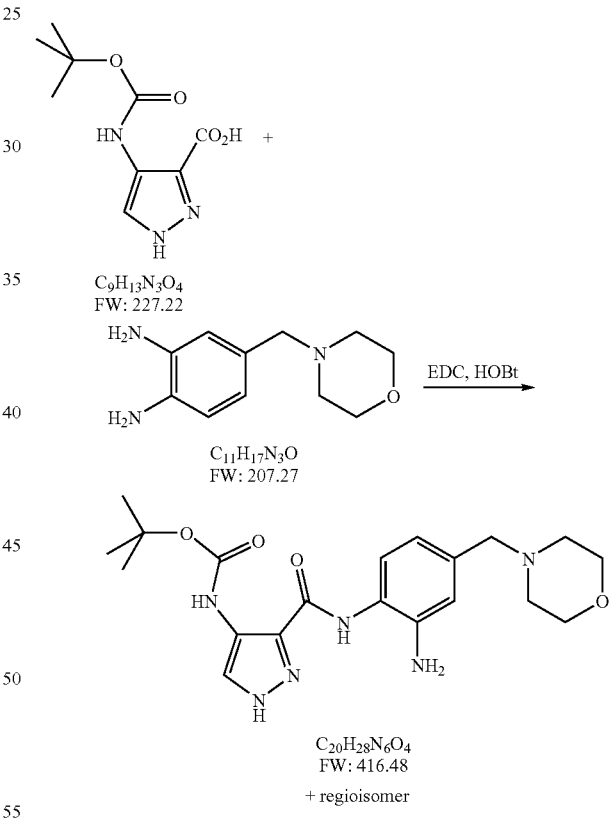

+ regioisomer 4-tert-Butoxycarbonylamino-1H-pyrazole-3-carboxylic acid (0.750 Kg, 3.30 mol, 1.0 wt), 4-morpholin-4-yl-methyl-benzene-1,2-diamine (0.752 Kg, 3.63 mol, 1.0 wt) and N,N'-dimethylformamide (11.25 L, 15.0 vol) were charged under nitrogen to a flange flask equipped with a mechanical stirrer and thermometer. 1-Hydroxybenzotriazole (HOBT, 0.540 Kg, 3.96 mol, 0.72 wt) was added at 15 to 25° C. N-(3-Dimethylaminopropyl)-N'-ethylcarbodiimide (EDC, 0.759 Kg, 3.96 mol, 1.01 wt) was added at 15 to 25° C. and the mixture was stirred at this temperature for 16 to 24 hours. Reaction completion was determined by $^1$H NMR analysis.

The reaction mixture was concentrated under vacuum at 35 to 45° C. The residue was partitioned between ethyl acetate (7.50 L, 10.0 vol) and sat. aq. sodium hydrogen carbonate solution (8.03 L, 10.7 vol) and the layers were separated. The organic phase was washed with brine (3.75 L, 5.0 vol), dried over magnesium sulfate (1.00 Kg, 1.33 wt) and filtered. The filter-cake was washed with ethyl acetate (1.50 L, 2.0 vol). The combined filtrate and wash were concentrated under vacuum at 35 to 45° C. to give [3-(2-amino-4-morpholin-4-ylmethyl-phenylcarbamoyl)-1H-pyrazol-4-yl]-carbamic acid tert-butyl ester (1.217 Kg, 88.6%) as a dark brown solid.

potassium carbonate (1.355 Kg, 9.08 mol, 1.0 wt) was charged portionwise at this temperature. The suspension was stirred until gas evolution ceased and was then filtered. The filter-cake was washed with ethanol (1.35 L, 1.0 vol) and the filtrates retained. The filter-cake was slurried with ethanol (4.00 L, 3.0 vol) at 15 to 25° C. for 20 to 40 minutes and the mixture was filtered. The filter-cake was washed with ethanol (1.35 L, 1.0 vol) and the total combined filtrates were concentrated under vacuum at 35 to 45° C. Ethanol (4.00 L, 3.0 vol) was charged to the residue and removed under vacuum at 35 to 45° C. Tetrahydrofuran (5.90 L, 4.4 vol) was added to the residue and stirred for 10 to 20 minutes at 15 to 25° C. The resulting solution was filtered, the filter-cake was washed with tetrahydrofuran (1.35 L, 1.0 vol) and the combined filtrates were concentrated under vacuum at 35 to 45° C. Tet- Stage 8: Preparation of 3-(5-morpholin-4-ylmethyl-1H-benzoimidazol-2-yl)-1H-pyrazol-4-ylamine

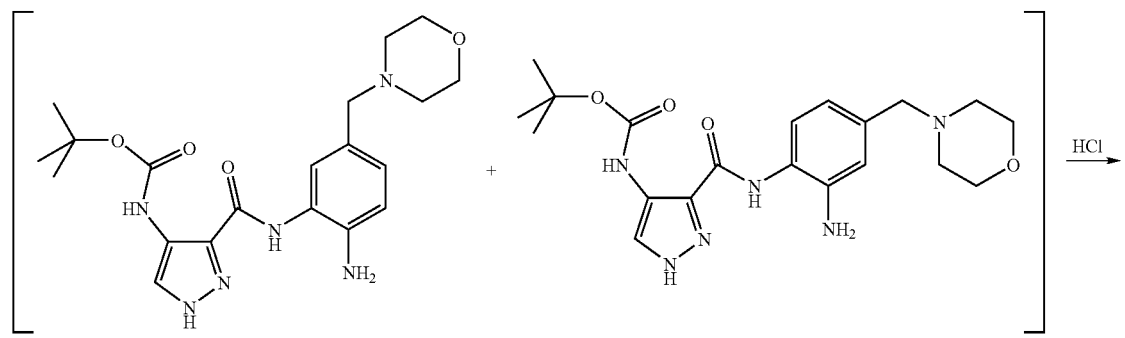

$C_{20}H_{28}N_6O_4$
FW: 416.48
As a mixture of two regioisomers

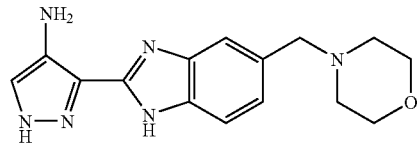

$C_{15}H_{18}N_6O$
FW: 298.35

[3-(2-Amino-4-morpholin-4-ylmethyl-phenylcarbamoyl)-1H-pyrazol-4-yl]-carbamic acid tert-butyl ester (1.350 Kg, 3.24 mol, 1.0 wt) and ethanol (6.75 L, 5.0 vol) were charged to a flange flask equipped with a mechanical stirrer, condenser and thermometer. Conc. aq. hydrochloric acid (1.10 L, 13.2 mol, 0.80 vol) was added at 15 to 30° C. under nitrogen and the contents were then heated to 70 to 80° C. and maintained at this temperature for 16 to 24 hours. A second portion of hydrochloric acid (0.11 L, 1.32 mol, 0.080 vol) was added at 70 to 80° C. and the reaction was heated for a further 4 hours. Reaction completion was determined by HPLC analysis. The reaction mixture was cooled to 10 to 20° C. and rahydrofuran (5.40 L, 4.0 vol) was charged to the concentrate and removed under vacuum at 35 to 45° C. Tetrahydrofuran (5.40 L, 4.0 vol) was charged to the concentrate and removed under vacuum at 35 to 45° C. to give the desired product, 3-(5-morpholin-4-ylmethyl-1H-benzoimidazol-2-yl)-1H-pyrazol-4-ylamine (0.924 Kg, 95.5%, 82.84% by HPLC area) as a purple foam.

Stage 9: Preparation of 7-morpholin-4-ylmethyl-2,4-dihydro-1,2,4,5a,10-pentaaza-cyclopentaralfluoren-5-one

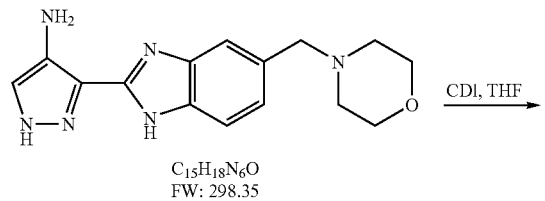

$C_{15}H_{18}N_6O$
FW: 298.35

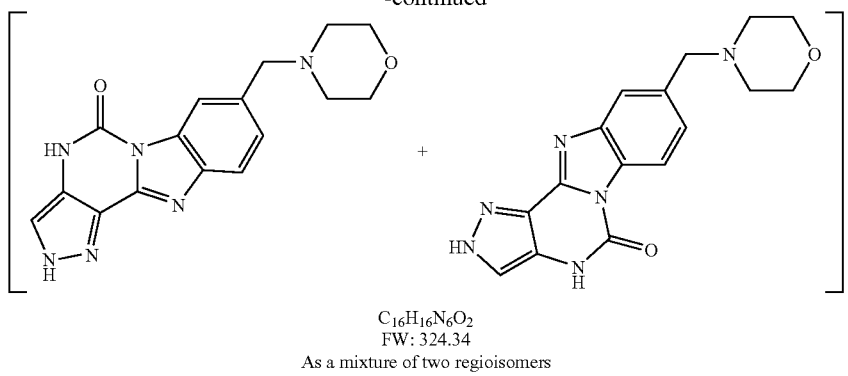

C₁₆H₁₆N₆O₂
FW: 324.34
As a mixture of two regioisomers 3-(5-Morpholin-4-ylmethyl-1H-benzoimidazol-2-yl)-1H-pyrazol-4-ylame (0.993 Kg, 3.33 mol, 1.0 wt) and tetrahydrofuran (14.0 L, 15.0 vol) were charged to a flange flask equipped with a mechanical stirrer, condenser and thermometer. The contents were stirred under nitrogen at 15 to 25° C. and 1,1'-carbonyldiimidazole (0.596 Kg, 3.67 mol, 0.60 wt) was added. The contents were then heated to 60 to 70° C. and stirred at this temperature for 16 to 24 hours. Reaction completion was determined by TLC analysis. The mixture was cooled to 15 to 20° C. and filtered. The filter-cake was washed with tetrahydrofuran (4.00 L, 4.0 vol) and pulled dry for 15 to 30 minutes. The solid was dried under vacuum at 35 to 45° C. to yield 7-morpholin-4-ylmethyl-2,4-dihydro-1,2,4,5a,10-pentaaza-cyclopenta[a]fluoren-5-one (0.810 Kg, 75.0% th, 92.19% by HPLC area) as a purple solid.

7-Morpholin-4-ylmethyl-2,4-dihydro-1,2,4,5a,10-pentaaza-cyclopenta[a]fluoren-5-one (0.797 Kg, 2.46 mol, 1.0 wt) and 1-methyl-2-pyrrolidinone (2.40 L, 3.0 vol) were charged to a flange flask equipped with a mechanical stirrer, condenser and thermometer. Cyclopropylamine (0.279 Kg, 4.88 mol, 0.351 wt) was added at 15 to 30° C. under nitrogen. The contents were heated to 95 to 105° C. and stirred at this temperature for 16 to 24 hours. Reaction completion was determined by ¹H NMR analysis. The reaction mixture was cooled to 10 to 20° C. and ethyl acetate (8.00 L, 10.0 vol) and sat. aq. sodium chloride (2.50 L, 3.0 vol) were charged, the mixture was stirred for 2 to 5 minutes and the layers separated. The organic phase was stirred with sat. aq. sodium chloride (5.00 L, 6.0 vol) for 25 to 35 minutes, the mixture filtered and the filter-cake washed with ethyl acetate (0.40 L, 0.5 vol). The filter-cake was retained and the filtrates were transferred to a separating funnel and the layers separated. The procedure was repeated a further 3 times and the retained solids were combined with the organic phase and the mixture Stage 10: Preparation of 1-cyclopropyl-3-[3-(5-morpholin-4-ylmethyl-1H-benzoimidazol-2-yl)-1H-pyrazol-4-yl]-urea

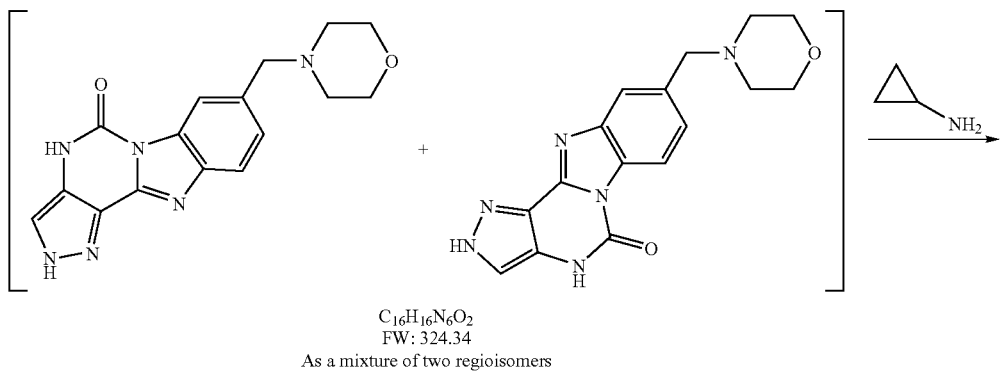

C₁₆H₁₆N₆O₂
FW: 324.34
As a mixture of two regioisomers

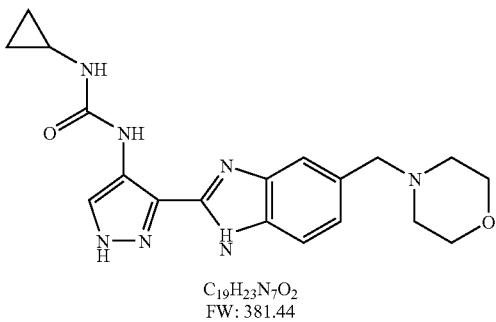

C₁₉H₂₃N₇O₂
FW: 381.44 concentrated to dryness under vacuum at 35 to 45° C. The concentrate was dissolved in propan-2-ol (8.00 L, 10.0 vol) at 45 to 55° C. and activated carbon (0.080 Kg, 0.1 wt) was charged. The mixture was stirred at 45 to 55° C. for 30 to 40 minutes and then hot filtered at 45 to 55° C. The filter-cake was washed with propan-2-ol (0.40 L, 0.5 vol). Activated carbon (0.080 L, 0.1 wt) was charged to the combined filtrates and wash and the mixture stirred at 45 to 55° C. for 30 to 40 minutes. The mixture was hot filtered at 45 to 55° C. and the filter-cake washed with propan-2-ol (0.40 L, 0.5 vol). The filtrates and wash were concentrated under vacuum at 35 to 45° C. Ethyl acetate (8.00, 10.0 vol) and water (2.20 L, 3.0 vol) were charged to the concentrate at 25 to 35° C. and the mixture stirred for 1 to 2 minutes. The layers were separated and the organic phase was concentrated under vacuum at 35 to 45° C. Ethyl acetate (4.00 L, 5.0 vol) was charged to the residue and concentrated under vacuum at 35 to 45° C. Ethyl acetate (4.00 L, 5.0 vol) was charged to the residue and the mixture was stirred for 2 to 20 hours at 15 to 25° C. The mixture was cooled to and aged at 0 to 5° C. for 90 to 120 minutes and then filtered. The filter-cake was washed with ethyl acetate (0.80 L, 1.0 vol) and pulled dry for 15 to 30 minutes. The solid was dried under vacuum at 35 to 45° C. to yield 1-cyclopropyl-3-[3-(5-morpholin-4-ylmethyl-1H-benzoimidazol-2-yl)-1H-pyrazol-4-yl]-urea (0.533 Kg, 56.8%, 93.20% by HPLC area) as a brown solid.

Several batches of Stage 9 product were processed in this way and the details of the quantities of starting material and product for each batch are set out in Table 1A.

TABLE 1A

Yields from urea formation step - Stage 10

| Batch | Input (g) of 7-Morpholin-4-ylmethyl-2,4-dihydro-1,2,4,5a,10-pentaaza-cyclopenta[a]fluoren-5-one | Input (g) of 1-cyclopropyl-3-[3-(5-morpholin-4-ylmethyl-1H-benzoimidazol-2-yl)-1H-pyrazol-4-yl]-urea | Chemical purity by HPLC area |
|---|---|---|---|
| 1 | 680 | 442 | 91.80 |
|   |     | 55.2% th, 64.9% w/w |       |
| 2 | 882 | 487 | 91.21 |
|   |     | 47.0% th, 56.6% w/w |       |
| 3 | 879 | 445 | 91.66 |
|   |     | 43.0% th, 50.6% w/w |       |
| 4 | 797 | 533 | 93.20 |
|   |     | 56.8% th, 66.8% w/w |       |

Stage 11: Preparation of 1-cyclopropyl-3-[3-(5-morpholin-4-ylmethyl-1H-benzoimidazol-2-yl)-1H-pyrazol-4-yl]-urea L-lactic acid salt

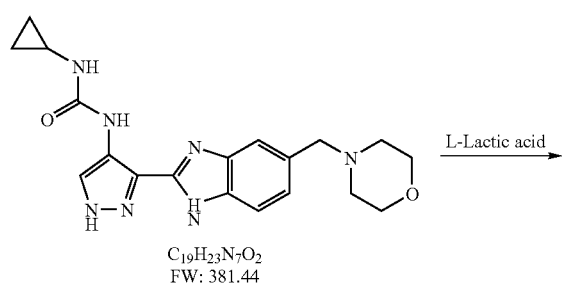

$C_{19}H_{23}N_7O_2$
FW: 381.44

-continued

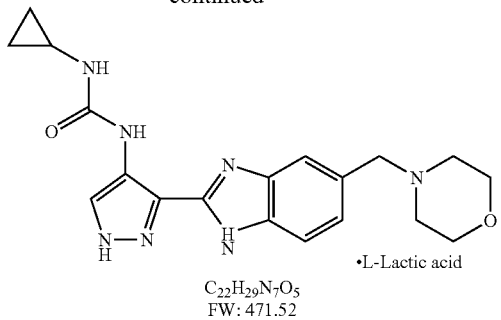

•L-Lactic acid $C_{22}H_{29}N_7O_5$
FW: 471.52

1-Cyclopropyl-3-[3-(5-morpholin-4-ylmethyl-1H-benzoimidazol-2-yl)-1H-pyrazol-4-yl]-urea (1.859 Kg, 4.872 mol, 1.0 wt), propan-2-ol (9.00 L, 5.0 vol) and ethyl acetate (8.00 L, 4.5 vol) were charged to a flange flask equipped with a mechanical stirrer and thermometer. The contents were stirred under nitrogen and L-lactic acid (0.504 Kg, 5.59 mol, 0.269 wt) was added at 15 to 25° C. followed by a line rinse of ethyl acetate (0.90 L, 0.5 vol). The mixture was stirred at 15 to 25° C. for 120 to 140 minutes. The solid was isolated by filtration, the filter-cake washed with ethyl acetate (2×2.00 L, 2×1.0 vol) and pulled dry for 20 to 40 minutes. The filter-cake was dissolved in ethanol (33.00 L, 17.7 vol) at 75 to 85° C., cooled to 65 to 70° C. and the solution clarified through glass microfibre paper. The filtrates were cooled to and aged at 15 to 25° C. for 2 to 3 hours. The crystallised solid was isolated by filtration, the filter-cake washed with ethanol (2×1.00 L, 2×0.5 vol) and pulled dry for at least 30 minutes. The solid was dried under vacuum at 35 to 45° C. to yield 1-cyclopropyl-3-[3-(5-morpholin-4-ylmethyl-1H-benzoimidazol-2-yl)-1H-pyrazol-4-yl]-urea L-lactic acid salt (1.386 Kg, 58.7% th, 99.47% by HPLC area,) as a dark pink uniform solid.

$^1$H NMR data (400 MHz, CD$_3$OD) δ 8.08 (s, 1H, pyrazole-CH), 7.66 (s, 1H, aryl-CH), 7.60 (d, J=8.0 Hz, 1H, aryl-CH), 7.29 (d, J=8.5 Hz, 1H, aryl-CH), 4.15 (q, J=7.0 Hz, 1H, lactate-CH), 3.96 (s, 2H, benzyl-CH$_2$), 3.79-3.77 (m, 4H, morpholino-(CH$_2$)$_2$), 2.82-2.80 (m, 4H, morpholino-(CH$_2$)$_2$), 2.74-2.68 (m, 1H, cyclopropyl-CH), 1.38 (d, J=7.0 Hz, 3H, lactate-CH$_3$), 0.98 (br s, 2H, cyclopropyl-CH$_2$), 0.68 (br s, 2H, cyclopropyl-CH$_2$).

The infra-red spectrum of the lactate salt (KBr disc method) included characteristic peaks at 3229, 2972 and 1660 cm$^{-1}$.

Without wishing to be bound by any theory, it is believed that the infra red peaks can be assigned to structural components of the salt as follow:

| Peak: | Due to: |
|---|---|
| 3229 cm$^{-1}$ | N—H |
| 2972 cm$^{-1}$ | aliphatic C—H |
| 1660 cm$^{-1}$ | urea C=O |

Example 66B

Stage 1: Preparation of 1-cyclopropyl-3-[3-(5-morpholin-4-ylmethyl-1H-benzoimidazol-2-yl)-1H-pyrazol-4-yl]-urea

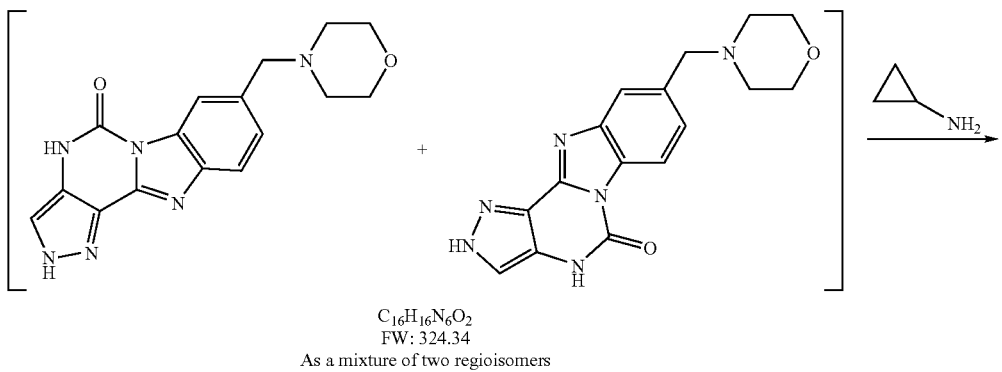

7-Morpholin-4-ylmethyl-2,4-dihydro-1,2,4,5a,10-pentaaza-cyclopenta[a]fluoren-5-one (1.0 wt, prepared as outlined above in Example 66A) and a solvent such as n-butanol, butyronitrile, glycol or toluene (3.0 vol) can be charged to a flange flask equipped with a mechanical stirrer, condenser and thermometer. Cyclopropylamine (0.351 wt) can be added at temperature such as 15 to 30° C. under an inert atmosphere e.g. nitrogen. The contents can be heated to 40 to 105° C., in particular 40-80° C. and stirred at this temperature for 16 to 24 hours. Reaction completion can be determined by ¹H NMR analysis. The reaction mixture can then be cooled to 10 to 20° C. The product can then be isolated by organic-aqueous extraction method as outlined above in Example 66A, or an alternative method of isolation may be employed such as the addition of an anti-solvent, for example n-heptanes, to the reaction mixture. This could allow the reaction product to precipitate with subsequent isolation by filtration. The solid can then be dried under vacuum at 35 to 45° C. to yield 1-cyclopropyl-3-[3-(5-morpholin-4-ylmethyl-1H-benzoimidazol-2-yl)-1H-pyrazol-4-yl]-urea. At this stage the solid can be purified by recrystallisation from an appropriate solvent, preferably a Class 2 or 3 solvent[1]. In addition, alternative methods of purification aside from recrystallisation may be employed for purification of the product such as flash column chromatography or filtration through a plug of silica gel or reverse-phase silica gel.

[1] Class 3 and Class 2 solvents are as outlined Q3C—Tables and List in Guidance for Industry Q3C Impurities: Residual Solvents (November 2003, CDER, CBER, FDA, ICH) and as further outlined in Impurities: Guideline for Residual Solvents (1997, ICH).

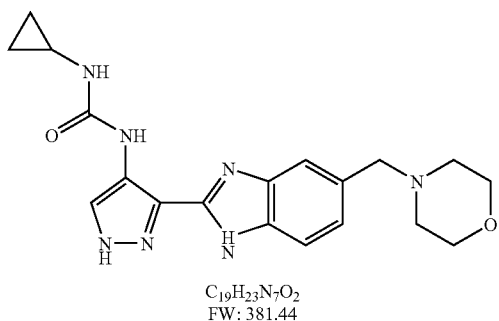

Stage 2: Preparation of 1-cyclopropyl-3-[3-(5-morpholin-4-ylmethyl-1H-benzoimidazol-2-yl)-1H-pyrazol-4-yl]-urea L-lactic acid salt

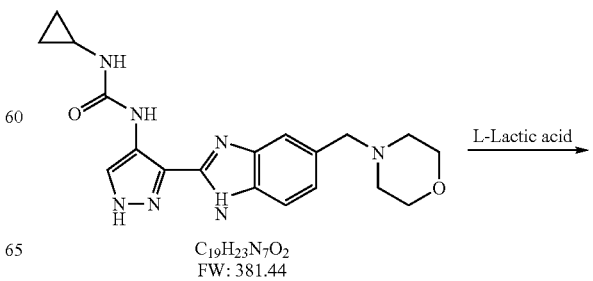

-continued

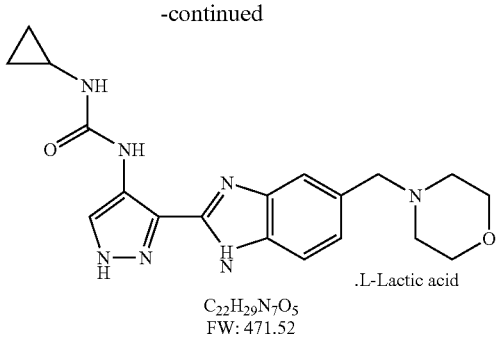

C<sub>22</sub>H<sub>29</sub>N<sub>7</sub>O<sub>5</sub>
FW: 471.52

1-Cyclopropyl-3-[3-(5-morpholin-4-ylmethyl-1H-benzoimidazol-2-yl)-1H-pyrazol-4-yl]-urea (1.0 wt), in a Class 2 or Class 3 solvent, in particular a Class 3 solvent such as aqueous ethanol (5.0-10.0 vol), can be charged to a flange flask equipped with a mechanical stirrer and thermometer. The contents are stirred under an inert atmosphere e.g. nitrogen and L-lactic acid (0.269 wt) can be added at 15 to 25° C. followed by a line rinse of the appropriate solvent such as aqueous ethanol (0.5 vol). The mixture can be stirred at 15 to 25° C. for 120 to 140 minutes. The solid may be isolated by filtration or by use of addition of anti-solvent such as n-butanol to bring the salt out of solution and then isolated by filtration. The filter-cake can be washed with the appropriate solvent (2×1.0 vol) and pulled dry for 20 to 40 minutes. The filter-cake can then be dissolved in a Class 2 or Class 3 solvent, or mixture thereof, in particular a Class 3 solvent (~3-60 vol) at 40 to 150° C., cooled to 40 to 70° C. and the solution clarified through glass microfibre paper. The filtrates can be cooled to and aged at 15 to 25° C. for 2 to 3 hours. The crystallised solid can be isolated by filtration, the filter-cake washed with the appropriate solvent (2×0.5-2 vol) and pulled dry for at least 30 minutes. The solid can then be dried under vacuum at 35 to 45° C. to yield 1-cyclopropyl-3-[3-(5-morpholin-4-ylmethyl-1H-benzoimidazol-2-yl)-1H-pyrazol-4-yl]-urea L-lactic acid salt. In addition, alternative methods of purification aside from recrystallisation may be employed for purification of the product such as flash column chromatography or filtration through a plug of silica gel or reverse-phase silica gel.

Example 66C

Further to the above examples, the preparation of 1-cyclopropyl-3-[3-(5-morpholin-4-ylmethyl-1H-benzoimidazol-2-yl)-1H-pyrazol-4-yl]-urea L-lactic acid salt can be completed using the revised procedures outlined below.

Stage 1: Preparation of 1-cyclopropyl-3-[3-(5-morpholin-4-ylmethyl-1H-benzoimidazol-2-yl)-1H-pyrazol-4-yl]-urea

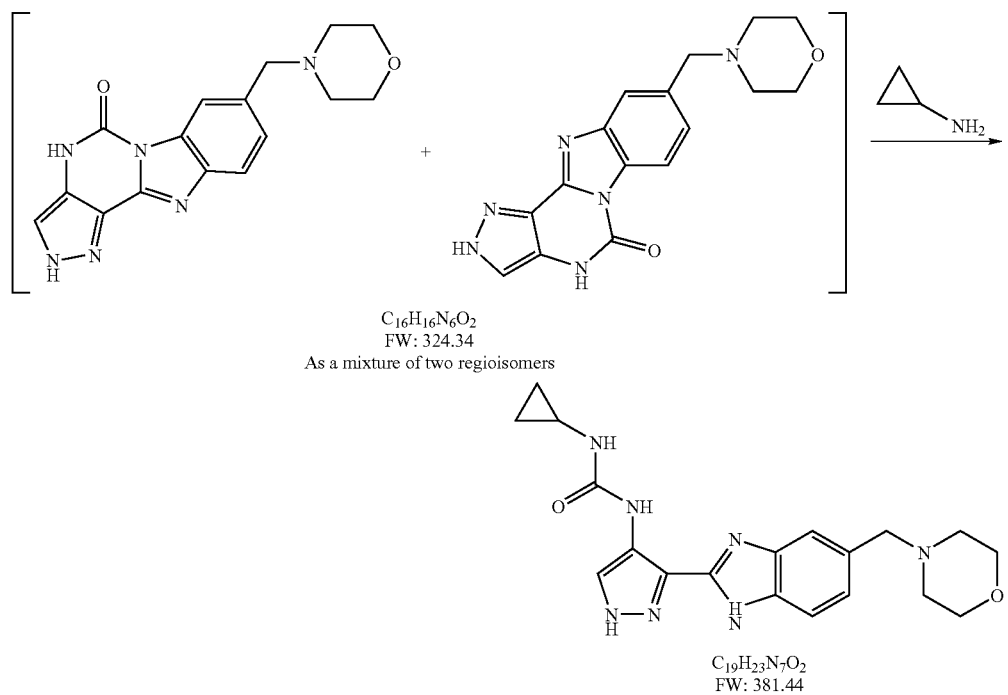

7-Morpholin-4-ylmethyl-2,4-dihydro-1,2,4,5a,10-pentaaza-cyclopenta[a]fluoren-5-one (1.0 wt, prepared as outlined above in Example 66A) and 1-methyl-2-pyrrolidinone (3.0 vol) are charged to a suitably sized flange flask equipped with a mechanical stirrer, condenser and thermometer. Cyclopropylamine (0.351 wt) is added at 15 to 30° C. under nitrogen. The contents are then heated to 95 to 105° C. and stirred at this temperature until the reaction is judged complete by $^1$H NMR analysis. Once complete, the reaction mixture is cooled to 16 to 25° C. and added slowly (approximately 2 to 3 hours) to stirred ca. 13% w/w sodium chloride solution (11.5 vol) whilst maintaining the mixture at 16 to 25° C. A precipitate is formed. The transfer of the reaction mixture is completed with a 1-methyl-2-pyrrolidinone (0.5 vol) rinse at 16 to 25° C. The precipitated solid is collected by filtration, washed with water (0.5 vol) and pulled dry on the filter until deemed suitable for handling. The solid is suspended in ethyl acetate (5.0 vol) and water (6.0 vol) and stirred at 16 to 25° C. for 60 to 70 minutes. The solid is collected by filtration, sequentially washed with ethyl acetate (1.0 vol) and mixed heptanes (2×2.0 vol) and dried on the filter until deemed suitable for handling. The solid is suspended in ethyl acetate (4.0 vol) and stirred at 15 to 25° C. for at least 60 minutes. The solid is collected by filtration, washed with ethyl acetate (1.0 vol) and pulled dry on the filter to yield crude 1-cyclopropyl-3-[3-(5-morpholin-4-ylmethyl-1H-benzoimidazol-2-yl)-1H-pyrazol-4-yl]-urea (60 to 80% w/w) as a dark brown/red solid.

Crude 1-cyclopropyl-3-[3-(5-morpholin-4-ylmethyl-1H-benzoimidazol-2-yl)-1H-pyrazol-4-yl]-urea (1.0 wt) is dissolved in propan-2-ol (15 vol) at 45 to 55° C. and activated carbon (DARCO KB) (0.2 wt) is charged. The mixture is stirred at 45 to 55° C. for 60 to 70 minutes and then hot filtered at 45 to 55° C. The filter-cake is washed with propan-2-ol (2.5 vol). Activated carbon (DARCO KB) (0.2 wt) is charged to the combined filtrate and wash and the mixture stirred at 45 to 55° C. for 60 to 70 minutes. The mixture is hot filtered at 45 to 55° C. and the filter-cake is washed with propan-2-ol (2.5 vol). The combined filtrate and wash are concentrated under vacuum at 35 to 45° C. to yield the desired product, 1-cyclopropyl-3-[3-(5-morpholin-4-ylmethyl-1H-benzoimidazol-2-yl)-1H-pyrazol-4-yl]-urea, as a brown foam in 65 to 100% w/w yield.

Stage 2: Preparation of 1-cyclopropyl-3-[3-(5-morpholin-4-ylmethyl-1H-benzoimidazol-2-yl)-1H-pyrazol-4-yl]-urea L-lactic acid salt Using material generated from the alternative procedure in Example 66C Stage 1 (above), the salt formation procedure can be performed as in Example 66A Stage 11 (above), to give 1-cyclopropyl-3-[3-(5-morpholin-4-ylmethyl-1H-benzoimidazol-2-yl)-1H-pyrazol-4-yl]-urea L-lactic acid salt as an off-white solid.

Example 67

Synthesis of Crystalline Free Base and Crystalline Salt Forms of 1-Cyclopropyl-3-[3-(5-Morpholin-4-ylmethyl-1H-Benzoimidazol-2-yl)-1H-Pyrazol-4-yl]-Urea A. Preparation of 1-Cyclopropyl-3-[3-(5-Morpholin-4-ylmethyl-1H-Benzoimidazol-2-yl)-1H-Pyrazol-4-yl]-Urea free base A sample of crude 1-cyclopropyl-3-[3-(5-morpholin-4-ylmethyl-1H-benzoimidazol-2-yl)-1H-pyrazol-4-yl]-urea free base was prepared as outlined in Example 60 and initially purified by column chromatography on silica gel, eluting with EtOAc-MeOH (98:2-80:20). A sample of the free base obtained was then recrystallised from hot methanol to give crystalline material of 1-cyclopropyl-3-[3-(5-morpholin-4-ylmethyl-1H-benzoimidazol-2-yl)-1H-pyrazol-4-yl]-urea free base.

B. Preparation of 1-Cyclopropyl-3-[3-(5-Morpholin-4-ylmethyl-1H-Benzoimidazol-2-yl)-1H-Pyrazol-4-yl]-Urea free base dihydrate A sample of crude 1-cyclopropyl-3-[3-(5-morpholin-4-ylmethyl-1H-benzoimidazol-2-yl)-1H-pyrazol-4-yl]-urea free base was dissolved in THF and then concentrated in vacuo to a minimum volume (~4 volumes). To the solution was added water dropwise (2-4 volumes) until the solution became turbid. A small amount of THF was added to re-establish solution clarity and the mixture left to stand overnight to give a crystalline material which was air-dried to give 1-cyclopropyl-3-[3-(5-morpholin-4-ylethyl-1H-benzoimidazol-2-yl)-1H-pyrazol-4-yl]-urea free base dihydrate.

C. Preparation of 1-Cyclopropyl-3-[3-(5-Morpholin-4-ylmethyl-1H-Benzoimidazol-2-yl)-1H-Pyrazol-4-yl]-Urea hydrochloride salt A sample of crude 1-cyclopropyl-3-[3-(5-morpholin-4-ylmethyl-1H-benzoimidazol-2-yl)-1H-pyrazol-4-yl]-urea free base was dissolved in the minimum amount of MeOH and then diluted with EtOAc. To the solution at 0° C. was slowly added 1.1 equivalents of HCl (4M solution in dioxane). Following addition, solid precipitated from solution which was collected by filtration. To the solid was added MeOH and the mixture reduced in vacuo. To remove traces of residual MeOH the residue was evaporated from water and then dried at 60° C./0.1 mbar to give the hydrochloride salt.

D. Preparation of 1-Cyclopropyl-3-[3-(5-Morpholin-4-ylmethyl-1H-Benzoimidazol-2-yl)-1H-Pyrazol-4-yl]-Urea ethanesulfonate salt To a solution of 1-cyclopropyl-3-[3-(5-morpholin-4-ylmethyl-1H-benzoimidazol-2-yl)-1H-pyrazol-4-yl]-urea free base in MeOH-EtOAc was added 1 equivalent of ethanesulfonic acid. The mixture was stirred at ambient temperature and then reduced in vacuo. The residue was taken up in MeOH and to the solution was added Et$_2$O. Mixture left to stand for 72 h and the solid formed collected by filtration and dried to give 1-cyclopropyl-3-[3-(5-morpholin-4-ylmethyl-1H-benzoimidazol-2-yl)-1H-pyrazol-4-yl]-urea ethanesulfonate salt.

E. Preparation of 1-Cyclopropyl-3-[3-(5-Morpholin-4-ylmethyl-1H-Benzoimidazol-2-yl)-1H-Pyrazol-4-yl]-Urea methanesulfonate salt To a solution of 1-cyclopropyl-3-[3-(5-morpholin-4-ylmethyl-1H-benzoimidazol-2-yl)-1H-pyrazol-4-yl]-urea free base (394 mg) in MeOH-EtOAc was added 1 equivalent of methanesulfonic acid (67 µl). A solid was formed which was collected by filtration, washing with EtOAc. The solid was dissolved in the minimum amount of hot MeOH, allowed to cool and then triturated with Et$_2$O. The solid was left to stand for 72 h and then collected by filtration, washing with MeOH, to give 1-cyclopropyl-3-[3-(5-morpholin-4-ylmethyl-1H-benzoimidazol-2-yl)-1H-pyrazol-4-yl]-urea methanesulfonate salt.

Example 68

Characterisation of 1-Cyclopropyl-3-[3-(5-Morpholin-4-ylmethyl-1H-Benzoimidazol-2-yl)-1H-Pyrazol-4-yl]-Urea Free Base and Salts Various forms of 1-cyclopropyl-3-[3-(5-morpholin-4-ylmethyl-1H-benzoimidazol-2-yl)-1H-pyrazol-4-yl]-urea were characterised. The forms selected for characterisation were identified from studies which primarily investigated extent of polymorphism and salt stability. The salts selected for further characterisation were the L-lactate salt, free base dihydrate, esylate salt, free base and hydrochloride salt.

A1. Differential Scanning Calorimetry (DSC):

Thermograms were collected on a TA instrument Q1000 equipped with a 50 position auto-sampler. The energy and temperature calibration standard was indium. Samples were heated at a rate of 10° C./minute from 10 to 250° C. A nitrogen purge of 30 ml/min was maintained over the sample. Between 2 and 10 mg of sample was used (unless otherwise stated) and all samples were enclosed in an aluminium pan with a pinhole in the lid.

| Identity | Melting Point (° C.) |
|---|---|
| L-lactate salt (prepared as described in Example 66A) | Onset at 190° C. Minimum at 194.6° C. |
| Free base dihydrate | Desolvates (peaking at 110° C.) |
| Esylate salt | None seen (up to 350° C.) |
| Free base | 193° C. |
| Hydrochloride salt | 190° C. |

A2. Further Differential Scanning Calorimetry (DSC):

Thermograms were collected on a Mettler Toledo 821e Differential Scanning Calorimeter. Samples were heated at a rate of 10° C./minute from 40° C. to 300° C. A nitrogen purge of 80 ml/min was maintained over the sample. Approximately 5-10 mg of sample was used and all samples were enclosed in a suitable high pressure pan (e.g. small aluminum, medium pressure aluminum or high pressure gold plated pan).

| Identity | Melting Point (° C.) |
|---|---|
| L-lactate salt (as prepared as described in Example 66A) | Minimum at 195.7° C. |
| L-lactate salt (as prepared from Example 66A) | Minimum at 196.3° C. |

B. Thermogravimetric Analysis (TGA):

Thermograms were collected on a TA Instruments Q500. Samples were heated at a rate of 10° C./minute. A nitrogen purge of 100 ml/minute was maintained over the sample. Typically 5-20 mg of sample was loaded into a tared, open aluminium pan.

| Identity | Observation |
|---|---|
| L-lactate salt | Loss of 1.7% unbound solvent, melt with degradation at 190° C. |
| Free base dihydrate | Weight loss (prior to degradation) of 4.1% w/w (corresponds to 1 equivalent of water) |
| Esylate salt | Loss of 4% unbound solvent, no other clearly identifiable features. |
| Free base | Loss of 1.7% unbound solvent, melt with degradation at 193° C. |
| Hydrochloride salt | Loss of 5.4% unbound solvent, melt with degradation at 190° C. |

C. Polarised light microscopy

Samples were studied on a Leica LM/DM microscope with a digital camera for image capture. A small amount of sample was mounted in immersion oil on a glass slide and covered with a glass cover slip. The individual particles were separated as well as possible and viewed with 50-500× magnification and partially crossed polars, coupled to a λ wave-plate.

| Identity | Observation |
|---|---|
| L-lactate salt | Irregular crystalline particles |
| Free base dihydrate | Irregular crystalline particles |
| Esylate salt | Irregular crystalline particles |
| Free base | Acicular crystalline particles |
| Hydrochloride salt | Irregular crystalline particles |

D. XRPD (X-Ray Powder Diffraction)

D5000

An XRPD study was carried out on a Siemens D5000 diffractometer using CuKα radiation (40 kV, 40 mA), θ-θ goniometer, automatic divergence and receiving slits, a graphite secondary monochromator and a scintillation counter. The data were collected over an angular range of 2° to 30° 2θ in continuous scan mode using a step size of either 0.02° 2θ or 0.005° 2θ and a step time of 1 second.

Samples, run under ambient conditions, were prepared as flat plate specimens using powder as received without grinding. Approximately 25-50 mg of the sample was gently packed into 12 mm diameter, 0.5 mm deep cavity cut into a polished, zero-background (510) silicon wafer (The Gem Dugout, 1652 Princeton Drive, Pennsylvania State College, Pa. 16803, USA). All XRPD analyses were performed using the Diffrac Plus XRD Commander software v2.3.1.

Bruker AXS C2 GADDS Diffractometer (Used for Samples Recovered from GVS)

X-ray powder diffraction patterns for the samples were acquired on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm.

Beam divergence, i.e. the effective size of the X-ray beam on the sample, was approximately 4 mm. A θ-θ continuous scan mode was employed with a sample to detector distance of 20 cm which gives an effective 2θ range of 3.2-29.8°. A typical exposure time of a sample would be 120 s.

Samples were prepared as flat plate specimens using powder as received without grinding. Approximately 1-2 mg of the sample was lightly pressed on a glass slide to obtain a flat surface.

The XRPD trace was recorded for the L-lactate salt and the free base. The traces show good signal to noise ratio, and indicate crystalline material.

E. Gravimetric Vapour Sorption (GVS):

All samples were run on a Hiden IGASorp moisture sorption analyser running CFRSorp software. The sample size was ca. 10-25 mg. A moisture adsorption/desorption isotherm was performed as outlined below. The sample was loaded and unloaded at room humidity and temperature (ca. 40% RH, 25° C.) and analysed afterwards by XRPD (using a Bruker AXS C2 GADDS system).

The standard isotherm run was a single cycle starting at 40% RH.

The humidity was stepped as follows:
40, 50, 60, 70, 80, 90
85, 75, 65, 55, 45, 35, 25, 15, 5, 0
10, 20, 30, 40

(i) L-Lactate Salt

The GVS isotherm for the L-lactate salt indicates that the sample does not display hygroscopic behaviour and does not form a hydrate. The XRPD trace for the sample following the GVS experiment is concordant with that of the input material, indicating that no phase change occurred during the experiment.

(ii) Free Base

During the experiment the sample weight differs by approximately 9% between 0% R.H and 95% R.H. This indicates that the sample is hygroscopic in nature.

Example 69

Determination of the crystal structure of 1-Cyclopropyl-3-[3-(5-Morpholin-4-ylmethyl-1H-Benzoimidazol-2-yl)-1H-Pyrazol-4-yl]-Urea dihydrate free base by X-ray diffraction The crystal used for the diffraction experiment was colourless and of irregular shape with dimensions 0.2×0.2×0.2 mm$^3$. It was obtained by precipitation of water solution of esylate salt with THF in a liquid-liquid diffusion experiment. The equivalence of such sample and the same crystal form prepared from free base (using water as anti-solvent with a range of solvents such as alcohols e.g. ethanol, ketones such as methyl ethyl ketone and ethers such as THF and dioxane) was established by comparison of X-ray powder diffraction pattern of both samples. Crystallographic data were collected at 101(2) K using CuKα radiation (λ=1.5418 Å) from a Rigaku rotating anode RU3HR, Osmic blue confocal optics, AFC9 ¼ χ goniometer and a Rigaku Jupiter CCD detector. Images were collected in four ω scans, one at 2θ=30° and three scans at 2θ=90° with a detector to crystal distance of 67 mm. Data collection was controlled by CrystalClear software and images were processed and scaled by Dtrek. Although absorption coefficient was moderate (μ32 0.82 mm$^{-1}$) data were corrected using 4$^{th}$ order Fourier absorption correction to compensate for glue and crystal holder (micromount) absorption. It was found that the crystals belong to a monclinic space group P2$_1$/n (# 14) with crystal lattice parameters a=7.66 (10), b=15.18 (10), c=17.71 (10) Å, β=98.53 (2)°, α=γ=90°. The numbers in brackets represents the deviation (s.u., standard uncertainty).

The crystal structure was solved using direct methods implemented in SHELXS-97. Intensity data for a total of 2822 unique reflections in a resolution range from 11.5-0.89 Å (3.85<θ<60.01) were used in the refinement of 274 crystallographic parameters by SHELXL-97. Final statistical parameters were: wR2=0.2416 (all data), R$_F$=0.0866 (data with I>2σ(I)) and goodness of fit S=1.145.

One molecule of free base and two water molecules were found in the asymmetric unit. The elemental composition of the asymmetric unit was C$_{19}$H$_{26}$N$_7$O$_4$ and the calculated density of the crystals is 1.36 Mg/m$^3$. Hydrogen atoms were generated on geometrical grounds while the location of heteroatom bound hydrogen atoms was confirmed by inspection of Fo-Fc difference maps. The positional and thermal parameters of hydrogen atoms were constricted to ride on corresponding non-hydrogen atoms. The thermal motion of non-hydrogen atoms was modelled by anisotropic thermal factors (see FIG. 1).

The crystal structure contains one intramolecular (N22-H . . . N14 2.898 Å) and seven intermolecular hydrogen bonds (see FIG. 2). 1-Cyclopropyl-3-[3-(5-morpholin-4-ylmethyl-1H-benzoimidazol-2-yl)-1H-pyrazol-4-yl]-urea molecules are linked together into chains along crystallographic b axis by two H-bonds: N7-H . . . O24 2.761 Å and N25-H . . . N2 3.310 Å. Benzimidazole moieties from two chains stack together at distance of 3.5-3.6 Å. The network of 1-cyclopropyl-3-[3-(5-morpholin-4-ylmethyl-1H-benzoimidazol-2-yl)-1H-pyrazol-4-yl]-urea molecules form pockets occupied by four water molecules, two and two being related by the centre of symmetry. Three H-bonds link 1-cyclopropyl-3-[3-(5-morpholin-4-ylmethyl-1H-benzoimidazol-2-yl)-1H-pyrazol-4-yl]-urea molecules with water molecules, one to 1$^{st}$ water molecule (O1W1-H . . . N16 2.845 Å) and remaining two to 2$^{nd}$ water molecule (N1-H . . . O1W2 2.875 Å and O1W2-H . . . O19 2.746 Å). Water molecules are involved in mutual interaction through another two H-bonds: O1W1-H . . . O1W2 2.884 Å and O1W2-H . . . O1W1 2.771 Å.

Figure 2:
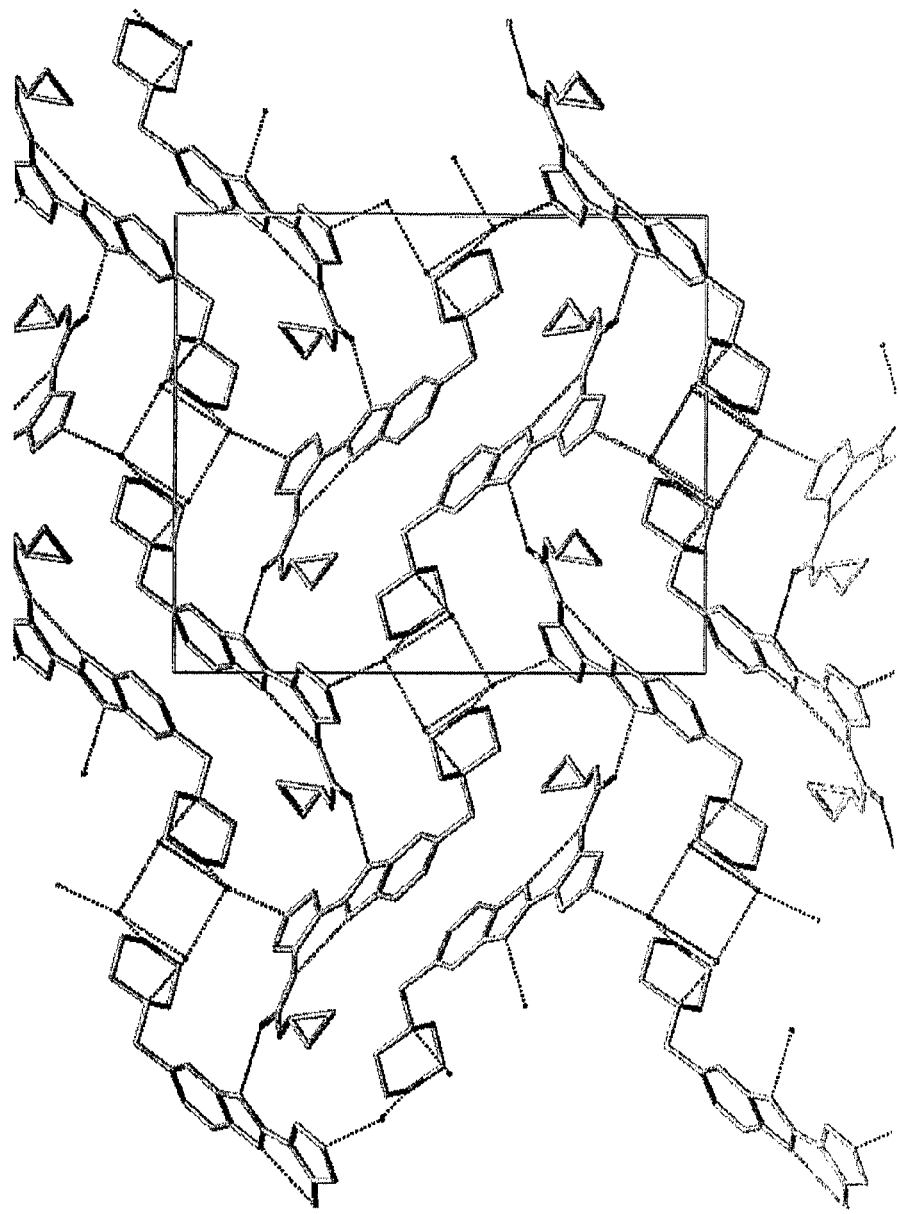
FIG. 2 shows a packing diagram of the free base dihydrate of 1-cyclopropyl-3-[3-(5-morpholin-4-ylmethyl-1H-benzoimidazol-2-yl)-1H-pyrazol-4-yl]-urea as described in Example 69 below.

A thermal ellipsoid representation of the structure generated by the X-ray diffraction study is provided in FIG. 1 and packing diagram is in FIG. 2.

The coordinates for the atoms making up the structure of the 1-cyclopropyl-3-[3-(5-morpholin-4-ylmethyl-1H-benzoimidazol-2-yl)-1H-pyrazol-4-yl]-urea free base dihydrate are as set out in Table 2. The numbers in brackets represents the deviation (s.u., standard uncertainty).

TABLE 2

| | |
|---|---|
| _cell_length_a | 7.662(10) |
| _cell_length_b | 15.184(10) |
| _cell_length_c | 17.711(10) |
| _cell_angle_alpha | 90.00 |
| _cell_angle_beta | 98.53(2) |
| _cell_angle_gamma | 90.00 |
| _cell_measurement_temperature | 101(2) | loop_
  _atom_site_label
  _atom_site_type_symbol
  _atom_site_fract_x
  _atom_site_fract_y
  _atom_site_fract_z
  _atom_site_U_iso_or_equiv
  _atom_site_adp_type
  _atom_site_occupancy
  _atom_site_symmetry_multiplicity
  _atom_site_calc_flag
N1 N 0.4468(4) 0.0332(2) 0.71441(19) 0.0274(9) Uani 1 1 d
H1 H 0.5453 0.0189 0.6973 0.033 Uiso 1 1 calc
N2 N 0.3749(4) −0.01642(19) 0.76559(19) 0.0253(8) Uani 1 1 d
C3 C 0.2277(5) 0.0286(2) 0.7751(2) 0.0237(9) Uani 1 1 d
C4 C 0.2074(6) 0.1060(2) 0.7308(2) 0.0246(9) Uani 1 1 d
C5 C 0.3539(5) 0.1058(3) 0.6923(2) 0.0254(10) Uani 1 1 d
H5 H 0.3822 0.1490 0.6572 0.030 Uiso 1 1 calc
C6 C 0.1101(5) −0.0035(2) 0.8265(2) 0.0213(9) Uani 1 1 d
N7 N 0.1457(5) −0.0752(2) 0.87205(19) 0.0268(9) Uani 1 1 d
H7 H 0.2403 −0.1087 0.8758 0.032 Uiso 1 1 calc
C8 C 0.0015(6) −0.0852(2) 0.9119(2) 0.0251(10) Uani 1 1 d
C9 C −0.0262(6) −0.1443(2) 0.9695(2) 0.0266(10) Uani 1 1 d
H9 H 0.0553 −0.1898 0.9865 0.032 Uiso 1 1 calc
C10 C −0.1833(5) −0.1319(2) 1.0008(2) 0.0258(10) Uani 1 1 d
C11 C −0.3006(6) −0.0649(3) 0.9758(2) 0.0295(10) Uani 1 1 d
H11 H −0.4052 −0.0590 0.9982 0.035 Uiso 1 1 calc
C12 C −0.2704(6) −0.0064(3) 0.9194(2) 0.0321(11) Uani 1 1 d
H12 H −0.3527 0.0387 0.9023 0.039 Uiso 1 1 calc
C13 C −0.1115(6) −0.0163(2) 0.8878(2) 0.0261(10) Uani 1 1 d
N14 N −0.0434(4) 0.03474(19) 0.83324(19) 0.0254(8) Uani 1 1 d
C15 C −0.2143(5) −0.1900(2) 1.0676(2) 0.0263(10) Uani 1 1 d
H15A H −0.1009 −0.1979 1.1018 0.032 Uiso 1 1 calc
H15B H −0.2963 −0.1593 1.0970 0.032 Uiso 1 1 calc
N16 N −0.2871(5) −0.2772(2) 1.04532(18) 0.0268(8) Uani 1 1 d
C17 C −0.4708(6) −0.2702(3) 1.0075(2) 0.0303(10) Uani 1 1 d
H17A H −0.4749 −0.2350 0.9602 0.036 Uiso 1 1 calc
H17B H −0.5421 −0.2395 1.0416 0.036 Uiso 1 1 calc
C18 C −0.5484(6) −0.3603(3) 0.9879(2) 0.0344(11) Uani 1 1 d
H18A H −0.6723 −0.3540 0.9631 0.041 Uiso 1 1 calc
H18B H −0.4814 −0.3896 0.9513 0.041 Uiso 1 1 calc
O19 O −0.5428(4) −0.41359(18) 1.05435(16) 0.0343(8) Uani 1 1 d
C20 C −0.3636(6) −0.4216(3) 1.0925(3) 0.0344(11) Uani 1 1 d
H20A H −0.2914 −0.4518 1.0584 0.041 Uiso 1 1 calc
H20B H −0.3617 −0.4580 1.1390 0.041 Uiso 1 1 calc
C21 C −0.2855(6) −0.3338(3) 1.1140(2) 0.0287(10) Uani 1 1 d
H21A H −0.3537 −0.3048 1.1503 0.034 Uiso 1 1 calc
H21B H −0.1626 −0.3413 1.1397 0.034 Uiso 1 1 calc
N22 N 0.0659(4) 0.16310(19) 0.72860(18) 0.0242(8) Uani 1 1 d
H22 H −0.0267 0.1453 0.7484 0.029 Uiso 1 1 calc
C23 C 0.0617(5) 0.2451(2) 0.6976(2) 0.0247(9) Uani 1 1 d
O24 O 0.1870(4) 0.27405(17) 0.66702(16) 0.0304(8) Uani 1 1 d
N25 N −0.0851(4) 0.2937(2) 0.70242(19) 0.0270(8) Uani 1 1 d

TABLE 2-continued

H25 H −0.0807 0.3509 0.6948 0.032 Uiso 1 1 calc
C26 C −0.2479(6) 0.2563(3) 0.7194(3) 0.0320(11) Uani 1 1 d
H26 H −0.3061 0.2121 0.6820 0.038 Uiso 1 1 calc
C27 C −0.3687(6) 0.3144(3) 0.7561(2) 0.0346(11) Uani 1 1 d
H27A H −0.4974 0.3069 0.7404 0.041 Uiso 1 1 calc
H27B H −0.3304 0.3757 0.7681 0.041 Uiso 1 1 calc
C28 C −0.2705(6) 0.2417(3) 0.8022(3) 0.0370(11) Uani 1 1 d
H28A H −0.3387 0.1896 0.8144 0.044 Uiso 1 1 calc
H28B H −0.1716 0.2585 0.8421 0.044 Uiso 1 1 calc
O1W1 O −0.0371(4) −0.37444(18) 0.97522(18) 0.0392(8) Uani 1 1 d
H1W1 H 0.0243 −0.4072 1.0168 0.047 Uiso 1 1 d
H2W1 H −0.1218 −0.3425 0.9983 0.047 Uiso 1 1 d
O1W2 O 0.1516(4) −0.4721(2) 1.1013(2) 0.0421(9) Uani 1 1 d
H1W2 H 0.113(7) −0.509(4) 1.067(3) 0.051 Uiso 1 1 d
H2W2 H 0.2534 −0.4527 1.0856 0.051 Uiso 1 1 d

Example 70

Determination of the XRPD pattern of 1-cyclopropyl-3-[3-(5-morpholin-4-ylmethyl-1H-benzoimidazol-2-yl)-1H-pyrazol-4-yl]-urea free base Samples for X-ray powder diffraction (XRPD) data collection were gently ground by marble mortar and loaded into a crystallographic capillary (from Hampton Research, Quartz or Glass Type 10, 0.4 or 0.7 mm diameter). Diffraction patterns were collected at room temperature using CuKα radiation (k=1.5418 Å) from a Rigaku rotating anode RU3HR, Osmic blue confocal optics, ¼ χ goniometer and a Rigaku HTC image plate detector. 2D Images were collected while spinning ϕ axis with a detector to crystal distance of 250 mm. Data collection was controlled by CrystalClear software and 2D images were converted to 1D plot (2θ vs. Intensity) by Datasqueeze (intensity averaged over the azimuthal angle 0<χ<360° for 2θ range 3-30° in 0.01° or 0.02° steps). In house program AstexXRPD was used for manipulation and visualisation of 1D XRPD patterns.

The XRPD pattern and relative intensity of peaks do not change between different crystallisation batches which is consistent with the presence of only one crystal form.

Figure 3:
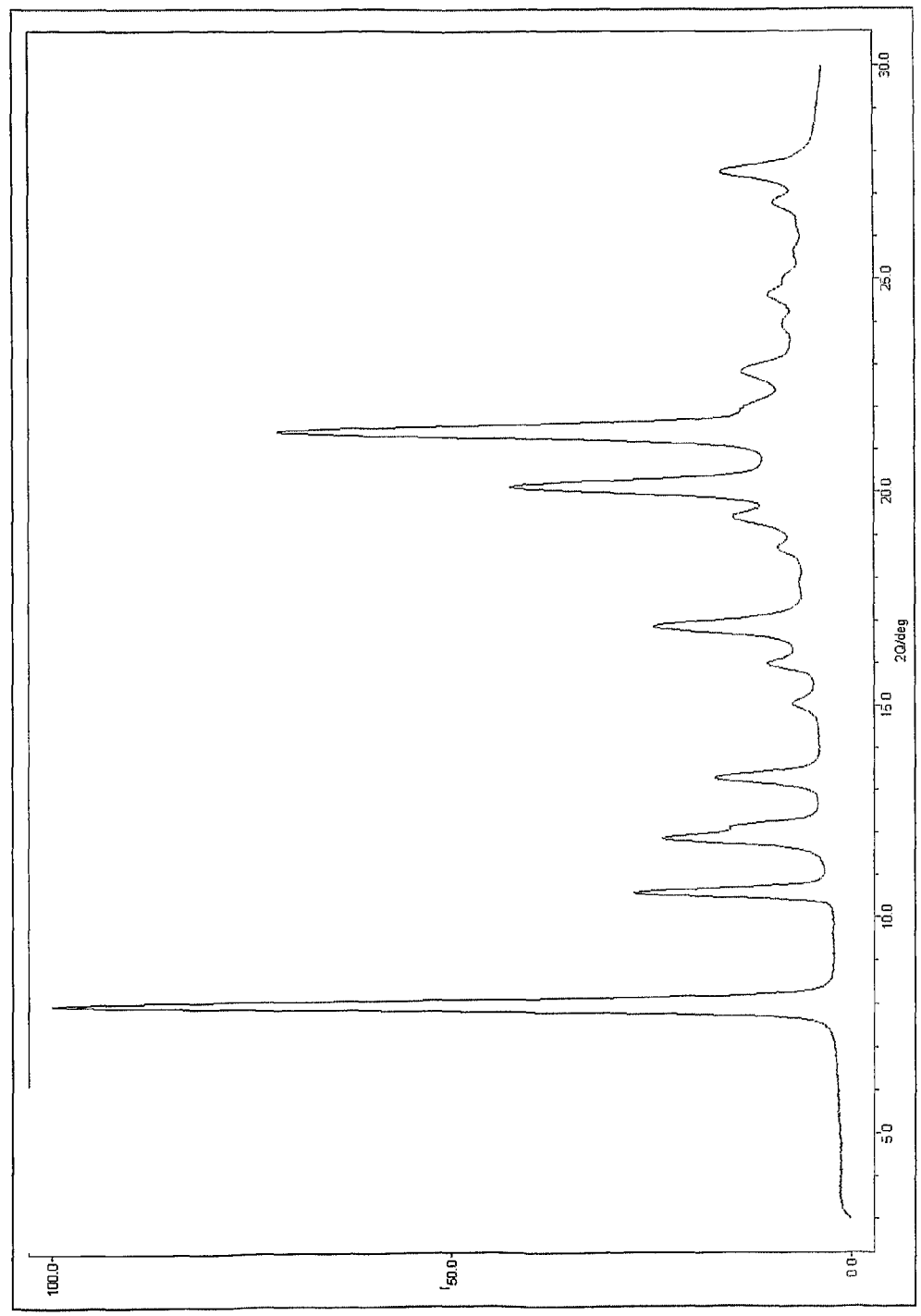
FIG. 3 shows the XRPD pattern of the free base of 1-cyclopropyl-3-[3-(5-morpholin-4-ylmethyl-1H-benzoimidazol-2-yl)-1H-pyrazol-4-yl]-urea as described in Example 70 below.

The XRPD pattern for the FB1 form of 1-cyclopropyl-3-[3-(5-morpholin-4-ylmethyl-1H-benzoimidazol-2-yl)-1H-pyrazol-4-yl]-urea free base is provided in FIG. 3 and details of the main peaks are listed in Table 3.

TABLE 3

2θ, d-spacing and relative intensity of main peaks.

| 2θ/° | d/Å | I |
|---|---|---|
| 7.97 | 11.09 | 100 |
| 10.60 | 8.35 | 26 |
| 11.87 | 7.46 | 23 |
| 12.13 | 7.30 | 15 |
| 13.30 | 6.66 | 16 |
| 15.04 | 5.89 | 6 |
| 15.97 | 5.55 | 9 |
| 16.85 | 5.26 | 24 |
| 18.68 | 4.75 | 8 |
| 19.40 | 4.58 | 14 |
| 20.10 | 4.42 | 42 |
| 21.40 | 4.15 | 72 |
| 21.92 | 4.05 | 13 |
| 22.81 | 3.90 | 13 |
| 23.92 | 3.72 | 8 |
| 24.62 | 3.62 | 9 |

TABLE 3-continued

2θ, d-spacing and relative intensity of main peaks.

| 2θ/° | d/Å | I |
|---|---|---|
| 24.98 | 3.56 | 8 |
| 26.78 | 3.33 | 9 |
| 27.52 | 3.24 | 15 |

Example 71

Determination of the Crystal Structure of 1-Cyclopropyl-3-[3-(5-Morpholin-4-ylmethyl-1H-Benzoimidazol-2-yl)-1H-Pyrazol-4-yl]-Urea lactate salt A single crystal form of 1-cyclopropyl-3-[3-(5-morpholin-4-ylmethyl-1H-benzoimidazol-2-yl)-1H-pyrazol-4-yl]-urea L-lactate salt has been identified. The crystal used for the diffraction experiment was a colourless prism with dimensions 0.1×0.1×0.1 mm$^3$ obtained by evaporation from ethanol. Crystallographic data were collected at 97 K using CuKα radiation (λ=1.5418 Å) from a Rigaku rotating anode RU3HR, Osmic blue confocal optics, AFC9 ¼χ goniometer and a Rigaku Jupiter CCD detector. Images were collected in five ω scans, one at 2θ=15° and four scans at 2θ=90° with a detector to crystal distance of 67 mm. Data collection was controlled by CrystalClear software and images were processed and scaled by Dtrek. Although absorption coefficient was moderate (μ=0.78 mm$^{-1}$) data were corrected using 4$^{th}$ order Fourier absorption correction to compensate for glue and crystal holder (micromount) absorption. It was found that the crystals belong to an orthorhombic space group P2$_1$2$_1$2$_1$ (# 19) with crystal lattice parameters a=9.94 (10), b=15.03 (10), c=16.18 (10) Å, α=β=γ=90°. The numbers in brackets represents the deviation (s.u., standard uncertainty). One short room temperature scan was taken to check crystal lattice parameters and symmetry. It was found that symmetry is the same as at 97 (2) K and crystal lattice parameters are similar (room temperature a=10.08, b=15.22, c=16.22 Å).

The crystal structure was solved using direct methods implemented in SHELXS-97. Absolute configuration was selected to match L-lactate configuration used in crystallisation experiment. Intensity data for a total of 3417 unique reflections in a resolution range from 11-0.9 Å (4.01<θ<58.92) were used in the refinement of 308 crystallographic parameters by SHELXL-97. Final statistical parameters were: wR2=0.2275 (all data), R$_F$=0.0817 (data with I>2σ(I)) and goodness of fit S=1.076.

One molecule of protonated free base and one L-lactate anion were found in the asymmetric unit. The elemental composition of the asymmetric unit was C$_{22}$H$_{29}$N$_7$O$_5$ and the calculated density of the crystals is 1.30 Mg/m$^3$. Hydrogen atoms were generated on geometrical grounds while the location of heteroatom bound hydrogen atoms was confirmed by inspection of Fo-Fc difference maps. The positional and thermal parameters of hydrogen atoms were constricted to ride on corresponding non-hydrogen atoms. The thermal motion of non-hydrogen atoms was modelled by anisotropic thermal factors (see FIG. 4).

The crystal structure contains one intramolecular (N22-H . . . N14 2.852 Å) and seven intermolecular hydrogen bonds forming complex 3D network (see FIG. 5). Two of intermolecular H-bonds, N7-H . . . O24 2.800 Å and N25-H . . . N2 3.004 Å, link 1-cyclopropyl-3-[3-(5-morpholin-4-ylmethyl-1H-benzoimidazol-2-yl)-1H-pyrazol-4-yl]-urea molecules into chains along crystallographic c axis.

L-lactate anions are linked into chains along crystallographic a axis by H-bond O3L-H . . . O1L 2.626 Å. Two bifurcated H-bonds join 1-cyclopropyl-3-[3-(5-morpholin-4-ylmethyl-1H-benzoimidazol-2-yl)-1H-pyrazol-4-yl]-urea cations and L-lactate anions. Protonated morpholine nitrogen atom interacts with both carboxyl oxygen atoms (N16-H . . . O1L 3.125 Å and N16-H . . . O2L 2.625 Å), while pyrazole N1 nitrogen is H donor to O2L and O3L (N1-H . . . O2L 2.882 Å, N1-H . . . O3L 2.740 Å).

Figure 4:
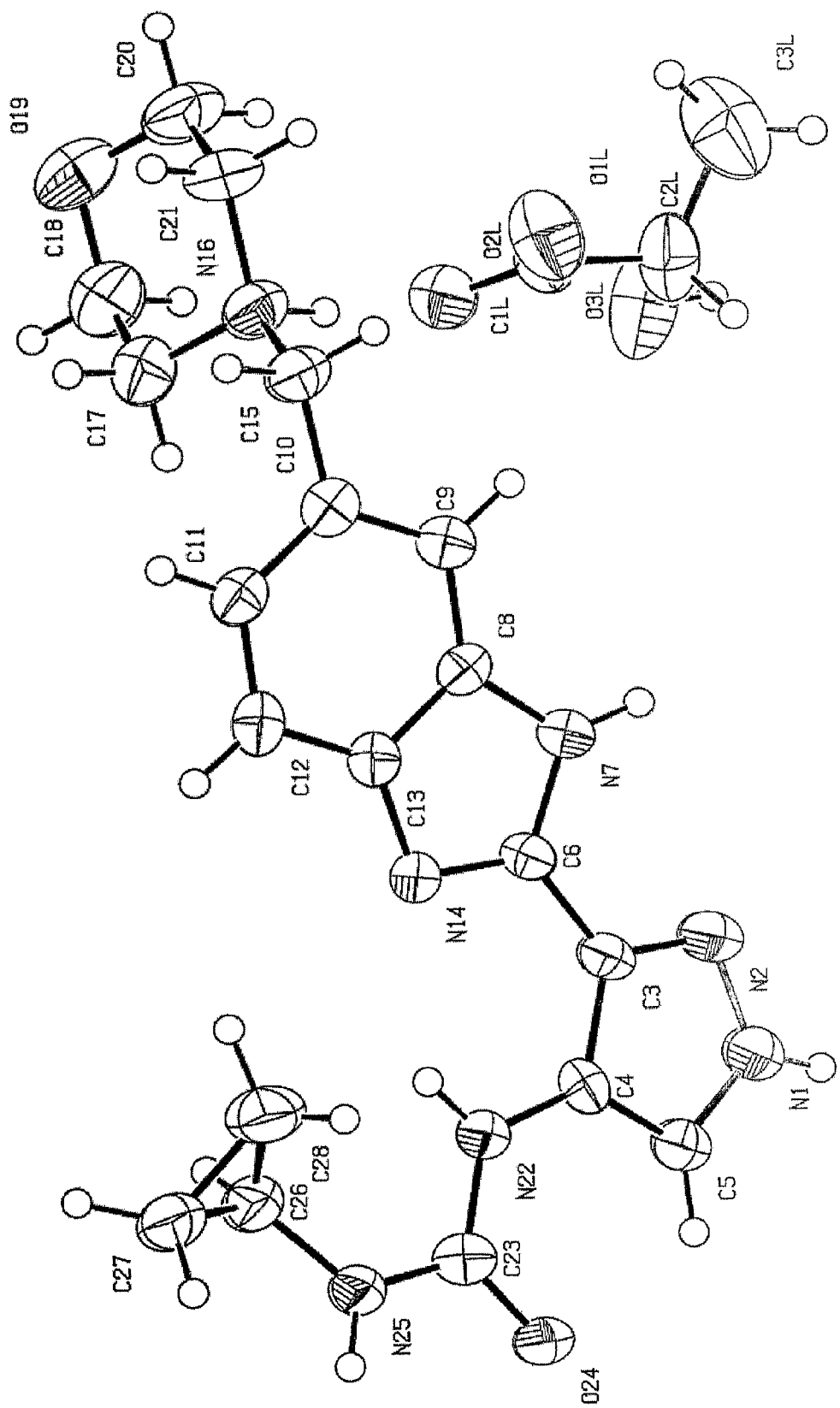
FIG. 4 shows a thermal ellipsoid plot of the L-lactate salt of 1-cyclopropyl-3-[3-(5-morpholin-4-ylmethyl-1H-benzoimidazol-2-yl)-1H-pyrazol-4-yl]-urea as described in Example 71 below.
Figure 5:
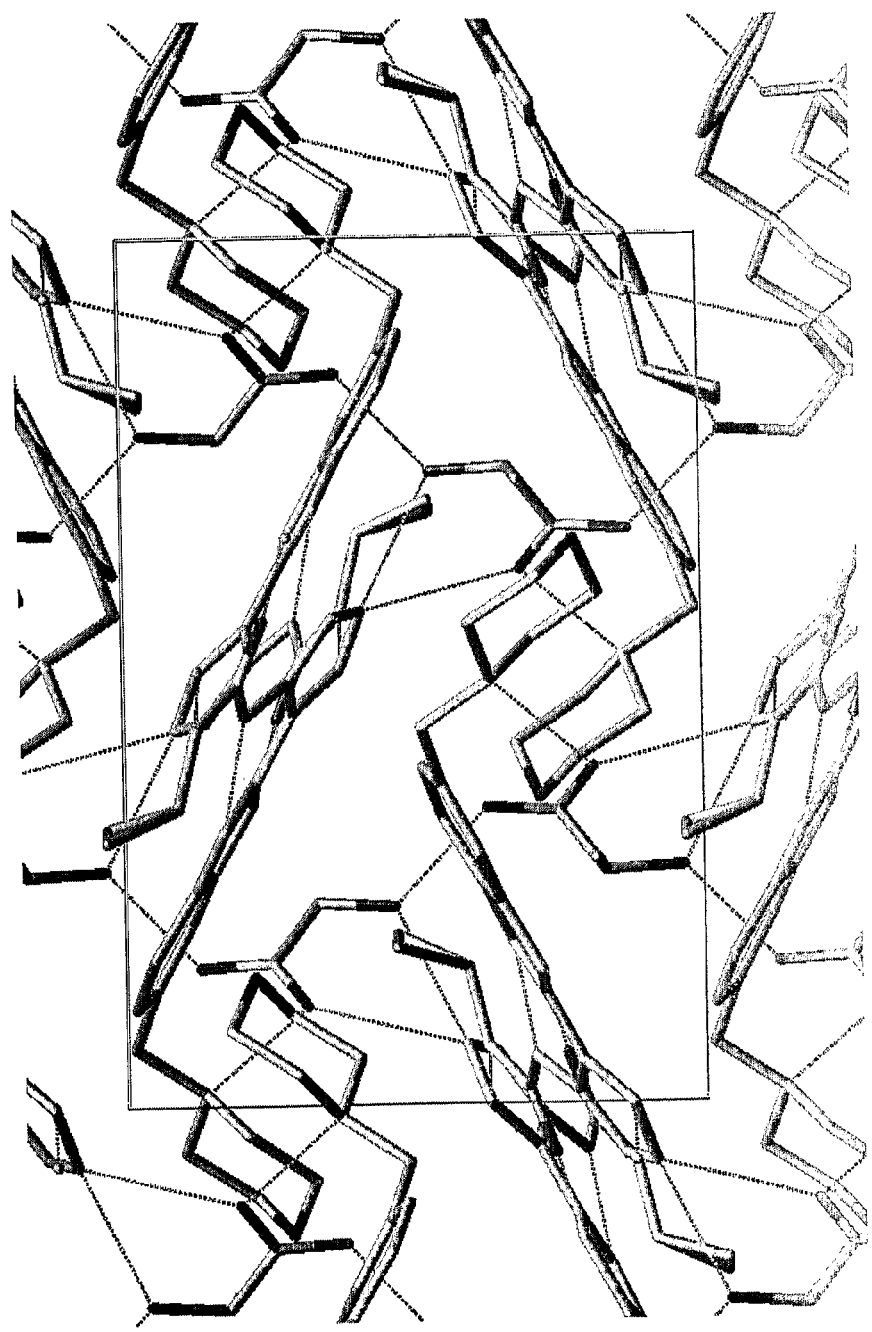
FIG. 5 shows a packing diagram of the L-lactate salt of 1-cyclopropyl-3-[3-(5-morpholin-4-ylmethyl-1H-benzoimidazol-2-yl)-1H-pyrazol-4-yl]-urea as described in Example 71 below.

A thermal ellipsoid representation of the structure generated by the X-ray diffraction study is provided in FIG. 4 and packing diagram is in FIG. 5.

The coordinates for the atoms making up the structure of 1-cyclopropyl-3-[3-(5-morpholin-4-ylmethyl-1H-benzoimidazol-2-yl)-1H-pyrazol-4-yl]-urea lactate salt are as set out in Table 4. The numbers in brackets represents the deviation (s.u., standard uncertainty).

TABLE 4

```
_cell_length_a                    9.941(10)
_cell_length_b                    15.034(10)
_cell_length_c                    16.175(10)
_cell_angle_alpha                 90.00
_cell_angle_beta                  90.00
_cell_angle_gamma                 90.00
_cell_measurement_temperature     97(2)
loop_
  _atom_site_label
  _atom_site_type_symbol
  _atom_site_fract_x
  _atom_site_fract_y
  _atom_site_fract_z
  _atom_site_U_iso_or_equiv
  _atom_site_adp_type
  _atom_site_occupancy
  _atom_site_symmetry_multiplicity
  _atom_site_calc_flag
N1   N 0.9111(5) 0.4310(3) 0.5668(2) 0.0509(12) Uani 1 1 d
H1   H 0.9653 0.3878 0.5824 0.061 Uiso 1 1 calc
N2   N 0.8702(5) 0.4971(3) 0.6177(2) 0.0503(12) Uani 1 1 d
C3   C 0.7902(5) 0.5479(3) 0.5704(3) 0.0395(11) Uani 1 1 d
C4   C 0.7795(6) 0.5130(3) 0.4891(3) 0.0431(12) Uani 1 1 d
C5   C 0.8601(5) 0.4380(3) 0.4893(3) 0.0449(12) Uani 1 1 d
H5   H 0.8766 0.3991 0.4441 0.054 Uiso 1 1 calc
C6   C 0.7254(5) 0.6280(3) 0.6003(3) 0.0404(12) Uani 1 1 d
N7   N 0.7166(4) 0.6504(3) 0.6825(2) 0.0428(10) Uani 1 1 d
H7   H 0.7473 0.6201 0.7250 0.051 Uiso 1 1 calc
C8   C 0.6485(5) 0.7316(3) 0.6840(3) 0.0413(11) Uani 1 1 d
C9   C 0.6136(5) 0.7875(3) 0.7496(3) 0.0443(12) Uani 1 1 d
H9   H 0.6337 0.7722 0.8052 0.053 Uiso 1 1 calc
C10  C 0.5477(6) 0.8667(3) 0.7300(3) 0.0482(12) Uani 1 1 d
C11  C 0.5166(5) 0.8863(3) 0.6481(3) 0.0495(13) Uani 1 1 d
H11  H 0.4708 0.9403 0.6364 0.059 Uiso 1 1 calc
C12  C 0.5495(6) 0.8304(3) 0.5826(3) 0.0508(13) Uani 1 1 d
H12  H 0.5264 0.8449 0.5272 0.061 Uiso 1 1 calc
C13  C 0.6186(5) 0.7510(3) 0.6021(3) 0.0428(12) Uani 1 1 d
N14  N 0.6671(4) 0.6851(3) 0.5497(2) 0.0434(10) Uani 1 1 d
C15  C 0.5154(6) 0.9337(3) 0.7949(3) 0.0529(14) Uani 1 1 d
H15A H 0.4767 0.9027 0.8434 0.064 Uiso 1 1 calc
H15B H 0.4462 0.9749 0.7733 0.064 Uiso 1 1 calc
N16  N 0.6353(5) 0.9869(3) 0.8225(3) 0.0504(11) Uani 1 1 d
H16  H 0.6962 0.9472 0.8458 0.060 Uiso 1 1 calc
C17  C 0.7050(7) 1.0325(4) 0.7543(4) 0.0652(16) Uani 1 1 d
H17A H 0.6420 1.0734 0.7260 0.078 Uiso 1 1 calc
H17B H 0.7370 0.9882 0.7135 0.078 Uiso 1 1 calc
C18  C 0.8234(7) 1.0844(4) 0.7881(4) 0.0732(18) Uani 1 1 d
H18A H 0.8887 1.0426 0.8130 0.088 Uiso 1 1 calc
H18B H 0.8689 1.1157 0.7421 0.088 Uiso 1 1 calc
O19  O 0.7835(5) 1.1470(3) 0.8481(3) 0.0804(14) Uani 1 1 d
C20  C 0.7191(8) 1.1040(4) 0.9155(4) 0.0724(19) Uani 1 1 d
H20A H 0.6921 1.1492 0.9568 0.087 Uiso 1 1 calc
H20B H 0.7835 1.0629 0.9423 0.087 Uiso 1 1 calc
C21  C 0.5984(6) 1.0533(4) 0.8886(3) 0.0619(16) Uani 1 1 d
H21A H 0.5299 1.0950 0.8668 0.074 Uiso 1 1 calc
H21B H 0.5591 1.0218 0.9366 0.074 Uiso 1 1 calc
N22  N 0.7055(5) 0.5524(3) 0.4260(2) 0.0455(10) Uani 1 1 d
```

TABLE 4-continued

```
H22  H 0.6642 0.6028 0.4368 0.055 Uiso 1 1 calc
C23  C 0.6930(6) 0.5175(4) 0.3483(3) 0.0475(13) Uani 1 1 d
O24  O 0.7394(4) 0.4431(2) 0.32976(19) 0.0524(10) Uani 1 1 d
N25  N 0.6245(5) 0.5675(3) 0.2934(2) 0.0506(11) Uani 1 1 d
H25  H 0.5979 0.5428 0.2468 0.061 Uiso 1 1 calc
C26  C 0.5929(6) 0.6602(3) 0.3080(3) 0.0512(13) Uani 1 1 d
H26  H 0.6709 0.7017 0.3144 0.061 Uiso 1 1 calc
C27  C 0.4712(6) 0.6964(4) 0.2675(3) 0.0580(15) Uani 1 1 d
H27A H 0.4182 0.6557 0.2321 0.070 Uiso 1 1 calc
H27B H 0.4743 0.7589 0.2481 0.070 Uiso 1 1 calc
C28  C 0.4692(7) 0.6806(4) 0.3585(3) 0.0642(17) Uani 1 1 d
H28A H 0.4156 0.6298 0.3794 0.077 Uiso 1 1 calc
H28B H 0.4718 0.7331 0.3954 0.077 Uiso 1 1 calc
C1L  C 0.7508(6) 0.8367(4) 0.9477(3) 0.0521(14) Uani 1 1 d
O1L  O 0.6267(5) 0.8403(3) 0.9593(3) 0.0793(14) Uani 1 1 d
O2L  O 0.8130(4) 0.8862(3) 0.8976(2) 0.0595(11) Uani 1 1 d
C2L  C 0.8308(7) 0.7682(4) 0.9940(4) 0.0692(17) Uani 1 1 d
H2L  H 0.7934 0.7082 0.9802 0.083 Uiso 1 1 calc
O3L  O 0.9655(5) 0.7716(3) 0.9651(4) 0.0935(17) Uani 1 1 d
H3L  H 1.0127 0.7353 0.9918 0.140 Uiso 1 1 calc
C3L  C 0.8189(9) 0.7814(7) 1.0854(5) 0.108(3) Uani 1 1 d
H3L1 H 0.7804 0.7279 1.1106 0.162 Uiso 1 1 calc
H3L2 H 0.7603 0.8324 1.0966 0.162 Uiso 1 1 calc
H3L3 H 0.9082 0.7925 1.1088 0.162 Uiso 1 1 calc
```

Example 72

1-Cyclopropyl-3-[3-(5-Morpholin-4-ylmethyl-1H-Benzoimidazol-2-yl)-1H-Pyrazol-4-yl]-Urea salt stability at 40° C. 75% RH Approximately 15 mg of samples for the stability study were gently ground by marble mortar and transferred to a Petri dish in a thin layer. Samples were then placed in sealed containers containing saturated NaCl solution with an excess of undissolved NaCl. This in turn was placed into an incubator held at 40° C. to provide an environment of 40° C. and #75% relative humidity (RH). Samples were analysed by X-ray powder diffraction (XRPD) in regular intervals.

Samples for XRPD data collection were loaded into crystallographic capillary (from Hampton Research, made of Quartz, diameter=0.4 mm). Diffraction patterns were collected at room temperature using CuKα radiation ($\lambda$=1.5418 Å) from a Rigaku rotating anode RU3HR, Osmic blue confocal optics, ¼ χ goniometer and a Rigaku HTC image plate detector. 2D Images were collected while spinning φ axis with a detector to crystal distance of 250 mm. Data collection was controlled by CrystalClear software and 2D images were converted to 1D plot (2θ vs. Intensity) by Datasqueeze (intensity averaged over the azimuthal angle $0 \leq \chi \leq 360°$ for 2θ range 3-30° in 0.01° steps). In house program AstexXRPD was used for manipulation and visualisation of 1D XRPD patterns.

XRPD patterns of the lactate salt, free base (FB1) and dihydrate free base (FB2) do not change over the period of 1-2 month while exposed to 40° C. and 75% RH. The XRPD patterns of the starting and stability tested samples of lactate salt, free base (FB1) and dihydrate free base (FB2) are provided in FIG. 6-8.

Figure 6:
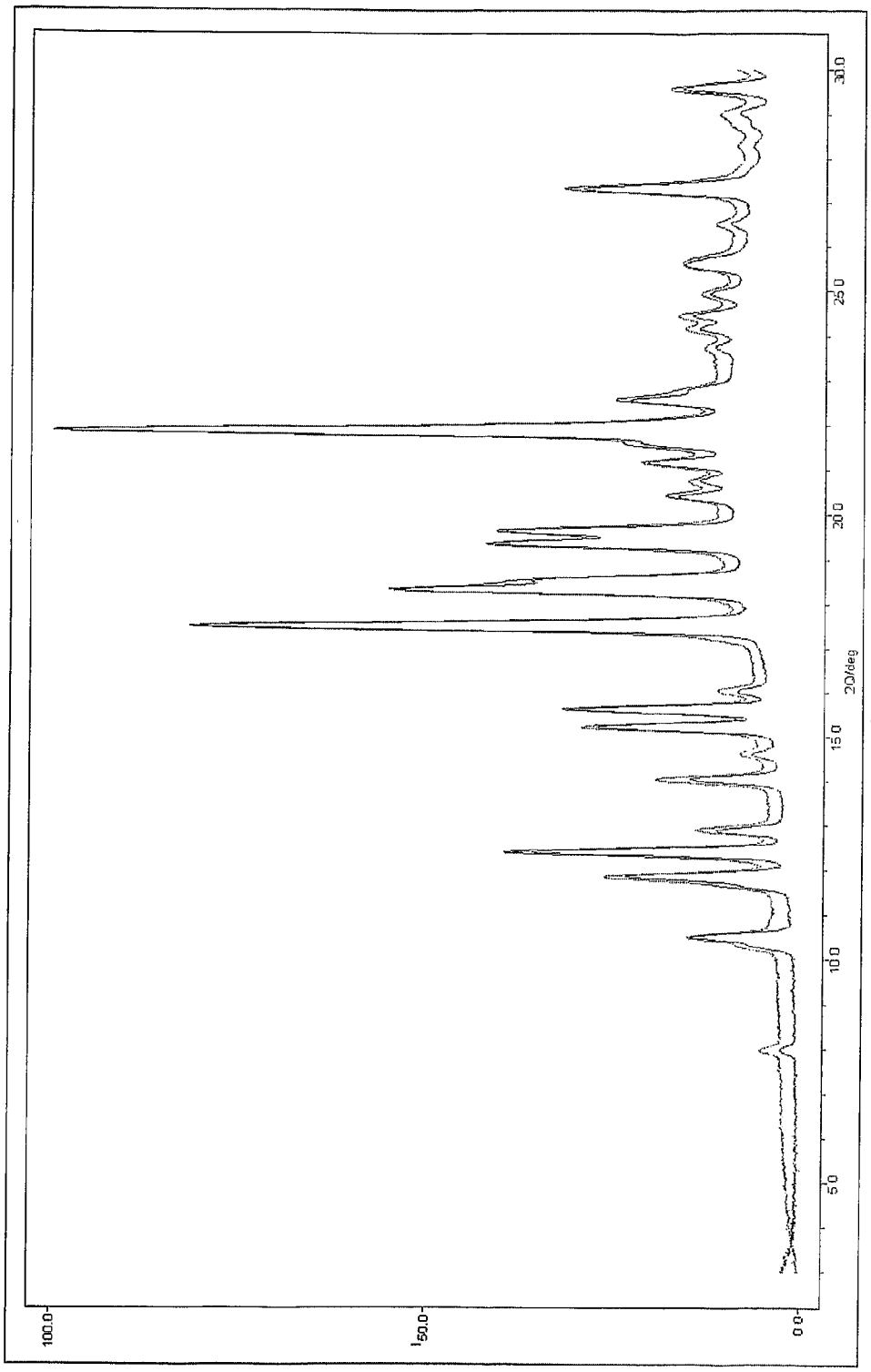
FIG. 6 shows the XRPD patterns of starting and stability tested samples of the L-lactate salt of 1-cyclopropyl-3-[3-(5-morpholin-4-ylmethyl-1H-benzoimidazol-2-yl)-1H-pyrazol-4-yl]-urea as described in Example 72 below.
Figure 7:
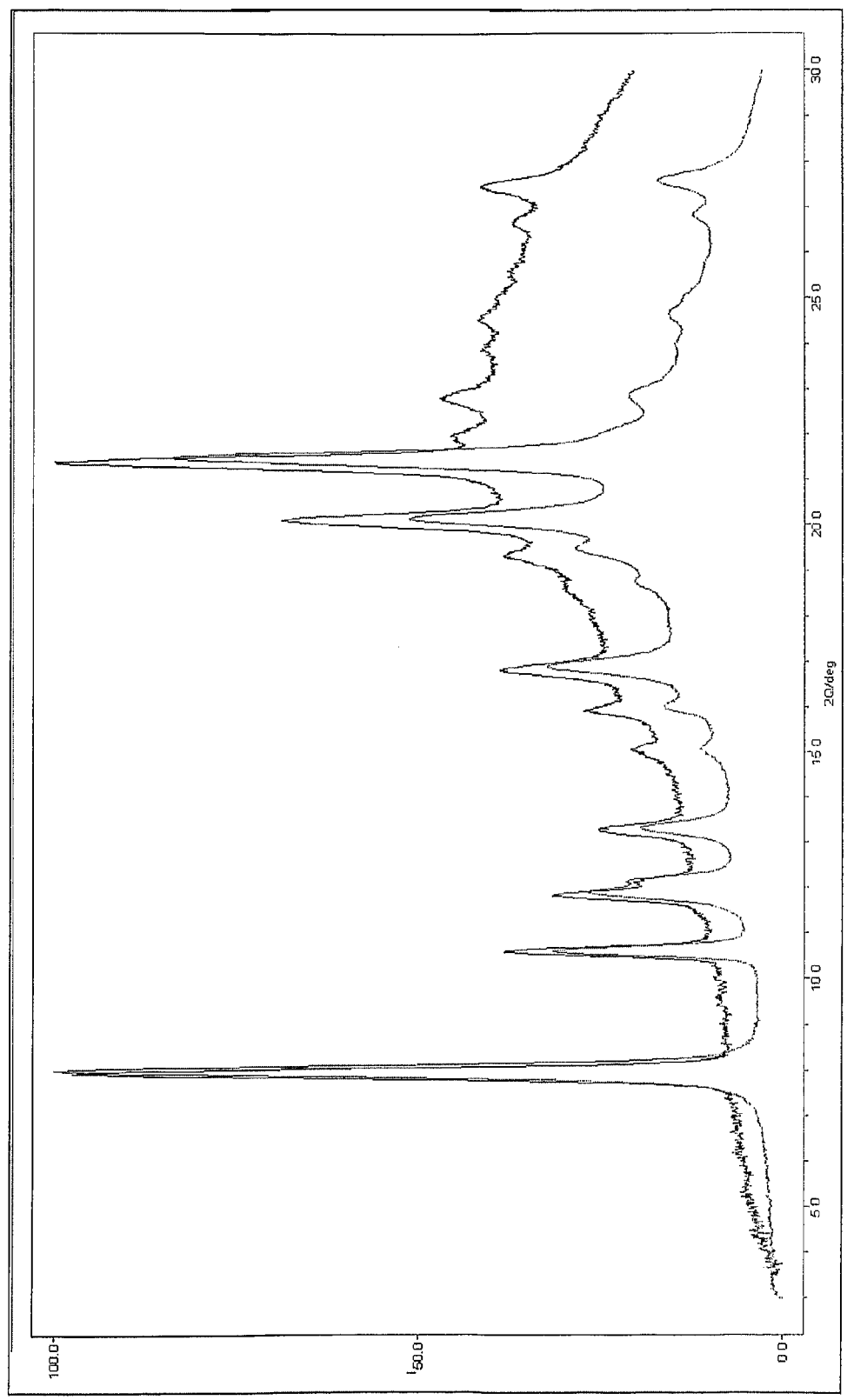
FIG. 7 shows the XRPD patterns of starting and stability tested samples of the free base (FB1) of 1-cyclopropyl-3-[3-(5-morpholin-4-ylmethyl-1H-benzoimidazol-2-yl)-1H-pyrazol-4-yl]-urea as described in Example 72 below.

The XRPD pattern for the L-lactate salt of 1-cyclopropyl-3-[3-(5-morpholin-4-ylmethyl-1H-benzoimidazol-2-yl)-1H-pyrazol-4-yl]-urea free base is provided in FIG. 6 and the details of the main peaks are listed in Table 5.

TABLE 5

| 2Θ/° | d/Å | I |
|---|---|---|
| 8.00 | 11.05 | 3 |
| 10.30 | 8.58 | 7 |
| 10.50 | 8.42 | 15 |
| 11.55 | 7.66 | 8 |
| 11.85 | 7.46 | 23 |
| 12.40 | 7.13 | 35 |
| 12.90 | 6.86 | 11 |
| 14.00 | 6.32 | 15 |
| 14.60 | 6.06 | 6 |
| 15.20 | 5.83 | 27 |
| 15.60 | 5.68 | 30 |
| 16.00 | 5.54 | 9 |
| 17.50 | 5.06 | 81 |
| 18.30 | 4.85 | 54 |
| 18.50 | 4.79 | 36 |
| 19.30 | 4.60 | 41 |
| 19.60 | 4.53 | 40 |
| 20.40 | 4.35 | 16 |
| 20.75 | 4.28 | 14 |
| 21.15 | 4.20 | 20 |
| 21.60 | 4.11 | 22 |
| 21.85 | 4.07 | 100 |
| 22.50 | 3.95 | 23 |
| 22.75 | 3.91 | 15 |
| 23.70 | 3.75 | 12 |
| 24.15 | 3.68 | 14 |
| 24.40 | 3.65 | 15 |
| 24.90 | 3.57 | 13 |
| 25.60 | 3.48 | 16 |
| 26.50 | 3.36 | 10 |
| 27.30 | 3.26 | 29 |
| 28.30 | 3.15 | 6 |
| 29.00 | 3.08 | 9 |
| 29.50 | 3.03 | 15 |

Figure 8:
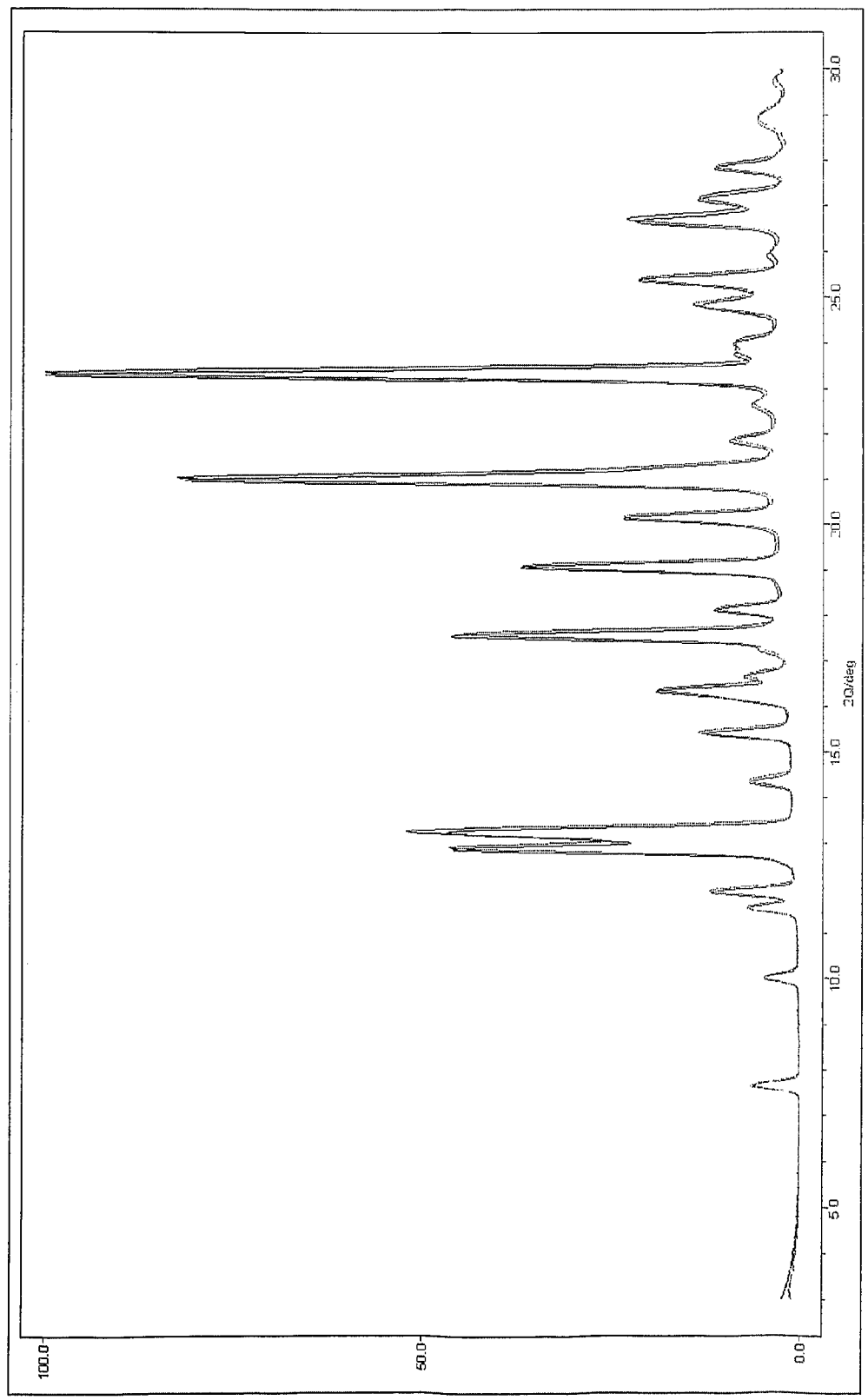
FIG. 8 shows the XRPD patterns of starting and stability tested samples of the free base dihydrate (FB2) of 1-cyclopropyl-3-[3-(5-morpholin-4-ylmethyl-1H-benzoimidazol-2-yl)-1H-pyrazol-4-yl]-urea as described in Example 72 below.

The XRPD pattern for the dihydrate free base FB2 form of 1-cyclopropyl-3-[3-(5-morpholin-4-ylmethyl-1H-benzoimidazol-2-yl)-1H-pyrazol-4-yl]-urea free base is provided in FIG. 8 and details on main peaks are listed in Table 6.

TABLE 6

| 2Θ/° | d/Å | I |
|---|---|---|
| 7.50 | 11.78 | 8 |
| 10.00 | 8.84 | 5 |
| 11.50 | 7.69 | 9 |
| 11.90 | 7.43 | 13 |
| 12.80 | 6.91 | 48 |
| 13.20 | 6.70 | 44 |
| 14.20 | 6.23 | 9 |
| 15.40 | 5.75 | 17 |
| 16.20 | 5.47 | 24 |
| 16.60 | 5.34 | 13 |
| 17.00 | 5.21 | 11 |
| 17.40 | 5.09 | 52 |
| 18.00 | 4.93 | 20 |
| 19.00 | 4.67 | 48 |
| 20.00 | 4.44 | 31 |
| 20.80 | 4.27 | 76 |
| 21.15 | 4.20 | 30 |
| 21.75 | 4.08 | 22 |
| 22.60 | 3.93 | 20 |
| 23.10 | 3.85 | 100 |
| 23.55 | 3.78 | 22 |
| 23.95 | 3.71 | 22 |
| 24.90 | 3.57 | 26 |
| 25.30 | 3.52 | 35 |
| 26.65 | 3.34 | 34 |
| 27.00 | 3.30 | 24 |
| 27.80 | 3.21 | 22 |
| 28.85 | 3.09 | 18 |
| 29.35 | 3.04 | 14 |

BIOLOGICAL ACTIVITY

Example 73

Measurement of Activated CDK2/CyclinA Kinase Inhibitory Activity Assay ($IC_{50}$)

Compounds of the invention were tested for kinase inhibitory activity using the following protocol.

Activated CDK2/CyclinA (Brown et al, Nat. Cell Biol., 1, pp 438-443, 1999; Lowe, E. D., et al Biochemistry, 41, pp 15625-15634, 2002) is diluted to 125 μM in 2.5× strength assay buffer (50 mM MOPS pH 7.2, 62.5 mM β-glycerophosphate, 12.5 mM EDTA, 37.5 mM $MgCl_2$, 112.5 mM ATP, 2.5 mM DTT, 2.5 mM sodium orthovanadate, 0.25 mg/ml bovine serum albumin), and 10 μl mixed with 10 μl of histone substrate mix (60 μl bovine histone H1 (Upstate Biotechnology, 5 mg/ml), 940 μl $H_2O$, 35 μCi $\gamma^{33}$P-ATP) and added to 96 well plates along with 5 μl of various dilutions of the test compound in DMSO (up to 2.5%). The reaction is allowed to proceed for 2 to 4 hours before being stopped with an excess of ortho-phosphoric acid (5 μl at 2%). $\gamma^{33}$P-ATP which remains unincorporated into the histone H1 is separated from phosphorylated histone H1 on a Millipore MAPH filter plate. The wells of the MAPH plate are wetted with 0.5% orthophosphoric acid, and then the results of the reaction are filtered with a Millipore vacuum filtration unit through the wells. Following filtration, the residue is washed twice with 200 μl of 0.5% orthophosphoric acid. Once the filters have dried, 20 μl of Microscint 20 scintillant is added, and then counted on a Packard Topcount for 30 seconds. The % inhibition of the CDK2 activity is calculated and plotted in order to determine the concentration of test compound required to inhibit 50% of the CDK2 activity ($IC_{50}$).

Example 74

Measurement of Activated CDK1/CyclinB Kinase Inhibitory Activity Assay ($IC_{50}$)

CDK1/CyclinB assay is identical to the CDK2/CyclinA above except that CDK1/CyclinB (Upstate Discovery) is used and the enzyme is diluted to 6.25 nM.

Example 75

Aurora A Kinase Assays

Aurora A kinase activity can be determined using a Dissociative Enhanced Lanthanide Fluoro Immuno Assay (DELFIA) with a GSK3-derived biotinylated peptide. The amount of phosphorylated peptide produced is quantified by means of a phospho-specific primary antibody and europium-labelled anti-rabbit IgG antibody using time-resolved fluorescence at $\lambda_{ex}$=337 nm, $\lambda_{em}$=620 nm.

Kinase Reaction:

Assay reactions are set up in 96 well plates in a total reaction volume of 25 μl with 0.5 nM Aurora A (Upstate Discovery), 3 μM Biotin-CGPKGPGRRGRRRTSSFAEG, 15 μM ATP and various dilutions of compound in 10 mM MOPS, pH 7.0, 0.1 mg/ml BSA, 0.001% Brij-35, 0.5% glycerol, 0.2 mM EDTA, 10mM $MgCl_2$, 0.01% β-mercaptoethanol & 2.5% DMSO. The reaction is allowed to proceed for 60 minutes at room temperature before stopping with 100 μl STOP buffer containing 100 mM EDTA, 0.05% Surfact-Amps20 (Pierce) and 1× Blocker™ BSA in TBS (Pierce).

Detection Step:

The reaction mixture is then transferred to a 96-well Neutravidin-coated plate (Pierce) and incubated for 30 minutes to capture the biotinylated peptide. After washing 5 times with 200 μl TBST buffer per well, a mixture of anti-phospho-(Ser/Thr)-AKT substrate antibody (Cell Signalling Technology) and Eu—$N_1$ anti-rabbit IgG (Perkin Elmer) is added to all wells and left for 1 hour. After a further washing step, DELFIA enhancement solution (Perkin Elmer) is added to all wells. After an incubation of 5 minutes, the wells are counted on a Fusion plate reader.

Example 76

Aurora B Kinase Assays

Kinase Reaction:
Assay reactions are set up in 96 well plates in a total reaction volume of 25 μl with 5 nM AuroraB (ProQinase), 3 μM Biotin-CGPKGPGRRGRRRTSSFAEG, 15 μM ATP and various dilutions of compound in 25 mM TRIS pH 8.5, 0.1 mg/ml BSA, 0.025% Surfact-Amps 20, 5 mM $MgCl_2$, 1 mM DTT, & 2.5% DMSO. The reaction is allowed to proceed for 90 minutes at room temperature before stopping with 100 μl STOP buffer containing 100 mM EDTA, 0.05% Surfactamps20 (Pierce) and 1× Blocker™ BSA in TBS (Pierce). The detection step is carried out as described for AuroraA.

Example 77

GSK3-B Kinase Inhibitory Activity Assay

GSK3-β (Upstate Discovery) are diluted to 7.5 nM in 25 mM MOPS, pH 7.00, 25 mg/ml BSA, 0.0025% Brij-35, 1.25% glycerol, 0.5 mM EDTA, 25 mM $MgCl_2$, 0.025% β-mercaptoethanol, 37.5 mM ATP and 10 μl mixed with 10 μl of substrate mix. The substrate mix for GSK3-β is 12.5 μM phospho-glycogen synthase peptide-2 (Upstate Discovery) in 1 ml of water with 35 μCi γ$^{33}$P-ATP. Enzyme and substrate are added to 96 well plates along with 5 μl of various dilutions of the test compound in DMSO (up to 2.5%). The reaction is allowed to proceed for 3 hours (GSK3-β) before being stopped with an excess of ortho-phosphoric acid (5 μl at 2%). The filtration procedure is as for Activated CDK2/CyclinA assay above.

Example 78

A. Other Kinase Inhibitory Activity Assays

The inhibitory activity against these enzymes was assayed at Upstate Discovery Ltd. Enzymes were prepared at 10× final concentration in enzyme buffer (as described in table below). Enzymes were then incubated in assay buffer with various substrates and $^{33}$P-ATP (~500 cpm/pmol) as described in the table.

The reaction was initiated by the addition of Mg/ATP. The reaction was allowed to proceed for 40 minutes at room temperature before being stopped with 5 μl of a 3% phosphoric acid solution. Ten μl of the reaction mix was transferred to either a filtermatA or P30 filtermat and washed three times in 75 mM phosphoric acid and once in methanol before being dried for scintillation counting.

Compounds were tested at the concentrations detailed below in duplicate against all kinases and the percent activity compared to control was calculated. Where inhibition was high an IC50 was determined.

| Enzyme | Enzyme Buffer | Assay Buffer | Substrate | ATP Concentration (μM) |
|---|---|---|---|---|
| c-abl | A | A | 50 μM EAIYAAPFAKKK | 45 |
| c-abl (T315I) | A | A | 50 μM EAIYAAPFAKKK | 10 |
| Cdk3 | A | A | 0.1 mg/ml Histone H1 | 200 |
| Cdk6 | A | A | 0.1 mg/ml Histone H1 | 200 |
| Cdk7 | A | A | 500 μM peptide | 90 |
| Cdk9 | A | A | 100 μM KTFCGTPEYLAPEVRREPRILSEE EQEMFRDFDYIADWC | 45 |
| Chk1 | A | A | 200 μM KKKVSRSGLYRSPSMPENLNRPR | 90 |
| Chk2 | A | A | 200 μM KKKVSRSGLYRSPSMPENLNRPR | 70 |
| Flt3 | A | A | 50 μM EAIYAAPFAKKK | 200 |
| Jak2 | A | A | 100 μM KTFCGTPEYLAPEVRREPRILSEE EQEMFRDFDYIADWC | 45 |
| PDK1 | B | B | 100 μM KTFCGTPEYLAPEVRREPRILSEE EQEMFRDFDYIADWC | 10 |
| VEGFR2 (KDR) | A | A | 0.33 mg/ml myelin basic protein | 90 |

-continued

| Enzyme | Enzyme Assay Buffer | Assay Buffer | Substrate | ATP Concentration (μM) |
|---|---|---|---|---|

Enzyme buffers were:
A: 20 mM MOPS pH 7.0, 1 mM EDTA, 0.1% β-mercaptoethanol, 0.01% Brij-35, 5% glycerol, 1 mg/ml BSA
B: 50 mM Tris pH 7.5, 0.05% β-mercaptoethanol, 1 mg/ml BSA
Assay buffers were:
A: 8 mM MOPS pH 7.0, 0.2 mM EDTA, 10 mM Mg acetate
B: 50 mM Tris pH 7.5, 0.1% β-mercaptoethanol, 10 mM Mg acetate

B. Further Kinase Inhibitory Activity Assays

The inhibitory activity against these enzymes was assayed at Upstate Discovery Ltd. Enzymes were prepared at 10× final concentration in enzyme buffer (as described in table below). Enzymes were then incubated in assay buffer with various substrates and $^{33}$P-ATP (~500 cpm/pmol) as described in the table.

The reaction was initiated by the addition of Mg/ATP. The reaction was allowed to proceed for 40 minutes at room temperature before being stopped with 5 μl of a 3% phosphoric acid solution. Ten μl of the reaction mix was transferred to either a filtermat A or P30 filtermat and washed three times in 75 mM phosphoric acid and once in methanol before being dried for scintillation counting.

Compounds were tested at the concentrations detailed below in duplicate against all kinases and the percent activity compared to control was calculated. Where inhibition was high, an IC50 was determined.

| Enzyme | Enzyme Buffer | Assay Buffer | Substrate | ATP Concentration (μM) |
|---|---|---|---|---|
| cSRC | A | A | 250 μM KVEKIGEGTYGVVYK | 200 |
| EpbB2 | A | C | 0.1 mg/ml poly(Glu, Tyr) 4:1 | 10 |
| EpbB4 | A | C | 0.1 mg/ml poly(Glu, Tyr) 4:1 | 10 |
| FGFR3 | A | C | 0.1 mg/ml Poly (Glu, Tyr) | 15 |
| Jak3 | A | A | 500 μM GGEEEEYFELVKKKK | 10 |
| Ret | A | A | 250 μM KKKSPGEYYNIEFG | 70 |

Enzyme buffers were:
A: 20 mM MOPS pH 7.0, 1 mM EDTA, 0.1% β-mercaptoethanol, 0.01% Brij-35, 5% glycerol, 1 mg/ml BSA
Assay buffers were:
A: 8 mM MOPS pH 7.0, 0.2 mM EDTA, 10 mM Mg acetate
C: 8 mM MOPS, pH 7, 0.2 mM EDTA, 10 mM $MnCl_2$, 10 mM Mg acetate

C. EGFR and PDGFR Kinase Inhibitory Activity Assays

The inhibitory activity against the EGFR and PDGFR-beta enzymes was determined. Enzymes (from Upstate) were prepared at 2× final concentration in 1× kinase assay buffer (as described below). Enzymes were then incubated with test compounds, biotinylated Flt3 substrate (biotin—DNEY-FYV) (Cell Signalling Technology Inc.) and ATP. The 60 ul reaction was allowed to proceed for 60 minutes (EGFR) or 2.5 hrs (PDGFR-beta) at room temperature on a plate shaker at 900 rpm before being stopped with 20 μl of 55 mM EDTA, pH 8. Twenty μl of 5× detection mix (50 mM HEPES, pH 7.5, 0.5 M KF, 0.1% BSA, 11.34 nM Eu-anti-pY (PT66) (PerkinElmer), 94 nM SA-XL665 (Cisbio)) was then added to each well and the plate sealed and incubated at room temperature for one hour on a plate shaker at 900 rpm. The plate was then read on a Packard Fusion plate reader in TRF mode.

| Enzyme | 1 × Assay Buffer | Flt3 substrate concentration | ATP concentration |
|---|---|---|---|
| EGFR | A | 0.15 uM | 0.9 uM |
| PDGFR-beta | B | 0.15 uM | 30 uM |

Kinase Assay buffers were:
A: 20 mM HEPES pH 7.5, 10 mM $MnCl_2$, 0.1 mg/ml BSA, 0.01% Triton X-100, 1 mM DTT, 0.1 mM Sodium orthovanadate
B: 20 mM MOPS pH 7.0, 10 mM $MnCl_2$, 0.01% Triton X-100, 1 mM DTT, 0.1 mM Sodium orthovanadate

Example 79

P450 Method

The potency of a compound against CYP450s 1A2, 2C9, 2C19, 3A4 and 2D6 was determined using the PanVera Vivid Cyp450 screening kits available from Invitrogen (Paisley, UK). CYPs are supplied in the form of baculosomes containing the CYP450 and NADPH reductase. Substrates are the fluorescent Vivid substrates. Final reaction mixtures were as follows:

1A2

100 mM potassium phosphate, pH 8, 1% methanol, 2 μM 1A2 Blue vivid substrate, 100 μM NADP$^+$, 4 nM CYP450 1A2, 2.66 mM glucose-6-phosphate, 0.32 U/ml glucose-6-phosphate dehydrogenase.

2C9

50 mM potassium phosphate, pH 8, 1% methanol, 2 μM Green vivid substrate, 100 μM NADP$^+$, 8 nM CYP450 2C9, 2.66 mM glucose-6-phosphate, 0.32 U/ml glucose-6-phosphate dehydrogenase.

2C19

50 mM potassium phosphate, pH 8, 1% methanol, 8 μM Blue vivid substrate, 100 μM NADP⁺, 4 nM CYP450 2C19, 2.66 mM glucose-6-phosphate, 0.32 U/ml glucose-6-phosphate dehydrogenase.

3A4

100 mM potassium phosphate, pH 8, 1% methanol, 10 μM 3A4 Blue vivid substrate, 100 μM NADP⁺, 2.5 nM CYP450 3A4, 2.66 mM glucose-6-phosphate, 0.32 U/ml glucose-6-phosphate dehydrogenase.

2D6

100 mM potassium phosphate, pH 8, 1% methanol, 5 μM 2D6 Blue vivid substrate, 100 μM NADP⁺, 5 nM CYP450 2D6, 2.66 mM glucose-6-phosphate, 0.32 U/ml glucose-6-phosphate dehydrogenase.

Fluorescence was monitored for 20 min at 30 s intervals on a Molecular Devices Spectramax Gemini reader. Excitation and emission wavelengths were 390 nm and 460 nm for 1A2, 2C19 and 3A4, 390 nm and 485 μm for 2D6 and 485 μm and 530 nm for 2C9. Initial rates were determined from progress curves. Compounds were made up in methanol and tested against the CYP450s at a concentration of 10 μM.

Example 80

Anti-Proliferative Activity

The anti-proliferative activities of compounds of the invention can be determined by measuring the ability of the compounds to inhibition of cell growth in a number of cell lines. Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. In addition, any morphological changes are recorded. Cell lines can be obtained from the ECACC (European Collection of cell Cultures).

In particular, compounds of the invention were tested against the HCT-116 cell line (ECACC Reference: 91091005) derived from human colon carcinoma.

The compound of the invention was found to have IC₅₀ values of less than 1 μM in this assay. In addition it was found to have the minimum concentration at which polyploidy or multinucleation is observed of less than 100 nM.

Example 81

A. General Colony Forming Assay Protocol

The effect of various treatment treatments of compounds on adherent tumour cell lines was assessed in a clonogenic assay.

Cells were seeded at a concentration of 75 to 100 cells/ml relevant culture media onto 6 or 24 well tissue culture plates and allowed to recover for 16 h.

Compound or vehicle control (DMSO) was added to duplicate wells to give a final DMSO concentration of 0.1%. Following compound addition, colonies were allowed to grow out for between 10 and 14 days for optimum discrete colony counting. Colonies were fixed in 2 ml Carnoys fixative (25% Acetic Acid, 75% Methanol) and stained in 2 ml 0.4% w/v crystal violet. The number of colonies in each well were counted. Only multi-cellular colonies of approximately 50 cells or more which show proliferation from a single cell to a colony of many cells (i.e. complete cell cycles including successful cytokinesis) were scored. Single multi-nucleated (polyploid) cells were not scored. IC50 values were calculated by sigmoidal dose-response (variable slope) IC50 curves using Prism Graphpad Software.

B. Colony Forming Assay Protocol for 1-Cyclopropyl-3-[3-(5-morpholin-4-ylmethyl-1H-benzoimidazol-2-yl)-1H-pyrazol-4-yl]-urea The effect of various treatment treatments of 1-cyclopropyl-3-[3-(5-morpholin-4-ylmethyl-1H-benzoimidazol-2-yl)-1H-pyrazol-4-yl]-urea on A2780, A549, HCT 116, HCT 116 N7, HT-29, MCF7, MIA-Pa-Ca-2, SW620 cell lines was assessed in a clonogenic assay.

Cells were seeded at a concentration of 75 to 100 cells/ml relevant culture media onto 6 or 24 well tissue culture plates and allowed to recover for 16 h.

| Cell Line | Media | Comments |
|---|---|---|
| HCT 116 | DMEM + 10% FBS + GLUTAMAX I | |
| HCT 116 N7 | DMEM + 10% FBS + GLUTAMAX I + 0.4 mg/ml G418 | |
| HT-29 | McCoy'5a + 10% FBS + 2 mM L-Glutamine | |
| SW620 | L-15 + 10% FBS + GLUTAMAX I | Atmospheric $CO_2$ |
| A2780 | RPMI 1640 + 2 mM Glutamine + 10% FBS | |
| A549 | DMEM + 10% FBS + GLUTAMAX I | |
| MCF7 | EMEM + 10% FBS + 2 mM L-Glutamine + 1% NEAA | |
| MIA-Pa—Ca-2 | DMEM + 10% FBS + GLUTAMAX I | |

1-Cyclopropyl-3-[3-(5-morpholin-4-ylmethyl-1H-benzoimidazol-2-yl)-1H-pyrazol-4-yl]-urea or vehicle control (DMSO) was added to duplicate wells to give a final DMSO concentration of 0.1%. Following compound addition, colonies were allowed to grow out for between 10 and 14 days for optimum discrete colony counting. Colonies were fixed in 2 ml Carnoys fixative (25% Acetic Acid, 75% Methanol) and stained in 2 ml 0.4% w/v crystal violet. The number of colonies in each well were counted. Only multi-cellular colonies of approximately 50 cells or more which show proliferation from a single cell to a colony of many cells (i.e. complete cell cycles including successful cytokinesis) were scored. Single multi-nucleated (polyploid) cells were not scored. IC50 values were calculated by sigmoidal dose-response (variable slope) IC50 curves using Prism Graphpad Software.

Inhibitory Effect on Tumour Cell Colony Formation

| Origin | Origin | IC50 (nM) | p53 Status* |
|---|---|---|---|
| Colon | HCT 116 | 13 | + |
| | HCT 116 N7 | 14 | − |
| | HT-29 | 11 | − |
| | SW620 | 14 | − |

-continued

| Origin | Origin | IC50 (nM) | p53 Status* |
|---|---|---|---|
| Ovarian | A2780 | 7.7 | + |
| Lung | A549 | 12 | + |
| Breast | MCF7 | 20 | + |
| Pancreatic | MIA-Pa—Ca-2 | 7.8 | − |

*+ indicates expression of wild type p53; − indicates no expression of p53 or that p53 is non-functional.

Example 82

Western Blotting Assay to Determine the Inhibition of Phosphorylation of the Downstream Substrates of JAK2 (e.g. Stat5) and Bcr-Abl (e.g. CRKL) in Erythroleukemia (HEL) and Chronic Myelogenous Leukaemia (K562) Cells Following compound treatment at a final concentration of 0.1% DMSO, cells were harvested and lysed in ice cold triton lysis buffer. Lysates were cleared by centrifugation and a sample of the supernatant removed for protein determination. Equivalent amounts of protein lysate had SDS sample buffer and DTT added and were boiled for 5 minutes.

Samples were resolved by SDS PAGE, blotted onto nitrocellulose filters, blocked with 5% non-fat milk or equivalent blocking buffer and incubated overnight with the specific antibodies to phosphorylated and non-phosphorylated proteins at 4° C. Secondary antibodies used were anti-rabbit and anti-mouse IgG, HRP linked (Cell Signalling Technology) and detection achieved using ECL$^{PLUS}$ reagents (Amersham Bioscience). Alternatively secondary antibodies used were IRDye® conjugated and detection achieved using the Odyssey Infrared Imaging System (LI-COR Biosciences).

Using this protocol, it was shown that the phosphorylation of direct downstream substrates of JAK2 (e.g. Stat5) and Bcr-Abl (e.g. CRKL) in erythroleukemia (HEL) and chronic myelogenous leukaemia (K562) cells respectively is inhibited when cells are treated with 1-cyclopropyl-3-[3-(5-morpholin-4-ylmethyl-1H-benzoimidazol-2-yl)-1H-pyrazol-4-yl]-urea. The results are set out in the table below.

| Downstream substrates | Kinase | 1-Cyclopropyl-3-[3-(5-morpholin-4-ylmethyl-1H-benzoimidazol-2-yl)-1H-pyrazol-4-yl]-urea |
|---|---|---|
| Histone H3 phosphorylation | Aurora | 10-30 nM |
| crkl phosphorylation | BCR-abl | ~10000 nM |
| STAT5 phosphorylation | JAK2 | 100-300 nM |

PHARMACEUTICAL FORMULATIONS

Example 83

(i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

(v) Injectable formulation III

A formulation for i.v. delivery by injection or infusion can be prepared by dissolving the compound of formula (I) (e.g. in a salt form) in water at 20 mg/ml. The vial is then sealed and sterilised by autoclaving.

(vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(viii) Lyophilised Formulation I

Aliquots of formulated compound of formula (I) or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(viii) Lyophilised Formulation II

Aliquots of formulated compound of formula (I) or s salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation for use in i.v. administration III

An aqueous buffered solution is prepared by dissolving 1-cyclopropyl-3-[3-(5-morpholin-4-ylmethyl-1H-benzoimidazol-2-yl)-1H-pyrazol-4-yl]-urea L-lactic acid salt at a concentration of 12.86 mg/ml in a 0.02M citric acid buffer corrected to a pH of 4.5 with sodium hydroxide or hydrochloric acid.

The buffered solution is filled, with filtration to remove particulate matter, into a container (such as class 1 glass vials) which is then partially sealed (e.g. by means of a Florotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle: for example Freezing—freeze to −40° C. over 2 hours and hold at −40° C. for 3 hours.

Primary drying—ramp −40° C. to −30° C. over 8 hours and hold at −30° C. for 7 hours.

Secondary drying—ramp to +30° C. over 4 hours and hold at +30° C. for 8-10 hours On completion of the freeze drying cycle the vials are back filled with nitrogen to atmospheric pressure, stoppered and secured (e.g. with an aluminium crimp). For intravenous administration, the freeze dried solid can be reconstituted into a pharmaceutically acceptable excipient, such as 0.9% saline or 5% dextrose. The solution can be dosed as is, or can be injected into an infusion bag (containing a pharmaceutically acceptable excipient, such as 0.9% saline or 5% dextrose), before administration.

(x) Subcutaneous Injection Formulation

A composition for sub-cutaneous administration is prepared by mixing a compound of the formula (I), or a salt thereof as defined herein, with pharmaceutical grade corn oil to give a concentration of 5 mg/ml. The composition is sterilised and filled into a suitable container.

(xi) Lyophilised Formulation for use in i.v. administration IV

An aqueous buffered solution is prepared by dissolving 13 mg/ml of 1-cyclopropyl-3-[3-(5-morpholin-4-ylmethyl-1H-benzoimidazol-2-yl)-1H-pyrazol-4-yl]-urea L-lactic acid salt (equivalent to 10 mg of free base) in 20 mg/ml citric acid anhydrous buffer corrected to a pH of 4.5 with 2M aqueous sodium hydroxide or 2M aqueous hydrochloric acid.

5 ml of the solution of 1-cyclopropyl-3-[3-(5-morpholin-4-ylmethyl-1H-benzoimidazol-2-yl)-1H-pyrazol-4-yl]-urea L-lactic acid salt (containing 65.9 mg of the L-lactate salt which equates to 52 mg the free base) in approximately 100 mM (e.g. 104 mM) citrate buffer pH 4.5 was filled into 20 ml type I glass vials and lyophilised. The solution is freeze dried using a suitable cycle for example:

| Step | Cycle stage | Temperature (° C.) | Pressure (mbar) | Time (min) |
|---|---|---|---|---|
| 1 | Ramp | −40 | n/a | 120 |
| 2 | Freezing | −40 | n/a | 110 |
| 3 | Hold | −40 | 0.133 | 60 |
| 4 | Ramp | 0 | 0.133 | 90 |
| 5 | Primary drying | 0 | 0.133 | 1380 |
| 6 | Ramp | 35 | 0 | 150 |
| 7 | Secondary drying | 35 | 0 | 360 |
| 8 | Ramp | 45 | 0 | 45 |
| 9 | Secondary drying | 45 | 0 | 360 |
| 10 | Finish | | | Vials stoppered to 95% atmosphere with (pure) nitrogen. |

On completion of the freeze drying cycle the vials are back-filled with nitrogen to around atmospheric pressure (e.g. just below (95%)), stoppered and secured (e.g. with an aluminium crimp). For intravenous administration, the freeze dried solid can be reconstituted into a pharmaceutically acceptable excipient, such as 0.9% saline or 5% dextrose. The solution can be dosed as is, or can be injected into an infusion bag (containing a pharmaceutically acceptable excipient, such as 0.9% saline or 5% dextrose), before administration.

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method for the treatment of:
   A. a disease state or condition mediated by a kinase which is BCR-abl, VEGFR, PDGFR, EGFR, Flt3, JAK, C-abl, PDK1, Chk, FGFR, Ret, Eph, or Src; or
   B. a cancer in which the cancer cells thereof contain a drug resistant kinase mutation which is:
      (a) a threonine gatekeeper mutation; or
      (b) a drug-resistant gatekeeper mutation; or
      (c) an imatinib resistant mutation; or
      (d) a nilotinib resistant mutation; or
      (e) a dasatinib resistant mutation; or
      (f) a T670I mutation in KIT; or
      (g) a T674I mutation in PDGFR; or
      (h) T790M mutation in EGFR; or
      (i) a T315I mutation in abl; or
   C. a cancer which expresses a mutated molecular target which is a mutated form of BCRabl, c-kit, PDGF, EGF receptor or ErbB2;
   which method comprises administering to a patient in need thereof a therapeutically effective amount of a compound of the formula:

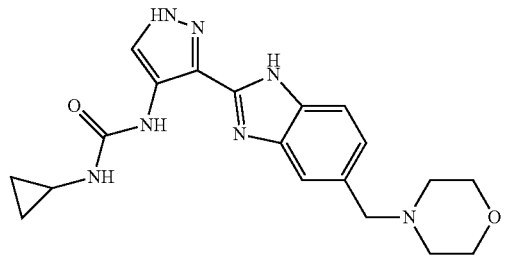 [SMILES: O=C(Nc1c[nH]nc1-c1nc2cc(CN3CCOCC3)ccc2[nH]1)NC1CC1]

or a salt, solvate, tautomer, or N-oxide thereof.

2. A method according to claim 1 comprising administering 1-cyclopropyl-3-[3-(5-morpholin-4-ylmethyl-1H-benzoimidazol-2-yl)-1H-pyrazol-4-yl]-urea or a salt thereof.

3. A method according to claim 2 wherein the salt is an L-lactate, D-lactate or citric acid salt.

4. A method as defined in claim 1, wherein said method is for the treatment of any one or more (in any combination) of diseases and conditions selected from ocular diseases or conditions; myeloproliferative disorders (MPD); juvenile myelomonocytic leukemia (JMML); Chronic Myelomonocytic Leukemias (CMML); megakaryocytic leukaemia (including megakaryocytic AML (AML M7)); Philadelphia chromosome-negative CML; imatinib resistant CML; nilotinib-resistant CML; dasatinib-resistant CML; gastrointestinal stromal tumours (GISTs); chronic myelomonocytic leukemia (CMML); the hypereosinophilic syndrome; dermatofibrosarcoma protuberans; Philadelphia chromosome positive malignancies; myeloproliferative syndrome; multiple myelomas, epithelial cancers, head and neck cancers, abnormalities in human skeletal development; thyroid cancers; and Hirschsprung's disease.

5. A method according to claim 1 wherein diseases or conditions (in any combination) are selected from myeloproliferative disorders (MPD); juvenile myelomonocytic leukemia (JMML); Chronic Myelomonocytic Leukemias (CMML); megakaryocytic leukaemia including megakaryocytic AML (AML M7); Philadelphia chromosome-negative CML; and imatinib resistant CML.

6. A method according to claim 1 wherein the disease state or condition is myelofibrosis with myeloid metaplasia (MMM).

7. A method for the diagnosis and treatment of a disease state or condition mediated by a kinase as defined in claim 1; which method comprises (i) screening a patient to determine whether a disease or condition from which the patient is or may be suffering is one which would be susceptible to treatment with a compound having activity against the kinase; and (ii) where it is indicated that the disease or condition is one from which the patient is thus susceptible, thereafter administering to the patient a compound as defined in claim 1 or a salt, solvate, tautomer, or N-oxide thereof.

8. A method for the diagnosis and treatment of a cancer in which the cancer cells thereof contain a drug resistant kinase mutation as defined in claim 1, which method comprises (i) screening a patient to determine whether a cancer from which the patient is or may be suffering is one in which the cancer cells thereof contain the drug resistant kinase mutation; and (ii) where it is indicated that the cancer cells do contain the drug resistant mutation, thereafter administering to the patient a compound as defined in claim 1 or a salt, solvate, tautomer, or N-oxide thereof.

9. A method for the diagnosis and treatment of a cancer which expresses a mutated molecular target which is a mutated form of BCRabl, c-kit, PDGF, EGF receptor or ErbB2; which method comprises (i) screening a patient to determine whether a cancer from which the patient is or may be suffering is one which expresses the said mutated molecular target; and (ii) where it is indicated that the cancer cells do express the said mutated molecular target, thereafter administering to the patient a compound as defined in claim 1 or a salt, solvate, tautomer, or N-oxide thereof.

10. A method according to claim 1 wherein the disease state or condition is a cancer selected from multiple myeloma, bladder, hepatocellular, oral squamous cell carcinoma, cervical, prostate and thyroid carcinomas, lung, breast, and colon cancers.

11. A method of modulating a cellular process by modulating the activity of a kinase selected from BCR-abl, VEGFR, PDGFR, EGFR, Flt3, JAK, C-abl, PDK1, Chk, FGFR, Ret, Eph, and Src using a compound as defined in claim 1 or a salt, solvate, tautomer, or N-oxide thereof.

12. A method for alleviating or reducing the incidence of a disease state or condition as defined in claim 1, which method comprises administering to a patient in need thereof a compound, in a therapeutically effective amount, as defined in claim 1 or a salt, solvate, tautomer, or N-oxide thereof.

13. A method according to claim 1 wherein the disease or condition is a myeloproliferative disorder (MPD) and the myeloproliferative disorder is polycythemia vera, essential thrombocythemia and idiopathic myelofibrosis.

14. A method according to claim 1 wherein the disease or condition is a Philadelphia chromosome positive malignancy and the Philadelphia chromosome positive malignancy is Philadelphia chromosome positive leukemia.

15. A method according to claim 3 wherein the salt is an L-lactate salt.

16. A method according to claim 2 wherein the salt is an L-lactate or citrate salt, or a mixture thereof.

17. A method according to claim 1 wherein the disease state or condition is multiple myeloma.

18. A method according to claim 17 comprising administering 1-cyclopropyl-3-[3-(5-morpholin-4-ylmethyl-1H-benzoimidazol-2-yl)-1H-pyrazol-4-yl]-urea or a salt thereof.

19. A method according to claim 18 wherein the salt is an L-lactate, D-lactate or citric acid salt.

20. A method according to claim 19 wherein the salt is an L-lactate salt.

21. A method according to claim 18 wherein the salt is an L-lactate or citrate salt, or a mixture thereof.

22. A method of treating multiple myeloma comprising administering a therapeutically effective amount of 1-cyclopropyl-3-[3-(5-morpholin-4-ylmethyl-1H-benzoimidazol-2-yl)-1H-pyrazol-4-yl]-urea or a salt, solvate, tautomer, or N-oxide thereof.

23. A method according to claim 22 comprising administering 1-cyclopropyl-3-[3-(5-morpholin-4-ylmethyl-1H-benzoimidazol-2-yl)-1H-pyrazol-4-yl]-urea or a salt thereof.

24. A method according to claim 23 wherein the salt is an L-lactate, D-lactate or citric acid salt.

25. A method according to claim 24 wherein the salt is an L-lactate salt.

26. A method according to claim 23 wherein the salt is an L-lactate or citrate salt, or a mixture thereof.

* * * * *